US010689428B2

(12) United States Patent
Reversade

(10) Patent No.: US 10,689,428 B2
(45) Date of Patent: *Jun. 23, 2020

(54) POLYPEPTIDES, NUCLEIC ACIDS AND USES THEREOF

(71) Applicant: AGENCY FOR SCIENCE, TECHNOLOGY AND RESEARCH, Singapore (SG)

(72) Inventor: Bruno Reversade, Singapore (SG)

(73) Assignee: Agency For Science, Technology And Research, Singapore (SG)

(*) Notice: Subject to any disclaimer, the term of this patent is extended or adjusted under 35 U.S.C. 154(b) by 0 days.

This patent is subject to a terminal disclaimer.

(21) Appl. No.: 15/865,950

(22) Filed: Jan. 9, 2018

(65) Prior Publication Data

US 2018/0265559 A1 Sep. 20, 2018

Related U.S. Application Data

(62) Division of application No. 15/101,304, filed as application No. PCT/SG2014/000574 on Dec. 3, 2014, now Pat. No. 9,902,761.

(60) Provisional application No. 61/911,276, filed on Dec. 3, 2013.

(51) Int. Cl.
| | |
|---|---|
| *C07K 14/575* | (2006.01) |
| *G01N 33/74* | (2006.01) |
| *C07K 16/26* | (2006.01) |
| *C07K 7/00* | (2006.01) |
| *C07K 14/46* | (2006.01) |
| *C12N 15/113* | (2010.01) |
| *A61K 38/00* | (2006.01) |

(52) U.S. Cl.
CPC .............. *C07K 14/575* (2013.01); *C07K 7/00* (2013.01); *C07K 14/46* (2013.01); *C07K 16/26* (2013.01); *C12N 15/113* (2013.01); *G01N 33/74* (2013.01); *A61K 38/00* (2013.01); *C07K 2317/30* (2013.01); *C07K 2317/34* (2013.01); *C12N 2310/14* (2013.01); *G01N 2333/575* (2013.01)

(58) Field of Classification Search
None
See application file for complete search history.

(56) References Cited

U.S. PATENT DOCUMENTS

| 9,309,314 | B2 * | 4/2016 | Reversade | G01N 33/74 |
| 9,902,761 | B2 * | 2/2018 | Reversade | G01N 33/74 |
| 2007/0258949 | A1 | 11/2007 | Lee et al. | |

FOREIGN PATENT DOCUMENTS

WO 2005/085280 A2 9/2005

OTHER PUBLICATIONS

Sato et al., "ELABELA-APJ axis protects from pressure overload heart failure and angiotensin II-induced cardiac lannage", Cardiovasc Res 113(7) 760-769 (2017).*
Murza et al., "Discovery and Structure-Activity Relationship of a Bioactive Fragment of ELABELA that Modulates /ascularand Cardiac Functions", J Med Chem 59(7) 2962-2972 (2016).*
Yang et al., "Elabela/Toddler Is an Endogenous Agonist of the Apelin APJ Receptor in the Adult Cardiovascular System, and Exogenous Administration of the Peptide Compensates for the Downregulation of Its Expression in Pulmonary Arterial Hypertension ", Circulation 135(12) 1160-1173 (2017).*
Cederlund et al., "Antimicrobial peptides important in innate immunity", FEBS J 278(20) 3942-3951 (2011).
Chng et al., "ELABELA: a hormone essential for heart development signals via the apelin receptor", Dev Cell 27(6) 672-680 (2013).
Church et al., "Lineage-specific biology revealed by a finished genome assembly of the mouse", PLoS Biol 7(5) e1000112 (2009).
Cummings et al., "Elevated plasma ghrelin levels in Prader Willi syndrome", Nat Med 8(7) 643-644 (2002).
Dalton, "Signaling networks in human pluripotent stem cells", Curr Opin Cell Biol 25(2) 241-246 (2013).
Firth et al., "The abundance of short proteins in the mammalian proteome", PLoS Genet 2(4) e52 (2006).
GenBank Accesion No. EB990333 16056400 ZF42 Danio rerio cDNA clone 4279044 mRNA sequence (May 26, 2006).
GenBank Accesion No. XM_001233479 Predicted: Gallus gallus uncharacterized LOC770154 (LOC770154) mRNA (Nov. 16, 2006).
GenBank Accession No. AK092578; Jul. 15, 2002.
GenBank Accession No. BG712694 pgl1n.pk013.i2 Normalized Liver Library Gallus gallus cDNA clone pgl1n.pk013.i2 5—similar to no significant hits (pLog(P) 4)G, mRNA sequence (May 8, 2001).
GenBank Accession No. BJ030019 NIBB Mochii normalized Xenopus neurula library Xenopus laevis cDNA clone XL001102 5—mRNA sequence (Dec. 5, 2001).
GenBank Accession No. DA868753 PROST2 *Homo Sapiens* cDNA clone PROTST20044251 5-, mRNA sequence (Dec. 3, 2005).
GenBank Accession No. DR729415 AGENCOURT_54833116 NICHD_XGC_Xenopus laevis cDNA clone Image: 797574 5-, mRNA sequence (Jun. 13, 2005).
GenBank Accession No. XP_001233480 Predicted: uncharacterized protein LOC770154 [Gallus gallus] (Jun. 19, 2013).

(Continued)

*Primary Examiner* — Maury A Audet
(74) *Attorney, Agent, or Firm* — Nixon Peabody LLP; Mark J. FitzGerald; Teresa A. Ptashka

(57) ABSTRACT

We describe an ELABELA polypeptide comprising a sequence CXXXRCXXXHSRVPFP (SEQ ID NO: 1), in which X signifies an amino acid residue, such as a sequence selected from the group consisting of: SEQ ID NO: 2 to SEQ ID NO: 18, preferably CLQRRCMPLHSRVPFP (SEQ ID NO: 2), or a fragment, homologue, variant or derivative thereof, which polypeptide is capable of maintaining self-renewal and/or pluripotency of a stem cell.

1 Claim, 120 Drawing Sheets

Specification includes a Sequence Listing.

(56) References Cited

OTHER PUBLICATIONS

GenBank Accession No. XP_005629510 Predicted: apelin receptor early endogenous ligan [Canis lupus familiaris] (Sep. 24, 2013).
GenBank Accession No. XP_008541294 Predicted: apelin receptor early endogenous ligand-like [Equus przewalskii] (Jul. 14, 2014).
GenBank Accession No. XP_008586594 Predicted: apelin receptor early endogenous ligand-like [Galeopterus iariegatus] (Jun. 22, 2014).
GenBank Accession No. XP_008683821 Predicted: apelin receptor early endogenous ligand [Ursus maritimus] (Aug. 4, 2014).
GenBank Accession No. XP_008770257 Predicted: apelin receptor early endogenous ligand [Rattus norvegicus] (Aug. 7, 2014).
GenBank Accession No. XP_008990755 Predicted: apelin receptor early endogenous ligand [Callithrix jacchus] (Sep. 2, 2014).
GenBank Accession No. XP_009270629 Predicted: apelin receptor early endogenous ligand-like [Aptenodytes forsteri] (Sep. 22, 2014).
GenBank Accession No. XP_009323552 Predicted: apelin receptor early endogenous ligand-like [Pygoscelis adeliae] (Sep. 26, 2014).
GenBank Accession No. XP_009473253 Predicted: apelin receptor early endogenous ligand-like, partial [Nipponia nippon] (Oct. 6, 2014).
GenBank Accession No. XP_010205212 Predicted: apelin receptor early endogenous ligand-like [Colius-striatus] (Nov. 7, 2014).
GenBank Accession No. XP_010328871 Predicted: apelin receptor early endogenous ligand [Saimiri boliviensis boliviensis] (Nov. 24, 2014).
GenBank Accession No. XP_010362890 Predicted: apelin receptor early endogenous ligand [Rhinopithecus roxellana] (Nov. 21, 2014).
Howe et al., "The zebrafish reference genome sequence and its relationship to the human genome", Nature 496 (7446) 498-503 (2013).
Hughes et al., "Proteomics of human embryonic stem cells", Proteomics 11(4) 675-690 (2011).
Miura et al., "Monitoring early differentiation events in human embryonic stem cells by massively parallel signature sequencing and expressed sequence tag scan", Stem Cells Dev 13(6) 694-715 (2004).
Montague et al., "Congenital leptin deficiency is associated with severe early-onset obesity in humans", Nature 387 (6636) 903-908 (1997).
Murza et al., "Discovery and Structure-Activity Relationship of a Bioactive Fragment of ELABELA that Modulates Vascular and Cardiac Functions", J Med Chem 59(7) 2962-2972 (2016).
Nishino et al., "Hypocretin (orexin) deficiency in human narcolepsy", Lancet 355(9197) 39-40 (2000).
Ota et al., "Complete sequencing and characterization of 21,243 full-length human cDNAs", Nat Genet 36(1) 40-45 (2004).
Peyron et al., "A mutation in a case of early onset narcolepsy and a generalized absence of hypocretin peptides in human narcoleptic brains", Nat Med 6(9) 991-997 (2000).
Rasmussen et al., "Crystal structure of the human beta2 adrenergic G-protein-coupled receptor", Nature 450(7168) 383-387 (2007).
Sato et al., "ELABELA-APJ axis protects from pressure overload heart failure and angiotensin II-induced cardiac damage", Cardiovasc Res 113(7) 760-769 (2017).
Van Den Pol, "Neuropeptide transmission in brain circuits", Neuron 76(1) 98-115 (2012).
Vassilatis et al., "The G protein-coupled receptor repertoires of human and mouse", Proc Natl Acad Sci USA 100(8) 4903-4908 (2003).

* cited by examiner

FIGURE 5F

|                | $ela^{br13}$ | $ela^{br15}$ | $ela^{br21}$ |
|---|---|---|---|
| mutant embryos | 670 | 1087 | 1664 |
| mutant adults  | 25  | 9    | 17   |
| escapee %      | 3.7 | 0.8  | 1.0  |

FIGURE 7A

|  |  | Isoelectric Point |
|---|---|---|
| ELA | GQRPVNLTMRRKLRKHNCLQRRCMPLHSRVPFP | 12.1 |
| APLN | LVQPRGSRNGPGPWQGGRRKFRRQRPRLSHKGPMPF | 12.8 |

FIGURE 9A

Hs.105196 biaised towards blastocyst

| embroid body | 0 | 0 / 69969 |
|---|---|---|
| blastocyst | 97 | 6 / 61448 |
| fetus | 1 | 1 / 556978 |
| neonate | 0 | 0 / 31070 |

Cardiac Differentiation act CASPASE 3  DAPI

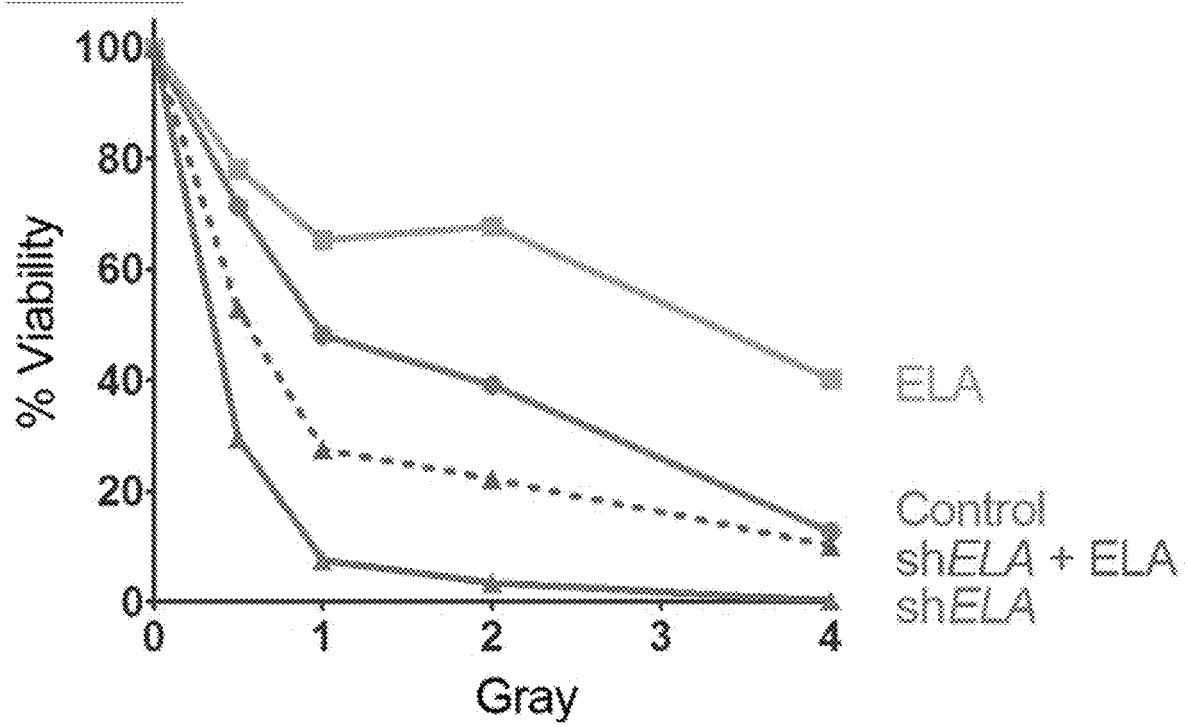

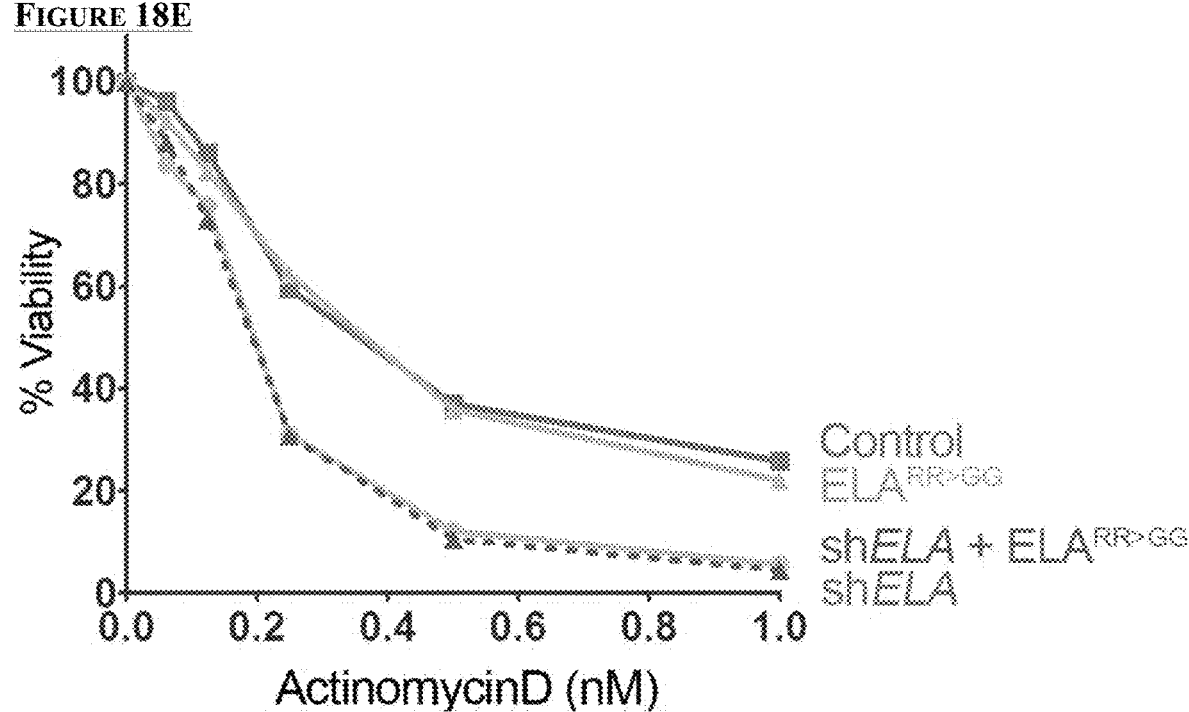

Genomic

Protein

Ela^WT   MRFQPLFWVFFIFAMSLLFISEQKPVNFPRRRKLYRHNCFRRRCIPLHSRVPFP.

Ela^Δ    MRFQPLFWVFFIFAMSLLFISEQKPENL.

FIGURE 19B

♀ $Ela^{\Delta/+}$ × ♂ $Ela^{\Delta/+}$

|  | $Ela^{+/+}$ | $Ela^{\Delta/+}$ | $Ela^{\Delta/\Delta}$ |
|---|---|---|---|
| Weaning | 31 | 65 | 18 |

$Ela^{\Delta/\Delta}$ underrepresented ($\chi 2$= 0.074)

POLYPEPTIDES, NUCLEIC ACIDS AND USES THEREOF

CROSS-REFERENCE TO RELATED APPLICATIONS

This application is of co-pending application Ser. No. 15/101,304 filed Jun. 2, 2016 which is a National Phase Entry Application under 35 U.S.C. § 371 of International Application No. PCT/SG2014/000574 filed Dec. 3, 2014, and claims benefit under 35 U.S.C. § 119 of U.S. Provisional Application Ser. No. 61/911,276 filed Dec. 3, 2013, the contents of which are incorporated herein by reference in their entireties. Reference is also made to U.S. application Ser. No. 14/496,600 filed Sep. 25, 2014, the content of which is herein incorporated by reference in its entirety.

FIELD

The present invention relates to the fields of medicine, cell biology, molecular biology and genetics. This invention relates to the field of medicine.

SEQUENCE LISTING

The instant application contains a Sequence Listing which has been submitted in ASCII format via EFS-Web and is hereby incorporated by reference in its entirety. Said ASCII copy, created on Mar. 31, 2016, is named 049595-087230-Sequence-Listing.txt and is 64,922 bytes in size.

BACKGROUND

Hormonal peptides are an important class of secreted signaling molecules. Endogenous peptides are most notable for their functions in innate defense as antimicrobial peptides (Cederlund et al., 2011), in immune regulation as chemokines (Bonecchi et al., 2009) and in modulation of behavior as neuropeptides (van den Pol, 2012). Deficiencies in hormonal peptides are the cause of several human diseases, the most prominent being the loss of INSULIN or INSULIN resistance in diabetes mellitus. Deficiency in the neuropeptide HYPOCRETIN causes narcolepsy (Nishino et al., 2000; Peyron et al., 2000) while anomalies in the regulation of the appetite and satiety hormones LEPTIN (Montague et al., 1997) and GHRELIN are the underlying causes for congenital obesity and hyperphagia in Prader-Willi syndrome (Cummings et al., 2002).

The discovery of new peptide-encoding genes is challenging, since their open reading frames (ORFs) are small and often overlooked by size-biased ORF prediction algorithms. This limitation has lead to their under-prediction or classification as non-coding transcripts (Frith et al., 2006). Equally challenging is the matching of these hormones to their cognate cell surface receptors. The vast majority of small signaling peptides are known to bind and signal through G-coupled protein receptors (GPCRs), the largest family of cell surface receptors (Rasmussen et al., 2007). GPCRs can be broadly classified into two categories based on the source of their ligands (Vassilatis et al., 2003). Chemosensory-GPCRs sense environmental cues such as odorants, tastants and pheromones, while endo-GPCRs transduce signals originating from endogenous compounds such as peptide hormones, amines, nucleosides or lipids. Recent studies estimate the number of endo-GPCRs in the human genome to be close to 370 (Vassilatis et al., 2003). Approximately 140 of these (40%) have no known ligands and are therefore orphaned GPCR receptors. As such, the discovery and pairing of novel endogenous hormones to their cognate receptors remains a considerable endeavour.

Whereas many peptide hormones have been characterized and shown to play key roles in adult physiology, an involvement for these tiny signaling molecules during early development has not been established. During embryogenesis, six key signaling pathways namely WNT, BMP/NODAL, FGF/IGF, NOTCH, HEDGEHOG and HIPPO are crucial for embryonic patterning. In particular IGF/FGF and NODAL are essential for maintaining pluripotency in human embryonic stem cells (hESCs) (Dalton, 2013). Aside from INSULIN/IGF, FGF and TGFβ/ACTIVIN/NODAL, no other soluble factors have been isolated from feeder or hESC-conditioned media and proven to be necessary for hESC culture (Hughes et al., 2011).

To our knowledge, no hormonal peptide has ever been implicated in maintaining the self-renewal capacity of hESCs or their ability to differentiate into any of the three embryonic germ layers.

SUMMARY

According to a $1^{st}$ aspect of the present invention, we provide an ELABELA polypeptide. The ELABELA polypeptide may comprise a sequence CXXXRCXXXHSRVPFP (SEQ ID NO: 1). X may signify an amino acid residue.

We also provide a fragment, homologue, variant or derivative of such a polypeptide.

The polypeptide, fragment, homologue, variant or derivative of such a polypeptide may have an activity, such as a biological activity of an ELABELA polypeptide.

For example, the polypeptide may be capable of maintaining self-renewal of a stem cell. It may be capable of maintaining pluripotency of a stem cell. It may be capable of maintaining growth of a stem cell. It may be capable of promoting growth of a stem cell. It may be capable of inhibiting apoptosis. It may be capable of binding to the cell surface of an embryonic stem cell. It may be capable of bias differentiation of a stem cell toward an endodermal or mesodermal lineage. It may be capable of binding to apelin receptor (APLNR). It may be capable of binding to CXCR4 receptor. It may be capable of activating the PI3K/AKT pathway. It may be capable of cardioprotection. It may be capable of restoration or maintenance of cardiac function during ischemia and/or reperfusion. It may be capable of reducing oxidative stress. It may be capable of reducing infarct size. It may be capable of inhibiting HIV infection.

It may be capable of doing any combination of these, or all of these.

The ELABELA polypeptide may comprise a basic residue at or about position-7 upstream of the sequence CXXXRCXXXHSRVPFP (SEQ ID NO: 1).

The ELABELA polypeptide may comprise a sequence SEQ ID NO: 162 (CXXXRCXXXHSRVPFP), in which X represents an amino acid residue, and in which position 1 of SEQ ID NO: 162 comprises a basic amino acid residue, preferably K or R;

The ELABELA polypeptide may comprise a basic residue at or about position-8 upstream of the sequence CXXXRCXXXHSRVPFP (SEQ ID NO: 1).

The basic residue may comprise K (lysine). It may comprise R (arginine).

The ELABELA polypeptide may comprise a sequence SEQ ID NO: 163 (XXXXXXXXCXXXRCXXXHSRVPFP), in which X represents an amino acid residue, and in which position 1 of SEQ ID NO: 163 comprises a basic amino acid residue, preferably K or R.

The ELABELA polypeptide may comprise a pair of basic residues at or about positions -7 and -8 upstream of the sequence CXXXRCXXXHSRVPFP (SEQ ID NO: 1). The pair of basic residues may comprise KK. They may comprise KR. They may comprise RK. They may comprise RR.

The ELABELA polypeptide may comprise a sequence SEQ ID NO: 163 (XXXXXCXXXRCXXXHSRVPFP), in which X represents an amino acid residue, in which positions 1 and 2 of SEQ ID NO: 163 comprise a pair of basic amino acid residues, preferably KK, KR, RK or RR.

The ELABELA polypeptide may comprise a sequence selected from the group consisting of: SEQ ID NO: 2 to SEQ ID NO: 18. The ELABELA polypeptide may comprise a human ELABELA sequence shown as SEQ ID NO: 2.

The ELABELA polypeptide may further comprise a signal sequence. The signal sequence may comprise a human ELABELA signal sequence such as shown in SEQ ID NO: 19.

The ELABELA polypeptide may comprise a sequence selected from the group consisting of: SEQ ID NO: 20 to SEQ ID NO: 36. The ELABELA polypeptide may comprise a human ELABELA sequence shown as SEQ ID NO: 20.

The ELABELA polypeptide may comprise an intramolecular covalent bond between the cysteine residues at positions 1 and 6, with reference to the numbering in the sequence CXXXRCXXXHSRVPFP (SEQ ID NO: 1). The ELABELA polypeptide may be such that one or both cysteine residues comprise a reduced cysteine, for example having a sulfhydryl group.

The ELABELA polypeptide may comprise a mutation of the residue at position 31. The ELABELA polypeptide may comprise a mutation of the residue at position 32. The ELABELA polypeptide may comprise a R31G substitution. The ELABELA polypeptide may comprise a R31A substitution. The ELABELA polypeptide may comprise a K31G substitution. The ELABELA polypeptide may comprise a K31A substitution. The ELABELA polypeptide may comprise an R32G substitution. The ELABELA polypeptide may comprise an R32A substitution. The ELABELA polypeptide may comprise a K32G substitution. The ELABELA polypeptide may comprise a K32A substitution. The residue numbering may be by reference to the position numbering of a human ELABELA sequence shown as SEQ ID NO: 20.

There is provided, according to a $2^{nd}$ aspect of the present invention, a nucleic acid comprising a sequence capable of encoding an ELABELA polypeptide as set out above.

The ELABELA nucleic acid may comprise a nucleic acid sequence shown in any of SEQ ID NO. 37 to SEQ ID NO: 46. The ELABELA nucleic acid may comprise a human ELABELA nucleic acid sequence SEQ ID NO: 37 or SEQ ID NO: 42.

We provide, according to a $3^{rd}$ aspect of the present invention, a vector such as an expression vector comprising such a nucleic acid according. We further provide a host cell such as a bacterial, fungal or yeast cell comprising such a vector or such a nucleic acid. We further provide a transgenic non-human animal comprising such a host cell, such a vector or such a nucleic acid. The transgenic non-human animal may comprise a mammal. The transgenic non-human animal may comprise a mouse.

As a $4^{th}$ aspect of the present invention, there is provided an antibody or an antigen-binding fragment thereof.

The antibody or antigen-binding fragment thereof may be capable of specifically binding to a polypeptide comprising the sequence CMPLHSRVPFP (SEQ ID NO: 52).

The antibody or antigen-binding fragment thereof may be capable of specifically binding to a polypeptide comprising the sequence QRPVNLTMRRKLRKHNC (SEQ ID NO: 53).

The antibody or antigen-binding fragment thereof may be capable of specifically binding to a polypeptide comprising the sequence QRPVNLTMRRKLRKHNCLQRRCMPLHSRVPFP (SEQ ID NO: 2).

The antibody or antigen-binding fragment thereof may be capable of specifically binding to an ELABELA polypeptide as set out above.

The antibody or antigen-binding fragment thereof may be capable of specifically binding to an ELABELA polypeptide encoded by a nucleic acid as set out above.

The antibody or antigen-binding fragment thereof may be capable of specifically binding to an ELABELA polypeptide comprising the sequence of any of SEQ ID NOs: 1-36;

The antibody or antigen-binding fragment thereof may further optionally comprise a label.

While antibodies that bind them are provided, it should be understood that these antigenic polypeptide fragments can also be useful and are provided in their own right.

We provide, according to a $5^{th}$ aspect of the present invention, an shRNA or siRNA molecule capable of modulating any combination of the expression, amount or activity of an ELABELA polypeptide set out above. The shRNA or siRNA may comprise a sequence selected from the group consisting of: SEQ ID NO: 47 to SEQ ID NO: 51.

As a $6^{th}$ aspect of the present invention, there is provided a method of assaying a compound of interest. The method may comprise contacting an ELABELA polypeptide as set out above with a candidate compound and performing an assay to determine if the candidate compound binds to the ELABELA polypeptide. The method may comprise contacting an ELABELA polypeptide as set out above with a candidate compound and performing an assay to determine if the candidate compound modulates an activity of the ELABELA polypeptide. The assay may comprise contacting a cell expressing an ELABELA polypeptide as set out above with a candidate compound and performing an assay to determine if the candidate compound causes an elevated or reduced expression, amount or activity of the ELABELA polypeptide in or of the cell. The method may further comprise isolating or synthesising the compound of interest so identified.

We provide, according to a $7^{th}$ aspect of the present invention, a compound of interest identified, isolated or synthesised by a method as set out above.

The present invention, in a $8^{th}$ aspect, provides a method of down-regulating any combination of the expression, amount or activity of an ELABELA polypeptide. The method may comprise exposing the ELABELA polypeptide to an antibody or antigen-binding fragment thereof as described. The method may comprise exposing the ELABELA polypeptide to an shRNA or siRNA as described. The method may comprise exposing the ELABELA polypeptide to a compound of interest as described.

The present invention, in a $9^{th}$ aspect, provides an ELABELA polypeptide as described, a nucleic acid as described, a vector, host cell or transgenic non-human animal as described, an antibody or antigen-binding fragment thereof as described, an shRNA or siRNA molecule as described or a compound of interest as described for use in the treatment, prophylaxis or alleviation of an ELABELA associated condition.

The ELABELA associated condition may comprise cardiac dysfunction, hypertension, or a cardiovascular anomaly in blood pressure, cardiac contractility or fluid balance.

The ELABELA associated condition may comprise a cardiovascular disease such as cardiac hypertrophy, coronary artery disease (CAD), atherosclerosis, post-infarct treatment, myocardial ischemia-reperfusion injury or atrial fibrillation, coronary heart disease, heart failure, pulmonary arterial hypertension (PAH).

The ELABELA associated condition may comprise a condition associated with high blood pressure, such as hypertension, angina, congestive heart failure or erectile dysfunction.

The ELABELA associated condition may comprise a condition associated with HIV infection, such as AIDS in an individual.

According to an 10th aspect of the present invention, we provide an ELABELA polypeptide as described, a nucleic acid as described, a vector, host cell or transgenic non-human animal as described, an antibody or antigen-binding fragment thereof as described, an shRNA or siRNA molecule as described or a compound of interest as described for use in the treatment, prophylaxis or alleviation of an ELABELA associated condition, or for use as a vasodilator.

We provide, according to a 11th aspect of the invention, a method of manipulating a cell, the method comprising modulating, preferably up-regulating, any combination of the expression, amount or activity of an ELABELA polypeptide as described in or of the cell, such as by exposing the cell to an ELABELA polypeptide as described or introducing a nucleic acid as described or a vector as described into the cell.

There is provided, in accordance with a 12th aspect of the present invention, a method of maintaining or enhancing self-renewal and/or pluripotency in or of a stem cell, the method comprising manipulating a stem cell by a method as set out above.

The cell may comprise a stem cell. Up-regulation of the expression, amount or activity of an ELABELA polypeptide may result in maintenance or enhancement of self-renewal and/or pluripotency in or of the stem cell.

As an 13th aspect of the invention, we provide a method comprising detecting any combination of the expression, amount or activity of an ELABELA polypeptide in or of a cell, such as a stem cell, tissue, organ or organism.

We provide, according to a 14th aspect of the invention, there is provided a combination comprising a first part comprising a sequence MPLHSRVPFP (SEQ ID NO: 54) or QRPVNLTMRRKLRKHN (SEQ ID NO: 55) or both and a second part comprising a polypeptide of interest.

The combination may be such that the first part and the second part are covalently joined, such as by chemical conjugation. The combination may comprise a fusion protein comprising the first part and the second part.

According to a 15th aspect of the present invention, we provide an expression construct capable of expressing such a fusion protein.

There is provided, according to a 16th aspect of the present invention, a method of detecting or quantifying a polypeptide of interest, the method comprising producing a combination as described and detecting the presence of or quantifying the first part of the combination.

We provide, according to a 17th aspect of the present invention, a method of isolating a polypeptide of interest. The method may comprise producing a combination as described and exposing the combination to a molecule capable of specifically binding to the first part. The molecule capable of specifically binding to the first part may comprise an antibody or antigen-binding fragment thereof as set out above.

There is provided, according to a 18th aspect of the present invention, a method comprising conjugating or otherwise joining a polypeptide of interest to a sequence MPLHSRVPFP (SEQ ID NO: 54) or QRPVNLTMRRKLRKHN (SEQ ID NO: 55) or both.

We provide, according to a 19th aspect of the present invention a method of making an ELABELA polypeptide or fragment thereof, the method comprising: (a) expressing a nucleic acid encoding a sequence comprising CXXXRCXXXHSRVPFP (SEQ ID NO: 1) in a cell, in which X is an/any amino acid residue, and in which the polypeptide fragment maintains self-renewal, pluripotency, or both of a stem cell; or (b) using chemical synthesis to generate a synthetic polypeptide or fragment thereof comprising CXXXRCXXXHSRVPFP (SEQ ID NO: 1) or a fragment having the sequence of SEQ ID NO: 53.

There is provided, according to a 20th aspect of the present invention, An immunoassay kit for measuring or detecting ELABELA expression, the immunoassay kit comprising: (a) a coating antigen comprising one or more isolated antibodies or antigen-binding fragments thereof that specifically binds to one or more of the following: (i) a polypeptide comprising the sequence CMPLHSRVPFP (SEQ ID NO: 52); (ii) a polypeptide comprising the sequence QRPVNLTMRRKLRKHNC (SEQ ID NO: 53); (iii) a polypeptide comprising the sequence QRPVNLTMRRKLRKHNCLQRRCMPLHSRVPFP (SEQ ID NO: 2); or (iv) an ELABELA polypeptide comprising the sequence of any of SEQ ID NOs: 1-36; and (b) instructions for using said coating antigen.

The immunoassay kit may be such that the isolated antibodies or antigen-binding fragments thereof are labelled.

The immunoassay kit may further comprise an enzyme labelled reagent, a secondary antibody or antigen-binding fragment thereof that specifically binds to the isolated antibodies or antigen-binding fragments, a solid substrate, or any combination thereof.

BRIEF DESCRIPTION OF THE FIGURES

FIG. 1A. NANOG, POU5F1 and PRDM14 syn-expression groups share a common list of 33 genes which define a core human pluripotency network. ELA is one of these genes.

FIG. 1B. ELA, like POU5F1, is rapidly silenced in hESCs during embryoid body differentiation.

FIG. 1C. ELA encodes a conserved vertebrate protein of 54 amino-acids consisting of a secretory signal and a mature 32 amino-acid peptide. The carboxy terminus is invariant. White arrowhead: predicted signal peptide cleavage site between G22 and Q33. Double black arrowheads: possible FURIN cleavage sites after conserved di-arginines R31R32 and R42R43 motifs. N- and C-terminal epitopes chosen for α N and α C antibody production are noted. The α C antibody is designed to recognize all ELA peptides regardless of species. FIG. 1C discloses SEQ ID NOs: 20, 22, 25-28, and 30-33, respectively, in order of appearance.

FIG. 1D. Western blot for ELA which is translated, processed, secreted and recognized by the α C antibody as a 4 kDa single band when over-expressed in *Xenopus laevis* embryos. Brefeldin A-mediated inhibition of secretion blocks ELA processing.

FIG. 1E. The α C antibody recognizes both full-length ELA and processed ELA whereas the α N antibody is specific to the mature processed ELA peptide.

FIG. 2A. By immunofluorescence in hESCs, endogenous ELA marked with the α C antibody co-localizes with the trans-Golgi network marked by TGN46.

FIG. 2B. Soluble extracellular ELA in conditioned medium of hESCs can be depleted by siRNA mediated silencing and detected by a sandwich ELISA assay.

FIG. 2C. Over a period of 5 days, secreted ELA reaches nM concentrations in the supernatant of hESCs cultures as measured by ELISA. Over the same period, Dox-inducible shELA knockdown achieves nearly 85% depletion of extra-cellular ELA.

FIG. 2D. As judged by immunofluorescence shELA, but not shβ2M, causes hESCS colonies to gradually differentiate and lose pluripotency markers POU5F1, SSEA-3 and TRA-1-60.

FIG. 2E. Measured on the xCELLigence platform, shELA, but not shβ2M (inset) hESCs seeded as single cells exhibit significant growth impairment.

FIG. 2F. An average shELA hESCS colonies are twice as small relative to control hESCs.

FIG. 2G. shELA hESCs do not display overt changes in cell cycle progression following release from a double thymidine block at G1/S.

FIG. 2H. By FACs analysis, shELA, but not shβ2M, causes hESCS grown in single cells to undergo rapid apoptosis as judged by increased ANNEXIN V and activated CASPASE 3.

FIG. 3A. Recombinant synthetically-produced ELA, and mutant $ELA^{RR>GG}$ (R31G, R32G), with free termini and intramolecular cystine bond between conserved C39 and C44 residues.

FIG. 3B. By immunofluorescence, recombinant ELA, but not $ELA^{RR>GG}$, labeled with FITC is rapidly up-taken by hESCs.

FIG. 3C. By cell numbers, addition of exogenous ELA elicits increased growth of hESCs while shELA hESCs show reduced growth relative to untreated hESCs.

FIG. 3D. Relative to untreated hESCs, addition of exogenous ELA, but not mutant $ELA^{RR>GG}$, elicits increased survival of hESCs.

FIG. 3E. By real-time cell index analysis, supply of exogenous ELA, but not mutant $ELA^{RR>GG}$, affords increased growth of hESCs.

FIG. 3F. Exogenous ELA, but not mutant $ELA^{RR>GG}$, is sufficient to rescue the growth of shELA hESCs.

FIG. 3G. Affinity purified α C antibodies added to the medium of hESCs are sufficient to inhibit the growth of hESCs, demonstrating potent neutralizing activity.

FIG. 3H. The pro-growth and survival properties of recombinant ELA are specific to hESCs culture and are not seen on multipotent hECs, or unipotent human chondrosarcoma and primary fibroblast cells.

FIG. 3I. By qPCR, hESCs treated with recombinant ELA express significantly higher levels of mesendodermal markers. Conversely shELA hESCs have reduced levels of these same mesendodermal markers.

FIG. 3J. As judged by FACs, hESCs treated with recombinant ELA do not lose the stem cells cell surface markers SSEA-3 and TRA-1-60.

FIG. 3K. hESCs treated with recombinant ELA are not committed to mesendodermal lineages and can differentiate into all three germ layers upon embryoid differentiation as judged by qPCR analysis.

FIG. 4A. By whole mount in situ hybridization in zebrafish embryos, ela is found to be zygotically expressed and ubiquitous in the blastoderm. During gastrulation its expression becomes axial and is strongest in the neural tube.

FIG. 4B. qPCR analysis shows that, relative to actin, expression of ela is exclusively zygotic, peaking at 100% epiboly and absent by 4 days post-fertilization.

FIG. 4C. In zebrafish, ela consists of three exons located on chromosome 1. A custom pair of Zinc Finger Nucleases (ZFNs) targeting exon1 of ela was used to create an allelic series of mutations within the signal peptide of Ela. FIG. 4C discloses SEQ ID NO: 156.

FIG. 4D. Three distinct loss-of-function alleles were generated, the $ela^{br21}$ allele results in a unique 7 amino-acid in frame deletion in Ela's signal peptide. Alleles $ela^{br13}$ and $ela^{br15}$ caused premature stop codons and disrupt the reading frame resulting in no Ela mature peptide. FIG. 4D discloses SEQ ID NOs: 36 and 157-159, respectively, in order of appearance.

FIG. 4E. Relative to wildtype embryos, homozygous null $ela^{br13}$ embryos show defective epiboly movements and a constricted germ ring at the involuting margin at 70% epiboly.

FIG. 4F. At 100% epiboly, by RT-PCR endogenous ela and $ela^{br13}$ mRNA are of distinct size. By western blotting using the α C antibody, endogenous Ela is recognized in wt embryos and is absent in null $ela^{br13}$ siblings.

FIGS. 5A to 5F. ela Knockout Zebrafish Have Severe Cardiovascular Defects

FIG. 5A. Null $ela^{br21}$ larvae display pericardial oedema (white arrowheads), accumulated erythrocytes (red arrowheads), and have no blood circulation. Variable posterior anomalies are observed including loss of ventral fin (black arrowheads), tailbud duplications (inset) and extreme tail/trunk truncations (bottom embryo).

FIG. 5B. Loss of ela causes severe cardiac anomalies ranging from mild heart dysplasia to total heart agenesis as shown by H&E staining on sections from top and bottom embryos shown in A.

FIG. 5C. Null $ela^{br13}$ fish have severe reduction of cmlc1 expression which marks the developing heart.

FIG. 5D. Null $ela^{br13}$ fish display increased hematopoiesis as judged by the up-regulation of scl, a marker of blood precursors.

FIG. 5E. Classification of null $ela^{br13}$ larvae with varying degrees of tail defects. Class I are defined as having pericardial oedema and tail blood clot, class 2 have ventral fin defects, or tailbud duplications, in addition to class 1 phenotypes and class 3 larvae have all phenotypes of class 1 combined with mild to severe tail/trunk truncations.

FIG. 5F. Percentages of ela mutant fertile adults that were obtained from heterozygous intercrosses using all three alleles.

FIG. 6A. Relative to wt embryos, homozygous null $ela^{br13}$ embryos show convergence-extension defects resulting in delayed blastopore closure and thickened notochord (insets) as indicated by altered bra expression.

FIG. 6B. The loss of ela causes defective migration of mediolateral gata5 expressing cells, which mark mesendoderm cells that guide heart progenitors to the anterior lateral plate mesoderm.

FIG. 6C. ela mutant embryos show a more compact sox17 expression pattern than do wildtype embryos, sox17+ forerunners cells are not affected.

FIG. 6D. ela null embryos have approximately 40% less sox17+ cells than their heterozygous siblings at 75% epiboly.

FIG. 6E. Directed endoderm differentiation of shELA, but not control, hESCs is markedly impaired as judged by the reduction in SOX17 expression by immunofluorescence. Addition of recombinant ELA is sufficient to rescue this loss of endoderm differentiation potential in shELA hESCs.

FIG. 6F. Quantification of endodermal differentiation efficiency in control, shELA and shELA with ELA peptide hESCS after 5 days reveals a significant 45% reduction of SOX17 expression upon ELA depletion which can be entirely rescued by addition of exogenous ELA.

FIGS. 7A to 7H. ELA's Cognate Receptor for Endoderm Differentiation Is APLNR.

FIG. 7A. ELA and APELIN are very basic hormones with isoelectric points exceeding 12. FIG. 7A discloses SEQ ID NOs: 160-161, respectively, in order of appearance.

FIG. 7B. By Q-PCR, the onset of transcription of aplnra and aplnrb coincides with that of ela at the midblastula transition, apelin expression debuts 5 hours later during gastrulation.

FIG. 7C. Relative to control embryos, the expression of aplnra and aplnrb at 70% epiboly becomes stronger and confined to the most equatorial hypoblast in ela mutant (white arrowheads: specific aplnra expression in the animal pole).

FIG. 7D. Wildtype embryo with a beating heart and blood circulation at 6 days post fertilization, normal sox17 expression in definitive endoderm at 75% epiboly, no erythrocyte accumulation in the intermediate cell mass, and cmlc1 expression in the heart forming region at 30 hpf.

FIG. 7E. Aplnr morphants phenocopy ela mutant embryos, with no beating heart, loss of blood circulation at 6 days post fertilization, reduced sox17 expression in definitive endoderm at 75% epiboly, accumulation erythrocytes in the intermediate cell mass and loss of cmlc1 expression in the heart forming region at 30 hpf.

FIG. 7F. ela mutant embryos are anatomically indistinguishable from Aplnr morphants and have no beating heart nor blood circulation at 6 days post fertilization, show reduced sox17 expression in definitive endoderm at 75% epiboly, have accumulated erythrocytes in the intermediate cell mass, and no cmlc1 expression in the heart forming region at 30 hpf.

FIG. 7G. In 293T cells, overexpression of zebrafish aplnra or aplnrb or human APLNR is sufficient to confer cell surface binding to recombinant ELA conjugated to Alkaline-Phosphatase (AP-ELA).

FIG. 7H. In 293T cells, overexpression of zebrafish aplnrb, but not its mutant form grinch carrying the W90L missense mutation, or GPR15 an orphan GPCR closely related to APLNR, is enough to afford binding to recombinant ELA conjugated to Alkaline-Phosphatase (AP-ELA).

FIGS. 9A to 9H. Expression of ELA is Highest in Human Blastocysts and hESCs and is Under POU5F1 Control, related to FIG. 1.

FIG. 9A. According to Unigene, ELA is most highly expressed in pre-implantation human blastocysts.

FIG. 9B. According to GEO, ELA expression in the human pre-implantation embryo starts by the blastocyst stage consistent with a zygotic expression.

FIG. 9C. ELA expression in hESCs is downregulated following POU5F1 knockdown.

FIG. 9D. The promoter region of ELA (chr4:165,796,806-165,798,359) transfected in hESCs can only drive expression of a firefly luciferase reporter in the presence of its upstream POU5F1 enhancer (chr4:165,787,570-165,788,797).

FIG. 9E. ELA expression is rapidly downregulated in hESCs upon embryoid body differentiation.

FIG. 9F. ELA expression is rapidly downregulated in hESCs undergoing definitive endoderm differentiation.

FIG. 9G. ELA expression is rapidly downregulated in hESCs undergoing RA-mediated neuroectoderm differentiation.

FIG. 9H. ELA expression is initially downregulated in hESCs undergoing cardiac differentiation, but is re-expressed after day 5.

FIG. 10A. In hESCs, ELA partly co-localizes with TGN46 a maker of the trans-Golgi network.

FIG. 10B. The same Golgi staining pattern is observed using α N antibodies.

FIG. 10C. Endogenous ELA in hECs can be efficiently knocked down by siRNA-mediated depletion.

FIG. 10D. Endogenous ELA in hESCs can be efficiently knocked-down by inducible shRNA-mediated depletion. shRNA against β2M is used as a control against non-specific effects of doxycycline treatment or hairpin RNA expression.

FIG. 10E. When 10 million control or shELA hESCs were injected subcutaneously into SCID mice (n=6), only control, but not shEL hESCs gave rise to tumors by day 60.

FIG. 10F. shELA hESCs lose expression of pluripotency markers POU51 and NANOG upon serial passaging.

FIG. 10G. Single colony qPCR analysis of passage 4 shELA hESCs confirms downregulation of POU51 and NANOG.

FIG. 10H. shRNA-mediated depletion of ELA or β2M does not affect the number of cells going through S phase and incorporating EDU.

FIG. 11A. Dose-dependent response of hESCs to recombinant ELA peptide.

FIG. 11B. Addition of purified α N antibodies to hESCs medium inhibits endogenous ELA and causes similar effects as shELA knockdown. The neutralizing activity of α N antibodies can be competed out by addition of the mutant non-signaling $ELA^{RR>GG}$ peptide.

FIG. 12A. Wildtype larvae at 6 days post-fertilization.

FIG. 12B. The 7 amino-acid in frame mutant $ela^{br21}$ allele causes identical phenotypes as the two frameshift mutants $ela^{br13}$ and $ela^{br15}$.

FIG. 12C. The $ela^{br15}$ mutant fish are indistinguishable from the $ela^{br21}$ and $ela^{br15}$ alleles.

FIG. 12D. Overexpression of 200 pg of zebrafish ela ORF mRNA causes heart dysgenesis (open arrows) and accumulation of erythrocytes in the ICM (red arrows), similar to ela null fish.

FIG. 13A. ela$^{br21}$ and ela$^{br15}$ mutant fish show similar defects in sox17 expression pattern at 75% epiboly.

FIG. 13B. Directed endoderm differentiation of shELA, but not shβ2M and control hESCs, is markedly impaired as judged by the reduction in SOX17 expression.

FIG. 13C. Quantification of endodermal differentiation efficiency in control, shELA and shβ2M hESCS after directed differentiation reveals a significant 35% reduction of SOX17 expression upon ELA depletion.

FIG. 14A. H3K4me3 by Chip-Seq, transcript levels by RNA seq. and DNA methylation levels by MeDIP around the ELA and APLNR loci in hESCs. Data are extracted from the Human Epigenome Atlas (www.genboree.org).

FIG. 14B. qPCR analysis of APLNR transcript levels (normalized to GAPDH) in Day 0 undifferentiated hESCs compared to Day 3 differentiated mesoendoderm cells. APLNR transcript levels are significantly reduced by shRNA-mediated knockdown using two different constructs.

FIG. 14C. Day 0 undifferentiated hESCs are uniformly APLNR-negative, whereas levels of APLNR in Day 3 mesoendoderm cells are one log higher, as measured by FACs. Grey shaded histograms are cells stained only with the secondary antibody. These results are confirmed using a second line of hESCs HES3.

FIG. 14D. shAPLNR Day 3 mesoendoderm cells have significantly reduced cell surface APLNR levels. No changes are observed in Day 0 undifferentiated hESCs, confirming the absence of APLNR.

FIG. 14E. shAPLNR Day 3 mesoendoderm cells have significantly reduced AP-ELA binding. This reduction is proportional to the decrease in levels of cell surface APLNR. shAPLNR does not affect the levels of AP-ELA bound to Day 0 undifferentiated hESCs.

FIG. 14F. Undifferentiated shAPLNR hESCs do not show impaired growth compared to shControl hESCs, as measured on the xCELLigence platform.

FIG. 15A is a drawing showing a schematic of SILAC-based phosphoproteomic analysis to elucidate immediate signal transduction of ELA in hESCs.

FIG. 15B is a drawing showing a mass spectra of a PRAS40-derived peptide showing phosphorylation on T426 by ELA but not ELARR>GG, suggesting activation of the AKT pathway.

FIG. 15C is a drawing showing that hESCs pulsed with ELA show immediate activation of the PI3K/AKT pathway. The mTOR pathway, as indicated by phosphorylation of p70S6K, is activated downstream of AKT via the phosphorylation of PRAS40.

FIG. 15D is a drawing showing control and shELA hESCs grown in decreasing INSULIN concentrations for 24 hours, revealing the requirement for ELA-mediated AKT activation.

FIG. 15E is a drawing showing that activation of AKT by ELA is dependent on PI3K, and is abrogated by pan-PI3K inhibitors Ly294002 and Wortmannin.

FIG. 15F is a drawing showing that following release from a double thymidine block, shELA hESCs show an accumulation of cells in the G1 phase.

FIG. 16A is a drawing showing that ELA but not ELARR>GG or vehicle control activates AKT signaling in hESCs, with little to no activation of ERK and SMAD2.

FIG. 16B is a drawing showing ELA-mediated activation of AKT is not impaired in undifferentiated shAPLNR hESCs.

FIG. 16C is a drawing showing that at steady state, shELA hESCs but not control hESCs show an increase in G0/G1 residence, as revealed by EDU pulsing.

FIG. 16D is a drawing showing that shELA hESCs have a lower rate of protein synthesis when cultured in mTSER1, as shown by a lower rate of incorporation of labeled amino acids in response to in a pulse-chase experiment.

FIG. 17A to 17J are drawings showing that ELA protects against stress-induced apoptosis and partially replaces INSULIN (see also Figure S5)

FIG. 17A is a drawing showing that shELA hESCs are more sensitive to INSULIN deprivation than control hESCs. Exogenous ELA partially rescues the increased cell death caused by INSULIN deprivation.

FIG. 17B is a drawing showing that By real-time cell index analysis, ELA but not ELARR>GG can partially rescue the requirement for INSULIN in hESC growth medium.

FIG. 17C is a drawing showing that By FACS analysis, a larger proportion of shELA hESCs are positive for ANNEXIN V, which marks apoptotic cells.

FIG. 17D is a drawing showing that By FACS analysis, a larger proportion shELA hESCs are positive for activated CASPASE 3, which marks apoptotic cells.

FIG. 17E is a drawing showing that Activated CASPASE 3 can be detected in shELA hESCs by immunofluorescence but not in control hESCs.

FIG. 17F is a drawing showing that ELA-treated hESCs are more resistant to γ-irradiation compared to control hESCs. shELA hESCs are sensitized to γ-irradiation which can be rescued by addition of ELA.

FIG. 17G is a drawing showing that ELA prevents activation of CASPASE 3 and apoptosis following irradiation, but does not appear to affect the formation of gamma-H2AX foci, which mark double stranded breaks.

FIG. 17H is a drawing showing that ELA-treated hESCs are more resistant to low levels of Actinomycin D treatment, which induces transcriptional stress and p53-dependent cell death. shELA hESCs are more sensitive but can be rescued by addition of ELA.

FIG. 17I is a drawing showing that ELA lowers the levels of activated CASPASE 3/7 and apoptosis following Actinomycin D treatment in hESCs.

FIG. 17J is a drawing showing that elabr13null zebrafish embryos have higher levels of apoptosis relative to controls embryos at 24 hours post fertilization (hpf) as shown by the increased numbers of cells positive for activated Caspase 3 in head and trunk regions.

FIG. 18A to FIG. 18H are drawings showing that ELA protects against stress-induced apoptosis and partially replaces INSULIN FIG. 18A is a drawing showing that INSULIN is the main activator of the PI3K/AKT pathway in hESCs grown in TSER-E8.

FIG. 18B is a drawing showing that ELA but not ELARR>GG rescues the viability of hESCs in the absence of exogenous INSULIN.

FIG. 18C is a drawing showing that after 3 days of growth in the absence of INSULIN, only hESCs supplemented with exogenous ELA continue to grow. bFGF and TGFβ are present in the culture medium but cannot replace ELA.

FIG. 18D is a drawing showing that ELA protects against anoikis, which refers to apoptosis caused by cellular dissociation. ROCK inhibitor protects against anoikis, and ELA can partially replace it following cellular dissociation.

FIG. 18E is a drawing showing that ELARR>GG has no protective effect on Actinomycin D-treated hESCs.

FIG. 18F is a drawing showing that ELA does not affect the levels of P53, while shELA hESCs have reduced levels of the antiapoptotic protein MCL-1.

FIG. 18G is a drawing showing that ELA prevents activation of the mitochondria pathway of apoptosis, by inhibiting the insertion of anti-apoptotic protein BAX into the mitochondria membrane. Consequently, less CYTOCHROME C is released from the mitochondria into the cytoplasm in response to Actinomycin D.

FIG. 18H is a drawing showing that shELA hESCs have increased activated CASPASE 9, whereas ELA lowers the levels of activated effector CASPASE 9 and apoptosis following Actinomycin D treatment.

Figure 19A:
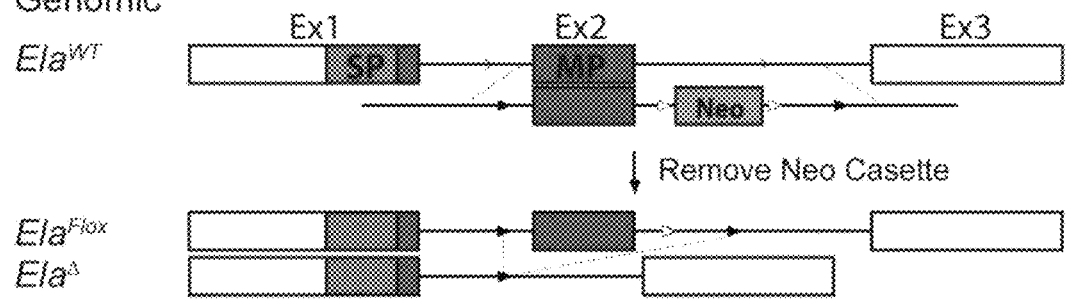

FIG. 19A is a drawing showing the genomic locus of the conditional Ela knockout (ElaFlox) mouse. Cre-mediated excision of Exon 2 flanked by lox sites (black triangles) generates a null allele (ElaΔ) which encodes for a truncated Ela peptide. (SP=Signal Peptide; MP=Mature Peptide)

FIG. 19B is a drawing showing that ElaΔ/+ intercrosses yield reduced numbers of Ela knockout mice at time of weaning, indicating partial embryonic lethality.

Figure 19C:

FIG. 19C is a drawing showing that Ela knockout embryos at e10.5 are hypovascular and growth-retarded, with large pericardial oedema indicating defects in heart development.

Figure 19D:
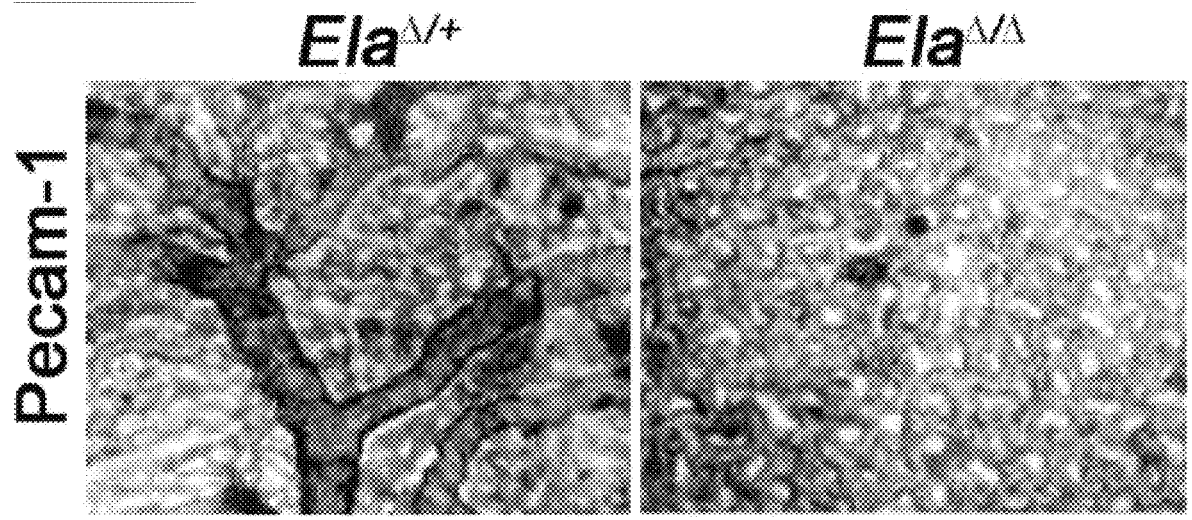

FIG. 19D is a drawing showing that vasculature in an Ela knockout yolk sac, as revealed by Pecam-1 staining, does not mature into a functional arbour like in ElaΔ/+ littermate control.

Figure 19E:
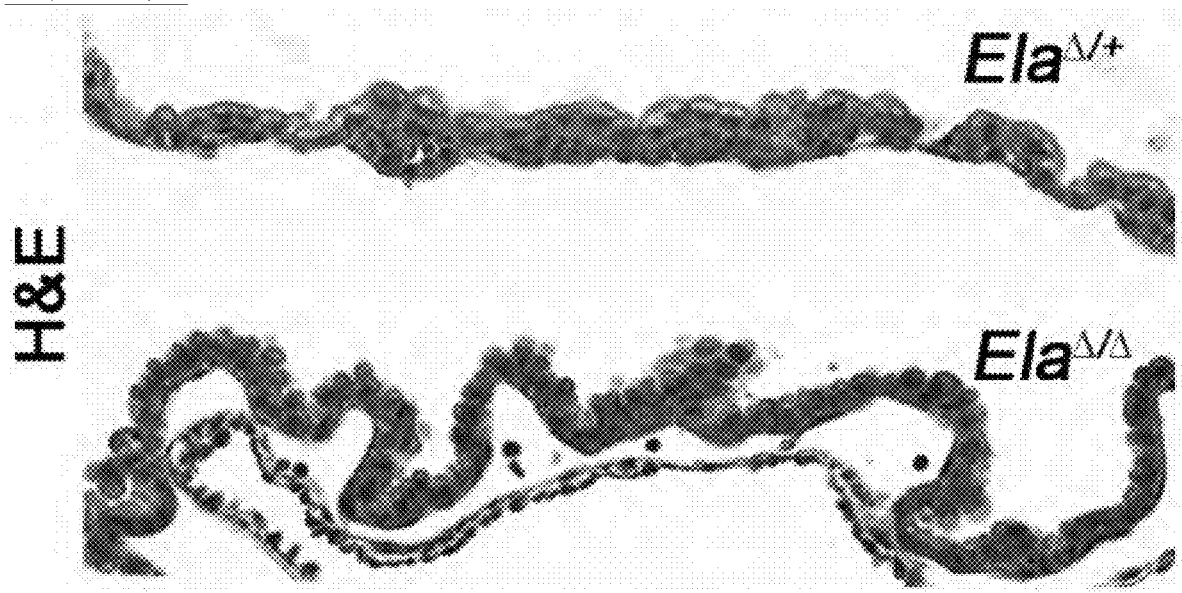

FIG. 19E is a drawing showing that different extraembryonic layers fail to adhere and mature to give rise to functional blood vessels in Ela knockout yolk sacs.

Figure 19F:
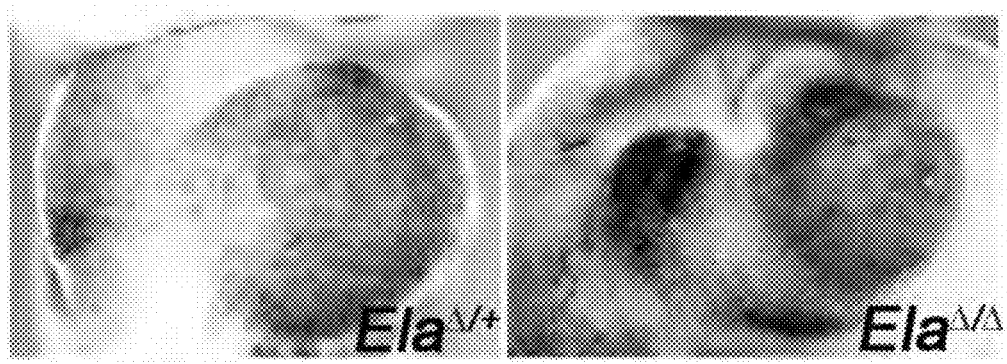

FIG. 19F is a drawing showing a frontal view of the heart in Ela knockout mice, stained with a blue dye for contrast, revealing abnormal heart tube development.

Figure 19G:
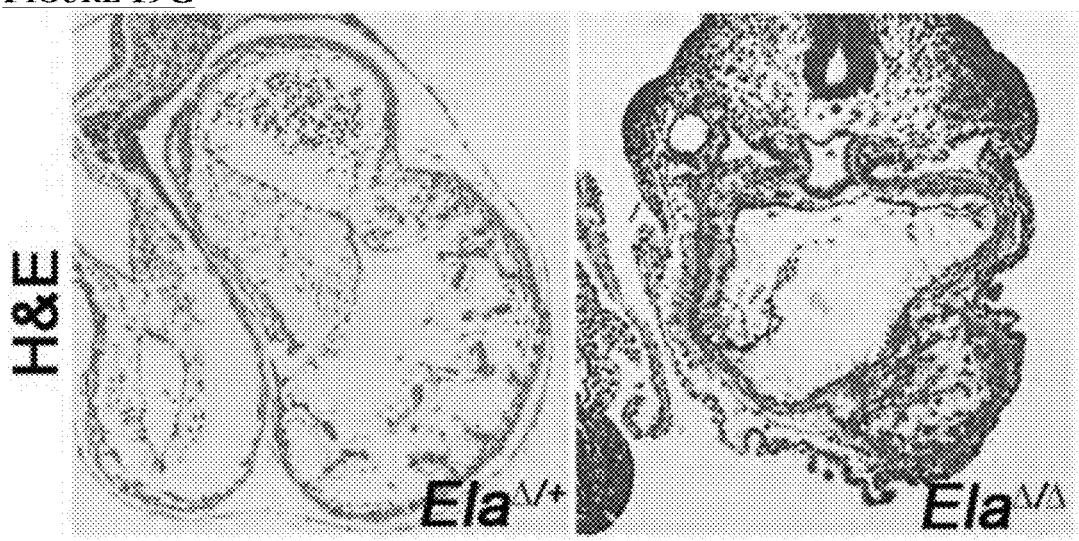

FIG. 19G is a drawing showing a cross-section view of an Ela knockout heart showed abnormal chamber septation and endocardial development compared to that of a control littermate.

Figure 20A:
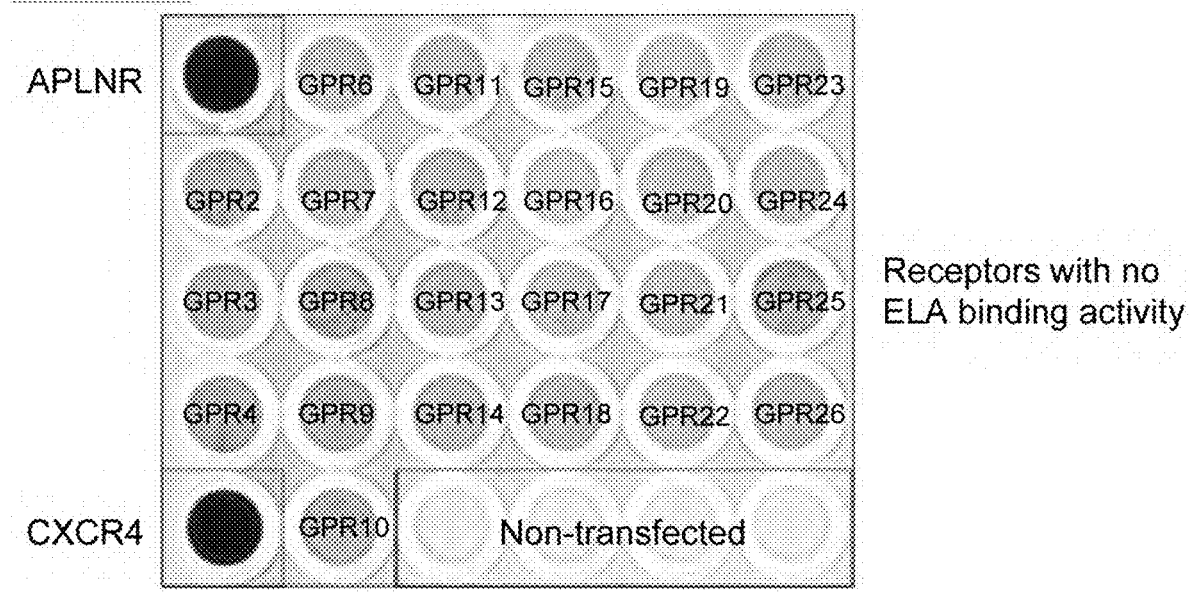

FIG. 20A is a drawing showing that like APLNR, the GPCR CXCR4, one of the most prominent HIV receptor, confers cell surface binding to ELA. Other tested GPCRs did not confer binding proving assay specificity.

Figure 20B:
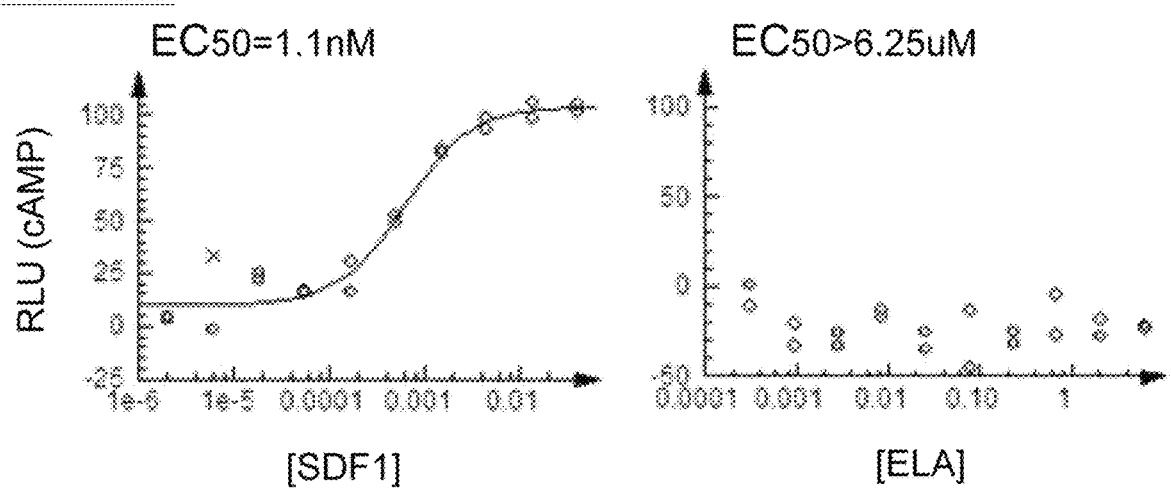

FIG. 20B is a drawing showing that unlike CXCR4's cognate ligand SDF1 (a.k.a CXCL12), ELA cannot activate CXCR4.

Figure 20C:
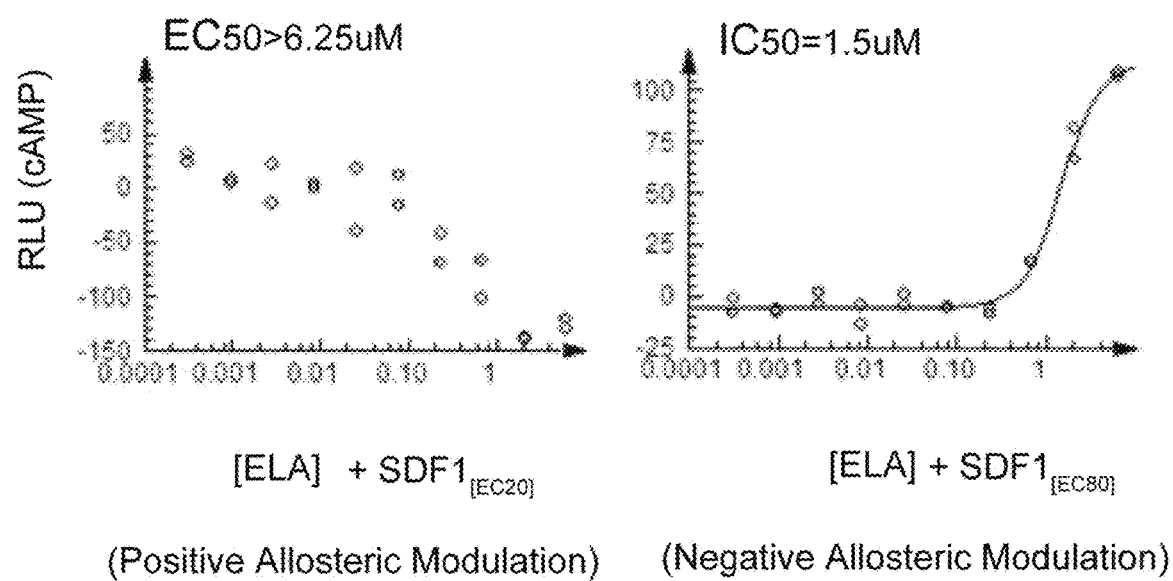

FIG. 20C is a drawing showing that ELA behaves as a CXCR4 antagonistic ligand, by preventing SDF1-mediated CXCR4 activation.

Figure 20D:
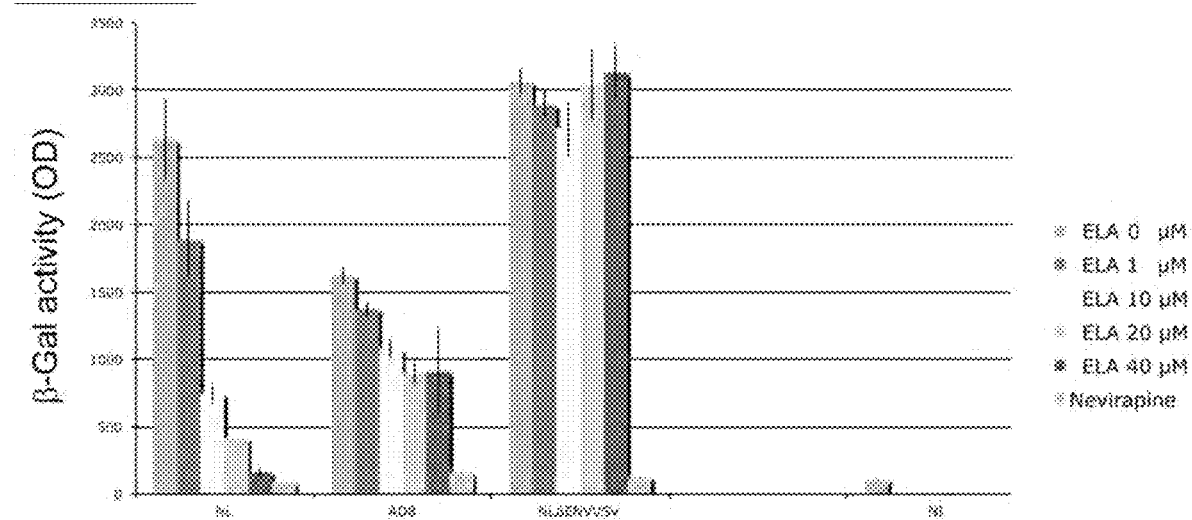

FIG. 20D is a drawing showing that ELA inhibits infection with NL (HIV-1 NL43: a CXCR4-tropic strain), but not with AD8 (HIV-1 NLAD8: a CCR5-tropic virus) or a VSV-G pseudotyped virus. HIV-1 infection is measured by a colorimetric assay (B-Gal activity) after 36-48 hrs of infection. ELA inhibits HIV at 10-40 µM. Nevirapine, a reverse transcriptase inhibitor, blocks all viruses tested.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; Using Antibodies: A Laboratory Manual: Portable Protocol NO. I by Edward Harlow, David Lane (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855. Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

SEQUENCE LISTINGS

SEQ ID NO: 1 shows a sequence of an ELABELA polypeptide signature sequence. SEQ ID NO: 2 shows a sequence of a *Homo* ELABELA mature polypeptide. SEQ ID NO: 3 shows a sequence of a *Peromyscus* ELABELA mature polypeptide. SEQ ID NO: 4 shows a sequence of a *Rattus* ELABELA mature polypeptide.

SEQ ID NO: 5 shows a sequence of a *Mus* ELABELA mature polypeptide. SEQ ID NO: 6 shows a sequence of a *Bos* ELABELA mature polypeptide. SEQ ID NO: 7 shows a sequence of a *Sus* ELABELA mature polypeptide. SEQ ID NO: 8 shows a sequence of a *Dasypus* ELABELA mature polypeptide. SEQ ID NO: 9 shows a sequence of a *Trichosurus* ELABELA mature polypeptide.

SEQ ID NO: 10 shows a sequence of a *Gallus* ELABELA mature polypeptide. SEQ ID NO: 11 shows a sequence of a *Gekko* ELABELA mature polypeptide. SEQ ID NO: 12 shows a sequence of a *Anolis* ELABELA mature polypeptide. SEQ ID NO: 13 shows a sequence of a *Xenopus* ELABELA mature polypeptide. SEQ ID NO: 14 shows a sequence of a *Ambystoma* ELABELA mature polypeptide.

SEQ ID NO: 15 shows a sequence of a *Oryzias* ELABELA mature polypeptide. SEQ ID NO: 16 shows a sequence of a *Callorhinchus* ELABELA mature polypeptide. SEQ ID NO: 17 shows a sequence of a *Oncorhynchus* ELABELA mature polypeptide. SEQ ID NO: 18 shows a sequence of a *Danio* ELABELA mature polypeptide.

SEQ ID NO: 19 shows a sequence of a Human ELABELA signal sequence. SEQ ID NO: 20 shows a sequence of a *Homo* ELABELA polypeptide with signal sequence (bold). SEQ ID NO: 21 shows a sequence of a *Peromyscus* ELABELA polypeptide with signal sequence (bold). SEQ ID NO: 22 shows a sequence of a *Rattus* ELABELA polypeptide with signal sequence (bold).

SEQ ID NO: 23 shows a sequence of a *Mus* ELABELA polypeptide with signal sequence (bold). SEQ ID NO: 24 shows a sequence of a *Bos* ELABELA polypeptide with signal sequence (bold). SEQ ID NO: 25 shows a sequence of a *Sus* ELABELA polypeptide with signal sequence (bold). SEQ ID NO: 26 shows a sequence of a *Dasypus* ELABELA polypeptide with signal sequence (bold). SEQ ID NO: 27 shows a sequence of a *Trichosurus* ELABELA polypeptide with signal sequence (bold).

SEQ ID NO: 28 shows a sequence of a *Gallus* ELABELA polypeptide with signal sequence (bold). SEQ ID NO: 29 shows a sequence of a *Gekko* ELABELA polypeptide with signal sequence (bold). SEQ ID NO: 30 shows a sequence of a *Anolis* ELABELA polypeptide with signal sequence (bold). SEQ ID NO: 31 shows a sequence of a *Xenopus* ELABELA polypeptide with signal sequence (bold). SEQ ID NO: 32 shows a sequence of a *Ambystoma* ELABELA polypeptide with signal sequence (bold).

SEQ ID NO: 33 shows a sequence of a *Oryzias* ELABELA polypeptide with signal sequence (bold). SEQ ID NO: 34 shows a sequence of a *Callorhinchus* ELABELA polypeptide with signal sequence (bold). SEQ ID NO: 35 shows a sequence of a *Oncorhynchus* ELABELA polypeptide with signal sequence (bold). SEQ ID NO: 36 shows a sequence of a *Danio* ELABELA polypeptide with signal sequence (bold).

SEQ ID NO: 37 shows a Human (*Homo sapiens*) ELABELA cDNA sequence. SEQ ID NO: 38 shows a Mouse (*Mus musculus*) ELABELA cDNA sequence. SEQ ID NO: 39 shows a Chicken (*Gallus gallus*) ELABELA cDNA sequence. SEQ ID NO: 40 shows a *Xenopus* (*Xenopus laevis*) ELABELA cDNA sequence. SEQ ID NO: 41 shows a Zebrafish (*Danio rerio*) ELABELA cDNA sequence.

SEQ ID NO: 42 shows a Human (*Homo sapiens*) ELABELA genomic sequence. SEQ ID NO: 43 shows a Mouse (*Mus musculus*) ELABELA genomic sequence. SEQ ID NO: 44 shows a Chicken (*Gallus gallus*) ELABELA genomic sequence. SEQ ID NO: 45 shows a *Xenopus* (*Xenopus laevis*) ELABELA genomic sequence. SEQ ID NO: 46 shows a Zebrafish (*Danio rerio*) ELABELA genomic sequence.

SEQ ID NO: 47 shows a Anti-ELABELA shRNA sequence A. SEQ ID NO: 48 shows a Anti-ELABELA shRNA sequence B. SEQ ID NO: 49 shows a Anti-ELABELA shRNA sequence C. SEQ ID NO: 50 shows a Anti-ELABELA shRNA sequence D. SEQ ID NO: 51 shows a Anti-ELABELA shRNA sequence E.

DETAILED DESCRIPTION

In describing the different ELABELA polypeptides variants encompassed by this document, the following nomenclature will be adopted for ease of reference:
(i) where the substitution includes a number and a letter, e.g., 31A, then this refers to [position according to the numbering system/substituted amino acid]. Accordingly, for example, the substitution of an amino acid to alanine in position 31 is designated as 31A;
(ii) where the substitution includes a letter, a number and a letter, e.g., R31A, then this refers to [original amino acid/position according to the numbering system/substituted amino acid]. Accordingly, for example, the substitution of arginine with alanine in position 31 is designated as R31A.

Where two or more possible substituents are possible at a particular position, this will be designated by contiguous letters, which may optionally be separated by slash marks "/", e.g., R31A/G or K32A/G. Where the relevant amino acid at a position can be substituted by any amino acid, this is designated by [position according to the numbering system/X], e.g., 31X.

Multiple mutations may be designated by being separated by slash marks "/", e.g. R31A/K32G representing mutations in position 31 and 32 substituting arginine with alanine and lysine with glycine respectively.

ELABELA

We disclose a previously unknown 54-amino acid hormone with a predicted signal peptide. The peptide hormone, together with its variants, homologues, derivatives and fragments will generally be referred to in this document as ELABELA (abbreviated to ELA). This peptide hormone is present in all vertebrate species.

Other names by which ELABELA is also known (given after our discovery) are ende, toddler and apela. The website www.elabela.com contains a repository of information on ELABELA.

In vivo, ELA expression is highest in the human blastocyst (hs.105196, LOC100506013), and has been reported to be rapidly down-regulated during hESC differentiation (Miura et al., 2004).

To our knowledge, the next earliest known peptide hormone to be expressed during embryogenesis is APELIN (APLN), the transcription of which begins during gastrulation in mice (D'Aniello et al., 2009). However, Apln knockout mice have no defects in early embryonic development (Kuba et al., 2007), which is inconsistent with the inactivation of its receptor Aplnr (also known as Apj or Agtrl1) whose loss leads to variable embryonic lethality due to growth retardation and cardiac malformations (Charo et al., 2009).

In zebrafish, mutations in the APLNR homologue aplnrb impair the migration of cardiac progenitors from the lateral plate mesoderm into the heart field. Because aplnra and aplnrb are expressed in early precursors of the endodermal lineage, hours before the onset of apln expression, it has been postulated that APLNR transduces the signal of an earlier hormone, yet to be discovered (Charo et al., 2009; Scott et al., 2007).

The Examples demonstrate that ELA is a novel secreted peptide hormone. Using zinc-finger-nuclease (ZFN)-mediated gene inactivation, we created an allelic series of ela null zebrafish, and show that it is essential for endoderm differentiation and heart morphogenesis.

ELABELA, its variants, homologues, derivatives and fragments, as well as modulators such as agonists and antagonists, may therefore be used for the treatment, prophylaxis or alleviation of an ELABELA associated condition. ELABELA associated conditions are described in further detail elsewhere in this document and may comprise a cardiac dysfunction or cardiovascular disease or a condition associated with high blood pressure for example.

The Examples show that Ela, and not Apln, is the first ligand recognized by Aplnr which mediates its effect for endoderm differentiation and subsequent cardiogenesis. However, in hESCs where APLNR is not expressed, we show that ELA serves as an endogenous signal that protects against apoptosis and maintains the self-renewal capacity of hESCs.

Together, our results unveil the existence of a hitherto uncharacterized hormone ELA that is indispensable for the self-renewal of cultured hESCs and critical in vivo for heart morphogenesis via the APLNR signaling pathway.

Example 19 demonstrates that ELA signals in a paracrine fashion in hESCS to maintain their self-renewal. ELA inhibition by shRNA or neutralizing antibodies causes cell death and reduced hESC growth.

Example 20 shows that synthetic ELA is sufficient to potentiate the growth and survival of hESCs in part by replacing INSULIN.

ELA's immediate signal transduction, revealed by SILAC phosphoproteomics, demonstrates that it activates the PI3K/AKT pathway which is indispensable to hESCs maintenance. This is shown in Example 48.

Accordingly, ELA protects against various cellular stress by preventing apoptosis in cultured hESCs and in vivo as evidenced with ela null embryos.

We propose that ELA, via an alternate cell-surface receptor, underwrites ESC self-renewal and constitutes one of the earliest survival factor secreted by the vertebrate embryo.

ELABELA Polypeptides

The methods and compositions described here make use of ELABELA polypeptides.

We demonstrate that ELABELA is expressed in a number of vertebrate species. We further demonstrate that ELABELA is highly conserved between species, and that the ELABELA polypeptide sequence comprises a number of conserved regions.

The sequence alignment below shows ELABELA proteins across 17 vertebrate species. Conserved residues are shown in bold and are also highlighted/shaded. Signal sequence is shown in italics. The sequences in Table D1 correspond to those in SEQ ID NO: 20 to 34 of the sequence listings. ("Invariant residues" consensus sequence disclosed as SEQ ID NO: 56).

```
Positions r/Homo
1--------------------------3131------39---
4344---48495051525354
Invariant residues
M----------------------------RKRK------C---RC---
HSRVPFP Homo
MRFQQFLFAFFIFIMSLLLISGQRPVNLTMRRKLRKHNCLQRRCMPL

HSRVPFP

Peromyscus
MRFQHYFLVFFIFAMSLLFITEQRPVNFPKKRKVYRHNCFRRRCVPL

HSRVPFP

Rattus
MRFQPLFWVFFIFAMSLLFITEEKSVNFPRRRKLYRHNCFRRRCISL

HSRVPFP

Mus
MRFQPLFWVFFIFAMSLLFISEQKPVNFPRRRKLYRHNCFRRRCIPL

HSRVPFP

Bos
MRFHQFFLLFVIFMLSLLLIHGQRQANLAMRRKLHRHNCLQRRCMPL

HSRVPFP

Sus
MRFRQFFLVFFIFMMNLLLICGQRPANLAVRRKLHRHNCLQRRCMPL

HSRVPFP

Dasypus
MKFQQFFYVFFVFIMSLLLINGQRPANLAMRRKLHRHNCFQRRCMPL

HSRVPFP

Trichosurus
MRFQLLITLFLFFTMGILLIDGQRPGNLALRRKPHRHICPQRRCMPL

HSRVPFP

Gallus
MRLRRLLCVVFLLLVSLLPAAAQRPANLALRRKLHRHNCSHRRCMPL

HSRVPFP

Gekko
MRLQLLLLTCFLILTGVLLGNGQRPANLSLRRKLHRQHCSHRRCMPL

HSRVPFP

Anolis
MRLQQLLLTWFLLLAGALLINGQRPANLASRRKLHRHHCSHRRCMPL

HSRVPFP

Xenopus
MDFQKLLYALFFILMSLLLINGQKPANLAQRRRIHRHNCFLKRCIPL

HSRVPFP

Ambystoma
MKWQKLLAILFWILMGALLVNGQRPVNAAHRRRLHRHNCSLRRCMPL

HSRVPFP

Oryzias
MRVWNLLYLLLLLAAALAPVFSARPDFLNLRRKYHRHHCLHRRCMPL

HSRVPFP

Callorhinchus
MRFQHLLHIILLLCTSLLLISGQKSGNSWRRKKMQRRNCWHRRCLPF

HSRVPFP
```

A number of sequences from other species show small variations in length:

For example, the *Oncorhynchus* ELABELA sequence (SEQ ID NO: 35) has a one amino-acid deletion between underlined TV residues. The missing or corresponding residue is Methionine 15 in the human sequence. This is within the signal peptide.

```
MRIISLLYLLLLVTVLGSVSSVRPDILNIRRRYHRHHCPHRRCMPL

HSRVPFP
```

As another example, the *Danio rerio* ELABELA sequence (SEQ ID NO: 36) has a four amino-acid insertion underlined as DKHG (SEQ ID NO: 57). These 4 residues are predicted to be kept in the mature peptide.

```
MRFFHPLYLLLLLLTVLVLISADKHGTKHDFLNLRRKYRRHNCPKK

RCLPLHSRVPF
```

In the broadest sense, an ELABELA polypeptide is a polypeptide that includes an "ELABELA signature" sequence. An ELABELA polypeptide may further comprise one or more activities, such as a biological activity of a native ELABELA polypeptide, as described in this document. As is clear from the sequence alignment, a number of ELABELA signatures are possible.

For example, an ELABELA signature may comprise the sequence HSRVPFP (SEQ ID NO: 57). Accordingly, as used in this document, the term "ELABELA polypeptide" may mean a polypeptide which comprises an HSRVPFP sequence (SEQ ID NO: 58). An ELABELA polypeptide comprising SEQ ID NO: 58 may comprise one or more biological activities of a native ELABELA polypeptide, such as maintaining self-renewal, pluripotency, or both of a stem cell, as described herein.

Alternatively, or in addition, an ELABELA signature may comprise the sequence RCXXXHSRVPFP (SEQ ID NO: 59). In this sense, therefore the term "ELABELA polypeptide" may mean a polypeptide which comprises an RCXXXHSRVPFP sequence (SEQ ID NO: 59), in which in which X represents any amino acid residue. An ELABELA polypeptide comprising SEQ ID NO: 59 may comprise one or more biological activities of a native ELABELA polypeptide, such as maintaining self-renewal, pluripotency, or both of a stem cell, as described herein.

In preferred embodiments, however, the ELABELA signature is intended to refer to a sequence CXXXRCXXXHSRVPFP (SEQ ID NO: 1), in which X signifies an amino acid residue. Accordingly, the term "ELABELA polypeptide" as used in this document is intended to refer to a sequence comprising a CXXXRCXXXHSRVPFP (SEQ ID NO: 1), in which X signifies an amino acid residue. An ELABELA polypeptide comprising SEQ ID NO: 1 may comprise one or more biological activities of a native ELABELA polypeptide, such as maintaining self-renewal, pluripotency, or both of a stem cell, as described herein.

For the purposes of this document, the term "ELABELA polypeptide" should also be taken to encompass any fragment, homologue, variant or derivative of such a polypeptide. Such ELABELA fragments, homologues, variants and derivatives are described in further detail elsewhere in this document. Such ELABELA fragments, homologues, variants and derivatives may comprise one or more biological activities of a native ELABELA polypeptide, such as maintaining self-renewal, pluripotency, or both of a stem cell, as described herein.

Figure 1A:
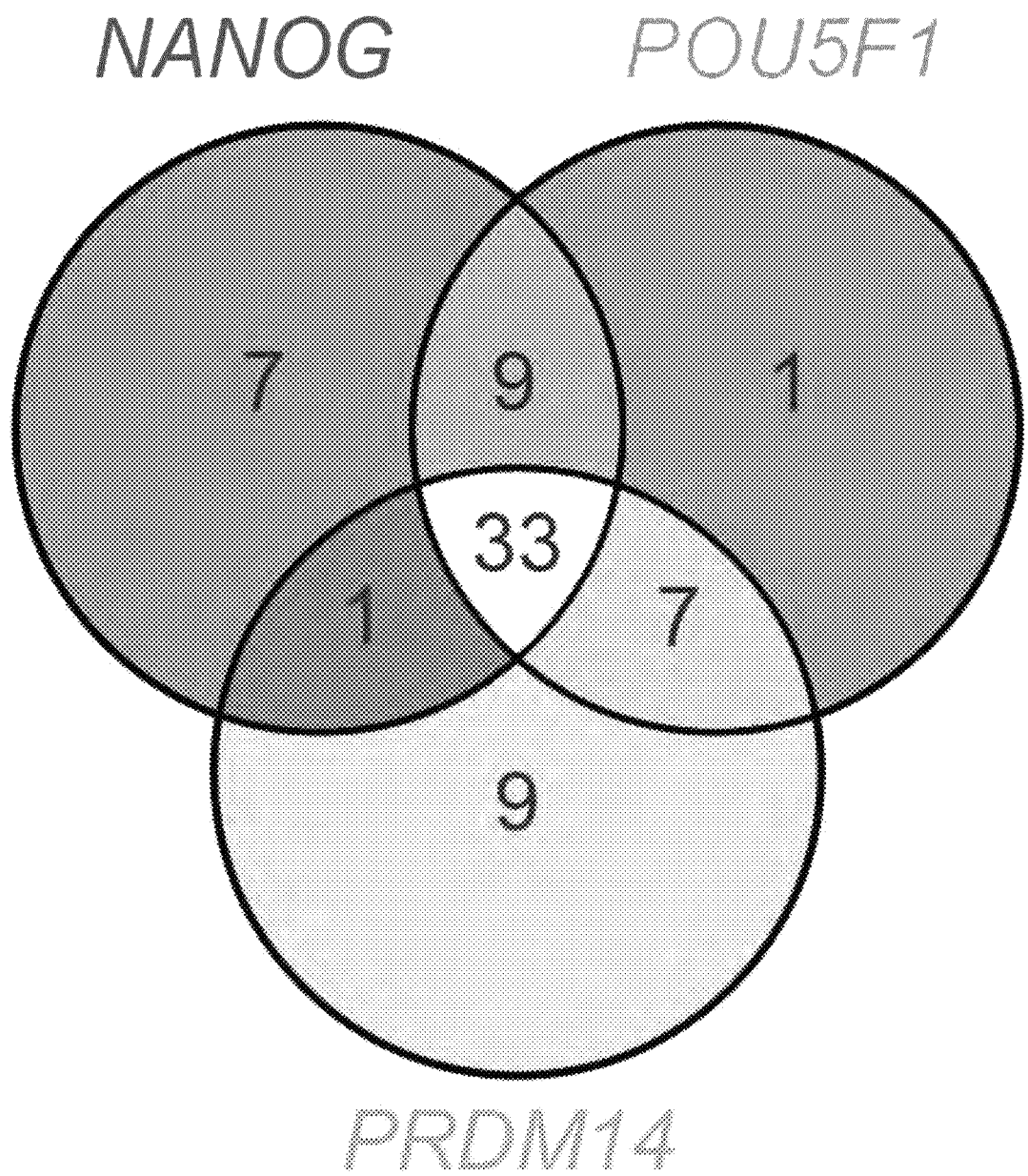
FIGS. 1A to 1E. Belonging to the Core Embryonic Pluripotency, ELA Encodes a Conserved Hormone.
Figure 1B:
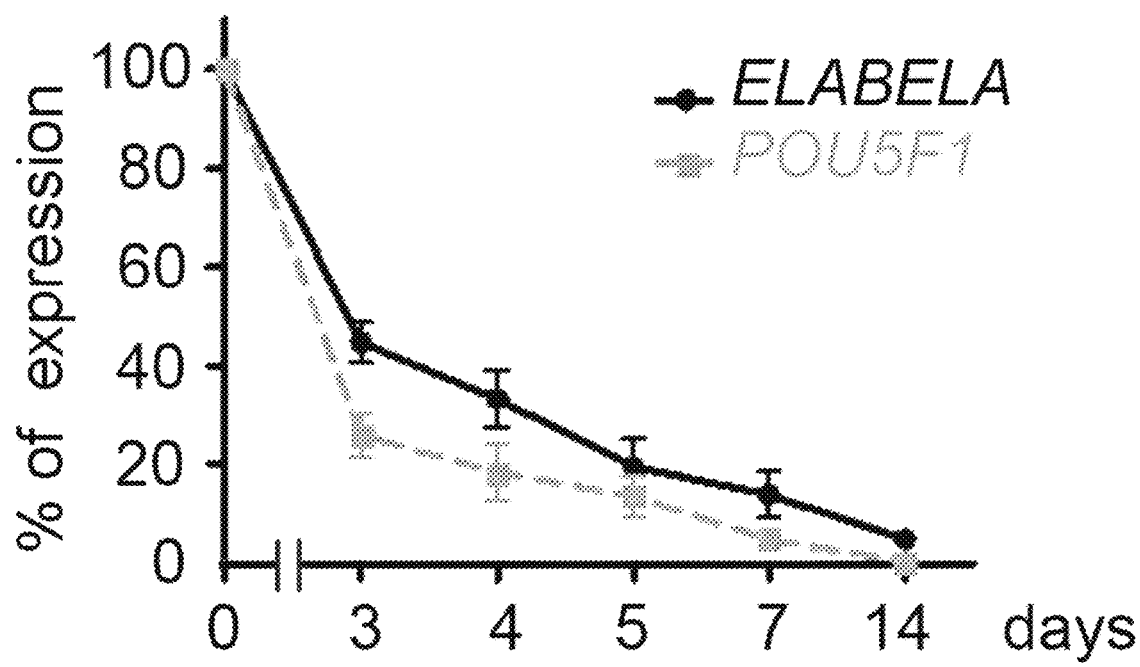
Figure 1C:
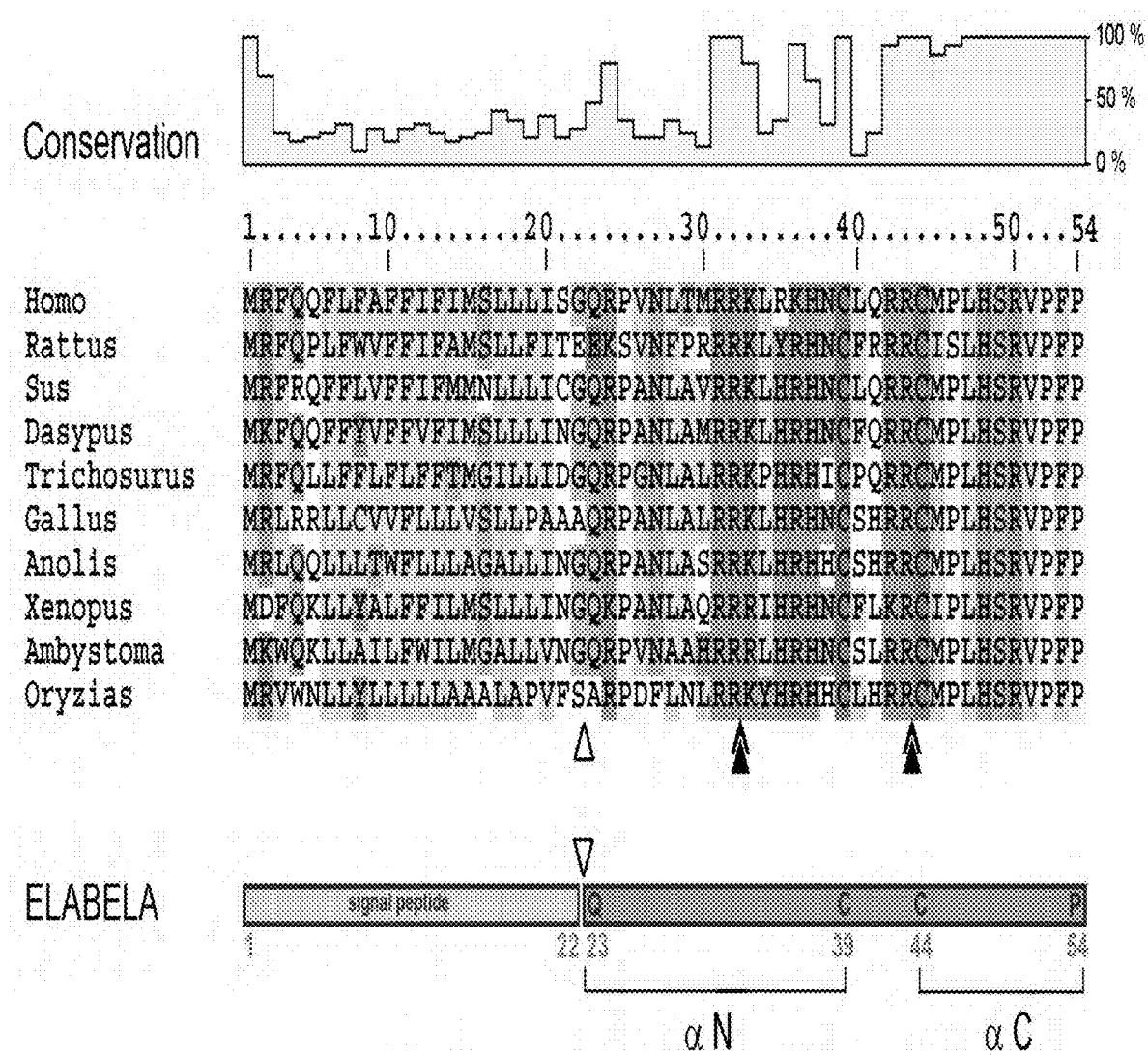

The ELABELA polypeptide encompassed by this document may therefore comprise a signature or conserved region from any of the vertebrate species in which ELABELA is expressed (see for example FIG. 1C and the sequence alignment above). Such signatures and conserved regions are set out as SEQ ID NO: 2 to SEQ ID NO: 18 and SEQ ID NOs: 60 to 76.

The ELABELA polypeptide may comprise a signature or conserved region from any species, for example: a *Homo* sequence CLQRRCMPLHSRVPFP (SEQ ID NO: 60); a *Peromyscus* sequence CFRRRCVPLHSRVPFP (SEQ ID NO: 61); a *Rattus* sequence CFRRRCISLHSRVPFP (SEQ ID NO: 62); a *Mus* sequence CFRRRCIPLHSRVPFP (SEQ ID NO: 63); a *Bos* sequence CLQRRCMPLHSRVPFP (SEQ ID NO: 64); a *Sus* sequence CLQRRCMPLHSRVPFP (SEQ ID NO: 65); a *Dasypus* sequence CFQRRCMPLHSRVPFP (SEQ ID NO: 66); a *Trichosurus* sequence CPQRRCMPLHSRVPFP (SEQ ID NO: 67); a *Gallus* ELABELA polypeptide sequence CSHRRCMPLHSRVPFP (SEQ ID NO: 68); a *Gekko* sequence CSHRRCMPLHSRVPFP (SEQ ID NO: 69); a *Anolis* sequence CSHRRCMPLHSRVPFP (SEQ ID NO: 70); a *Xenopus* sequence CFLKRCIPLHSRVPFP (SEQ ID NO: 71); a *Ambystoma* sequence CSLRRCMPLHSRVPFP (SEQ ID NO: 72); a *Oryzias* sequence CLHRRCMPLHSRVPFP (SEQ ID NO: 73); a *Callorhinchus* sequence CWHRRCLPFHSRVPFP (SEQ ID NO: 74); a *Oncorhynchus* sequence CPHRRCMPLHSRVPFP (SEQ ID NO: 75); a *Danio* sequence CPKKRCLPLHSRVPFP (SEQ ID NO: 76).

The ELABELA polypeptide may therefore comprise a signature from human ELABELA, i.e., CXXXRCXXXHSRVPFP (SEQ ID NO: 1) may comprise CLQRRCMPLHSRVPFP (SEQ ID NO: 60). It may comprise a signature from mouse ELABELA, i.e., CXXXRCXXXHSRVPFP (SEQ ID NO: 1) may comprise CFRRRCIPLHSRVPFP (SEQ ID NO: 63).

An ELABELA polypeptide comprising CLQRRCMPLHSRVPFP (SEQ ID NO: 60) or CFRRRCIPLHSRVPFP (SEQ ID NO: 63) may comprise one or more biological activities of a native ELABELA polypeptide, such as maintaining self-renewal, pluripotency, or both of a stem cell, as described herein.

A number of other residues may also be present in the ELABELA polypeptide. For example, the ELABELA polypeptide may comprise one or more basic residues upstream of the ELABELA signature sequence.

In particular, the ELABELA polypeptide may comprise a basic residue at or about position-7 upstream of the ELABELA signature sequence CXXXRCXXXHSRVPFP (SEQ ID NO: 1). The basic residue may comprise a lysine residue, or an arginine residue.

Accordingly, the ELABELA polypeptide may comprise a sequence (R/K) XXXXXXCXXXRCXXXHSRVPFP (SEQ ID NO: 77) where X represents any amino acid.

An ELABELA polypeptide comprising (R/K) XXXXXXCXXXRCXXXHSRVPFP (SEQ ID NO: 77) may comprise one or more biological activities of a native ELABELA polypeptide, such as maintaining self-renewal, pluripotency, or both of a stem cell, as described herein.

The ELABELA polypeptide may, alternatively or in addition, comprise a basic residue at or about position-8 upstream of the ELABELA signature sequence CXXXRCXXXHSRVPFP (SEQ ID NO: 1). The basic residue may comprise a lysine residue, or an arginine residue.

Accordingly, the ELABELA polypeptide may comprise a sequence (R/K) XXXXXXXCXXXRCXXXHSRVPFP (SEQ ID NO: 78) where X represents any amino acid. An ELABELA polypeptide comprising (R/K) XXXXXXX-CXXXRCXXXHSRVPFP (SEQ ID NO: 78) may comprise one or more biological activities of a native ELABELA polypeptide, such as maintaining self-renewal, pluripotency, or both of a stem cell, as described herein.

As noted above, the ELABELA polypeptide may comprise a pair of basic residues at or about positions-7 and -8 upstream of the ELABELA signature sequence CXXXRCXXXHSRVPFP (SEQ ID NO: 1), i.e., it may comprise a sequence (R/K) (R/K) XXXXXX-CXXXRCXXXHSRVPFP (SEQ ID NO: 79).

It will be evident that where the ELABELA polypeptide comprises a signal sequence (see below), position-8 upstream of the ELABELA signature sequence CXXXRCXXXHSRVPFP (SEQ ID NO: 1) corresponds to position 31 of a human ELABELA sequence (SEQ ID NO: 20) and position-7 upstream of the ELABELA signature sequence CXXXRCXXXHSRVPFP (SEQ ID NO: 1) corresponds to position 32 of a human ELABELA sequence (SEQ ID NO: 20).

The ELABELA polypeptide may comprise a sequence selected from the group consisting of: SEQ ID NO: 2 to SEQ ID NO: 18. The ELABELA polypeptide may comprise a human ELABELA sequence shown as SEQ ID NO: 2. It may comprise a mouse ELABELA sequence shown as SEQ ID NO: 5.

In some embodiments, the ELABELA polypeptide comprises a signal peptide or signal sequence. The skilled reader will appreciate that the presence of a signal peptide will allow the ELABELA peptide to be exported and secreted from a cell. The skilled reader will also know how to engineer such signal sequences into the sequences of ELABELA polypeptides described in this document.

ELABELA polypeptides comprising signal sequences may referred to in this document for convenience as "full length" polypeptides. They may be produced by including any known signal sequences, including the ELABELA signal sequences disclosed in this document in an ELABELA polypeptide to be produced.

The ELABELA polypeptide may comprise an ELABELA signal sequence from any suitable species, for example, *Homo* MRFQQFLFAFFIFIMSLLLISG (SEQ ID NO: 19); *Peromyscus* MRFQHYFLVFFIFAMSLLFITE (SEQ ID NO: 80); *Rattus* MRFQPLFWVFFIFAMSLLFITE (SEQ ID NO: 81); *Mus* MRFQPLFWVFFIFAMSLLFISE (SEQ ID NO: 82); *Bos* MRFHQFFLLFVIFMLSLLLIHG (SEQ ID NO: 83); *Sus* MRFRQFFLVFFIFMMNLLLICG (SEQ ID NO: 84); *Dasypus* MKFQQFFYVFFVFIMSLLLING (SEQ ID NO: 85); *Trichosurus* MRFQLLFFLFLFFTMGILLIDG (SEQ ID NO: 86); *Gallus* MRLRRLLCVVFLLLVSLLPAAA (SEQ ID NO: 87); *Gekko* MRLQLLLLTCFLILTGVLLGNG (SEQ ID NO: 88); *Anolis* MRLQQLLLTWFLLLAGALLING (SEQ ID NO: 89); *Xenopus* MDFQKLLYALFFILMSLLLING (SEQ ID NO: 90); *Ambystoma* MKWQKLLAILFWILMGALLVNG (SEQ ID NO: 91); *Oryzias* MRVWNLLYLLLLLAAALAPVFS (SEQ ID NO: 92); or *Callorhinchus* MRFQHLLHIILLLCTSLLLISG (SEQ ID NO: 93).

It may for example comprise a human ELABELA signal sequence shown as SEQ ID NO: 19, i.e., MRFQQFLFAFFIFIMSLLLISG.

Examples of "full length" or "native" ELABELA polypeptides are disclosed herein, and include any of the sequences set out as SEQ ID NO: 20 to SEQ ID NO: 36. In some embodiments, the ELABELA polypeptide may comprise or consist of a human ELABELA polypeptide having or comprising a sequence shown as SEQ ID NO: 20. It may comprise or consist of a mouse ELABELA polypeptide, such as the sequence having SEQ ID NO: 23.

The "ELABELA polypeptide" may comprise one or more activities of a native ELABELA polypeptide, such as one or more biological activities of a native ELABELA polypeptide. Such ELABELA activities are described in detail elsewhere in this document, and include, for example, the ability to maintain self-renewal or pluripotency, or both, of a cell such as a stem cell.

As noted above, homologues variants and derivatives thereof of any, some or all of these polypeptides are also included in the term "ELABELA polypeptide".

For example, an ELABELA polypeptide may comprise one or more reduced cysteines having a sulfhydryl group. The reduced cysteines may appear anywhere in the ELABELA amino acid sequence. For example, a cysteine at position 1 with reference to the numbering in the sequence CXXXRCXXXHSRVPFP (SEQ ID NO: 1) may comprise a reduced cysteine having a sulfhydryl group. A cysteine at position 6 may similarly comprise a reduced cysteine shaving a sulfhydryl group. The cysteine residues at both position 1 and position 6 may be so modified. The ELABELA polypeptide may comprise an intramolecular covalent bond between the cysteine residues at positions 1 and 6, with reference to the numbering in the sequence CXXXRCXXXHSRVPFP (SEQ ID NO: 1).

The position numberings above correspond respectively to position numbers 39 and 43 respectively in the human ELABELA polypeptide sequence MRFQQFLFAFFIFIMSLLLISGQRPVNLTMRRKLRKHNCLQRRCMPLHSRVPFP (SEQ ID NO: 20).

As another example, an ELABELA polypeptide may comprise one or more mutations of any of the sequences discussed in this document, such as those referred to as "ELABELA polypeptides". Such mutated sequences are described in further detail elsewhere in this document.

Included are an ELABELA polypeptide which comprises a mutation of a basic residue at position 31 of its sequence, with reference to the position numbering of a human ELABELA sequence shown as SEQ ID NO: 20. The basic residue at position 31 may be mutated to a neutral residue. For example, an arginine or lysine residue at position 31 may be mutated to an alanine or glycine residue.

The ELABELA polypeptide may comprise a mutation of a basic residue at position 32, with reference to the position numbering of a human ELABELA sequence shown as SEQ ID NO: 20. For example, the basic residue at position 32 may be mutated to a neutral residue. Thus, an arginine or lysine residue at position 32 may be mutated to an alanine or glycine residue.

The ELABELA polypeptide may comprise a mutant in which both of the basic residues set out above are so mutated. Thus, the ELABELA polypeptide may comprise an R31G, R31A, K31G or K31A substitution. The substitutions may comprise R32G, R32A, K32G or K32A. The ELABELA polypeptide may therefore comprise any one of the sequences: (R/K) (A/G) XXXXXXCXXXRCXXXHSRVPFP (SEQ ID NO: 94), (A/G) (R/K) XXXXXXCXXXRCXXXHSRVPFP (SEQ ID NO: 95) or (A/G) (A/G) XXXXXXCXXXRCXXXHSRVPFP (SEQ ID NO: 96).

As noted above, the position numbering is with reference to the position numbering of a human ELABELA sequence shown as SEQ ID NO: 20.

It will be appreciated that, with reference to the position numbering of a human ELABELA sequence shown as SEQ ID NO: 20, positions 31 and 32 correspond to positions-8 and -7 respectively with respect to the position numbering of the ELABELA signature sequence CXXXRCXXXHSRVPFP (SEQ ID NO: 1).

As each of the ELABELA polypeptide sequences described in this document necessarily comprise an ELABELA signature sequence, the skilled person will be able to establish the position numbering of any particular residue within ELABELA polypeptide sequence in his possession. That is to say, a skilled person will, given the information available in this document, and in other resources he has in his possession, be able to establish, in any ELABELA polypeptide sequence, the position numbering of any particular residue with reference to the human ELABELA sequence shown as SEQ ID NO: 20 or with reference to the position numbering of the ELABELA signature sequence CXXXRCXXXHSRVPFP (SEQ ID NO: 1) comprised in the ELABELA polypeptide.

ELABELA polypeptides may be used for a variety of means, for example, administration to an individual suffering from, or suspected to be suffering from an ELABELA associated condition, for the treatment thereof.

They may also be used for production or screening of anti-ELABELA agents such as specific ELABELA binding agents, in particular, anti-ELABELA antibodies. These are described in further detail elsewhere in this document.

The expression of ELABELA polypeptides may be detected for diagnosis or detection of an ELABELA associated condition.

ELABELA associated conditions are described in further detail elsewhere in this document.

We specifically provide for ELABELA polypeptide fragments comprising a sequence CXXXRCXXXHSRVPFP (SEQ ID NO: 1), where X is an/any amino acid residue, and where the polypeptide fragment maintains self-renewal, pluripotency, or both of a stem cell.

The fragment may be such that it does not comprise a sequence of SEQ ID NOs: 60-76.

An intramolecular covalent bond may be present between the cysteine residues at positions 1 and 6 of SEQ ID NO: 1, or one or both cysteine residues at positions 1 and 6 of SEQ ID NO: 1 may comprise a reduced cysteine having a sulfhydryl group, or both.

The ELABELA polypeptide fragment may further comprise a label. The label may comprise a radioisotope. The radioisotope may comprise $^{125}$I.

The polypeptide fragment may be derivatized.

The ELABELA polypeptide fragment may further comprise a signal sequence. The signal sequence may comprise SEQ ID NO: 19.

The fragment may further comprise seven additional amino acids at the N-terminus of SEQ ID NO: 1. The ELABELA polypeptide fragment may have a sequence of SEQ ID NO: 162 (XXXXXXXCXXXRCXXXHSRVPFP). Position 1 of SEQ ID NO: 162 may comprise a basic amino acid residue. X at positions 2-6, 8-10, and 13-15 may comprise an/any amino acid residue. The polypeptide fragment may be capable of maintaining self-renewal, pluripotency, or both of a stem cell.

The fragment may be such that it does not comprise a sequence of SEQ ID NOs: 181-197.

The basic residue at the position 1 may be selected from K or R.

The fragment may further comprise eight additional amino acids at the N-terminus of SEQ ID NO: 1. The ELABELA polypeptide fragment may have a sequence of SEQ ID NO: 163 (XXXXXXXXCXXXRCXXXH-SRVPFP). Position 1 of SEQ ID NO: 163 may comprise a basic amino acid residue. The X at positions 2-7, 9-11, and 14-17 may comprise an/any amino acid residue. The polypeptide fragment may be capable of maintaining self-renewal, pluripotency, or both of a stem cell.

The fragment may be such that it does not comprise a sequence of SEQ ID NOs: 164-180.

The basic residue at the position 1 may be selected from K or R.

The fragment may further comprise eight additional amino acids at the N-terminus of SEQ ID NO: 1. The ELABELA polypeptide fragment may comprise a sequence of SEQ ID NO: 163 (XXXXXXXXCXXXRCXXXH-SRVPFP). Positions 1 and 2 of SEQ ID NO: 163 may comprise a pair of basic amino acid residues. The X at positions 3-7, 10-12, and 15-17 may comprise an/any amino acid residue. The polypeptide fragment may be capable of maintaining self-renewal, pluripotency, or both of a stem cell.

The fragment may be such that it does not comprise a sequence of SEQ ID NOs: 164-180.

The pair of basic residues at positions 1 and 2 may be selected from KK, KR, RK, and RR.

Polypeptide

A "polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids.

"Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications.

ELABELA polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-inking, cyclization, disulfide bond formation, demethylation, formation of covalent cross-inks, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, *Proteins—Structure and Molecular Properties,* 2nd Ed., T. E. Creighton, W. H. Freeman and Company, New York, 1993 and Wold, F., *Posttranslational Protein Modifications: Perspectives and Prospects,* pgs. 1-12 in *Posttranslational Covalent Modification of Proteins,* B. C. Johnson, Ed., Academic Press, New York, 1983; Seifter et al., "Analysis for protein modifications and non-protein cofactors", *Meth Enzymol* (1990) 182:626-646 and Rattan et aL, "Protein Synthesis: Posttranslational Modifications and Aging", *Ann NY Acad Sci* (1992) 663:48-62.

An ELABELA polypeptide may comprise a fragment having the sequence of SEQ ID NO: 53. Such a fragment may comprise a pyroglutamate at the N-terminus. As understood by one of ordinary skill in the art, when glutamic acid or glutamine are at the N-terminus of a polypeptide, such as an ELABELA polypeptide fragment of SEQ ID NO: 53, they can spontaneously cyclize to form pyroglutamate. In some embodiments, the fragment having the sequence of SEQ ID NO: 53 may further comprise a label.

The term "polypeptide" includes the various synthetic peptide variations known in the art, such as a retroinverso D peptides. The peptide may be an antigenic determinant and/or a T-cell epitope. The peptide may be immunogenic in vivo. The peptide may be capable of inducing neutralising antibodies in vivo.

As applied to ELABELA, the resultant amino acid sequence may have one or more activities, such as biological activities in common with an ELABELA polypeptide, for example a human ELABELA polypeptide. ELABELA polypeptide activities are described in detail elsewhere in this document. As an example, an ELABELA homologue may be capable of maintaining self-renewal or pluripotency, or both, of a cell such as a stem cell.

In particular, the term "homologue" is intended to cover identity with respect to structure and/or function providing the resultant amino acid sequence has ELABELA activity. With respect to sequence identity (i.e. similarity), there may be at least 70%, such as at least 75%, such as at least 85%, such as at least 90% sequence identity. There may be at least 95%, such as at least 98%, sequence identity. These terms also encompass polypeptides derived from amino acids which are allelic variations of the ELABELA nucleic acid sequence.

Other ELABELA Polypeptides

ELABELA variants, homologues, derivatives and fragments are also of use in the methods and compositions described here.

The terms "variant", "homologue", "derivative" or "fragment" in relation to ELABELA include any substitution of, variation of, modification of, replacement of, deletion of or addition of one (or more) amino acid from or to a sequence. Unless the context admits otherwise, references to "ELABELA" includes references to such variants, homologues, derivatives and fragments of ELABELA. Such ELABELA variants, homologues, derivatives and fragments may comprise one or more biological activities of a native ELABELA polypeptide, such as maintaining self-renewal, pluripotency, or both of a stem cell, as described herein.

As used herein a "deletion" is defined as a change in either nucleotide or amino acid sequence in which one or more nucleotides or amino acid residues, respectively, are absent.

As used herein an "insertion" or "addition" is that change in a nucleotide or amino acid sequence which has resulted in the addition of one or more nucleotides or amino acid residues, respectively, as compared to the naturally occurring substance.

As used herein "substitution" results from the replacement of one or more nucleotides or amino acids by different nucleotides or amino acids, respectively.

ELABELA polypeptides as described here may also have deletions, insertions or substitutions of amino acid residues which produce a silent change and result in a functionally equivalent amino acid sequence.

Deliberate amino acid substitutions may be made on the basis of similarity in polarity, charge, solubility, hydrophobicity, hydrophilicity, and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the table below. Amino acids in the same block in the second column and in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

ELABELA polypeptides may further comprise heterologous amino acid sequences, typically at the N-terminus or C-terminus, such as the N-terminus.

Heterologous sequences may include sequences that affect intra or extracellular protein targeting (such as leader sequences). Heterologous sequences may also include sequences that increase the immunogenicity of the ELABELA polypeptide and/or which facilitate identification, extraction and/or purification of the polypeptides. Another heterologous sequence that may be used is a polyamino acid sequence such as polyhistidine which may be N-terminal. A polyhistidine sequence of at least 10 amino acids, such as at least 17 amino acids but fewer than 50 amino acids may be employed.

The ELABELA polypeptides may be in the form of the "mature" protein or may be a part of a larger protein such as a fusion protein. It is also possible to include an additional amino acid sequence which contains secretory or leader sequences, pro-sequences, sequences which aid in purification such as multiple histidine residues, or an additional sequence for stability during recombinant production.

The signal sequence (secretory sequence or leader sequence) may comprise the sequence MRFQQFLFAFFI-FIMSLLLISG (SEQ ID NO: 19). An example of an ELABELA polypeptide which comprises such a signal sequence is the full length human ELABELA polypeptide sequence shown as SEQ ID NO: 20.

ELABELA polypeptides as described here may be made by recombinant means, using known techniques. However they may also be made by synthetic means using techniques well known to skilled persons such as using chemical methods, such as solid phase synthesis.

Such polypeptides may also be produced as fusion proteins, for example to aid in extraction and purification. Examples of fusion protein partners include glutathione-S-transferase (GST), 6×His (SEQ ID NO: 97), GAL4 (DNA binding and/or transcriptional activation domains) and β-galactosidase.

It may also be convenient to include a proteolytic cleavage site between the fusion protein partner and the protein sequence of interest to allow removal of fusion protein sequences, such as a thrombin cleavage site. The fusion protein may be one which does not hinder the function of the protein of interest sequence.

The ELABELA polypeptides may be in a substantially isolated form. This term is intended to refer to alteration by the hand of man from the natural state. If an "isolated" composition or substance occurs in nature, it has been changed or removed from its original environment, or both. For example, a polynucleotide, nucleic acid or a polypeptide naturally present in a living animal is not "isolated," but the same polynucleotide, nucleic acid or polypeptide separated from the coexisting materials of its natural state is "isolated", as the term is employed herein.

It will however be understood that the ELABELA protein may be mixed with carriers or diluents which will not interfere with the intended purpose of the protein and still be regarded as substantially isolated. An ELABELA polypeptide may also be in a substantially purified form, in which case it will generally comprise the protein in a preparation in which more than 90%, for example, 95%, 98% or 99% of the protein in the preparation is an ELABELA polypeptide.

By aligning ELABELA sequences from different species, it is possible to determine which regions of the amino acid sequence are conserved between different species ("homologous regions"), and which regions vary between the different species ("heterologous regions").

An example of such an alignment is set out in FIG. 1C.

The ELABELA polypeptide may comprise a sequence which corresponds to at least part of a homologous region.

A homologous region shows a high degree of homology between at least two species. The two species may comprise for example human and another species, such as *Peromyscus, Rattus, Mus, Bos, Sus, Dasypus, Trichosurus, Gallus, Gekko, Anolis, Xenopus, Ambystoma, Oryzias, Callorhinchus, Oncorhynchus* or *Danio*.

The homologous region may for example show at least 70%, at least 80%, at least 90% or at least 95% identity at the amino acid level using the tests described above.

Examples of homologous regions are set out in this document and may comprise for example HSRVPFP (SEQ ID NO: 58), RCXXXHSRVPFP (SEQ ID NO: 59) or CXXXRCXXXHSRVPFP (SEQ ID NO: 1). Such homologous regions may comprise one or more biological activities of a native ELABELA polypeptide, such as maintaining self-renewal, pluripotency, or both of a stem cell, as described herein Peptides which comprise a sequence which corresponds to a homologous region may be used in therapeutic strategies as explained in further detail elsewhere in this document. Alternatively, the ELABELA peptide may comprise a sequence which corresponds to at least part of a heterologous region. A heterologous region shows a low degree of homology between at least two species.

ELABELA Homologues

The ELABELA polypeptides disclosed for use include homologous sequences obtained from any source, for example related viral/bacterial proteins, cellular homologues and synthetic peptides, as well as variants or derivatives thereof.

Thus polypeptides also include those encoding homologues of ELABELA from other species including animals such as mammals (e.g. mice, rats or rabbits), especially primates, more especially humans. More specifically, homologues include human homologues.

In the context of this document, a homologous sequence is taken to include an amino acid sequence which is at least 15, at least 20, at least 25, at least 30, at least 40, at least 50, at least 60, at least 70, at least 80 or at least 90% identical, such as at least 95 or at least 98% identical at the amino acid level, for example over at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 or more amino acids with the sequence of a relevant ELABELA sequence.

In particular, homology should typically be considered with respect to those regions of the sequence known to be essential for protein function rather than non-essential neighbouring sequences. This is especially important when considering homologous sequences from distantly related organisms.

Examples of such regions in ELABELA are shown underlined in the sequence below:

(R/K) (R/K) XXXXXXCXXXRCXXXHSRVPFP (SEQ ID NO: 79)

Although homology can also be considered in terms of similarity (i.e. amino acid residues having similar chemical properties/functions), in the context of the present document homology may be expressed in terms of sequence identity.

Homology comparisons can be conducted by eye, or more usually, with the aid of readily available sequence comparison programs. These publicly and commercially available computer programs can calculate % identity between two or more sequences.

% identity may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local identity or similarity.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, the default values may be used when using such software for sequence comparisons. For example when using the GCG Wisconsin Bestfit package (see elsewhere in this document) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Altschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). The GCG Bestfit program may be used.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). The public default values for the GCG package may be used, or in the case of other software, the default matrix, such as BLOSUM62.

Once the software has produced an optimal alignment, it is possible to calculate % homology, such as % sequence identity. The software typically does this as part of the sequence comparison and generates a numerical result.

The terms "variant" or "derivative" in relation to amino acid sequences includes any substitution of, variation of, modification of, replacement of, deletion of or addition of one (or more) amino acids from or to the sequence providing the resultant amino acid sequence retains substantially the same activity as the unmodified sequence, such as having at least the same activity as the ELABELA polypeptides. Such ELABELA variants and derivatives may comprise one or more biological activities of a native ELABELA polypeptide, such as maintaining self-renewal, pluripotency, or both of a stem cell, as described herein.

Polypeptides having the ELABELA amino acid sequence disclosed here, or fragments or homologues thereof may be modified for use in the methods and compositions described here. Typically, modifications are made that maintain the biological activity of the sequence. Amino acid substitutions may be made, for example from 1, 2 or 3 to 10, 20 or 30 substitutions provided that the modified sequence retains the biological activity of the unmodified sequence. Alternatively, modifications may be made to deliberately inactivate one or more functional domains of the polypeptides described here. Amino acid substitutions may include the use of non-naturally occurring analogues, for example to increase blood plasma half-life of a therapeutically administered polypeptide.

ELABELA Fragments

Polypeptides for use in the methods and compositions described here also include fragments of the full length sequence of any of the ELABELA polypeptides identified above. Fragments may comprise at least one epitope. Methods of identifying epitopes are well known in the art. Fragments will typically comprise at least 5 amino acids, such as at least 6, 7, 8, 9, 10, 15, 20, 25, 30, 35, 40, 45, 50, 55 or more amino acids.

Included are fragments comprising or consisting of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or more residues from a relevant ELABELA amino acid sequence.

Such ELABELA fragments may comprise one or more biological activities of a native ELABELA polypeptide, such as maintaining self-renewal, pluripotency, or both of a stem cell, as described herein.

We further describe peptides comprising a portion of an ELABELA polypeptide as described here. Thus, fragments of ELABELA and its homologues, variants or derivatives are included. The peptides may be between 2 and 60 amino acids, such as between 4 and 50 amino acids in length. The peptide may be derived from an ELABELA polypeptide as disclosed here, for example by digestion with a suitable enzyme, such as trypsin. Alternatively the peptide, fragment, etc may be made by recombinant means, or synthesised synthetically via chemical means, such as solid phase synthesis.

We therefore describe a method of making an ELABELA polypeptide or a fragment, the method comprising expressing a nucleic acid encoding a sequence comprising CXXXRCXXXHSRVPFP (SEQ ID NO: 1) in a cell, in which X is an or any amino acid residue, and in which the polypeptide fragment maintains self-renewal, pluripotency or both of a stem cell.

The cell expressing the nucleic acid encoding a sequence comprising CXXXRCXXXHSRVPFP (SEQ ID NO: 1) may be a bacterial, fungal or yeast cell.

The sequence comprising CXXXRCXXXHSRVPFP (SEQ ID NO: 1) may be selected from the group consisting of SEQ ID NOs: 2 to 36.

We further describe a method of making an ELABELA polypeptide or a fragment, the method comprising using chemical synthesis to generate a synthetic polypeptide comprising CXXXRCXXXHSRVPFP (SEQ ID NO: 1) or a fragment having the sequence of SEQ ID NO: 53, in which X is an or any amino acid residue, and in which the polypeptide fragment maintains self-renewal, pluripotency, or both of a stem cell.

The ELABELA polypeptide or fragment, derivative, homologue or variant may comprise a label. The label may comprise a radioisotope. The radioisotope may comprise $^{125}$I. the ELABELA polypeptide or fragment, derivative, homologue or variant may be derivatized.

Such ELABELA polypeptides, fragments, derivatives, homologues and variants may be used to generate probes to preferentially detect ELABELA expression, for example, through antibodies generated against such fragments. These antibodies would be expected to bind specifically to ELABELA, and are useful in the methods of diagnosis and treatment disclosed here.

ELABELA and its fragments, homologues, variants and derivatives, may be made by recombinant means. However they may also be made by synthetic means using techniques well known to skilled persons such as solid phase synthesis. The proteins may also be produced as fusion proteins, for example to aid in extraction and purification. Examples of fusion protein partners include glutathione-S-transferase (GST), 6×His (SEQ ID NO: 97), GAL4 (DNA binding and/or transcriptional activation domains) and β-galactosidase. It may also be convenient to include a proteolytic cleavage site between the fusion protein partner and the protein sequence of interest to allow removal of fusion protein sequences. The fusion protein may be one which will not hinder the function of the protein of interest sequence. Proteins may also be obtained by purification of cell extracts from animal cells.

The ELABELA polypeptides, variants, homologues, fragments and derivatives disclosed here may be in a substantially isolated form. It will be understood that such polypeptides may be mixed with carriers or diluents which will not interfere with the intended purpose of the protein and still be regarded as substantially isolated. An ELABELA variant, homologue, fragment or derivative may also be in a substantially purified form, in which case it will generally comprise the protein in a preparation in which more than 90%, e.g. 95%, 98% or 99% of the protein in the preparation is a protein.

The ELABELA polypeptides, variants, homologues, fragments and derivatives disclosed here may be labelled with a revealing label. The revealing label may be any suitable label which allows the polypeptide, etc to be detected. Suitable labels include radioisotopes, e.g. $^{125}$I, enzymes, antibodies, polynucleotides and linkers such as biotin. Labelled polypeptides may be used in diagnostic procedures such as immunoassays to determine the amount of a polypeptide in a sample. Polypeptides or labelled polypeptides may also be used in serological or cell-mediated immune assays for the detection of immune reactivity to said polypeptides in animals and humans using standard protocols.

ELABELA polypeptides, variants, homologues, fragments and derivatives disclosed here, optionally labelled, may also be fixed to a solid phase, for example the surface of an immunoassay well or dipstick. Such labelled and/or immobilised polypeptides may be packaged into kits in a suitable container along with suitable reagents, controls, instructions and the like. Such polypeptides and kits may be used in methods of detection of antibodies to the polypeptides or their allelic or species variants by immunoassay.

Immunoassay methods are well known in the art and will generally comprise: (a) providing a polypeptide comprising an epitope bindable by an antibody against said protein; (b) incubating a biological sample with said polypeptide under conditions which allow for the formation of an antibody-antigen complex; and (c) determining whether antibody-antigen complex comprising said polypeptide is formed.

The ELABELA polypeptides, variants, homologues, fragments and derivatives disclosed here may be used in in vitro or in vivo cell culture systems to study the role of their corresponding genes and homologues thereof in cell function, including their function in disease. For example, truncated or modified polypeptides may be introduced into a cell to disrupt the normal functions which occur in the cell.

The polypeptides may be introduced into the cell by in situ expression of the polypeptide from a recombinant expression vector (see elsewhere in this document). The expression vector optionally carries an inducible promoter to control the expression of the polypeptide.

The use of appropriate host cells, such as insect cells or mammalian cells, is expected to provide for such post-translational modifications (e.g. myristolation, glycosylation, truncation, lapidation and tyrosine, serine or threonine phosphorylation) as may be needed to confer optimal biological activity on recombinant expression products.

Such cell culture systems in which the ELABELA polypeptides, variants, homologues, fragments and derivatives disclosed here are expressed may be used in assay systems to identify candidate substances which interfere with or enhance the functions of the polypeptides in the cell.

We describe methods of making an ELABELA polypeptide or fragment thereof, the methods comprising: (a) expressing a nucleic acid encoding a sequence comprising CXXXRCXXXHSRVPFP (SEQ ID NO: 1) in a cell, wherein X is an/any amino acid residue, and wherein the polypeptide fragment maintains self-renewal, pluripotency, or both of a stem cell; or (b) using chemical synthesis to generate a synthetic polypeptide or fragment thereof comprising CXXXRCXXXHSRVPFP (SEQ ID NO: 1) or a fragment having the sequence of SEQ ID NO: 53, wherein X is an/any amino acid residue, and wherein the polypeptide fragment maintains self-renewal, pluripotency, or both of a stem cell.

The cell expressing the nucleic acid encoding a sequence comprising CXXXRCXXXHSRVPFP (SEQ ID NO: 1) may comprise a bacterial, fungal, or yeast cell.

The sequence comprising CXXXRCXXXHSRVPFP (SEQ ID NO: 1) may be selected from the group consisting of SEQ ID NOs: 2-36.

The ELABELA polypeptide or fragment thereof further may comprise a label. The label may comprise a radioisotope. The radioisotope may comprise $^{125}$I.

The polypeptide or fragment thereof may be derivatized.

ELABELA Polypeptide Activities

An ELABELA polypeptide according to this document may comprise one or more activities, such as biological activities of a native ELABELA polypeptide, such as a human ELABELA polypeptide having SEQ ID NO: 20. Such activity may be referred to for convenience as an "ELABELA activity" or an "ELABELA polypeptide activity".

Where reference is made to the "activity" or "biological activity" of a polypeptide such as ELABELA, these terms are intended to refer to the metabolic or physiological function of ELABELA, including similar activities or improved activities or these activities with decreased undesirable side effects.

For example, an ELABELA activity may comprise any activity of a native ELABELA polypeptide. It may comprise for example any physical, biochemical, enzymatic, biological etc activity of a native ELABELA polypeptide.

In particular, ELABELA activities, including activities of ELABELA polypeptides, fragments, variants, homologues and derivatives may include any one or more of the following:

ability to maintain self-renewal of a stem cell
ability to maintain pluripotency of a stem cell
ability to maintain growth of a stem cell
ability to promote growth of a stem cell
ability to inhibit apoptosis
ability to bind to the cell surface of an embryonic stem cell
ability to bias differentiation of a stem cell toward an endodermal or mesodermal lineage
ability to bind to apelin receptor (APLNR)
ability to bind to CXCR4 receptor
ability to activate the P13K/AKT pathway
cardioprotection, for example restoration or maintenance of cardiac function during ischemia and/or reperfusion
reduction of oxidative stress
reduction of infarct size
inhibition of HIV infection The ELABELA activity may include any one or more of the ability to maintain the growth potential of a stem cell, ability to maintain the clonogenicity of a stem cell and ability to maintain the survival of a stem cell.

The ELABELA activity may include one or both of the ability to be secreted by an embryonic stem cell and ability to be taken-up by an embryonic stem cell Also included are antigenic and immunogenic activities of ELABELA. Examples of such activities, and methods of assaying and quantifying these activities, are known in the art, and are described in detail later in this section.

Maintenance of Self-Renewal

The ELABELA polypeptide may have a property of a native ELABELA polypeptide comprising the ability to maintain self-renewal of a cell such as a stem cell.

Maintenance of Pluripotency

The ELABELA polypeptide may have a property of a native ELABELA polypeptide comprising the ability to maintain pluripotency of a cell such as a stem cell.

Assays for Maintenance of Self-Renewal/Pluripotency

Assays for maintenance of self-renewal and/or pluripotency are described in detail in the section below headed "MAINTENANCE OF SELF-RENEWAL OR PLURIPOTENCY".

Inhibition of Apoptosis

The ELABELA polypeptide may have a property of a native ELABELA polypeptide comprising the ability to inhibit apoptosis. The ELABELA polypeptide may have a property of a native ELABELA polypeptide comprising the ability to promote cell growth.

Assay for Promotion of Cell Growth/Inhibition of Apoptosis

Apoptosis inhibitory activity may be assayed as described in detail in Example 2 below.

Briefly, hESCs are dissociated into single cells using Accutase (Stem Cell Technologies) and plated in the presence of 10 μM Y-27632 (ROCK inhibitor) for 12 hours (Watanabe et al., 2007).

xCELLigence real time growth assays are performed, with 4000 cells plated per well of an E-plate (ACEA Biosciences) with media changes every 48 hours.

ELABELA polypeptide is added at 2.5 μM (or 10 μg/ml). Cell cycle studies are performed with Click-iT EDU staining kit (Invitrogen) and by performing a double thymidine block (2.5 mM thymidine; 16 hour block, 8 hour release, 16 hour block) followed by DAPI staining for DNA content at the indicated times following release.

Apoptosis assays are performed by plating control and Doxycycline-treated cells without Y-27632 onto matrigel for 6 hours, followed by harvesting and staining for Annexin V and activated Caspase 3.

The ELABELA polypeptide may be such that a concentration of 10 μM of ELABELA polypeptide exposed to human ES cells over a period of 120 hours increases the cell index of the human ES cells by at least 10%, at least 20%, at least 30%, at least 40%, at least 50%, at least 60%, at least 70%, at least 80%, at least 90%, at least 100%, at least 150%, at least 200% or more compared to control cells not exposed to ELABELA polypeptide.

The ELABELA polypeptide may be such that a concentration of 10 μM of ELABELA polypeptide exposed to human ES cells over a period of 120 hours increases the cell index of the human ES cells by 2.5 times or more, 3 times or more, 3.5 times or more, 4 times or more, 4.5 times or more, 5 times or more, 5.5 times or more, 6 times or more, 6.5 times or more, 7 times or more, 7.5 times or more, 8 times or more, 8.5 times or more, 9 times or more, 10 times or more, 15 times or more, 20 times or more, 30 times or more or 40 times or more compared to control cells not exposed to ELABELA polypeptide.

By the term "cell index" we mean the quantitative measure (such as the number) of viable cells at any given time compared to the initial number of cells seeded at the start of a cell culture assay (see Ke N, Wang X, Xu X, Abassi Y A. *The xCELLigence system for real-time and label-free monitoring of cell viability. Methods Mol Biol.* 2011; 740:33-43).

ES Cell Surface Binding

The ELABELA polypeptide may have a property of a native ELABELA polypeptide comprising the ability to bind to the cell surface of an ES cell.

Assay for ES Cell Surface Binding

ES cell surface binding activity assays may be performed with a number of methods known to the person skilled in the art, for example as described in Example 7 below.

ELABELA polypeptide may be exposed to embryonic stem cells such as hES cells and allowed to bind to their cognate cell surface receptors. hES cells may then be fixed and stained with an anti-ELABELA antibody, such as any of the antibodies having ELABELA polypeptide binding activity, as described in this document. Chromogenic methods to reveal antibody binding are known to the art, and may include alkaline phosphatase, digoxigenin, based methods etc. Confocal microscopy may be used to reveal cell-surface binding (as opposed to intracellular binding).

Apelin Receptor (APLNR) Binding

The ELABELA polypeptide may have a property of a native ELABELA polypeptide comprising the ability to bind to an apelin receptor (APLNR).

Assay for Apelin Receptor Binding

Apelin receptor binding assays are known in the art and are described in detail in, for example, Angela Giddings, Scott Runyon, James Thomas, Julianne Tajuba, Katherine Bortoff, Rangan Maitra (2010). *Development of a functional HTS assay for the APJ receptor. International Journal of High Throughput Screening*. Volume 2010:1 Pages 39-47.

CXCR4 Receptor Binding

The ELABELA polypeptide may have a property of a native ELABELA polypeptide comprising the ability to bind to a CXCR4 receptor.

Assay for CXCR4 Receptor Binding

Secreted ELABELA polypeptide-Alkaline Phosphatase (ELABELA polypeptide-AP) is produced by transfecting a construct encoding ELABELA polypeptide-AP into 293T cells, as described previously (Chng et al., 2013). Conditioned medium from ELA-AP expressing cells is then incubated for 3 hours with 293T cells transfected with plasmids encoding full length ORFs of CXCR4. Unbound ELABELA polypeptide-AP is washed away and cells are lysed with 1% Triton-X/PBS. Lysates are cleared and incubated with an AP substrate BCIP/NBT at 37° C. for 15 minutes. Optical density is read at 495 nm, and the intensity of blue coloration is directly proportional to the affinity of ELABELA polypeptide-AP to the overexpressed CXCR4 receptor.

Biasing Towards Endo or Mesodermal Lineages

The ELABELA polypeptide may have a property of a native ELABELA polypeptide comprising the ability to bias, poise or steer a pluripotent cell toward an endodermal or mesodermal lineage. The ELABELA polypeptide may poise a cell such as a stem cell towards the mesendoderm lineage without causing overt lineage commitment.

Assay for Ability to Bias Towards Endo or Mesodermal Lineages

Assays for mesoendodermal lineage bias are known in the art and are described for example in International (PCT) Patent Publication Number WO 2007/050043.

Assays for bias towards endodermal or mesodermal lineages may also be performed as described for example in Example 3 and Example 20 below.

Any suitable ES cell culture, such as a human ES cell line Shef4 cell line (Inniss and Moore, 2006), may be used. ES cells are cultured in the presence of a suitable concentration of ELABELA polypeptide (2.5 μM or 10 μg/ml) for a suitable amount of time such as 24 hours, 48 hours, 72 hours, 96 hours, 120 hours.

Following incubation, expression of mesendodermal markers including GATA6, GATA4, FOXA2, EOMES and BRA may be assayed by any suitable means, for example using RT-PCR, qPCR or immunofluorescence, for example.

Thus, RNA may be extracted using RNeasy kit (Invitrogen). qPCR reactions may be carried out using either Universal FastStart SYBR Green Mastermix (Roche) or using the Universal Probe Library system (Roche) in tandem with Taqman Fast Mastermix (Invitrogen).

Primer sequences for each of these markers are known in the art and are also listed in for example in Table E1 (Example 3).

Expression of cell surface markers such as SSEA3 and TRA-1-60 may be assayed to confirm that the ES cells do not lose stemness.

Cardioprotection

The ELABELA polypeptide may have a property of a native ELABELA polypeptide comprising cardioprotection. The cardioprotection may comprise restoration or maintenance of cardiac function during ischemia and/or reperfusion.

Cardioprotection may also be assayed as the ability to reduce infarct size. Reduction of infarct may be assayed in a mouse or pig model of myocardial ischemia and reperfusion injury.

Assay for Cardioprotection

Cardioprotection may for example be assayed using any one or more of the methods described in Examples 5, 10, 14 and 20 of International (PCT) Patent Publication WO 2009/105044.

Oxidative Stress

The ELABELA polypeptide may have a property of a native ELABELA polypeptide comprising the ability to reduce oxidative stress (or cytoprotection).

Assay for Oxidative Stress

The reduction of oxidative stress may for example be assayed using an in vitro assay of hydrogen peroxide ($H_2O_2$)-induced cell death. In summary, hydrogen peroxide ($H_2O_2$)-mediated oxidative stress is induced in human leukemic CEM cells and cell viability is monitored by Trypan blue-exclusion. Human leukemic CEM cells are incubated with ELABELA polypeptide (with saline as a control) and treated with 50 μM $H_2O_2$ to induce oxidative stress. Cell viability is assessed using Trypan Blue exclusion at 12, 24, 36 and 48 hours after $H_2O_2$ treatment.

The reduction of oxidative stress may further be assayed using an in vivo assay of DNA oxidation. In vivo oxidative stress may also be assayed as follows. Pigs are treated with the ELABELA polypeptide (with saline as a control). Tissue sections of pig heart are obtained. Nuclear oxidative stress in tissue sections of treated and untreated pigs is quantified by 8-OHdG immunostaining for oxidized DNA. The tissue sections are assayed for intense nuclear staining indicative of DNA oxidation and oxidative stress.

Reduction of Infarct Size

The ELABELA polypeptide may have a property of a native ELABELA polypeptide comprising the ability to reduce infarct size.

Assay for Infarct Size

Infarct size may for example be assayed using any one or more of the methods described in Examples 6 and 13 of of International (PCT) Patent Publication WO 2009/105044.

Inhibition of HIV Infection

The ELABELA polypeptide may have a property of a native ELABELA polypeptide comprising the ability inhibit any of the activities of HIV, including HIV infection.

Assay for HIV Inhibition

Assays for HIV inhibition may be performed as described in Example 56 below.

ELABELA Nucleic Acids

The methods and compositions described here may make use of ELABELA polynucleotides, ELABELA nucleotides and ELABELA nucleic acids, as well as variants, homologues, derivatives and fragments of any of these.

The terms "ELABELA polynucleotide", "ELABELA nucleotide" and "ELABELA nucleic acid" may be used interchangeably, and should be understood to specifically include both cDNA and genomic ELABELA sequences. These terms are also intended to include a nucleic acid sequence capable of encoding an ELABELA polypeptide and/or a fragment, derivative, homologue or variant of this. These terms are also intended to include a nucleic acid sequence which is a fragment, derivative, homologue or variant of an ELABELA polypeptide having a specific sequence disclosed in this document, for example as set out in the sequence listings.

Where reference is made to an ELABELA nucleic acid, this should be taken as a reference to a nucleic acid sequence capable of encoding an ELABELA polypeptide. Such nucleic acids may encode ELABELA polypeptides comprising one or more biological activities of a native ELABELA polypeptide, such as maintaining self-renewal, pluripotency, or both of a stem cell, as described herein.

For example, an ELABELA nucleic acid sequence may be capable of encoding a polypeptide comprising a sequence CXXXRCXXXHSRVPFP (SEQ ID NO: 1), in which X signifies an amino acid residue. The resulting encoded polypeptide sequence may comprise ELABELA activity, such as being capable of maintaining self-renewal and/or pluripotency of a stem cell.

An ELABELA nucleic acid may also be taken generally to refer to any member of the ELABELA family of nucleic acids.

ELABELA nucleic acids may for example be capable of encoding polypeptides comprising any of the sequences set out as SEQ ID NO: 2 to SEQ ID NO: 19. An ELABELA nucleic acid may be capable of encoding a polypeptide comprising a sequence CLQRRCMPLHSRVPFP (SEQ ID NO: 2).

Examples of ELABELA nucleic acids include those selected from the group consisting of SEQ ID NO: 37 to SEQ ID NO: 41 or SEQ ID NO: 42 to SEQ ID NO: 46. For example, a human ELABELA nucleic acid sequence having the sequence SEQ ID NO: 37 is disclosed.

Also included are any one or more of the nucleic acid sequences set out as "Other ELABELA nucleic acid sequences" elsewhere in this document.

For example, the ELABELA nucleic acid may comprise a human ELABELA sequence SEQ ID NO: 37.

ELABELA nucleic acids may be used for a variety of means, as described in this document. For example, ELABELA nucleic acids may be used treat an individual suffering from, or suspected to be suffering from an ELABELA associated condition, or to prevent such a condition or to alleviate any symptoms arising as a result of such a condition. They may be used to maintain or sustain pluripotency or self-renewal or both of a cell such as a stem cell. ELABELA nucleic acids may also be used for the expression or production of ELABELA polypeptides. Other uses will be evident to the skilled reader, and are also encompassed in this document.

The term "polynucleotide", as used in this document, generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

It will be understood by the skilled person that numerous nucleotide sequences can encode the same polypeptide as a result of the degeneracy of the genetic code.

As used herein, the term "nucleotide sequence" refers to nucleotide sequences, oligonucleotide sequences, polynucleotide sequences and variants, homologues, fragments and derivatives thereof (such as portions thereof). The nucleotide sequence may be DNA or RNA of genomic or synthetic or recombinant origin which may be double-stranded or single-stranded whether representing the sense or antisense strand or combinations thereof. The term nucleotide sequence may be prepared by use of recombinant DNA techniques (for example, recombinant DNA).

The term "nucleotide sequence" may mean DNA.

Other Nucleic Acids

We also provide nucleic acids which are fragments, homologues, variants or derivatives of ELABELA nucleic acids. The terms "variant", "homologue", "derivative" or "fragment" in relation to ELABELA nucleic acid include any substitution of, variation of, modification of, replacement of, deletion of or addition of one (or more) nucleic acids from or to the sequence of an ELABELA nucleotide sequence. Unless the context admits otherwise, references to "ELABELA" and "ELABELA nucleic acid", "ELABELA nucleotide sequence" etc include references to such variants, homologues, derivatives and fragments of ELABELA.

The resultant nucleotide sequence may encode a polypeptide having any one or more ELABELA activity. The term "homologue" may be intended to cover identity with respect to structure and/or function such that the resultant nucleotide sequence encodes a polypeptide which has ELABELA activity. For example, a homologue etc of ELABELA may have a increased expression level in cells from an individual suffering from an ELABELA associated condition compared to normal cells. With respect to sequence identity (i.e. similarity), there may be at least 70%, at least 75%, at least 85% or at least 90% sequence identity. There may be at least 95%, such as at least 98%, sequence identity to a relevant sequence such as any nucleic acid sequence shown in the sequence listings (e.g., an ELABELA sequence having SEQ ID NO: 37). These terms also encompass allelic variations of the sequences.

Variants, Derivatives and Homologues

ELABELA nucleic acid variants, fragments, derivatives and homologues may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of this document, it is to be understood that the polynucleotides may be modified by any method available in the art. Such modifications may be carried out in order to enhance the in vivo activity or life span of polynucleotides of interest.

Where the polynucleotide is double-stranded, both strands of the duplex, either individually or in combination, are encompassed by the methods and compositions described here. Where the polynucleotide is single-stranded, it is to be understood that the complementary sequence of that polynucleotide is also included.

The terms "variant", "homologue" or "derivative" in relation to a nucleotide sequence include any substitution of, variation of, modification of, replacement of, deletion of or addition of one (or more) nucleic acid from or to the sequence. Said variant, homologues or derivatives may code for a polypeptide having biological activity. Such fragments, homologues, variants and derivatives of ELABELA may comprise modulated activity, as set out above.

As indicated above, with respect to sequence identity, a "homologue" may have at least 5% identity, at least 10% identity, at least 15% identity, at least 20% identity, at least 25% identity, at least 30% identity, at least 35% identity, at least 40% identity, at least 45% identity, at least 50% identity, at least 55% identity, at least 60% identity, at least 65% identity, at least 70% identity, at least 75% identity, at least 80% identity, at least 85% identity, at least 90% identity, or at least 95% identity to the relevant sequence, such as any nucleic acid sequence shown in the sequence listings (e.g., an ELABELA sequence having SEQ ID NO: 37).

There may be at least 95% identity, at least 96% identity, at least 97% identity, at least 98% identity or at least 99% identity. Nucleotide identity comparisons may be conducted as described above. A sequence comparison program which may be used is the GCG Wisconsin Bestfit program described above. The default scoring matrix has a match value of 10 for each identical nucleotide and −9 for each mismatch. The default gap creation penalty is −50 and the default gap extension penalty is −3 for each nucleotide.

Hybridisation

We further describe nucleotide sequences that are capable of hybridising selectively to any of the sequences presented herein, or any variant, fragment or derivative thereof, or to the complement of any of the above. Nucleotide sequences may be at least 5, 10, or 15 nucleotides in length, such as at least 20, 30, 40 or 50 nucleotides in length.

The term "hybridization" as used herein shall include "the process by which a strand of nucleic acid joins with a complementary strand through base pairing" as well as the process of amplification as carried out in polymerase chain reaction technologies.

Polynucleotides capable of selectively hybridising to the nucleotide sequences presented herein, or to their complement, may be at least 40% homologous, at least 45% homologous, at least 50% homologous, at least 55% homologous, at least 60% homologous, at least 65% homologous, at least 70% homologous, at least 75% homologous, at least 80% homologous, at least 85% homologous, at least 90% homologous, or at least 95% homologous to the corresponding nucleotide sequences presented herein, such as any nucleic acid sequence shown in the sequence listings (e.g., an ELABELA sequence having SEQ ID NO: 37). Such polynucleotides may be generally at least 70%, at least 80 or 90% or at least 95% or 98% homologous to the corresponding nucleotide sequences over a region of at least 5, 10, 15 or 20, such as at least 25 or 30, for instance at least 40, 60 or 100 or more contiguous nucleotides.

The term "selectively hybridizable" means that the polynucleotide used as a probe is used under conditions where a target polynucleotide is found to hybridize to the probe at a level significantly above background. The background hybridization may occur because of other polynucleotides present, for example, in the cDNA or genomic DNA library being screening. In this event, background implies a level of signal generated by interaction between the probe and a non-specific DNA member of the library which is less than 10 fold, such as less than 100 fold as intense as the specific interaction observed with the target DNA. The intensity of interaction may be measured, for example, by radiolabelling the probe, e.g. with $^{32}P$ or $^{33}P$ or with non-radioactive probes (e.g., fluorescent dyes, biotin or digoxigenin).

Hybridization conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained elsewhere in this document.

Maximum stringency typically occurs at about Tm–5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridization can be used to identify or detect identical polynucleotide sequences while an intermediate (or low) stringency hybridization can be used to identify or detect similar or related polynucleotide sequences.

We provide nucleotide sequences that may be able to hybridise to the ELABELA nucleic acids, fragments, variants, homologues or derivatives under stringent conditions (e.g. 65° C. and 0.1×SSC (1×SSC=0.15 M NaCl, 0.015 M Na$_3$ Citrate pH 7.0)).

Generation of Homologues, Variants and Derivatives

Polynucleotides which are not 100% identical to the relevant sequences (e.g., a human ELABELA sequence having SEQ ID NO: 37) but which are also included, as well as homologues, variants and derivatives of ELABELA can be obtained in a number of ways. Other variants of the sequences may be obtained for example by probing DNA libraries made from a range of individuals, for example individuals from different populations. For example, ELABELA homologues may be identified from other individuals, or other species. Further recombinant ELABELA nucleic acids and polypeptides may be produced by identifying corresponding positions in the homologues, and synthesising or producing the molecule as described elsewhere in this document.

In addition, other viral/bacterial, or cellular homologues of ELABELA, particularly cellular homologues found in mammalian cells (e.g. rat, mouse, bovine and primate cells), may be obtained and such homologues and fragments thereof in general will be capable of selectively hybridising to human ELABELA. Such homologues may be used to design non-human ELABELA nucleic acids, fragments, variants and homologues. Mutagenesis may be carried out by means known in the art to produce further variety.

Sequences of ELABELA homologues may be obtained by probing cDNA libraries made from or genomic DNA libraries from other animal species, and probing such libraries with probes comprising all or part of any of the ELABELA nucleic acids, fragments, variants and homologues, or other fragments of ELABELA under conditions of medium to high stringency.

Similar considerations apply to obtaining species homologues and allelic variants of the polypeptide or nucleotide sequences disclosed here.

Variants and strain/species homologues may also be obtained using degenerate PCR which will use primers designed to target sequences within the variants and homologues encoding conserved amino acid sequences within the sequences of the ELABELA nucleic acids. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences. It will be appreciated by the skilled person that overall nucleotide homology between sequences from distantly related organisms is likely to be very low and thus in these situations degenerate PCR may be the method of choice rather than screening libraries with labelled fragments the ELABELA sequences.

In addition, homologous sequences may be identified by searching nucleotide and/or protein databases using search algorithms such as the BLAST suite of programs.

Alternatively, such polynucleotides may be obtained by site directed mutagenesis of characterised sequences, for example, ELABELA nucleic acids, or variants, homologues, derivatives or fragments thereof. This may be useful where for example silent codon changes are required to sequences to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

The polynucleotides described here may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 8, 9, 10, or 15, such as at least 20, for example at least 25, 30 or 40 nucleotides in length, and are also encompassed by the term "polynucleotides" as used herein.

Polynucleotides such as a DNA polynucleotides and probes may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Primers comprising fragments of ELABELA are particularly useful in the methods of detection of ELABELA expression, such as up-regulation of ELABELA expression, for example, as associated with an ELABELA associated condition. Suitable primers for amplification of ELABELA may be generated from any suitable stretch of ELABELA. Primers which may be used include those capable of amplifying a sequence of ELABELA which is specific.

Although ELABELA primers may be provided on their own, they are most usefully provided as primer pairs, comprising a forward primer and a reverse primer.

Longer polynucleotides will generally be produced using recombinant means, for example using a PCR (polymerase chain reaction) cloning techniques. This will involve making a pair of primers (e.g. of about 15 to 30 nucleotides), bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Polynucleotides or primers may carry a revealing label. Suitable labels include radioisotopes such as $^{32}P$ or $^{35}S$, digoxigenin, fluorescent dyes, enzyme labels, or other protein labels such as biotin. Such labels may be added to polynucleotides or primers and may be detected using by techniques known per se. Polynucleotides or primers or fragments thereof labelled or unlabeled may be used by a person skilled in the art in nucleic acid-based tests for detecting or sequencing polynucleotides in the human or animal body.

Such tests for detecting generally comprise bringing a biological sample containing DNA or RNA into contact with a probe comprising a polynucleotide or primer under hybridising conditions and detecting any duplex formed between the probe and nucleic acid in the sample. Such detection may be achieved using techniques such as PCR or by immobilising the probe on a solid support, removing nucleic acid in the sample which is not hybridised to the probe, and then detecting nucleic acid which has hybridised to the probe. Alternatively, the sample nucleic acid may be immobilised on a solid support, and the amount of probe bound to such a support can be detected. Suitable assay methods of this and other formats can be found in for example WO89/03891 and WO90/13667.

Tests for sequencing nucleotides, for example, the ELABELA nucleic acids, involve bringing a biological sample containing target DNA or RNA into contact with a probe comprising a polynucleotide or primer under hybridising conditions and determining the sequence by, for example the Sanger dideoxy chain termination method (see Sambrook et al.).

Such a method generally comprises elongating, in the presence of suitable reagents, the primer by synthesis of a strand complementary to the target DNA or RNA and selectively terminating the elongation reaction at one or more of an A, C, G or T/U residue; allowing strand elongation and termination reaction to occur; separating out according to size the elongated products to determine the sequence of the nucleotides at which selective termination has occurred. Suitable reagents include a DNA polymerase enzyme, the deoxynucleotides dATP, dCTP, dGTP and dTTP, a buffer and ATP. Dideoxynucleotides are used for selective termination.

ELABELA Control Regions

For some purposes, it may be necessary to utilise or investigate control regions of ELABELA. Such control regions include promoters, enhancers and locus control regions. By a control region we mean a nucleic acid sequence or structure which is capable of modulating the expression of a coding sequence which is operatively linked to it.

For example, control regions are useful in generating transgenic animals expressing ELABELA. Furthermore, control regions may be used to generate expression constructs for ELABELA. This is described in further detail elsewhere in this document.

Identification of control regions of ELABELA is straightforward, and may be carried out in a number of ways. For example, the coding sequence of ELABELA may be obtained from an organism, by screening a cDNA library using a human or mouse ELABELA cDNA sequence as a probe. 5' sequences may be obtained by screening an appropriate genomic library, or by primer extension as known in the art. Database searching of genome databases may also be employed. Such 5' sequences which are particularly of interest include non-coding regions. The 5' regions may be examined by eye, or with the aid of computer programs, to identify sequence motifs which indicate the presence of promoter and/or enhancer regions.

Furthermore, sequence alignments may be conducted of ELABELA nucleic acid sequences from two or more organisms. By aligning ELABELA sequences from different species, it is possible to determine which regions of the amino acid sequence are conserved between different species. Such conserved regions are likely to contain control regions for the gene in question (i.e., ELABELA). The mouse and human genomic sequences as disclosed here, for example, a mouse ELABELA genomic sequence, may be employed for this purpose. Furthermore, ELABELA homologues from other organisms may be obtained using standard methods of screening using appropriate probes generated from the mouse and human ELABELA sequences. The genome of the pufferfish (*Takifugu rubripes*) or zebrafish may also be screened to identify an ELABELA homologue; thus, several zebrafish sequences of ELABELA have been identified (noted above). Comparison of the 5' non-coding region of the Fugu or zebrafish ELABELA gene with a mouse or human genomic ELABELA sequence may be used to identify conserved regions containing control regions.

Deletion studies may also be conducted to identify promoter and/or enhancer regions for ELABELA.

The identity of putative control regions may be confirmed by molecular biology experiments, in which the candidate sequences are linked to a reporter gene and the expression of the reporter detected.

Modulation of ELABELA

We describe a method of manipulating a cell, the method comprising modulating, such as up-regulating, any combination of the expression, amount or activity of an ELABELA polypeptide in or of the cell. The method may comprise exposing the cell to an ELABELA polypeptide.

Alternatively, or in addition, ELABELA expression, amount or activity may be up-regulated by introducing an ELABELA expression construct (also known as an ELABELA construct) into the cell. The ELABELA expression construct or ELABELA construct may comprise an ELABELA nucleic acid or a vector (such as an expression vector) comprising an ELABELA nucleic acid sequence.

As a result of such manipulation, ELABELA expression, amount or activity in or of the cell may be up-regulated by at least 1%, at least 2%, at least 5%, at least 10%, at least 15%, at least 20%, at least 30%, at least 40%, at least 50%, at least 60%, at least 70%, at least 80%, at least 90%, or at least 100% or more compared to a cell which has not been subject to the manipulation.

The ELABELA expression, amount or activity in or of the cell may be up-regulated by at least 1×, at least 1.5×, at least 2×, at least 2.5×, at least 3×, at least 3.5×, at least 4×, at least 5×, at least 10×, at least 20×, at least 30×, at least 40×, at least 50× or more compared to a cell which has not been subject to the manipulation.

Mechanisms for delivery of such constructs, nucleic acids and vectors may comprise electroporation, calcium phosphate transformation or particle bombardment. However, transfer of the construct may be performed by any of the methods mentioned which physically or chemically permeabilize the cell membrane.

1. Electroporation

The ELABELA construct may be introduced into the cells via electroporation. Electroporation involves the exposure of a suspension of cells and DNA to a high-voltage electric discharge.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

It is contemplated that electroporation conditions for cells from different sources may be optimized. One may particularly with to optimize such parameters as the voltage, the capacitance, the time and the electroporation media composition. The execution of other routine adjustments will be known to those of skill in the art.

2. Particle Bombardment

One of the ways of transferring a naked DNA construct into cells involves particle bombardment. This method depends on the ability to accelerate DNA-coated microprojectiles to a high velocity allowing them to pierce cell membranes and enter cells without killing them (Klein et al., 1987). The microprojectiles used have consisted of biologically inert substances such as tungsten, platinum or gold beads.

It is contemplated that in some instances DNA precipitation onto metal particles would not be necessary for DNA delivery to a recipient cell using particle bombardment. It is contemplated that particles may contain DNA rather than be coated with DNA. Hence it is proposed that DNA-coated particles may increase the level of DNA delivery via particle bombardment but are not, in and of themselves, necessary.

Several devices for accelerating small particles have been developed. One such device relies on a high voltage discharge to generate an electrical current, which in turn provides the motive force (Yang et al., 1990). Another method involves the use of a Biolistic Particle Delivery System, which can be used to propel particles coated with DNA through a screen, such as stainless steel or Nytex screen, onto a filter surface covered with cells in suspension. The screen disperses the particles so that they are not delivered to the recipient cells in large aggregates. It is believed that a screen intervening between the projectile apparatus and the cells to be bombarded reduces the size of projectile aggregates and may contribute to a higher frequency of transformation by reducing the damage inflicted on the recipient cells by projectiles that are too large.

For the bombardment, cells in suspension may be concentrated on filters, or alternatively on solid culture medium. The cells to be bombarded are positioned at an appropriate distance below the macroprojectile stopping plate. If desired, one or more screens are also positioned between the acceleration device and the cells to be bombarded.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity or either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of primordial germ cells.

Accordingly, it is contemplated that one may wish to adjust various of the bombardment parameters in small scale studies to fully optimize the conditions. One may particularly wish to adjust physical parameters such as gap distance, flight distance, tissue distance and helium pressure. One may also optimize the trauma reduction factors by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art.

3. Viral Transformation a. Adenoviral Infection

One method for delivery of the ELABELA nucleic acid constructs involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a construct that has been cloned therein.

The vector comprises a genetically engineered form of adenovirus. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them suitable mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA.

Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. A suitable helper cell line is 293.

Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the methods and compositions described here. The adenovirus may be of any of the 42 different known serotypes or subgroups A-F. Adenovirus type 5 of subgroup C may be used as starting material in order to obtain the conditional replication-defective adenovirus vector for use in the methods and compositions described here. This is because Adenovirus type 5 is a human adenovirus about which a great deal of biochemical and genetic information is known, and it has historically been used for most constructions employing adenovirus as a vector.

As stated above, the typical vector according to the methods and compositions described here is replication defective and will not have an adenovirus E1 region. Thus, it will be most convenient to introduce the transforming construct at the position from which the E1-coding sequences have been removed. However, the position of insertion of the construct within the adenovirus sequences is not critical to the methods and compositions described here. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus growth and manipulation is known to those of skill in the art, and exhibits broad host range in vitro and in vivo. This group of viruses can be obtained in high titers, e.g., $10^9$-$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

b. AAV Infection

Adeno-associated virus (AAV) is an attractive vector system for use in the methods and compositions described hereas it has a high frequency of integration and it can infect nondividing cells, thus making it useful for delivery of genes into mammalian cells in tissue culture (Muzyczka, 1992). AAV has a broad host range for infectivity (Tratschin, et al., 1984; Laughlin, et al., 1986; Lebkowski, et al., 1988; McLaughlin, et al., 1988), which means it is applicable for use with the methods and compositions described here. Details concerning the generation and use of rAAV vectors are described in U.S. Pat. Nos. 5,139,941 and 4,797,368, each incorporated herein by reference.

Studies demonstrating the use of AAV in gene delivery include LaFace et al. (1988); Zhou et al. (1993); Flotte et al. (1993); and Walsh et al. (1994). Recombinant AAV vectors have been used successfully for in vitro and in vivo transduction of marker genes (Kaplitt, et al., 1994; Lebkowski, et al., 1988; Samulski, et al., 1989; Shelling and Smith, 1994; Yoder, et al., 1994; Zhou, et al., 1994; Hermonat and Muzyczka, 1984; Tratschin, et al., 1985; McLaughlin, et al., 1988) and genes involved in human diseases (Flotte, et al., 1992; Luo, et al., 1994; Ohi, et al., 1990; Walsh, et al., 1994; Wei, et al., 1994). Recently, an AAV vector has been approved for phase I human trials for the treatment of cystic fibrosis.

AAV is a dependent parvovirus in that it requires coinfection with another virus (either adenovirus or a member of the herpes virus family) to undergo a productive infection in cultured cells (Muzyczka, 1992). In the absence of coinfection with helper virus, the wild type AAV genome integrates through its ends into human chromosome 19 where it resides in a latent state as a provirus (Kotin et al., 1990; Samulski et al., 1991). rAAV, however, is not restricted to chromosome 19 for integration unless the AAV Rep protein is also expressed (Shelling and Smith, 1994). When a cell carrying an AAV provirus is superinfected with a helper virus, the AAV genome is "rescued" from the chromosome or from a recombinant plasmid, and a normal productive infection is established (Samulski, et al., 1989; McLaughlin, et al., 1988; Kotin, et al., 1990; Muzyczka, 1992).

Typically, recombinant AAV (rAAV) virus is made by cotransfecting a plasmid containing the gene of interest flanked by the two AAV terminal repeats (McLaughlin et al., 1988; Samulski et al., 1989; each incorporated herein by reference) and an expression plasmid containing the wild type AAV coding sequences without the terminal repeats, for example pIM45 (McCarty et al., 1991; incorporated herein by reference). The cells are also infected or transfected with adenovirus or plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions or cell lines containing the AAV coding regions and some or all of the adenovirus helper genes could be used (Yang et al., 1994a; Clark et al., 1995). Cell lines carrying the rAAV DNA as an integrated provirus can also be used (Flotte et al., 1995).

c. Retroviral Infection

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

d. Other Viral Vectors

Other viral vectors may be employed as ELABELA constructs in the methods and compositions described here. Vectors derived from viruses such as vaccinia virus (Ridgeway, 1988; Baichwal and Sugden, 1986; Coupar et al., 1988) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In still further embodiments, the ELABELA nucleic acids to be delivered are housed within an infective virus that has been engineered to express a specific binding ligand. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

4. Calcium Phosphate Co-Precipitation or DEAE-Dextran Treatment

In other embodiments, the ELABELA nucleic acid construct is introduced to the cells using calcium phosphate co-precipitation. Mouse primordial germ cells have been transfected with the SV40 large T antigen, with excellent results (Watanabe et al., 1997). Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

In another embodiment, the ELABELA expression construct is delivered into the cell using DEAE-dextran followed by polyethylene glycol. In this manner, reporter plasmids were introduced into mouse myeloma and erythroleukemia cells (Gopal, 1985).

5. Direct Microinjection or Sonication Loading

Further embodiments include the introduction of the ELABELA nucleic acid construct by direct microinjection or sonication loading. Direct microinjection has been used to introduce ELABELA nucleic acid constructs into Xenopus oocytes (Harland and Weintraub, 1985), and LTK.sup.-fibroblasts have been transfected with the thymidine kinase gene by sonication loading (Fechheimer et al., 1987).

6. Liposome Mediated Transformation

In a further embodiment, the ELABELA nucleic acid construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an ELABELA nucleic acid construct complexed with Lipofectamine (Gibco BRL).

Liposome-mediated nucleic acid delivery and expression of foreign DNA in vitro has been very successful (Nicolau and Sene, 1982; Fraley et al., 1979; Nicolau et al., 1987). Wong et al. (1980) demonstrated the feasibility of liposome-mediated delivery and expression of foreign DNA in cultured chick embryo, HeLa and hepatoma cells.

In certain embodiments, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1.

7. Adenoviral Assisted Transfection

In certain embodiments, the ELABELA nucleic acid construct is introduced into the cell using adenovirus assisted transfection. Increased transfection efficiencies have been reported in cell systems using adenovirus coupled systems (Kelleher and Vos, 1994; Cotten et al., 1992; Curiel, 1994), and the inventors contemplate using the same technique to increase transfection efficiencies.

8. Receptor Mediated Transfection

Still further ELABELA constructs that may be employed to deliver the ELABELA nucleic acid construct to the target cells are receptor-mediated delivery vehicles. These take advantage of the selective uptake of macromolecules by receptor-mediated endocytosis that will be occurring in the target cells. In view of the cell type-specific distribution of various receptors, this delivery method adds a degree of specificity. Specific delivery in the context of another mammalian cell type is described by Wu and Wu (1993; incorporated herein by reference).

Certain nucleic acid delivery constructs comprise a cell receptor-specific ligand and a DNA-binding agent. Others comprise a cell receptor-specific ligand to which the DNA construct to be delivered has been operatively attached. Several ligands have been used for receptor-mediated gene transfer (Wu and Wu, 1987; Wagner et al., 1990; Ferkol et al., 1993; Perales et al., 1994; Myers, EPO 0273085), which establishes the operability of the technique.

In other embodiments, the DNA delivery vehicle component may comprise a specific binding ligand in combination with a liposome. The nucleic acids to be delivered are housed within the liposome and the specific binding ligand is functionally incorporated into the liposome membrane. The liposome will thus specifically bind to the receptors of the target cell and deliver the contents to the cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the DNA delivery vehicle component of the delivery vehicles may be a liposome itself, which may comprise one or more lipids or glycoproteins that direct cell-specific binding. For example, Nicolau et al. (1987) employed lactosyl-ceramide, a galactose-terminal asialoganglioside, incorporated into liposomes and observed an increase in the uptake of the insulin gene by hepatocytes.

It is contemplated that the ELABELA nucleic acid described here can be specifically delivered into the target cells in a similar manner.

Down-Regulation of ELABELA

We describe a method of manipulating a cell, the method comprising down-regulating, any combination of the expression, amount or activity of an ELABELA polypeptide in or of the cell.

The method may comprise exposing the cell to an inhibitor of ELABELA activity. The method may comprise exposing the cell to an anti-ELABELA antibody or antigen-binding fragment thereof. Alternatively, or in addition, ELABELA expression, amount or activity may be down-regulated by introducing an ELABELA shRNA or siRNA into the cell.

As a result of such manipulation, ELABELA expression, amount or activity in or of the cell may be down-regulated by at least 1%, at least 2%, at least 5%, at least 10%, at least 15%, at least 20%, at least 30%, at least 40%, at least 50%, at least 60%, at least 70%, at least 80%, at least 90%, or at least 100% or more compared to a cell which has not been subject to the manipulation.

The ELABELA expression, amount or activity in or of the cell may be down-regulated by at least 1×, at least 1.5×, at least 2×, at least 2.5×, at least 3×, at least 3.5×, at least 4×, at least 5×, at least 10×, at least 20×, at least 30×, at least 40×, at least 50× or more compared to a cell which has not been subject to the manipulation.

Maintenance of Self-Renewal or Pluripotency

We disclose a method of maintaining or enhancing self-renewal or pluripotency, or both, in or of a stem cell. Such a method may comprise manipulating a stem cell by a method set out above.

We therefore describe a method of manipulating a stem cell by modulating, such as up-regulating, any combination of the expression, amount or activity of an ELABELA polypeptide in or of the stem cell. The method may comprise exposing the stem cell to an ELABELA polypeptide.

Alternatively, or in addition, ELABELA expression, amount or activity may be up-regulated in the stem cell by introducing an ELABELA expression construct (also known as an ELABELA construct) into the cell. The ELABELA expression construct or ELABELA construct may comprise an ELABELA nucleic acid or a vector (such as an expression vector) comprising an ELABELA nucleic acid sequence. Methods of introducing such constructs are set out in detail in the immediately preceding section.

Maintenance of Pluripotency

Cells treated by the methods and compositions described here retain pluripotency. In other words, such cells retain at least one characteristic of a stem cell, such as a vertebrate, mammalian, primate or human stem cell. Such cells may retain the characteristic after one or more passages. They may do so after a plurality of passages.

The pluripotency or stem cell characteristic may comprise a morphological characteristic, immunohistochemical characteristic, a molecular biological characteristic, etc. The characteristic may comprise a biological activity.

Stem Cell Characteristics

The cells treated by our methods, in which pluripotency is retained, may display any of the following stem cell characteristics.

Stem cells may display increased expression of Oct4/POU5F1, TRA-1-160 and/or SSEA-1. Expression of any one or more of Flk-1, Tie-2 and c-kit may be decreased.

Stem cells which are self-renewing may display a shortened cell cycle compared to stem cells which are not self-renewing.

Stem cells may display defined morphology. For example, in the two dimensions of a standard microscopic image, human embryonic stem cells display high nuclear/cytoplasmic ratios in the plane of the image, prominent nucleoli, and compact colony formation with poorly discernable cell junctions.

Stem cells may also be characterized by expressed cell markers as described in further detail below.

Expression of Pluripotency Markers

The biological activity that is retained may comprise expression of a pluripotency marker.

Stage-specific embryonic antigens (SSEA) are characteristic of certain embryonic cell types. Antibodies for SSEA markers are available from the Developmental Studies Hybridoma Bank (Bethesda Md.). Other useful markers are detectable using antibodies designated Tra-1-60 and Tra-1-81 (Andrews et al., Cell Lines from Human Gem Cell Tumors, in E. J. Robertson, 1987, supra). Human embryonic stem cells are typically SSEA-1 negative and SSEA-4 positive. hEG cells are typically SSEA-1 positive. Differentiation of pPS cells in vitro results in the loss of SSEA-4, TRA-1-60, and TRA-1-81 expression and increased expression of SSEA-1. pPS cells can also be characterized by the presence of alkaline phosphatase activity, which can be detected by fixing the cells with 4% paraformaldehyde, and then developing with Vector Red as a substrate, as described by the manufacturer (Vector Laboratories, Burlingame Calif.).

Embryonic stem cells are also typically telomerase positive and OCT-4/POU5F1 positive. Telomerase activity can be determined using TRAP activity assay (Kim et al., Science 266:2011, 1997), using a commercially available kit (TRAPeze® XK Telomerase Detection Kit, Cat. s7707; Intergen Co., Purchase N.Y.; or TeloTAGGG™ Telomerase PCR ELISA plus, Cat. 2,013,89; Roche Diagnostics, Indianapolis). hTERT expression can also be evaluated at the mRNA level by RT-PCR. The LightCycler TeloTAGGG™ hTERT quantification kit (Cat. 3,012,344; Roche Diagnostics) is available commercially for research purposes.

Any one or more of these pluripotency markers, including FOXD3, PODXL, alkaline phosphatase, POU5F1 (also known as OCT-4), SSEA-3, SSEA-4 and TRA-1-60, etc, may be retained by the cells produced by the methods and compositions described here.

Detection of markers may be achieved through any means known in the art, for example immunologically. Histochemical staining, flow cytometry (FACs), Western Blot, enzyme-linked immunoassay (ELISA), etc may be used.

Flow immunocytochemistry may be used to detect cell-surface markers. immunohistochemistry (for example, of fixed cells or tissue sections) may be used for intracellular or cell-surface markers. Western blot analysis may be conducted on cellular extracts. Enzyme-linked immunoassay may be used for cellular extracts or products secreted into the medium.

For this purpose, antibodies to the pluripotency markers as available from commercial sources may be used.

Antibodies for the identification of stem cell markers including the Stage-Specific Embryonic Antigens 1 and 4 (SSEA-1 and SSEA-4) and Tumor Rejection Antigen 1-60 and 1-81 (TRA-1-60, TRA-1-81) may be obtained commercially, for example from Chemicon International, Inc (Temecula, Calif., USA). The immunological detection of these antigens using monoclonal antibodies has been widely used to characterize pluripotent stem cells (Shamblott M. J. et. al. (1998) PNAS 95: 13726-13731; Schuldiner M. et. al. (2000). PNAS 97: 11307-11312; Thomson J. A. et. al. (1998). Science 282: 1145-1147; Reubinoff B. E. et. al. (2000). Nature Biotechnology 18: 399-404; Henderson J. K. et. al. (2002). Stem Cells 20: 329-337; Pera M. et. al. (2000). J. Cell Science 113: 5-10.).

The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods. Sequence data for the particular markers listed in this disclosure can be obtained from public databases such as GenBank (URL www.ncbi.nlm.nih.gov:80/entrez). See U.S. Pat. No. 5,843,780 for further details.

Substantially all of the cells treated by the methods and compositions described here, or a substantial portion of them, may express the marker(s). For example, the percentage of cells that express the marker or markers may be 50% or more, 60% or more, 70% or more, 80% or more, 90% or more, 93% or more, 95% or more, 97% or more, 97% or more, 99% or more, or substantially 100%.

Cell Viability

The biological activity may comprise cell viability after treatment by the methods and compositions described here, or after propagation following treatment. Cell viability may be assayed in various ways, for example by Trypan Blue exclusion.

A protocol for vital staining follows. Place a suitable volume of a cell suspension (20-200 μL) in appropriate tube add an equal volume of 0.4% Trypan blue and gently mix, let stand for 5 minutes at room temperature. Place 10 μl of stained cells in a hemocytometer and count the number of viable (unstained) and dead (stained) cells. Calculate the average number of unstained cells in each quadrant, and multiply by $2 \times 10^4$ to find cells/ml. The percentage of viable cells is the number of viable cells divided by the number of dead and viable cells.

The viability of cells may be 50% or more, 60% or more, 70% or more, 80% or more, 90% or more, 93% or more, 95% or more, 97% or more, 97% or more, 99% or more, or substantially 100%.

Karyotype

The cells treated by the methods and compositions described here, in which pluripotency is enhanced or induced, may retain a normal karyotype during or after propagation. A "normal" karyotype is a karyotype that is identical, similar or substantially similar to a karyotype of a parent stem cell from which the propagule is derived, or one which varies from it but not in any substantial manner. For example, there should not be any gross anomalies such as translocations, loss of chromosomes, deletions, etc.

Karyotype may be assessed by a number of methods, for example visually under optical microscopy. Karyotypes may be prepared and analyzed as described in McWhir et al. (2006), Hewitt et al. (2007), and Gallimore and Richardson (1973). Cells may also be karyotyped using a standard G-banding technique (available at many clinical diagnostics labs that provides routine karyotyping services, such as the Cytogenetics Lab at Oakland Calif.) and compared to published stem cell karyotypes.

All or a substantial portion of cells treated by the methods and compositions described here may retain a normal karyotype. This proportion may be 50% or more, 60% or more, 70% or more, 80% or more, 90% or more, 93% or more, 95% or more, 97% or more, 97% or more, 99% or more, or substantially 100%.

Pluripotency

The cells treated by our methods may retain the capacity to differentiate into all three embryonic lineages, i.e., endoderm, ectoderm and mesoderm. Methods of induction of stem cells to differentiate each of these lineages are known in the art and may be used to assay the capability of the cells to differentiate. All or a substantial portion of the treated cells may retain this ability. This may be 50% or more, 60% or more, 70% or more, 80% or more, 90% or more, 93% or more, 95% or more, 97% or more, 97% or more, 99% or more, or substantially 100% of the treated cells.

Co-Culture and Feeders

Our methods may comprise culturing stem cells in the presence or absence of co-culture. The term "co-culture" refers to a mixture of two or more different kinds of cells that are grown together, for example, stromal feeder cells. The two or more different kinds of cells may be grown on the same surfaces, such as particles or cell container surfaces, or on different surfaces. The different kinds of cells may be grown on different particles or container surfaces.

Feeder cells, as the term is used in this document, may mean cells which are used for or required for cultivation of cells of a different type. In the context of stem cell culture, feeder cells have the function of securing the survival, proliferation, and maintenance of ES-cell pluripotency. ES-cell pluripotency may be achieved by directly co-cultivating the feeder cells. Alternatively, or in addition, the feeder cells may be cultured in a medium to condition it. The conditioned medium may be used to culture the stem cells.

The inner surface of the container such as a culture dish may be coated with a feeder layer of mouse embryonic skin cells that have been treated so they will not divide. The feeder cells release nutrients into the culture medium which are required for ES cell growth. The stem cells may be grown in such coated containers.

The feeder cells may themselves be grown on particles. They may be seeded on particles in a similar way as described for stem cells. The stem cells to be propagated may be grown together with or separate from such feeder particles. The stem cells may therefore be grown on a layer on such feeder cell coated particles. On the other hand, the stem cells may be grown on separate particles. Any combinations of any of these arrangements are also possible, for example, a culture which comprises feeder cells grown on particles, particles with feeder cells and stem cells, and particles with stem cells growing. These combinations may be grown in containers with a feeder layer or without.

Arrangements in which feeder cells are absent or not required are also possible. For example, the cells may be grown in medium conditioned by feeder cells or stem cells.

Media and Feeder Cells

Media for isolating and propagating pluripotent stem cells can have any of several different formulas, as long as the cells obtained have the desired characteristics, and can be propagated further.

Suitable sources are as follows: Dulbecco's modified Eagles medium (DMEM), Gibco #11965-092; Knockout Dulbecco's modified Eagles medium (KO DMEM), Gibco #10829-018; 200 mM L-glutamine, Gibco #15039-027; non-essential amino acid solution, Gibco 11140-050; beta-mercaptoethanol, Sigma # M7522; human recombinant basic fibroblast growth factor (bFGF), Gibco #13256-029. Exemplary serum-containing embryonic stem (ES) medium is made with 80% DMEM (typically KO DMEM), 20% defined fetal bovine serum (FBS) not heat inactivated, 0.1 mM non-essential amino acids, 1 mM L-glutamine, and 0.1 mM beta-mercaptoethanol. The medium is filtered and stored at 4 degrees C. for no longer than 2 weeks. Serum-free embryonic stem (ES) medium is made with 80% KO DMEM, 20% serum replacement, 0.1 mM non-essential amino acids, 1 mM L-glutamine, and 0.1 mM beta-mercaptoethanol. An effective serum replacement is Gibco #10828-028. The medium is filtered and stored at 4 degrees C. for no longer than 2 weeks. Just before use, human bFGF is added to a final concentration of 4 ng/mL (Bodnar et al., Geron Corp, International Patent Publication WO 99/20741).

The media may comprise Knockout DMEM media (Invitrogen-Gibco, Grand Island, N.Y.), supplemented with 10% serum replacement media (Invitrogen-Gibco, Grand Island, N.Y.), 5 ng/ml FGF2 (Invitrogen-Gibco, Grand Island, N.Y.) and 5 ng/ml PDGF AB (Peprotech, Rocky Hill, N.J.).

Feeder cells (where used) may be propagated in mEF medium, containing 90% DMEM (Gibco #11965-092), 10% FBS (Hyclone #30071-03), and 2 mM glutamine. mEFs are propagated in T150 flasks (Coming #430825), splitting the cells 1:2 every other day with trypsin, keeping the cells subconfluent. To prepare the feeder cell layer, cells are irradiated at a dose to inhibit proliferation but permit synthesis of important factors that support human embryonic stem cells (.about.4000 rads gamma irradiation). Six-well culture plates (such as Falcon #304) are coated by incubation at 37 degrees C. with 1 mL 0.5% gelatin per well overnight, and plated with 375,000 irradiated mEFs per well. Feeder cell layers are typically used 5 h to 4 days after plating. The medium is replaced with fresh human embryonic stem (hES) medium just before seeding pPS cells.

Conditions for culturing other stem cells are known, and can be optimized appropriately according to the cell type. Media and culture techniques for particular cell types referred to in the previous section are provided in the references cited.

Serum Free Media

The methods and compositions described here may include culture of cells such as stem cells in a serum-free medium.

The term "serum-free media" may comprise cell culture media which is free of serum proteins, e.g., fetal calf serum. Serum-free media are known in the art, and are described for example in U.S. Pat. Nos. 5,631,159 and 5,661,034. Serum-free media are commercially available from, for example, Gibco-BRL (Invitrogen).

The serum-free media may be protein free, in that it may lack proteins, hydrolysates, and components of unknown composition. The serum-free media may comprise chemically-defined media in which all components have a known chemical structure. Chemically-defined serum-free media may be used as it provides a completely defined system which eliminates variability allows for improved reproducibility and more consistent performance, and decreases possibility of contamination by adventitious agents.

The serum-free media may comprise Knockout DMEM media (Invitrogen-Gibco, Grand Island, N.Y.).

The serum-free media may be supplemented with one or more components, such as serum replacement media, at a concentration of for example, 5%, 10%, 15%, etc. The serum-free media may be supplemented with 10% serum replacement media from Invitrogen-Gibco (Grand Island, N.Y.).

The serum-free medium in which the dissociated or disaggregated embryonic stem cells are cultured may comprise one or more growth factors. A number of growth factors are known in the art, including FGF2, IGF-2, Noggin, Activin A, TGF beta 1, HRG1 beta, LIF, S1P, PDGF, BAFF, April, SCF, Flt-3 ligand, Wnt3A and others. The growth factor(s), may be used at any suitable concentration such as between 1 pg/ml to 500 ng/ml.

Stem Cells

As used in this document, the term "stem cell" refers to a cell that on division faces two developmental options: the daughter cells can be identical to the original cell (self-renewal) or they may be the progenitors of more specialised cell types (differentiation). The stem cell is therefore capable of adopting one or other pathway (a further pathway exists in which one of each cell type can be formed). Stem cells are therefore cells which are not terminally differentiated and are able to produce cells of other types.

Stem cells as referred to in this document may include totipotent stem cells, pluripotent stem cells, and multipotent stem cells. They also specifically include induced pluripotent stem cells (iPS).

Totipotent Stem Cells

The term "totipotent" cell refers to a cell which has the potential to become any cell type in the adult body, or any cell of the extraembryonic membranes (e.g., placenta). Thus, the only totipotent cells are the fertilized egg and the first 4 or so cells produced by its cleavage.

Pluripotent Stem Cells

"Pluripotent stem cells" are true stem cells, with the potential to make any differentiated cell in the body. However, they cannot contribute to making the extraembryonic membranes which are derived from the trophoblast. Several types of pluripotent stem cells have been found.

Embryonic Stem Cells

Embryonic Stem (ES) cells may be isolated from the inner cell mass (ICM) of the blastocyst, which is the stage of embryonic development when implantation occurs.

Embryonic Germ Cells

Embryonic Germ (EG) cells may be isolated from the precursor to the gonads in aborted fetuses.

Embryonic Carcinoma Cells

Embryonic Carcinoma (EC) cells may be isolated from teratocarcinomas, a tumor that occasionally occurs in a gonad of a fetus. Unlike the first two, they are usually aneuploid. All three of these types of pluripotent stem cells can only be isolated from embryonic or fetal tissue and can be grown in culture. Methods are known in the art which prevent these pluripotent cells from differentiating.

Adult Stem Cells

Adult stem cells comprise a wide variety of types including neuronal, skin and the blood forming stem cells which are the active component in bone marrow transplantation. These latter stem cell types are also the principal feature of umbilical cord-derived stem cells. Adult stem cells can mature both in the laboratory and in the body into functional, more specialised cell types although the exact number of cell types is limited by the type of stem cell chosen.

Multipotent Stem Cells

Multipotent stem cells are true stem cells but can only differentiate into a limited number of types. For example, the bone marrow contains multipotent stem cells that give rise to all the cells of the blood but not to other types of cells. Multipotent stem cells are found in adult animals. It is thought that every organ in the body (brain, liver) contains them where they can replace dead or damaged cells.

Methods of characterising stem cells are known in the art, and include the use of standard assay methods such as clonal assay, flow cytometry, long-term culture and molecular biological techniques e.g. PCR, RT-PCR and Southern blotting.

In addition to morphological differences, human and murine pluripotent stem cells differ in their expression of a number of cell surface antigens (stem cell markers). Markers for stem cells and methods of their detection are described elsewhere in this document (under "Maintenance of Stem Cell Characteristics").

Screening for Anti-ELABELA Agents

Identifying ELABELA Modulators, Agonists and Antagonists Antagonists, in particular, small molecules may be used to specifically inhibit ELABELA for use as anti-ELABELA agents.

We disclose a method of assaying a compound of interest, the method comprising contacting an ELABELA polypeptide with a candidate compound and performing an assay to determine if the candidate compound binds to the ELABELA polypeptide.

We further disclose a method of assaying a compound of interest, the method comprising contacting an ELABELA polypeptide with a candidate compound and performing an assay to determine if the candidate compound modulates an activity of the ELABELA polypeptide.

We further disclose a method of assaying a compound of interest, the method comprising contacting a cell expressing an ELABELA polypeptide with a candidate compound and performing an assay to determine if the candidate compound causes an elevated or reduced expression, amount or activity of the ELABELA polypeptide in or of the cell.

The compound of interest so identified may then be isolated or chemically synthesised.

We therefore disclose ELABELA antagonists and small molecule ELABELA inhibitors, as well as assays for screening for these. Antagonists of ELABELA may be screened by detecting modulation, such as down regulation, of binding or other ELABELA activity. We therefore provide a compound capable of down-regulating the expression, amount or activity ELABELA polypeptide. Such a compound may be used in the methods and compositions described here for treating or preventing an ELABELA associated condition.

ELABELA may therefore be used to assess the binding of small molecule substrates and ligands in, for example, cells, cell-free preparations, chemical libraries, and natural product mixtures. These substrates and ligands may be natural substrates and ligands or may be structural or functional mimetics. See Coligan et al., *Current Protocols in Immunology* 1(2): Chapter 5 (1991). Furthermore, screens may be conducted to identify factors which influence the expression of ELABELA, in particular in an ELABELA associated condition.

In general, the assays for agonists and antagonists rely on determining the effect of candidate molecules on one or more activities of ELABELA. An assay may involve assaying ELABELA activity in the presence of a candidate molecule, and optionally in the absence of the candidate molecule, or in the presence of a molecule known to inhibit or activate an ELABELA activity.

Expression of ELABELA may be modulated, such as up-regulated in an ELABELA associated condition. Therefore, it may be desirous to find compounds and drugs which stimulate the expression and/or activity of ELABELA, or which can inhibit the function of this protein. In general, agonists and antagonists may be employed for therapeutic and prophylactic purposes for an ELABELA associated condition.

By "down-regulation" we include any negative effect on the behaviour being studied; this may be total or partial. Thus, where binding is being detected, candidate antagonists are capable of reducing, ameliorating, or abolishing the binding between two entities. The down-regulation of binding (or any other activity) achieved by the candidate molecule may be at least 10%, such as at least 20%, at least 30%, at least 40%, at least 50%, at least 60%, at least 70%, at least 80%, at least 90% or more compared to binding (or whichever activity) in the absence of the candidate molecule. Thus, a candidate molecule suitable for use as an antagonist is one which is capable of reducing by 10% more the binding or other activity.

The term "compound" refers to a chemical compound (naturally occurring or synthesised), such as a biological macromolecule (e.g., nucleic acid, protein, non-peptide, or organic molecule), or an extract made from biological materials such as bacteria, plants, fungi, or animal (particularly mammalian) cells or tissues, or even an inorganic element or molecule. The compound may be an antibody.

Examples of potential antagonists of ELABELA include antibodies, small molecules, nucleotides and their analogues, including purines and purine analogues, oligonucleotides, stapled peptides or proteins which are closely related to a binding partner of ELABELA, e.g., a fragment of the binding partner, or small molecules which bind to the ELABELA polypeptide but do not elicit a response, so that the activity of the polypeptide is prevented, etc.

Screening Kits

The materials necessary for such screening to be conducted may be packaged into a screening kit.

Such a screening kit is useful for identifying agonists, antagonists, ligands, receptors, substrates, enzymes, etc. for ELABELA polypeptides or compounds which decrease or enhance the production of ELABELA. The screening kit may comprise: (a) an ELABELA polypeptide; (b) a recombinant cell expressing an ELABELA polypeptide; or (c) an antibody to ELABELA polypeptide. The screening kit may comprise a library. The screening kit may comprise any one or more of the components needed for screening, as described elsewhere in this document. The screening kit may optionally comprise instructions for use.

Screening kits may also be provided which are capable of detecting ELABELA expression at the nucleic acid level. Such kits may comprise a primer for amplification of ELABELA, or a pair of primers for amplification. The primer or primers may be chosen from any suitable sequence, for example a portion of the ELABELA sequence. Methods of identifying primer sequences are well known in the art, and the skilled person will be able to design such primers with ease. The kits may comprise a nucleic acid probe for ELABELA expression, as described in this document. The kits may also optionally comprise instructions for use.

Rational Design

Rational design of candidate compounds likely to be able to interact with ELABELA may be based upon structural studies of the molecular shapes of an ELABELA polypeptide. One means for determining which sites interact with specific other proteins is a physical structure determination, e.g., X-ray crystallography or two-dimensional NMR techniques. These will provide guidance as to which amino acid residues form molecular contact regions. For a detailed description of protein structural determination, see, e.g., Blundell and Johnson (1976) *Protein Crystallography*, Academic Press, New York.

Polypeptide Binding Assays

Modulators and antagonists of ELABELA activity or expression may be identified by any means known in the art.

In their simplest form, the assays may simply comprise the steps of mixing a candidate compound with a solution containing an ELABELA polypeptide to form a mixture, measuring activity of ELABELA polypeptide in the mixture, and comparing the activity of the mixture to a standard.

Furthermore, molecules may be identified by their binding to ELABELA, in an assay which detects binding between ELABELA and the putative molecule.

One type of assay for identifying substances that bind to an ELABELA polypeptide described here involves contacting the ELABELA polypeptide, which is immobilised on a solid support, with a non-immobilised candidate substance determining whether and/or to what extent the ELABELA polypeptide of interest and candidate substance bind to each other. Alternatively, the candidate substance may be immobilised and the ELABELA polypeptide as set out in this document non-immobilised.

The binding of the substance to the ELABELA polypeptide can be transient, reversible or permanent. The substance may bind to the polypeptide with a Kd value which is lower than the Kd value for binding to control polypeptides (e.g., polypeptides known to not be involved in an ELABELA associated condition). The Kd value of the substance may be 2 fold less than the Kd value for binding to control polypeptides, such as a Kd value 100 fold less or a Kd 1000 fold less than that for binding to the control polypeptide.

In an example assay method, the ELABELA polypeptide may be immobilised on beads such as agarose beads. Typically this may be achieved by expressing the ELABELA polypeptide as a GST-fusion protein in bacteria, yeast or higher eukaryotic cell lines and purifying the GST-ELABELA fusion protein from crude cell extracts using glutathione-agarose beads (Smith and Johnson, 1988; *Gene* 67(10):31-40). As a control, binding of the candidate substance, which is not a GST-fusion protein, to an immobilised polypeptide may be determined in the absence of the ELABELA polypeptide. The binding of the candidate substance to the immobilised ELABELA polypeptide may then be determined. This type of assay is known in the art as a GST pulldown assay. Again, the candidate substance may be immobilised and the ELABELA polypeptide non-immobilised.

It is also possible to perform this type of assay using different affinity purification systems for immobilising one of the components, for example Ni-NTA agarose, histidine-tagged components as well as antibody-based affinity chromatography.

Binding of the polypeptide to the candidate substance may be determined by a variety of methods well-known in the art. For example, the non-immobilised component may be labeled (with for example, a radioactive label, an epitope tag or an enzyme-antibody conjugate). Alternatively, binding may be determined by immunological detection techniques. For example, the reaction mixture can be Western blotted and the blot probed with an antibody that detects the non-immobilised component. ELISA techniques may also be used.

Candidate substances are typically added to a final concentration of from 1 to 1000 nmol/ml, such as from 1 to 100 nmol/ml. In the case of antibodies, the final concentration used is typically from 100 to 500 µg/ml, such as from 200 to 300 µg/ml.

Modulators and antagonists of ELABELA may also be identified by detecting modulation of binding between ELA- BELA and any molecule to which this polypeptide binds, or modulation of any activity consequential on such binding or release.

Cell Based Assays

A cell based assay may simply test binding of a candidate compound wherein adherence to the cells bearing the ELABELA polypeptide is detected by means of a label directly or indirectly associated with the candidate compound or in an assay involving competition with a labelled competitor.

Further, these assays may test whether the candidate compound results in a signal generated by binding to the ELABELA polypeptide, using detection systems appropriate to the cells bearing the polypeptides at their surfaces. Inhibitors of activation are generally assayed in the presence of a known agonist and the effect on activation by the agonist by the presence of the candidate compound is observed.

Another method of screening compounds utilises eukaryotic or prokaryotic host cells which are stably transformed with recombinant DNA molecules expressing a library of compounds. Such cells, either in viable or fixed form, can be used for standard binding-partner assays. See also Parce et al. (1989) Science 246:243-247; and Owicki et al. (1990) Proc. Nat'l Acad. Sci. USA 87; 4007-4011, which describe sensitive methods to detect cellular responses.

Competitive assays are particularly useful, where the cells expressing the library of compounds are contacted or incubated with a labelled antibody known to bind to an ELABELA polypeptide, such as $^{125}$I-antibody, and a test sample such as a candidate compound whose binding affinity to the binding composition is being measured. The bound and free labelled binding partners for the ELABELA polypeptide are then separated to assess the degree of binding. The amount of test sample bound is inversely proportional to the amount of labelled antibody binding to the ELABELA polypeptide.

Any one of numerous techniques can be used to separate bound from free binding partners to assess the degree of binding. This separation step could typically involve a procedure such as adhesion to filters followed by washing, adhesion to plastic following by washing, or centrifugation of the cell membranes.

The assays may involve exposing a candidate molecule to a cell, such as a colon, lung, squamous cell including lip, larynx, vulva, cervix and penis, pancreatic, brain, oesophageal, stomach, bladder, kidney, skin, ovary, prostate and testicular cell, and assaying expression of ELABELA by any suitable means. Molecules which down-regulate the expression of ELABELA in such assays may be optionally chosen for further study, and used as drugs to down-regulate ELABELA expression. Such drugs may be usefully employed to treat or prevent an ELABELA associated condition.

cDNA encoding ELABELA protein and antibodies to the proteins may also be used to configure assays for detecting the effect of added compounds on the production of ELABELA mRNA and protein in cells. For example, an ELISA may be constructed for measuring secreted or cell associated levels of ELABELA polypeptide using monoclonal and polyclonal antibodies by standard methods known in the art, and this can be used to discover agents which may inhibit or enhance the production of ELABELA protein (also called antagonist or agonist, respectively) from suitably manipulated cells or tissues. Standard methods for conducting screening assays are well understood in the art.

Activity Assays

Assays to detect modulators or antagonists typically involve detecting modulation of any activity of ELABELA, in the presence, optionally together with detection of modulation of activity in the absence, of a candidate molecule.

Assays which detect specific biological activities of ELABELA, such as phosphatase activity, may be used. The assays typically involve contacting a candidate molecule (e.g., in the form of a library) with ELABELA whether in the form of a polypeptide, a nucleic acid encoding the polypeptide, or a cell, organelle, extract, or other material comprising such, with a candidate modulator. The relevant activity of ELABELA (such as phosphatase activity, as described elsewhere in this document) may be detected, to establish whether the presence of the candidate modulator has any effect.

Phosphatase assays are known in the art and are described in Wu et al (2004), Int J Biochem Cell Biol. 36(8):1542-53 and Alonso et al (2004). J Biol Chem. 20; 279(34):35768-74. Such assays comprise assaying the ability of ELABELA to de-phosphorylate a suitable substrate such as p-nitrophenyl phosphate, or as oligopeptides containing phospho-tyrosine and phospho-threonine residues. The assays may be performed in the presence or absence of a candidate modulator and the appropriate activity detected to detect modulation of ELABELA activity and hence identification of a candidate modulator and/or antagonist of ELABELA.

Promoter binding assays to detect candidate modulators which bind to and/or affect the transcription or expression of ELABELA may also be used. Candidate modulators may then be chosen for further study, or isolated for use. Details of such screening procedures are well known in the art, and are for example described in, *Handbook of Drug Screening*, edited by Ramakrishna Seethala, Prabhavathi B. Fernandes (2001, New York, N.Y., Marcel Dekker, ISBN 0-8247-0562-9).

The screening methods described here may employ in vivo assays, although they may be configured for in vitro use. In vivo assays generally involve exposing a cell comprising ELABELA to the candidate molecule. In in vitro assays, ELABELA is exposed to the candidate molecule, optionally in the presence of other components, such as crude or semi-purified cell extract, or purified proteins. Where in vitro assays are conducted, these may employ arrays of candidate molecules (for example, an arrayed library). In vivo assays may be employed. Therefore, the ELABELA polypeptide may be comprised in a cell, such as heterologously. Such a cell may be a transgenic cell, which has been engineered to express ELABELA as described above.

Where an extract is employed, it may comprise a cytoplasmic extract or a nuclear extract, methods of preparation of which are well known in the art.

It will be appreciated that any component of a cell comprising ELABELA may be employed, such as an organelle. One embodiment utilises a cytoplasmic or nuclear preparation, e.g., comprising a cell nucleus which comprises ELABELA as described. The nuclear preparation may comprise one or more nuclei, which may be permeabilised or semi-permeabilised, by detergent treatment, for example.

Thus, in a specific embodiment, an assay format may include the following: a multiwell microtitre plate is set up to include one or more cells expressing ELABELA polypeptide in each well; individual candidate molecules, or pools of candidate molecules, derived for example from a library, may be added to individual wells and modulation of ELABELA activity measured. Where pools are used, these may be subdivided in to further pools and tested in the same manner. ELABELA activity, for example binding activity or transcriptional co-activation activity, as described elsewhere in this document may then be assayed.

Alternatively or in addition to the assay methods described above, "subtractive" procedures may also be used to identify modulators or antagonists of ELABELA. Under such "subtractive" procedures, a plurality of molecules is provided, which comprises one or more candidate molecules capable of functioning as a modulator (e.g., cell extract, nuclear extract, library of molecules, etc), and one or more components is removed, depleted or subtracted from the plurality of molecules. The "subtracted" extract, etc, is then assayed for activity, by exposure to a cell comprising ELABELA (or a component thereof) as described.

Thus, for example, an 'immunodepletion' assay may be conducted to identify such modulators as follows. A cytoplasmic or nuclear extract may be prepared from a suitable cell. The extract may be depleted or fractionated to remove putative modulators, such as by use of immunodepletion with appropriate antibodies. If the extract is depleted of a modulator, it will lose the ability to affect ELABELA function or activity or expression. A series of subtractions and/or depletions may be required to identify the modulators or antagonists.

It will also be appreciated that the above "depletion" or "subtraction" assay may be used as a preliminary step to identify putative modulatory factors for further screening. Furthermore, or alternatively, the "depletion" or "subtraction" assay may be used to confirm the modulatory activity of a molecule identified by other means (for example, a "positive" screen as described elsewhere in this document) as a putative modulator.

Candidate molecules subjected to the assay and which are found to be of interest may be isolated and further studied. Methods of isolation of molecules of interest will depend on the type of molecule employed, whether it is in the form of a library, how many candidate molecules are being tested at any one time, whether a batch procedure is being followed, etc.

The candidate molecules may be provided in the form of a library. In one embodiment, more than one candidate molecule may be screened simultaneously. A library of candidate molecules may be generated, for example, a small molecule library, a polypeptide library, a nucleic acid library, a library of compounds (such as a combinatorial library), a library of antisense molecules such as antisense DNA or antisense RNA, an antibody library etc, by means known in the art. Such libraries are suitable for high-throughput screening. Different cells comprising ELABELA may be exposed to individual members of the library, and effect on the ELABELA activity determined. Array technology may be employed for this purpose. The cells may be spatially separated, for example, in wells of a microtitre plate.

In an embodiment, a small molecule library is employed. By a "small molecule", we refer to a molecule whose molecular weight may be less than about 50 kDa. In particular embodiments, a small molecule may have a molecular weight which is less than about 30 kDa, such as less than about 15 kDa or less than 10 kDa or so. Libraries of such small molecules, here referred to as "small molecule libraries" may contain polypeptides, small peptides, for example, peptides of 20 amino acids or fewer, for example, 15, 10 or 5 amino acids, simple compounds, etc.

Alternatively or in addition, a combinatorial library, as described in further detail elsewhere in this document, may be screened for modulators or antagonists of ELABELA. Assays for ELABELA activity are described above.

Libraries

Libraries of candidate molecules, such as libraries of polypeptides or nucleic acids, may be employed in the screens for ELABELA antagonists and inhibitors described here. Such libraries are exposed to ELABELA protein, and their effect, if any, on the activity of the protein determined.

Selection protocols for isolating desired members of large libraries are known in the art, as typified by phage display techniques. Such systems, in which diverse peptide sequences are displayed on the surface of filamentous bacteriophage (Scott and Smith (1990 supra), have proven useful for creating libraries of antibody fragments (and the nucleotide sequences that encoding them) for the in vitro selection and amplification of specific antibody fragments that bind a target antigen. The nucleotide sequences encoding the $V_H$ and VI, regions are linked to gene fragments which encode leader signals that direct them to the periplasmic space of E. coli and as a result the resultant antibody fragments are displayed on the surface of the bacteriophage, typically as fusions to bacteriophage coat proteins (e.g., pIII or pVIII). Alternatively, antibody fragments are displayed externally on lambda phage capsids (phagebodies). An advantage of phage-based display systems is that, because they are biological systems, selected library members can be amplified simply by growing the phage containing the selected library member in bacterial cells. Furthermore, since the nucleotide sequence that encodes the polypeptide library member is contained on a phage or phagemid vector, sequencing, expression and subsequent genetic manipulation is relatively straightforward.

Methods for the construction of bacteriophage antibody display libraries and lambda phage expression libraries are well known in the art (McCafferty et al. (1990) supra; Kang et al. (1991) Proc. Natl. Acad. Sci. U.S.A., 88: 4363; Clackson et al. (1991) Nature, 352: 624; Lowman et al. (1991) Biochemistry, 30: 10832; Burton et al. (1991) Proc. Natl. Acad. Sci U.S.A., 88: 10134; Hoogenboom et al. (1991) Nucleic Acids Res., 19: 4133; Chang et al. (1991) J Immunol., 147: 3610; Breitling et al. (1991) Gene, 104: 147; Marks et al. (1991) supra; Barbas et al. (1992) supra; Hawkins and Winter (1992) J. Immunol., 22: 867; Marks et al., 1992, J Biol. Chem., 267: 16007; Lerner et al. (1992) Science, 258: 1313, incorporated herein by reference). Such techniques may be modified if necessary for the expression generally of polypeptide libraries.

One approach has been the use of scFv phage-libraries (Bird, R. E., et al. (1988) Science 242: 423-6, Huston et al., 1988, Proc. Natl. Acad. Sci U.S.A., 85: 5879-5883; Chaudhary et al. (1990) Proc. Natl. Acad. Sci U.S.A., 87: 1066-1070; McCafferty et al. (1990) supra; Clackson et al. (1991) supra; Marks et al. (1991) supra; Chiswell et al. (1992) Trends Biotech., 10: 80; Marks et al. (1992) supra). Various embodiments of scFv libraries displayed on bacteriophage coat proteins have been described. Refinements of phage display approaches are also known, for example as described in WO96/06213 and WO92/01047 (Medical Research Council et al.) and WO97/08320 (Morphosys, supra), which are incorporated herein by reference.

Alternative library selection technologies include bacteriophage lambda expression systems, which may be screened directly as bacteriophage plaques or as colonies of lysogens, both as previously described (Huse et al. (1989) Science, 246: 1275; Caton and Koprowski (1990) Proc. Natl. Acad. Sci. U.S.A., 87; Mullinax et al. (1990) Proc. Natl. Acad. Sci. U.S.A., 87: 8095; Persson et al. (1991) Proc. Natl. Acad. Sci. U.S.A., 88: 2432) and are of use in the methods and compositions described here. These systems may be used to screen a large number of different members of a library, in the order of about $10^6$ or even more. Other screening systems rely, for example, on direct chemical synthesis of library members. One early method involves the synthesis of peptides on a set of pins or rods, such as described in WO84/03564. A similar method involving peptide synthesis on beads, which forms a peptide library in which each bead is an individual library member, is described in U.S. Pat. No. 4,631,211 and a related method is described in WO92/00091. A significant improvement of the bead-based methods involves tagging each bead with a unique identifier tag, such as an oligonucleotide, so as to facilitate identification of the amino acid sequence of each library member. These improved bead-based methods are described in WO93/06121.

Another chemical synthesis method involves the synthesis of arrays of peptides (or peptidomimetics) on a surface in a manner that places each distinct library member (e.g., unique peptide sequence) at a discrete, predefined location in the array. The identity of each library member is determined by its spatial location in the array. The locations in the array where binding interactions between a predetermined molecule (e.g., a receptor) and reactive library members occur is determined, thereby identifying the sequences of the reactive library members on the basis of spatial location. These methods are described in U.S. Pat. No. 5,143,854; WO90/15070 and WO92/10092; Fodor et al. (1991) *Science*, 251: 767; Dower and Fodor (1991) *Ann. Rep. Med. Chem.*, 26: 271.

Other systems for generating libraries of polypeptides or nucleotides involve the use of cell-free enzymatic machinery for the in vitro synthesis of the library members. In one method, RNA molecules are selected by alternate rounds of selection against a target ligand and PCR amplification (Tuerk and Gold (1990) *Science*, 249: 505; Ellington and Szostak (1990) *Nature*, 346: 818). A similar technique may be used to identify DNA sequences which bind a predetermined human transcription factor (Thiesen and Bach (1990) *Nucleic Acids Res.*, 18: 3203; Beaudry and Joyce (1992) *Science*, 257: 635; WO92/05258 and WO92/14843). In a similar way, in vitro translation can be used to synthesise polypeptides as a method for generating large libraries. These methods which generally comprise stabilised polysome complexes, are described further in WO88/08453, WO90/05785, WO90/07003, WO91/02076, WO91/05058, and WO92/02536. Alternative display systems which are not phage-based, such as those disclosed in WO95/22625 and WO95/11922 (Affymax) use the polysomes to display polypeptides for selection. These and all the foregoing documents also are incorporated herein by reference.

Combinatorial Libraries

Libraries, in particular, libraries of candidate molecules, may suitably be in the form of combinatorial libraries (also known as combinatorial chemical libraries).

A "combinatorial library", as the term is used in this document, is a collection of multiple species of chemical compounds that consist of randomly selected subunits. Combinatorial libraries may be screened for molecules which are capable of inhibiting ELABELA.

Various combinatorial libraries of chemical compounds are currently available, including libraries active against proteolytic and non-proteolytic enzymes, libraries of agonists and antagonists of G-protein coupled receptors (GP-CRs), libraries active against non-GPCR targets (e.g., integrins, ion channels, domain interactions, nuclear receptors, and transcription factors) and libraries of whole-cell oncology and anti-infective targets, among others. A comprehensive review of combinatorial libraries, in particular their construction and uses is provided in Dolle and Nelson (1999), *Journal of Combinatorial Chemistry*, Vol 1 No 4, 235-282. Reference is also made to Combinatorial peptide library protocols (edited by Shmuel Cabilly, Totowa, N.J.: Humana Press, c1998. *Methods in Molecular Biology* v. 87). Specific combinatorial libraries and methods for their construction are disclosed in U.S. Pat. No. 6,168,914 (Campbell, et al), as well as in Baldwin et al. (1995), "Synthesis of a Small Molecule Library Encoded with Molecular Tags," J. Am. Chem. Soc. 117:5588-5589, and in the references mentioned in those documents.

In one embodiment, the combinatorial library which is screened is one which is designed to potentially include molecules which interact with a component of the cell to influence gene expression. For example, combinatorial libraries against chromatin structural proteins may be screened. Other libraries which are useful for this embodiment include combinatorial libraries against histone modification enzymes (e.g., histone acetylation or histone methylation enzymes), or DNA modification, for example, DNA methylation or demethylation.

Further references describing chemical combinatorial libraries, their production and use include those available from the URL http://www.netsci.org/Science/Combichem/, including The Chemical Generation of Molecular Diversity. Michael R. Pavia, Sphinx Pharmaceuticals, A Division of Eli Lilly (Published July, 1995); Combinatorial Chemistry: A Strategy for the Future—MDL Information Systems discusses the role its Project Library plays in managing diversity libraries (Published July, 1995); Solid Support Combinatorial Chemistry in Lead Discovery and SAR Optimization, Adnan M. M. Mjalli and Barry E. Toyonaga, Ontogen Corporation (Published July, 1995); Non-Peptidic Bradykinin Receptor Antagonists From a Structurally Directed Non-Peptide Library. Sarvajit Chakravarty, Babu J. Mavunkel, Robin Andy, Donald J. Kyle*, Scios Nova Inc. (Published July, 1995); Combinatorial Chemistry Library Design using Pharmacophore Diversity Keith Davies and Clive Briant, Chemical Design Ltd. (Published July, 1995); A Database System for Combinatorial Synthesis Experiments—Craig James and David Weininger, Daylight Chemical Information Systems, Inc. (Published July, 1995); An Information Management Architecture for Combinatorial Chemistry, Keith Davies and Catherine White, Chemical Design Ltd. (Published July, 1995); Novel Software Tools for Addressing Chemical Diversity, R. S. Pearlman, Laboratory for Molecular Graphics and Theoretical Modeling, College of Pharmacy, University of Texas (Published June/July, 1996); Opportunities for Computational Chemists Afforded by the New Strategies in Drug Discovery: An Opinion, Yvonne Connolly Martin, Computer Assisted Molecular Design Project, Abbott Laboratories (Published June/July, 1996); Combinatorial Chemistry and Molecular Diversity Course at the University of Louisville: A Description, Arno F. Spatola, Department of Chemistry, University of Louisville (Published June/July, 1996); Chemically Generated Screening Libraries: Present and Future. Michael R. Pavia, Sphinx Pharmaceuticals, A Division of Eli Lilly (Published June/July, 1996); Chemical Strategies For Introducing Carbohydrate Molecular Diversity Into The Drug Discovery Process. Michael J. Sofia, Transcell Technologies Inc. (Published June/July, 1996); Data Management for Combinatorial Chemistry. Maryjo Zaborowski, Chiron Corporation and Sheila H. DeWitt, Parke-Davis Pharmaceutical Research, Division of Warner-Lambert Company (Published November, 1995); and The Impact of High Throughput Organic Synthesis on R&D in Bio-Based Industries, John P. Devlin (Published March, 1996).

Techniques in combinatorial chemistry are gaining wide acceptance among modern methods for the generation of new pharmaceutical leads (Gallop, M. A. et al., 1994, J. Med. Chem. 37:1233-1251; Gordon, E. M. et al., 1994, J. Med. Chem. 37:1385-1401.). One combinatorial approach in use is based on a strategy involving the synthesis of libraries containing a different structure on each particle of the solid phase support, interaction of the library with a soluble receptor, identification of the 'bead' which interacts with the macromolecular target, and determination of the structure carried by the identified 'bead' (Lam, K. S. et al., 1991, Nature 354:82-84). An alternative to this approach is the sequential release of defined aliquots of the compounds from the solid support, with subsequent determination of activity in solution, identification of the particle from which the active compound was released, and elucidation of its structure by direct sequencing (Salmon, S. E. et al., 1993, Proc. Natl. Acad. Sci. USA 90:11708-11712), or by reading its code (Kerr, J. M. et al., 1993, J. Am. Chem. Soc. 115:2529-2531; Nikolaiev, V. et al., 1993, Pept. Res. 6:161-170; Ohlmeyer, M. H. J. et al., 1993, Proc. Natl. Acad. Sci. USA 90:10922-10926).

Soluble random combinatorial libraries may be synthesized using a simple principle for the generation of equimolar mixtures of peptides which was first described by Furka (Furka, A. et al., 1988, Xth International Symposium on Medicinal Chemistry, Budapest 1988; Furka, A. et al., 1988, 14th International Congress of Biochemistry, Prague 1988; Furka, A. et al., 1991, Int. J. Peptide Protein Res. 37:487-493). The construction of soluble libraries for iterative screening has also been described (Houghten, R. A. et al. 1991, Nature 354:84-86). K. S. Lam disclosed the novel and unexpectedly powerful technique of using insoluble random combinatorial libraries. Lam synthesized random combinatorial libraries on solid phase supports, so that each support had a test compound of uniform molecular structure, and screened the libraries without prior removal of the test compounds from the support by solid phase binding protocols (Lam, K. S. et al., 1991, Nature 354:82-84).

Thus, a library of candidate molecules may be a synthetic combinatorial library (e.g., a combinatorial chemical library), a cellular extract, a bodily fluid (e.g., urine, blood, tears, sweat, or saliva), or other mixture of synthetic or natural products (e.g., a library of small molecules or a fermentation mixture).

A library of molecules may include, for example, amino acids, oligopeptides, polypeptides, proteins, or fragments of peptides or proteins; nucleic acids (e.g., antisense; DNA; RNA; or peptide nucleic acids, PNA); aptamers; or carbohydrates or polysaccharides. Each member of the library can be singular or can be a part of a mixture (e.g., a compressed library). The library may contain purified compounds or can be "dirty" (i.e., containing a significant quantity of impurities).

Commercially available libraries (e.g., from Affymetrix, ArQule, Neose Technologies, Sarco, Ciddco, Oxford Asymmetry, Maybridge, Aldrich, Panlabs, Pharmacopoeia, Sigma, or Tripose) may also be used with the methods described here.

In addition to libraries as described above, special libraries called diversity files can be used to assess the specificity, reliability, or reproducibility of the new methods. Diversity files contain a large number of compounds (e.g., 1000 or more small molecules) representative of many classes of compounds that could potentially result in nonspecific detection in an assay. Diversity files are commercially available or can also be assembled from individual compounds commercially available from the vendors listed above.

Antibodies

Anti-ELABELA agents, including antagonists or modulators of ELABELA, which may be used to regulate the activity of this protein (for example, for methods of treating or preventing diseases such as an ELABELA associated condition as described in this document) may include antibodies against the ELABELA protein.

We therefore provide for antibodies which bind to an ELABELA polypeptide, fragment, homologue, variant or derivative thereof. Such antibodies may be useful in detecting ELABELA expression, and in particular in diagnosing an ELABELA associated disease or condition. Other antibodies include those which have therapeutic activity, i.e., which are may be used in a therapeutic manner to treat, manage or prevent any ELABELA associated disease or condition.

An antibody against ELABELA may be generated by any means known in the art, from the ELABELA sequences disclosed in this document.

For example, an anti-ELABELA antibody may be generated against an ELABELA polypeptide as disclosed in this document, or a polypeptide encoded by an ELABELA nucleic acid as disclosed in this document, such as any of the ELABELA sequences set out in the sequence listing.

An antibody against ELABELA may be generated as described in the Examples, by immunisation with a peptide CMPLHSRVPFP (SEQ ID NO: 52) corresponding to amino acid residues (44-54) of human ELABELA.

Antibodies against a polypeptide comprising the sequence MRFQQFLFAFFIFIMSLLLISG (SEQ ID NO: 19) or QRPVNLTMRRKLRKHNC (SEQ ID NO: 53); or a polypeptide comprising the sequence QRPVNLTMRRKLRKHNCLQRRCMPLHSRVPFP (SEQ ID NO: 2) may also be generated as anti-ELABELA antibodies.

Furthermore, antibodies which are specific for ELABELA may be generated against any suitable epitope, for example, an epitope derived from the ELABELA protein. The sequence of a suitable fragment of ELABELA may comprise residues HSRVPFP (SEQ ID NO: 58), RCXXXHSRVPFP (SEQ ID NO: 59) or CXXXRCXXXHSRVPFP (SEQ ID NO: 1) of ELABELA and any epitope from this sequence may be used for the generation of specific ELABELA antibodies.

We therefore disclose isolated antibodies or antigen-binding fragments thereof which are capable of specifically binding to one or more of the following:

(a) a polypeptide comprising the sequence CMPLHSRVPFP (SEQ ID NO: 52);
(b) a polypeptide comprising the sequence QRPVNLTMRRKLRKHNC (SEQ ID NO: 53);
(c) a polypeptide comprising the sequence QRPVNLTMRRKLRKHNCLQRRCMPLHSRVPFP (SEQ ID NO: 2);
(d) a polypeptide comprising the sequence of any of SEQID NOs: 1 to 36.

The isolated antibodies or antigen-binding fragments thereof may further comprise a label, such as a radiolabel, such as $^{125}I$.

For the purposes of this document, the term "antibody" refers to complete antibodies or antibody fragments capable of binding to a selected target. Unless specified to the contrary, the term includes but is not limited to, polyclonal, monoclonal, natural or engineered antibodies including chimeric, CDR-grafted and humanised antibodies, and artificially selected antibodies produced using phage display or alternative techniques. The term also includes single chain, Fab fragments and fragments produced by a Fab expression library. Such fragments include fragments of whole antibodies which retain their binding activity for a target substance, Fv, F(ab') and F(ab')2 fragments, as well as single chain antibodies (scFv), fusion proteins and other synthetic proteins which comprise the antigen-binding site of the antibody. Small fragments, such as Fv and ScFv, possess properties for diagnostic and therapeutic applications on account of their small size and consequent superior tissue distribution.

The antibodies and fragments thereof may be humanised antibodies, for example as described in EP-A-239400. Furthermore, antibodies with fully human variable regions (or their fragments), for example, as described in U.S. Pat. Nos. 5,545,807 and 6,075,181 may also be used.

The anti-ELABELA antibody may comprise a neutralising antibody. Neutralizing antibodies, i.e., those which inhibit any biological activity of ELABELA, may be used for diagnostics and therapeutics.

The antibodies described here may be altered antibodies comprising an effector protein such as a label. Labels which allow the imaging of the distribution of the antibody in vivo or in vitro may be used. Such labels may be radioactive labels or radioopaque labels, such as metal particles, which are readily visualisable within an embryo or a cell mass. Moreover, they may be fluorescent labels or other labels which are visualisable on tissue samples.

Antibodies may be produced by standard techniques, such as by immunisation or by using a phage display library. Such an antibody may be capable of binding specifically to the ELABELA protein or homologue, fragment, etc.

Polyclonal Antibodies

If polyclonal antibodies are desired, a selected mammal or vertebrate species (e.g., chicken, mouse, rabbit, goat, horse, camel etc.) may be immunised with an immunogenic composition comprising an ELABELA polypeptide or peptide. Depending on the host species, various adjuvants may be used to increase immunological response. Such adjuvants include, but are not limited to, Freund's, mineral gels such as aluminium hydroxide, and surface active substances such as lysolecithin, pluronic polyols, polyanions, peptides, oil emulsions, keyhole limpet hemocyanin, and dinitrophenol. BCG (Bacilli Calmette-Guerin) and *Corynebacterium parvum* are potentially useful human adjuvants which may be employed if purified the substance amino acid sequence is administered to immunologically compromised individuals for the purpose of stimulating systemic defence.

Serum from the immunised animal is collected and treated according to known procedures. If serum containing polyclonal antibodies to an epitope obtainable from an ELABELA polypeptide contains antibodies to other antigens, the polyclonal antibodies can be purified by immunoaffinity chromatography. Techniques for producing and processing polyclonal antisera are known in the art. In order that such antibodies may be made, we also provide ELABELA amino acid sequences or fragments thereof haptenised to another amino acid sequence for use as immunogens in animals or humans.

Monoclonal Antibodies

Monoclonal antibodies directed against epitopes obtainable from an ELABELA polypeptide or peptide can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against orbit epitopes can be screened for various properties; i.e., for isotype and epitope affinity.

Monoclonal antibodies may be prepared using any technique which provides for the production of antibody molecules by continuous cell lines in culture. These include, but are not limited to, the hybridoma technique originally described by Koehler and Milstein (1975 Nature 256:495-497), the trioma technique, the human B-cell hybridoma technique (Kosbor et al (1983) Immunol Today 4:72; Cote et al (1983) Proc Natl Acad Sci 80:2026-2030) and the EBV-hybridoma technique (Cole et al., *Monoclonal Antibodies and Cancer Therapy*, pp. 77-96, Alan R. Liss, Inc., 1985).

Recombinant DNA technology may be used to improve the antibodies as described here. Thus, chimeric antibodies may be constructed in order to decrease the immunogenicity thereof in diagnostic or therapeutic applications. Such techniques comprise splicing of mouse antibody genes to human antibody genes to obtain a molecule with appropriate antigen specificity and biological activity (Morrison et al (1984) Proc Natl Acad Sci 81:6851-6855; Neuberger et al (1984) Nature 312:604-608; Takeda et al (1985) Nature 314:452-454). Moreover, immunogenicity may be minimised by humanising the antibodies by CDR grafting [see European Patent Application 0 239 400 (Winter)] and, optionally, framework modification [EP 0 239 400].

Alternatively, techniques described for the production of single chain antibodies (U.S. Pat. No. 4,946,779) can be adapted to produce the substance specific single chain antibodies.

Antibodies, both monoclonal and polyclonal, which are directed against epitopes obtainable from an ELABELA polypeptide or peptide are particularly useful in diagnosis. Monoclonal antibodies, in particular, may be used to raise anti-idiotype antibodies. Anti-idiotype antibodies are immunoglobulins which carry an "internal image" of the substance and/or agent against which protection is desired. Techniques for raising anti-idiotype antibodies are known in the art. These anti-idiotype antibodies may also be useful in therapy.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833-3837), and Winter G and Milstein C (1991; Nature 349:293-299).

Antibody fragments which contain specific binding sites for the polypeptide or peptide may also be generated. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse W D et al (1989) Science 256:1275-1281).

Techniques for the production of single chain antibodies (U.S. Pat. No. 4,946,778) can also be adapted to produce single chain antibodies to ELABELA polypeptides. Also, transgenic mice, or other organisms including other mammals, may be used to express humanized antibodies.

The above-described antibodies may be employed to isolate or to identify clones expressing the polypeptide or to purify the polypeptides by affinity chromatography.

Recombinant Techniques of Antibody Production

Recombinant DNA technology may be used to produce the antibodies according to established procedure, in bacterial or mammalian cell culture. The selected cell culture system may secrete the antibody product.

Therefore, we disclose a process for the production of an antibody comprising culturing a host, e.g. *E. coli* or a mammalian cell, which has been transformed with a hybrid vector comprising an expression cassette comprising a promoter operably linked to a first DNA sequence encoding a signal peptide linked in the proper reading frame to a second DNA sequence encoding said antibody protein, and isolating said protein.

Multiplication of hybridoma cells or mammalian host cells in vitro is carried out in suitable culture media, which are the customary standard culture media, for example Dulbecco's Modified Eagle Medium (DMEM) or RPMI 1640 medium, optionally replenished by a mammalian serum, e.g. foetal calf serum, or trace elements and growth sustaining supplements, e.g. feeder cells such as normal mouse peritoneal exudate cells, spleen cells, bone marrow macrophages, 2-aminoethanol, insulin, transferrin, low density lipoprotein, oleic acid, or the like. Multiplication of host cells which are bacterial cells or yeast cells is likewise carried out in suitable culture media known in the art, for example for bacteria in medium LB, NZCYM, NZYM, NZM, Terrific Broth, SOB, SOC, 2×YT, or M9 Minimal Medium, and for yeast in medium YPD, YEPD, Minimal Medium, or Complete Minimal Dropout Medium.

In vitro production provides relatively pure antibody preparations and allows scale-up to give large amounts of the desired antibodies. Techniques for bacterial cell, yeast or mammalian cell cultivation are known in the art and include homogeneous suspension culture, e.g. in an airlift reactor or in a continuous stirrer reactor, or immobilised or entrapped cell culture, e.g. in hollow fibres, microcapsules, on agarose microbeads or ceramic cartridges.

Large quantities of the desired antibodies can also be obtained by multiplying mammalian cells in vivo. For this purpose, hybridoma cells producing the desired antibodies are injected into histocompatible mammals to cause growth of antibody-producing tumours. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane, and, after one to two weeks, ascitic fluid is taken from the animals.

The foregoing, and other, techniques are discussed in, for example, Kohler and Milstein, (1975) Nature 256:495-497; U.S. Pat. No. 4,376,110; Harlow and Lane, Antibodies: a Laboratory Manual, (1988) Cold Spring Harbor, incorporated herein by reference. Techniques for the preparation of recombinant antibody molecules are described in the above references and also in, for example, EP 0623679; EP 0368684 and EP 0436597, which are incorporated herein by reference.

The cell culture supernatants are screened for the desired antibodies, such as by immunofluorescent staining of PGCs or other pluripotent cells, such as ES or EG cells, by immunoblotting, by an enzyme immunoassay, e.g. a sandwich assay or a dot-assay, or a radioimmunoassay.

For isolation of the antibodies, the immunoglobulins in the culture supernatants or in the ascitic fluid may be concentrated, e.g. by precipitation with ammonium sulphate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-) affinity chromatography, e.g. affinity chromatography with the antigen, or fragments thereof, or with Protein-A.

Hybridoma cells secreting the monoclonal antibodies are also provided. Hybridoma cells may be genetically stable, secrete monoclonal antibodies of the desired specificity and can be activated from deep-frozen cultures by thawing and recloning.

Also included is a process for the preparation of a hybridoma cell line secreting monoclonal antibodies directed to the ELABELA polypeptide, characterised in that a suitable mammal, for example a Balb/c mouse, is immunised with a one or more ELABELA polypeptides, or antigenic fragments thereof; antibody-producing cells of the immunised mammal are fused with cells of a suitable myeloma cell line, the hybrid cells obtained in the fusion are cloned, and cell clones secreting the desired antibodies are selected. For example spleen cells of Balb/c mice immunised with ELABELA are fused with cells of the myeloma cell line PAI or the myeloma cell line Sp2/0-Ag14, the obtained hybrid cells are screened for secretion of the desired antibodies, and positive hybridoma cells are cloned.

We describe a process for the preparation of a hybridoma cell line, characterised in that Balb/c mice are immunised by injecting subcutaneously and/or intraperitoneally between 10 and $10^7$ and $10^8$ cells expressing ELABELA and a suitable adjuvant several times, e.g. four to six times, over several months, e.g. between two and four months, and spleen cells from the immunised mice are taken two to four days after the last injection and fused with cells of the myeloma cell line PAI in the presence of a fusion promoter, such as polyethylene glycol. The myeloma cells may be fused with a three- to twentyfold excess of spleen cells from the immunised mice in a solution containing about 30% to about 50% polyethylene glycol of a molecular weight around 4000. After the fusion the cells are expanded in suitable culture media as described hereinbefore, supplemented with a selection medium, for example HAT medium, at regular intervals in order to prevent normal myeloma cells from overgrowing the desired hybridoma cells.

Recombinant DNAs comprising an insert coding for a heavy chain variable domain and/or for a light chain variable domain of antibodies directed to ELABELA as described hereinbefore are also disclosed. By definition such DNAs comprise coding single stranded DNAs, double stranded DNAs consisting of said coding DNAs and of complementary DNAs thereto, or these complementary (single stranded) DNAs themselves.

Furthermore, DNA encoding a heavy chain variable domain and/or for a light chain variable domain of antibodies directed to ELABELA can be enzymatically or chemically synthesised DNA having the authentic DNA sequence coding for a heavy chain variable domain and/or for the light chain variable domain, or a mutant thereof. A mutant of the authentic DNA is a DNA encoding a heavy chain variable domain and/or a light chain variable domain of the above-mentioned antibodies in which one or more amino acids are deleted or exchanged with one or more other amino acids. The modification(s) may be outside the CDRs of the heavy chain variable domain and/or of the light chain variable domain of the antibody. Such a mutant DNA is also intended to be a silent mutant wherein one or more nucleotides are replaced by other nucleotides with the new codons coding for the same amino acid(s). Such a mutant sequence is also a degenerated sequence. Degenerated sequences are degenerated within the meaning of the genetic code in that an unlimited number of nucleotides are replaced by other nucleotides without resulting in a change of the amino acid sequence originally encoded. Such degenerated sequences may be useful due to their different restriction sites and/or frequency of particular codons which are preferred by the specific host, particularly E. coli, to obtain an optimal expression of the heavy chain murine variable domain and/or a light chain murine variable domain.

The term mutant is intended to include a DNA mutant obtained by in vitro mutagenesis of the authentic DNA according to methods known in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

Also disclosed are recombinant DNAs comprising an insert coding for a heavy chain murine variable domain of an antibody directed to ELABELA fused to a human constant domain g, for example γ1, γ2, γ3 or γ4, such as γ1 or γ4. Likewise recombinant DNAs comprising an insert coding for a light chain murine variable domain of an antibody directed to ELABELA fused to a human constant domain κ or λ, such as κ are also disclosed.

In another embodiment, we disclose recombinant DNAs coding for a recombinant polypeptide wherein the heavy chain variable domain and the light chain variable domain are linked by way of a spacer group, optionally comprising a signal sequence facilitating the processing of the antibody in the host cell and/or a DNA coding for a peptide facilitating the purification of the antibody and/or a cleavage site and/or a peptide spacer and/or an effector molecule.

The DNA coding for an effector molecule is intended to be a DNA coding for the effector molecules useful in diagnostic or therapeutic applications. Thus, effector molecules which are toxins or enzymes, especially enzymes capable of catalysing the activation of prodrugs, are particularly indicated. The DNA encoding such an effector molecule has the sequence of a naturally occurring enzyme or toxin encoding DNA, or a mutant thereof, and can be prepared by methods well known in the art.

Antibodies

The terms "antibody" and "immunoglobulin", as used in this document, may be employed interchangeably where the context permits. These terms include fragments of proteolytically-cleaved or recombinantly-prepared portions of an antibody molecule that are capable of selectively reacting with or recognising ELABELA or an epitope thereof, such as an epitope of ELABELA bound by 209.

Non limiting examples of such proteolytic and/or recombinant fragments include Fab, F(ab')2, Fab', Fv fragments, and single chain antibodies (scFv) containing a VL and VH domain joined by a peptide linker. These Fvs may be covalently or non-covalently linked to form antibodies having two or more binding sites.

By "ScFv molecules" we mean molecules wherein the VH and VL partner domains are linked via a flexible oligopeptide. A general review of the techniques involved in the synthesis of antibody fragments which retain their specific binding sites is to be found in Winter & Milstein (1991) Nature 349, 293-299.

Whole antibodies, and F(ab')2 fragments are "bivalent". By "bivalent" we mean that the said antibodies and F(ab') fragments have two antigen combining sites. In contrast, Fab, Fv, ScFv and dAb fragments are monovalent having only one antigen combining site.

The anti-ELABELA antibody may comprise a high affinity antibody with an off rate from $10^{-2}$ s$^{-1}$ to $10^{-4}$ s$^{-1}$. The off rate may be about $2\times10^{-4}$ s$^1$.

The term "off-rate" as used in this document refers to the dissociation rate ($k_{off}$) of an antibody such as an anti-ELABELA antibody disclosed here. It may be measured using BIA evaluation software (Pharmacia). A low off rate is desirable as it reflects the affinity of an Fab fragment for an antigen.

The term "affinity" is defined in terms of the dissociation rate or off-rate ($k_{off}$) of an antibody such as an anti-ELABELA antibody. The lower the off-rate the higher the affinity that a an antibody such as an anti-ELABELA antibody has for an antigen such as ELABELA.

The anti-ELABELA antibody may comprise a peptide per se or form part of a fusion protein.

The anti-ELABELA antibodies described here include any antibody that comprise ELABELA binding activity, such as binding ability to intracellular ELABELA or binding to the same epitope bound by 209 as the case may be.

The anti-ELABELA antibodies also include the entire or whole antibody, whether mouse, humanised or human, such antibody derivatives and biologically-active fragments. These may include antibody fragments with ELABELA binding activity that have amino acid substitutions or have sugars or other molecules attached to amino acid functional groups, etc.

The anti-ELABELA antibody may comprise isolated antibody or purified antibody. It may be obtainable from or produced by any suitable source, whether natural or not, or it may be a synthetic anti-ELABELA antibody, a semi-synthetic anti-ELABELA antibody, a derivatised anti-ELABELA antibody or a recombinant anti-ELABELA antibody.

Where the anti-ELABELA antibody is a non-native anti-ELABELA antibody, it may include at least a portion of which has been prepared by recombinant DNA techniques or an anti-ELABELA antibody produced by chemical synthesis techniques or combinations thereof.

The term "derivative" as used in this document includes chemical modification of an anti-ELABELA antibody. Illustrative of such modifications would be replacement of hydrogen by an alkyl, acyl, or amino group, for example. The sequence of the anti-ELABELA antibody may be the same as that of the naturally occurring form or it may be a variant, homologue, fragment or derivative thereof.

Antibody Variable Regions

The term "variable region", as used in this document, refers to the variable regions, or domains, of the light chains (VL) and heavy chains (VH) which contain the determinants for binding recognition specificity and for the overall affinity of the antibody against ELABELA (or variant, homologue, fragment or derivative), as the case may be.

The variable domains of each pair of light (VL) and heavy chains (VH) are involved in antigen recognition and form the antigen binding site. The domains of the light and heavy chains have the same general structure and each domain has four framework (FR) regions, whose sequences are relatively conserved, connected by three complementarity determining regions (CDRs). The FR regions maintain the structural integrity of the variable domain. The CDRs are the polypeptide segments within the variable domain that mediate binding of the antigen.

The term "constant region", as used in this document, refers to the domains of the light (CL) and heavy (CH) chain of the antibody (or variant, homologue, fragment or derivative) which provide structural stability and other biological functions such as antibody chain association, secretion, transplacental mobility, and complement binding, but which are not involved with binding an ELABELA epitope. The amino acid sequence and corresponding exon sequences in the genes of the constant region will be dependent upon the species from which it is derived. However, variations in the amino acid sequence leading to allotypes are relatively limited for particular constant regions within a species. An "allotype" is an antigenic determinant (or epitope) that distinguishes allelic genes.

The variable region of each chain is joined to the constant region by a linking polypeptide sequence. The linkage sequence is coded by a "J" sequence in the light chain gene, and a combination of a "D" sequence and a "J" sequence in the heavy chain gene.

Antibody: Variable Region Sequences

Anti-ELABELA antibodies, according to the methods and compositions described here, may be generated from these variable region sequences by methods known in the art. For example, the heavy and light chain sequences may be recombined into a constant sequence for a chosen antibody, through recombinant genetic engineering techniques which are known to the skilled person.

Constant region sequences are known in the art, and are available from a number of databases, such as the IMGT/LIGM-DB database (described in Giudicelli et al, 2006, Nucleic Acids Research 34(Database Issue):D781-D784 and LeFranc et al (1995) *LIGM-DB/IMGT: An Integrated Database of Ig and TcR, Part of the Immunogenetics Database*. Annals of the New York Academy of Sciences 764 (1), 47-47 doi:10.1111/j.1749-6632.1995.tb55805.x) and the IMGT/GENE-DB database (described in Giudicelli et al, 2005, Nucleic Acids Res. 2005 Jan. 1; 33(Database issue): D256-61). IMGT/LIGM-DB and IMGT/GENE-DB are part of the ImMunoGeneTics Database located at www.ebi.ac.uk/imgt/.

Methods for combining variable regions with given sequences and constant regions to produce whole antibodies are known in the art and are described for example in Example 16 and in Hanson et al., (2006). *Respiratory Research*, 7:126. Fragments of whole antibodies such as Fv, F(ab') and F(ab')$_2$, fragments or single chain antibodies (scFv) may be produced by means known in the art.

Using the disclosed sequences and the methods described in the literature, for example, the heavy and light chains of the variable region of antibody 209, having the sequences shown above, may be transgenically fused to a mouse IgG constant region sequence to produce a mouse monoclonal anti-ELABELA antibody.

Uses

Anti-ELABELA antibodies may be used in method of detecting an ELABELA polypeptide present in biological samples by a method which comprises: (a) providing an anti-ELABELA antibody; (b) incubating a biological sample with said antibody under conditions which allow for the formation of an antibody-antigen complex; and (c) determining whether antibody-antigen complex comprising said antibody is formed.

Suitable samples include extracts from tissues such as brain, breast, ovary, lung, colon, pancreas, testes, liver, muscle and bone tissues or from neoplastic growths derived from such tissues. In particular, a sample may comprise a tissue such as a colon, lung, squamous cell including lip, larynx, vulva, cervix and penis, pancreatic, brain, oesophageal, stomach, bladder, kidney, skin, ovary, prostate and testicular tissue from an individual suspected to be suffering from a relevant an ELABELA associated disease.

Antibodies may be bound to a solid support and/or packaged into kits in a suitable container along with suitable reagents, controls, instructions and the like.

Antibody Delivery

The antibodies against the ELABELA protein may be delivered into a cell by means of techniques known in the art, for example by the use of liposomes, polymers, (e.g., polyethylene glycol (PEG), N-(2-hydroxypropyl) methacrylamide (HPMA) copolymers, polyamidoamine (PAMAM) dendrimers, HEMA, linear polyamidoamine polymers etc) etc. The immunoglobulins and/or antibodies may also be delivered into cells as protein fusions or conjugates with a protein capable of crossing the plasma membrane and/or the nuclear membrane. For example, the immunoglobulin and/or target may be fused or conjugated to a domain or sequence from such a protein responsible for the translocational activity. Translocation domains and sequences may include domains and sequences from the HIV-1-trans-activating protein (Tat), *Drosophila* Antennapedia homeodomain protein and the herpes simplex-1 virus VP22 protein.

Detection and Diagnostic Methods

Detection of Expression of ELABELA

We describe methods of detecting the expression of ELABELA, including ELABELA polypeptides, ELABELA nucleic acids and variants, homologues, derivatives and fragments thereof, etc.

ELABELA expression may be detected as a means to determine the quantity of ELABELA or its activity. ELABELA expression may be detected in or of a cell, such as a stem cell. Detection of ELABELA expression may also be conducted on a sample comprising a cell tissue, an organ or part or all of an organism.

Expression of ELABELA in an ELABELA association condition may be modulated, such as up-regulated when compared to normal tissue. Accordingly, we provide for a method of diagnosis of an ELABELA associated condition, comprising detecting modulation of expression of ELABELA, such as modulation or up-regulation of expression of ELABELA in a cell or tissue of an individual.

Detection of ELABELA expression, activity or amount may be used to provide a method of determining the state of a cell. Thus, a cell of interest may be one with high levels of ELABELA expression, activity or amount compared to a normal cell. Similarly, a cell of interest may be one with low levels ELABELA expression, activity or amount compared to a normal cell.

Detection of ELABELA may also be used to determine whether a cell is a cell of interest. Thus, a high level of ELABELA expression, amount or activity of ELABELA in the cell may be detected. Similarly, a low level of ELABELA expression, amount or activity may also be detected in a cell.

It will be appreciated that if the level of ELABELA varies with the aggressiveness of an ELABELA associated condition, that detection of ELABELA expression, amount or activity may also be used to predict a survival rate of an individual with an ELABELA associated condition, i.e., high levels of ELABELA indicating a lower survival rate or probability and low levels of ELABELA indicating a higher survival rate or probability, both as compared to individuals or cognate populations with normal levels of ELABELA. Detection of expression, amount or activity of ELABELA may therefore be used as a method of prognosis of an individual with an ELABELA associated condition.

Detection of ELABELA expression, amount or level may be used to determine the likelihood of success of a particular therapy in an individual with an ELABELA associated condition.

The diagnostic methods described in this document may be combined with the therapeutic methods described. Thus, we provide for a method of treatment, prophylaxis or alleviation of an ELABELA associated condition in an individual, the method comprising detecting modulation of expression, amount or activity of ELABELA in a cell of the individual and administering an appropriate therapy to the individual based on the aggressiveness of the ELABELA associated condition. The therapy may comprise an anti-ELABELA agent as described elsewhere.

The presence and quantity of ELABELA polypeptides and nucleic acids may be detected in a sample as described in further detail elsewhere in this document. Thus, the ELABELA associated diseases can be diagnosed by methods comprising determining from a sample derived from a subject an abnormally decreased or increased expression, amount or activity, such as a increased expression, amount or activity, of the ELABELA polypeptide or ELABELA mRNA.

The sample may comprise a cell or tissue sample from an organism or individual suffering or suspected to be suffering from a disease associated with increased, reduced or otherwise abnormal ELABELA expression, amount or activity, including spatial or temporal changes in level or pattern of expression, amount or activity. The level or pattern of expression, amount or activity of ELABELA in an organism suffering from or suspected to be suffering from such a disease may be usefully compared with the level or pattern of expression, amount or activity in a normal organism as a means of diagnosis of disease.

The sample may comprise a cell or tissue sample from an individual suffering or suspected to be suffering from an ELABELA associated condition, such as a tissue or cell sample of any of those tissues or cells.

In some embodiments, an increased level of expression, amount or activity of ELABELA is detected in the sample. The level of ELABELA may be increased to a significant extent when compared to normal cells, or cells from an individual known not to be suffering from an ELABELA associated condition. Such cells may be obtained from the individual being tested, or another individual, such as those matched to the tested individual by age, weight, lifestyle, etc.

In some embodiments, the level of expression, amount or activity of ELABELA is increased by 10%, 20%, 30% or 40% or more. In some embodiments, the level of expression, amount or activity of ELABELA is increased by 45% or more, such as 50% or more, as judged by cDNA hybridisation.

The expression, amount or activity of ELABELA may be detected in a number of ways, as known in the art, and as described in further detail elsewhere in this document. Typically, the amount of ELABELA in a sample of tissue from an individual is measured, and compared with a sample from an unaffected individual. Both ELABELA nucleic acid, as well as ELABELA polypeptide levels may be measured.

Detection of the amount, activity or expression of ELABELA may be used to grade an ELABELA associate condition. For example, a high level of amount, activity or expression of ELABELA may indicate an aggressive ELABELA associate condition. Similarly, a low level of amount, activity or expression of ELABELA may indicate a non-aggressive ELABELA associate condition.

Levels of ELABELA gene expression may be determined using a number of different techniques.

Measuring Expression of ELABELA at the RNA Level

ELABELA gene expression can be detected at the RNA level.

In one embodiment therefore, we disclose a method of detecting the presence of a nucleic acid comprising an ELABELA nucleic acid in a sample, by contacting the sample with at least one nucleic acid probe which is specific for the ELABELA nucleic acid and monitoring said sample for the presence of the ELABELA nucleic acid. For example, the nucleic acid probe may specifically bind to the ELABELA nucleic acid, or a portion of it, and binding between the two detected; the presence of the complex itself may also be detected.

Thus, in one embodiment, the amount of ELABELA nucleic acid in the form of ELABELA mRNA may be measured in a sample. ELABELA mRNA may be assayed by in situ hybridization, Northern blotting and reverse transcriptase—polymerase chain reaction. Nucleic acid sequences may be identified by in situ hybridization, Southern blotting, single strand conformational polymorphism, PCR amplification and DNA-chip analysis using specific primers. (Kawasaki, 1990; Sambrook, 1992; Lichter et al, 1990; Orita et al, 1989; Fodor et al., 1993; Pease et al., 1994).

ELABELA RNA may be extracted from cells using RNA extraction techniques including, for example, using acid phenol/guanidine isothiocyanate extraction (RNAzol B; Biogenesis), or RNeasy RNA preparation kits (Qiagen). Typical assay formats utilising ribonucleic acid hybridisation include nuclear run-on assays, RT-PCR and RNase protection assays (Melton et al., Nuc. Acids Res. 12:7035. Methods for detection which can be employed include radioactive labels, enzyme labels, chemiluminescent labels, fluorescent labels and other suitable labels.

Each of these methods allows quantitative determinations to be made, and are well known in the art. Decreased or increased ELABELA expression, amount or activity can therefore be measured at the RNA level using any of the methods well known in the art for the quantitation of polynucleotides. Any suitable probe from an ELABELA sequence, for example, any portion of a suitable human ELABELA sequence may be used as a probe. Sequences for designing ELABELA probes may include a sequence having SEQ ID NO: 37 to 41, or a portion thereof.

Typically, RT-PCR is used to amplify RNA targets. In this process, the reverse transcriptase enzyme is used to convert RNA to complementary DNA (cDNA) which can then be amplified to facilitate detection.

Many DNA amplification methods are known, most of which rely on an enzymatic chain reaction (such as a polymerase chain reaction, a ligase chain reaction, or a self-sustained sequence replication) or from the replication of all or part of the vector into which it has been cloned.

Many target and signal amplification methods have been described in the literature, for example, general reviews of these methods in Landegren, U. et al., Science 242:229-237 (1988) and Lewis, R., *Genetic Engineering News* 10:1, 54-55 (1990).

For example, the polymerase chain reaction may be employed to detect ELABELA mRNA.

The "polymerase chain reaction" or "PCR" is a nucleic acid amplification method described inter alia in U.S. Pat. Nos. 4,683,195 and 4,683,202. PCR can be used to amplify any known nucleic acid in a diagnostic context (Mok et al., 1994, *Gynaecologic Oncology* 52:247-252). Self-sustained sequence replication (3SR) is a variation of TAS, which involves the isothermal amplification of a nucleic acid template via sequential rounds of reverse transcriptase (RT), polymerase and nuclease activities that are mediated by an enzyme cocktail and appropriate oligonucleotide primers (Guatelli et al., 1990, *Proc. Natl. Acad. Sci. USA* 87:1874). Ligation amplification reaction or ligation amplification system uses DNA ligase and four oligonucleotides, two per target strand. This technique is described by Wu, D. Y. and Wallace, R. B., 1989, *Genomics* 4:560. In the Qβ Replicase technique, RNA replicase for the bacteriophage Qβ, which replicates single-stranded RNA, is used to amplify the target DNA, as described by Lizardi et al., 1988, *Bio/Technology* 6:1197.

A PCR procedure basically involves: (1) treating extracted DNA to form single-stranded complementary strands; (2) adding a pair of oligonucleotide primers, wherein one primer of the pair is substantially complementary to part of the sequence in the sense strand and the other primer of each pair is substantially complementary to a different part of the same sequence in the complementary antisense strand; (3) annealing the paired primers to the complementary sequence; (4) simultaneously extending the annealed primers from a 3' terminus of each primer to synthesize an extension product complementary to the strands annealed to each primer wherein said extension products after separation from the complement serve as templates for the synthesis of an extension product for the other primer of each pair; (5) separating said extension products from said templates to produce single-stranded molecules; and (6) amplifying said single-stranded molecules by repeating at least once said annealing, extending and separating steps.

Reverse transcription-polymerase chain reaction (RT-PCR) may be employed. Quantitative RT-PCR may also be used. Such PCR techniques are well known in the art, and may employ any suitable primer from an ELABELA sequence.

Alternative amplification technology can also be exploited. For example, rolling circle amplification (Lizardi et al., 1998, *Nat Genet* 19:225) is an amplification technology available commercially (RCAT™) which is driven by DNA polymerase and can replicate circular oligonucleotide probes with either linear or geometric kinetics under isothermal conditions. A further technique, strand displacement amplification (SDA; Walker et al., 1992, *Proc. Natl. Acad. Sci. USA* 80:392) begins with a specifically defined sequence unique to a specific target.

Measuring Expression of ELABELA at the Polypeptide Level

ELABELA expression can be detected at the polypeptide level.

In a further embodiment, therefore, ELABELA expression, amount or activity may be detected by detecting the presence or amount of ELABELA polypeptide in a sample. This may be achieved by using molecules which bind to ELABELA polypeptide. Suitable molecules/agents which bind either directly or indirectly to the ELABELA polypeptide in order to detect its presence include naturally occurring molecules such as peptides and proteins, for example antibodies, or they may be synthetic molecules.

Thus, we disclose a method of detecting the presence of an ELABELA polypeptide by contacting a cell sample with an antibody capable of binding the polypeptide and monitoring said sample for the presence of the polypeptide.

For example, the ELABELA polypeptide may be detected using an anti-ELABELA antibody. Such antibodies may be made by means known in the art (as described in further detail elsewhere in this document).

Detection of ELABELA may conveniently be achieved by monitoring the presence of a complex formed between the antibody and the ELABELA polypeptide, or monitoring the binding between the polypeptide and the antibody. Methods of detecting binding between two entities are known in the art, and include FRET (fluorescence resonance energy transfer), surface plasmon resonance, etc.

Standard laboratory techniques such as immunoblotting as described above can be used to detect altered levels of ELABELA protein, as compared with untreated cells in the same cell population.

Gene expression may also be determined by detecting changes in post-translational processing of ELABELA polypeptides or post-transcriptional modification of ELABELA nucleic acids. For example, differential phosphorylation of ELABELA polypeptides, the cleavage of ELABELA polypeptides or alternative splicing of ELABELA RNA, and the like may be measured. Levels of expression of gene products such as ELABELA polypeptides, as well as their post-translational modification, may be detected using proprietary protein assays or techniques such as 2D polyacrylamide gel electrophoresis.

Assay techniques that can be used to determine levels of ELABELA protein in a sample derived from a host are well-known to those of skill in the art. Antibodies can be assayed for immunospecific binding by any method known in the art.

The immunoassays which can be used include but are not limited to competitive and non-competitive assay systems using techniques such as western blots, radioimmunoassays, ELISA, sandwich immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays. Such assays are routine in the art (see, for example, Ausubel et al., eds, 1994, *Current Protocols in Molecular Biology*, Vol. 1, John Wiley & Sons, Inc., New York, which is incorporated by reference herein in its entirety).

We describe immunoassay kits for measuring or detecting ELABELA expression. The immunoassay kits may comprise
(a) a coating antigen;
(b) one or more isolated antibodies or antigen-binding fragments thereof that specifically binds to one or more of the following:
(i) a polypeptide comprising the sequence CMPLHSRVPFP (SEQ ID NO: 52);
(ii) a polypeptide comprising the sequence QRPVNLTMRRKLRKHNC (SEQ ID NO: 53);
(iii) a polypeptide comprising the sequence QRPVNLTMRRKLRKHNCLQRRCMPLHSRVPFP (SEQ ID NO: 2);
(iv) a polypeptide comprising the sequence of any of SEQID NOs: 1 to 36; and
(c) instructions for use.

The isolated antibodies or antigen-binding fragments may be labelled, such as with a radiolabel, for example $^{125}$I.

The immunoassay kit may further comprise an enzyme labelled reagent, a secondary antibody capable of specifically binding to the isolated antibodies or antigen-binding fragments, a solid substrate, or any combination of these.

The specimen may be assayed for polypeptides/proteins by immunohistochemical and immunocytochemical staining (see generally Stites and Terr, Basic and Clinical Immunology, Appleton and Lange, 1994), ELISA, RIA, immunoblots, Western blotting, immunoprecipitation, functional assays and protein truncation test. Other assay methods include radioimmunoassays, competitive-binding assays, Western Blot analysis and ELISA assays.

ELISA assays are well known to those skilled in the art. Both polyclonal and monoclonal antibodies may be used in the assays. Where appropriate other immunoassays, such as radioimmunoassays (RIA) may be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, 1992.

Diagnostic Kits

We also provide diagnostic kits for detecting an ELABELA associated condition in an individual, or susceptibility to such an ELABELA associated condition in an individual.

The diagnostic kit may comprise means for detecting expression, amount or activity of ELABELA in the individual, by any means as described in this document. The diagnostic kit may therefore comprise any one or more of the following: an ELABELA polynucleotide or a fragment thereof; a complementary nucleotide sequence to ELABELA nucleic acid or a fragment thereof; an ELABELA polypeptide or a fragment thereof, or an antibody to an ELABELA, such as comprising an anti-ELABELA antibody against ELABELA, e.g., an anti-peptide antibody human ELABELA antibody.

The diagnostic kit may comprise instructions for use, or other indicia. The diagnostic kit may further comprise means for treatment or prophylaxis of an ELABELA associated condition, such as any of the compositions described in this document, or any means known in the art for treating such an ELABELA associated condition. In particular, the diagnostic kit may comprise an anti-ELABELA agent as described, for example obtained by screening. The diagnostic kit may comprise a therapeutic drug. The therapeutic drug may also comprise an anti-ELABELA antibody.

Immunoassays

We describe immunoassay kits for measuring or detecting ELABELA expression, the immunoassay kits comprising: (a) a coating antigen comprising one or more isolated antibodies or antigen-binding fragments thereof that specifically binds to one or more of the following: (i) a polypeptide comprising the sequence CMPLHSRVPFP (SEQ ID NO: 52); (ii) a polypeptide comprising the sequence QRPVNLTMRRKLRKHNC (SEQ ID NO: 53); (iii) a polypeptide comprising the sequence QRPVNLTMRRKLRKHNCLQRRCMPLHSRVPFP (SEQ ID NO: 2); or (iv) an ELABELA polypeptide comprising the sequence of any of SEQ ID NOs: 1-36; and (b) instructions for using said coating antigen.

The isolated antibodies or antigen-binding fragments thereof may be labelled.

The kit may further comprise an enzyme labelled reagent, a secondary antibody that specifically binds to the isolated antibodies or antigen-binding fragments, a solid substrate, or any combination thereof.

Prophylactic and Therapeutic Methods

We disclose methods of treating an abnormal condition, such as an ELABELA associated condition, related to insufficient or excessive amounts of ELABELA expression or activity. Methods of preventing an ELABELA associated condition (i.e., prophylaxis) also suitably employ the same or similar approaches.

In general terms, our methods involve manipulation of cells, by modulating (such as down-regulating) the expression, amount or activity of ELABELA in the cell. A step of detecting modulated ELABELA expression, amount or activity in a cell may be conducted before or after the manipulation step. The detection step may detect up-regulated or down-regulated ELABELA expression, amount or activity. Any of the methods of modulating or down-regulating ELABELA, as described in detail elsewhere in this document, may be used.

The method may comprise exposing the cell to a suitable siRNA, shRNA or chimera RNAi. Examples of siRNA and shRNA are set out in the sequence listing. For example, any of the shRNA sequences shown as SEQ ID NO: 47 to SEQ ID NO: 51 may be employed to down-regulate ELABELA mRNA expression.

Chimera RNA interference (chimera RNAi) is process by which small interfering RNA/DNA chimera triggers the destruction of mRNA for the original gene. Chimer RNAi is described in detail in Ui-Tei K et al., 2008, Nucleic Acids Res., April 2008; 36: 2136-2151, Naito al. Nucleic Acids Res., July 2005; 33: W589-W591, Ui-Tei K et al., 2004, Nucleic Acids Res. 2004 Feb. 9; 32(3):936-48 and Naito et al. Nucleic Acids Res. 2004 Jul. 1; 32 (Web Server issue): W124-9.

The method may also comprise exposing the cell to an anti-ELABELA antibody capable of specifically binding to ELABELA. Such an antibody may comprise any anti-ELABELA antibody, as described elsewhere in this document.

Where ELABELA is associated with aggressiveness of an ELABELA associated condition, the level of ELABELA may be detected in a cell of an individual with an ELABELA associated condition, and the aggressiveness of the ELABELA associated condition assessed. A high level of ELABELA amount, expression or activity compared with a normal cell may indicate an aggressive an ELABELA associated condition, and a stronger or harsher therapy may therefore be required and chosen. Similarly, a lower level may indicate a less aggressive therapy.

The approaches described here may be used for therapy of any ELABELA related disease in general. ELABELA related diseases are described in detail elsewhere in this document.

An ELABELA related disease is defined as being "treated" if a condition associated with the disease is significantly inhibited (i.e., by 50% or more) relative to controls. The inhibition may be by at least 75% relative to controls, such as by 90%, by 95% or 100% relative to controls. By the term "treatment" we mean to also include prophylaxis or alleviation of an ELABELA associated condition.

One possible approach for therapy of an ELABELA associated conditions or disorders is to express anti-sense constructs directed against ELABELA polynucleotides as described here, and administering them to cells or individuals suffering from an ELABELA associated condition.

Anti-sense constructs may be used to inhibit gene function to prevent growth or progression in a proliferative cell. Antisense constructs, i.e., nucleic acid, such as RNA, constructs complementary to the sense nucleic acid or mRNA, are described in detail in U.S. Pat. No. 6,100,090 (Monia et al.), and Neckers et al., 1992, *Crit Rev Oncog* 3(1-2):175-231, the teachings of which document are specifically incorporated by reference.

In a particular example, an ELABELA associated condition may be treated or prevented by reducing the amount, expression or activity of ELABELA in whole or in part, for example by siRNAs capable of binding to and destroying ELABELA mRNA. We specifically provide for an anti-ELABELA agent which downregulates ELABELA by RNA interference. The anti-ELABELA agent may comprise a Small Interfering RNA (siRNA) or Short Hairpin RNA (shRNA).

RNA interference (RNAi) is a method of post transcriptional gene silencing (PTGS) induced by the direct introduction of double-stranded RNA (dsRNA) and has emerged as a useful tool to knock out expression of specific genes in a variety of organisms. RNAi is described by Fire et al., *Nature* 391:806-811 (1998). Other methods of PTGS are known and include, for example, introduction of a transgene or virus. Generally, in PTGS, the transcript of the silenced gene is synthesised but does not accumulate because it is rapidly degraded. Methods for PTGS, including RNAi are described, for example, in the Ambion.com world wide web site, in the directory "/hottopics/", in the "rnai" file.

Suitable methods for RNAi in vitro are described herein. One such method involves the introduction of siRNA (small interfering RNA). Current models indicate that these 21-23 nucleotide dsRNAs can induce PTGS. Methods for designing effective siRNAs are described, for example, in the Ambion web site described above. RNA precursors such as Short Hairpin RNAs (shRNAs) can also be encoded by all or a part of the ELABELA nucleic acid sequence.

Alternatively, double-stranded (ds) RNA is a powerful way of interfering with gene expression in a range of organisms that has recently been shown to be successful in mammals (Wianny and Zernicka-Goetz, 2000, *Nat Cell Biol* 2:70-75). Double stranded RNA corresponding to the sequence of an ELABELA polynucleotide can be introduced into or expressed in oocytes and cells of a candidate organism to interfere with ELABELA activity.

Other methods of modulating ELABELA gene expression are known to those skilled in the art and include dominant negative approaches. Thus, another approach is to use non-functional variants of ELABELA polypeptide in this document that compete with the endogenous gene product resulting in inhibition of function.

One example of a non-functional variant of ELABELA is a mutation to alanine or glycine of an arginine or lysine residue at a position 31 or 32—or both—of (or corresponding to) the human ELABELA sequence SEQ ID NO: 20.

ELABELA gene expression may also be modulated by as introducing peptides or small molecules which inhibit gene expression or functional activity. Thus, compounds identified by the assays described here as binding to or modulating, such as down-regulating, the amount, activity or expression of ELABELA polypeptide may be administered to cells to prevent the function of ELABELA polypeptide. Such a compound may be administered along with a pharmaceutically acceptable carrier in an amount effective to down-regulate expression or activity ELABELA, or by activating or down-regulating a second signal which controls ELABELA expression, activity or amount, and thereby alleviating the abnormal condition.

Suitable antibodies against ELABELA polypeptide as described herein may also be used as therapeutic agents.

Alternatively, gene therapy may be employed to control the endogenous production of ELABELA by the relevant cells such as embryonic or adult stem cells in the subject. For example, a polynucleotide encoding an ELABELA siRNA or a portion of this may be engineered for expression in a replication defective retroviral vector, as discussed elsewhere in this document. The retroviral expression construct may then be isolated and introduced into a packaging cell transduced with a retroviral plasmid vector containing RNA encoding an anti-ELABELA siRNA such that the packaging cell now produces infectious viral particles containing the sequence of interest. These producer cells may be administered to a subject for engineering cells in vivo and regulating expression of the ELABELA polypeptide in vivo. For overview of gene therapy, see Chapter 20, Gene Therapy and other Molecular Genetic-based Therapeutic Approaches, (and references cited therein) in Human Molecular Genetics, T Strachan and A P Read, BIOS Scientific Publishers Ltd (1996).

In some embodiments, the level of ELABELA is decreased in a stem cell. Furthermore, in such embodiments, treatment may be targeted to, or specific to, stem cells. The expression of ELABELA may be specifically decreased only in diseased stem cells, and not substantially in other non-diseased stem cells. In these methods, expression of ELABELA may be not substantially reduced in other cells, i.e., cells which are not stem cells. Thus, in such embodiments, the level of ELABELA remains substantially the same or similar in non-stem cells in the course of or following treatment.

Stem cell specific reduction of ELABELA levels may be achieved by targeted administration, i.e., applying the treatment only to the stem cells and not other cells. However, in other embodiments, down-regulation of ELABELA expression in stem cells (and not substantially in other cell or tissue types) is employed. Such methods may make use of stem specific expression vectors, for stem specific expression of for example siRNAs, as known in the art.

ELABELA Related Conditions

"ELABELA related condition", as the term is used in this document, is intended to encompass any cardiac dysfunction, hypertension, or a cardiovascular anomaly in blood pressure, cardiac contractility or fluid balance.

The term "ELABELA related condition" is also intended to encompass any cardiovascular disease such as cardiac hypertrophy, coronary artery disease (CAD), atherosclerosis, post-infarct treatment, myocardial ischemia-reperfusion injury or atrial fibrillation, coronary heart disease, heart failure, pulmonary arterial hypertension (PAH).

"ELABELA related condition" may also include a condition associated with high blood pressure, such as hypertension, angina, congestive heart failure or erectile dysfunction.

"ELABELA related condition" may also include a condition associated with HIV infection, such as AIDS in an individual.

For example, the methods and compositions described here may be used to prevent, treat or alleviate any of the conditions or diseases set out below:

Heart Disease

Heart disease is an umbrella term for a variety for different diseases affecting the heart. As of 2007, it is the leading cause of death in the United States, England, Canada and Wales, killing one person every 34 seconds in the United States alone. Heart disease includes any of the following.

Coronary Heart Disease

Coronary artery disease is a disease of the artery caused by the accumulation of atheromatous plaques within the walls of the arteries that supply the myocardium. Angina pectoris (chest pain) and myocardial infarction (heart attack) are symptoms of and conditions caused by coronary heart disease. Over 459,000 Americans die of coronary heart disease every year. In the United Kingdom, 101,000 deaths annually are due to coronary heart disease.

Cardiomyopathy

Cardiomyopathy is the deterioration of the function of the myocardium (i.e., the actual heart muscle) for any reason. People with cardiomyopathy are often at risk of arrhythmia and/or sudden cardiac death. Extrinsic cardiomyopathies—cardiomyopathies where the primary pathology is outside the myocardium itself comprise the majority of cardiomyopathies. By far the most common cause of a cardiomyopathy is ischemia.

The World Health Organization includes as specific cardiomyopathies: Alcoholic cardiomyopathy, coronary artery disease, congenital heart disease, nutritional diseases affecting the heart, ischemic (or ischaemic) cardiomyopathy, hypertensive cardiomyopathy, valvular cardiomyopathy, inflammatory cardiomyopathy.

Also included are:

Cardiomyopathy secondary to a systemic metabolic disease

Intrinsic cardiomyopathies (weakness in the muscle of the heart that is not due to an identifiable external cause)

Dilated cardiomyopathy (DCM, the most common form, and one of the leading indications for heart transplantation. In DCM the heart (especially the left ventricle) is enlarged and the pumping function is diminished)

Hypertrophic cardiomyopathy (HCM or HOCM, a genetic disorder caused by various mutations in genes encoding sarcomeric proteins. In HCM the heart muscle is thickened, which can obstruct blood flow and prevent the heart from functioning properly).

Arrhythmogenic right ventricular cardiomyopathy (ARVC, which arises from an electrical disturbance of the heart in which heart muscle is replaced by fibrous scar tissue. The right ventricle is generally most affected)

Restrictive cardiomyopathy (RCM, which is the least common cardiomyopathy. The walls of the ventricles are stiff, but may not be thickened, and resist the normal filling of the heart with blood).

Noncompaction Cardiomyopathy—the left ventricle wall has failed to properly grow from birth and such has a spongy appearance when viewed during an echocardiogram.

Cardiovascular Disease

Cardiovascular disease is any of a number of specific diseases that affect the heart itself and/or the blood vessel system, especially the veins and arteries leading to and from the heart. Research on disease dimorphism suggests that women who suffer with cardiovascular disease usually suffer from forms that affect the blood vessels while men usually suffer from forms that affect the heart muscle itself. Known or associated causes of cardiovascular disease include diabetes mellitus, hypertension, hyperhomocysteinemia and hypercholesterolemia.

Types of cardiovascular disease include atherosclerosis

Ischaemic Heart Disease

Ischaemic heart disease is disease of the heart itself, characterized by reduced blood supply to the organs. This occurs when the arteries that supply the oxygen and the nutrients gets stopped and the heart will not get enough of the oxygen and the nutrients and will eventually stop beating.

Heart Failure

Heart failure, also called congestive heart failure (or CHF), and congestive cardiac failure (CCF), is a condition that can result from any structural or functional cardiac disorder that impairs the ability of the heart to fill with or pump a sufficient amount of blood throughout the body. Cor pulmonale is a failure of the right side of the heart.

Hypertensive Heart Disease

Hypertensive heart disease is heart disease caused by high blood pressure, especially localised high blood pressure. Conditions that can be caused by hypertensive heart disease include: left ventricular hypertrophy, coronary heart disease, (Congestive) heart failure, hypertensive cardiomyopathy, cardiac arrhythmias, inflammatory heart disease, etc.

Inflammatory heart disease involves inflammation of the heart muscle and/or the tissue surrounding it. Endocarditis comprises inflammation of the inner layer of the heart, the endocardium. The most common structures involved are the heart valves. Inflammatory cardiomegaly. Myocarditis comprises inflammation of the myocardium, the muscular part of the heart.

Valvular Heart Disease

Valvular heart disease is disease process that affects one or more valves of the heart. The valves in the right side of the heart are the tricuspid valve and the pulmonic valve. The valves in the left side of the heart are the mitral valve and the aortic valve. Included are aortic valve stenosis, mitral valve prolapse and valvular cardiomyopathy.

[The above text is adapted from Heart disease. (2009, February 3). In Wikipedia, The Free Encyclopedia. Retrieved 06:33, Feb. 20, 2009, from http://en.wikipedia.org/w/index.php?title=Heart_disease&oldid=268290924]

Pharmaceutical Compositions and Administration

While it is possible for the anti-ELABELA agent, including an ELABELA nucleic acid, polypeptide, fragment, homologue, variant or derivative thereof, modulator, agonist or antagonist, a structurally related compound, or an acidic salt of either to be administered alone, the active ingredient may be formulated as a pharmaceutical formulation.

We therefore also disclose pharmaceutical compositions comprising an anti-ELABELA agent. Such pharmaceutical compositions are useful for delivery of the anti-ELABELA agent such as in the form of a composition as described, to an individual for the treatment or alleviation of symptoms as described.

A pharmaceutical composition in the context of the present document is a composition of matter comprising at least an anti-ELABELA agent as an active ingredient.

The pharmaceutical formulations comprise an effective amount of the anti-ELABELA agent together with one or more pharmaceutically-acceptable carriers. An "effective amount" is the amount sufficient to alleviate at least one symptom of a disease as described.

The effective amount will vary depending upon the particular disease or syndrome to be treated or alleviated, as well as other factors including the age and weight of the patient, how advanced the disease etc state is, the general health of the patient, the severity of the symptoms, and whether the anti-ELABELA agent is being administered alone or in combination with other therapies.

Suitable pharmaceutically acceptable carriers are well known in the art and vary with the desired form and mode of administration of the pharmaceutical formulation. For example, they can include diluents or excipients such as fillers, binders, wetting agents, disintegrators, surface-active agents, lubricants and the like. Typically, the carrier is a solid, a liquid or a vaporizable carrier, or a combination thereof. Each carrier should be "acceptable" in the sense of being compatible with the other ingredients in the formulation and not injurious to the patient. The carrier should be biologically acceptable without eliciting an adverse reaction (e.g. immune response) when administered to the host.

The active ingredient(s) of a pharmaceutical composition is contemplated to exhibit therapeutic activity, for example, in the alleviation of an ELABELA associated condition. Dosage regimes may be adjusted to provide the optimum therapeutic response. For example, several divided doses may be administered daily or the dose may be proportionally reduced as indicated by the exigencies of the therapeutic situation.

The active compound may be administered in a convenient manner such as by the oral, intravenous (where water soluble), intramuscular, subcutaneous, intranasal, intradermal or suppository routes or implanting (e.g. using slow release molecules). Depending on the route of administration, the active ingredient may be required to be coated in a material to protect said ingredients from the action of enzymes, acids and other natural conditions which may inactivate said ingredient.

The anti-ELABELA agent may be administered alone, or in combination with other therapeutic agents. Other therapeutic agents suitable for use herein are any compatible drugs that are effective for the intended purpose, or drugs that are complementary to the agent formulation. The formulation utilized in a combination therapy may be administered simultaneously, or sequentially with other treatment, such that a combined effect is achieved.

Oral Administration

In some embodiments, the inhibitor of ELABELA activity, expression or amount is provided as an oral composition and administered accordingly. The dosage of the inhibitor of ELABELA activity, expression or amount may be between about 1 mg/day to about 10 mg/day.

The pharmaceutical composition can be administered in an oral formulation in the form of tablets, capsules or solutions. An effective amount of the oral formulation is administered to patients 1 to 3 times daily until the symptoms of the disease alleviated.

The effective amount of agent depends on the age, weight and condition of a patient. In general, the daily oral dose of agent is less than 1200 mg, and more than 100 mg. The daily oral dose may be about 300-600 mg. Oral formulations are conveniently presented in a unit dosage form and may be prepared by any method known in the art of pharmacy. The composition may be formulated together with a suitable pharmaceutically acceptable carrier into any desired dosage form. Typical unit dosage forms include tablets, pills, powders, solutions, suspensions, emulsions, granules, capsules, suppositories. In general, the formulations are prepared by uniformly and intimately bringing into association the agent composition with liquid carriers or finely divided solid carriers or both, and as necessary, shaping the product. The active ingredient can be incorporated into a variety of basic materials in the form of a liquid, powder, tablets or capsules to give an effective amount of active ingredient to treat the disease.

The composition may be suitably orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. The amount of active compound in such therapeutically useful compositions in such that a suitable dosage will be obtained.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier.

Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound may be incorporated into sustained-release preparations and formulations.

Injectable or Intravenous Administration

In some embodiments, the anti-ELABELA agent is provided as an injectable or intravenous composition and administered accordingly. The dosage of the anti-ELABELA agent inhibitor may be between about 5 mg/kg/2 weeks to about 10 mg/kg/2 weeks. The anti-ELABELA agent inhibitor may be provided in a dosage of between 10-300 mg/day, such as at least 30 mg/day, less than 200 mg/day or between 30 mg/day to 200 mg/day.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene gloycol, and the like), suitable mixtures thereof, and vegetable oils. The proper fluidity can be maintained, for example, by the use of a coating such as lecithin, by the maintenance of the required particle size in the case of dispersion and by the use of superfactants.

Topical Administration

The pharmaceutical compositions disclosed here include those suitable for topical and oral administration. Topical formulations may be used where the tissue affected is primarily the skin or epidermis (for example, psoriasis, eczema and other epidermal diseases).

The topical formulations include those pharmaceutical forms in which the composition is applied externally by direct contact with the skin surface to be treated. A conventional pharmaceutical form for topical application includes a soak, an ointment, a cream, a lotion, a paste, a gel, a stick, a spray, an aerosol, a bath oil, a solution and the like. Topical therapy is delivered by various vehicles, the choice of vehicle can be important and generally is related to whether an acute or chronic disease is to be treated. As an example, an acute skin proliferation disease generally is treated with aqueous drying preparations, whereas chronic skin proliferation disease is treated with hydrating preparations. Soaks are the easiest method of drying acute moist eruptions. Lotions (powder in water suspension) and solutions (medications dissolved in a solvent) are ideal for hairy and intertriginous areas. Ointments or water-in-oil emulsions, are the most effective hydrating agents, appropriate for dry scaly eruptions, but are greasy and depending upon the site of the lesion sometimes undesirable. As appropriate, they can be applied in combination with a bandage, particularly when it is desirable to increase penetration of the agent composition into a lesion. Creams or oil-in-water emulsions and gels are absorbable and are the most cosmetically acceptable to the patient. (Guzzo et al, in Goodman & Gilman's Pharmacological Basis of Therapeutics, 9th Ed., p. 1593-15950 (1996)). Cream formulations generally include components such as petroleum, lanolin, polyethylene glycols, mineral oil, glycerin, isopropyl palmitate, glyceryl stearate, cetearyl alcohol, tocopheryl acetate, isopropyl myristate, lanolin alcohol, simethicone, carbomen, methylchlorisothiazolinone, methylisothiazolinone, cyclomethicone and hydroxypropyl methylcellulose, as well as mixtures thereof.

Other formulations for topical application include shampoos, soaps, shake lotions, and the like, particularly those formulated to leave a residue on the underlying skin, such as the scalp (Arndt et al, in Dermatology In General Medicine 2:2838 (1993)).

In general, the concentration of the composition in the topical formulation is in an amount of about 0.5 to 50% by weight of the composition, such as about 1 to 30%, about 2-20%, or about 5-10%. The concentration used can be in the upper portion of the range initially, as treatment continues, the concentration can be lowered or the application of the formulation may be less frequent. Topical applications are often applied twice daily. However, once-daily application of a larger dose or more frequent applications of a smaller dose may be effective. The stratum corneum may act as a reservoir and allow gradual penetration of a drug into the viable skin layers over a prolonged period of time.

In a topical application, a sufficient amount of active ingredient must penetrate a patient's skin in order to obtain a desired pharmacological effect. It is generally understood that the absorption of drug into the skin is a function of the nature of the drug, the behaviour of the vehicle, and the skin. Three major variables account for differences in the rate of absorption or flux of different topical drugs or the same drug in different vehicles; the concentration of drug in the vehicle, the partition coefficient of drug between the stratum corneum and the vehicle and the diffusion coefficient of drug in the stratum corneum. To be effective for treatment, a drug must cross the stratum corneum which is responsible for the barrier function of the skin. In general, a topical formulation which exerts a high in vitro skin penetration is effective in vivo. Ostrenga et al (J. Pharm. Sci., 60:1175-1179 (1971) demonstrated that in vivo efficacy of topically applied steroids was proportional to the steroid penetration rate into dermatomed human skin in vitro.

A skin penetration enhancer which is dermatologically acceptable and compatible with the agent can be incorporated into the formulation to increase the penetration of the active compound(s) from the skin surface into epidermal keratinocytes. A skin enhancer which increases the absorption of the active compound(s) into the skin reduces the amount of agent needed for an effective treatment and provides for a longer lasting effect of the formulation. Skin penetration enhancers are well known in the art. For example, dimethyl sulfoxide (U.S. Pat. No. 3,711,602); oleic acid, 1,2-butanediol surfactant (Cooper, J. Pharm. Sci., 73:1153-1156 (1984)); a combination of ethanol and oleic acid or oleyl alcohol (EP 267,617), 2-ethyl-1,3-hexanediol (WO 87/03490); decyl methyl sulphoxide and Azone® (Hadgraft, Eur. J. Drug. Metab. Pharmacokinet, 21:165-173 (1996)); alcohols, sulphoxides, fatty acids, esters, Azone®, pyrrolidones, urea and polyoles (Kalbitz et al, Pharmazie, 51:619-637 (1996));

Terpenes such as 1,8-cineole, menthone, limonene and nerolidol (Yamane, J. Pharmacy & Pharmocology, 47:978-989 (1995)); Azone® and Transcutol (Harrison et al, Pharmaceutical Res. 13:542-546 (1996)); and oleic acid, polyethylene glycol and propylene glycol (Singh et al, Pharmazie, 51:741-744 (1996)) are known to improve skin penetration of an active ingredient.

Levels of penetration of an agent or composition can be determined by techniques known to those of skill in the art. For example, radiolabeling of the active compound, followed by measurement of the amount of radiolabeled compound absorbed by the skin enables one of skill in the art to determine levels of the composition absorbed using any of several methods of determining skin penetration of the test compound. Publications relating to skin penetration studies include Reinfenrath, W G and G S Hawkins. The Weaning Yorkshire Pig as an Animal Model for Measuring Percutaneous Penetration. In: Swine in Biomedical Research (M. E. Tumbleson, Ed.) Plenum, N.Y., 1986, and Hawkins, G. S. Methodology for the Execution of In Vitro Skin Penetration Determinations. In: Methods for Skin Absorption, B W Kemppainen and W G Reifenrath, Eds., CRC Press, Boca Raton, 1990, pp. 67-80; and W. G. Reifenrath, Cosmetics & Toiletries, 110:3-9 (1995).

For some applications, a long acting form of agent or composition may be administered using formulations known in the arts, such as polymers. The agent can be incorporated into a dermal patch (Junginger, H. E., in Acta Pharmaceutica Nordica 4:117 (1992); Thacharodi et al, in Biomaterials 16:145-148 (1995); Niedner R., in Hautarzt 39:761-766 (1988)) or a bandage according to methods known in the arts, to increase the efficiency of delivery of the drug to the areas to be treated.

Optionally, the topical formulations described here can have additional excipients for example; preservatives such as methylparaben, benzyl alcohol, sorbic acid or quaternary ammonium compound; stabilizers such as EDTA, antioxidants such as butylated hydroxytoluene or butylated hydroxanisole, and buffers such as citrate and phosphate.

Parenteral Administration

The active compound may also be administered parenterally or intraperitoneally. Dispersions can also be prepared in glycerol, liquid polyethylene glycols, and mixtures thereof and in oils. In some embodiments, the dispersions may be prepared in 30% Capsitol (CyDex, Inc., Lenexa, Kans., USA). Capsitol is a polyanionic β-cyclodextrin derivative with a sodium sulfonate salt separated from the lipophilic cavity by a butyl ether spacer group, or sulfobutylether (SBE). The cyclodextrin may be SBE7-β-CD.

Adjuvants

The composition may be administered in an adjuvant, co-administered with enzyme inhibitors or in liposomes. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin. Liposomes include water-in-oil-in-water CGF emulsions as well as conventional liposomes.

Prevention of Microorganism Growth

Under ordinary conditions of storage and use, these preparations may contain a preservative to prevent the growth of microorganisms.

The prevention of the action of microorganisms can be brought about by various antibacterial and antifungal agents, for example, parabens, chlorobutanol, phenol, sorbic acid, thirmerosal, and the like. In many cases, it is possible to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compound in the required amount in the appropriate solvent with various of the other ingredients enumerated above, as required, followed by filtered sterilisation. Generally, dispersions are prepared by incorporating the sterilised active ingredient into a sterile vehicle which contains the basic dispersion medium and the required other ingredients from those enumerated above. In the case of sterile powders for the preparation of sterile injectable solutions, the methods of preparation may include vacuum drying and the freeze-drying technique which yield a powder of the active ingredient plus any additional desired ingredient from previously sterile-filtered solution thereof.

Pharmaceutically Acceptable Carrier

As used herein "pharmaceutically acceptable carrier and/or diluent" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

Dosage Unit Forms

Pharmaceutical compositions may be formulated in dosage unit form for ease of administration and uniformity of dosage.

Dosage unit form as used herein refers to physically discrete units suited as unitary dosages for the subjects to be treated; each unit containing a predetermined quantity of active material calculated to produce the desired therapeutic effect in association with the required pharmaceutical carrier. The specification for the novel dosage unit forms are dictated by and directly dependent on (a) the unique characteristics of the active material and the particular therapeutic effect to be achieved, and (b) the limitations inherent in the art of compounding such as active material for the treatment of disease in living subjects having a diseased condition in which bodily health is impaired.

The principal active ingredients are compounded for convenient and effective administration in effective amounts with a suitable pharmaceutically acceptable carrier in dosage unit form. In the case of compositions containing supplementary active ingredients, the dosages are determined by reference to the usual dose and manner of administration of the said ingredients.

ELABELA Combinations

ELABELA polypeptides as disclosed in this document may be combined with a molecule of interest. They may be conjugated to a molecule of interest. Alternatively, or in addition, one or more fusion proteins may be produced comprising an ELABELA polypeptide together with a molecule of interest such as a polypeptide of interest.

Such combinations are referred to generally in this document as "ELABELA combinations".

We disclose an ELABELA combination comprising a first part comprising an ELABELA polypeptide and a second part comprising a molecule of interest. The ELABELA polypeptide may comprise any sequence disclosed in this document, for example, a sequence MPLHSRVPFP (SEQ ID NO: 54) or QRPVNLTMRRKLRKHN (SEQ ID NO: 55) or both.

The combination may be such that the first part comprising an ELABELA polypeptide is coupled, fused, mixed, combined, or otherwise joined to a second part comprising a molecule of interest.

As noted above, the combination may be such that the first part and the second part are covalently joined. Such covalent joining may for example be achieved by chemical conjugation. Alternatively, or in addition, the combination may comprise a fusion protein comprising the first part and the second part, where the molecule of interest comprises a polypeptide. We further disclose an expression construct capable of expressing such a fusion protein.

The generation of such combinations of ELABELA polypeptides and molecules of interest may aid in the tracking, quantitation, extraction or purification of the molecule of interest. In other words, the ELABELA polypeptide may act as a "flag" peptide. Flag peptides are known in the art and include for example glutathione-S-transferase (GST), 6×His (SEQ ID NO: 97), GAL4 (DNA binding and/or transcriptional activation domains) and β-galactosidase.

The ELABELA combination may be tracked, quantitated, extracted, purified etc by means of any agent capable of binding to an ELABELA polypeptide, such as the anti-ELABELA antibodies disclosed elsewhere in this document.

Where ELABELA combinations are produced as fusion proteins, it may also be convenient to include a proteolytic cleavage site between the ELABELA polypeptide and the protein sequence of interest so as to allow removal of fusion protein sequences, such as a thrombin cleavage site.

The coupling, etc between the ELABELA polypeptide and the molecule of interest in the ELABELA combination may be permanent or transient. It may involve covalent or non-covalent interactions (including ionic interactions, hydrophobic forces, Van der Waals interactions, etc). The exact mode of coupling is not important. Accordingly, where reference is made to "comprising", "conjugation", "coupling", etc, these references should be taken to include any form of interaction between the ELABELA polypeptide and the molecule of interest.

ELABELA Fusion Proteins

For example, the ELABELA combination may be a molecule of interest such as a polypeptide of interest which is provided as a fusion protein with the ELABELA polypeptide. An expression vector may be constructed by standard recombinant DNA technology to include a nucleotide sequence capable of expressing an ELABELA polypeptide together with a nucleotide sequence capable of expressing a polypeptide of interest, such that a fusion protein is expressed comprising the ELABELA polypeptide of interest fused to the polypeptide of interest. The expression vector may be transfected or transformed into a suitable host for large scale production of fusion protein, by means known in the art (and as described in detail elsewhere in this document). Purification of the fusion protein may also be carried out by known means.

Alternatively, or in addition, and as discussed above, the ELABELA polypeptide may be physically associated with the molecule of interest, and attached to it by chemical conjugation.

The ELABELA polypeptide of the combination or conjugate or fusion protein etc may comprise the whole ELABELA molecule, or fragments of it. It may for example comprise the native ELABELA, or any ELABELA polypeptide as disclosed above. The molecule of interest portion may comprise any molecule of interest, whether proteinaceous or not. Where the molecule of interest is proteinaceous in nature (i.e., a polypeptide of interest), it may be conjugated to the ELABELA polypeptide portion by means of covalent bonds, for example, amide bonds (for example, as a fusion protein).

Furthermore, protein-protein conjugation also provides a convenient and alternative choice for conjugation between the ELABELA polypeptide portion and the molecule of interest portion. Any suitable means of conjugation, for example, chemical conjugation may be used to couple the ELABELA polypeptide and the molecule of interest. Crosslinkers, for example, heterobifunctional cross linkers are known in the art, and may be used. Furthermore, other conjugation agents, for example, poly-lactic acid (PLA) and polyethylene glycol (PEG) may also be employed.

Chemical Coupling

As noted above, the ELABELA polypeptide may be coupled to the molecule of interest by a number of methods. Crosslinkers are divided into homobifunctional crosslinkers, containing two identical reactive groups, or heterobifunctional crosslinkers, with two different reactive groups. Heterobifunctional crosslinkers allow sequential conjugations, minimizing polymerization.

Any of the homobifunctional or heterobifunctional crosslinkers presented in the table below may be used to couple the ELABELA polypeptide with the molecule of interest to produce an ELABELA polypeptide-molecule of interest conjugate.

Coupling

The molecule of interest may be attached or coupled to the ELABELA polypeptide by a number of methods. For example, the molecule of interest may be coupled to the ELABELA polypeptide by the use of cyanogen bromide.

Chemical crosslinkers are used to covalently modify proteins for studying ligand-receptor interactions, conformational changes in tertiary structure, or for protein labeling. Crosslinkers are divided into homobifunctional crosslinkers, containing two identical reactive groups, or heterobifunctional crosslinkers, with two different reactive groups. Heterobifunctional crosslinkers allow sequential conjugations, minimizing polymerization.

Homobifunctional

| Reagent | code No. | Modified Group | Solubility | Comments | Refs |
|---|---|---|---|---|---|
| BMME | 442635-Y | —SH | DMF, Acetone | Homobifunctional crosslinker useful for formation of conjugates via thiol groups. | Weston, P. D., et al. 1980. Biochem. Biophys Acta. 612, 40. |
| BSOCOES | 203851-Y | —NH2 | Water | Base cleavable crosslinker useful for studying receptors and mapping surface polypeptide antigens on lymphocytes. | Howard, A. D., et al. 1985. J. Biol. Chem.260, 10833. |
| DSP | 322133-Y | —NH2 | Water | Thiol cleavable crosslinker used to immobilize proteins on supports containing amino groups. | Lee, W. T., and Conrad, D. H. 1985. J. Immunol.134, 518. |
| DSS | 322131-Y | —NH2 | Water | Non-cleavable, membrane impermeable crosslinker widely used for conjugating radiolabeled ligands to cell surface receptors and for detecting conformational changes in membrane proteins. | D'Souza, S. E., et al. 1988. J. Biol. Chem.263, 3943. |
| EGS | 324550-Y | —NH2 | DMSO | Hydroxylamine cleavable reagent for crosslinking and reversible immobilization of proteins through their primary amine groups. Useful for studying structure-function relationships. | Geisler, N., et al. 1992. Eur. J. Biochem.206, 841. 14. Moenner, M., et al. 1986. Proc. Natl. Acad. Sci. USA83, 5024. |
| EGS, Water Soluble | 324551-Y | —NH2 | Water | Water soluble version of EGS that reacts rapidly with dilute proteins at neutral pH. Crosslinked proteins are readily cleaved with hydroxylamine at pH 8.5 for 3-6 hours, 37° C. | Yanagi, T., et al. 1989. Agric. Biol. Chem.53, 525. |
| Glutaraldehyde | 354400-Y | —OH | Water | Used for crosslinking proteins and polyhydroxy materials. Conjugates haptens to carrier proteins; also used as a tissue fixative. | Harlow, E., and Lane, D. 1988. Antibodies: A Laboratory Manual, Cold Spring Harbor Publications, N.Y., p. 349. |
| SATA | 573100-Y | —NH2 | DMSO | Introduces protected thiols via primary amines. When treated with hydroxylamine, yields a free sulhydryl group that can be conjugated to maleimide-modified proteins. | Duncan, R. J. S., et al. 1983. Anal. Biochem.132, 68. |

Heterobifunctional

| Reagent | code No. | Modified Group | Solubility | Comments | Refs |
|---|---|---|---|---|---|
| GMBS | 442630-Y | —NH2, —SH | DMSO | Heterobifunctional crosslinker useful for preparing enzyme-antibody conjugates (for example beta-gal-IgG) and for immobilizing enzymes on solid supports. | Kitagwa, T., et al. 1983. J. Biochem.94, 1160.19. Rusin, K. M., et al. 1992. Biosens. Bioelectron.7, 367. |
| MBS | 442625-Y 442626-Y | —NH2, —SH —NH2, —SH | DMSO, Water | Thiol cleavable, heterobifunctional reagent especially useful for preparing peptide-carrier conjugates and conjugating toxins to antibodies. | Green, N., et al. 1982. Cell 28, 477. |
| PMPI | 528250-Y | —SH2, —OH | DMSO, DMF | Used in the preparation of alkaline phosphatase conjugates of estradiol, progesterone, serine-enriched peptides, and vitamin B12. | Aithal, H. N., et al. 1988. J. Immunol. Methods112, 63. |
| SMCC | 573114-Y 573115-Y | —NH2, —SH —NH2, —SH | DMF, AN Acetonitrile Water | Heterobifunctional reagent for enzyme labeling of antibodies and antibody fragments. The cyclohexane bridge provides extra stability to the maleimide group. Ideal reagent for preserving enzyme activity and antibody specificity after coupling. | Annunziato, M. E., et al. 1993. Bioconjugate Chem.4, 212. |
| SPDP | 573112-Y | —NH2, —SH | DMF, AN Acetonitrile | Introduces protected thiol groups to amine groups. Thiolated proteins can be coupled to a second molecule via an iodoacetamide or maleimide group, or to a second pyridyldisulfide containing molecule. | Caruelle, D., et al. 1988. Anal. Biochem.173, 328. |

Each of these reagents may be obtained from a number of manufacturers, for example, from Calbiochem (code No. in column 2), or Piece Chemical Company.

The molecule of interest may be activated prior to coupling, to increase its reactivity. For example, the molecule of interest may be activated using chloroacetic acid followed by coupling using EDAC/NHS—OH. Molecules of interest may also be activated using hexane di isocyanate to give primary amino group. Such activated molecule of interest may be used in combination with any hetero bifunctional cross linker. The molecule of interest in certain embodiments is activated using divinyl sulfon. Such activated molecule of interest comprise moieties which can react with amino or thiol groups, on a peptide, for example.

The molecule of interest may also be activated using tresyl chloride, giving moieties which are capable of reacting with amino or thiol groups. The molecule of interest may also be activated using cyanogen chloride, giving moieties which can react with amino or thiol groups Peptide Coupling The ELABELA polypeptides may be coupled to the molecule of interest by peptide coupling techniques as described in detail in this section.

Peptides can be obtained by solid phase synthesis methods. The first stage of the technique, first introduced by Merrifield (R. B. Merrifield, Solid Phase Peptide Synthesis. The synthesis of a Tetrapeptide., J. Am. Chem. Soc. 85, page 2149-2154, (1963) and R. B. Merrifield, Solid Phase Synthesis, Science 232, page 341-347, (1986)) consists of peptide chain assembly with protected amino acid derivatives on a polymeric support. The second stage of the technique is the cleavage of the peptide from the support with the concurrent cleavage of all side chain protecting groups to give the crude free peptide. To achieve larger peptides, these processes can be repeated sequentially.

The flexibility of the method allows the synthesis of long, short and branched peptides, including peptides with natural and un-natural occurring amino acids, different linkers and so-called spacers. The spacers typically being of polyethylenglycol, PEG derivatives or polyalkanes or homo poly amino acids. The solid phase synthesis method allows for the preparation of peptides terminated with reactive functionalities, for example free thiols, for chemo selective coupling schemes to the molecule of interest material.

A sequence of amino acids can be repeated in the final peptide sequence to enhance the immunoreactivity with a specific antibody. The repetitive and reactive sequence can be spaced with irrelevant amino acid sequences in a linear peptide. Also, by synthesizing branched or dendritic peptide constructs, like the multiple antigen peptides (MAP), the immuno reactivity can be enhanced.

For a review of the general methodology, including the different chemical protection schemes and solid and soluble supports, see for example G. Barany, N. Kneib-Cordonier, D. G. Mullen, Solid-phase peptide synthesis: A silver anniversary report, Int. J. Peptide Protein Res. 30, page 705-739, (1987), and G. B. Fields, R. L. Noble, Solid phase peptide synthesis utilizing 9-fluorenylmethoxycarbonyl amino acids, Int. J. Peptide Protein Res. 35, page 161-214 (1990)

Other methods for obtaining peptides include enzymatic fragment ligation, genetic engineering techniques as for example site-directed mutagenesis. Genetic engineering of oligonucleotides, PCR-products, or cloned fragments of DNA material encoding relevant amino acid sequence using standard DNA cloning techniques has been a well-established methods of obtaining polypeptides. Alternatively, the peptides can be obtained after isolation from natural sources, such as by protein purification and digestion.

Conjugation of the target molecule (for example, peptide) may be achieved by forming covalent bonds or using strong binding pairs, for example ion binding, biotin-avidin. Examples of other binding entities than streptavidin, avidin and derivatives and biotin and biotin analogues, are the leucine zipper domain of AP-1 (Jun and fos), hexa-his (metal chelate moiety), hexa-hat GST (glutathione S-Transferase) glutathione affinity, trivalent vancomycin, D-Ala-D-Ala, lectines that binds to a diversity of compounds, including carbohydrates, lipids and proteins, for example Con A (*Canavalia ensiformis*), concanavalin A and WGA (Whet germ agglutinin) and tetranectin or Protein A or G. These and other methods are well known to any skilled in the art of conjugation.

Covalent conjugation confers allows increased resistance to degradation.

The coupling method useful for conjugation is dependent on the chemical structure of the target and the partner involved. Typical chemical reagents used are so-called zero length cross linkers, homobifunctional, heterobifunctional or polymeric cross linkers.

Zero length cross linkers like 1-Ethyl-3-(3-dimethylaminopropyl) carbodiimide (EDAC) or 1-cyclohexyl-3-(2-morpholinoethyl)carbodiimide metho-p-toluenesulfonate (CHMC) and other carbodiimides can facilitate direct coupling between for example Glu or Asp to Lysine residues and for example the N terminus of a peptide.

Homobifunctional cross linkers like glutar(di)aldehydes, imidates, bis-diazotized benzidines, bis(imido esters), bis(succinimidyl esters), diisocyanates, diacid chlorides, divinylsulfone or similar, allows amino or hydroxyl groups to be bound covalent together through a short linker molecule. Formaldehyde or glutar(di)aldehyde can also facilitate cross-linking between the ELABELA polypeptide and the molecule of interest.

The use of heterobifunctional cross linkers is described in more detail for cross linking the ELABELA polypeptide to the molecule of interest by a methodology known to any skilled in the art of conjugation.

Heterobifunctional cross linkers allow greater control over the cross-linking than methods which rely on for example homobifunctional cross linkers.

The most common schemes for forming a heteroconjugate involve the indirect coupling of an amine group on one bio molecule to a thiol group on a second bio molecule, usually by a two- or three-step reaction sequence. The high reactivity of thiols and their relative rarity in many biomolecules make thiol groups ideal targets for controlled chemical cross-linking.

If a thiol group is not present, thiol goups can be introduced by several methods. One common method including the use of succinimidyl 3-(2-pyridyldithio)propionate (SPDP) followed by reduction of the 3-(2-pyridyldithio) propionyl conjugate with DTT or TCEP. Reduction releases the chromophore 2-pyridinethione, which can be used to determine the degree of thiolation.

Alternatively, the degree of thiolation can be measured using 5,5'-dithiobis-(2-nitrobenzoic acid) (DTNB, Ellman's reagent) which stoichiometrically yields the chromophore 5-mercapto-2-nitrobenzoic acid upon reaction with a thiol group.

Heterobifunctional cross linkers typically contain an activated carboxyl group at one end which can react with amino groups and a maleimido or iodoacetamide group at the opposite end which reacts readily with the sulfhydryl group of cysteine residues.

Two frequently used heterobifunctional crosslinkers are N-gamma-Maleimidobutyryloxysuccinimide ester (GMBS) and Succinimidyl 4-(N-maleimidomethyl)cyclohexane-1-carbonate (SMCC).

It should be understood, that the cross linker may contain a photoactivated reactive moiety. The photo reactive moiety acts as a masked reactive group. By using a photoactive coupling method, it is possible to bring the target molecule into specific part of for example the molecule of interest before using the photo reactive group for the covalent coupling.

Typically, the peptide is synthesized with a single cysteine residue at either the N- or C-termini. Alternatively, the internal Cys residues or Cys residues on a linker can be used. If the peptide contains no thiol group, then one or more can be introduced using one of several thiolation methods, typically by modifying one of the amino groups.

It should be understood that coupling of target probes, like for example peptides, are not limited by the use of thiol selective coupling schemes.

Other useful chemical moieties for both chemo selective or random conjugation schemes include carboxyl, hydroxyl, aromatic, phenolic or amino groups. Especially amino groups are useful, as they are very reactive at relevant pH, can form strong chemical bonds and are widely distributed in biological material.

The possibility to employ conjugation schemes using the amino group in the N-termini of peptides, including the amino group in the side chain of lysine or polylysine is of special relevance to the compositions and methods described here.

The cross linker is first reacted with the amino groups on the molecule of interest, followed by removal of the unreacted cross linker using for example a decanting or centrifugation. The activated carrier is then reacted with the Cys-containing peptide. Excess peptide is removed using for example a desalting column, dialysis, filtration or centrifugation. The amount of peptide or cross linker attached can be assessed by various direct or indirect analytical methods.

The conjugation sequence can be reversed by first attaching the heterobifunctional cross linker to the peptide, before attaching to thiols on the molecule of interest.

During conjugation reaction, the free thiols are often protected against spontaneous oxidation by the addition of EDTA, EGTA or tributylphosphine or similar or by using a protective atmosphere.

Other methods of covalent cross-linking include the use of homo or heterofunctionel polymeric cross linkers. Examples of reagents include tresyl or vinylsulfone activated dextrans or activated polyacrylic acid polymers or derivatives. Especially divinyl is preferred for activation of for example hydroxyl groups on the molecule of interest, as the resulting second vinylsulfone is highly reactive towards thiols.

The amount of coupled peptide can be determined by several methods, including incorporating one beta-alanine residue immediately adjacent to the cysteine residue on the peptide. Amino acid analysis may then be used to determine the amount of beta-alanine present after purification of the resulting conjugate.

The cross linkers may offer the possibility to include a tracer or detectable moiety. This moiety can be used to measure the amount of cross linker bound to the bio molecule. The tracer can be fluorescent, radioactive, a hapten or any other detectable molecule.

Further Aspects

Further aspects and embodiments of the invention are now set out in the following numbered Paragraphs; it is to be understood that the invention encompasses these aspects:

Paragraph 1.

An ELABELA polypeptide fragment comprising a sequence CXXXRCXXXHSRVPFP (SEQ ID NO: 1), wherein X is an/any amino acid residue, and wherein the polypeptide fragment maintains self-renewal, pluripotency, or both of a stem cell.

Paragraph 2.

The ELABELA polypeptide fragment of Paragraph 1, wherein the fragment does not comprise a sequence of SEQ ID NOs: 60-76.

Paragraph 3.

The ELABELA polypeptide fragment of Paragraph 1, wherein (a) an intramolecular covalent bond is present between the cysteine residues at positions 1 and 6 of SEQ ID NO: 1, or (b) one or both cysteine residues at positions 1 and 6 of SEQ ID NO: 1 comprise a reduced cysteine having a sulfhydryl group.

Paragraph 4.

The ELABELA polypeptide fragment of Paragraph 1, further comprising a label.

Paragraph 5.

The ELABELA polypeptide fragment of Paragraph 4, wherein the label is a radioisotope.

Paragraph 6.

The ELABELA polypeptide fragment of Paragraph 5, wherein the radioisotope is 125I.

Paragraph 7.

The ELABELA polypeptide fragment of Paragraph 1, wherein the polypeptide fragment is derivatized.

Paragraph 8.

The ELABELA polypeptide fragment of Paragraph 1, further comprising a signal sequence.

Paragraph 9.

The ELABELA polypeptide fragment of Paragraph 8, wherein the signal sequence comprises SEQ ID NO: 19.

Paragraph 10.

The ELABELA polypeptide fragment of Paragraph 1, wherein the fragment further comprises seven additional amino acids at the N-terminus of SEQ ID NO: 1, said ELABELA polypeptide fragment having a sequence of SEQ ID NO: 162 (XXXXXXXCXXXRCXXXHSRVPFP), wherein position 1 of SEQ ID NO: 162 is a basic amino acid residue, wherein the X at positions 2-6, 8-10, and 13-15 is an/any amino acid residue, and wherein the polypeptide fragment maintains self-renewal, pluripotency, or both of a stem cell.

Paragraph 11.

The ELABELA polypeptide fragment of Paragraph 10, wherein the fragment does not comprise a sequence of SEQ ID NOs: 181-197.

Paragraph 12.

The ELABELA polypeptide fragment of Paragraph 10, wherein the basic residue at the position 1 is selected from K or R.

Paragraph 13.

The ELABELA polypeptide fragment of Paragraph 1, wherein the fragment further comprises eight additional amino acids at the N-terminus of SEQ ID NO: 1, said ELABELA polypeptide fragment having a sequence of SEQ ID NO: 163 (XXXXXXXXCXXXRCXXXHSRVPFP), wherein position 1 of SEQ ID NO: 163 is a basic amino acid residue, wherein the X at positions 2-7, 9-11, and 14-17 is an/any amino acid residue, and wherein the polypeptide fragment maintains self-renewal, pluripotency, or both of a stem cell.

Paragraph 14.

The ELABELA polypeptide fragment of Paragraph 13, wherein the fragment does not comprise a sequence of SEQ ID NOs: 164-180.

Paragraph 15.

The ELABELA polypeptide fragment of Paragraph 13, wherein the basic residue at the position 1 is selected from K or R.

Paragraph 16.

The ELABELA polypeptide fragment of Paragraph 1, wherein the fragment further comprises eight additional amino acids at the N-terminus of SEQ ID NO: 1, said ELABELA polypeptide fragment having a sequence of SEQ ID NO: 163 (XXXXXXXXCXXXRCXXXHSRVPFP), wherein positions 1 and 2 of SEQ ID NO: 163 are a pair of basic amino acid residues, wherein the X at positions 3-7, 10-12, and 15-17 is an/any amino acid residue, and wherein the polypeptide fragment maintains self-renewal, pluripotency, or both of a stem cell.

Paragraph 17.

The ELABELA polypeptide fragment of Paragraph 16, wherein the fragment does not comprise a sequence of SEQ ID NOs: 164-180.

Paragraph 18.

The ELABELA polypeptide fragment of Paragraph 16, wherein the pair of basic residues at positions 1 and 2 is selected from KK, KR, RK, and RR.

Paragraph 19.

A method of making an ELABELA polypeptide or fragment thereof, the method comprising: (a) expressing a nucleic acid encoding a sequence comprising CXXXRCXXXHSRVPFP (SEQ ID NO: 1) in a cell, wherein X is an/any amino acid residue, and wherein the polypeptide fragment maintains self-renewal, pluripotency, or both of a stem cell; or (b) using chemical synthesis to generate a synthetic polypeptide or fragment thereof comprising CXXXRCXXXHSRVPFP (SEQ ID NO: 1) or a fragment having the sequence of SEQ ID NO: 53, wherein X is an/any amino acid residue, and wherein the polypeptide fragment maintains self-renewal, pluripotency, or both of a stem cell.

Paragraph 20.

The method of Paragraph 19, wherein the cell expressing the nucleic acid encoding a sequence comprising CXXXRCXXXHSRVPFP (SEQ ID NO: 1) is a bacterial, fungal, or yeast cell.

Paragraph 21.

The method of Paragraph 19, wherein the sequence comprising CXXXRCXXXHSRVPFP (SEQ ID NO: 1) is selected from the group consisting of SEQ ID NOs: 2-36.

Paragraph 22.

The method of Paragraph 19, wherein the ELABELA polypeptide or fragment thereof further comprises a label.

Paragraph 23.

The method of Paragraph 22, wherein the label is a radioisotope.

Paragraph 24.

The method of Paragraph 23, wherein the radioisotope is 125I.

Paragraph 25.

The method of Paragraph 19, wherein the polypeptide or fragment thereof is derivatized.

Paragraph 26.

An isolated antibody or antigen-binding fragment thereof that specifically binds to one or more of the following: (a) a polypeptide comprising the sequence CMPLHSRVPFP (SEQ ID NO: 52); (b) a polypeptide comprising the sequence QRPVNLTMRRKLRKHNC (SEQ ID NO: 53); (c) a polypeptide comprising the sequence QRPVNLTMR-RKLRKHNCLQRRCMPLHSRVPFP (SEQ ID NO: 2); and (d) an ELABELA polypeptide comprising the sequence of any of SEQ ID NOs: 1-36.

Paragraph 27.

The isolated antibody or antigen-binding fragment thereof of Paragraph 26, further comprising a label.

Paragraph 28.

An immunoassay kit for measuring or detecting ELA-BELA expression, the immunoassay kit comprising: (a) a coating antigen comprising one or more isolated antibodies or antigen-binding fragments thereof that specifically binds to one or more of the following: (i) a polypeptide comprising the sequence CMPLHSRVPFP (SEQ ID NO: 52); (ii) a polypeptide comprising the sequence QRPVNLTMRRKL-RKHNC (SEQ ID NO: 53); (iii) a polypeptide comprising the sequence QRPVNLTMRRKLRKHNCLQRRCMPLH-SRVPFP (SEQ ID NO: 2); or (iv) an ELABELA polypeptide comprising the sequence of any of SEQ ID NOs: 1-36; and (b) instructions for using said coating antigen.

Paragraph 29.

The immunoassay kit of Paragraph 28, wherein the isolated antibodies or antigen-binding fragments thereof are labelled.

Paragraph 30.

The immunoassay kit of Paragraph 28, further comprising an enzyme labelled reagent, a secondary antibody that specifically binds to the isolated antibodies or antigen-binding fragments, a solid substrate, or any combination thereof.

EXAMPLES

Example 1. Materials and Methods: Accession Codes

The human ELABELA gene and its vertebrate homologs are accessible with the following Ensembl IDs: *Homo sapiens*: ENSG00000248329. *Mus musculus*: ENS-MUSG0000007430. *Gallus gallus*: ENS-GALG00000023444. *Xenopus laevis*: no gene ID exists yet but defined as UniGene Xl.40684. *Danio rerio*: ENS-DARG00000094729.

Example 2. Materials and Methods: Cell Culture and Assays

The Shef4 cell line was used throughout and exhibits standard morphological and surface marker characteristics of hESCs and a normal 46XY karyotype (Inniss and Moore, 2006). Feeder-free hESCs were cultured in clumps in mTSER1 (Stem Cell Technologies) on Matrigel (BD 354277).

Primary human fibroblasts, SW1353 chondrosarcoma (ATCC) and NTERA2 hECs (a gift from Barbara Knowles and Davor Solter) were grown in Dulbecco's modified Eagle's medium (DMEM) with 10% FBS (Hyclone), 2 mM GlutaMAX™ (Invitrogen) and 1 mM sodium pyruvate.

hESCs were dissociated into single cells using Accutase (Stem Cell Technologies) and plated in the presence of 10 µM Y-27632 (ROCK inhibitor) for 12 hours (Watanabe et al., 2007).

For xCELLigence real time growth assays, 4000 cells were plated per well of an E-plate (ACEA Biosciences) with media changes every 48 hours.

Recombinant ELA was added at 2.5 uM (or 10 µg/ml). Cell cycle studies were performed with Click-iT EDU staining kit (Invitrogen) and by performing a double thymidine block (2.5 mM thymidine; 16 hour block, 8 hour release, 16 hour block) followed by DAPI staining for DNA content at the indicated times following release.

To assay the signaling pathway activated by ELA, hESCs were dissociated and plated in mTSER1 for 48 hours, followed by a 2-hour starvation in DMEM/F12. Synthetically produced ELA or $ELA^{RR>GG}$ peptides, dialyzed against PBS to remove any residual synthesis buffers, were added at a final concentration of 5 uM (or as indicate(D) for the indicated period of time. Where applicable, PI3K inhibitors LY294002 (5 uM) and Wortmannin (1 uM) were added 30 minutes before pulsing with ELA peptides. Cells were lysed with PhosphoSafe™ (Millipore) for SDS-PAGE.

Apoptosis assays were performed by plating control and Doxycycline-treated cells without Y-27632 onto matrigel for 6 hours, followed by harvesting and staining for Annexin V and activated CASPASE3.

To induce apoptosis, hESCs were treated with the indicated doses of ActinomycinD (Sigma) or ionizing radiation followed by Aqueous One Cell Titer (Promega) or CAS-PASE GLO3/7 (Promega) assays 12 hours post-treatment.

For insulin replacement assays, SHEF4 or HESC3 hESCs were cultured in TSER-E5 (Stem Cell Technologies) supplemented with TGF-β (5 ng/ml, R&D Systems) and bFGF (100 ng/ml, Invitrogen) with and without INSULIN (10 ug/ml, SIGMA).

Embryoid body differentiation was performed by plating 1 million cells per well of an Aggrewell 400 plate in Aggrewell Medium (Stem Cell Technologies) followed by harvesting and replating into low-adhesion plates (Corning).

After the indicated time periods, embryoid bodies were harvested and RNA extracted using RNeasy kit (Invitrogen). qPCR reactions were carried out using either Universal FastStart SYBR Green Mastermix (Roche) or using the Universal Probe Library system (Roche) in tandem with Taqman Fast Mastermix (Invitrogen). Primer sequences can be found in Table E1.

TABLE E1

List of qPCR Primers

| Trans-cript | Forward (SEQ ID NOs: 98 to 114) | Reverse (SEQ ID NOs: 114 to 131) | UPL Probe |
|---|---|---|---|
| Human ||||
| POU5F1 | agcaaaacccggaggagt tc | ccacatcggcctgtgtata | 35 |
| ELABELA | cacgagtacccttccct ga | ggctgggtgtctttccttc | 35 |
| NANOG | tccagcagatgcaagaac tc | ttgctattcttcggccagt t | 87 |
| GATA4 | ggaagcccaagaacctga at | gctggagttgctggaagc | 69 |

TABLE E1-continued

List of qPCR Primers

| Transcript | Forward (SEQ ID NOs: 98 to 114) | Reverse (SEQ ID NOs: 114 to 131) | UPL Probe |
|---|---|---|---|
| GATA6 | aatacttcccccacaaca caa | ctctcccgcaccagtcat | 90 |
| FOXA2 | cgccctactcgtacatct cg | agcgtcagcatcttgttgg | 9 |
| EOMES | gtggggaggtcgaggttc | tgttctggaggtccatggt ag | 6 |
| BRA | gctgtgacaggtacccaa cc | catgcaggtgagttgtcag aa | 23 |
| NESTIN | tgcgggctactgaaaagt tc | tgtaggccctgtttctcct g | 76 |
| GAPDH | agccacatcgctcagaca c | gcccaatacgaccaaatcc | 60 |
| APLNR | atcttgaccctccctgga at | atggggagactaggctgtg a | 63 |
| PAX6 | aatgggcggagttatgat acc | catatcaggttcacttccg gg | NA |
| SOX17 | ABI Taqman Assay s00751752_s1 | | NA |
| NKX2.5 | ABI Taqman Assay Hs00231763_m1 | | NA |

Zebrafish

| | | | |
|---|---|---|---|
| actin | gatcttcactccccttgt tca | ggcagcgatttcctcatc | NA |
| apln | gctgtgttcagccagtgc t | ttctgccgcaaaggagtc | NA |
| aplnra | cgtctgctactgcttcat cg | gcttttctggtcttcctt gc | NA |
| aplnrb | cctcttgcgctatggact tc | gcctgcaatccagtaggtc t | NA |
| elabela | ttcttccacccgctgtat ct | ccggagcatcataaaacct c | NA |

Example 3. Materials and Methods: shRNA and siRNA-Mediated ELA Knockdown

To generate stable inducible knockdown of ELA in hESCs, the sequence GTGATTCTCGTGCCTCAAC (SEQ ID NO: 132) targeting the 3'UTR of ELA was cloned into pSUPERIOR (Oliogoengine) and nucleofected (Lonza) into Shef4$_{TetR5}$ hESCs (Zafarana et al., 2009). Neomycin-resistant cells were clonally expanded and assayed for doxycycline (20 ng/ml)-inducible knockdown. Data from one representative clone (Shef4$_{TetR5\ shELA}$) are shown in this paper. Shef4$_{TetR5\ shβ2M}$ were derived as previously described (Zafarana et al., 2009). Unless otherwise stated, ELA knockdown was induced on Day-4 with 20 ng/ml doxycycline to generate shELA cells.

Anti-ELA siRNAs were produced by RNase III (New England Biolabs) cleavage of double stranded full-length ELA mRNA produced by T7 in vitro transcription (Applied Biosystems). siRNAs were transfected into hESCs with Lipofectamine RNAiMax (Invitrogen) for 48-72 hours prior to assay.

POU5F1 Knockdown

Inducible knockdown of POU5F1 in Shef4$_{TetR5}$ was performed as previously reported by Zarafana and colleagues (Zafarana et al., 2009). Briefly, Shef4$_{TetR5\ shPOU5F1}$ hESCs were cultured in the presence (shPOU5F1) or absence (Control) of 5 ng/ml doxycycline for the indicated durations and harvested for qPCR analysis.

Example 4. Materials and Methods: Antibodies

Polyclonal antibodies were raised against a human N-terminal epitope (nh2-QRPVNLTMRRKLRKHNC) (SEQ ID NO: 53), C-terminal epitope (CMPLHSRVPFP-cooh) (SEQ ID NO: 53) or whole mature ELABELA peptide with an intramolecular cystine bond (nh2-QRPVNLTMRRKL-RKHNCLQRRCMPLHSRVPFP-cooh) (SEQ ID NO: 2) and peptide-affinity purified from rabbit and goat sera.

For extracellular neutralizing assays, the rabbit α N and α C affinity purified antibodies were dialysed into PBS overnight at 4° C. and added to the hESCs culture at 10 µg/mL. For western blotting and immunofluoresence assays, ELA antibodies were used at 1 µg/mL. All other antibodies are commercially available: TGN-46 (Serotec # AHP500GT); SSEA-3 (Stem Cell Tech #60061AD); TRA-1-60 (BD #560173); SOX17 (R&D # AF1924); POU5F1 (SCBT # sc-5279).

Example 5. Materials and Methods: Embryological Methods

Protocols for fertilization, microinjections, secretion assay and whole-mount in situ hybridization (WISH) are at our protocol website (http://www.reversade.com-a.googlepages.com/protocols/) and are also set out below.

In vitro Fertilization of *Xenopus* Eggs

Nathalie Escande-Beillard, March 2009

This protocol describes the in vitro fertilization of *Xenopus* eggs, to obtain large amounts of synchronous and dejellyed embryos ready for microinjections and experimental manipulations.

Day 1—Inducing Ovulation

1. Proven breeders *Xenopus laevis* pigmented and albinos are purchased from Nasco (http://www.enasco.com/xenopus/).

2. Choose female's breeders with a big belly and a red cloaca as these are usually signs of readiness to lay.

3. Inject 800 units (800 µl) of Human Chorionic Gonadotropin (HCG) into the dorsal lymph sac of a female frog. Inject half volume in each side. Place the needle posteriorly, at the level of the hindlimb near the lateral line sense organs. Penetrate the skin with a firm push and then hold the syringe almost parallel to the back.

4. Place the frogs in separate bucket fill with charcoal-filtered water and cover.

5. Frogs kept at room temperature (23° C.) begin laying eggs about 9-10 hours after induction of ovulation, whereas frogs kept at 15° C. begin laying eggs approximately 14 hours after injection.

6. After ovulation, frog needs to rest 3 months before being induced again.

Day 2—In Vitro Fertilization

1. In the morning, put the female in 1× High Salt Barth's solution diluted with charcoal filtered water. Keep them in separate bucket.

2. After 1-2 hours start to collect eggs. If the frogs lay well, it is possible to collect eggs every 1 hour. To collect eggs use a pipetman outfitted with a 25 ml pipette that has had a little bit of its tip sawed off with a hacksaw. Always have the pipetman set to the slow setting while collecting the eggs. As much as possible try to avoid any perturbations of the eggs at all points during the process of fertilization. Pipet the eggs into a 100 mm glass petri dish, trying to limit as much as possible the amount of buffer, covering about one third the surface of the plate. Carefully pipette off any extraneous buffer.

3. Label glass petri dishes according to which frog the eggs came from on the side of the bottom dish and the top of the lid. It is very important to know which frog gives good eggs.

4. Sacrifice male and excise testes. Keep testis at 4° C. in 1.5 ml eppendorf tube.

5. Draw off as much 1× High Salt Barth as possible using a Pasteur pipette and tilting the dish. Using Kimwipes, suck up as much buffer as possible (keeping the dish tilted).

6. Add about 1 ml of Steinberg's solution to a 1.5 ml eppendorf tube. Cut off a small piece of the testis and mince with scissors in the tube. Add about 5-10 drops of this solution onto the eggs. Mince fresh testis every time.

7. Cover the dish and incubate at room temperature for 5 minutes.

8. Carefully add 0.1× Barth. Submerge any floating eggs with your prewet fingertip. Cover the dish and note the time of fertilization on the dish lid. Sperm enters eggs as you add 0.1× Barth. Incubate for 20 minutes at room temperature. Note the embryos should rotate and the future animal pole (pigmented side) should face up.

9. Decant water, removing excess water with a pasteur pipette. Add fresh Cysteine Solution, gently pushing submerging any floating eggs with your finger (put finger into the cysteine before touching eggs to prevent them from sticking to finger).

Incubate for 8 minutes at room temperature. This step allows the complete removal of the jelly surrounding the eggs.

10. Decant and add fresh Cysteine Solution. Incubate 3 minutes.

11. Decant Cysteine Solution and wash at least 6 times with 0.1× Barth.

12. Incubate the eggs in 0.1× Barth. The embryos cultured at room temperature should be at 2-cell stage, 1 hour 20 minutes after fertilization (step #7).

13. Note that embryos are cultured in 0.1× Barth in 50 mm plastic petri dishes lined with a cushion of 1% agarose solution.

14. Do not forget to return back female in regular tank at the end of day 2.

Solutions

10× High Salt Barth's Solution

Fill a 4 L beaker to 3 L with nanopure water and add following:

| Compound | Amount | Final concentration |
|---|---|---|
| NaCl | 256 g | 1.095 M |
| KCl | 3 g | 10 mM |
| NaHCO3 | 8 g | 24 mM |
| MgSO4•7H2O | 8 g | 8 mM |
| Hepes | 95.2 g | 100 mM |

Add the following dropwise after dissolving each in 25 ml nanopure water:

| Compound | Amount | Final concentration |
|---|---|---|
| Ca(NO3)2•4H2O | 3.2 g | 3.4 mM |
| CaCl2•2H2O | 2.4 g | 4 mM | pH to 7.7 with HCl. Bring to 4 L with nanopure water. When making a 1× dilution, add 1 ml of 5% Ampicillin per liter.

10× Barth's Solution

Fill 500 ml beaker to 350 ml with nanopure water and add following:

| Compound | Amount | Final concentration |
|---|---|---|
| NaCl | 26 g | 889 mM |
| KCl | 0.38 g | 10 mM |
| NaHCO3 | 1 g | 24 mM |
| Hepes | 11.9 g | 100 mM |

Add the following dropwise after dissolving each in 25 ml nanopure water:

| Compound | Amount | Final concentration |
|---|---|---|
| MgSO4•7H2O | 1 g | 8 mM |
| Ca(NO3)2•4H2O | 0.4 g | 3.3 mM |
| CaCl2•2H2O | 0.3 g | 4.1 mM |

Bring to pH 7.6 with NaOH. Bring to 500 ml with nanopure H2O. When making the 1× and 0.1× dilutions, add 1 ml of 5% Ampicillin per liter.

10× Steinberg's Solution

Fill 1 liter beaker to 800 ml with nanopure water

| Compound | Amount | Final concentration |
|---|---|---|
| NaCl | 34 g | 581 mM |
| KCl | 0.5 g | 6.7 mM |
| Ca(NO3)2•4H2O | 0.8 g | 3.3. mM |
| MgSO4•7H2O | 2 g | 8 mM |
| Kanamycin | 0.1 g | 0.01% |
| Tris Base | 6 g | 50 mM | pH to 7.35-7.45 with HCl. adjust volume to 1 liter with nanopure H2O

2% Cysteine Solution

Fill a 1 L beaker to 800 mL with 0.1× Barth's. Add 20 g L-Cysteine Hydrochloride Monohydrate. pH to 7.8 with NaOH. Bring to 1 liter with 0.1× Barth's 5% Ampicillin Dissolve 5 grams Ampicillin in 100 ml nanopure H2O. Filter sterilize, make 1 ml aliquots in 1.5 ml eppendorf tubes, and store at −20° C.

Preparation of Agarose Petri Dishes

Dissolve Agarose to 1% in water, melt in microwave and add Kanamycin (100 μg/ml). Pour petri dishes with 5 ml of the Agarose solution. Once cooled down and congealed at room temperature, petri dishes are stored at 4° C.

Chemicals

1. Human Chorionic Gonadotropin 10 000 units/vial, reconstituted with 10 ml of water.

Keep at 4° C. Sigma # CG10-IVL.

2. Cysteine Hydrochloride Monohydrate. Sigma # C7880-500G.

3. Ampicillin. Sigma # A9518.

Microinjection of *Xenopus* Embryos

This protocol describes the microinjections of *Xenopus* embryos for gain- and loss-of-function studies using Morpholinos, DNA, mRNA, Protein or other chemicals.

Day 1—Injections

1. Embryos for micro-injections are obtained following In Vitro Fertilization of *Xenopus* Eggs described here: http://www.reversade.com-a.googlepages.com/protocols 2. Pull needles made of borosilicate glass capillaries using a micropipette puller. Place pulled needles in safe box as they are delicate.

3. Link needle to Microinjector with plastic tubing and place assembled needle onto Micromanipulator.

4. Under a Stereoscopic Microscope calibrate needle by successively cutting small segments of its fine end with forceps. 1× Barth solution can be used for calibration purposes.

For cytoplasmic injections calibrate needle so that it delivers 4 nl in 1 second with an injection pressure between 20 and 25 PSI. Needles that are too thin will clog easily and be difficult to fill. Needles that are too large will damage embryos upon injection and lead to leakage of cytoplasm.

4'. For blastocoele injections calibrate needle so that it delivers 50 nl in 2 seconds with an injection pressure between 20 and 25 PSI.

5. Once calibrated, empty and start filling needle with desired solution.

To fill, carefully place needle into yellow tip containing a few uL of solution to inject. Monitor progression of solution inside capillary. Stop before air is drawn.

6. Prepare agarose Petri dish filled with 1× Barth. Gently pipette embryos with eyedropper into 1× Barth Dish. Adjust magnification, focus, lighting, chair position and rest your forearms on bunch. You are ready to inject.

7. Bring filled needle close to embryo, hold embryo in position with forceps, and gently insert needle through chorion and cytoplasmic membrane. Once inside, inject by pressing foot pedal linked to Microinjector. In 1 second 4 nL will be delivered to the embryo. Remove needle by holding embryo. Microinject each blastomere at the 4-cell stage if all embryo is targeted.

7'. For blastocoele injections, culture embryo until they reach stage 7 to 8. Place in 1× Barth and microinject in blastocoele cavity, situated just underneath animal cap. You should see embryo expand as 50 nl are delivered into blastocoele.

8. Once embryos have been injected in 1× Barth, transfer them into fresh 0.1× Barth dish. Label lid of dish. Do not forget to keep uninjected embryos. Control embryos should be from the same fertilization batch and mother frog.

9. Culture embryos in 0.1× Barth at 13° C. (not below) to slow down development or up to 22° C. for faster development.

Day 2—Look after Your Embryos

1. Everyday remove dead embryos. De-chorionate using fine forceps and place embryos in fresh dish filled with 0.1× Barth using an eyedropper.

2. By stage 20, it is preferable to culture embryos in 1× Steinberg.

3. To fix embryos, drop embryos with eyedropper in 2 ml of MEMFA in glass vial. Fix for 2 hours at room temperature or overnight at 4° C. with gentle rocking.

4. Dehydrate through a methanol series (25%, 50%, 75%, 2×100% in PBS 1×). Embryos can be stored in 100% methanol at −20° C.

5. For *Xenopus* Whole Mount In Situ Hybridization follow protocol described here: http://www.reversade.com-a.googlepages.com/protocols Solutions 10× Barth's Solution Fill 500 ml beaker to 350 ml with nanopure water and add following:

| Compound | Amount | Final concentration |
| --- | --- | --- |
| NaCl | 26 g | 889 mM |
| KCl | 0.38 g | 10 mM |
| NaHCO3 | 1 g | 24 mM |
| Hepes | 11.9 g | 100 mM |

Add the following dropwise after dissolving each in 25 ml nanopure water:

| Compound | Amount | Final concentration |
| --- | --- | --- |
| MgSO4•7H2O | 1 g | 8 mM |
| Ca(NO3)2•4H2O | 0.4 g | 3.3 mM |
| CaCl2•2H20 | 0.3 g | 4.1 mM |

Bring to pH 7.6 with NaOH. Bring to 500 ml with nanopure H2O. When making the 1× and 0.1× dilutions, add 1 ml of 5% Ampicillin per liter.

10× Steinberg's Solution

Fill 1 liter beaker to 800 ml with nanopure water

| Compound | Amount | Final concentration |
| --- | --- | --- |
| NaCl | 34 g | 581 mM |
| KCl | 0.5 g | 6.7 mM |
| Ca(NO3)2•4H2O | 0.8 g | 3.3. mM |
| MgSO4•7H2O | 2 g | 8 mM |
| Kanamycin | 0.1 g | 0.01% |
| Tris Base | 6 g | 50 mM | pH to 7.35-7.45 with HCl. Adjust volume to 1 liter with nanopure $H_2O$

10×MEM

To make 1 L

| | | |
| --- | --- | --- |
| 209.26 g | MOPS (pH 7.4) | 100 mM |
| 9.36 g | EGTA | 2 mM |
| 1.2 g | MgSO4 | 1 mM |

Adjust pH to 7.4 with 10 M NaOH, filter and store at 4° C.

MEMFA 1×

Prepare a small volume of 1× each time. For 100 ml: 10 ml of 10×MEM, 10 ml of Formaldehyde (37%), 80 ml of Water.

Agarose Petri Dishes

Dissolve Agarose to 1% in water, melt in microwave and add Kanamycin (100 µg/ml). Pour Petri dishes with 5 ml of the Agarose solution. Once congealed at room temperature, Petri dishes are stored at 4° C.

Instruments

Needle puller: SUTTER INSTRUMENT CO. Flaming/brown Micropipette puller MODEL P-97

Needles: World Precision Instruments, Inc. Borosilicate Glass Capillaries Item number: TW100-6

Microinjectors: Harvard APPARATUS PLI-100 OR NARISHIGE IM 300 Microinjector

Micromanipulator: Singer Instruments Mk1 Micromanipulator

Stereomicroscope: Leica MZ12.5 or MZ9.5

Light Source: Leica CLS 150X

Forceps: Rustless DUMOXEL #3 or #5 FST by DUMONT Switzerland

Eyedropper: Fisher Scientific Pipet Straight Med Drop FIS #13-700

Glass Vial: Fisher Scientific Vial ST W/Closure 1DR FIS #03-399-25B

*Xenopus* Whole Mount In Situ Hybridization

ISH is a method used to determine the spatio-temporal expression pattern of a gene.

Synthesis of Antisense RNA Probe

1. Linearize DNA plasmid by digesting with a suitable enzyme. Check for complete digestion by running 1 µl of DNA on agarose gel. **All conditions should be RNase free: use gloves and filtered tips.
2. Phenol:Chloroform extract and ethanol precipitate DNA or use a Kit for cleaning DNA.
3. Resuspend DNA in a suitable volume of RNase free water to get approximately 0.5 or 1 µg/µl. Measure DNA concentration (nanodrop).
4. Set up transcription reaction: 1000-2000 ng DNA, 4 µl 10× Transcription Buffer, 4 µl Labelling Mix (Digoxigenin), 1 µl RNA guard (40 U/µl), 4 µl RNA polymerase (20 U/µl), RNAse free Water to 40 µl
5. Incubate for 4-5 hours at 37° C.
6. Treat with DNase for 20 min at 37° C. (1 unit of enzyme/µg DNA).
7. Remove unincorporated, free nucleotides with Quick Spin Columns:
   First remove top cap from column and then bottom cap to avoid air bubbles.
   Spin for 5 minutes at 4° C., 1800 rpm in a swing bucket centrifuge.
   Remove eluate and spin for an additional 5 minutes.
   Put columns in new (labeled) tubes, add transcription reaction making sure to add it directly on the center of the column while not disrupting resin with the pipette tip.
   Spin for 15 minutes at 4° C., 1800 rpm.
8. Quantify RNA yield with nanodrop to determine how much to use for the ISH.
9. Run a gel with 1 µl to verify expected size and quality of probes General Notes All recipes and most chemicals used are listed with their vendor and catalog number at the end of this protocol. Very important to work in RNAse free conditions. Use gloves and filtered tips from the fixation step to the end of hybridization.

Day 1

All steps in Day 1 are done ON ICE except for Proteinase K treatment (step #3). Use at least 2 ml of buffer for each wash, unless indicated.

1. Rehydrate the embryos through a methanol series in PBSw (75%, 50%, 25%). Each rehydration step is incubated for 5 minutes.
2. Wash 3× with PBSw, 5 minutes each.
3. Treat embryos for 8 minutes with 10 µg/ml Proteinase K in PBSw at room temperature (1 ml per tube). Staining for highly expressed genes requires less digestion, but longer digestion may help for genes with lower expression. Do not exceed 8 minutes !
4. Stop digestion by washing with 2 mg/ml glycine in PBSw.
5. Do a fast wash with PBSw, and then wash 2× with PBSw, 5 minutes each.
6. Refix embryos in 5 ml of 4% paraformaldehyde/0.2% glutaraldehyde in PBSw for 15 minutes. Make the buffer fresh each time.
7. Do a fast wash with PBSw, and then wash 3× with PBSw, 5 minutes each.
8. Wash in 1 ml of 50% PBSw/50% Hybridization Solution for 3 minutes.
9. Wash in 1 ml of Hybridization Solution (100%) for 3 minutes. Embryos can also be stored at this step in Hybridization Solution at −20° C.
10. Replace 1 ml Hybridization Solution with 400 µl Hybridization Solution and prehybridize for 3 hours at 65° C.
11. Denature appropriate amount of probe in 100 µl Hybridization Solution at 95° C. for 5 minutes. Put on ice, vortex and add this mix to the embryos and hybridize overnight at 70° C.

Day 2

1. Remove probe/hybridization mix and replace with 800 µl Hybridization Solution. Wash for 5 minutes at 70° C.
2. Add 400 µl 2×SSC (pH4.5) to each vial. Incubate 5 minutes at 70° C.
3. Repeat the previous step 2 more times (final volume=800 µl+400 µl+400 µl+400 µl=2000 µl). Incubate at 70° C. for 5 minutes each time.
4. Remove the mix and wash 2× with 2×SSC (pH7)/0.1% CHAPS at 70° C. for 30 minutes.
5. Wash 2× in MAB at room temperature for 10 minutes each.
6. Wash 2× in MAB at 70° C. for 30 minutes each.
7. Wash 2× in PBS at room temperature for 10 minutes each.
8. Wash in PBSw at room temperature for 5 minutes.
9. Incubate the embryos in 1 ml Antibody Buffer (without antibody) at 4° C., rocking, for a minimum of 2 hours.
10. At this time also pre-block the antibody in Antibody Buffer at 4° C., rocking for 2 hours: Anti-Dig—Alkaline Phosphatase dilute 1:5000 from a stock of 150 units/200 ul. Anti-Dig—Peroxidase dilute 1:200 from a stock of 150 units/ml.
11. Replace Antibody Buffer with 1.5 ml of pre-blocked antibody. Incubate with rocking at 4° C. overnight. Check embryos to make sure all are immersed in solution (not stuck in lid of glass).

Day 3

1. Fast wash embryos with 0.1% BSA in PBSw.
2. Wash 5× in 0.1% BSA in PBSw, with rocking, 1 hour each wash at room temperature.
3. Wash 2× in PBSw for 30 minutes each, at room temperature.
4. Wash 2× in AP1 Buffer for BM Purple staining for 10 minutes each.
5. Replace AP1 Buffer with 1 ml BM Purple, cover with Aluminium foil and incubate with rocking until desired staining is reached. Check embryos to make sure all are immersed in solution (not stuck in lid of glass). Staining time will vary depending on the level of expression and probe quality. It is recommended to let the reaction take place at 4° C., overnight. At room temperature embryos will tend to get more background.

Day 4

1. Stop staining reaction by washing 2 times in Stop Solution for 15 minutes each. Rinse caps as well.
2. Dehydrate through a methanol series (25%, 50%, 75%, 2×100%). Embryos can be stored in methanol at −20° C.
3. Optional: to remove pigmentation or excess background and to enhance contrast, embryos can be bleached with 3 ml of fresh bleaching solution. To speed up the process, place tubes on aluminium foil and under intense neon light several hours to overnight.
4. Put back embryos in methanol 100%.

Solutions

When diluting 10× stock solution use DEPC treated water and filter. All other buffers are made using DEPC treated water and then filter.

DEPC Treated Buffers or Water

Add 0.1% DEPC. Incubate with agitation until it is completely dissolved and autoclave.

10×PBS 80 g NaCl, 2 g KCl, 14.4 g Na$_2$HPO4, 2.4 g KH2PO4, 800 ml distilled Water (DDW). Dissolve, pH to 7.4, add DDW to 1 L, DEPC treat and autoclave.

PBSw

PBS with 0.1% Tween-20. DEPC treat and autoclave.

20×SSC 175.3 g NaCl, 88.2 g Sodium Citrate, 800 ml DDW. Dissolve, pH to 7.0, add DDW to 1 L, DEPC treat and autoclave.

4% Paraformaldehyde

Dissolve paraformaldehyde in fresh PBS (4 g for 100 ml). Heat at 60° C. and mix until completely dissolved. Cool on ice, filter, aliquot and store at −20° C.

Hybridization Solution

Make 1 L, filter, aliquot and store at −20° C. 10 g Boehringer Block, 500 ml Formamide, 250 ml 20×SSC. Heat at 65° C. for 1 hour. 120 ml DEPC treated water, 100 ml Torula RNA (10 mg/ml in water; filtered), 2 ml Heparin (50 mg/ml in 1×SSC), 5 ml 20% Tween-20, 10 ml 10% CHAPS, 10 ml 0.5M EDTA

MAB 100 mM Maleic Acid, 150 mM NaCl pH 7.5

Boehringer Blocking Solution (10%)

Dissolve Boehringer blocking reagent in maleic acid buffer (MAB) (10 g for 100 ml). Heat and vortex frequently to dissolve completely. Store at −20° C. as a stock solution.

Antibody Buffer

10% heat inactivated goat serum, 10% Boehringer blocking stock solution. 80% PBSw. Heat at 70° C. for 10 minutes, vortex, cool on ice and filter. Aliquot and store at −20° C.

AP1 Buffer 0.1M NaCl, 0.1M Tris pH 9.5, 50 mM MgCl2

Stop Solution 100 mM Tris pH 7.4, 1 mM EDTA

Bleaching Solution

2/3 Methanol 100%, 1/3 Hydroxide Peroxide 31.5% (final 10.5%), Make fresh each time.

Chemicals for Making the Probe

Dig RNA Labelling Mix (10×)—Roche #1277073, Flu RNA Labelling Mix (10×)—Roche #1685619, Transcription Buffer (10×)—Roche #1465384, RNA Guard—Roche #3335399, T3 RNA Polymerase—Roche #1031163, T7 RNA Polymerase—Roche #881767, SP6 RNA Polymerase—Roche #810274, Quick Spin Columns—Roche #1274015, QIAquick Gel Extraction Kit—Qiagen #28706

Chemicals for ISH

Boehringer Block—Roche #1096176, Proteinase K—Gibco #25530-049, Anti Dig-AP—Roche #1093274, Anti Flu-AP—Roche #1426338, Anti Dig-POD—Roche #1207733, Anti Flu-POD—Roche #1426346, BM Purple—Roche #1442074, Hydrogen Peroxide 31.5%—Calbiochem #386790.

ZFNs were purchased from Sigma-Aldrich. 250 pg of mRNAs encoding the ZFN pair were injected into 1-cell stage embryos. ZFN binding sites within exon 1 are as follows: 5'_TCCACCCGCTGTATCT_3' (SEQ ID NO: 133) and 5'_GCTGCTGCTGACAGT_3' (SEQ ID NO: 134). Sequencing primers flanking the mutation sites are: forward 5'_AACACTTGCTGAGAGCGACAG_3' (SEQ ID NO: 135), reverse 5'_AGATGTGGTGGTGTTGAGTAGC_3' (SEQ ID NO: 136). For ela overexpression, 200 pg of SP6-transcribed zebrafish ela capped mRNA (Applied Biosystems) was injected into 1-cell stage zebrafish embryos. Translation blocking MOs used for aplnra and aplnrb have been described previously (Scott et al., 2007; Zeng et al., 2007) and were purchased from Gene tools (Oregon, USA). Embryos were injected at 1-cell stage with a combination of 1 ng of aplnra MO and 0.5 ng of aplnrb MO (Zeng et al., 2007). Information on probes used for q-PCR and WISH can be found in Tables E1 and E2. Zebrafish embryos at 100% epiboly were dechorionated and processed for western blotting as previously described (Link et al., 2006). For the *Xenopus* secretion assay, 16 ng of SP6-transcribed human ELA capped mRNA (Applied Biosystems) was injected into each cell of 4-cell stage embryos. At stage 8, embryos were dechorionated and dissociated in CMFM medium with 5 mM EDTA. Cell pellets of 10 embryos were transferred into 1.5 mL tubes and allowed to secrete for 24 hours at room temperature in 40 µl of fresh CMFM medium with or without BFA. The conditioned supernatant was carefully depleted of all cells before SDS-PAGE electrophoresis on 16.5% Tris-Tricine precast gels (BioRad).

ISH Probes

TABLE E2

In situ Hybridisation Probes.

| | Forward (SEQ ID NOs: 137 to 140) | Reverse (SEQ ID NOs: 141 to 144) |
|---|---|---|
| aplnra | atggagccaacgccggaat | tcacactttggtggccagc |
| aplnrb | atgaatgccatggacaacat | tcacaccttcgtagccagc |
| cmlc1 | acacacatcccagccttttc | ccaatttcattcggcaatct |
| ela | ccatccctcagaggacagag | catgtttggcagcagtagga |

| | References |
|---|---|
| bra | (Schulte-Merker et al., 1994) |
| gata5 | (Reiter et al., 1999) |
| scl | (Schoenebeck and Yelon, 2007) |
| sox17 | (Alexander and Stainier, 1999) |

Example 6. Materials and Methods: ELISA

For sandwich ELISA assays, goat a C antibody (4 µg/ml) was used as the capture antibody and blocked with 3% BSA in PBS-Tween (0.05% v/v). hESCs were cultured for 24 hours in mTSER1 and supernatants harvested and incubated with the capture antibody for 1 hour at room temperature. After 5 washes with PBST, rabbit α C (0.8 µg/mL) followed by anti-rabbit HRP (Jackson Immunolabs, 0.12 µg/ml) in 3% BSA/PBST were used for detection with 3,3',5,5'-Tetramethylbenzidine chromogenic substrate. Recombinant ELA peptide of known concentration (Pierce BCA Protein Assay kit) was used to generate a standard curve.

Example 7. Materials and Methods: AP-ELA Binding Assay

An AP-ELA fusion construct was generated by cloning the mature C-terminal 32-mer of ELA in frame with the 3' end of the alkaline phosphatase ORF containing an N-terminal signal sequence from Xenopus Chordin (Reversade and De Robertis, 2005). This construct was transfected into 293T cells with Fugene HD (Promega) and allowed to secrete for 48 hours into serum-free media (Pro293a CDM, Lonza). The resulting supernatant was incubated with test cells for 3 hours, washed 3 times with PBS, lysed, and heated at 65° C. to inactivate endogenous alkaline phosphatases. Lysates were then incubated with BM Purple (Roche) at 37° C. for chromogenic development.

Example 8. Materials and Methods: Statistical Analysis

To analyze the statistical significance of differences between group means, two-tailed unpaired Student's T-test was used throughout the study. Significance levels are denoted by * ($p<0.05$);  ($p<0.01$), * ($p<0.001$).

Unless otherwise indicated, all values were expressed as mean±SEM. Comparison of means were performed using two-tailed Student's unpaired t-test in Prism GraphPad, with significance levels indicated as follows: n.s. $p>0.05$; * $p\leq0.05$;  $p\leq0.01$; * $p\leq0.001$.

Example 9. Materials and Methods: DNA Constructs and Site-Directed Mutagenesis Zebrafish aplnra, aplnrb and elabela ORFs were cloned from 80%-epiboly cDNA into vector pCS2+ between restriction sites BamHI and XbaI. Human APLNR and GPR15 ORFs were cloned from human genomic DNA into pCS2+ between restriction sites BamHI and XbaI. Primers used can be found on Table E3. aplnrb$^{grinch}$ (aplnb$^{W90L}$) was generated using QuikChange Site-directed Mutagenesis kit (Stratagene), with the following primer pair:

(SEQ ID NO: 145)
5'_CTTTGTGGTGACCCTGCCCCTGTTGGCCGTCTACACTGCTCTG_3'
and (SEQ ID NO: 146)
5'_CAGAGCAGTGTAGACGGCCAACAGGGGCAGGGTCACCACAAAG_3'.

Cloning Primers

TABLE E3

List of cloning primers

| Forward (SEQ ID NOs: 147, 148, 137, 138 and 149) | Reverse (SEQ ID NOs: 150, 151, 141, and 152) |
|---|---|

| Human | | |
|---|---|---|
| APLNR | atggaggaaggtggtgat tttga | ggagacccttgtggttgactag |
| GPR15 | atggacccagaagaaact tcag | ttagagtgacacagacctcttcc |
| Zebrafish | | |
| aplnra | atggagccaacgccgg aat | tcacactttggtggccagc |
| aplnrb | atgaatgccatggaca acat | tcacaccttcgtagccagc |
| ela | atgagattcttccacccgc | tcaagggaaaggtactctggag |

Example 10. Materials and Methods: siRNA-Mediated ELA Knockdown

Anti-ELA siRNAs were produced by RNase III (New England Biolabs) cleavage of double stranded full-length ELA mRNA produced by T7 in vitro transcription (Applied Biosystems). siRNAs were transfected into hESCs with Lipofectamine RNAiMax (Invitrogen) for 48-72 hours prior to assay.

Example 11. Materials and Methods: POU5F1 Knockdown

POU5F1 is also known as OCT-4. Inducible knockdown of POU5F1 in Shef4$_{TetR5}$ was performed as previously reported by Zarafana and colleagues (Zafarana et al., 2009). Briefly, Shef4$_{TetR5\ shPOU5F1}$ hESCs were cultured in the presence (shPOU5F1) or absence (Control) of 5 ng/ml doxycycline for the indicated durations and harvested for qPCR analysis.

Example 12. Materials and Methods: Luciferase Reporter Assay

The ELA promoter situated between coordinates chr4: 165,796,806-165,798,359 (hg19) was amplified from human genomic DNA and cloned upstream of a firefly luciferase reporter gene in pGL3basic (Promega) to generate pGL3-ELA$_{promoter}$. To generate pGL3-ELA$_{promoter+POU5F1enhancer}$, the POU5F1 enhancer region situated between coordinates chr4:165,787,570-165,788,797 (hg19) containing several POU5F1 putative binding sites as predicted by TRANSFAC (Matys et al., 2006) was cloned from human genomic DNA and inserted 5' of the ELA promoter in pGL3-ELA$_{promoter}$. These constructs were nucleofected into hESCs (Human Stem Cell Nucleofector® kit, Lonza) together with pRL-CMV (Promega) for 24 hours. Normalized firefly activity was measured using Dual-Glo® Luciferase Assay System (Promega).

Example 13. Materials and Methods: Teratoma Analysis

Shef4$_{TetR5-shELA}$ cells were cultured in the presence (shELA) or absence (Control) of 20 ng/ml doxycycline for 3 passages (4 days/passage). Cells were harvested with Accutase (Stemcell Technologies) and resuspended in 1 part Matrigel to 2 parts mTSER1. 10 million cells in 200 μl were injected subcutaneously into the right hind paunches of SCID mice. shELA-injected mice were fed doxycycline (20 μg/ml) for 3 weeks following injection. Mice were sacrificed 60 days post-injection for tumor analysis.

Example 14. Materials and Methods: Directed Endoderm Differentiation

Shef4$_{TetR5-shELA}$ and Shef4$_{TetR5-sh\beta2M}$ cells were cultured in the presence (shELA and shβ2M respectively) or absence (Control) of 20 ng/ml doxycycline for 1 passage (4 days) and dissociated with Accutase. 0.6 million cells were plated into each well of a matrigel-coated 6 well dish in the presence of 10 uM Y-27632 in mTSER1. 24 hours later, the media was changed to Endo differentiation media 1 [RPMI 1640 (Gibco), 1× B-27 supplement (Invitrogen), 50 ng/ml of Activin A (R&D Systems), 25 ng/ml BMP4 (R&D Systems) and 50 ng/ml bFGF (Invitrogen)] for 3 days. On day 3, the media was changed to Endo differentiation media 2 (RPMI 1640, B27, 50 ng/ml Activin) for 2 more days of culture. Rescue experiments were performed by adding 2.5 uM of ELA peptide to Shef4$_{TetR5-shELA}$ concurrently with doxycycline up to day 3, when the ELA peptide is no longer necessary as judged by downregulation of endogenous ELA.

On day 5, cells were fixed with 4% paraformaldehyde and stained with a SOX17 (AF1924, R&D Systems) and DAPI. For each well, three different randomly selected fields were imaged and the number of nuclei staining positive of SOX17 and DAPI were counted using a custom macro in ImageJ. A minimum of two wells per condition was used for each experiment, and a minimum of two independent experiments were performed to generate the results.

Example 15. Materials and Methods: shRNA-Mediated Knockdown of APLNR

Lentiviral constructs encoding shRNA hairpins were prepared as previously described (Tiscornia et al., 2006a). Briefly, L-CMV-GFP-NheI vector was modified by replacing the CMV-GFP with PGK-GFP-P2A PURO cassette for stable expression in hESCs. Validated shRNA sequences (shAPLNR-1: 5' ACACGTACCGGGACTATGA 3' (SEQ ID NO: 153), shAPLNR-2: 5' CCATCATGCTGACCTGTTA 3' (SEQ ID NO: 154) and Control: 5' GACCTCTGCGC-CTAATTAT 3' (SEQ ID NO: 155)) were cloned into NheI site along with the along with H1 promoter. Lentiviral particles were prepared as described (Tiscornia et al., 2006b). HES3 human embryonic stem cells were transduced with 2TU of lentiviruses and selected with 2 ug/ml puromycin for 2 weeks on feeder free culture system.

Example 16. Materials and Methods: Mesoendoderm Differentiation of hESC

To obtain hESC-derived cells that express APLNR, we adopted a protocol for cardiac differentiation, which was stopped at Day 3 when APLNR expression peaks (Lian et al., 2013). We refer to this intermediary cell type as Day 3-differentiated mesoendoderm. Briefly, Shef4 and HES3 hESCs were dissociated with Accutase, and 0.14 million cells were plated into each well of a Matrigel-coated 24 well plate in the presence of 5 μM Y-27632 in mTSER1. The media was changed daily for 4 days with mTSER1 until the cells became 90% confluent. On Day 0, mTSER1 was then replaced with differentiation media [RPMI 1640, B-27 supplement with no insulin (Invitrogen)] with 9 μM of GSK3β inhibitor CHIR99201 (BioVision) for 24 hours. The cells were further grown for 2 days in RPMI+B27 without insulin until Day 3, when they were used for qPCR, flow cytometry and AP-binding assays.

Example 17. Materials and Methods: Flow Cytometry

Cells were resuspended to 2.5 million/ml and stained with 5 μg/ml of a APLNR (mAB856, R&D Systems) in PBS/5% FBS/1 mM EDTA for 30 minutes on ice, followed by wash in buffer, and stain with a mouse-IgG-Alexa Fluo488 (Molecular Probes) for 30 minutes on ice. Flow cytometry was carried out on LSRII (Becton Dickinson) and data analysis was performed with FlowJo (Treestar Inc.).

Figure 9B:
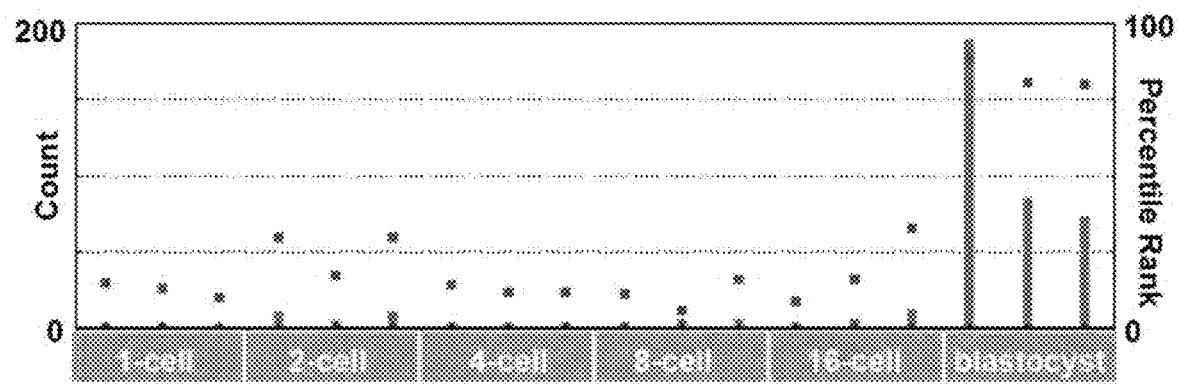
Figure 9C:
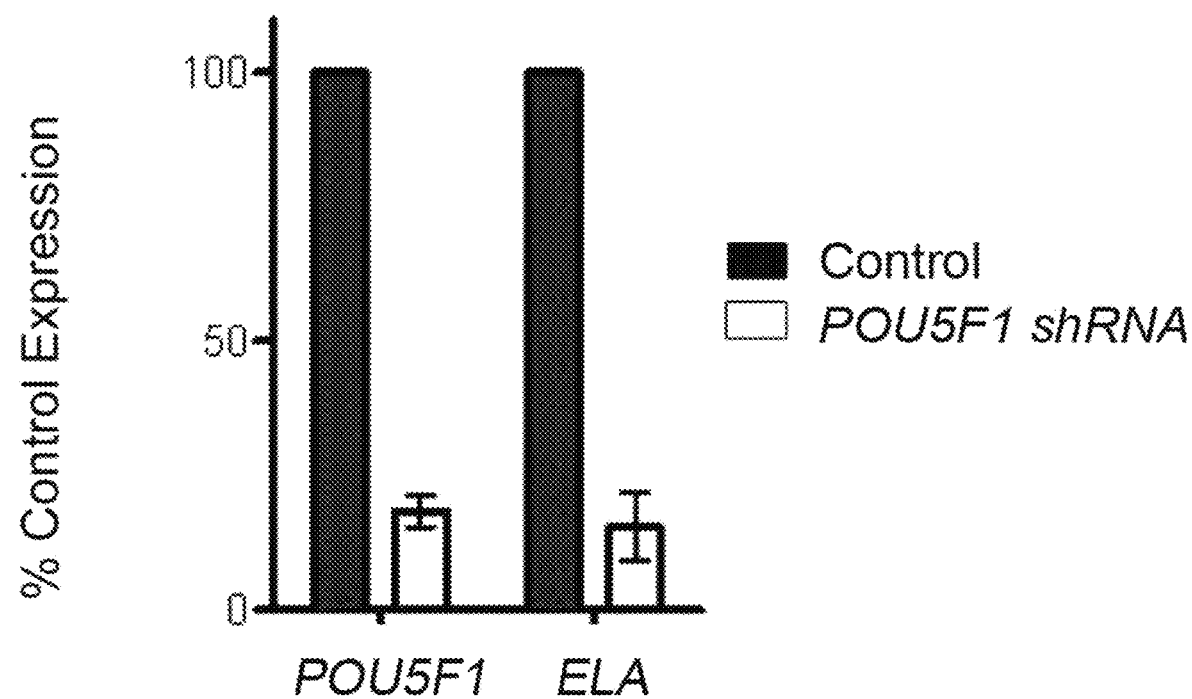
Figure 9D:
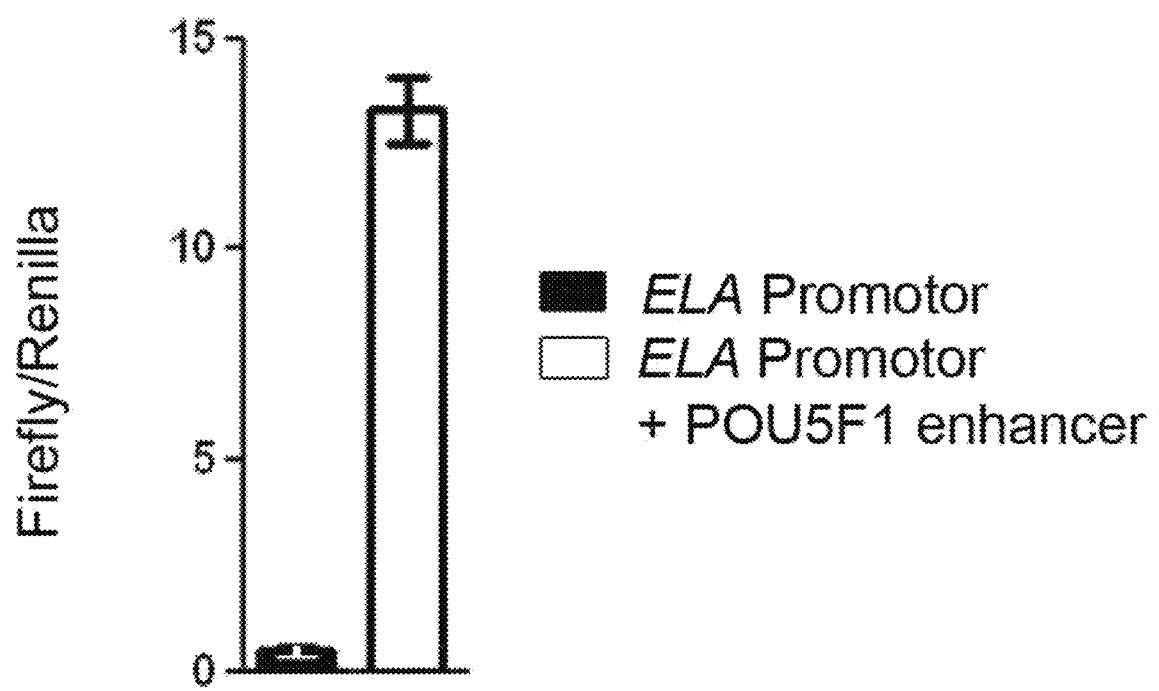
Figure 9E:
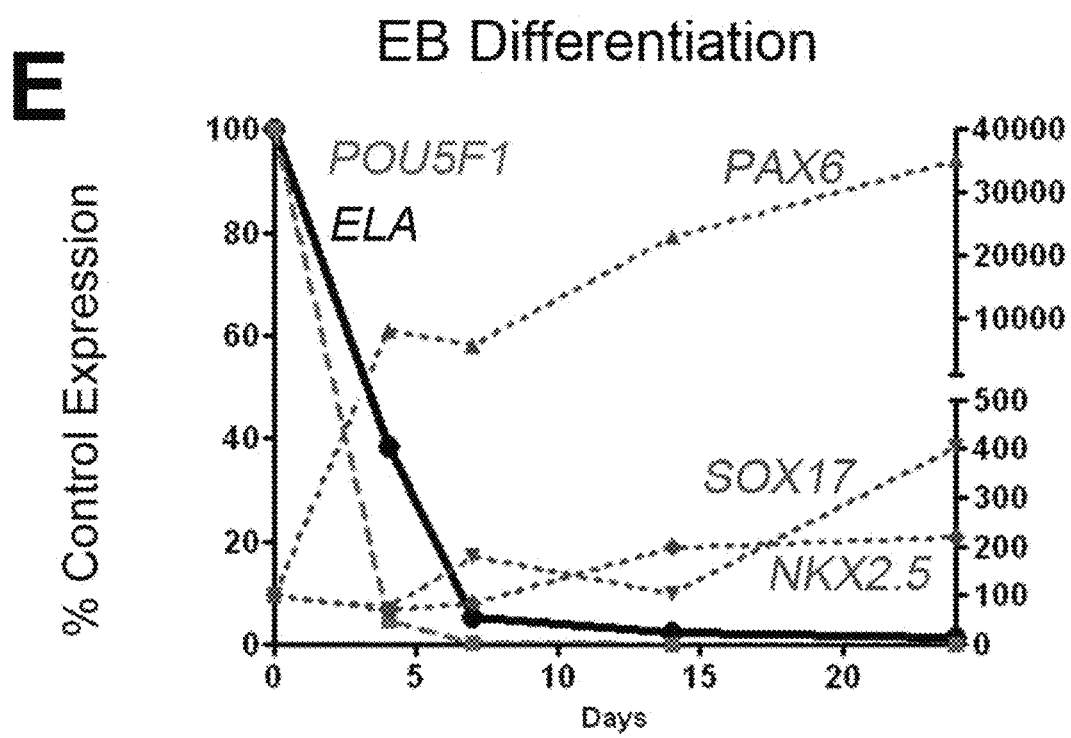
Figure 9F:
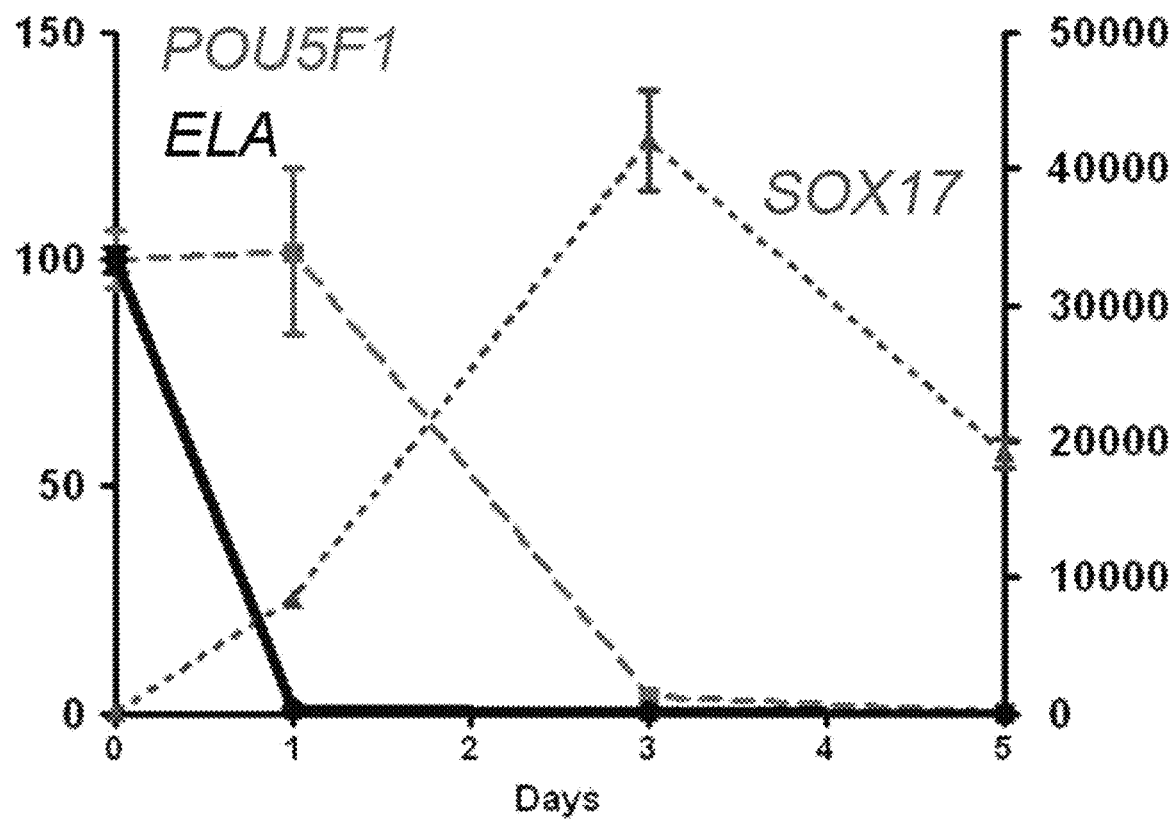
Figure 9G:
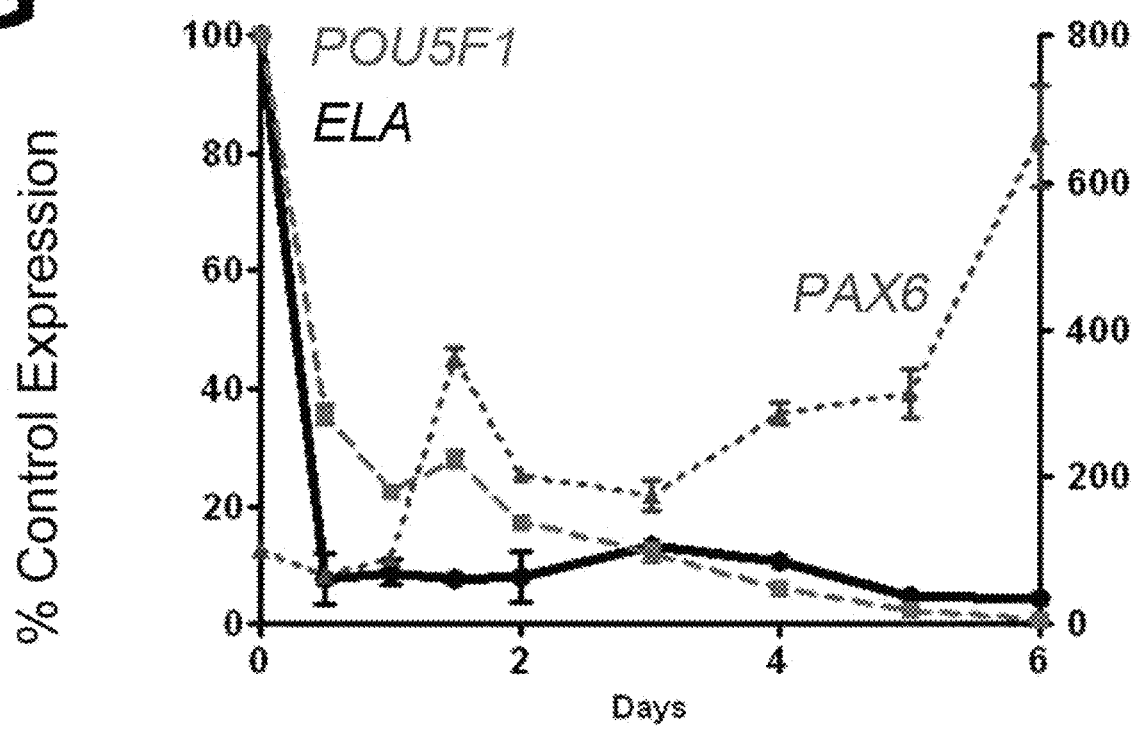
Figure 9H:
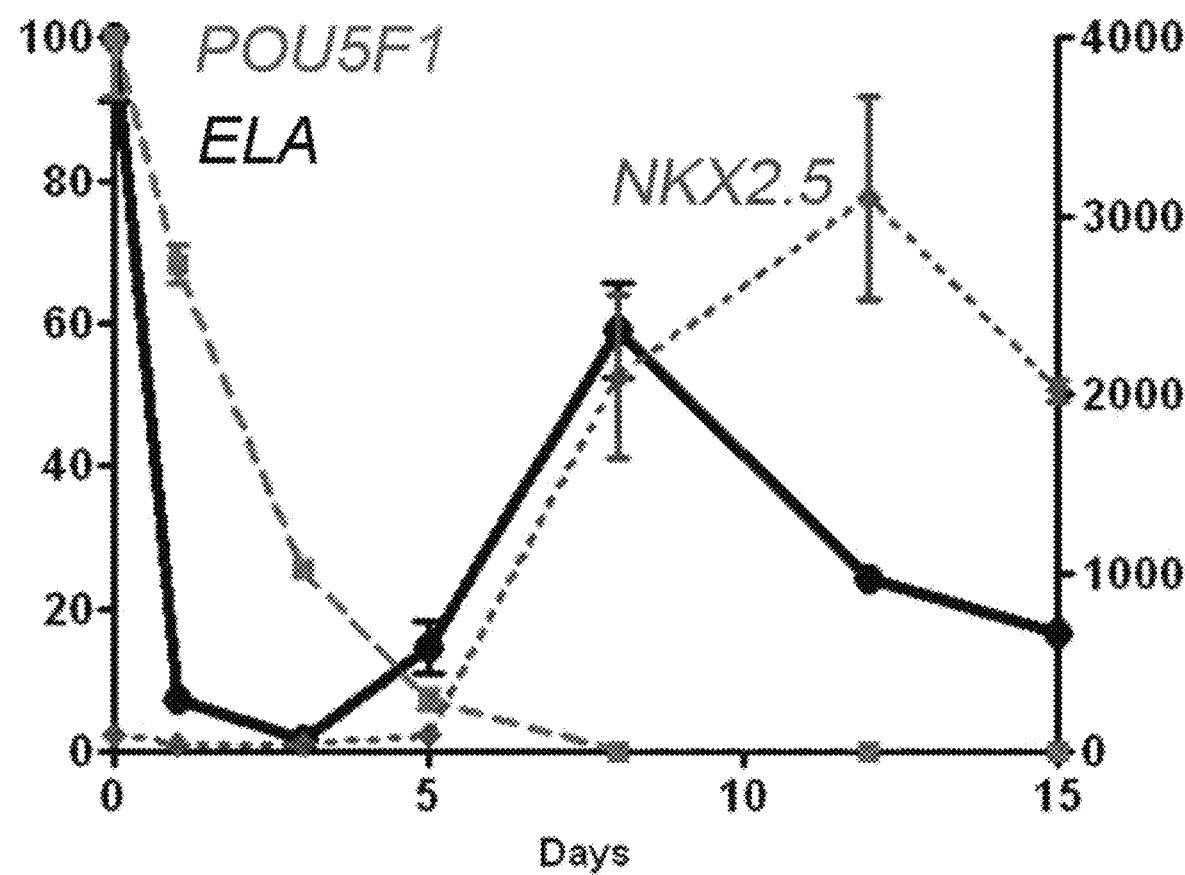

Example 18. Results: ELA is a Conserved Hormone Associated with Human Embryonic Pluripotency Within the human pluripotency circuitry network, which we delineated as the core intersection of the syn-expression groups (Day et al., 2009; Niehrs and Pollet, 1999) of NANOG, POU5F1 and PRDM14, lies a list of 33 transcripts (FIG. 1A), six of which are still unknown or uncharacterized. One, AK092578, was previously reported to be specific to undifferentiated hESCs (Miura et al., 2004). According to UniGene, this transcript is conspicuously expressed in human blastocysts before implantation (FIG. 9A and FIG. 9B). Its expression is dependent on an active POU5F1 regulatory element 10 kb upstream of its promoter and is downregulated in POU5F1-depleted hESCs (FIG. 9C and FIG. 9D). Consistent with this, ELA transcription is highest in undifferentiated hESCs and becomes rapidly silenced during embryoid body, endodermal, RA-mediated neuronal and cardiac directed differentiation (FIG. 1B, FIG. 9E to FIG. 9H).

These data validate that EKA expression is correlated with the undifferentiated state of hESCs and is associated with the pre-implantation human development.

Figure 1D:
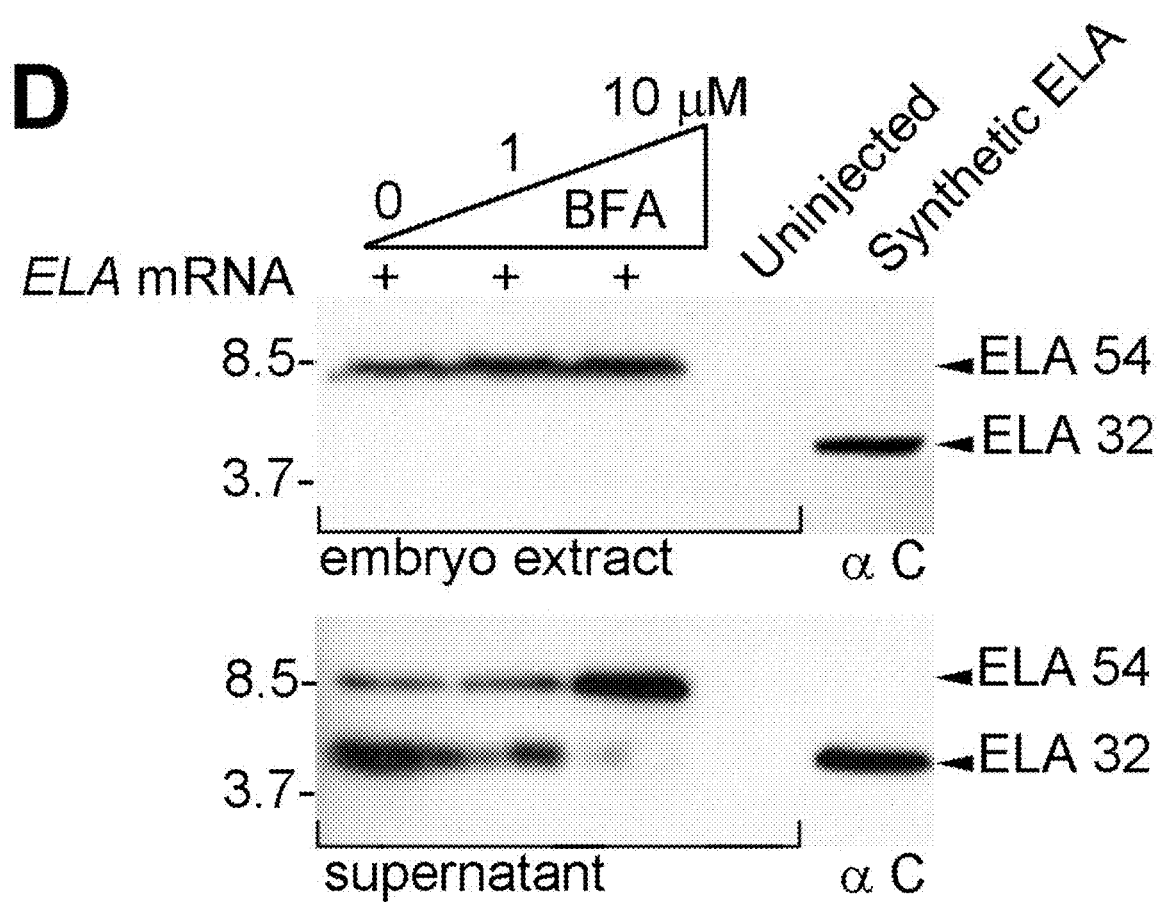

Human ELA consists of 3 exons on chromosome 4 that generates a transcript annotated as a non-coding RNA. However, ELA mRNA contains a conserved ORF which encodes a predicted polypeptide of 54 amino acids (FIG. 1C). Phylogenetic analysis revealed that this polypeptide is a highly conserved protein with a predicted N-terminal signal sequence of 22 residues (FIG. 1C). Along with a pair of conserved cysteines, the last 13 residues are nearly invariant in all vertebrate species (FIG. 1C). Based on this prediction, we raised antibodies against the N- and C-termini of the predicted mature ELA peptide (referred hereafter as α N and α C antibodies) (FIG. 1C). To confirm that ELA is processed for secretion, human ELA ORF mRNA was microinjected in 4-cell stage *Xenopus laevis* embryos. After 10 hours of secretion, we confirmed that ELA was translated, processed and secreted by embryos using the α C antibody (FIG. 1D). In the supernatant, processed ELA was of the same size as a synthetically produced recombinant ELA. Increasing amounts of Brefeldin A (BFA), an antibiotic that blocks the exit of secretory proteins from the endoplasmic reticulum, was able to block ELA processing and secretion (FIG. 1D). Unlike the α C antibody, which recognizes both full-length and processed ELA, the α N antibody was specific to mature ELA, indicating that its epitope is revealed once the signal peptide is cleaved (FIG.

1E). Taken together, these data confirm that ELA belongs to the pluripotency network of hESCs and encodes a potentially soluble mature peptide with a molecular weight of less than 4 kDa.

Figure 2A:
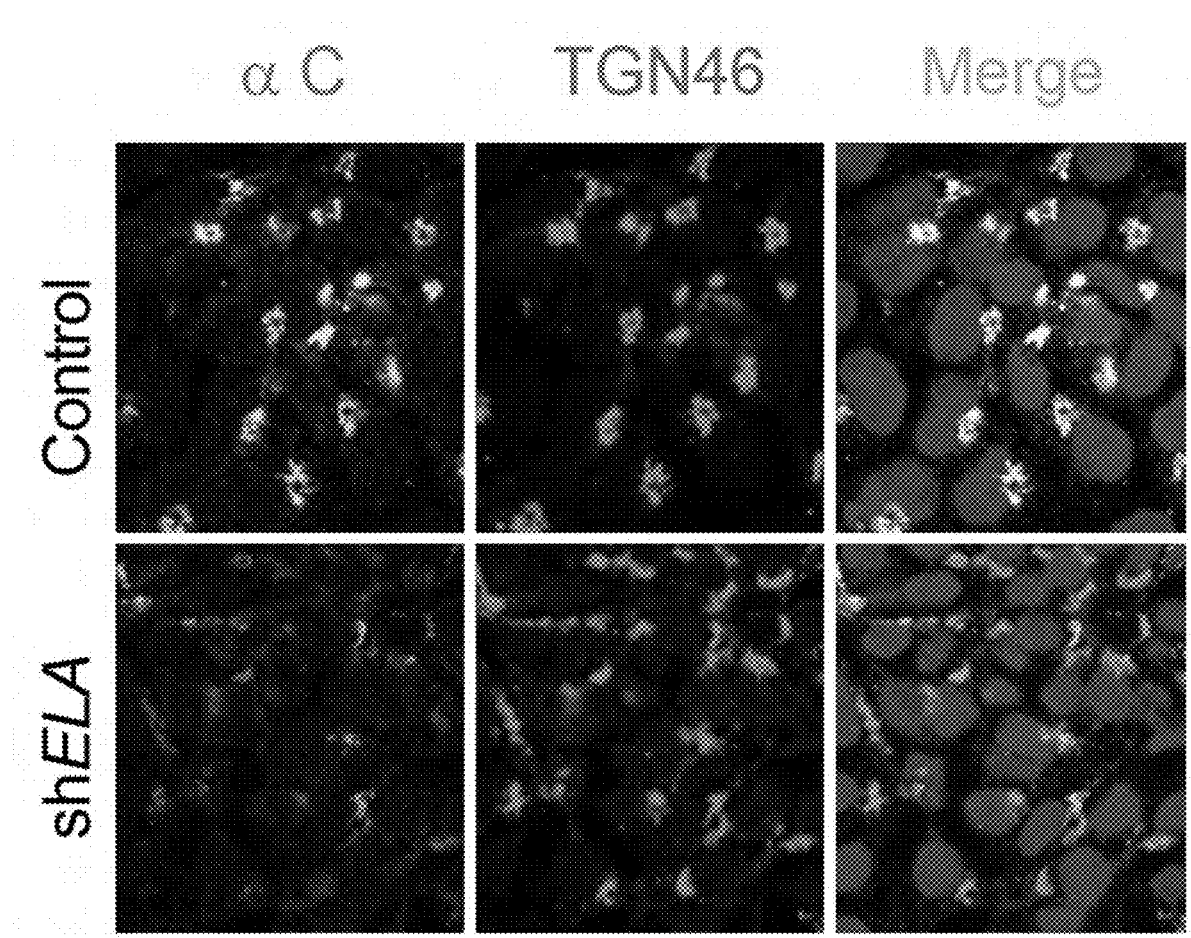
FIGS. 2A to 2H. ELA is an Endogenous Hormone Secreted by hESCs and Essential for their Survival.
Figure 2B:
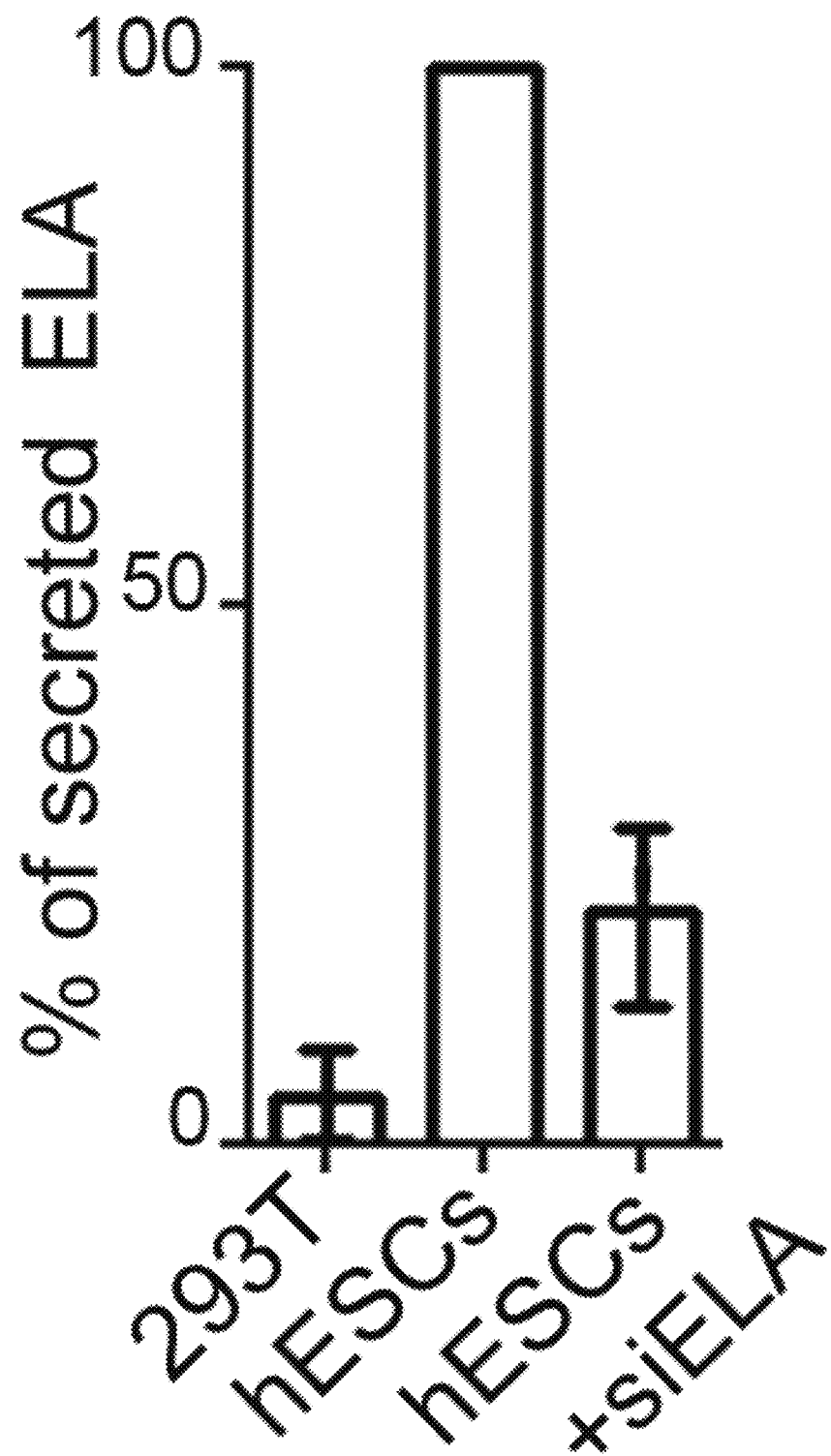
Figure 10A:
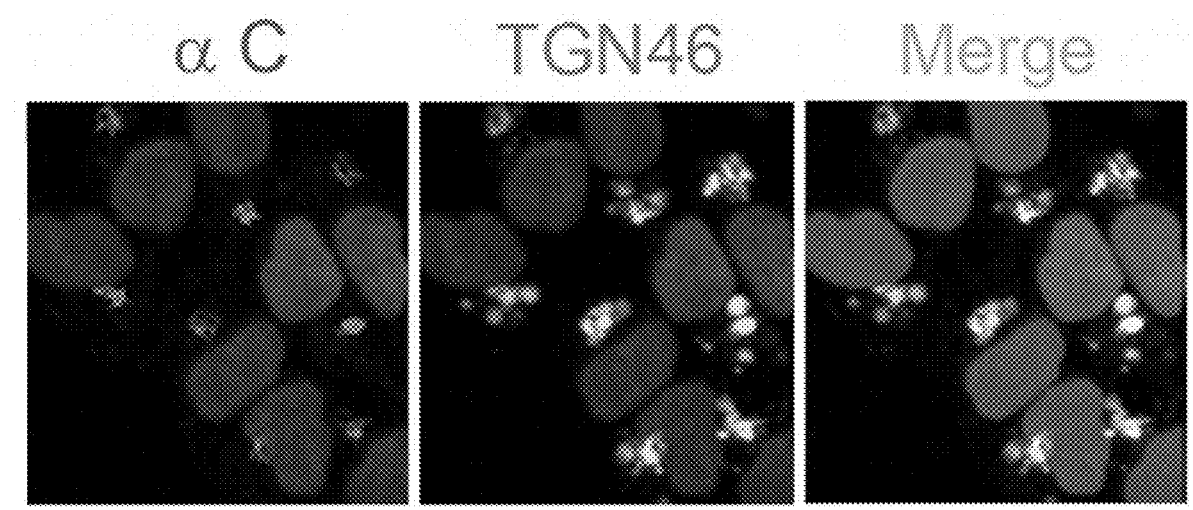
FIGS. 10A to 10H. ELA is Localized to the Golgi in hESCs and its knockdown Compromises Pluripotency, related to FIG. 2.
Figure 10B:
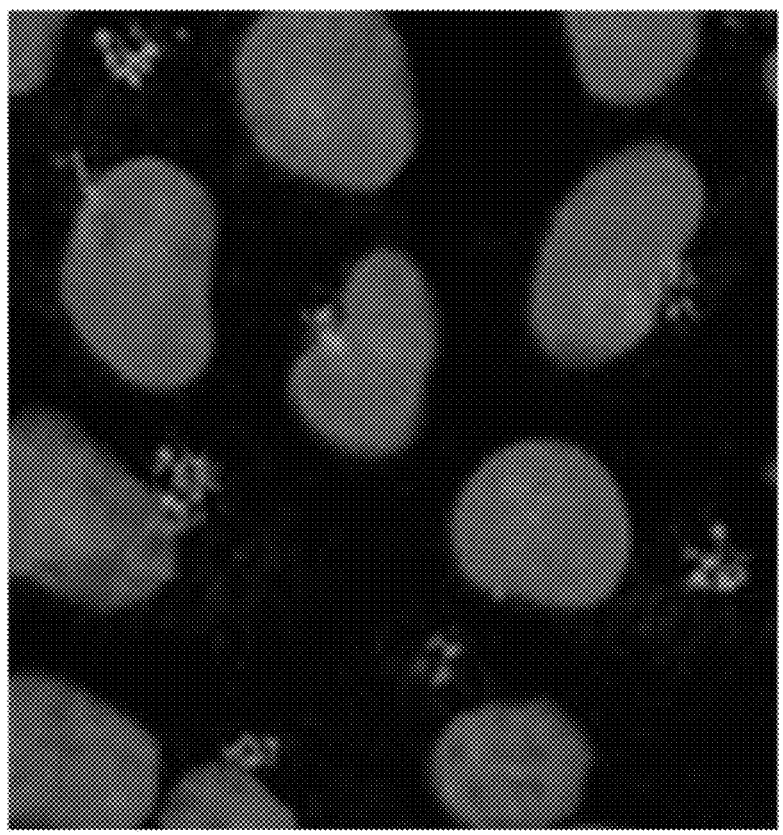
Figure 10C:
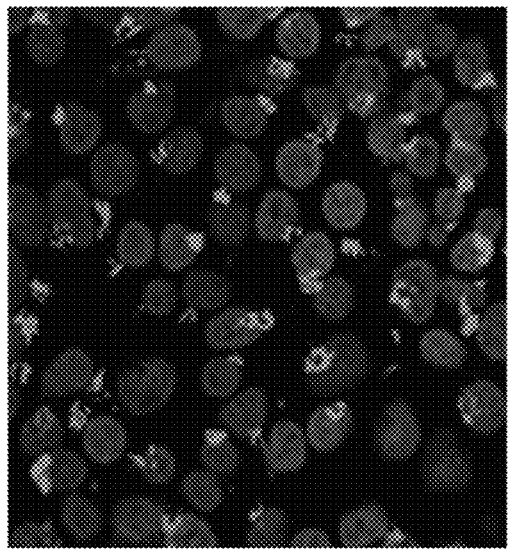
Figure 10C:
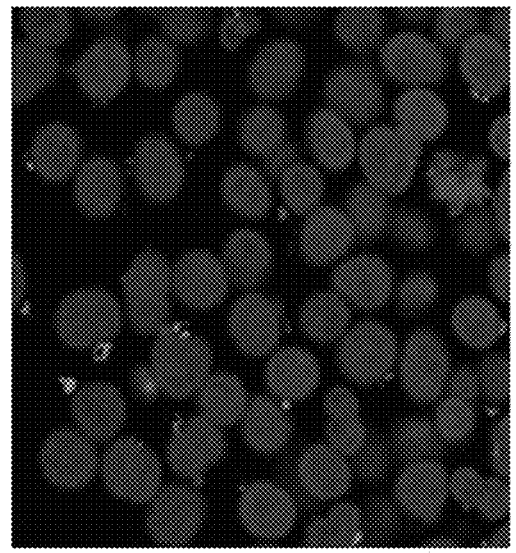

Example 19. Results: ELA is Secreted by hESCs and is Needed for their Self-Renewal ELA is a bona fide endogenous protein because it is detectable by immunofluorescence using the α N and C antibodies in hESCs and in related human embryonic carcinoma cells (hECs) (FIG. 2A and FIG. 10A to FIG. 10C). ELA staining was highest in the Golgi apparatus as evidenced by co-localization with TGN46, a marker of the trans-Golgi network, but is also found in the cytoplasm (FIG. 2A and FIG. 10A). This staining is specific, as it was markedly reduced upon siRNA- and shRNA-mediated ELA knockdown in both pluripotent cell types (FIG. 2A and FIG. 10C). We confirmed that endogenous ELA was indeed secreted because it is readily detected in the supernatant of cultured hESCs using a sandwich ELISA assay (FIG. 2B). We estimated that over a period of 5 days, soluble endogenous ELA reached nanomolar range concentrations in the supernatant of hESCs (FIG. 2C).

Figure 2C:
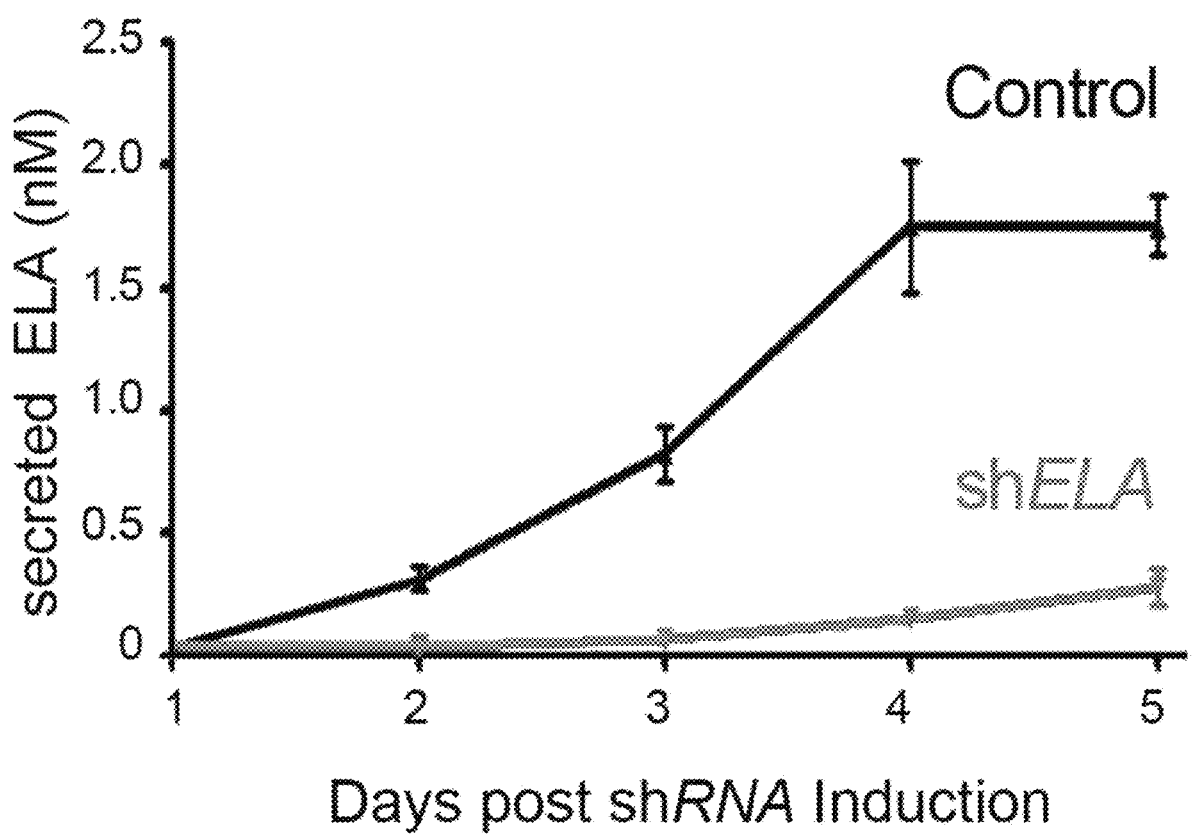
Figure 2D:
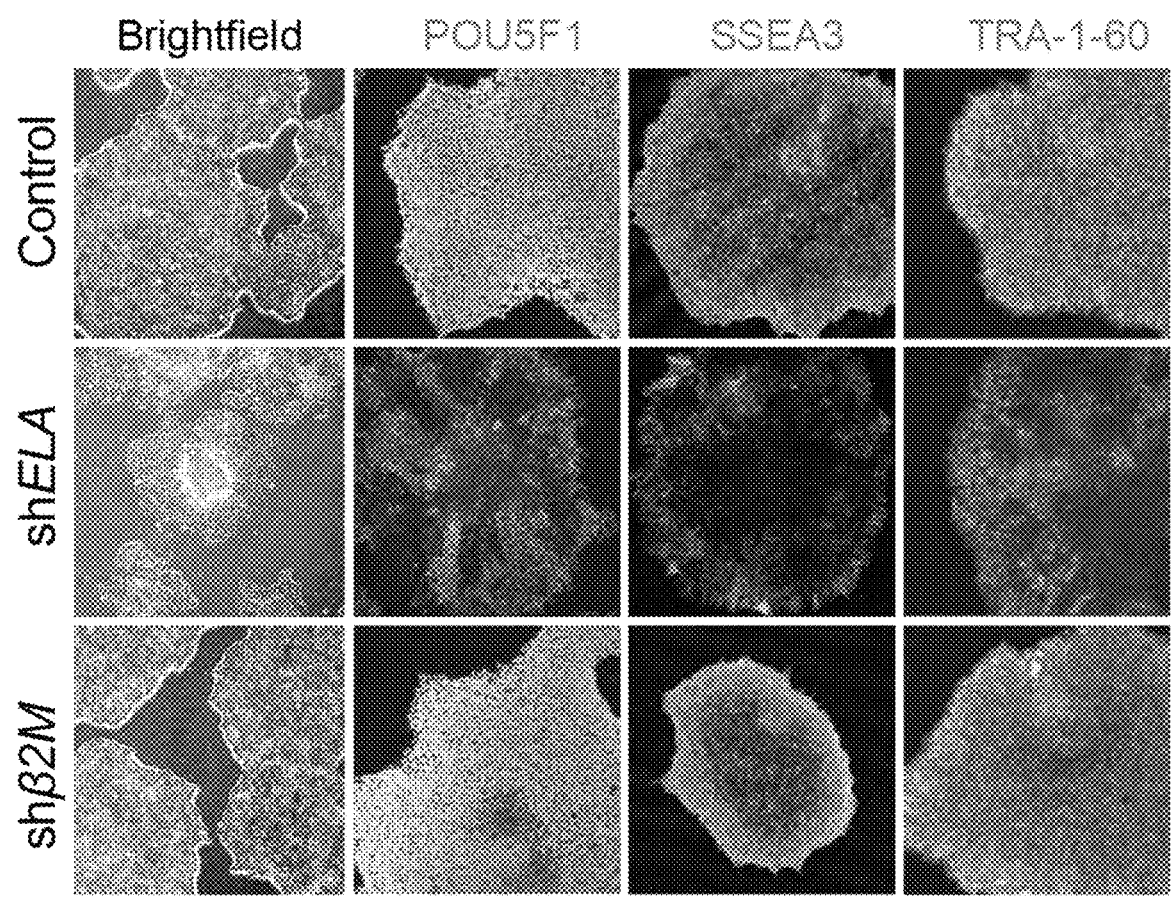
Figure 2E:
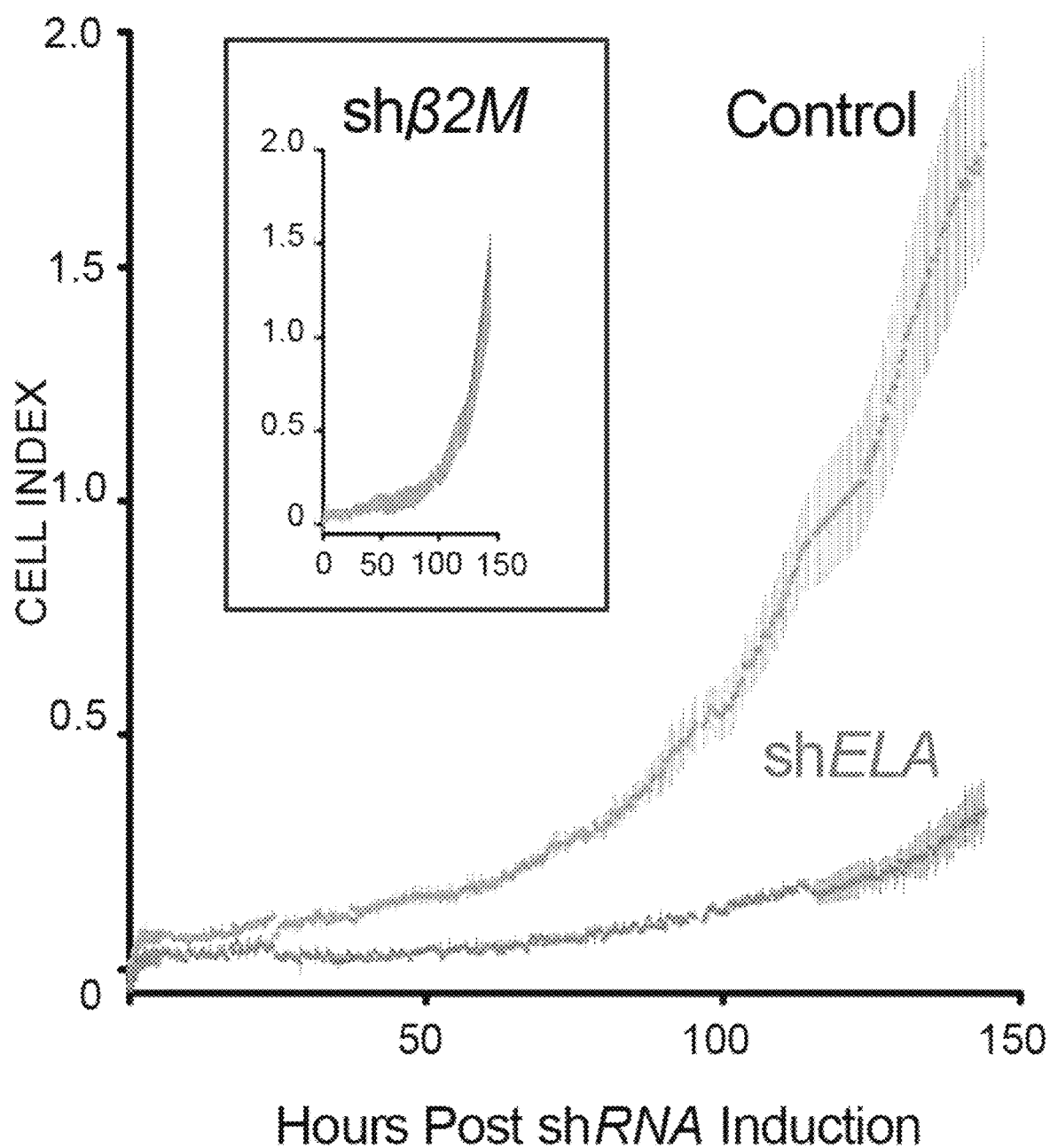
Figure 2F:
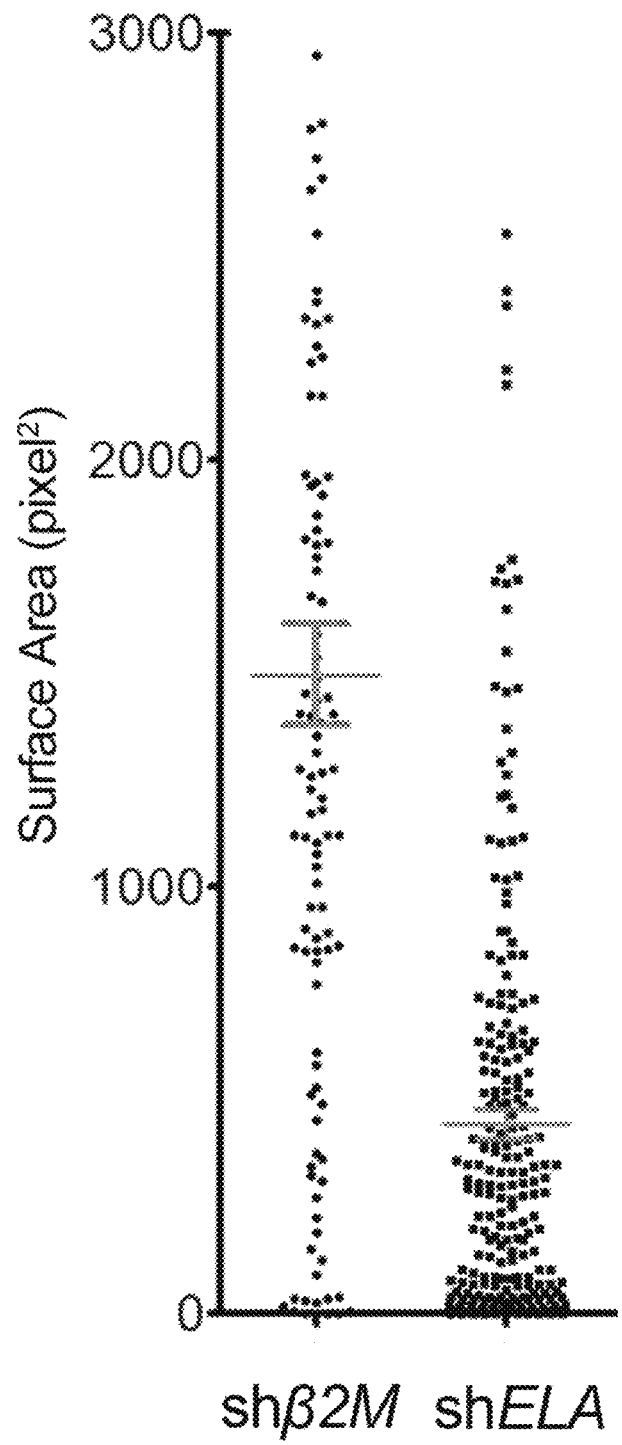
Figure 10D:
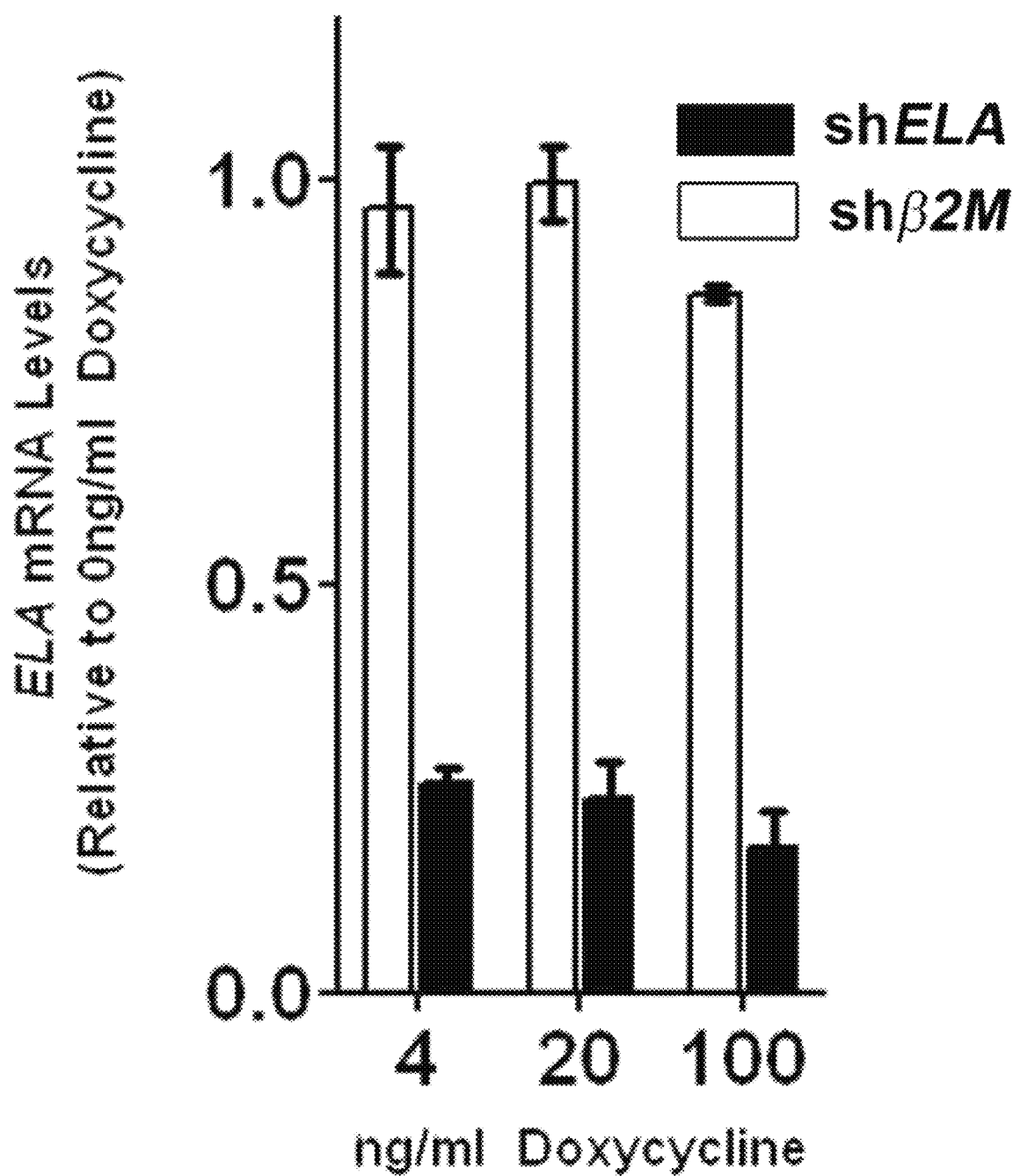
Figure 10E:
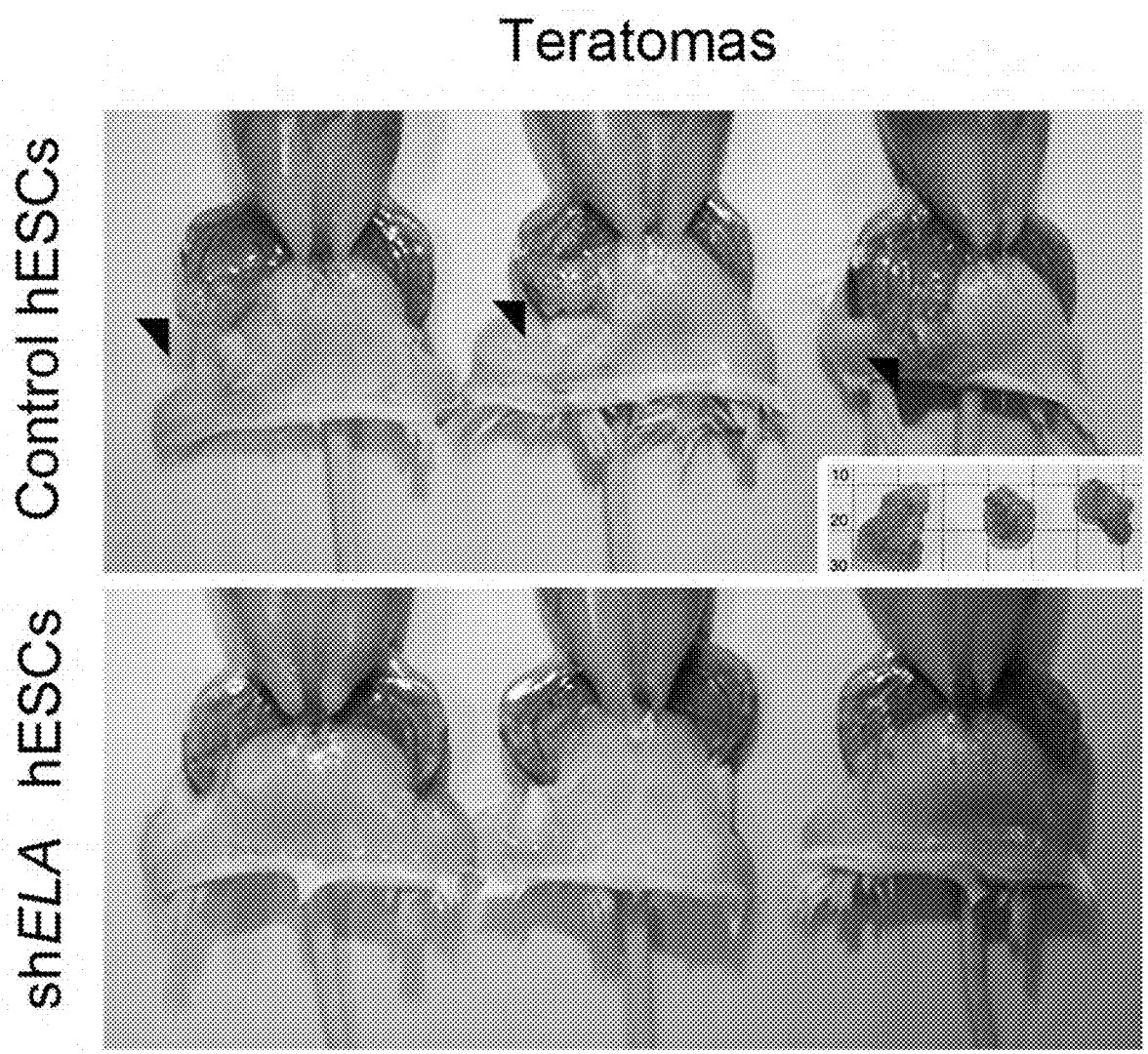
Figure 10F:
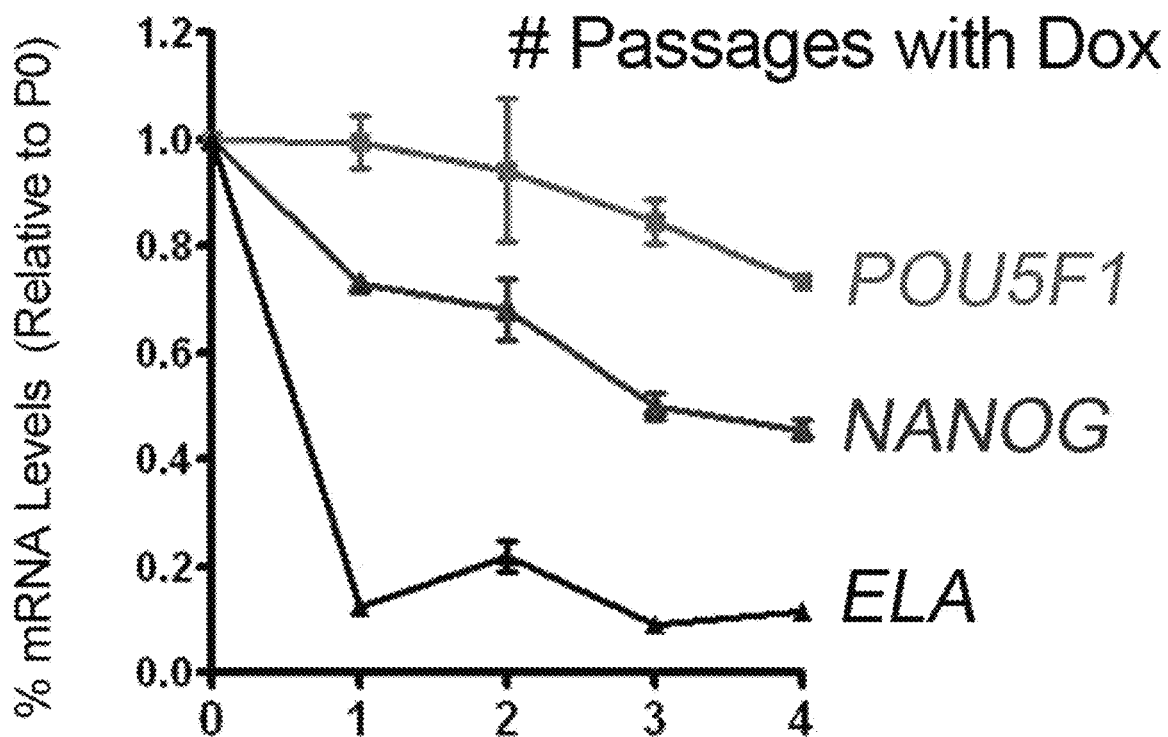
Figure 10G:
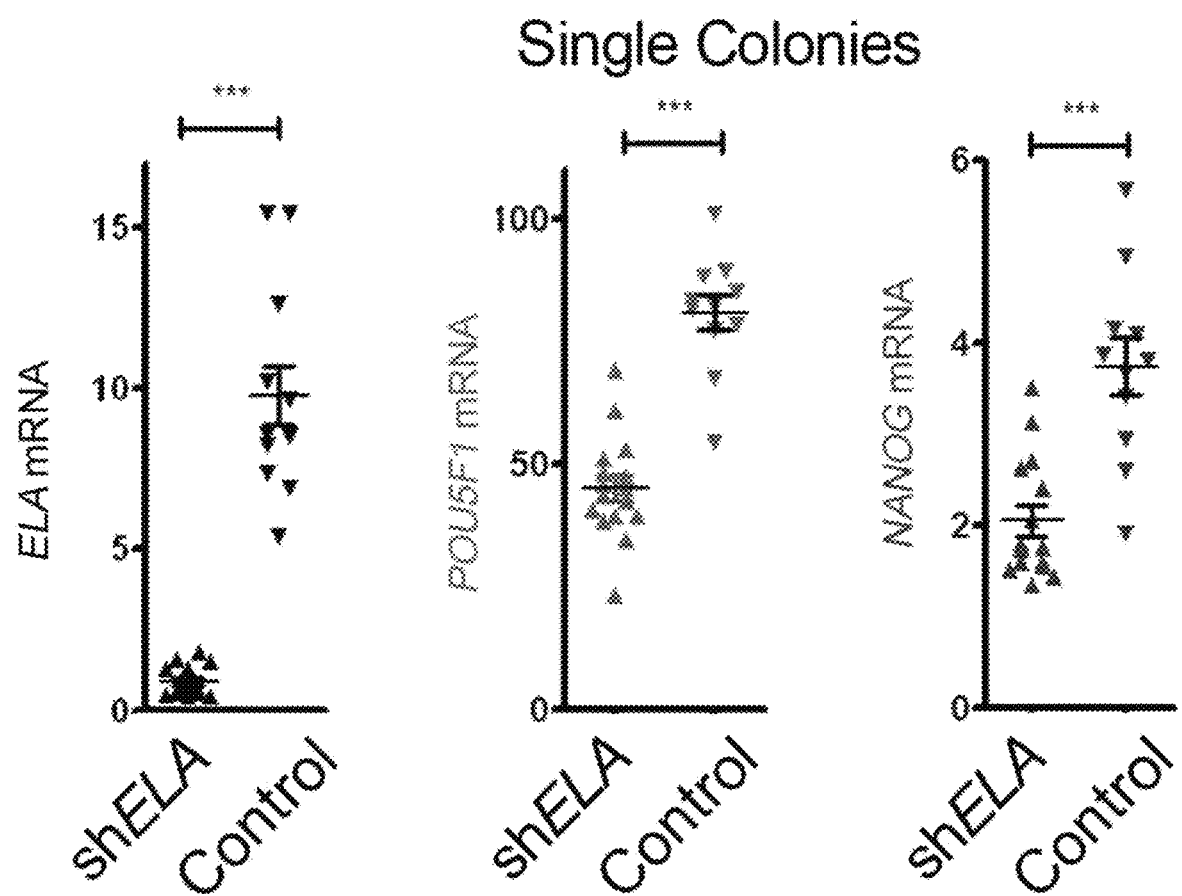

To assess ELA function, we next generated stable doxycycline-inducible shRNA knockdown hESCs against ELA and a non-essential gene β2-MICROGLOBULIN (β2M) (FIG. 10D) (Zafarana et al., 2009). shELA knockdown achieved approximately 85% depletion of extracellular ELA relative to control levels (FIG. 2C). Prolonged depletion of ELA, but not β2M, resulted in a gradual loss of hESCs colony morphology and a downregulation of pluripotency markers POU5F1, NANOG, SSEA3 and TRA-1-60 (FIG. 2D, FIG. 10F and FIG. 10G). shELA hESCs injected into SCID mice did not form teratomas as did control hESCs (FIG. 10E). In line with these results, shELA hESCs displayed markedly reduced growth rates compared to control and shβ2M hESCs when seeded as single cells as shown by real-time cell index analysis (FIG. 2E). This index serves a proxy for cell numbers, which is proportional to the surface area occupied (FIG. 2E). Slower growth rates were also documented in shELA hESC colonies that were on average less than half the size of shβ2M hESCs (FIG. 2F).

Altogether these findings argue that the hormonal peptide ELA made by hESCs is key to their self-renewal and maintenance in culture.

Figure 2G:
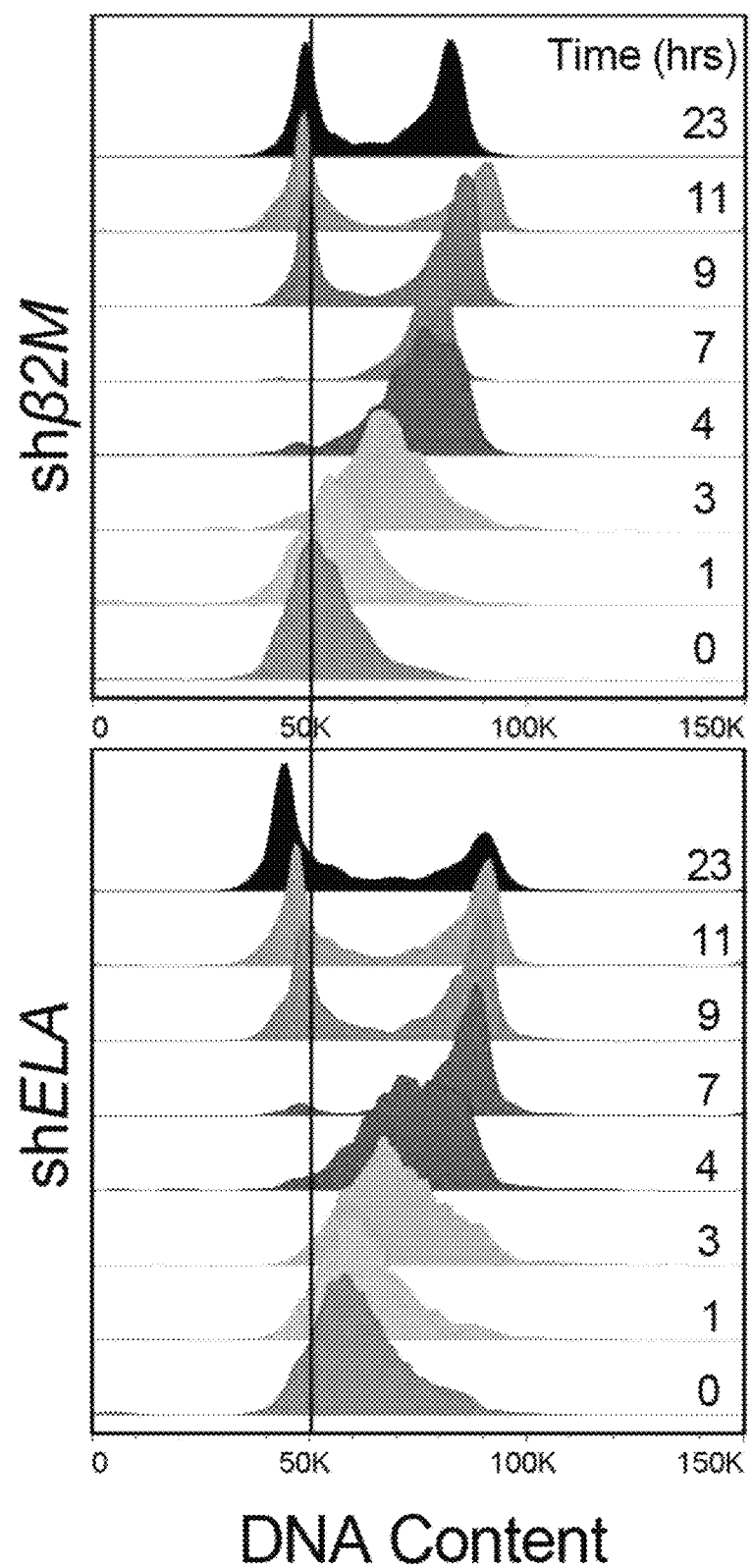
Figure 2H:
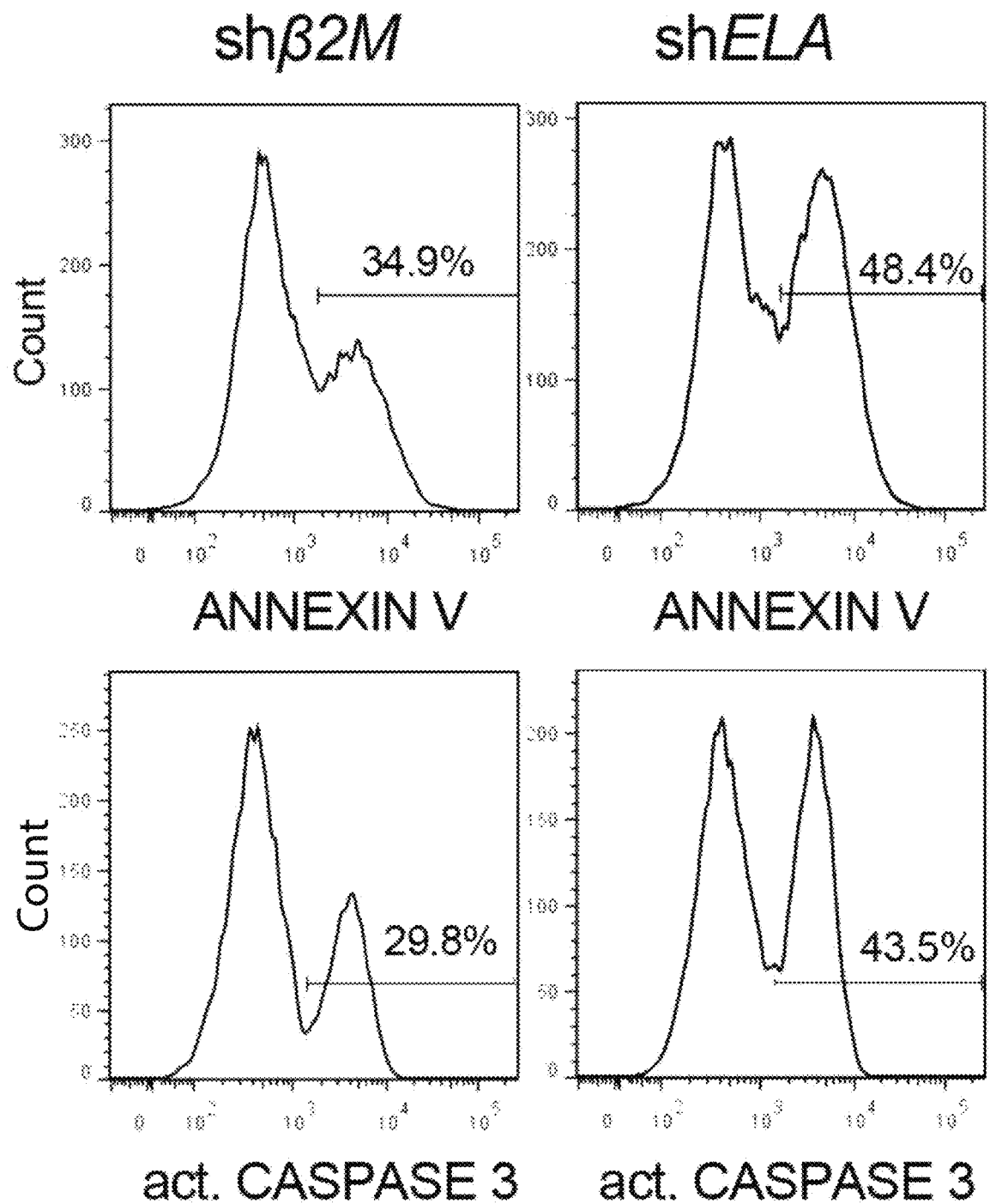
Figure 10H:
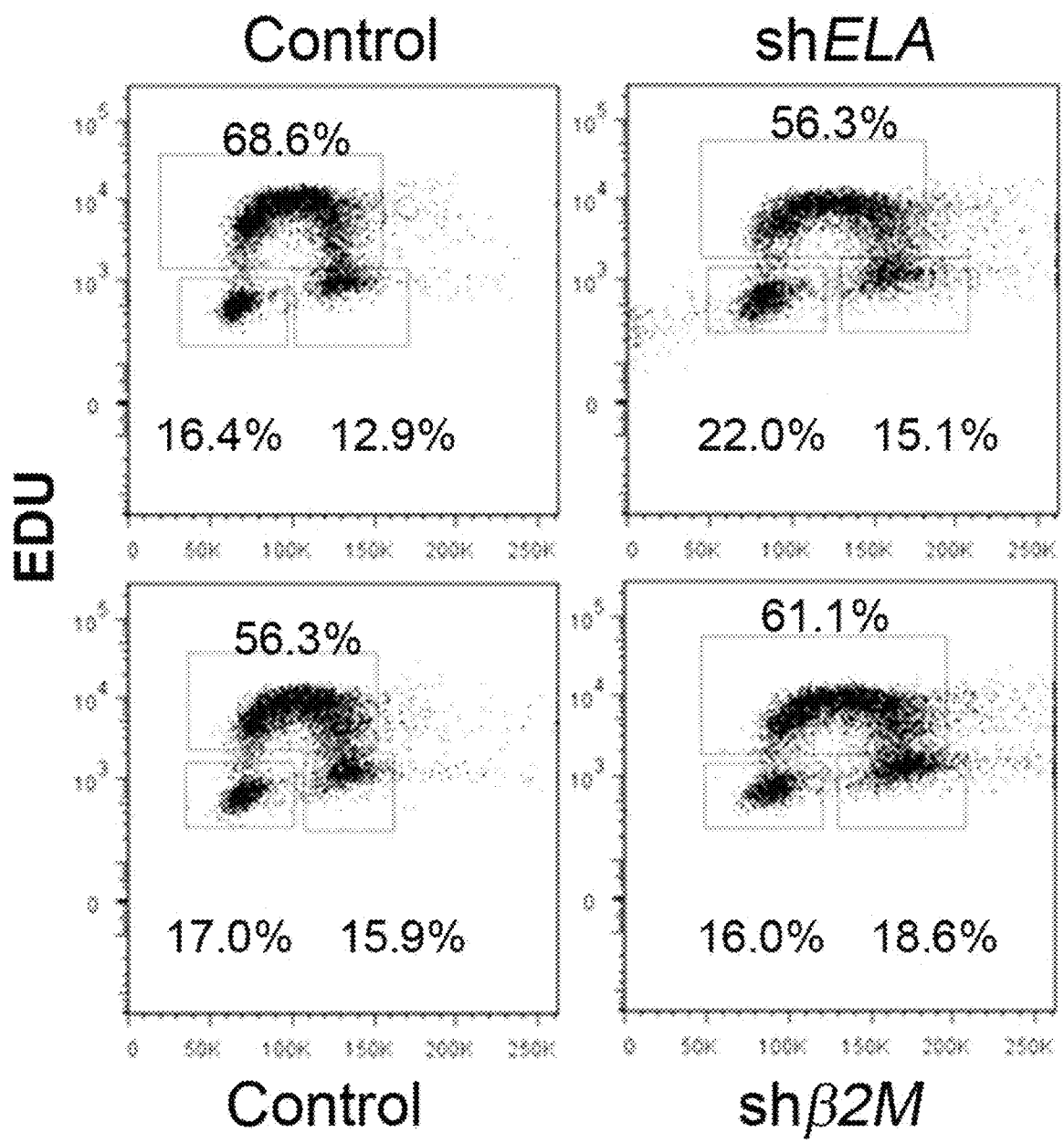

This impairment in cell numbers was not due to the activation of G1/S checkpoint or lengthened G0 residence, as evidenced by EDU staining (FIG. 10H). Cell cycle analysis following release from a double thymidine block, which synchronizes hESCs in the G1 phase, confirmed this result (FIG. 2G). Rather, shELA hESCs underwent apoptosis at a significantly higher rate compared to control hESCs, as revealed by an approximately 40% increase in the number of ANNEXIN V and activated CASPASE 3-positive cells (FIG. 2H).

We conclude from these observations that ELA is an endogenous secreted peptide that is essential for the survival and self-renewal of hESCs and that its depletion triggers apoptosis and gradual differentiation.

Figure 3A:
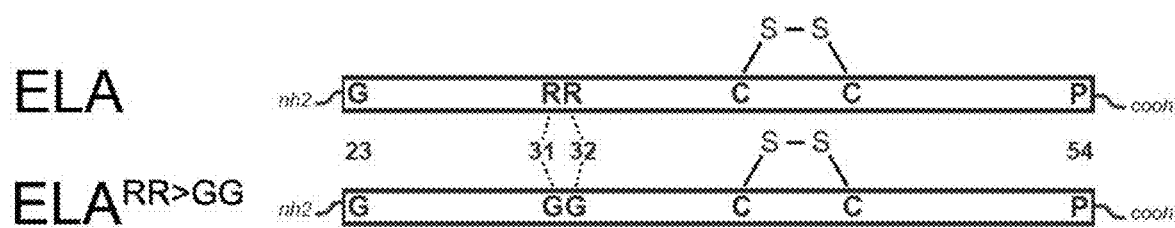
FIGS. 3A to 3K. Recombinant ELA Promotes hESCs Growth and Primes Cells Towards Mesendoderm Lineages.

Example 20. Results: Exogenous ELA Promotes Growth and Primes hESCs Towards Mesendoderm Lineages We next assessed the bioactivity of mature ELA. To this end we synthetically produced recombinant mature ELA at 98% purity as a 32 amino-acid peptide bearing an intramolecular cystine bond between cysteine residues 39 and 44 (FIG. 3A).

Figure 3B:
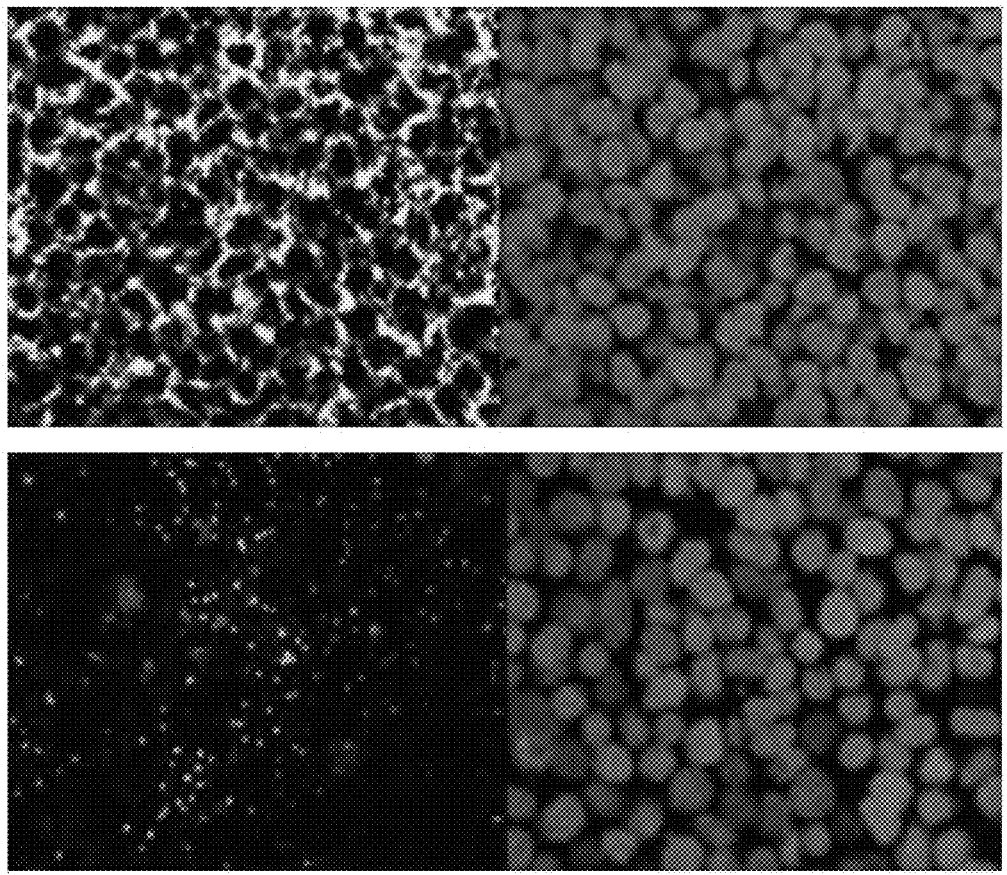

This recombinant FITC-labeled ELA was rapidly up-taken by hESCs (FIG. 3B). We found that mutation of two invariant arginines into glycines (R31G and R32G) completely abolished the uptake of recombinant ELA (FIGS. 3A and 3B).

Figure 3C:
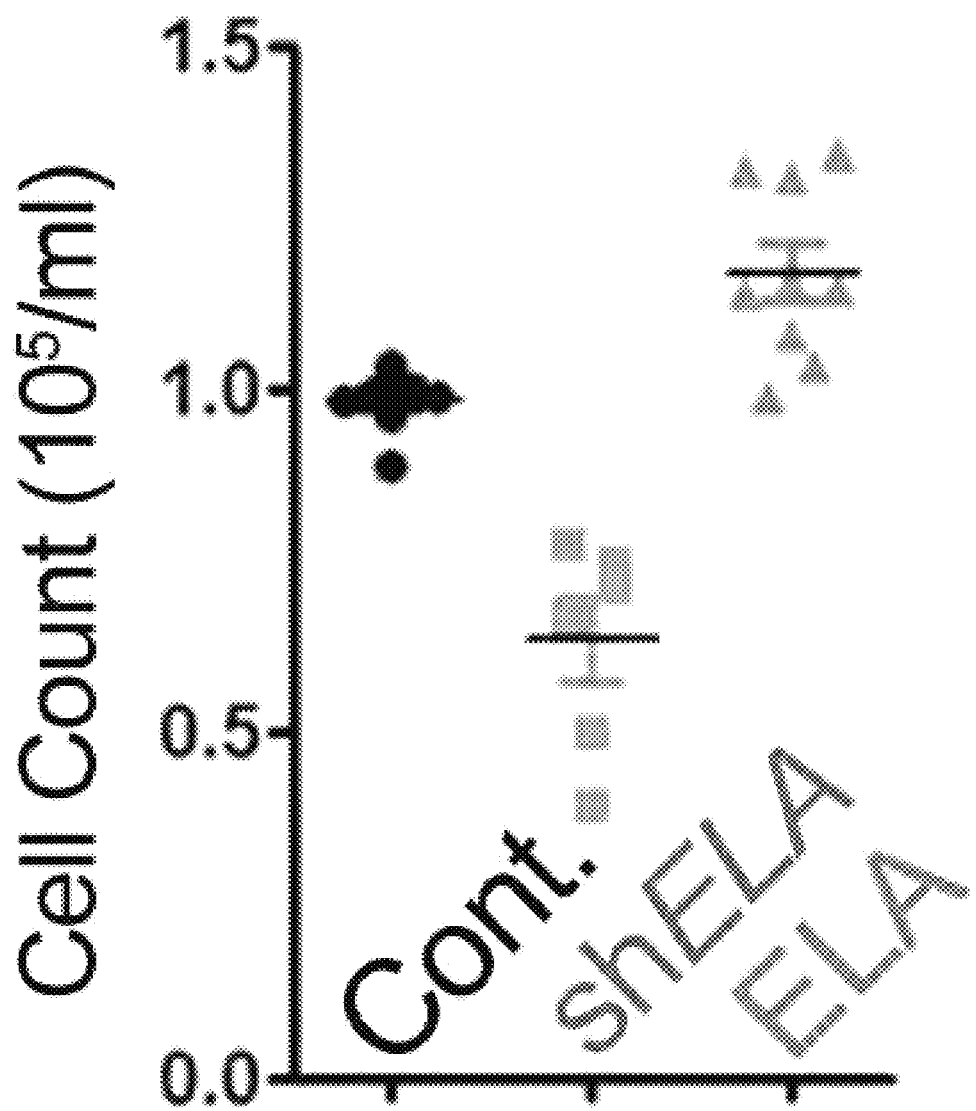
Figure 3D:
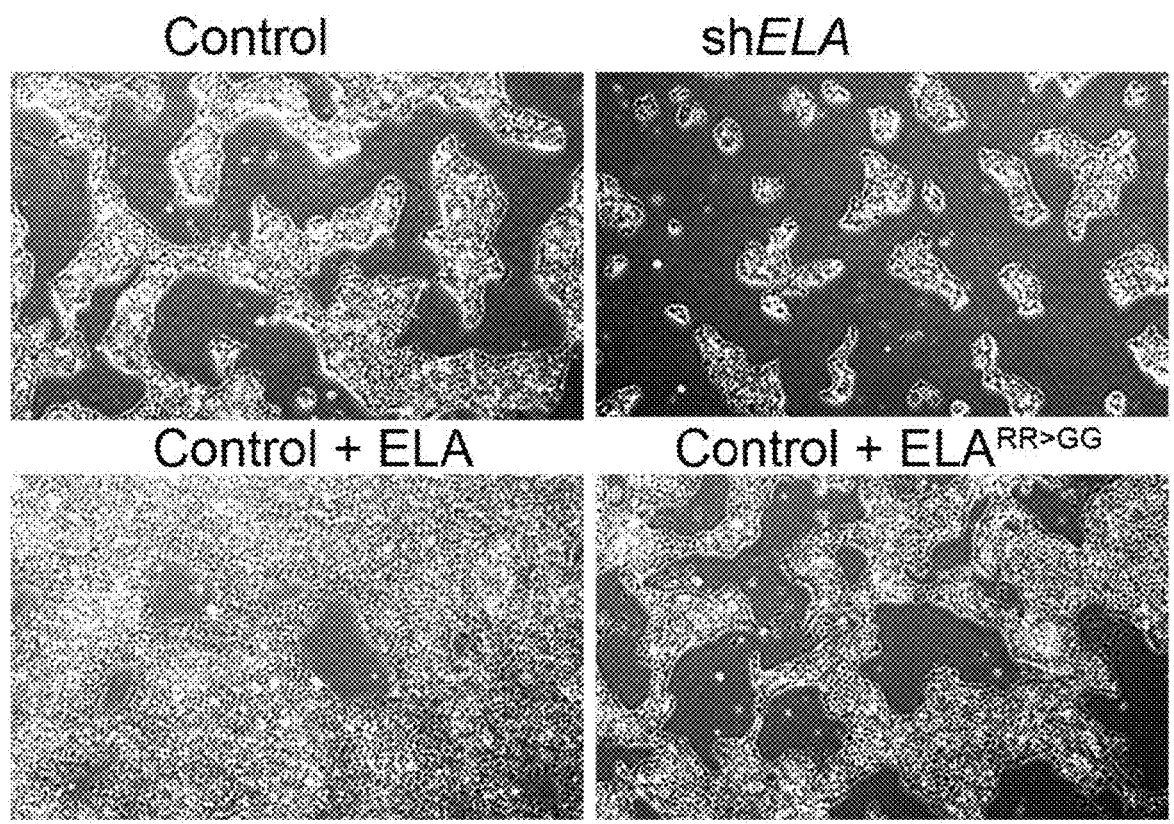
Figure 3E:
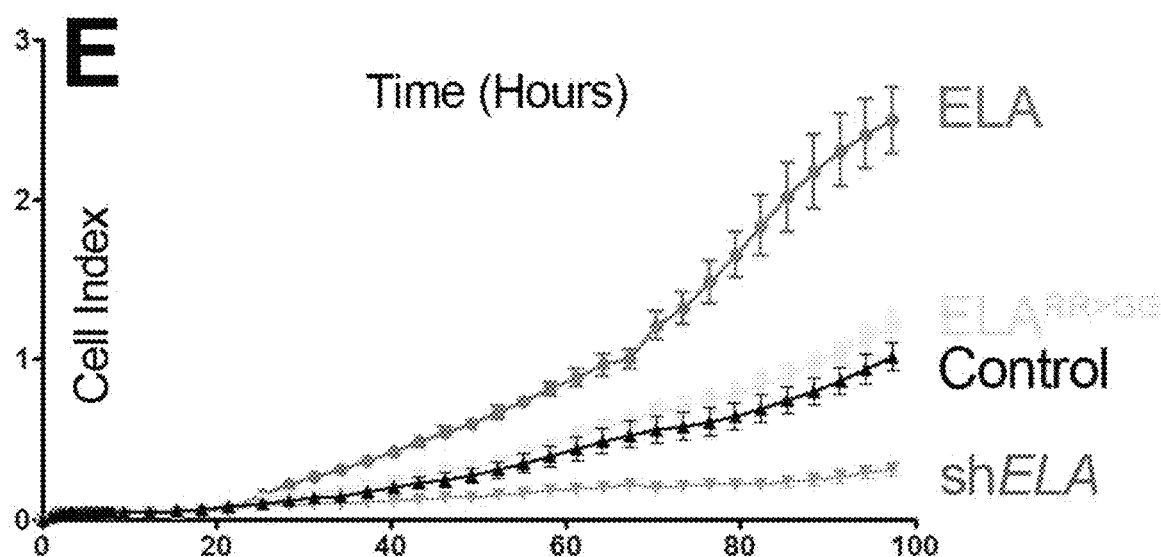
Figure 3F:
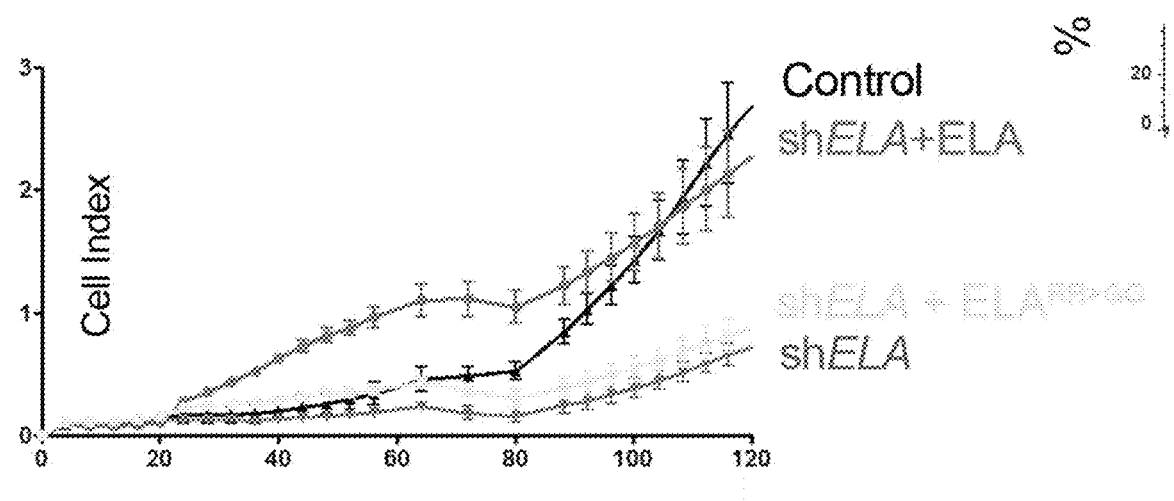
Figure 11A:
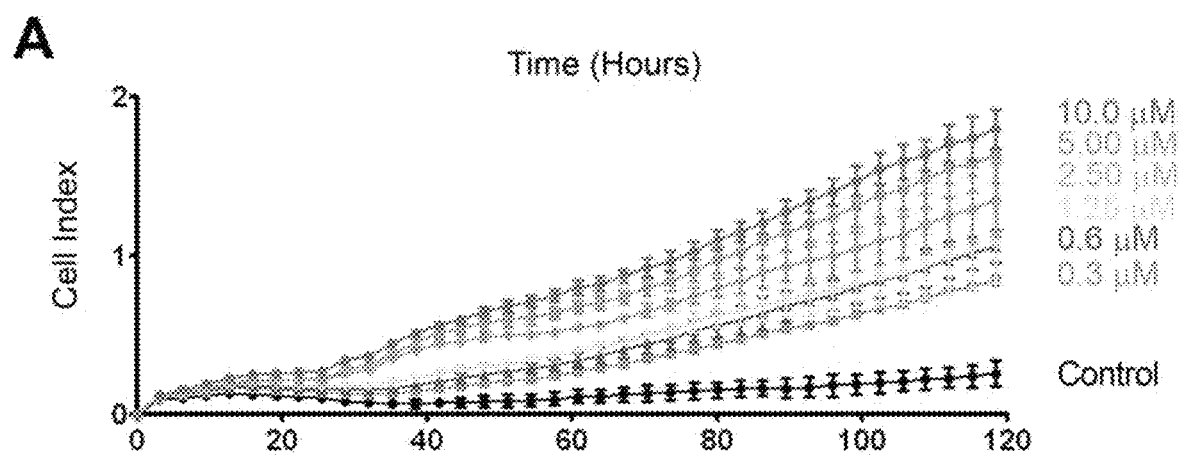
FIGS. 11A to 11B. In hESCs, Recombinant ELA is Bioactive and endogenous ELA can be Neutralized by the α N Antibody, related to FIGS. 3A to 3K.

While shELA hESCs showed reduced growth, hESCs pulsed with ELA peptide showed dose-dependent enhanced growth relative to untreated cells. This was independently documented by cell counts (FIG. 3C), colony size (FIG. 3D) and by real-time measurement of cell indices (FIG. 3E and FIG. 11A). The doubly mutated ELA mutant peptide (referred to as $ELA^{RR>GG}$) was without effect in these assays (FIGS. 3D and 3E). Notably, the growth of shELA hESCs was entirely rescued to normal levels by addition of recombinant ELA, but not $ELA^{RR>GG}$, showing that ELA can exert its role wholly as a non-cell autonomous factor (FIG. 3F).

Figure 3G:
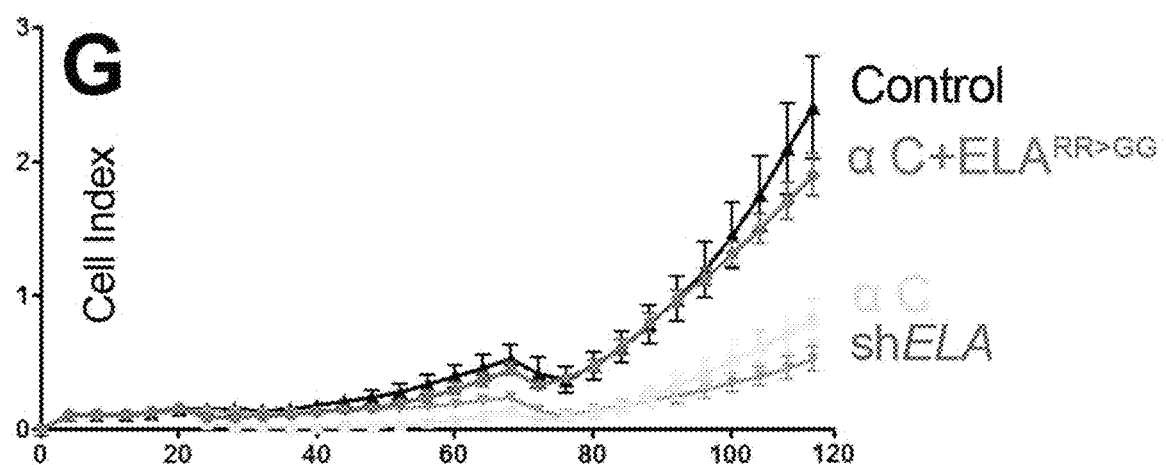
Figure 3H:
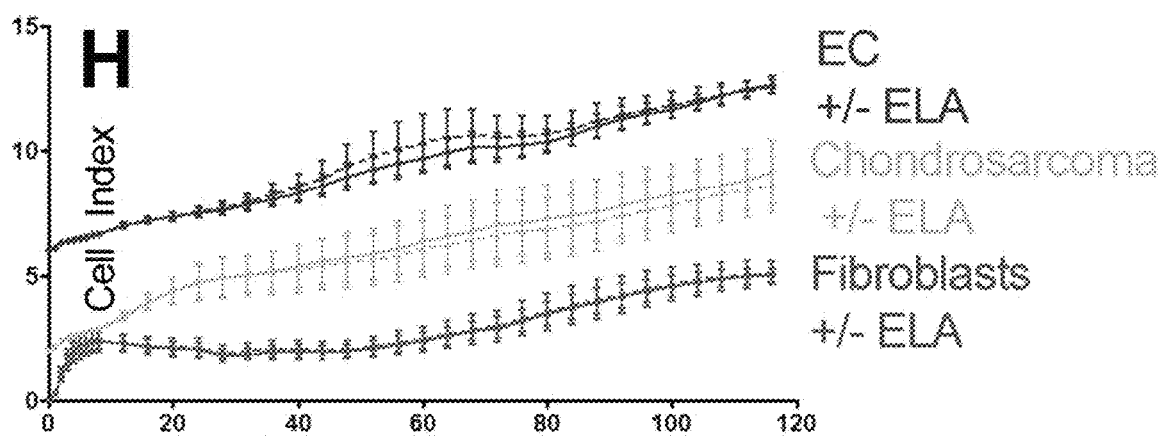
Figure 11B:
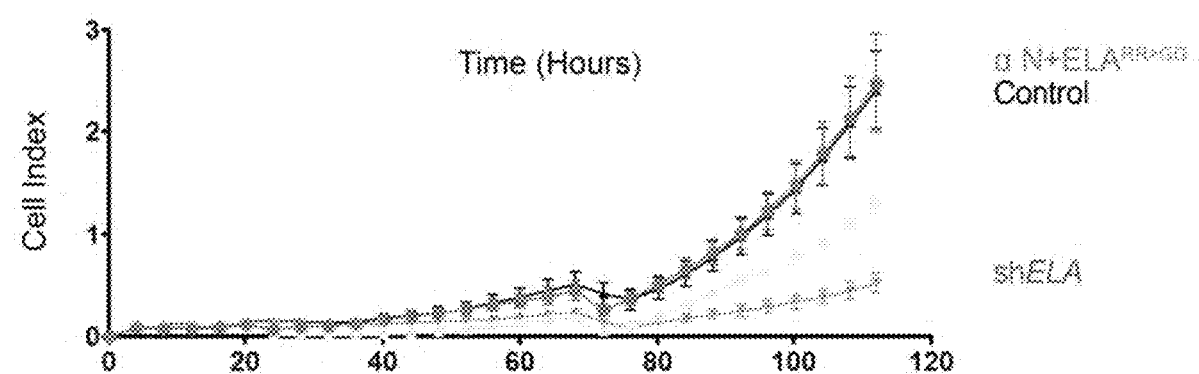

We therefore hypothesized that its direct inhibition in the extracellular space should yield similar results as its depletion at the mRNA level. Indeed, we found that addition of affinity-purified α C and N antibodies to hESC medium recapitulated the effects of shELA (FIG. 3G and FIG. 11B), indicating that these antibodies have potent ELA-neutralizing activity. The non-signaling mutant $ELA^{RR>GG}$ peptide was used as a competitive inhibitor of the α C antibody to prove the specificity of this assay (FIG. 3G). It is noteworthy that recombinant ELA exerted activity only on hESCs cultures and no other differentiated cell types including hECs, a human chondrosarcoma cell line or primary human fibroblasts (FIG. 3H).

We conclude from these data that exogenous ELABELA is sufficient to enhance the growth of hESCs.

Figure 3I:
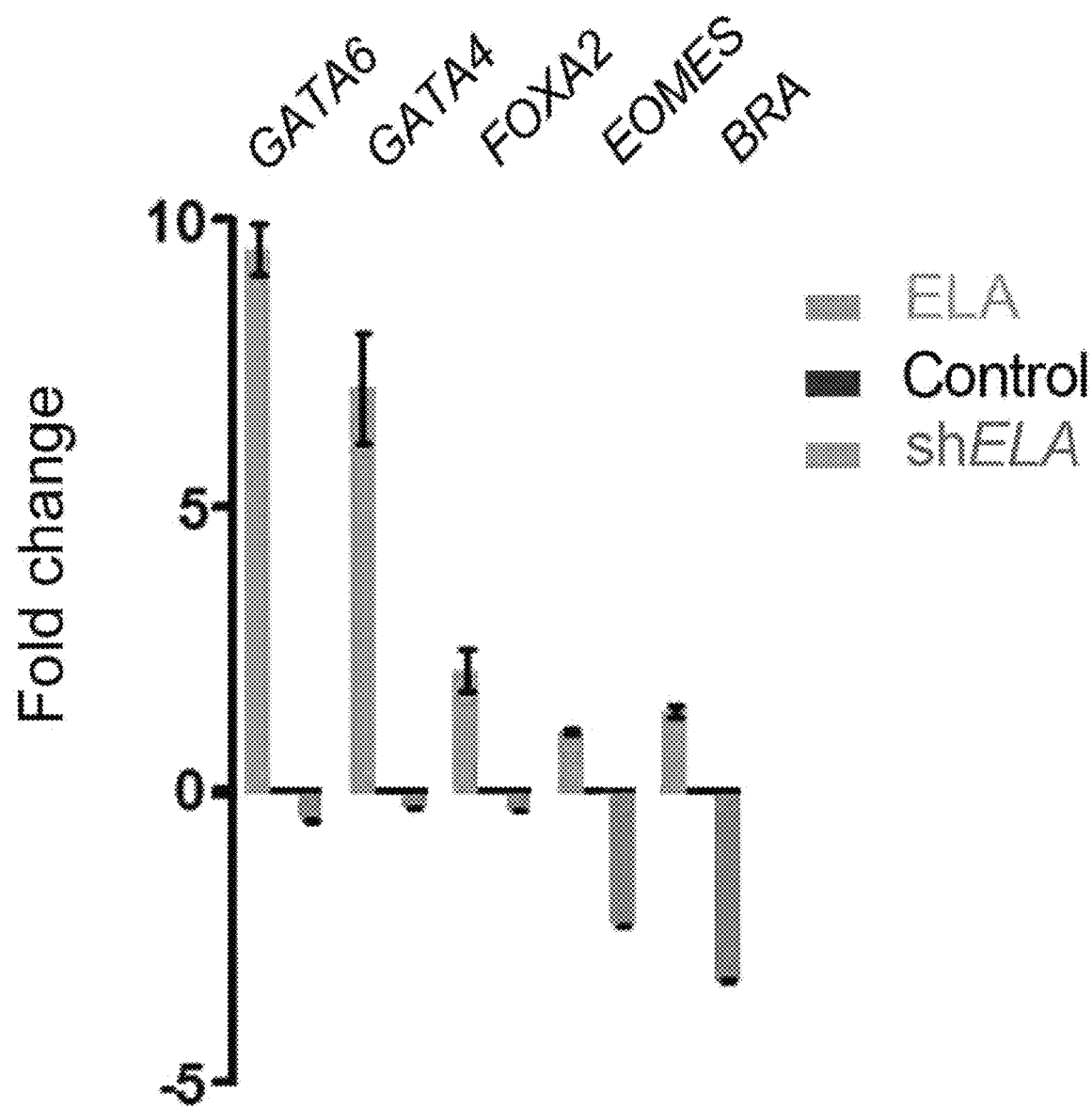
Figure 3J:
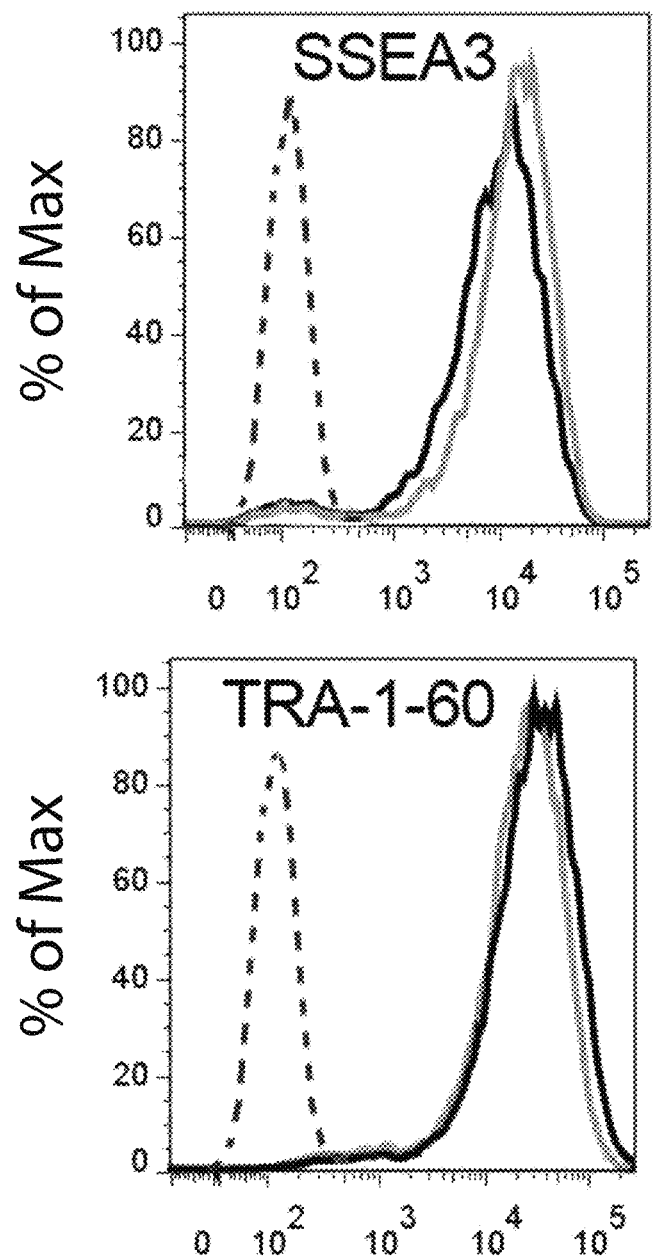
Figure 3K:
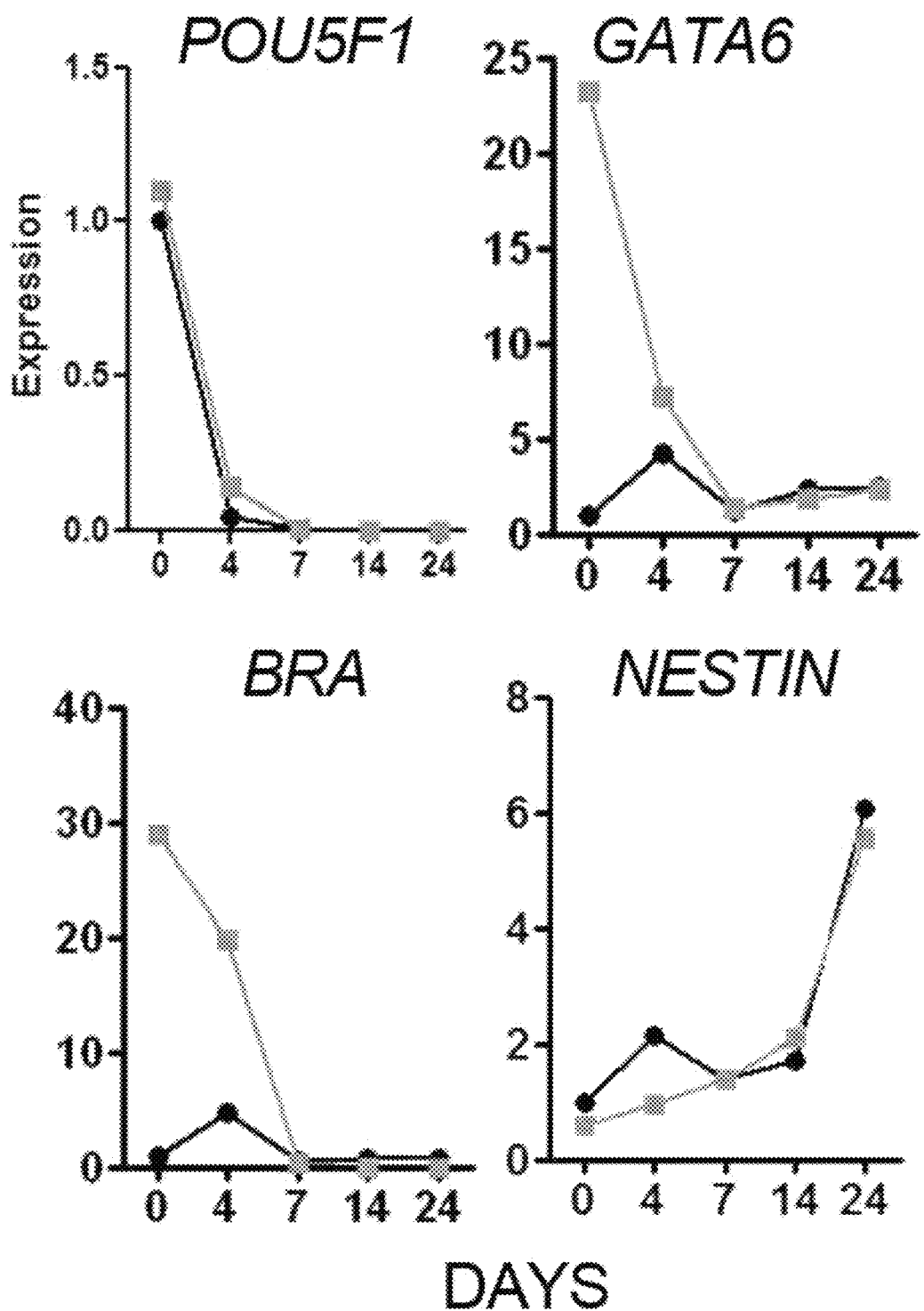

We observed that in the presence of elevated ELA, following the addition of exogenous ELA peptide to hESC cultures, mesendodermal genes including GATA6, GATA4, FOXA2, EOMES and BRA were consistently upregulated. These same markers were conversely downregulated in shELA hESCs (FIG. 3I). In spite of this, hESCs did not appear to lose stemness, as judged by the unchanged levels of cell surface markers SSEA3 and TRA-1-60 (FIG. 3J). This priming towards mesendoderm did not represent a permanent lineage commitment, since ELA-treated hESCs were not biased towards mesoderm or endoderm lineages during embryoid body differentiation and could equally express NESTIN a neuroectodermal marker (FIG. 3K). Taken together, these data suggest that mature ELA functions as an extracellular factor able to elicit enhanced growth and survival of hESCs. Upon overexpression, ELA poises hESCs towards the mesendoderm lineage but without causing overt lineage commitment.

Example 21. Results: Creating an Allelic Series of ela Mutants in Zebrafish

Figure 4A:
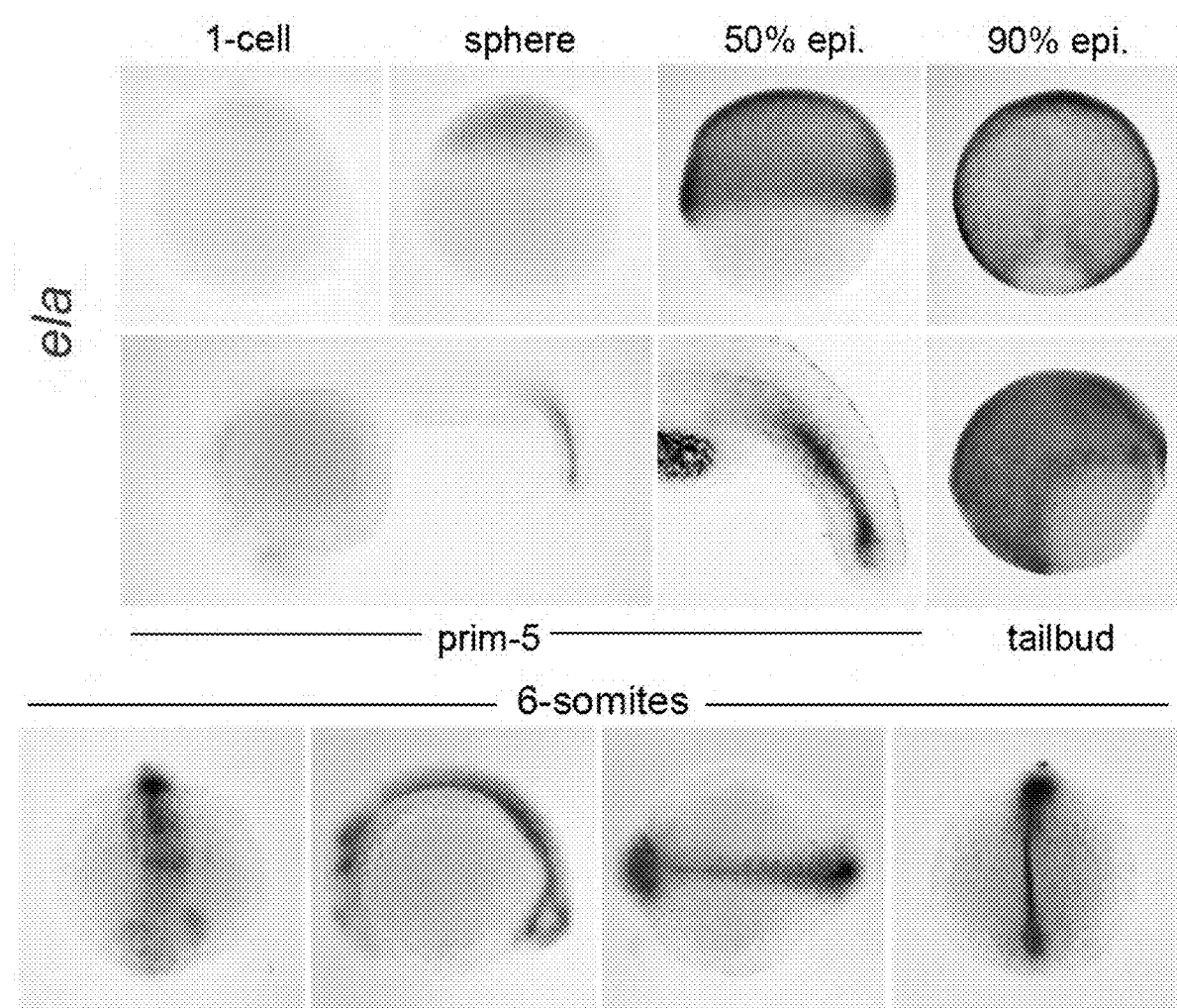
FIGS. 4A to 4F. Generation of an Allelic Series of Mutant ela Zebrafish
Figure 4B:
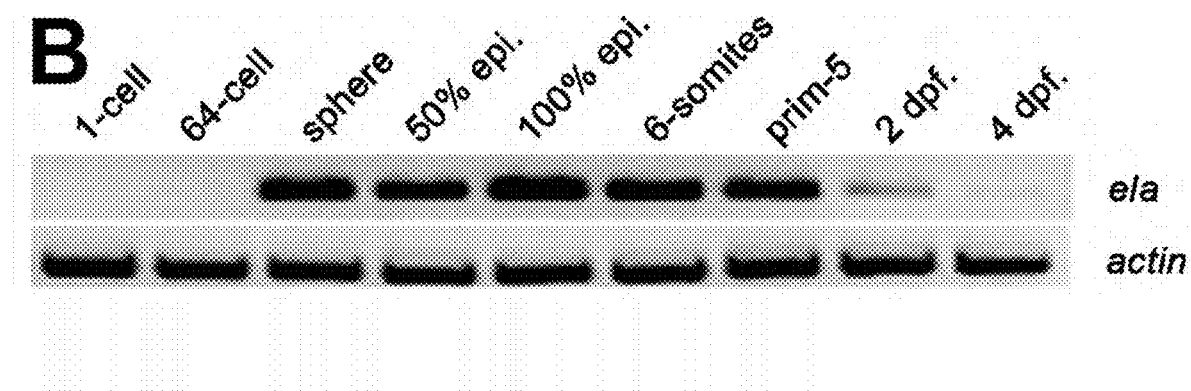
Figures 4C, 4D:
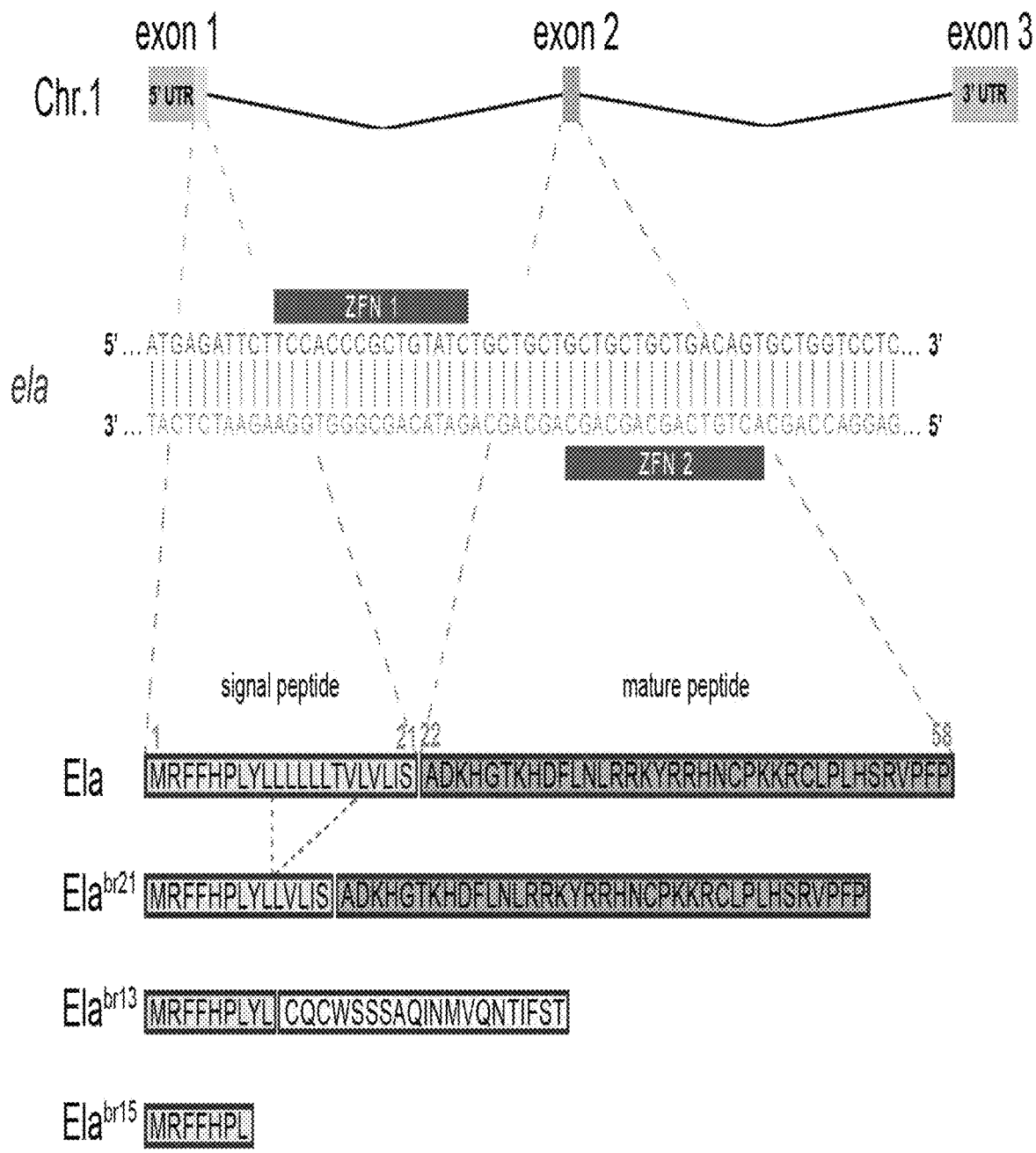

During zebrafish embryogenesis, ela is expressed from the mid-blastula transition (MBT) to 3 days post-fertilization (FIGS. 4A and 4B). Without any measurable maternal contribution, ela is ubiquitous in dividing cells of the blastoderm before becoming restricted after gastrulation to axial structures with most prominent expression in the neural tube (FIG. 4A). ela is located on chromosome 1 and also consists of 3 exons (FIG. 4C). To document the exact function and requirement for ela in vivo, we designed and injected custom ZFNs to induce double-stranded breaks in exon 1 of ela, which codes for its signal peptide. Screening of the F1 generation allowed us to identify an allelic series (FIG. 4D) of heterozygous ela fish that were selected and backcrossed at least five times before phenotypic analysis was undertaken.

Figure 4E:
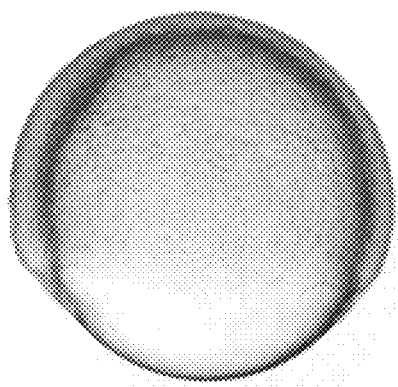
Figure 4E:
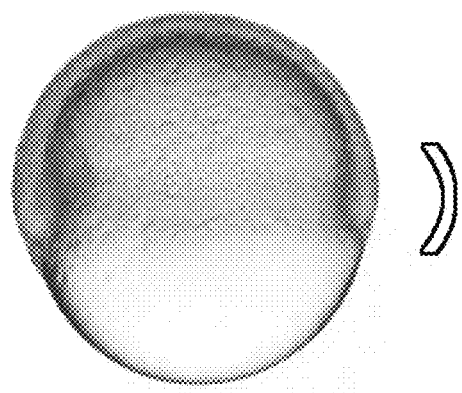
Figure 4F:
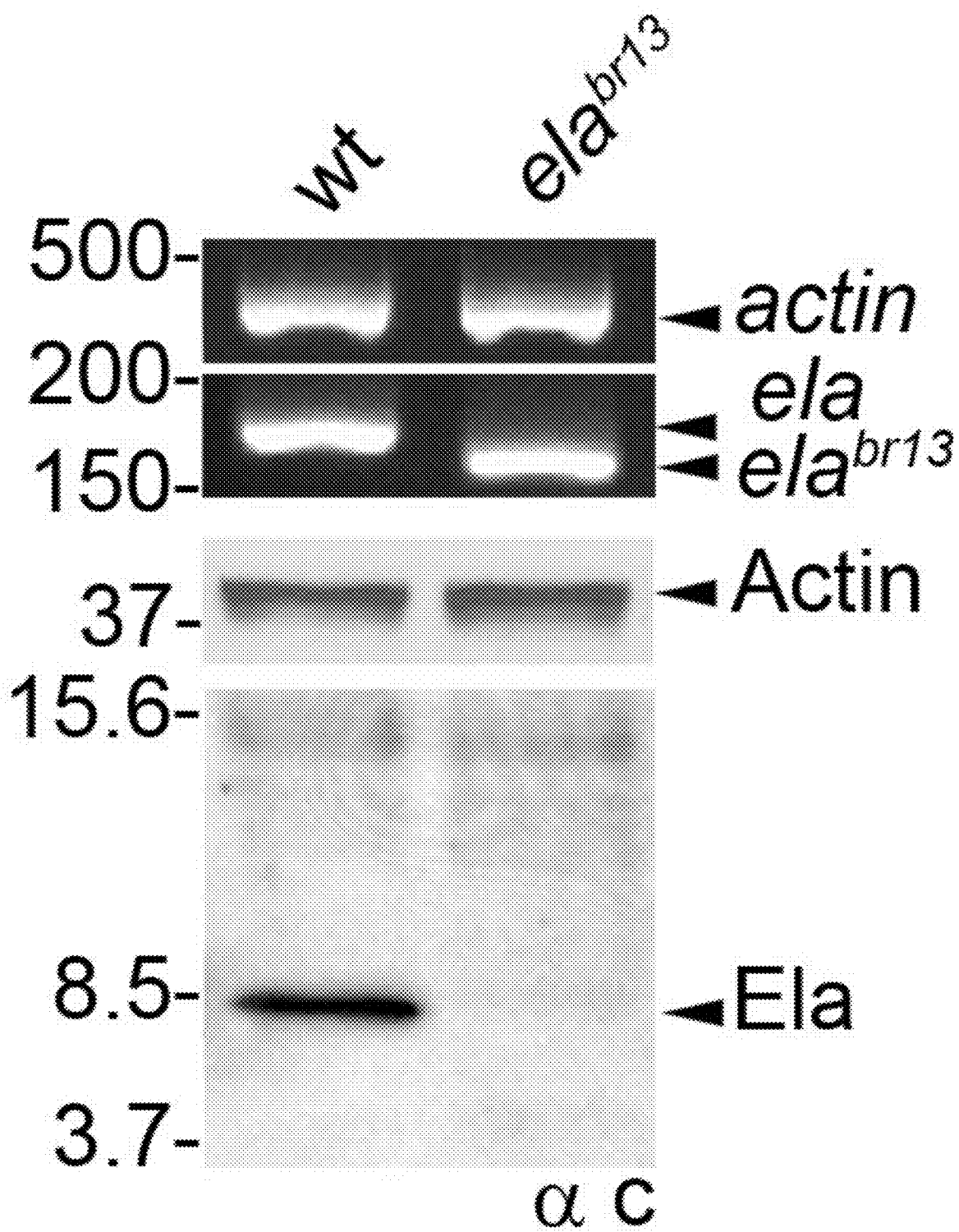

We analyzed 3 distinct ela alleles. $ela^{br21}$ is a 21 bp deletion causing a unique 7 amino acid in-frame deletion within the signal peptide but which leaves the mature peptide intact. $ela^{br13}$ and $ela^{br15}$ are frameshift alleles caused by deletion of 13 and 15 bp, respectively, that disrupt the entire mature Ela peptide (FIG. 4D). ela null embryos developed normally up to 50% epiboly, after which migration anomalies were observed in the germ ring; ela null embryos were easily scored by eye using the "rough" and constricted appearance of the involuting marginal layer at the shield stage (FIG. 4E). At 100% epiboly, when ela expression peaks (FIG. 4B), we confirmed by RT-PCR that $ela^{br13}$ mRNA was shorter than that of wildtype ela mRNA (FIG. 4F), which is consistent with its biallelic genomic deletion. By western blotting using α C antibodies, the endogenous Ela full-length protein could be detected in extracts of wt embryos but was absent from $ela^{br13}$ embryos (FIG. 4F).

Figure 5A:
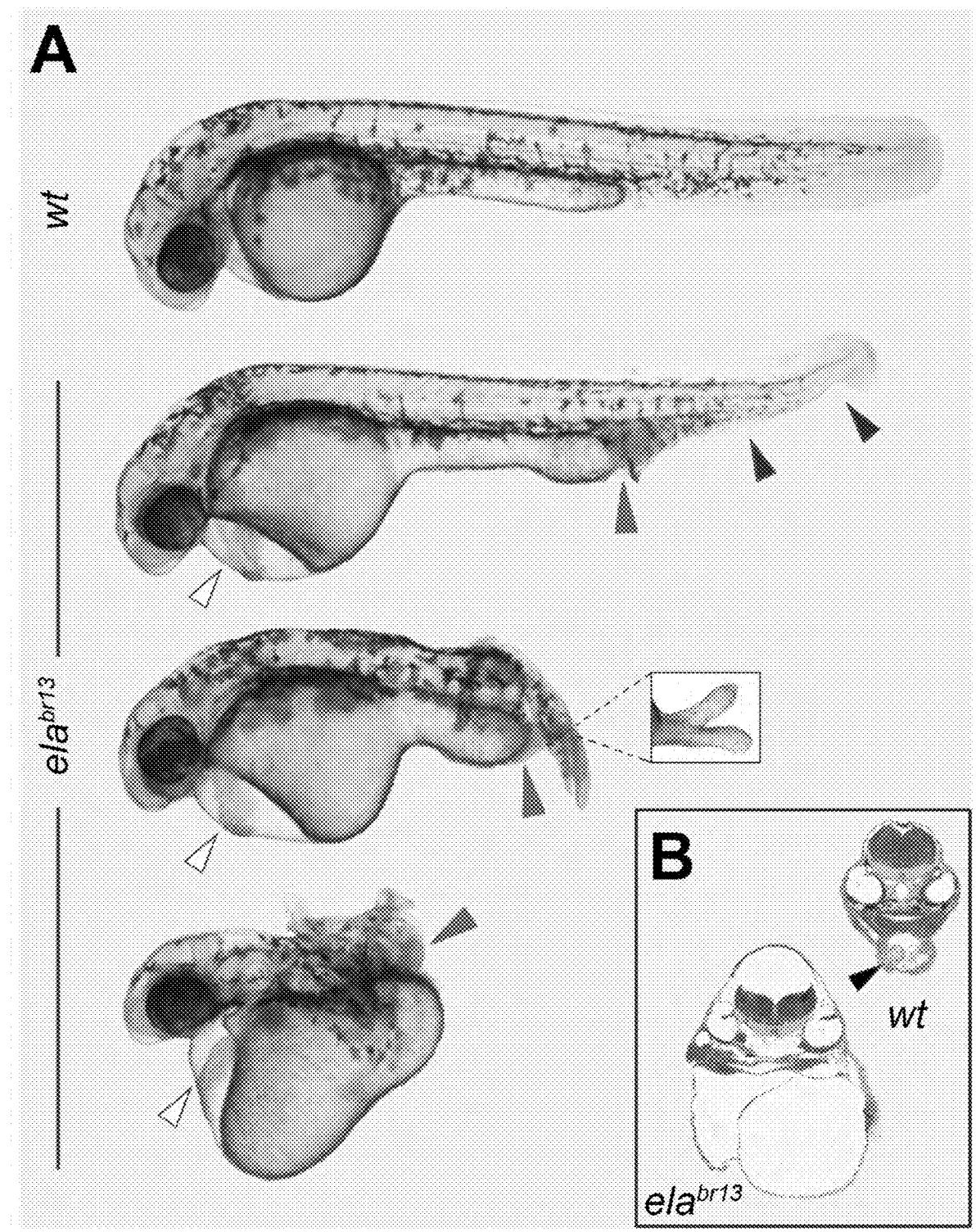
Figure 5B:
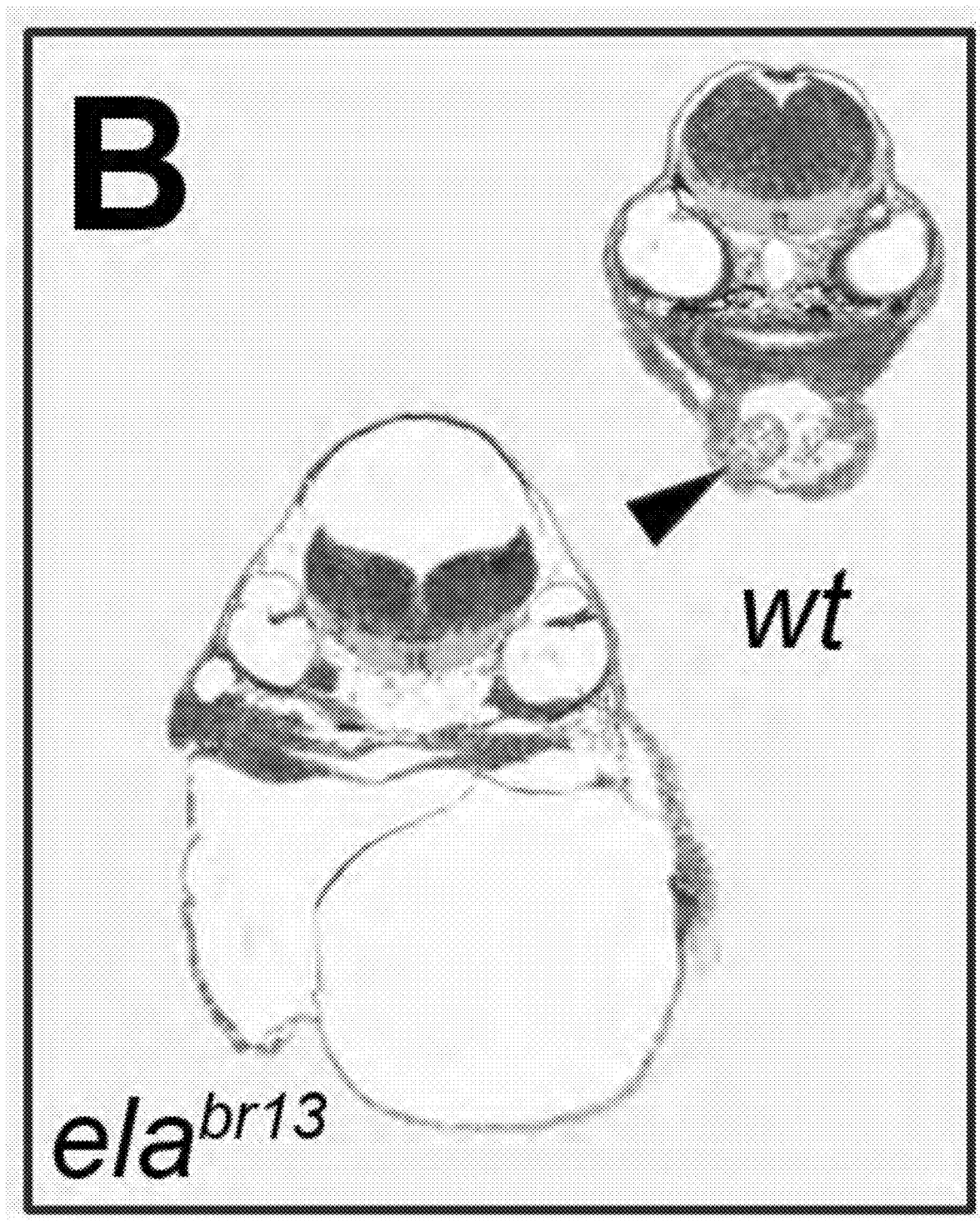
Figure 5C:
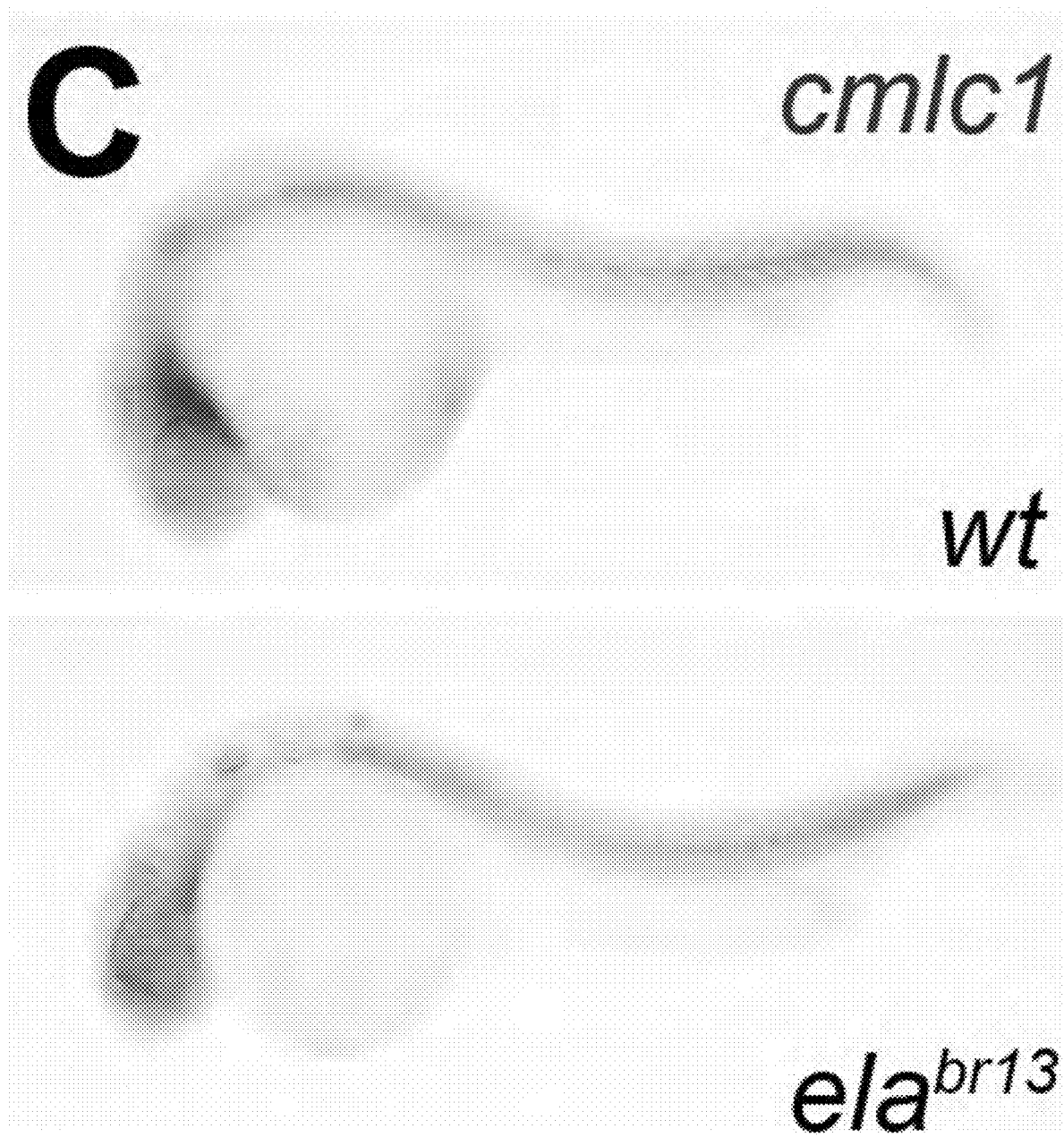
Figure 5D:
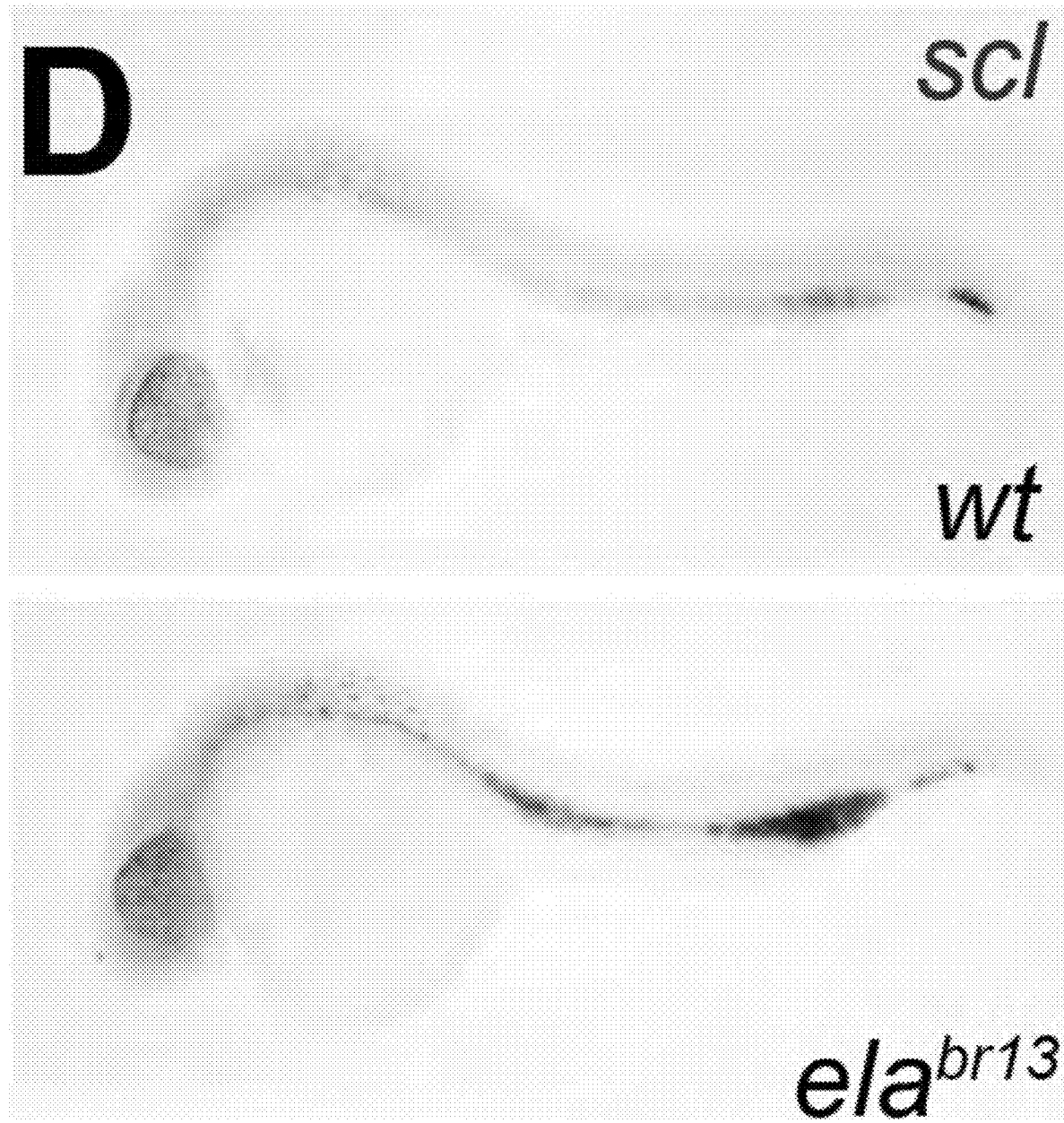

Example 22. Results: Loss of ela Causes Embryonic Lethality Due to Heart Dysgenesis All ela homozygous mutant fish showed similar phenotypes and were of expected Mendelian recessive ratios (FIG. 5A and FIG. 12A to FIG. 12C), suggesting that the three alleles behave as loss-of-function mutants. ela heterozygous fish were ostensibly normal, while ela null fish presented with severe cardiac dysplasia ranging from rudimentary heart to no heart (FIG. 5A, FIG. 5B and FIG. 12A to FIG. 12C). Loss, or severe reduction of embryonic heart marker cmlc1 was seen in more than 95% of ela null embryos (n>370) regardless of the allele analyzed (FIG. 5C). No blood circulation was observed and excess erythrocytes accumulated at the intermediate cell mass (ICM) (FIG. 5A), which was confirmed by sc/upregulation in ela mutant embryos relative to heterozygous siblings (FIG. 5D).

Figure 5E:
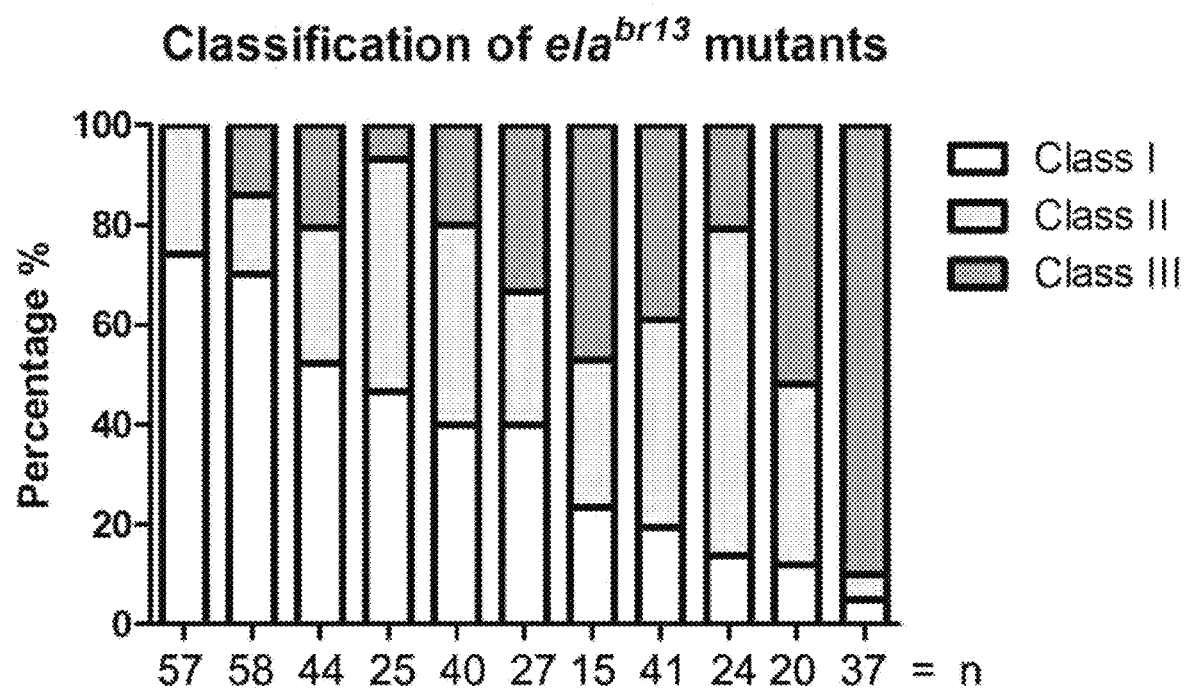
Figure 12A:
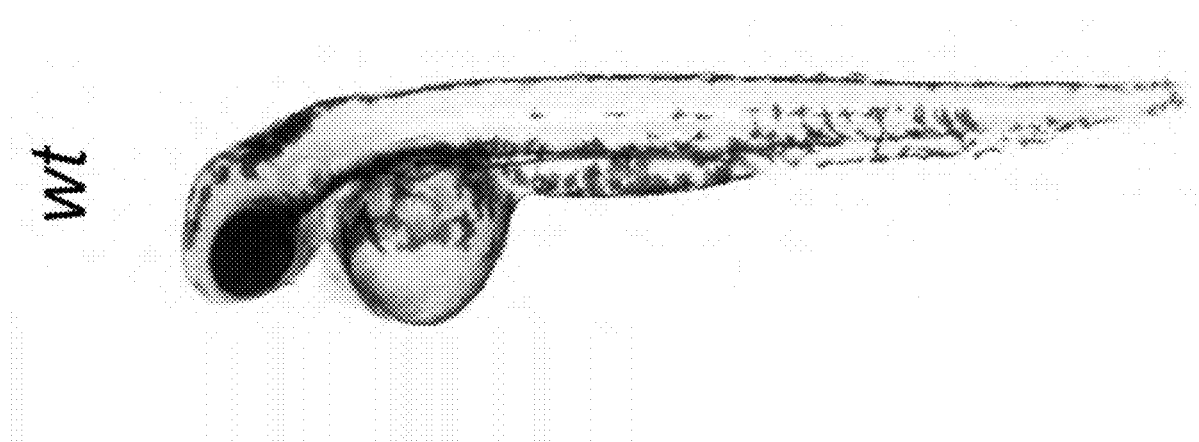
FIGS. 12A to 12D. Homozygous $ela^{br21}$ and $ela^{br15}$ mutant fish have Identical Phenotypes, related to FIG. 5.
Figure 12B:
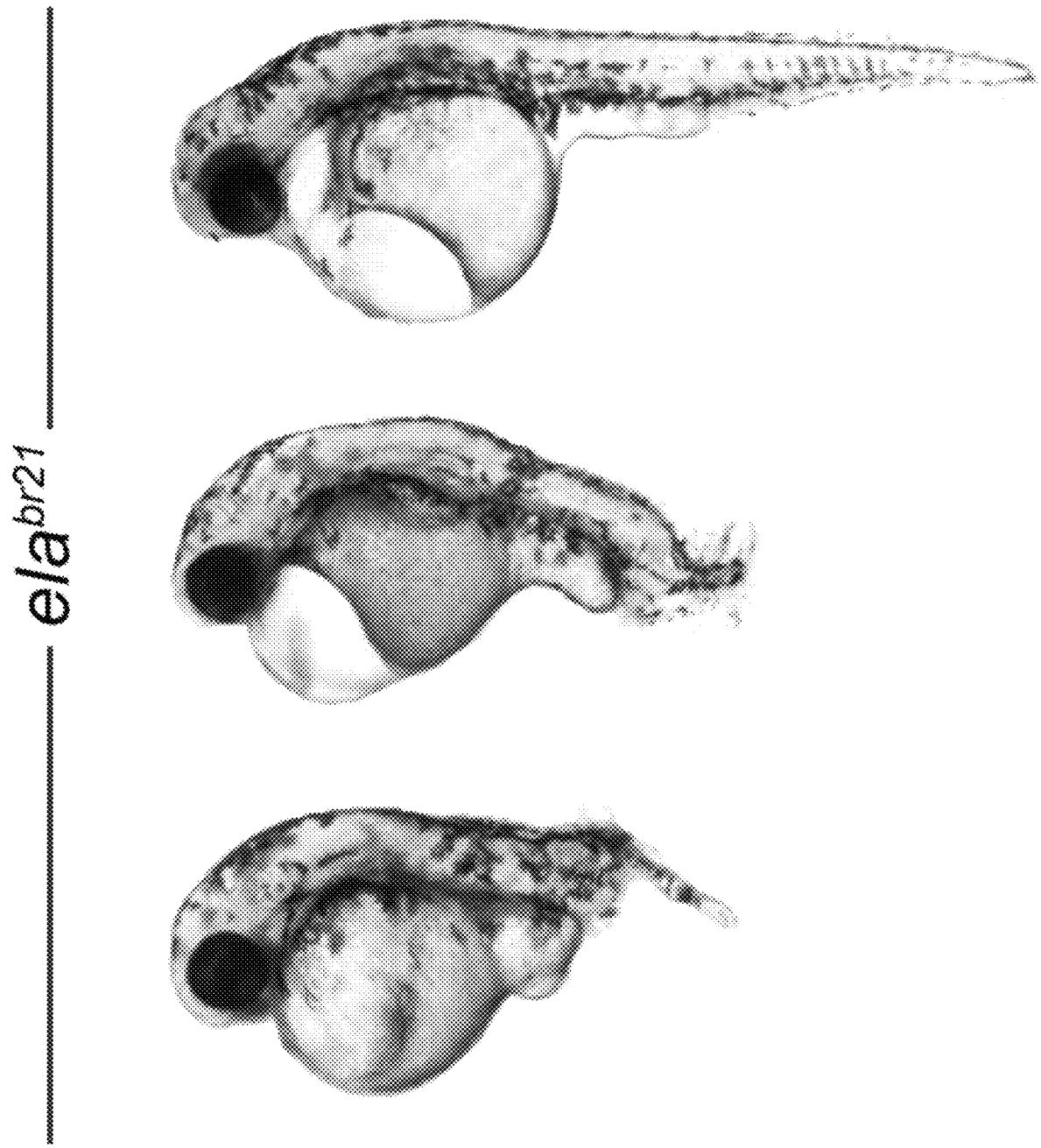
Figure 12C:
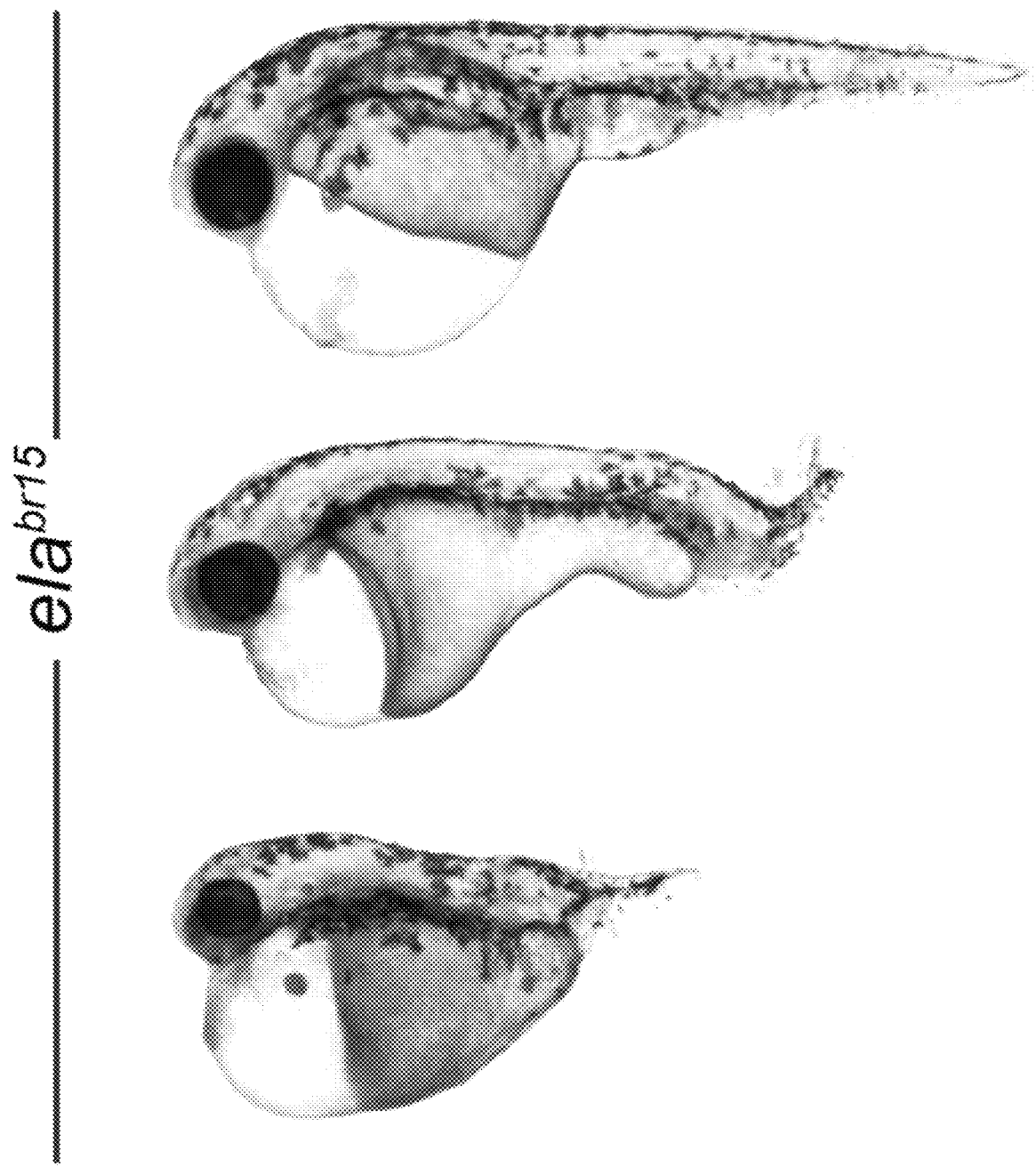
Figure 12D:
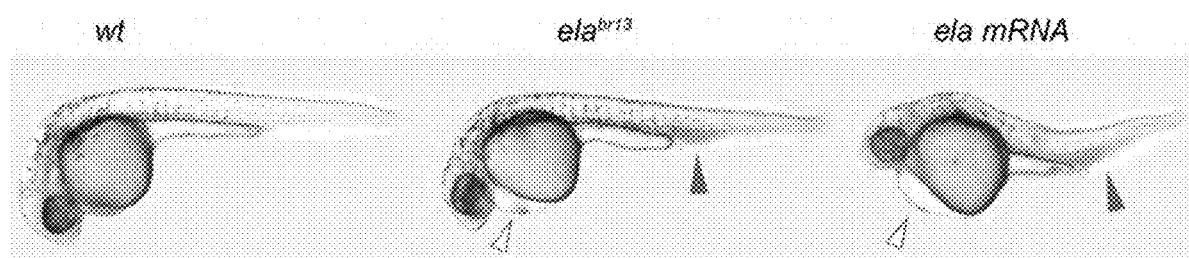

In addition, ela mutant larvae displayed variable posterior truncations, and at times, tailbud duplications. Posterior tissue defects ranged from loss of ventral fin to complete tail and trunk truncations (FIG. 5A). Unexpectedly, similar phenotypes were also observed upon ela mRNA overexpression (FIG. 12D). Thousands of ela null embryos from all three genotypes were obtained and scored into 3 classes according to the severity of tail defects (FIGS. 5A and 5E). We observed that the relative proportions of each class varied greatly among heterozygous crosses (FIG. 5E) and even among different clutches of embryos born to identical parents (data not shown), suggesting notable phenotypic variance in tail development but not in heart morphogenesis. Remarkably, a very low percentage of ela null mutants develop to fertile adults (FIG. 5F), ruling out any maternal ela effects and permitting homozygous crosses to yield 100% null clutches. These 3 ela loss-of-function alleles show that truncation of one third of the Ela signal peptide causes identical phenotypes as frameshift mutations, indicating that Ela requires an intact signal peptide to be functional in vivo. Moreover, these recessive ela alleles suggest that lowering Ela levels by half is of no obvious consequence whereas its total absence is incompatible with heart development, hematopoiesis and to a lesser extent for tail elongation.

Figure 6A:
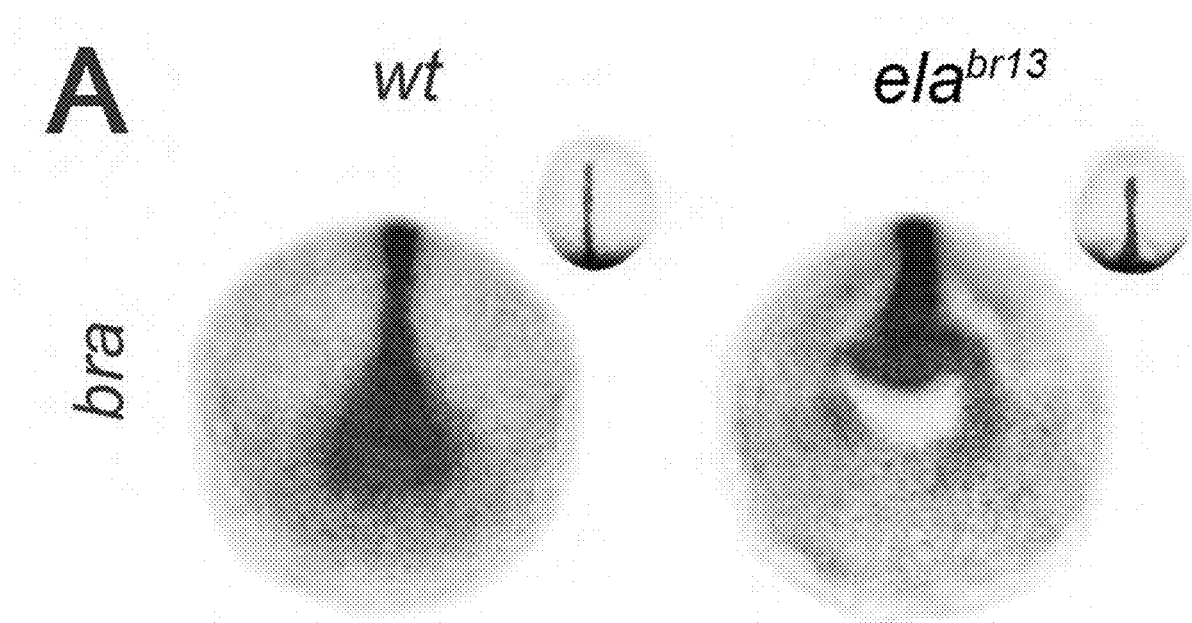
FIGS. 6A to 6F. ELA is Essential for Endoderm Differentiation
Figure 6B:
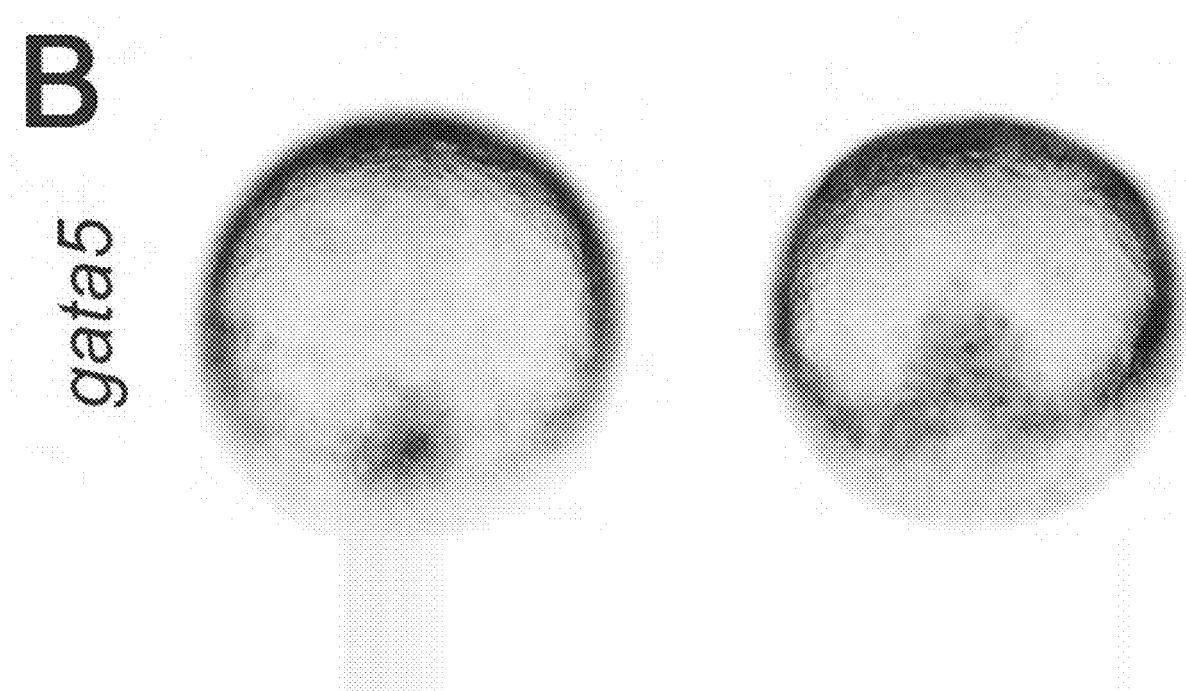
Figure 6C:
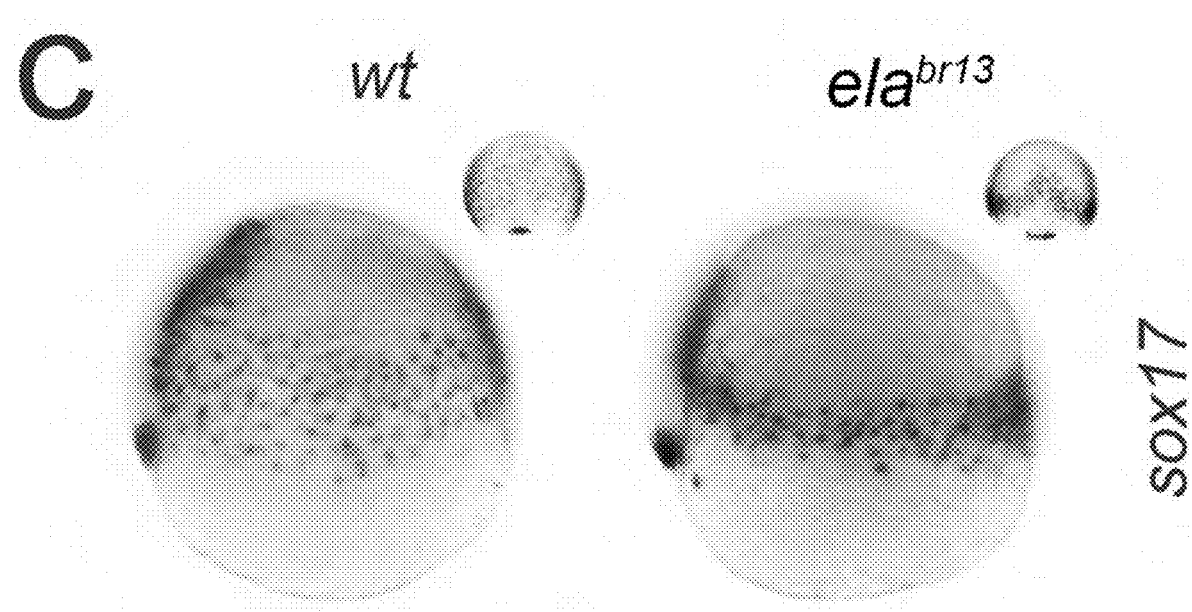
Figure 6D:
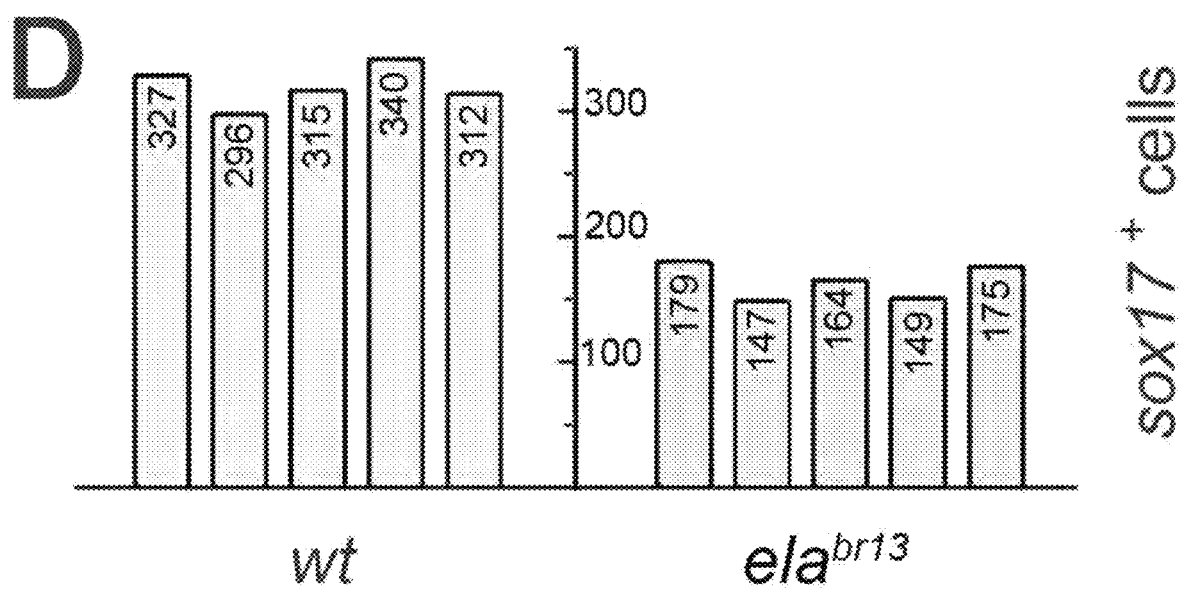
Figure 13A:
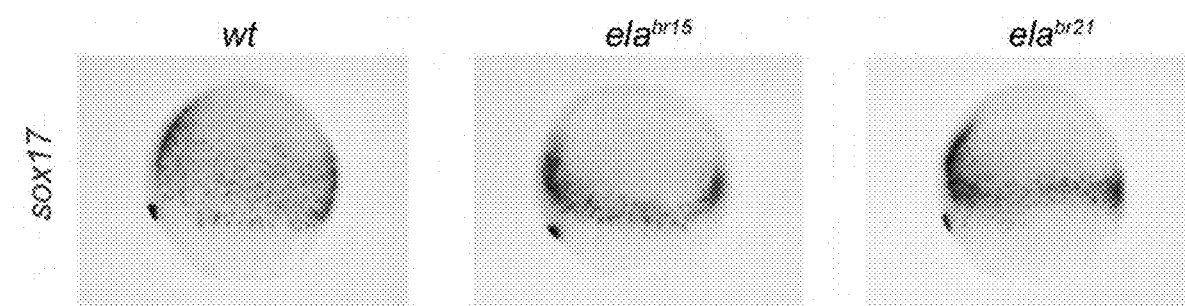
FIGS. 13A to 13C. Endoderm Differentiation is Defective in ela mutant fish and ELA-depleted hESCs, related to FIG. 6.

Example 23. Results: ELA is Required for Proper Endoderm Differentiation in Zebrafish and hESCs In order to understand the embryological origin of the severe cardiac defects observed in ela mutant fish, we analyzed by whole-mount in situ hybridization a series of markers for all three embryonic germ layers. Most prominently, ela mutant gastrulae displayed specific defects in the mesendodermal lineage (FIG. 6A-D). Mesoderm, marked by bra, exhibited impaired epiboly movements presumably caused by convergent-extension anomalies. At 100% epiboly ela mutant embryos were delayed and had an open blastopore with a shorter and thicker notochord relative to wildtype (wt) embryos (FIG. 6A). The expression of gata5, which marks mesendoderm and promotes the development of cardiovascular progenitor cells (CPCs), was distinctly altered in ela embryos compared to wt embryos at 75% epiboly; instead of marking a discrete axial population of cells in the heart-forming region, ela null embryos displayed a distinctive chevron shape around the organizer that was continuous with the marginal gata5-expressing cells (FIG. 6B). Expression of sox17, which marks definitive endodermal precursors, was equally chevron-shaped in the dorsal side, although sox17 forerunner cells were unaltered by the absence of ela (FIG. 6C and FIG. 13A). We observed a significant reduction in the total number of $sox17^+$ cells at 75% epiboly, which on average were reduced by 30 to 40% compared to wt or ela heterozygous siblings (FIG. 6D).

Figure 6E:
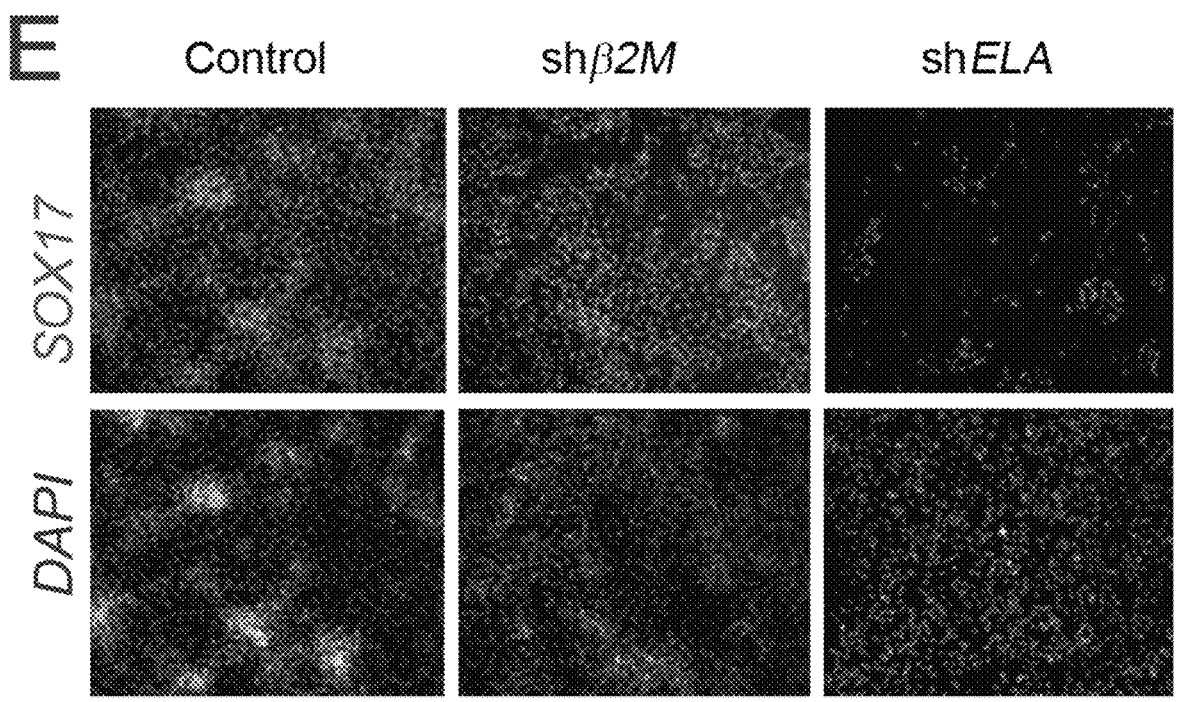
Figure 6F:
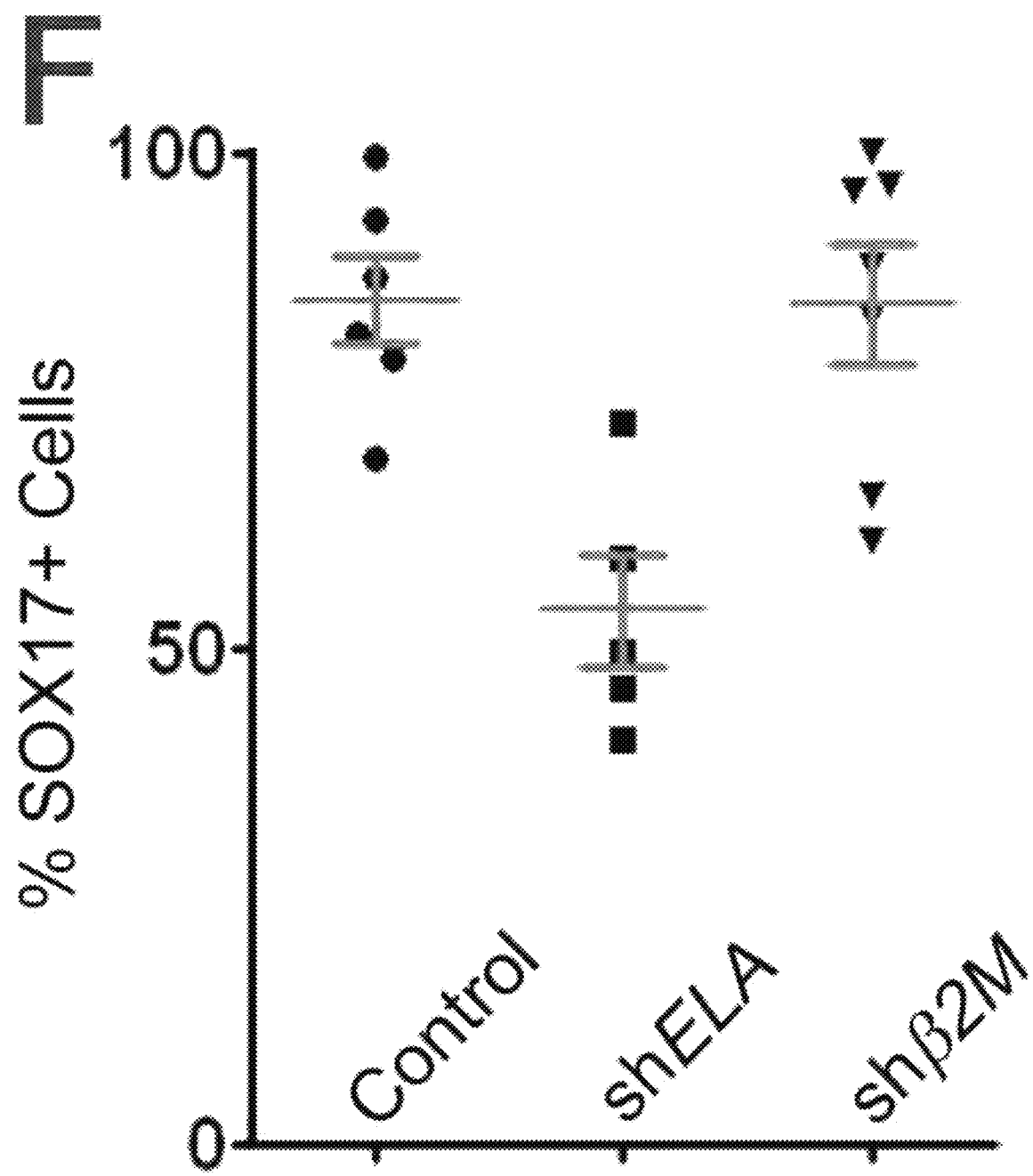
Figure 13B:
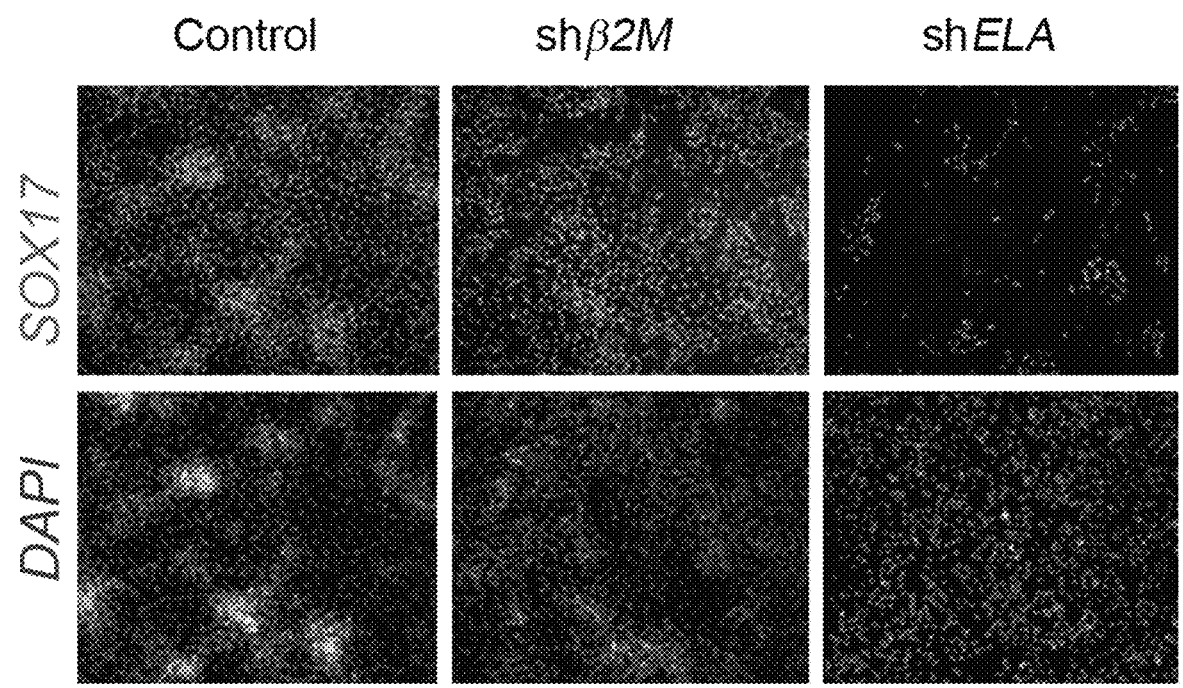
Figure 13C:
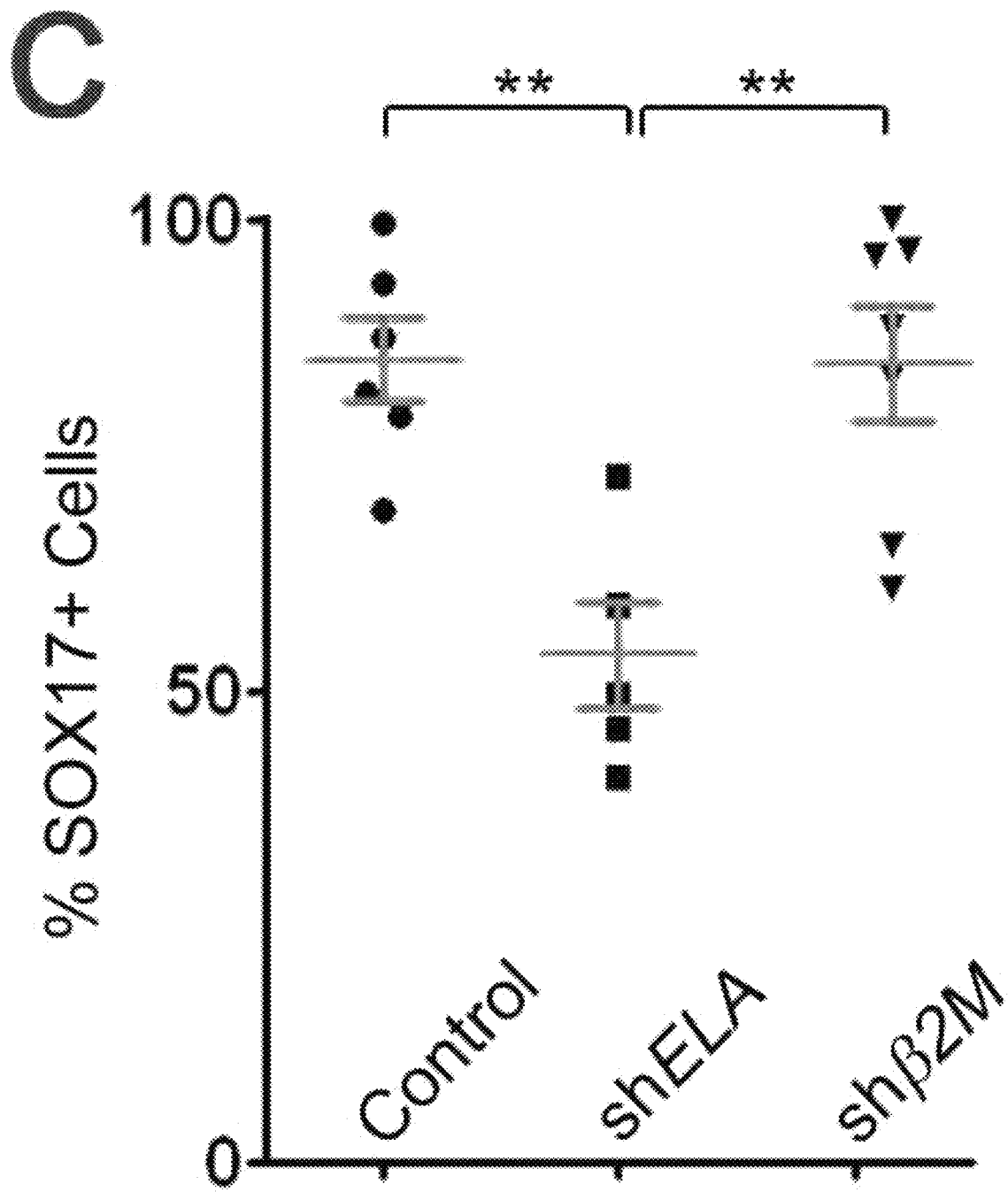

To test whether human ELA is similarly required for endoderm differentiation of hESCs, we differentiated hESCs for 5 days and counted the number of $SOX17^+$ definitive endoderm cells. We observed impaired endoderm differentiation of shELA but not shβ2M or control hESCs (FIG. 6E, FIG. 13B and FIG. 13C). shELA hESCs showed a significant 45% reduction over control in the number of $SOX17^+$ cells which could be entirely rescued by addition of the recombinant ELA peptide (FIG. 6F). We conclude that ELA is essential both in vivo and in vitro for embryonic pluripotency and for the proper differentiation of endodermal precursors.

Figure 7B:
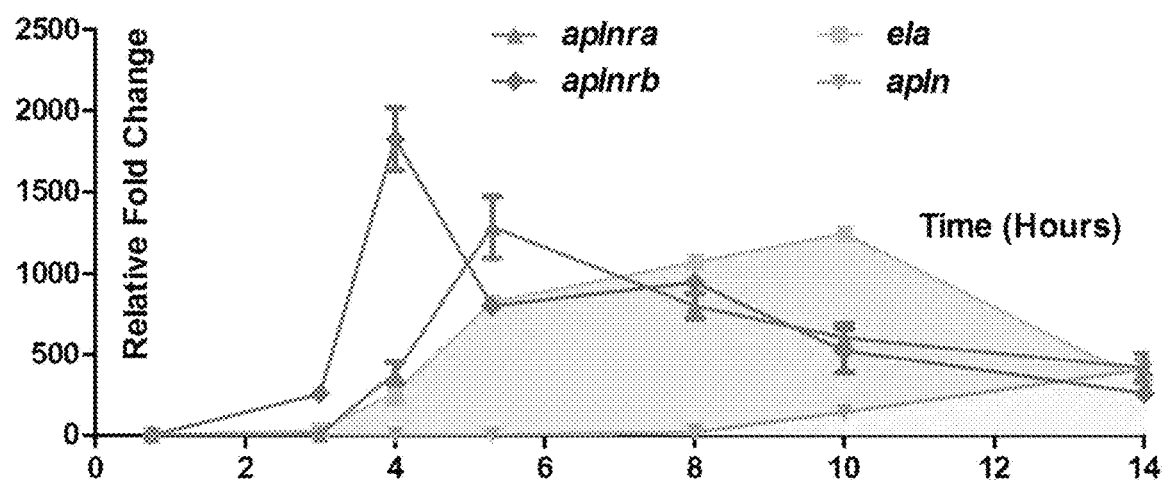
Figure 7C:
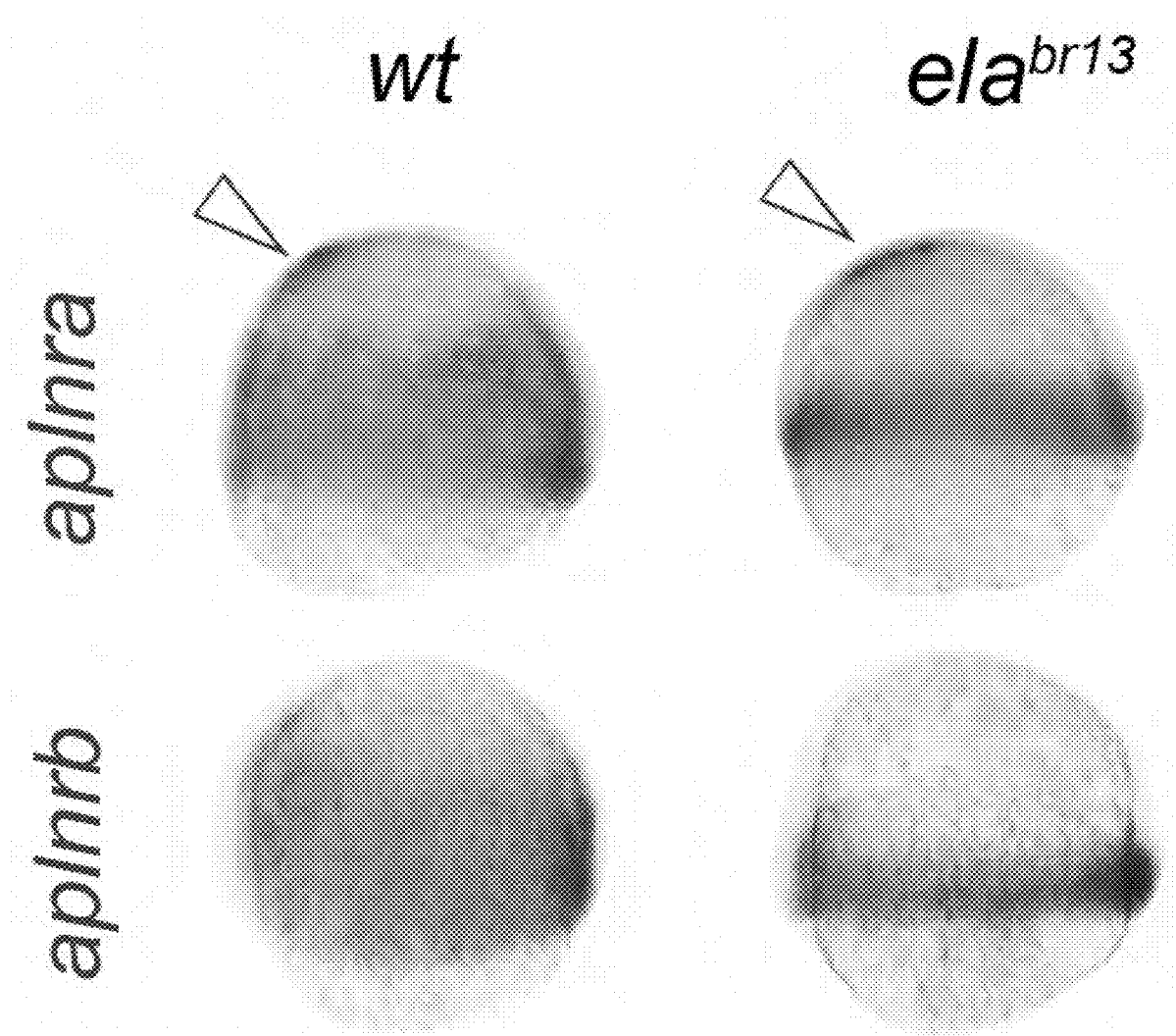
Figure 7D:
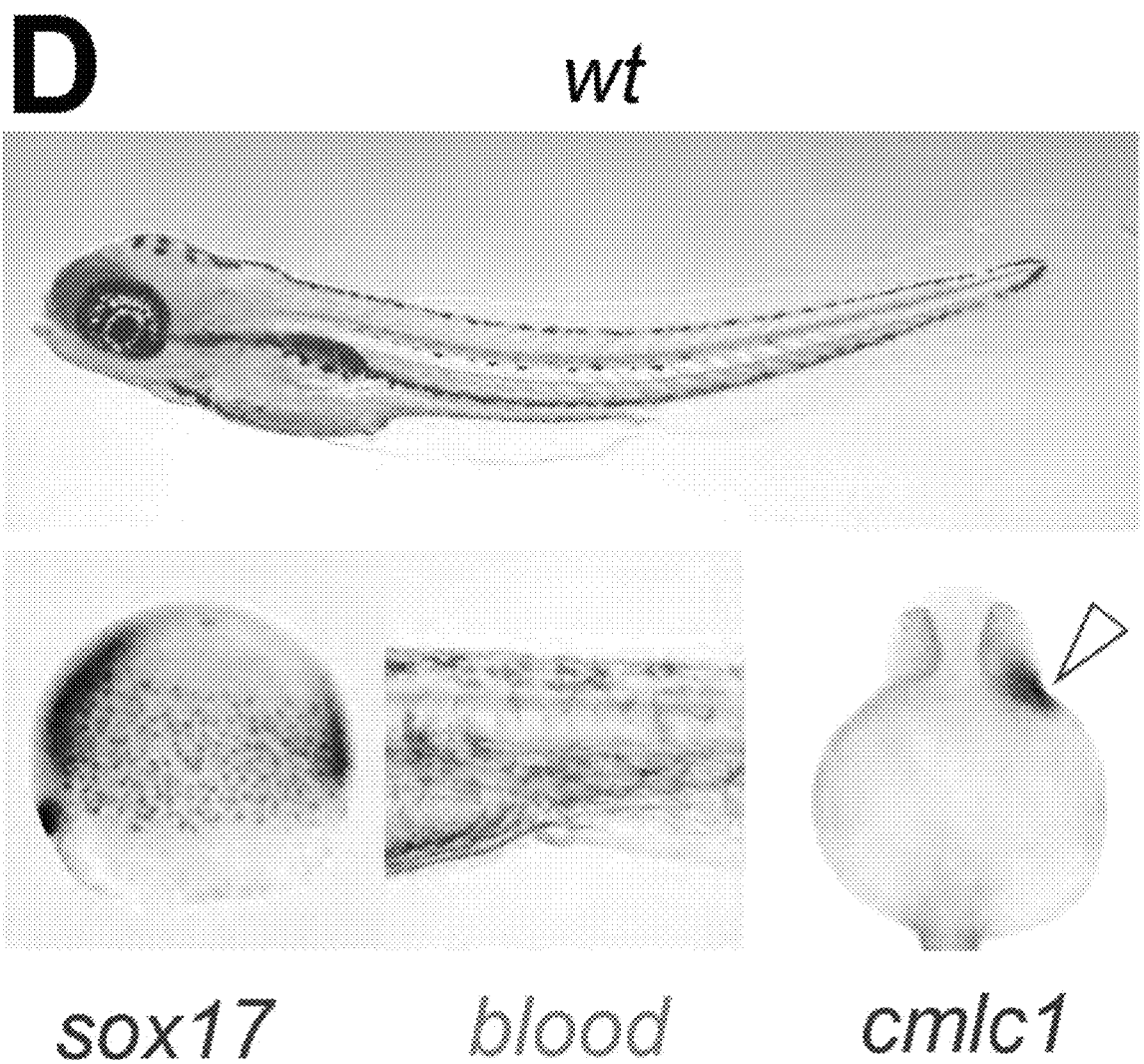
Figure 7E:
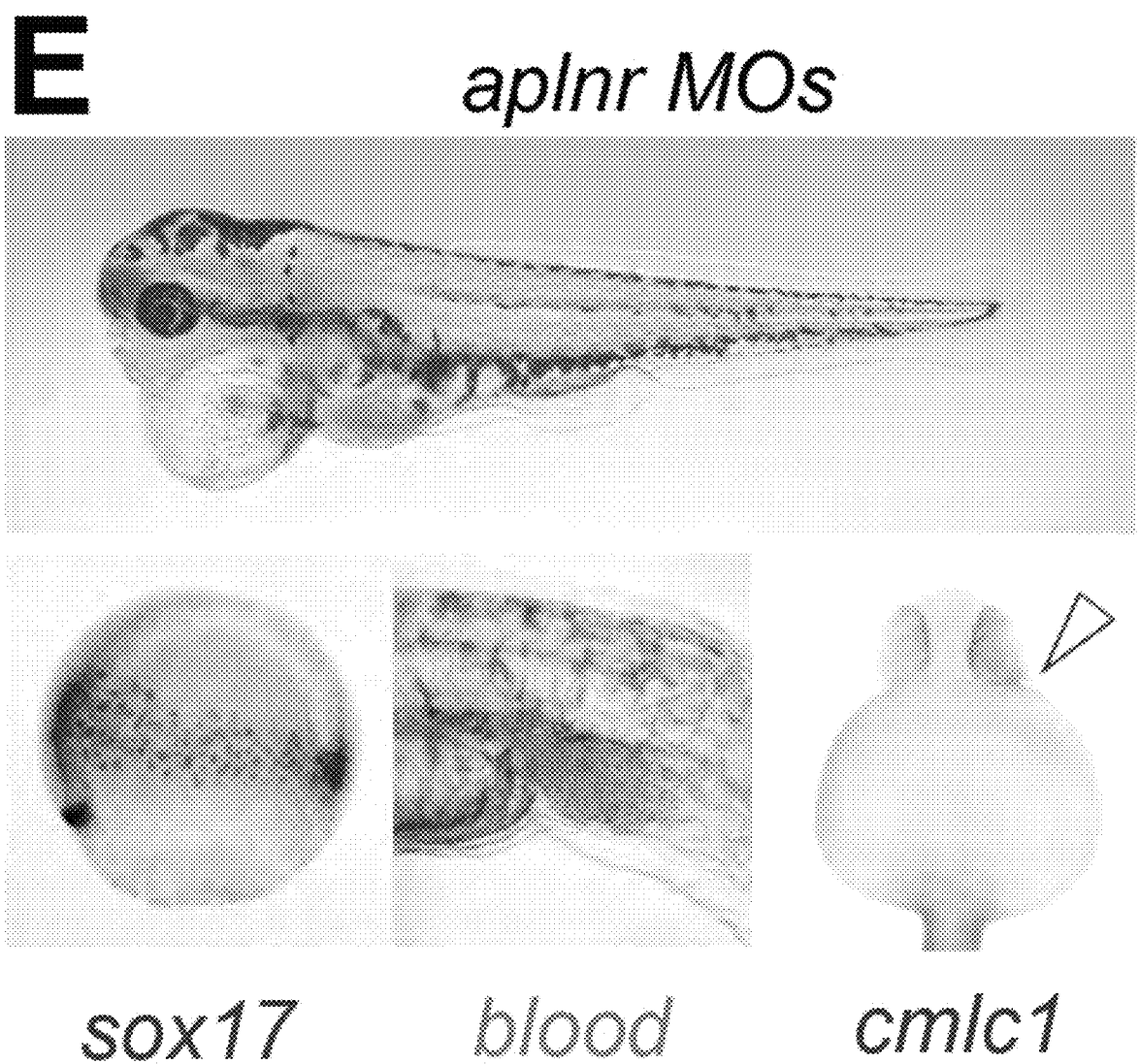
Figure 7F:
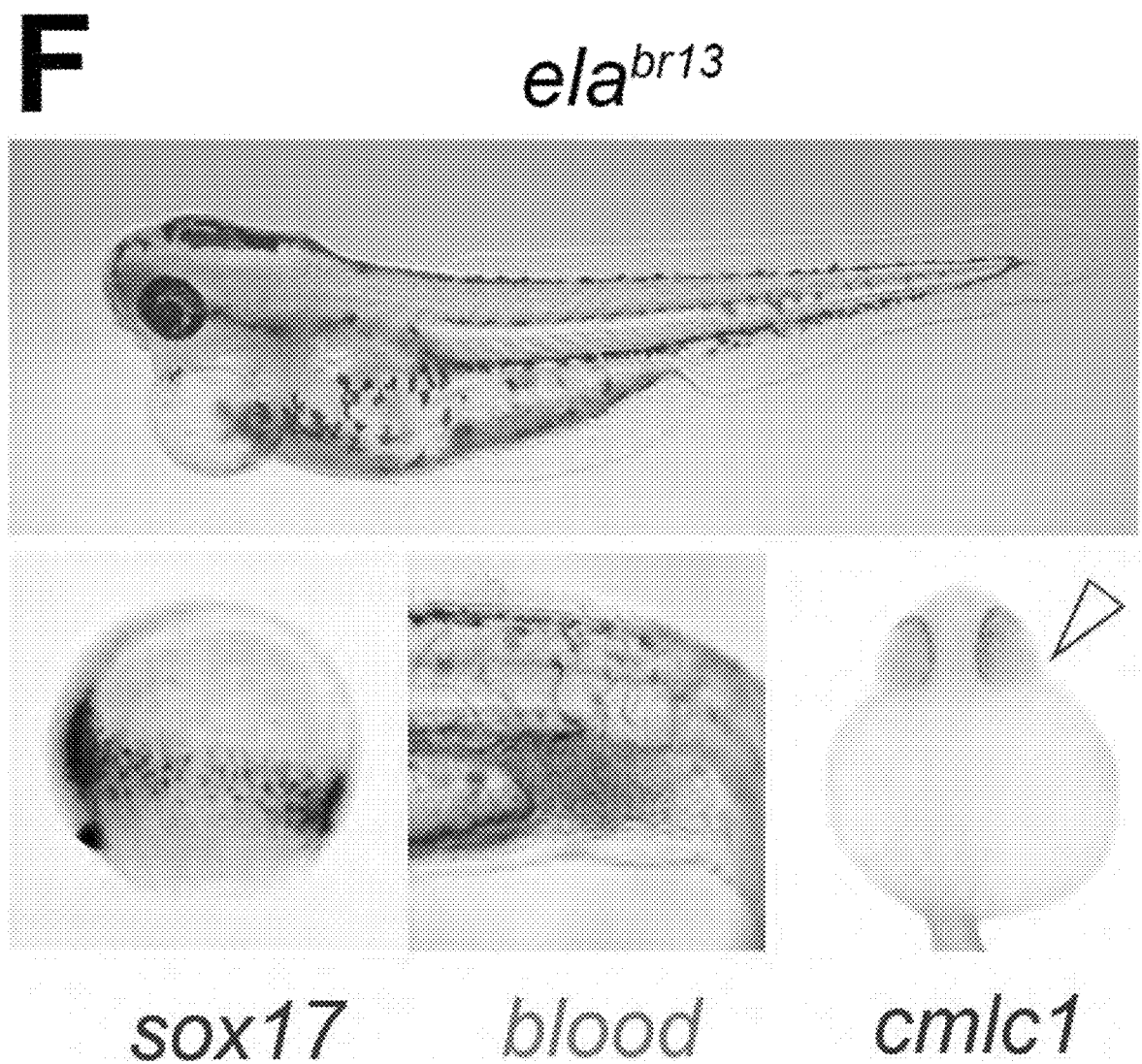
Figure 7G:
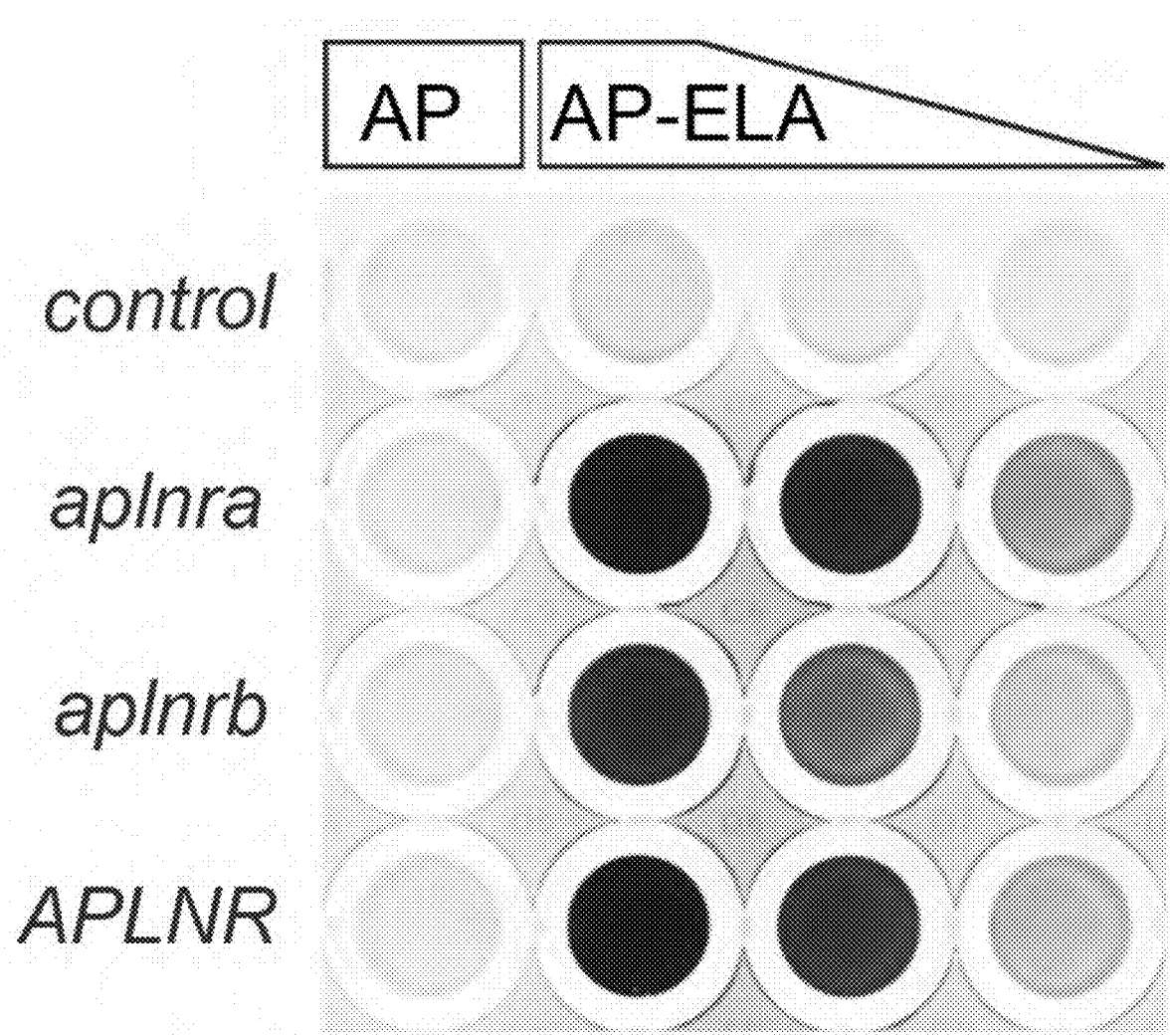
Figure 7H:
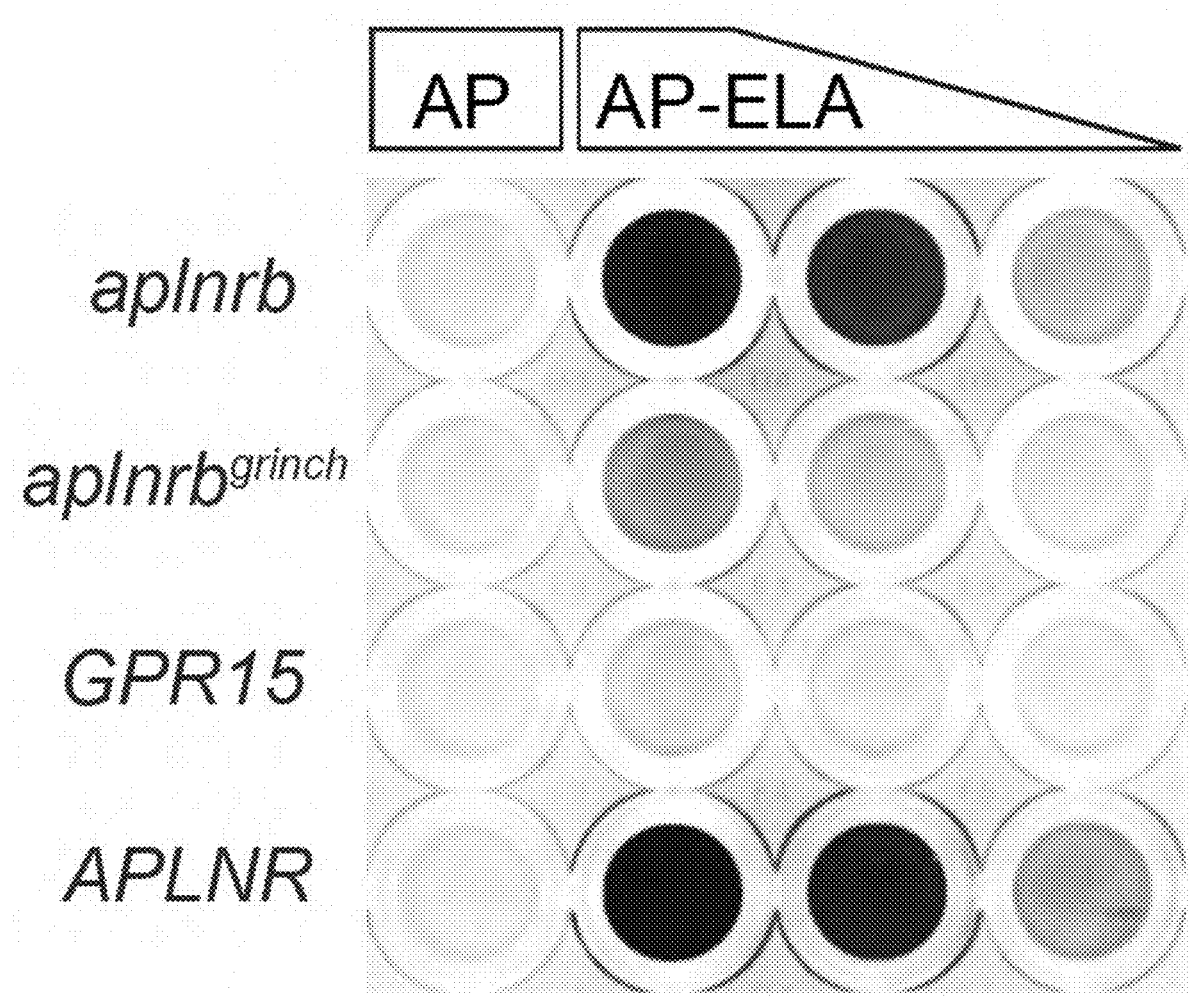
Figure 8:
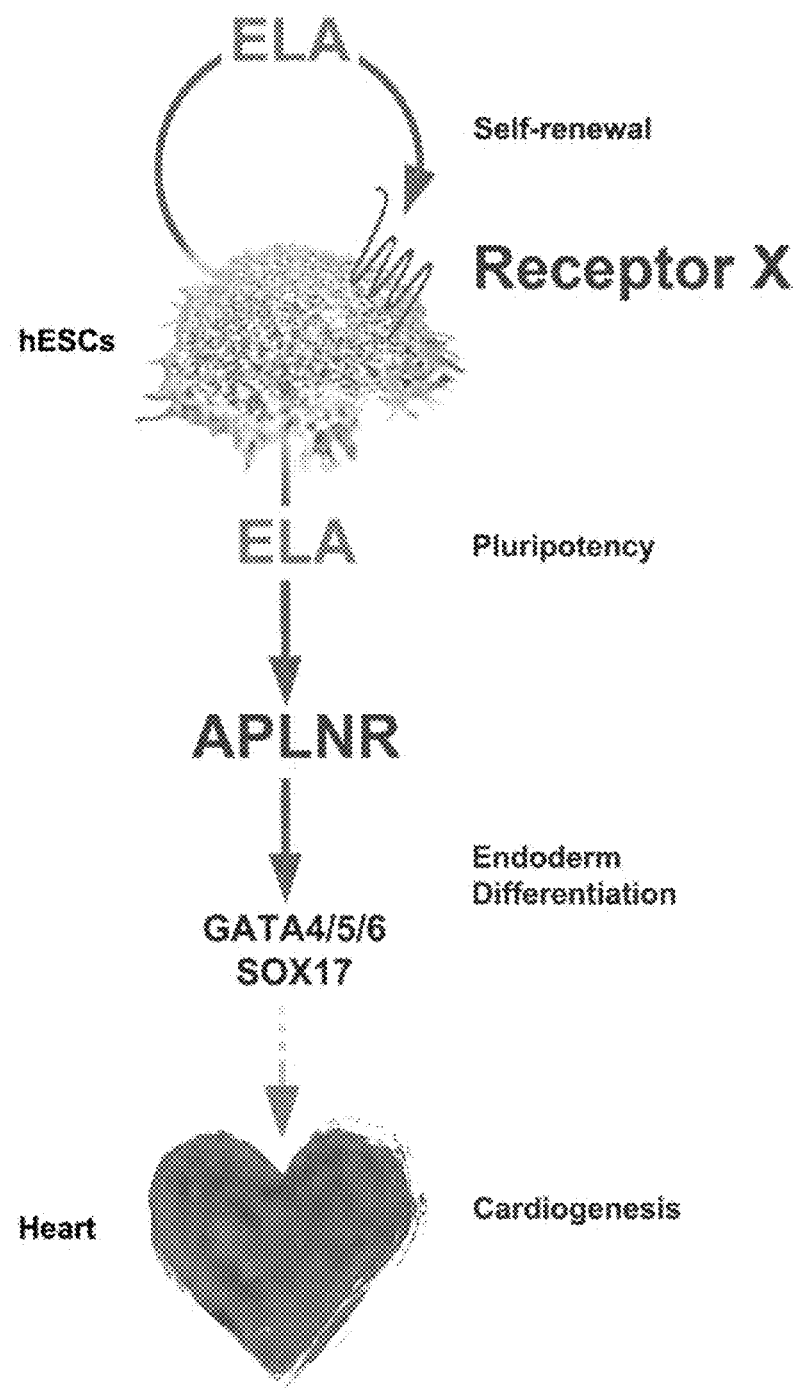
FIG. 8. Graphical abstract.

Example 24. Results: APLNR is the Cognate Receptor for ELA During Heart Development Hormonal peptides signal through G-protein coupled Receptors (GPCRs). One such GPCR, the apelin receptor (APLNR), has been implicated in heart development in fish and mice. The zebrafish mutant grinch, which carries a recessive W90L missense mutation in aplnrb, and Aplnr knockout mice both have defects in cardiac morphogenesis (Charo et al., 2009; Scott et al., 2007). Unexpectedly however, loss of APLN, the accepted ligand for APLNR does not recapitulate the phenotype of grinch in zebrafish or Aplnr null mice. We surmised that ELA might be the long sought-after alternate and earlier ligand for APLNR (Charo et al., 2009; Scott et al., 2007). Unlike most other hormones that have near neutral isoelectric points, ELA and APLN are rich in basic residues and have isoelectric points above 12 (FIG. 7A), suggesting they might share a common receptor. For ELA to be the first ligand of APLNR, we contended that it should: 1) be expressed concomitantly with aplnr before the onset of gastrulation; 2) be expressed in, or adjacent to, aplnr-expressing cells; 3) phenocopy aplnr mutants and 4) bind to APLNR on the surface of cells. Consistent with previous reports, the onset of aplnra and aplnrb coincides with that of ela at MBT, whereas apln expression begins 5 hours later during gastrulation (FIG. 7B). Cells expressing aplnra and aplnrb are in the hypoblast (Zeng et al., 2007), just beneath the overlying enveloping layer where ela is ubiquitously transcribed (FIGS. 4A and 7C). We found that the expression of aplnra and aplnrb was also responsive to the loss of ela, displaying a more condensed pattern at the margin relative to wt embryos (FIG. 7C). Phenotypically, and using an array of markers, we found that aplnr morphants were indistinguishable from ela null embryos. Both exhibited pericardial oedema with markedly reduced cmlc1 expression and accumulation of erythrocytes in the ICM at 30 hours post fertilization (hpf). By six days, all ela mutant and aplnr morphant embryos had cardiac dysplasia with little to no blood circulation (FIG. 7D-7F). These in vivo data demonstrate that loss of ela phenocopies the loss of aplnr, arguing that they form a ligand-receptor pair in vivo. Lastly, overexpression of zebrafish aplnra/b and human APLNR in HEK293T cells, which do not express APLNR and do not bind ELA, was sufficient to afford cell-surface binding to ELA conjugated to Alkaline Phosphatase (AP-ELA) (FIG. 7G). In contrast aplnrb$^{grinch}$ was unable to bind AP-ELA nor could GPR15 (FIG. 7H), an orphan GPCR closely related to APLNR (Vassilatis et al., 2003). These results suggest that extracellular ELA can bind APLNR in a native cellular context. Taken together, our results strongly support the notion that ELA, and not APLN, is the first agonist of APLNR which in tandem direct endodermal differentiation for cardiac development.

Figure 14A:
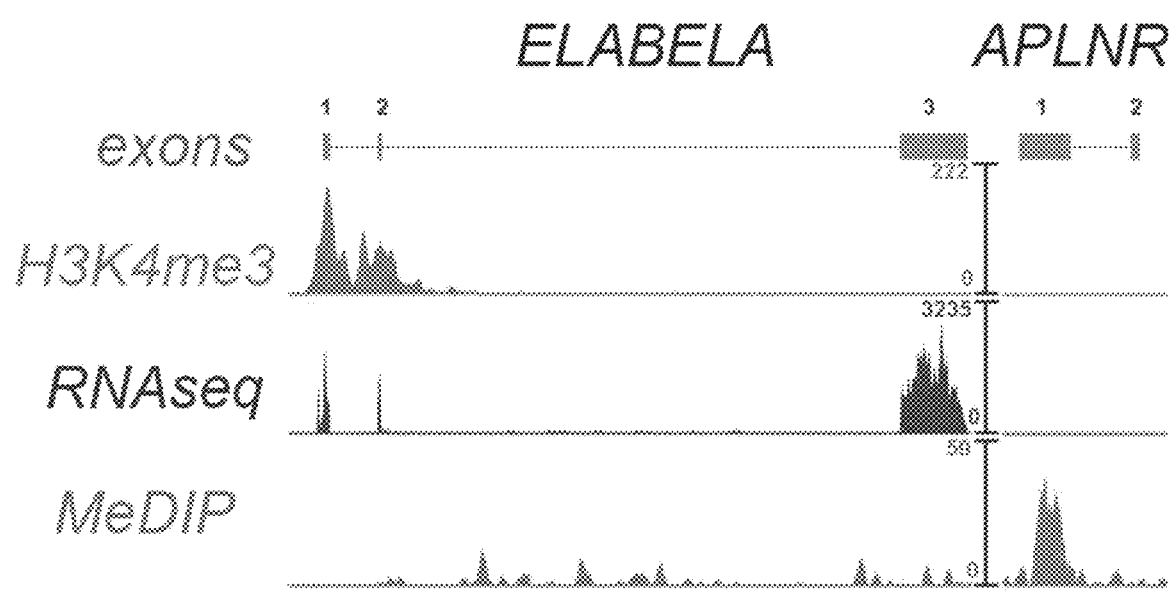
FIGS. 14A to 14F. APLNR is Necessary for ELA Binding but is Not the ELA Receptor in hESCs, related to FIG. 7.
Figure 14B:
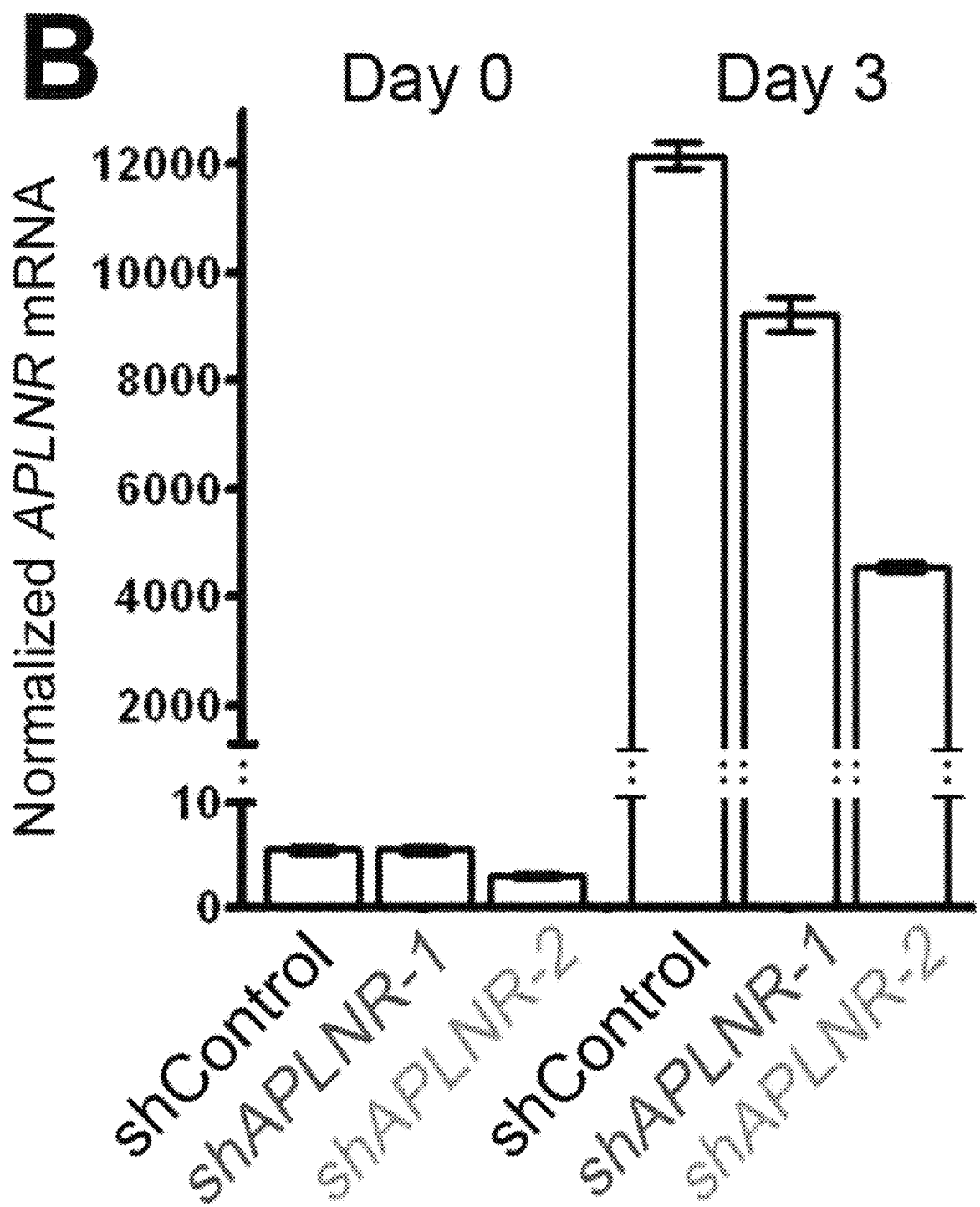
Figure 14C:
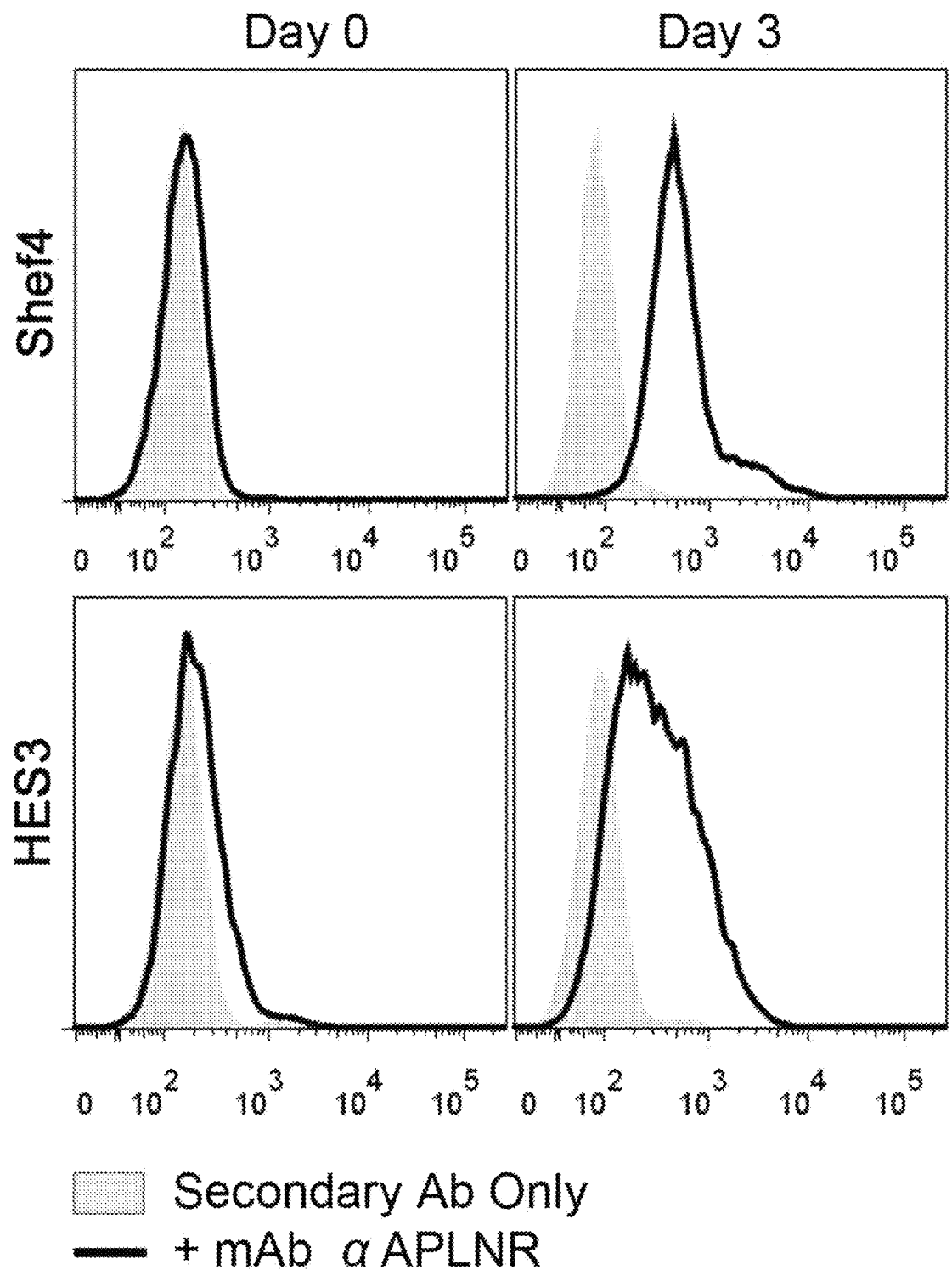
Figure 14D:
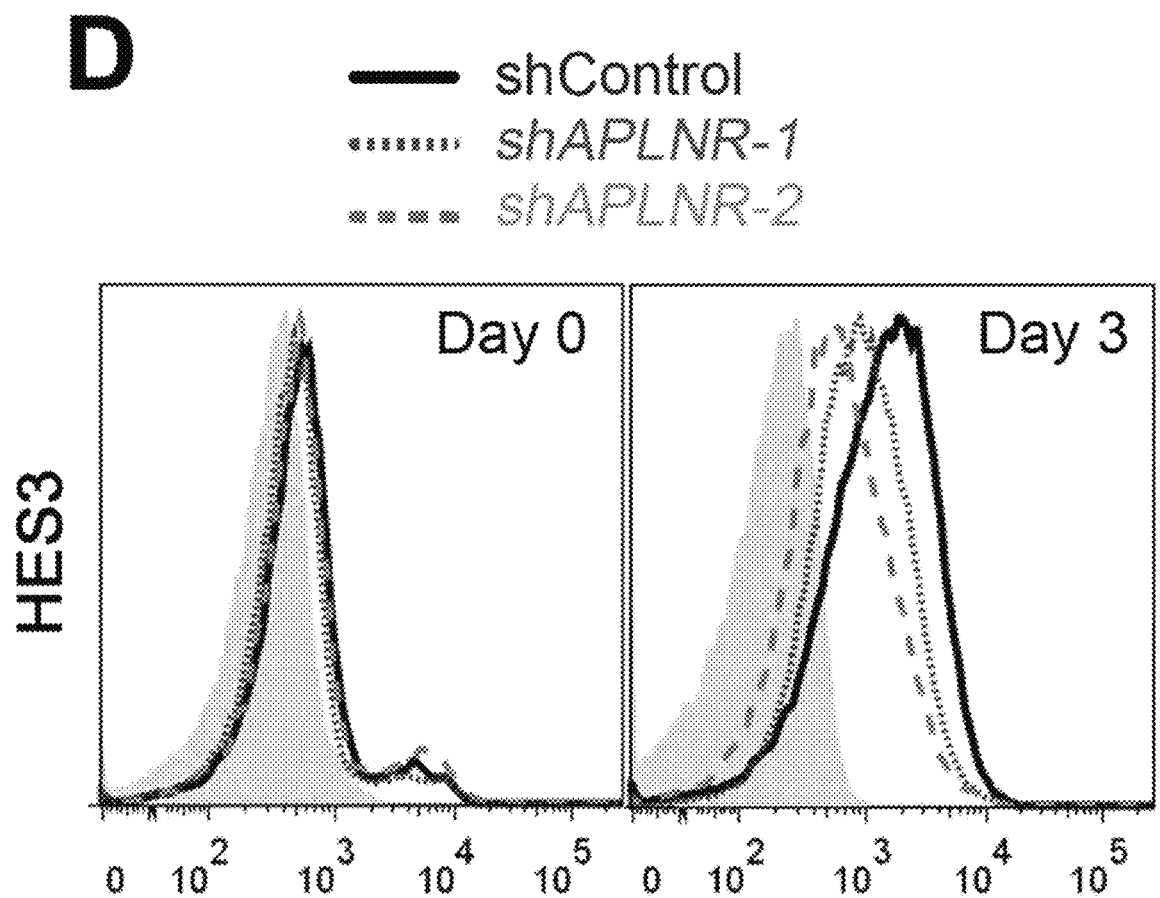
Figure 14E:
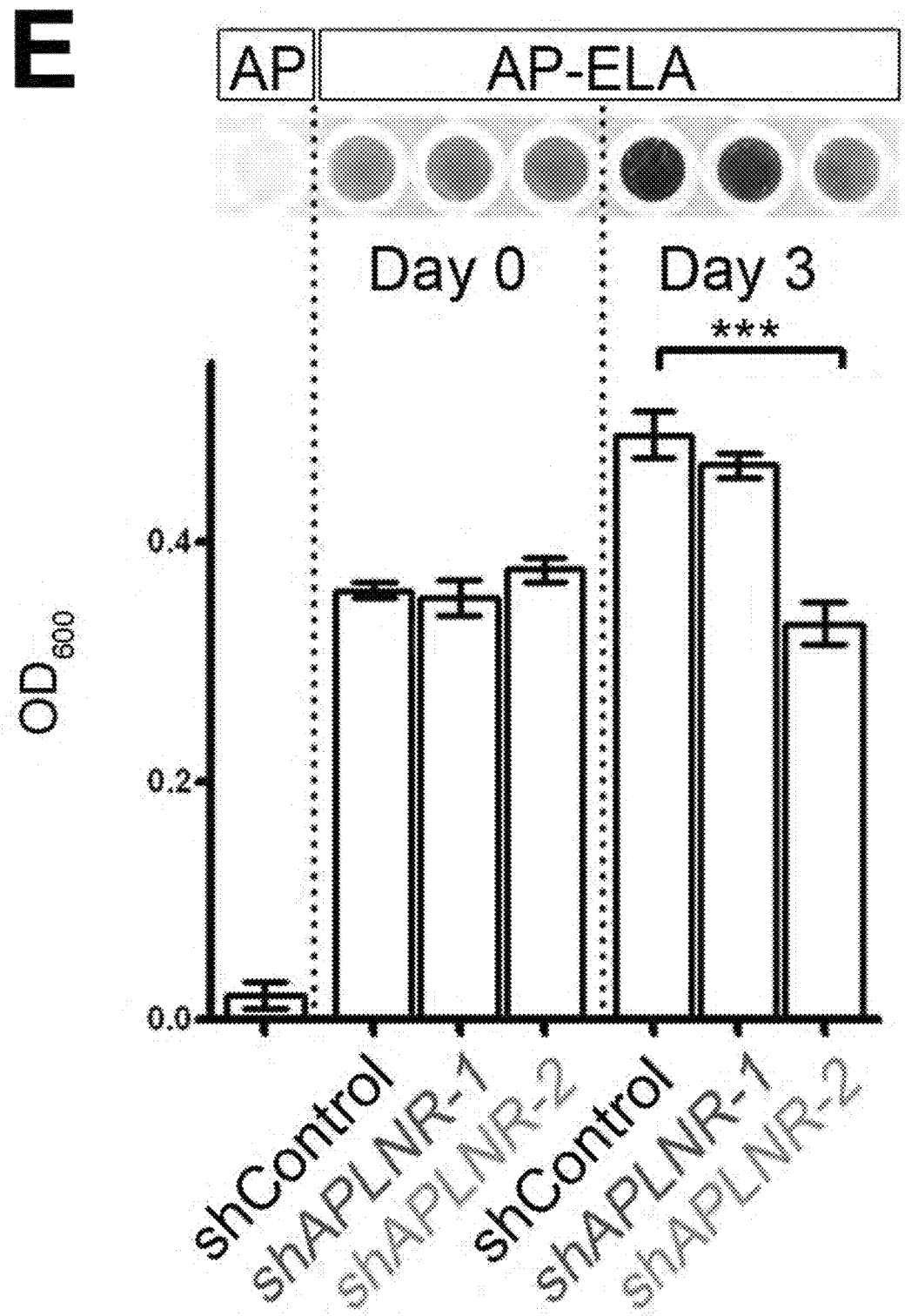
Figure 14F:
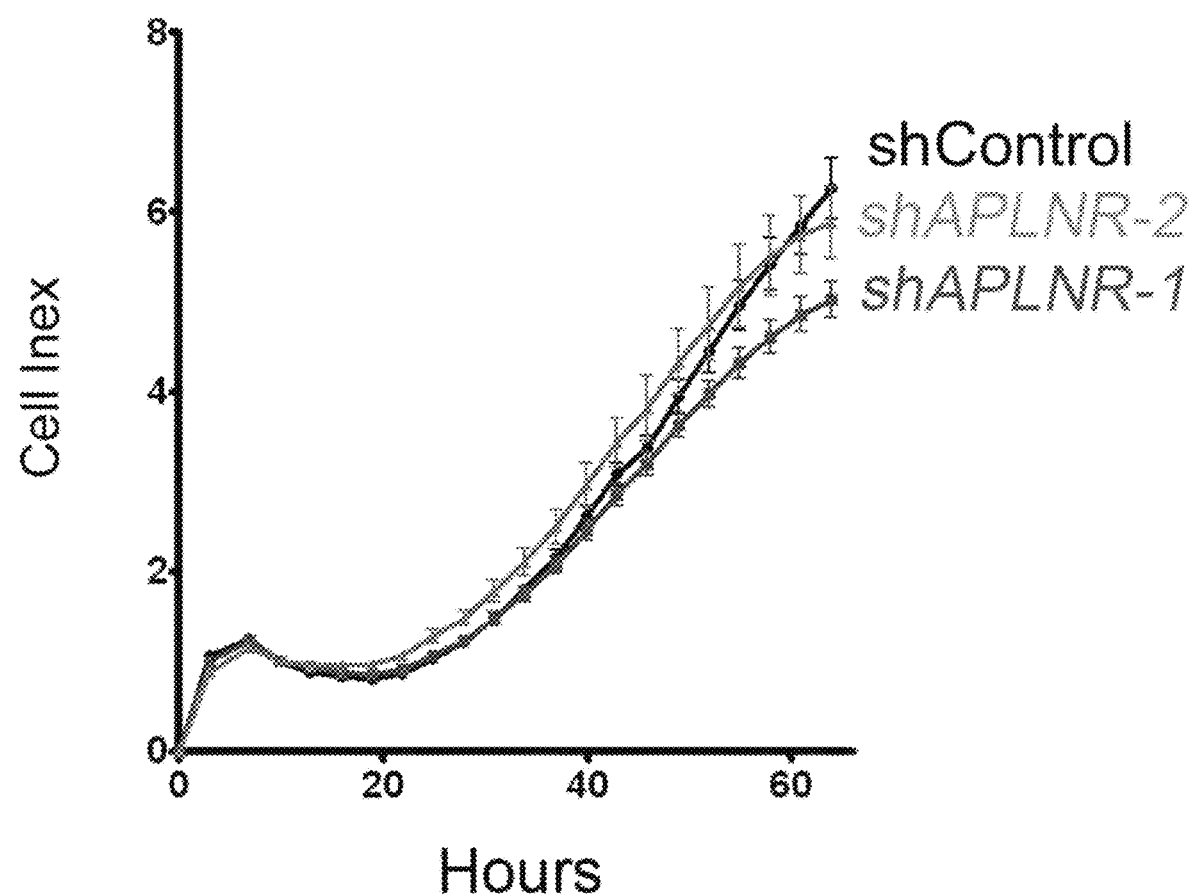

Unexpectedly, APLNR is reported to be absent in hESCs (Vodyanik et al., 2010; Yu et al., 2012), arguing that it is not the ELA receptor mediating hESCs self-renewal. Unlike ELA, which is marked by H3K4me3 and actively transcribed in hESCs, APLNR is methylated and not transcribed (FIG. 14A). We confirmed the absence of APLNR transcripts in the Shef4 and HES3 hESC lines by qPCR and flow cytometry. In contrast, APLNR transcripts were upregulated about 2500-fold upon mesendoderm differentiation, when cell surface APLNR becomes robustly detectable (FIG. 14B and FIG. 14C). Notwithstanding, we performed shRNA-mediated depletion of APLNR in hESCs to ensure that trace levels of APLNR in hESCs could not account for cell surface binding of ELA. Depletion of APLNR in hESCs (FIG. 14B and FIG. 14D) could not reduce binding of AP-ELA to undifferentiated hESCs, but was sufficient to significantly diminish the levels of AP-ELA bound to hESC-derived mesendoderm cells (FIG. 14E). These data suggest that while APLNR is both necessary and sufficient to confer cell surface binding to ELA in differentiated cells, it is not the endogenous receptor for ELA in undifferentiated hESCs. Consistent with this conclusion, the growth of shAPLNR hESCs was not compromised (FIG. 14F), unlike that of shELA hESCs. From these experiments, we predict that an alternate ELA receptor exists in hESCs and is responsible for maintaining embryonic self-renewal.

Example 25. Discussion

Our work has uncovered a new peptide hormone with potent embryonic signaling activity. We surmise that more will surface as careful examinations of multi-exonic transcripts are screened for the existence of phylogenetically conserved small ORFs. Encoded by a transcript believed to be a non-coding RNA, ELABELA is in fact the precursor for a small secreted peptide found in all vertebrate species. Its mature form ELA, is central to self-renewal of hESCs and required for endoderm differentiation. In vivo, ela specifically affects the mesendodermal lineage where its activity, transduced by APLNR, brings about the migration and differentiation of the cardiac lineage. The identity of ELA's receptor in hESCs is unknown and is the subject of intense investigation.

Example 26. Discussion: Regulation of Embryonic Pluripotency by Secreted Factors A disproportionate emphasis has been placed on transcription factors for the maintenance of the pluripotency circuit. In recent years, a plethora of transcription factors has been shown to be critical for the pluripotent state and to enhance reprogramming (Takahashi and Yamanaka, 2006). However, no novel secreted factors, along with NODAL/BMP and IGF/FGF that are established factors for pluripotency, have been discovered in the last 20 years. Here we present evidence that one such extracellular molecule, ELA exists and plays an important role in stemness. Unlike FGFs which needs to be added exogenously, or secreted by feeder cells to maintain pluripotency in hESCs, ELA is endogenously synthesized, secreted and taken up by hESCs in an autocrine and/or paracrine fashion in self-sufficient quantities. The reason why such molecules are needed is not entirely clear but the fact that inhibition of ELA causes rapid apoptosis suggests that it serves as a pro-survival factor to counteract the high levels of spontaneous apoptosis that are inherent to hESCs, particularly following dissociation (Wang et al., 2009; Watanabe et al., 2007). In line with this, we note that the depletion of ELA in hESCs grown as single cells is more detrimental than hESCs grown in colonies. Alternatively, this might point to the extracellular activity of the peptide, which may be more readily captured in a paracrine manner by hESC colonies than it is by single cells. Also, we note that while endogenous ELA is present in hESC-conditioned media in the nM range, our recombinant peptide, although specific, is bioactive only in the μM range. This finding suggests existence of possible post-translational modifications on endogenous ELA that are required for its full potency, as is the case for GHRELIN (Kojima et al., 1999).

Our observation that recombinant ELA is rapidly taken up by hESCs and that endogenous ELA can be found in the cytoplasm suggests that it has a dedicated receptor in these cells. We do not favor the possibility that ELA behaves a self-penetrating peptide despite its very basic amino-acid make-up (Green and Loewenstein, 1988) because its rapid cellular uptake is only observed in hESCs and not in other tested cell types. APLNR is silent in hESCs (FIG. 14A to FIG. 14C), we therefore believe that another cell surface receptor mediates ELA activity in hESCs.

Example 27. Discussion: The ELA-APLNR Axis in Cardiovascular Development

Stainier and colleagues have shown that although aplnr is required prior to the onset of gastrulation for proper cardiac morphogenesis, its known ligand apln is not expressed until mid-gastrulation (Scott et al., 2007). Similarly in mice, several groups have reported that the knockouts of Apln and Aplnr are not functionally allelic, as would be expected if a linear and exclusive ligand-receptor relationship linked Apln to Aplnr. This has led some to hypothesize that Aplnr may have ligand-independent functions and recent reports have shown that Aplnr can respond to stretch in the absence of Apln (Scimia et al., 2012). An alternate and non mutually-exclusive explanation for this phenomenon invokes the existence of a second ligand for APLNR. Our results strongly suggest that ELA fulfills this role in early zebrafish embryogenesis, where ela phenocopies the loss of aplnr and directs the migration and amplification of endodermal precursors for proper cardiac ontogeny.

At present, it is unclear if APLN and ELA signal through APLNR to elicit identical signaling cascades and therefore partly compensate for one another. With respect to cardiovascular development however, we note that apln zebrafish morphants or apln mouse knockouts do not display overt congenital cardiac anomalies (Kuba et al., 2007; Scott et al., 2007). The ELA-APLNR axis thus appears to be exclusive for cardiac development and APLN may be insufficient either due to diverging signaling downstream of APLNR, or simply due to incompatible spatiotemporal patterns of expression.

How ela in the epibolyzing blastoderm affects the migration and differentiation of aplnr-expressing endodermal precursors in the hypoblast is not clear. Our analysis places ela upstream of gata5, one of the earliest markers of mesendodermal cells, which fails to coalesce at the midline in ela mutants. Mutation in gata5 in faust zebrafish demonstrates that this transcription factor is required for precardiac mesoderm to migrate to the embryonic midline (Reiter et al., 1999). The myocardium lineage which is one of the first paraxial cell populations to migrate into the anterior lateral plate mesoderm (ALPM) is very sensitive to changes in the endoderm lineage, which is specified by the Nodal pathway (Schier, 2003). Our loss-of-function alleles place signaling by Ela upstream, or in parallel to the endodermal-mediated pathway for heart morphogenesis. Ela may be required for the correct proliferation of endoderm precursor cells as judged by their decreased numbers in ela mutant fish. Alternatively, or concurrently, Ela may behave as a chemotactic stimulus that promotes the timely migration of endodermal cells towards the midline, who in turn guide the cardiovascular progenitor cells (CPCs) towards the APLM and render them competent to initiate cardiogenesis.

Example 28. Discussion: Polygamy of Ligand-Receptor Pairing

One receptor, multiple ligands. The TGFβ ligands ACTIVIN and NODAL have distinct spatiotemporal expression during development which allows for the same set of receptors to be activated sequentially. In the case of ELA and APLN, likewise, differences in tissue and timing of expression could potentially expand the utility of the APLNR signaling cascade. However, unlike ACTIVIN and NODAL which are structurally related TGFβ cytokines, ELA and APLN do not share sequence homology besides being both very basic proteins. A similar scenario exists within the world of small peptides, where for instance for the Calcitonin-gene-related peptide (CGRP) and adrenomedullin (AM) hormone both signal through the same GPCR calcitonin-receptor-like receptor (CRLR) depending on which member of the single membrane-spanning RAMP protein is present. By interacting with RAMP1, CRLR acquires a high affinity for CGRP, whereas by interacting with RAMP2 or RAMP3, CRLR acquires a high affinity for AM (McLatchie et al., 1998). This system enables one receptor to transduce the signals of multiple ligands.

Example 29. Discussion: One Ligand, Multiple Receptors

While ELA signaling appears to be mediated by the APNLR during heart development, we find that APLNR is not expressed in hESCs where ELA has potent bioactivity. This would not be unprecedented and examples abound of ligands signaling through distinct receptors in a context- and tissue-dependent manner. For instance, WNT ligands signal primarily through GPCRs of the FRIZZLED family (Niehrs, 2012) but also via RTK such as ROR for convergent-extension movements (Hikasa et al., 2002). Likewise, ELA signals through APLNR to direct cardiac progenitor migration in the early embryo whereas it may signal through an as-yet unidentified receptor in hESCs to promote self-renewal and growth. This putative "ménage à quatre" suggests the existence of a delicate and fine-tuned relationship between ELA, APLN, APLNR and ELA's hESC-specific receptor which will warrant the investigation of tissue specific inactivation of single and double ligand and receptor mutants.

Example 30. Discussion: Future Directions

Besides its expression in the pre-implantation human embryo, ELA mRNA is also found in the adult prostate and kidney in humans. It will be interesting to examine its role in these exocrine glands as well. Although quite speculative at this stage, several forward-looking statements can be made with respect to the possible therapeutic value of recombinant ELA. Assuming that ELA signals through APLNR in adults it will be important to assess if this hormone is endowed with potent cardioprotective and vasodilatory properties as is APLN (Ashley et al., 2005; Maguire et al., 2009) and therefore serve as a novel therapeutic peptide for cardiac repair/regeneration and blood pressure control. In this regard ELA may serve as a potent inducer of cardiac lineages in vitro and along this line, potential loss-of-function ELA alleles may be associated with cardiovascular diseases in the general human population. Coincidentally, since APLNR permits entry of the HIV-1 by serving as a co-receptor (Zou et al., 2000), it will be interesting to determine if, a non-signaling version of ELA may serve as a means to alter and possibly slow-down AIDS' progression.

Example 31. ELABELA Polypeptide has Cardioprotective Activity

To demonstrate that ELABELA polypeptide confers cardioprotection, we use a mouse or pig model of ischemia and reperfusion injury.

Study Design for Mouse Study

Myocarial ischaemia is induced by 30 minutes left coronary artery (LCA) occlusion and subsequent reperfusion.

Mice are treated with ELABELA polypeptide via the tail vein, 5 minutes before reperfusion. Infarct size is assessed the following day (24 hours after reperfusion).

Study Design for Pig Study

Thirty female Dalland Landrace pigs (60-70 kg; IDDLO, Lelystad, The Netherlands), all pretreated with clopidogrel 75 mg/day for 3 days and amiodarone 400 mg/day for 10 days, are randomly assigned to ELABELA polypeptide, non-ELABELA polypeptide, or saline treatment.

The saline group is added to assess a potential effect of fresh, non-conditioned culture medium. In all pigs, MI is induced by 75 minutes of proximal left circumflex coronary artery (LCxCA) ligation and 4 hours of subsequent reperfusion. An ischemic period of 75 minutes is selected to inflict severe myocardial injury without inducing completely transmural myocardial infarction. The 4 hour reperfusion period is used, because infarct size measurement using TTC staining is most reliable after 3 hours of reperfusion (Birnbaum et al., 1997).

After longer periods of reperfusion, it becomes more difficult to assess oxidative stress status and apoptotic mechanisms. Treatment is initiated 5 minutes before the onset of reperfusion by intravenous infusion of ELABELA polypeptide (1.0 ml, 2.0 mg protein) non-ELABELA polypeptide or saline. Immediately following reperfusion, an additional intracoronary bolus ELABELA polypeptide (4.0 ml, 8.0 mg protein), non-ELABELA polypeptide or saline is given. Myocardial infarct size and function are assessed 4 hours after reperfusion.

MI and Operational Procedure

During the entire operation, ECG, Systemic Arterial Pressure, and capnogram are monitored continuously. Under general anesthesia as described before (Timmers et al 2007), a median sternotomy is performed and two introduction sheets are inserted in the carotid arteries for a 6 Fr guiding catheter and an 8 Fr conductance catheter (CD Leycom, Zoetermeer, the Netherlands).

The distal tip of a Swan Ganz catheter is placed into the pulmonary artery via the internal jugular vein. Transonic flow probes (Transonic Systems Inc, Ithaca, N.Y.) are placed around the proximal aorta and LCxCA to measure cardiac output and coronary flow, and a wire is placed around the inferior caval vein to enable functional measurements under varying loading conditions for PV loops. After functional measurements, 10.000 IU of heparin are administered intravenously and sutures are tightened to occlude the proximal LCxCA. Internal defibrillation with 50 J is used when ventricular fibrillation occurred. After 75 minutes of ischemia, the LCxCA is reopened by release of the suture. Immediately following reperfusion, Nitroglycerine (0.1 mg to prevent no-reflow) is infused through the LCxCA via the guiding catheter, followed by intracoronary treatment with ELABELA polypeptide, non-ELABELA polypeptide or saline. After 4 hours of reperfusion, the final functional measurements are performed and the heart is explanted for infarct size analysis.

Mice are anesthetized with Fentanyl (0.05 mg/kg), Dormicum (5 mg/kg) and Domitor (0.5 mg/kg) and intubated using a 24-gauge intravenous catheter with a blunt end. Mice are artificially ventilated at a rate of 105 strokes/min using a rodent ventilator with a mixture of $O_2$ and $N_2O$ (1:2 vol/vol) to which isoflurane (2.5-3.0% vol/vol) is added. The mouse is placed on a heating pad to maintain the body temperature at 37° C. The chest is opened in the third intercostal space and an 8-0 prolene suture is used to occlude the left coronary artery (LCA) for 30 minutes. The chest is closed and the following day (24 hours later), the hearts are explanted for infarct size analysis.

Functional Measurements

The ECG, arterial pressure and cardiac output, are digitized at a sampling rate of 250 Hz and stored for offline analysis (Leycom CFL-512, CD Leycom). Left ventricular (LV) pressure and volume are measured using the conductance catheter method, as described previously (Timmers et al 2007). LV pressure and volume signals derived from the conductance catheter are displayed and acquired at a 250-Hz sampling rate with a Leycom CFL-512 (CD Leycom).

Data are acquired during steady state and during temporal caval vein occlusion, all with the ventilator turned off at end expiration. Analysis of the pressure-volume loops is performed with custom software as described previously (Steendijk et al 1998). In addition, short-axis epicardial ultrasound images (Prosound SSD-5000, 5-MHz probe UST-5280-5, Aloka Holding Europe AG, Zug, Switzerland) are obtained at the midpapillary muscle level. Wall thickness (WT) of the infarct area, remote area (septum) and LV internal area (LVia) are measured at end diastole (ED) and end systole (ES).

Systolic wall thickening (SWT) is calculated as [(WT (ES)−WT(ED))/WT(ED)]*100%, fractional area shortening (FAS) as [(LVia(ES)−LVia(ED))/LVia(ED)]*100%, and left ventricular ejection fraction (LVEF) as [(EDV−ESV)/EDV] *100%. The end-diastolic chamber stiffness is quantified by means of linear regression of the end-diastolic pressure-volume relationship. Echocardiography and PV loops are measured before MI, 1 hour after ischemia and 4 hours after reperfusion. To challenge stunned myocardium, additional measurements are performed during pharmaceutically induced stress by intravenous dobutamine infusion (2.5 µg/kg/min and 5.0 µg/kg/min).

Infarct Size

Just prior to excision of the heart, the LCxCA (pigs) or LCA (mice) is religated at exactly the same spot as for the induction of the MI. Evans blue dye is infused through the coronary system to delineate the area at risk (AAR). The heart is then excised, the LV is isolated and cut into 5 slices from apex to base.

The slices are incubated in 1% triphenyltetrazolium chloride (TTC, Sigma-Aldrich Chemicals, Zwijndrecht, the Netherlands) in 37° C. Sörensen buffer (13.6 g/L $KH_2PO_4$+ 17.8 g/L $Na_2H$ $PO_4.2H_2O$, pH 7.4) for 15 minutes to discriminate infarct tissue from viable myocardium.

All slices are scanned from both sides, and in each slide, the infarct area is compared with area at risk and the total area by use of digital planimetry software (Image J). After correction for the weight of the slices, infarct size is calculated as a percentage of the AAR and of the LV.

Example 32. ELABELA Polypeptide Protects Against Myocardial Ischaemia-Reperfusion Injury It is known that the APLN/APLNR (APELIN/APELIN Receptor) axis has protective effects in myocardial ischemia-reperfusion injury.

Accordingly, ELABELA constitutes an important therapeutic option for myocardial ischaemia-reperfusion injury.

Materials and Methods

The following publications describe experiments showing the role of a peptide hormone (APELIN) in protection against myocardial ischaemia-reperfusion injury:

Tao J, ZhuW, Li Y, et al. *Apelin-13 protects the heart against ischemia-reperfusion injury through inhibition of ER-dependent apoptotic pathways in a time-dependent fashion*. Am J Physiol Heart Circ Physiol 2011; 301:H1471-86.

Zeng X J, Zhang L K, Wang H X, Lu L Q, Ma L Q, Tang C S. *Apelin protects heart against ischemia/reperfusion injury in rat*. Peptides 2009; 30:1144-52.

Simpkin J C, Yellon D M, Davidson S M, Lim S Y, Wynne A M, Smith C C. *Apelin-13 and apelin-36 exhibit direct cardioprotective activity against ischemia-reperfusion injury*. Basic Res Cardiol 2007; 102:518-28.

The experiments described in the above publications are repeated, with the replacement of APELIN with ELABELA.

Results

When the above experiments are carried out, ELABELA administered during reperfusion is seen to significantly decrease infarct size in subjects hearts.

Without wishing to be bound by theory, we believe that administration of ELABELA protect hearts against ischemia-reperfusion injury through activation of PI3K/Akt and ERK pathways and/or may inhibit generation of reactive oxygen species.

ELABELA may therefore be used for treating, preventing or alleviating myocardial ischaemia reperfusion injury in an individual.

Example 33. ELABELA Polypeptide Protects Against Coronary Artery Disease

Materials and Methods

The following publications describe experiments showing the role of a peptide hormone (APELIN) in protection against coronary artery disease:

Azizi Y, Faghihi M, Imani A, Roghani M, Nazari A. Post-infarct treatment with [Pyr1]-apelin-13 reduces myocardial damage through reduction of oxidative injury and nitric oxide enhancement in the rat model of myocardial infarction. Peptides 2013; 46:76-82.

Li L, Zeng H, Chen J X. Apelin-13 increases myocardial progenitor cells and improves repair postmyocardial infarction. Am J Physiol Heart Circ Physiol 2012; 303:H605-18.

Pisarenko O I, Serebryakova L I, Pelogeykina Y A, et al. In vivo reduction of reperfusion injury to the heart with apelin-12 peptide in rats. Bull Exp Biol Med 2011; 152:79-82.

The experiments described in the above publications are repeated, with the replacement of APELIN with ELABELA.

Results

When the above experiments are carried out, injection of ELABELA to subjects is found to limit the myocardial infarction size and reduce damage to cardiomyocytes.

Without wishing to be bound by theory, we believe that the effects of ELABELA are achieved by significantly attenuating myocardial damage through the reduction of oxidative injury and enhancement of Nitric Oxide (NO) production.

In addition, ELABELA is found to promote angiogenesis and ameliorate cardiac repair postmyocardial infarction.

ELABELA may therefore be used for treating, preventing or alleviating coronary artery disease in an individual.

Example 34. ELABELA Polypeptide Protects Against Artherosclerosis

Materials and Methods

The following publication describes experiments showing the role of a peptide hormone (APELIN) in protection against artherosclerosis:

Chun H J, Ali Z A, Kojima Y, et al. *Apelin signaling antagonizes Ang II effects in mouse models of atherosclerosis. J Clin Invest* 2008; 118:3343-54.

The experiments described in the above publication are repeated, with the replacement of APELIN with ELABELA.

Results

When the above experiments are carried out, we find that, like APLN, ELABELA can protect against artherosclerosis. We find that ELABELA antagonizes the vascular disease-promoting actions of Ang II and mitigates the Ang II-mediated increase in atherosclerosis burden. It also is seen to inhibit abdominal aortic aneurysm formation and rupture.

ELABELA may therefore be used for treating, preventing or alleviating artheroscloersis in an individual.

Example 35. ELABELA Polypeptide Protects Against Heart Failure

According to the methods and compositions described here, ELABELA exhibits beneficial effects in the cardiovascular system and/or improves cardiac repair.

Accordingly, ELABELA may be used as, or as part of, therapeutic regimens to treat patients with heart failure.

Materials and Methods

The following publications describe experiments showing the role of a peptide hormone (APELIN) in protection against heart failure:

Scimia M C, Hurtado C, Ray S, Metzler S, Wei K, Wang J, Woods C E, Purcell N H, Catalucci D, Akasaka T, Bueno O F, Vlasuk G P, Kaliman P, Bodmer R, Smith L H, Ashley E, Mercola M, Brown J H, Ruiz-Lozano P. (2012), *APJ acts as a dual receptor in cardiac hypertrophy. Nature* 2012 Aug. 16; 488(7411):394-8.

Sato T, Suzuki T, Watanabe H, Kadowaki A, Fukamizu A, Liu P P, Kimura A, Ito H, Penninger J M, Imai Y, Kuba K. (2013) *Apelin is a positive regulator of ACE2 in failing hearts. J Clin Invest.* 2013 Nov. 1.

The experiments described in the above publications are repeated, with the replacement of APELIN with ELABELA.

Results

When the above experiments are carried out, we find that, like APLN, ELABELA is able to provide protection against heart failure.

Without wishing to be bound by theory, we believe that ELABELA crosstalks with the renin-angiotensin system via the Angiotensin-converting enzyme 2 (ACE2)/Ang II/Ang 1-7 axis to increase cardiac contractility and control heart failure.

Dysregulation of the ELA/APLNR system may therefore be involved in the predisposition to cardiovascular diseases. Accordingly, we propose that enhancing ELABELA action has important therapeutic effects.

Furthermore administration of ELABELA may be used to blunt cardiac hypertrophy as does APELIN following sustained pressure overload by transaortic constriction (TAC), a model for heart failure.

ELABELA may therefore be used for treating, preventing or alleviating heart failure in an individual.

Example 36. ELABELA Polypeptide Protects Against Hypertension

Like APELIN, we propose that ELABELA acts as a vasodilator and effectively lowers blood pressure. Accordingly, ELABELA may be used as, or as part of, therapeutic regimens to treat patients with hypertension.

Materials and Methods

The following publications describe experiments showing the role of a peptide hormone (APELIN) in protection against hypertension:

Tatemoto K, Takayama K, Zou M X, et al. *The novel peptide apelin lowers blood pressure via a nitric oxide-dependent mechanism. Regulatory Peptides.* 2001; 99(2-3): 87-92.

Cheng X, Cheng X S, Pang C C. *Venous dilator effect of apelin, an endogenous peptide ligand for the orphan APJ receptor, in conscious rats. European Journal of Pharmacology.* 2003; 470(3):171-175.

Japp A G, Cruden N L, Amer D A, et al. *Vascular effects of apelin in vivo in man. Journal of the American College of Cardiology.* 2008; 52(11):908-913.

The experiments described in the above publications are repeated, with the replacement of APELIN with ELABELA.

Results

When the experiments described above are carried out, it is found that administration of ELABELA causes a reduction in blood pressure. Without wishing to be bound by theory, we believe that it does so by functioning as an arterial and/or venous dilator via the nitric oxide-dependent pathway.

ELABELA may therefore be used for treating, preventing or alleviating hypertension in an individual.

Example 37. ELABELA Polypeptide Protects Against HIV Infection and AIDS

The identification of specific inhibitors of APLNR-mediated HIV-1 entry would greatly assist efforts to find new reagents to block HIV-1 infection.

Materials and Methods

The following publications describe experiments showing the role of a peptide hormone (APELIN) in protection against HIV infection and AIDS:

Cayabyab M, Hinuma S, Farzan M, Choe H, Fukusumi S, Kitada C, Nishizawa N, Hosoya M, Nishimura O, Messele T, Pollakis G, Goudsmit J, Fujino M, Sodroski J. (2000) *Apelin, the natural ligand of the orphan seven-transmembrane receptor APJ, inhibits human immunodeficiency virus type 1 entry. J Virol. December;* 74(24):11972-6.

Xuejun Fan, Naiming Zhou, Xiaoling Zhang, Muhammad Mukhtar, Zhixian Lu, Jianhua Fang, Garrett C. DuBois, and Roger J. Pomerantz. (2003) *Structural and Functional Study of the Apelin-13 Peptide, an Endogenous Ligand of the HIV-1 Coreceptor, APJ. Biochemistry* 42, 10163-10168 10163.

The experiments described in the above publications are repeated, with the replacement of APELIN with ELABELA.

Results

When the above experiments are performed, it is found that ELABELA prevents or slows-down HIV-1 entry.

ELABELA may be particularly useful for central nervous system infection in patients with HIV-1-induced dementia given that APLNR is widely expressed in the brain.

ELABELA may therefore be used for treating, preventing or alleviating HIV infection or AIDS, or both, in an individual.

Example 38. ELABELA Polypeptide Protects Against Pulmonary Arterial Hypertension The APLN/APLNR system plays a key role in the occurrence and development of cardiovascular diseases. Targeting the ELA/APLNR axis also represents a new class of potential therapeutic agents for pulmonary arterial hypertension (PAH).

Materials and Methods

The following publications describe experiments showing the role of a peptide hormone (APELIN) in protection against pulmonary arterial hypertension:

Alastalo T P, Li M, Perez Vde J, et al. *Disruption of PPARgamma/beta-catenin-mediated regulation of apelin impairs BMP-induced mouse and human pulmonary arterial EC survival. J Clin Invest* 2011; 121:3735-46.

Falcao-Pires I, Goncalves N, Henriques-Coelho T, Moreira-Goncalves D, Roncon Albuquerque Jr R, Leite-Moreira A F. *Apelin decreases myocardial injury and improves right ventricular function in monocrotaline-induced pulmonary hypertension. Am J Physiol Heart Circ Physiol* 2009; 296: H2007-14.

The experiments described in the above publications are repeated, with the replacement of APELIN with ELABELA.

Results

When the above experiments are performed, it is found that ELABELA alleviates symptoms of pulmonary arterial hypertension.

ELABELA may therefore be used for treating, preventing or alleviating pulmonary arterial hypertension in an individual.

Example 39. ELABELA Polypeptide Treats Erectile Dysfunction

Materials and Methods

The following publication describes experiments showing the role of a peptide hormone (APELIN) in treating erectile dysfunction:

Kwon M H, Tuvshintur B, Kim W J, Jin H R, Yin G N, Song K M, Choi M J, Kwon K D, Batbold D, Ryu J K, Suh J K. *Expression of the Apelin-APJ Pathway and Effects on Erectile Function in a Mouse Model of Vasculogenic Erectile Dysfunction. J Sex Med.* 2013 Apr. 11. doi: 10.1111/jsm.12158.

The experiments described in the above publications are repeated, with the replacement of APELIN with ELABELA.

Results

When the above experiments are performed, it is found that ELABELA provides a significant restoration of erectile function.

ELABELA may therefore be used for treating, preventing or alleviating erectile dysfunction in an individual.

Example 40. Materials and Methods: SILAC Cell Culture and Cell Lysis

SHEF4 hESCs were cultured in custom-made mTSER1 (Stem Cell Technologies) containing either stable medium isotopes of L-lysine-(2H4) (K4) and L-arginine-(13C6) (R6) or heavy isotope L-lysine-(13C615N2) (K8) and L-arginine-(13C615N4) (R10) for three passages to allow complete exchange of isotopes. Cells were then starved in DMEM/F12 for 2 hours, following by a 10 minute pulse with 5 uM of ELA or ELA$^{RR>GG}$. Cells were lysed in 9 M urea lysis buffer, consists of 20 mM HEPES (pH 8.0), 9 M urea, 1 mM activated sodium orthovanadate, 2.5 mM sodium pyrophosphate and 1 mM β-glycerophosphate. Equal amounts of cell lysates from medium (K4R6) and heavy (K8R10) cells were mixed. Experiments were carried out in four replicates as two Forward (medium cells ELA$^{RR>GG}$ versus heavy cells ELA) experiments and two Reverse (heavy cells ELA$^{RR>GG}$ versus medium cells ELA) experiments.

Example 41. Materials and Methods: Reduction, Alkylation and Digestion

About 1 mg protein in 9 M urea lysis buffer was reduced by the addition of ⅒ volume of 55 mM DTT to the cleared cell supernatant and incubated for 30 min at room temperature, followed by addition of 120 mM iodoacetamide at a volume equal to the DTT solution and incubated for 30 min at room temperature in the dark. The samples were then diluted 1.5-fold using 20 mM Hepes (pH8) to a final concentration of 6 M urea. LysC (Wako 129-02451) was added with a LysC to protein ratio of 1:100 and incubated at 37° C. overnight. The samples were further diluted to a final concentration of ~1 M urea using 20 mM Hepes (pH8). Sequencing-grade trypsin (Promega) was added with a trypsin to protein ratio of 1:50 (w/w). After 4 hours of digestion at 37° C., the peptide solution was cleaned up using a C18 cartridge (Waters Sep-Pak Vac RC Cartridge, 100 mg Sorbent per Cartridge). The amount of peptide obtained was measured using Nanodrop (ThermoScientific).

Example 42. Materials and Methods: IMAC Beads Preparation

IMAC beads were prepared as described with slight modifications (Ficarro et al., 2009). Briefly, 200 uL Ni-NTA agarose conjugates (Qiagen) was rinsed 3 times with 800 µl MilliQ H2O. Nickel was then striped from the resin by incubation with 800 µl of 100 mM EDTA pH 8.0 for 30 minutes at RT with mixing. Residual nickel was rinsed 3 times with 800 µl MilliQ H2O, followed by incubation with 800 µl of a 100 mM iron chloride solution for 30-45 minutes. The resin was washed 3 times with 800 µl MilliQ H2O, followed by rinsing 4 times with 800 µl 80% Acetonitrile/0.1% trifluoroacetic acid.

Example 43. Materials and Methods: Phosphopeptide Enrichment

Phosphopeptides were enriched from the tryptic peptides using IMAC beads. ~600 ug tryptic peptides were reconstituted in 600 uL 50% Acetonitrile/0.1% trifluoroacetic acid, followed by 1:1 dilution with 100% Acetonitrile/0.1% trifluoroacetic acid. The peptides were then incubated with 10 uL IMAC beads for 30 minutes with end-over-end rotation. The beads were then loaded onto a self-packed C18 StageTip (Rappsilber et al., 2007), which was conditioned with 200 uL methanol, washed with 100 uL 50% Acetonitrile/0.1% formic acid and equilibrated with 200 uL 1% formic acid beforehand. After being loaded onto the stage tip, the IMAC beads were washed with 100 uL 80% Acetonitrile/0.1% trifluoroacetic acid and 200 uL 1% formic acid. The phosphopeptides were eluted from the IMAC beads onto C18 membranes on the stage tip using 4×70 uL 500 mM dibasic sodium phosphate (pH 7.0), followed by washing using 200 uL 1% formic acid. The phosphopeptides were stored on the stage tip until they were ready to be analysed on LC-MS. The phosphopeptides were eluted from the C18 membranes with 60 uL 50% Acetonitrile/0.1% formic acid, dried using a speedvac and reconstituted in 24 µL of 0.1% formic acid.

Example 44. Materials and Methods: LC/MS Analysis

Reconsituted peptides were analysed using an EASY-nLC 1000 (Proxeon, Fisher Scientific) coupled a Q-Exactive (Thermo Fisher Scientific). Peptides were trapped onto a C18 pre-column and separated on a 50 cm analytical column (EASY-Spray Columns, Thermo Fisher Scientific) at 50° C. using a 245 min gradient ranging from 0 to 40% acetonitrile/0.1% formic acid, followed by a 10 min gradient ranging from 40 to 80% acetonitrile/0.1% formic acid and stayed at 80% acetonitrile/0.1% formic acid for 10 min. Samples were analyzed on a Q-Exactive (Thermo Fisher Scientific). Survey full scan MS spectra (m/z 310-2000) were acquired with a resolution of r=70,000, an AGC target of 3e6, and a maximum injection time of 10 ms. The twenty most intense peptide ions in each survey scan with an intensity threshold of 10,000, underfill ratio of 1% and a charge state ≥2 were isolated sequentially with an isolation window of 2 Th to a target value of 50,000, maximum injection time of 50 ms and fragmented in the high energy collision cell by high energy collision dissociation using a normalized collision energy of 25%. The MS/MS was acquired with a resolution of 17,500 and a starting mass of m/z 100. A dynamic exclusion was applied using an exclusion duration of 15 s.

Example 45. Materials and Methods: Identification and Quantification of Phosphopeptides Data were processed using MaxQuant (Version 1.3.0.5) (Cox and Mann, 2008; Cox et al., 2009) against uniprot 2014-04 human database containing 262 commonly observed contaminants. Database searches were performed with tryptic specificity allowing maximum two missed cleavages and two labeled amino acids as well as an initial mass tolerance of 6 ppm for precursor ions and 20 ppm for fragment ions. The default setting for the minimum length of peptide (seven amino acids) was used. Cysteine carbamidomethylation was searched as a fixed modification, and N-acetylation, oxidized methionine, phosphorylated serine/threonine/tyrosine were searched as variable modifications. Labeled arginine and lysine were specified as fixed or variable modifications, depending on the prior knowledge about the parent ion. SILAC peptide and protein quantification was performed using default settings. Maximum false discovery rates were set to 0.01 for both protein and peptide.

Example 46. Materials and Methods: Zebrafish Manipulation ela$^{br13}$ zebrafish were generated as previously described (Chng et al., 2013). ela$^{br13}$ and AB wildtype zebrafish were grown under standard conditions until 24 hour post-fertilization. Caspase3 staining was performed as described (Sorrells et al., 2013). Images were acquired on an Olympus FV1000 confocal microscope and a custom-made light-sheet-based fluorescent microcope (Swoger et al., 2014).

Example 47. Results: APLNR is not the ELA Receptor in hESCs

We and others have shown that ELA can serve as a cognate ligand to the cell surface Apelin Receptor (APLNR, a.k.a APJ) to mediate endoderm and subsequent heart morphogenesis. However, APLNR was reported to be absent in undifferentiated hESCs (Vodyanik et al., 2010; Yu et al., 2012). Unlike ELA, which is marked by H3K4me3 and actively transcribed, the APLNR locus is methylated and not transcribed in hESCs (FIG. 14A). We confirmed the absence of APLNR transcripts in both SHEF4 and HES3 hESC lines by qPCR and flow cytometry. In contrast, APLNR transcripts were upregulated nearly 2500-fold upon mesendoderm differentiation, when cell surface APLNR became robustly detectable (FIG. 14B and FIG. 14C). Notwithstanding, we performed shRNA-mediated depletion of APLNR in undifferentiated hESCs to ensure that trace levels of APLNR could not mediate the effects of ELA on hESCs. We adapted the ELA cell surface binding assay previously described to hESCs which readily bind recombinant AP-ELA (Chng et al., 2013). Undifferentiated shAPLNR hESCs had unchanged AP-ELA binding capacity, whereas shAPLNR hES-derived mesendoderm cells had significantly less cell surface retention of recombinant AP-ELA (FIG. 14B, FIG. 14C, FIG. 14D and FIG. 14E). These data suggest that while APLNR is necessary to confer cell surface binding to ELA in mesendoderm cells, it is not the receptor for ELA in undifferentiated hESCs. Consistent with this conclusion, the growth of shAPLNR hESCs was not compromised (FIG. 14F), unlike that of shELA hESCs. From these experiments, we surmise that an alternate ELA receptor exists in hESCs and is responsible for maintaining embryonic self-renewal.

Example 48. Results: ELA Activates the PI3K/AKT Pathway in hESCs

Figure 15A:
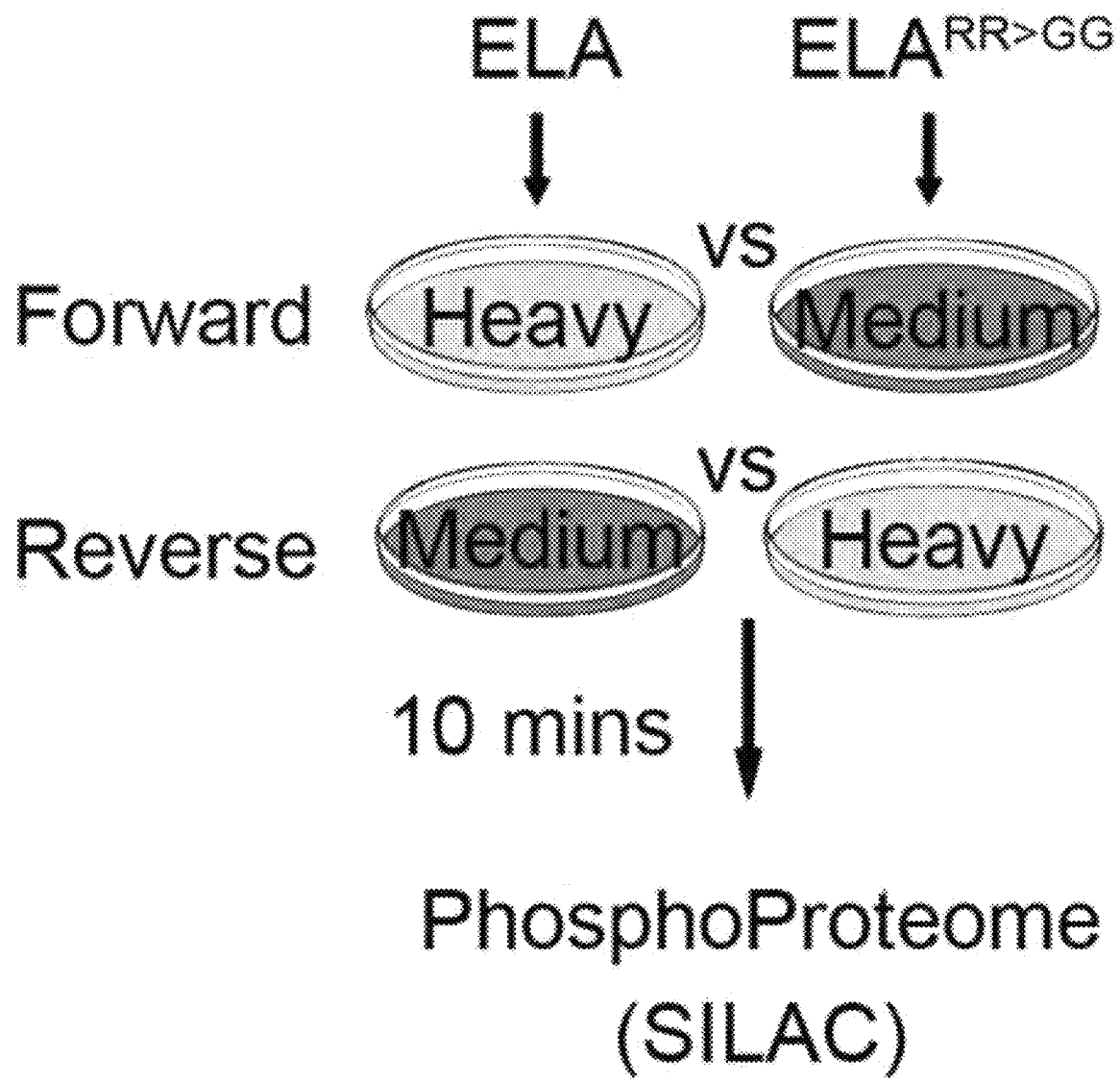
FIGS. 15A to FIG. 15F are drawings showing that ELA activates the essential PI3K/AKT pathway in hESCs.
Figure 15B:
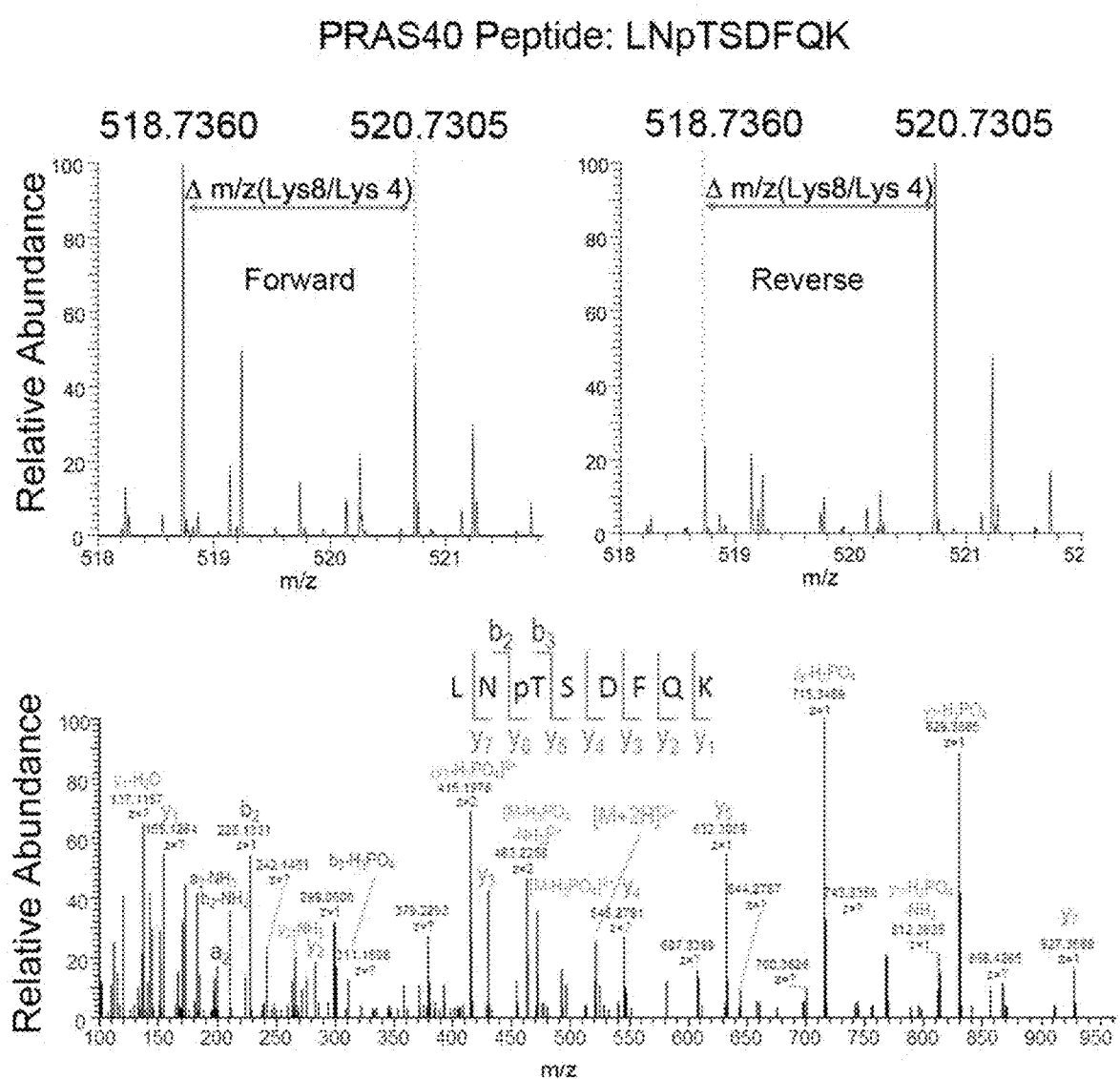
Figure 15C:
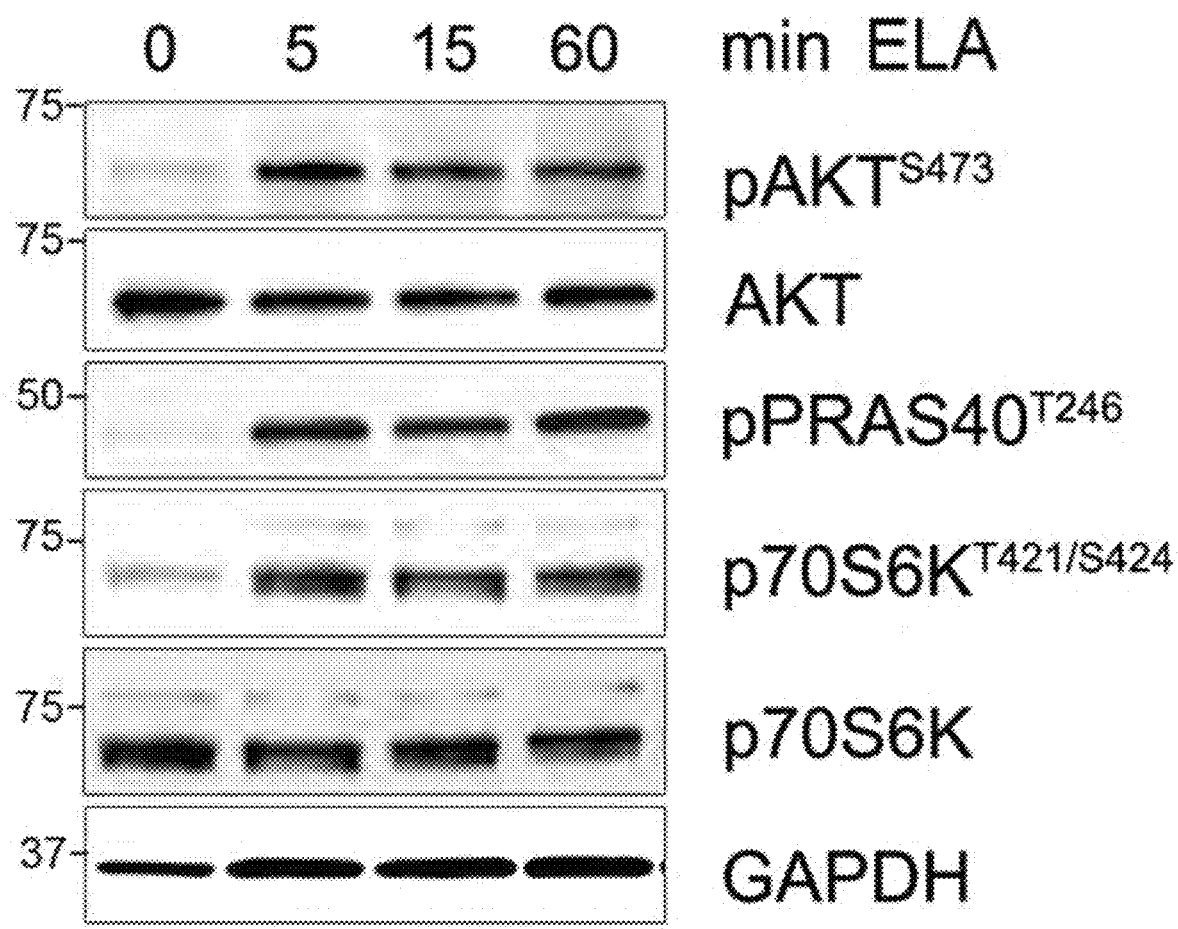
Figure 15D:
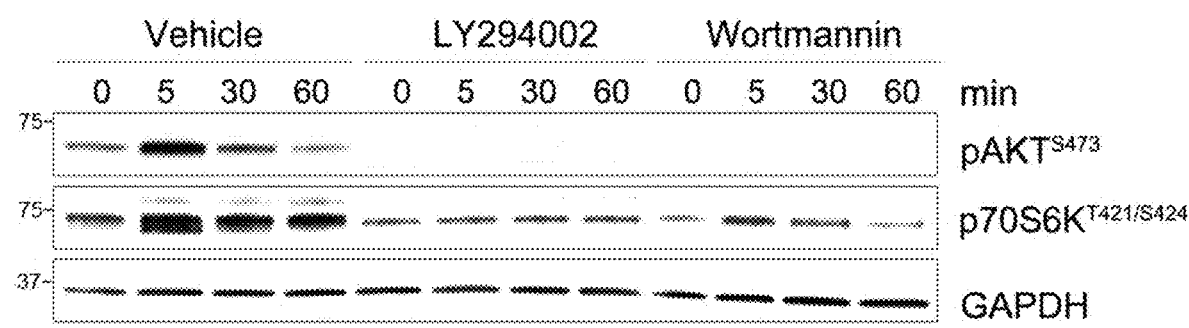
Figure 15E:
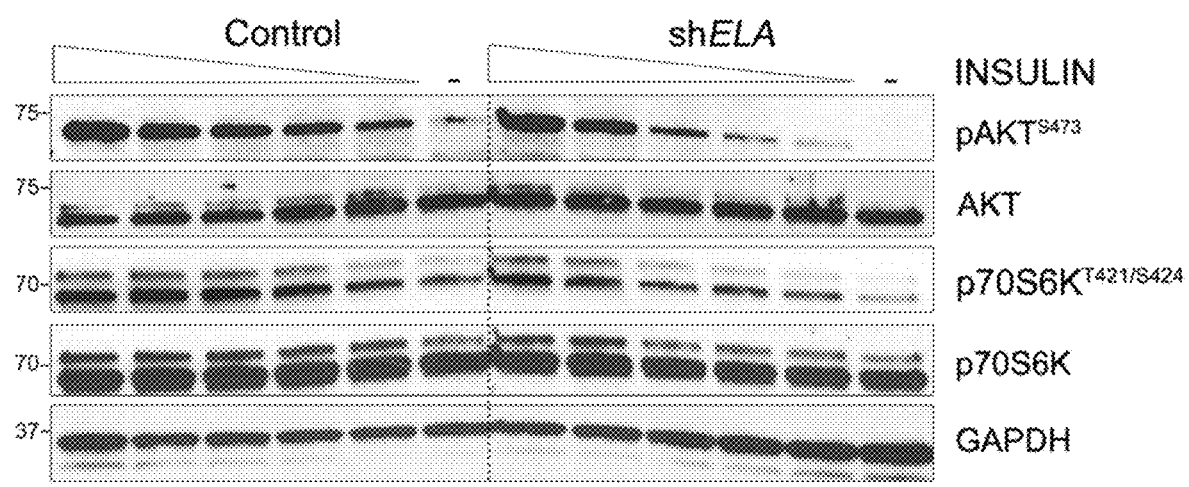
Figure 16A:
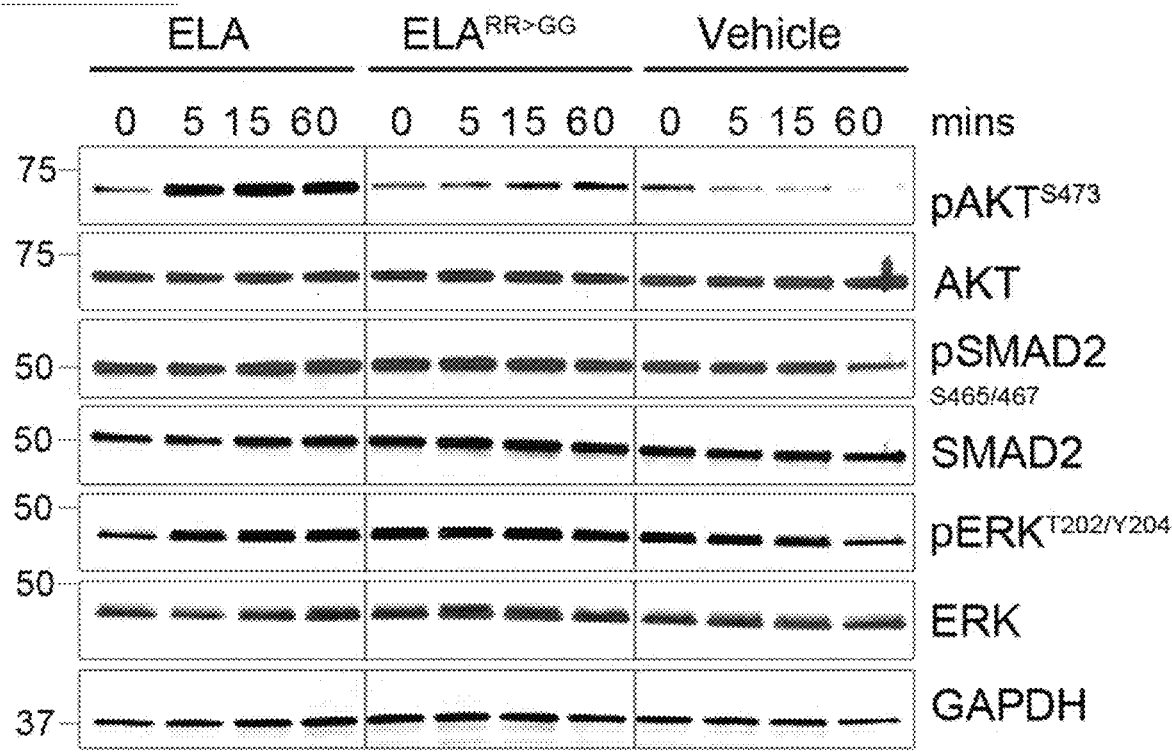
FIG. 16A to 16D are drawings showing that ELA is the endogenous signal for activation of PI3K/AKT in hESCs
Figure 16B:
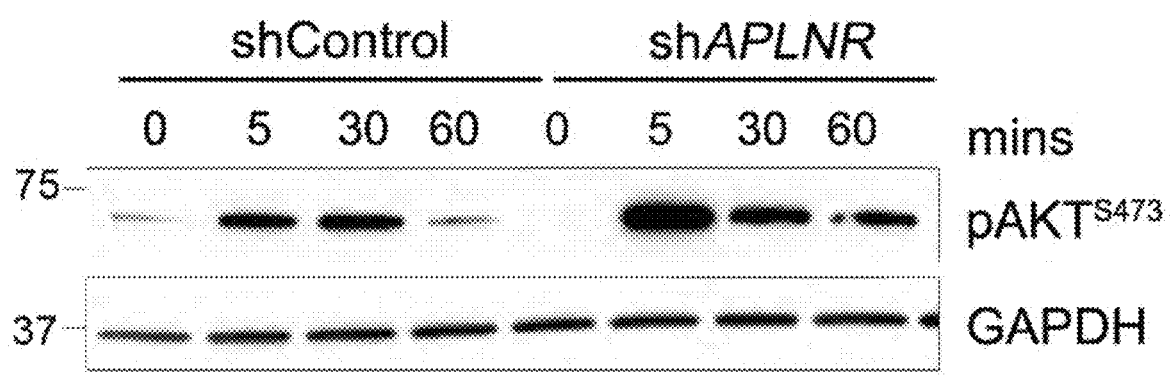
Figure 16C:
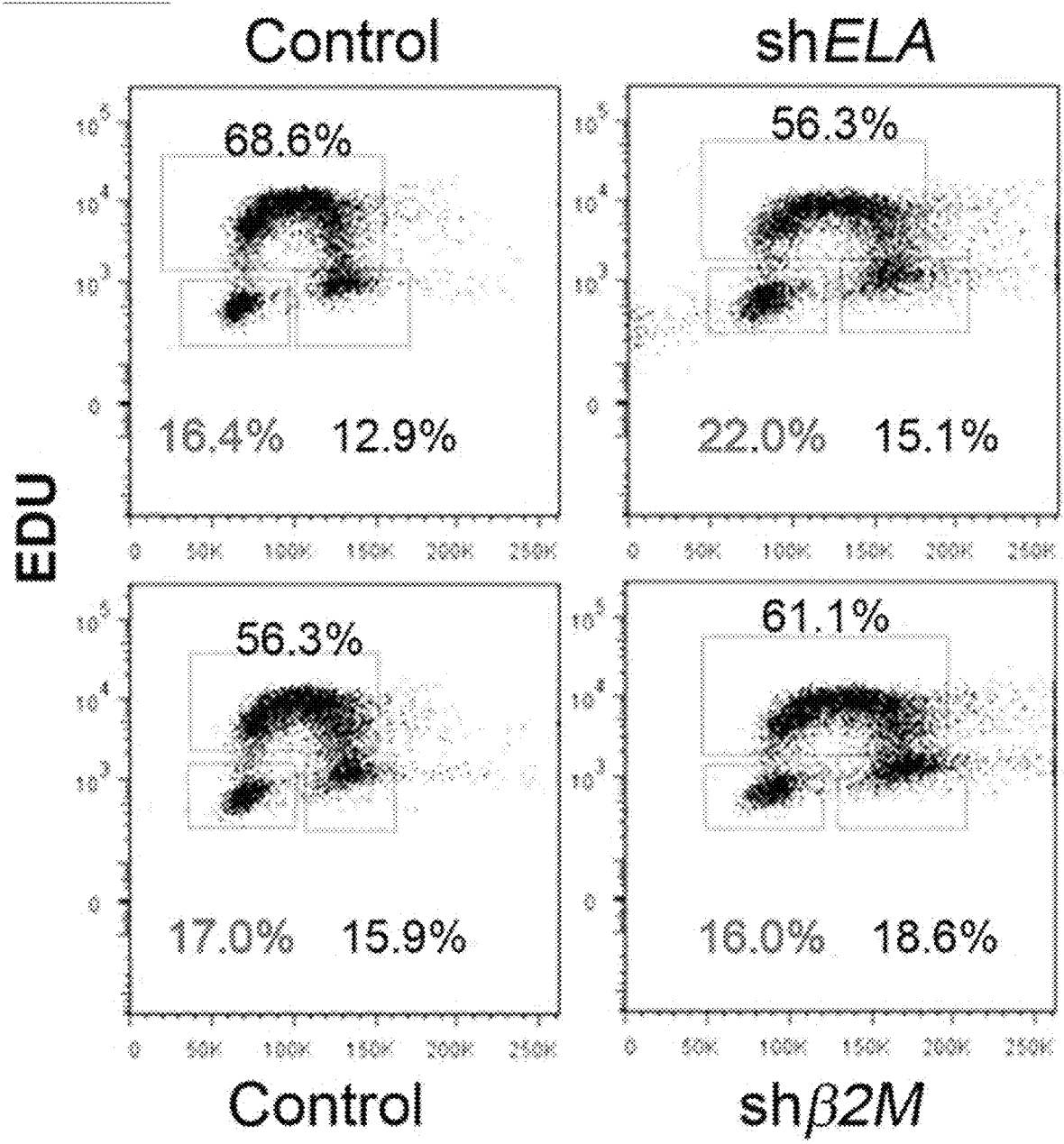

To delineate the immediate ELA signal transduction pathway in hESCs, we sought to find it direct downstream targets. Using a proteomic approach known as Stable Isotope Labeling by Amino acids in Cell culture (SILAC) (Cohen and Melton, 2011), we analyzed the phosphoproteome of hESCs pulsed with ELA for 10 minutes, using the inactive ELA$^{RR>GG}$ peptide as a baseline control (FIG. 15A). The experiment was performed twice in both forward and reverse configurations, and only hits that were replicated were further investigated. Among the top phosphopeptides activated by ELA, but not ELA$^{RR>GG}$, was LNpTSDFQK, derived from PRAS40 (proline-rich Akt substrate of 40 kDa a.k.a AKT1S1) (FIG. 15B). PRAS40 is a substrate of AKT, which is in turn activated by Phosphatidylinositol-4,5-bisphosphate 3-kinase (PI3K) (Vander Haar et al., 2007). This suggests that ELA can activate the PI3K/AKT pathway. Indeed, addition of recombinant ELA to hESCS was sufficient to trigger the immediate phosphorylation of AKT at serine 473, leading to phosphorylation of PRAS40 at threonine 246 (FIG. 15C). This was not observed in cells treated with mutant ELA$^{RR>GG}$ or vehicle control (FIG. 16A) and was abrogated by pre-treating the cells with pan-PI3K inhibitors LY249004 or Wortmannin (FIG. 15D) but not using sh-mediated APLNR depletion (FIG. 16C). This demonstrates that ELA activation of AKT is APLNR-independent and requires the PI3K. Once phosphorylated, PRAS40 becomes inactivated, relieving its repressive effect on the mammalian target of rapamycin (mTOR) signaling pathway (Sancak et al., 2007; Wang et al., 2012; Wang et al., 2007a). The subsequent activation of the mTORC1 complex is marked by phosphorylation of its prototypical substrate p70S6K (Peterson et al., 1999; Wang et al., 2007a) (FIG. 15C). Hence, ELA activates the PI3K/AKT pathway and subsequently the mTORC1 pathway. PI3K/AKT and mTOR are both potent regulators of growth and viability, and contribute integrally to the self-renewal capacity of hESCs (Armstrong et al., 2006; Zhou et al., 2009). Consistent with the loss of self-renewal and viability of shELA hESCs, we find that shELA hESCs indeed have lower levels of endogenous PI3K/AKT and mTOR activity, which can be revealed by gradually lowering levels of exogenous INSULIN in the growth media (FIG. 15E). These results suggest that the growth deficiency seen in shELA hESCs are attributable to the loss of paracrine and autocrine PI3K/AKT signaling mediated by ELA.

Figure 15F:
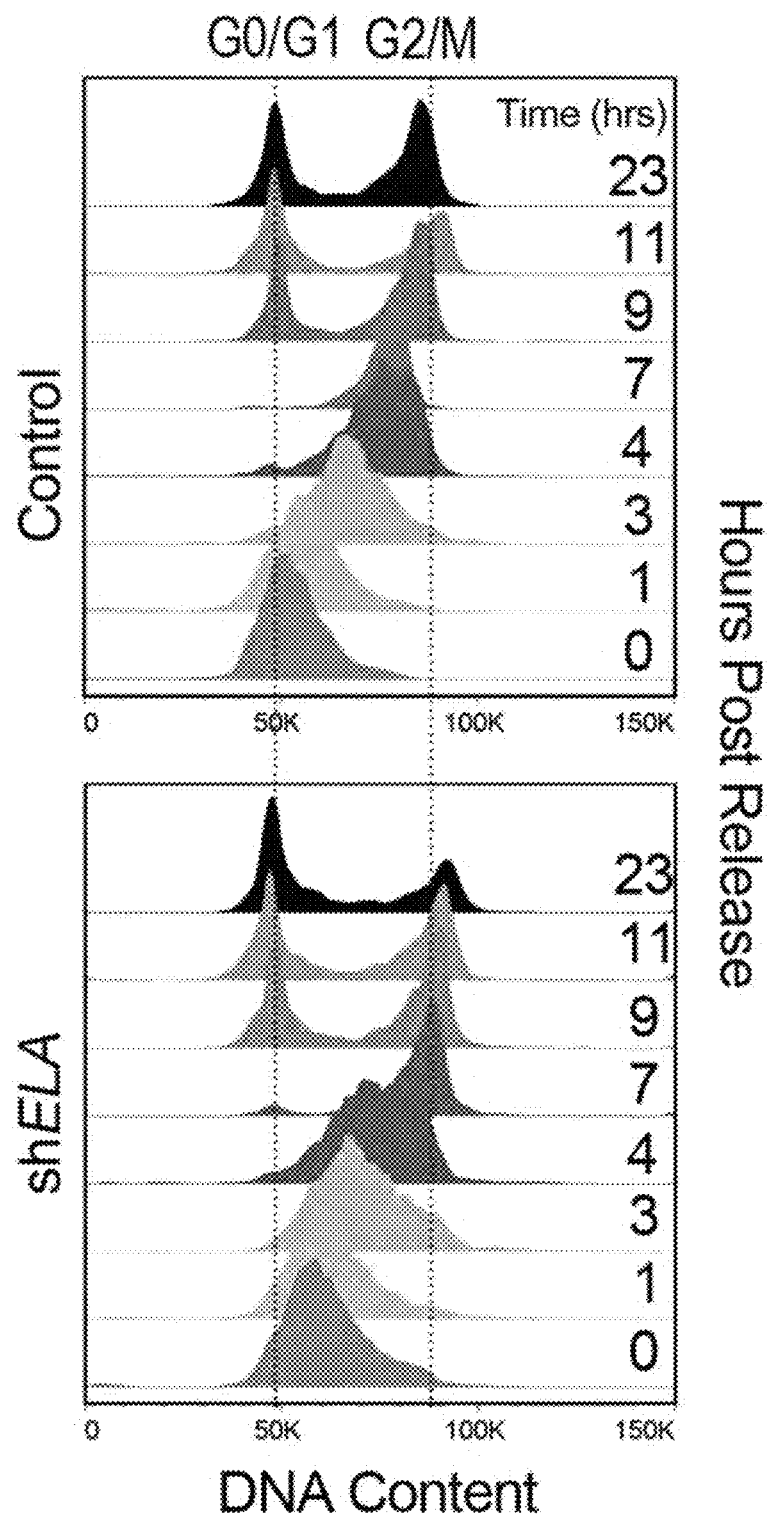
Figure 16D:
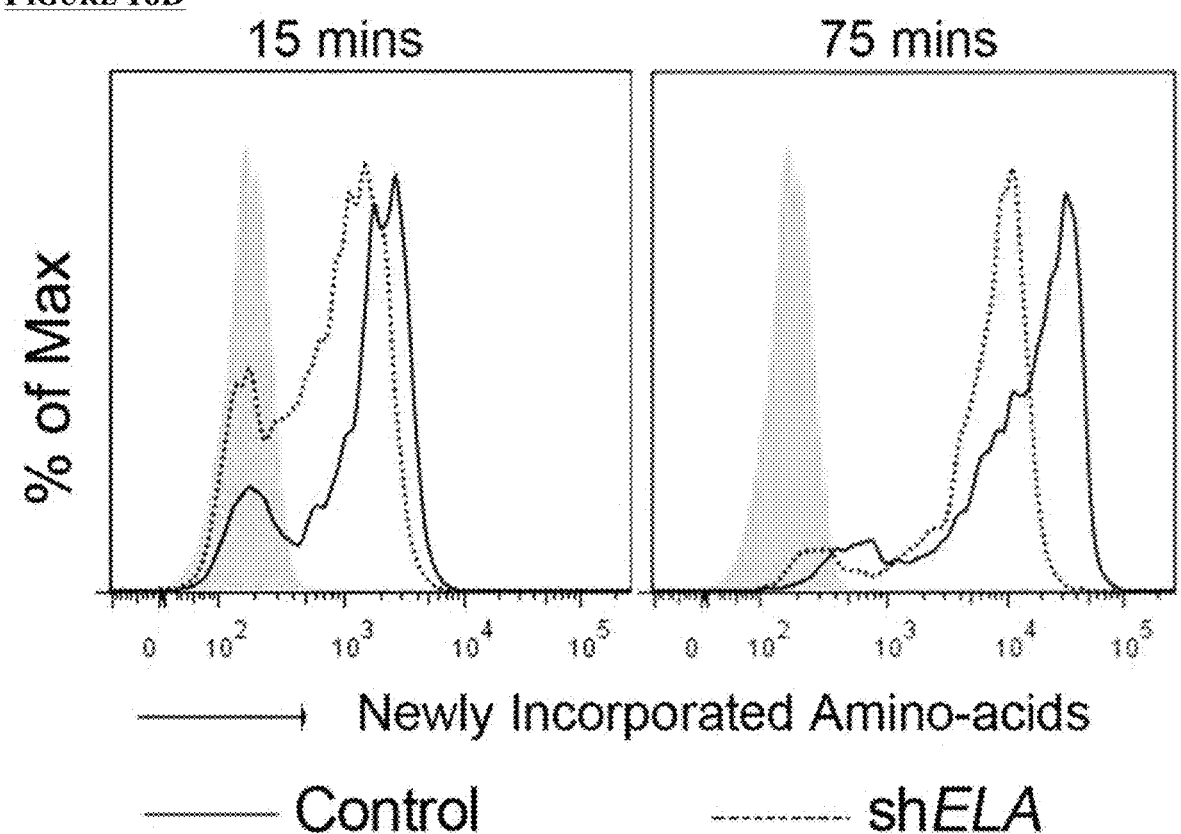

Example 49. Results: ELA Impacts Cell Cycle and Protein Translation Downstream of PI3K/AKT PI3K/AKT is upstream of an array of cellular processes involved in growth and proliferation (Brons et al., 2007). One such function is regulating the progression of cells through the G1/S transition during the cell cycle (Tesar et al., 2007). Embryonic stem cells have an abridged G1 phase compared to differentiated cells (Nichols and Smith, 2012). Unlike in mESCs, where Cyclin D is mostly inactive (Dreesen and Brivanlou, 2007), the pRB-CyclinD/CDK4/6 cascade in hESCs is operational (Dreesen and Brivanlou, 2007) and is indispensable for G1/S transition and pluripotency (Vanier et al., 2005; Voskas et al., 2014). Since PI3K/AKT is crucial for the post-transcriptional stabilization of CyclinD (Xu et al., 2005), we hypothesized that the loss of PI3K/AKT signaling in shELA cells would result in an accumulation of cells in the G1 phase. Careful analysis of the cell cycle of shELA hESCs following release from a double thymidine block revealed a noticeable increase of cells in G1 (FIG. 15F, black), and a small lag in transiting from G2/M back to G1/G0 (FIG. 15F, magenta). At steady state, EDU incorporation also revealed a similar accumulation of shELA hESCs in the G1/G0 phase (FIG. 16C). Consistent with impaired activation of mTOR downstream of AKT, shELA hESCs exhibited reduced protein synthesis (Vander Haar et al., 2007; Wang et al., 2012) as assayed by incorporation of fluorescently-labeled amino acids (FIG. 16D). These data suggest that one of the functions of ELA in hESCs consists of promoting cell cycle progression and optimal protein translation.

Figure 17A:
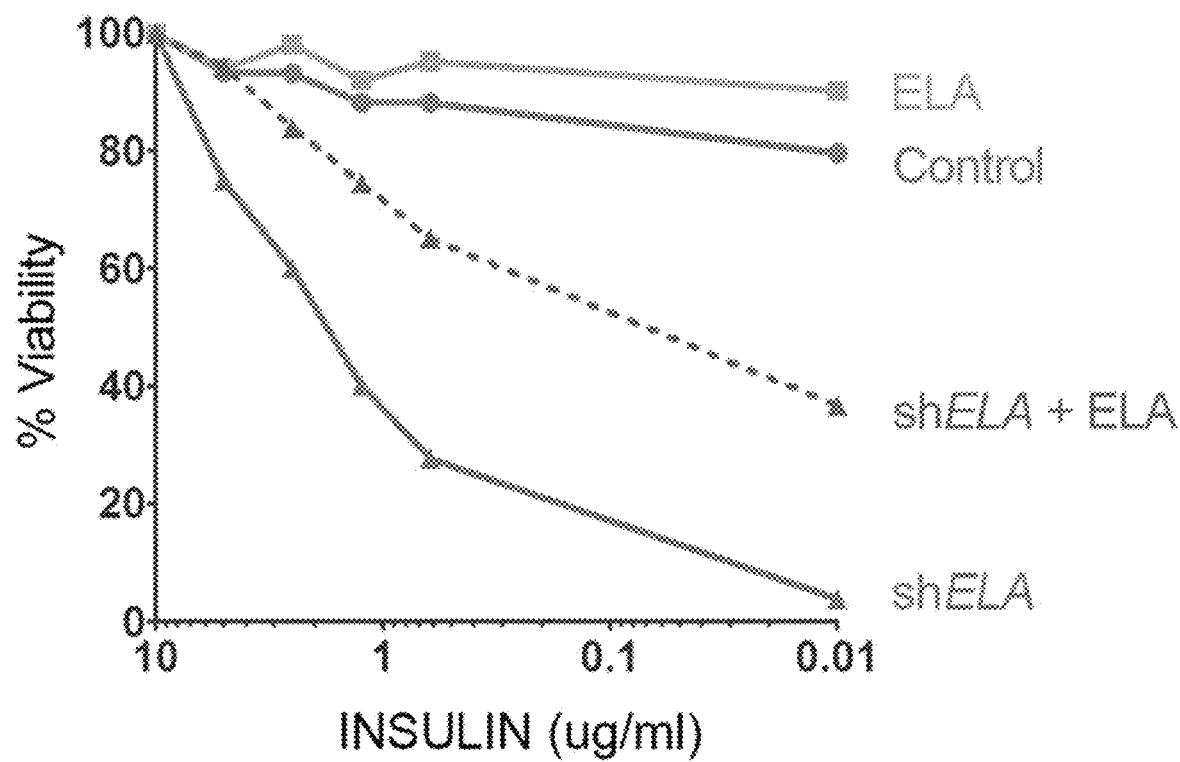
Figure 17B:
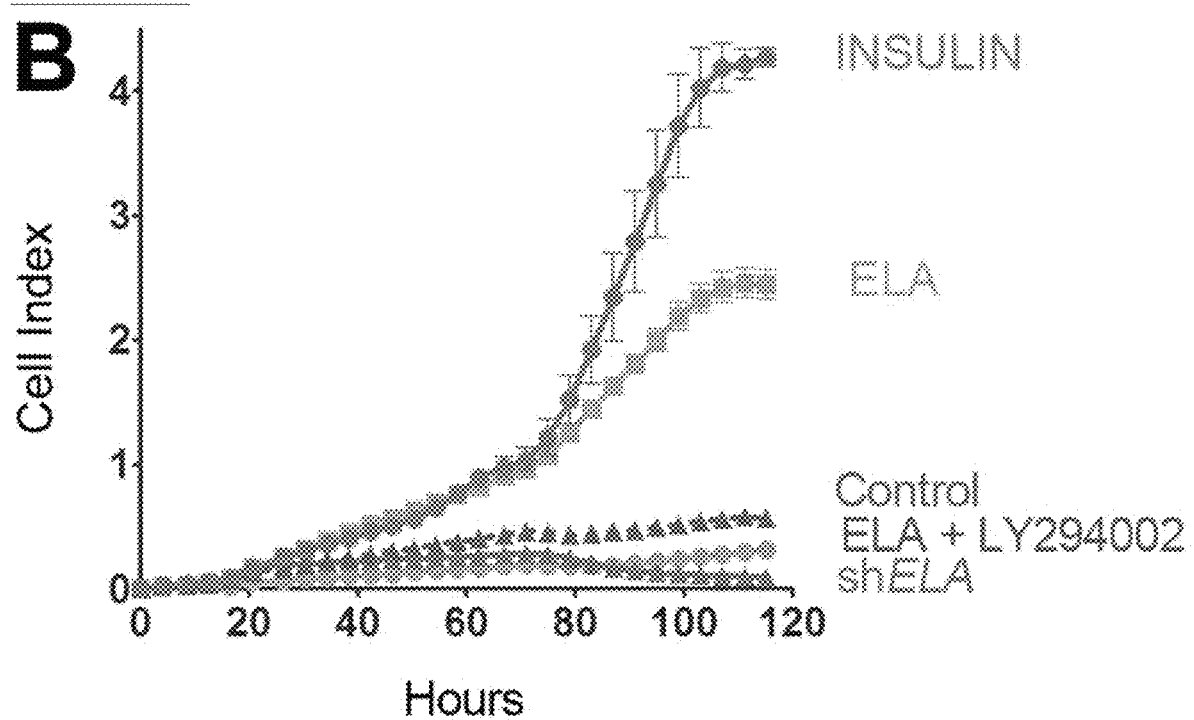
Figure 18A:
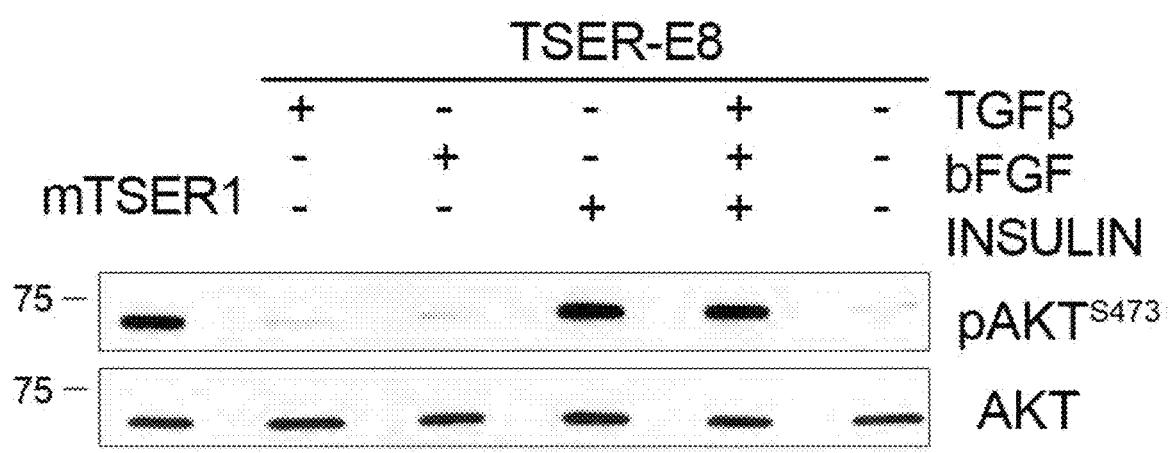
Figure 18B:
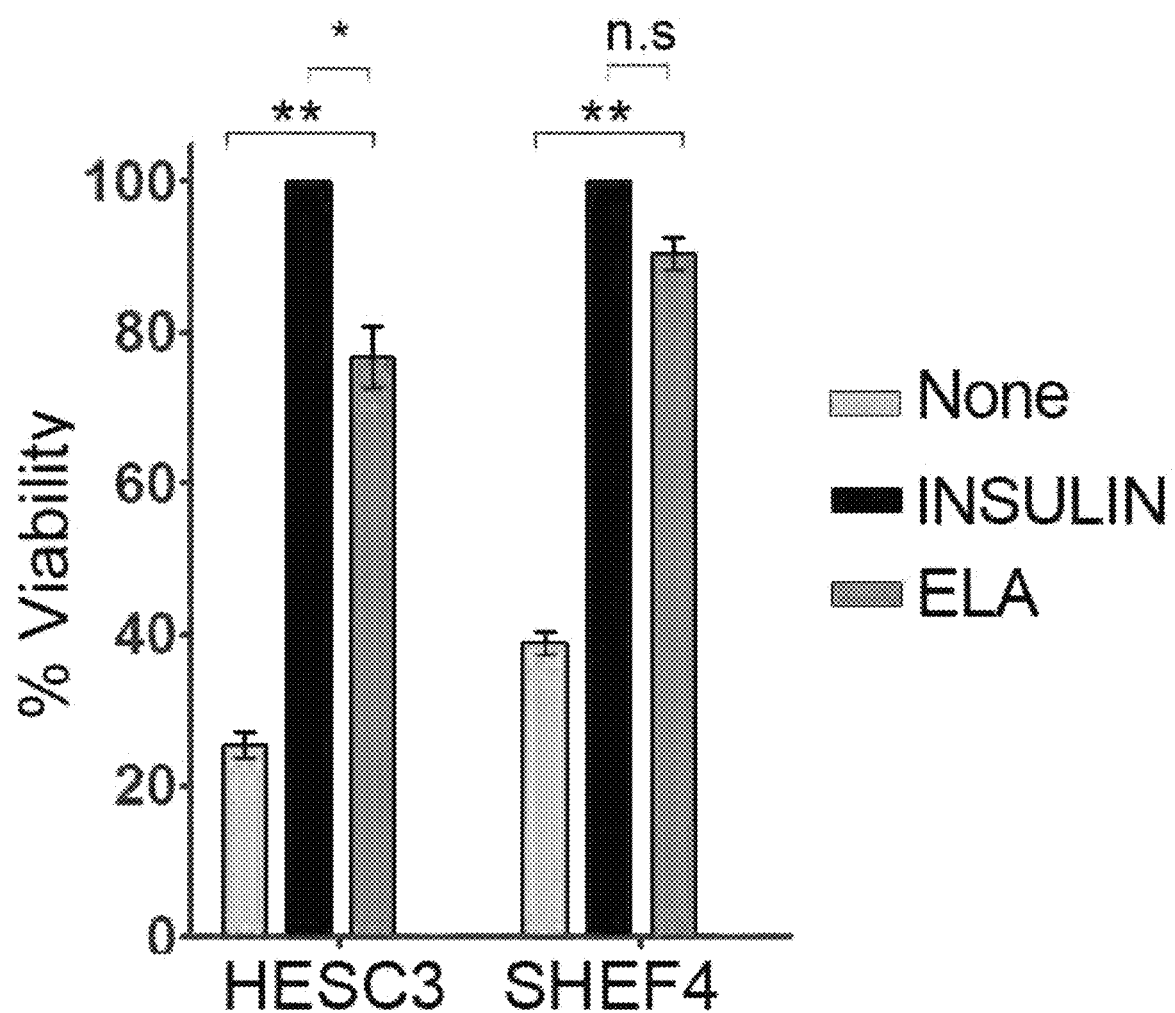
Figure 18C:
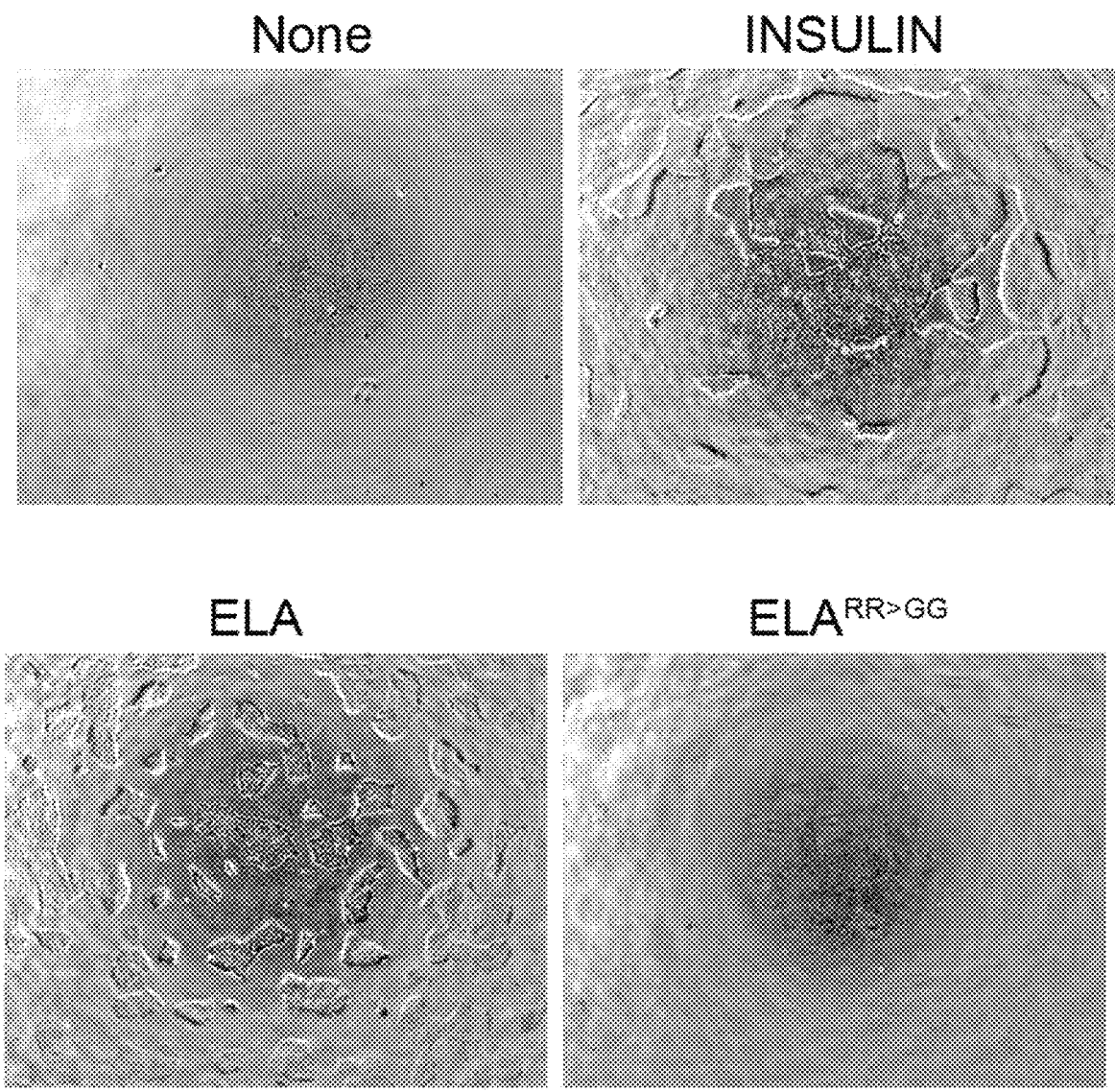

Example 50. Results: ELA Protects Against Apoptosis and Prevents Stress-induced Cell Death hESCs are dependent on exogenous INSULIN (Sancak et al., 2007) and autologously-derived IGF2 (Wang et al., 2007a), both of which activate the PI3K/AKT pathway to mediate self-renewal and prevent differentiation (Wang et al., 2007a). For this reason, mTSER1 medium (used in this study), and most formulations of hESC media (Armstrong et al., 2006; Peterson et al., 1999) contain high levels of INSULIN. To investigate the requirement for ELA, we cultured hESCs in a defined TSERe8 medium (Zhou et al., 2009) which only contains four growth factors: INSULIN, bFGF, TGFβ1 and TRANSFERRIN to allow precise control of its composition. We confirmed that INSULIN is the sole activator of AKT in this formulation (FIG. 18A). In two different hESCs lines SHEF4 and HESC3, we observed a high rate of cell death after 24 hours of growth in the absence of INSULIN. Addition of ELA provided an 80% to 90% rescue in cell viability, while ELA$^{RR>GG}$ exerted no effects (FIGS. 18B and 18C). On the contrary, we found that shELA hESCs are exquisitely sensitive to INSULIN deprivation compared to control hESCS, while addition of ELA provides an intermediate growth rescue (FIG. 17A). These results were confirmed by cell index measurements over 5 days, where ELA partially replaces INSULIN in a PI3K-dependent manner, since addition of LY294002 abrogated the rescuing effect of ELA (FIG. 17B). Hence, ELA, through activation of the PI3K/AKT pathway, partially replaces INSULIN in the growth media of hESCs.

Figure 17C:
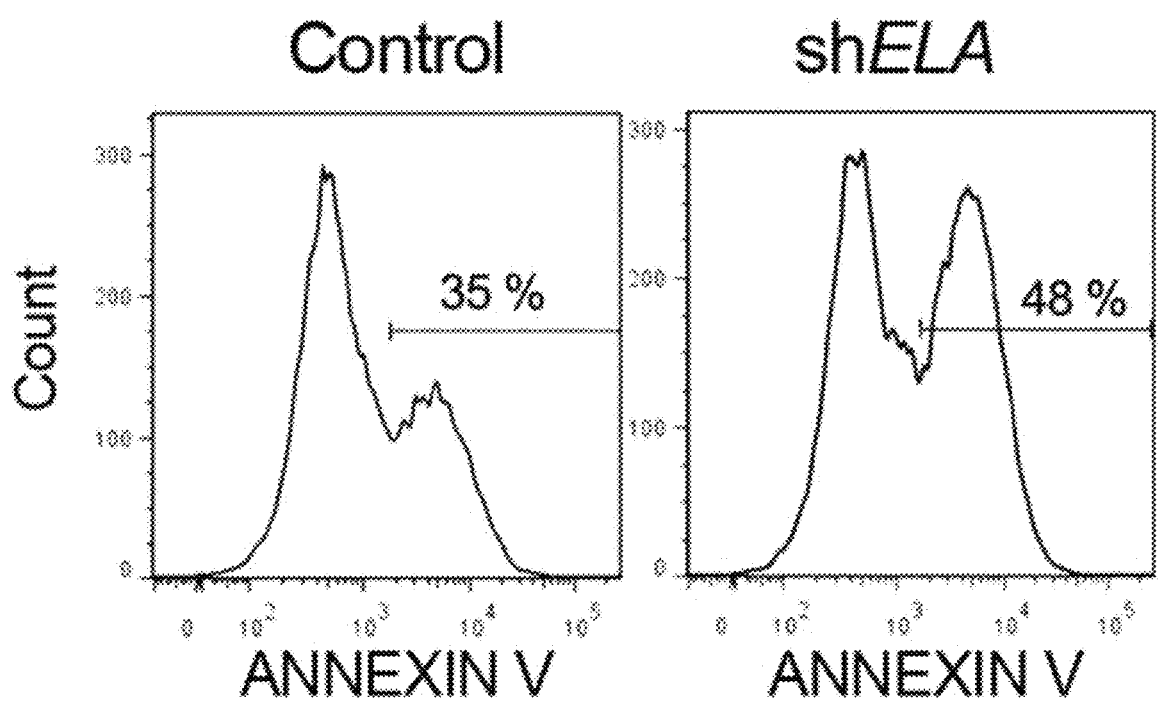
Figure 17D:
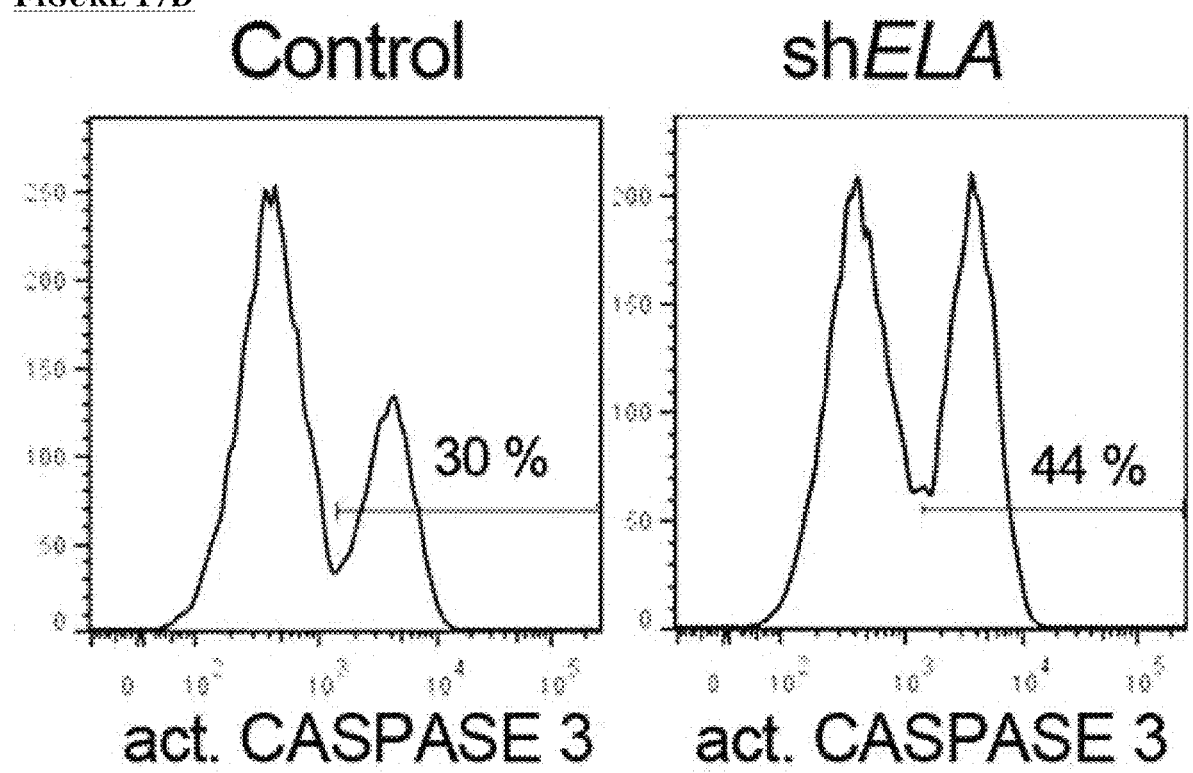
Figure 17E:
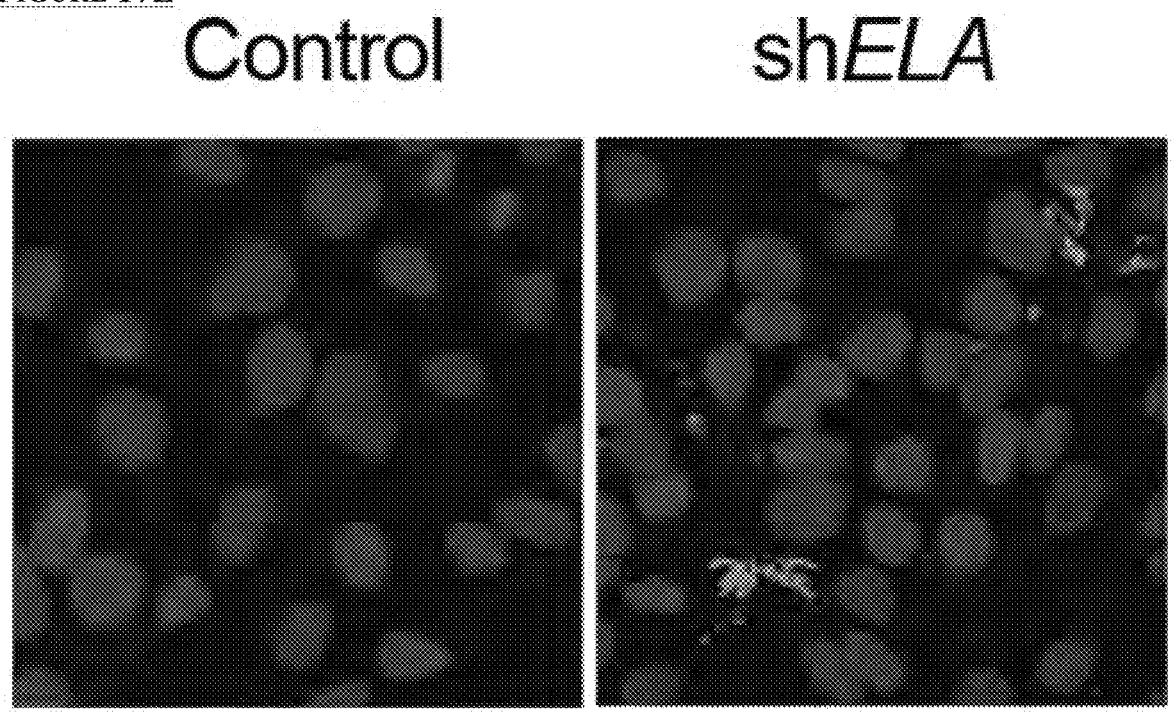
Figure 17G:
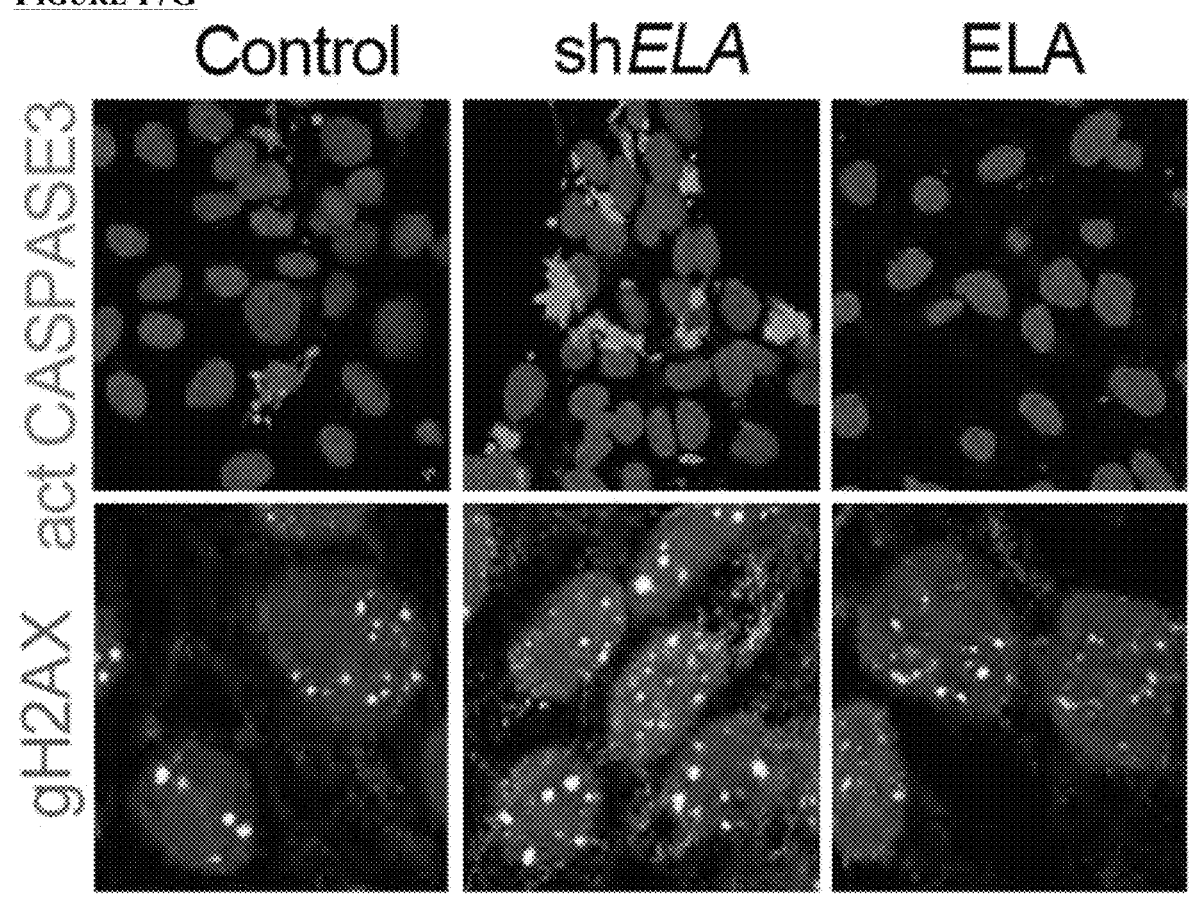
Figure 17H:
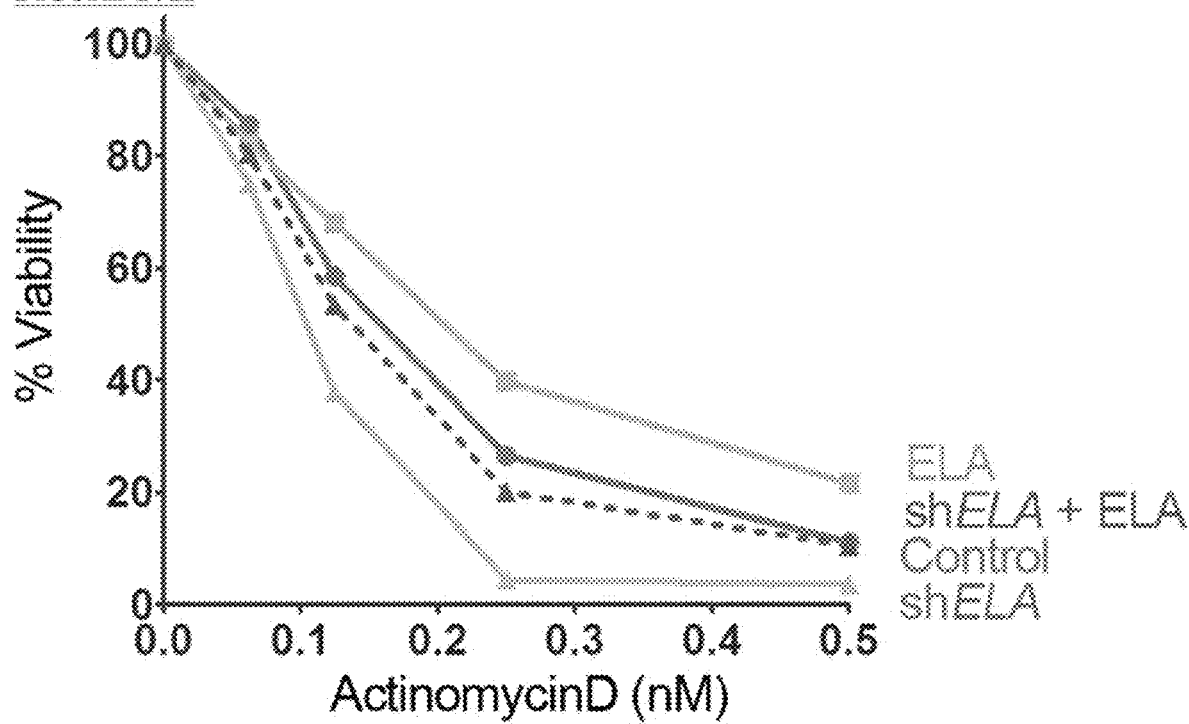
Figure 17I:
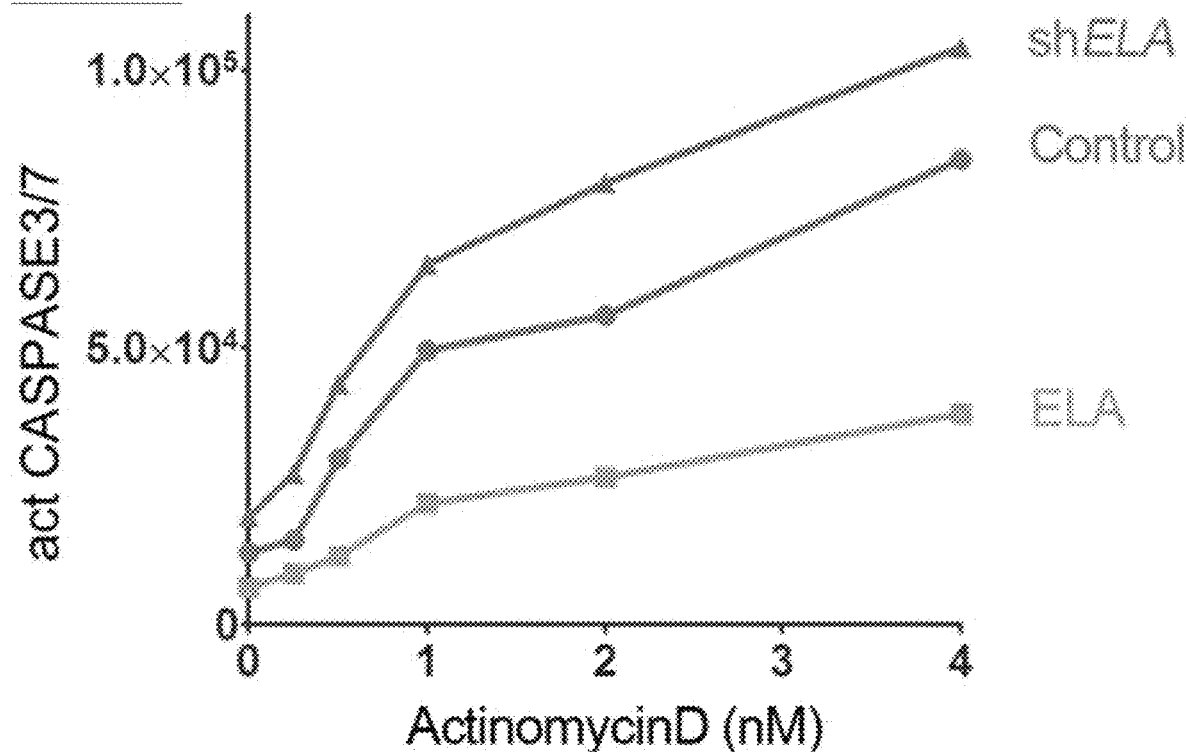
Figure 18D:
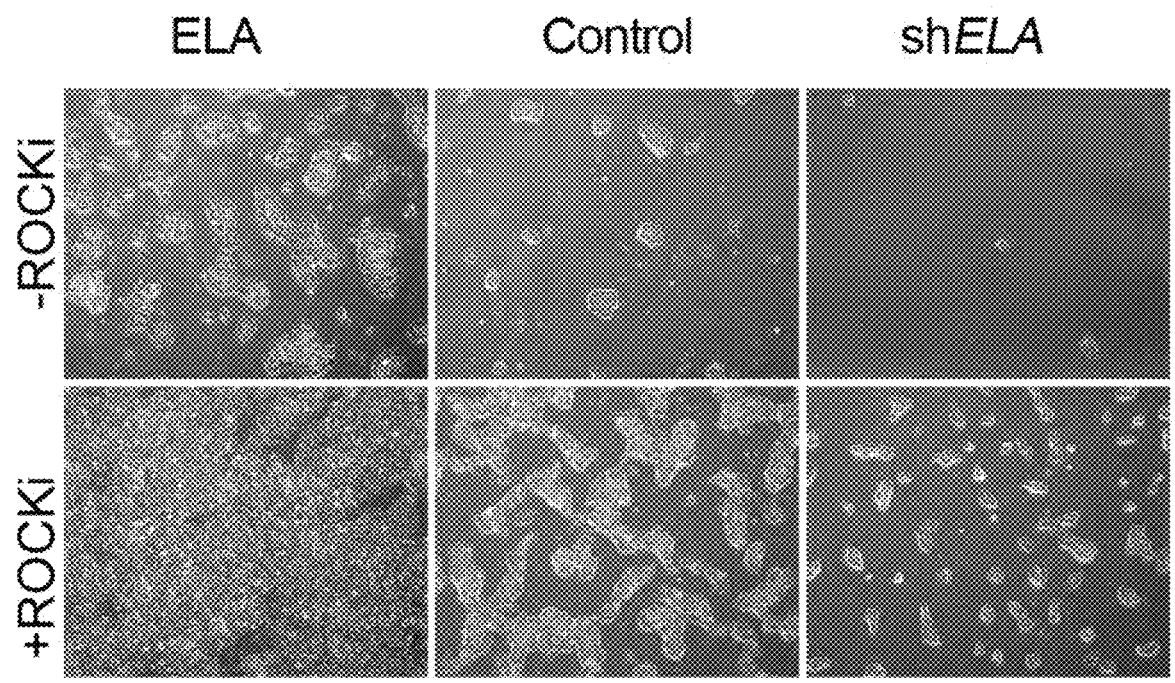
Figure 18F:
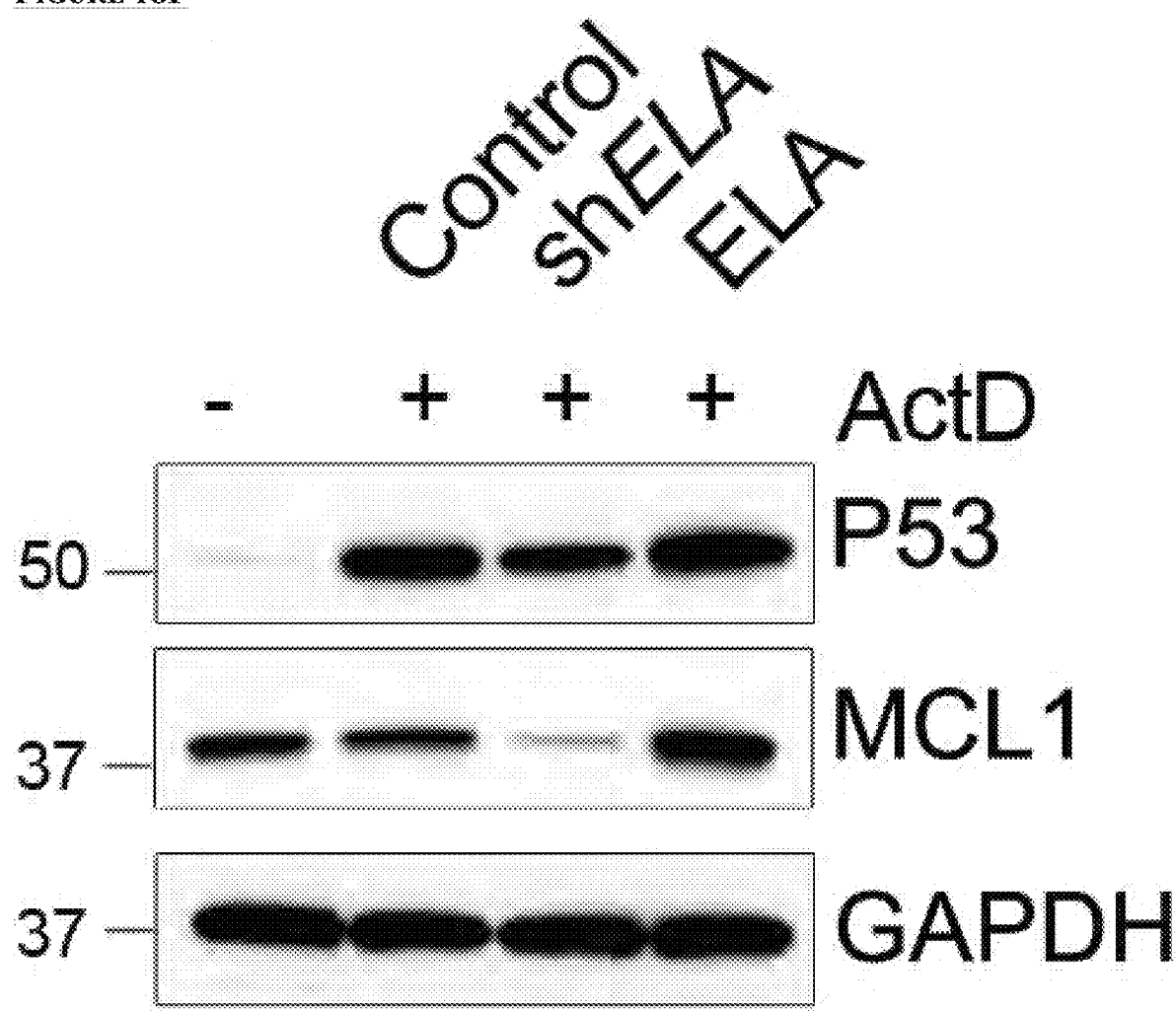
Figure 18G:
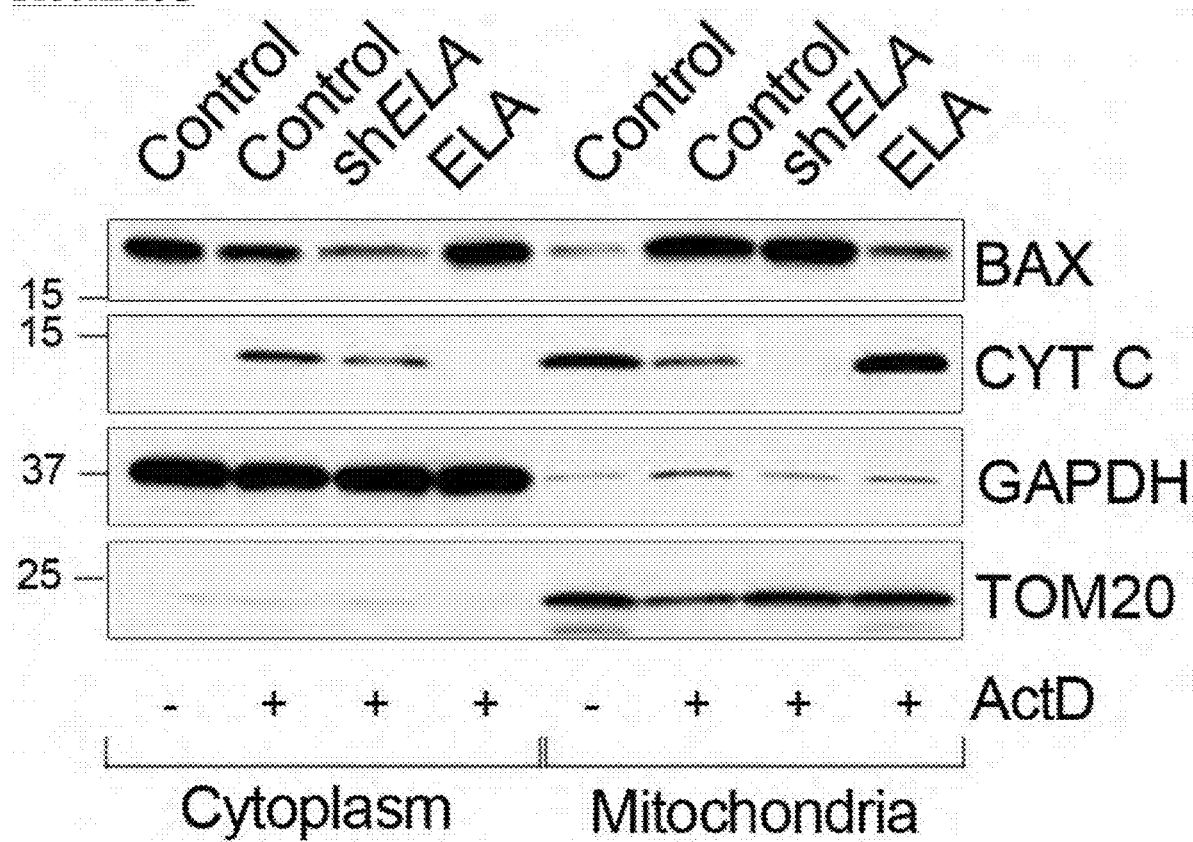
Figure 18H:
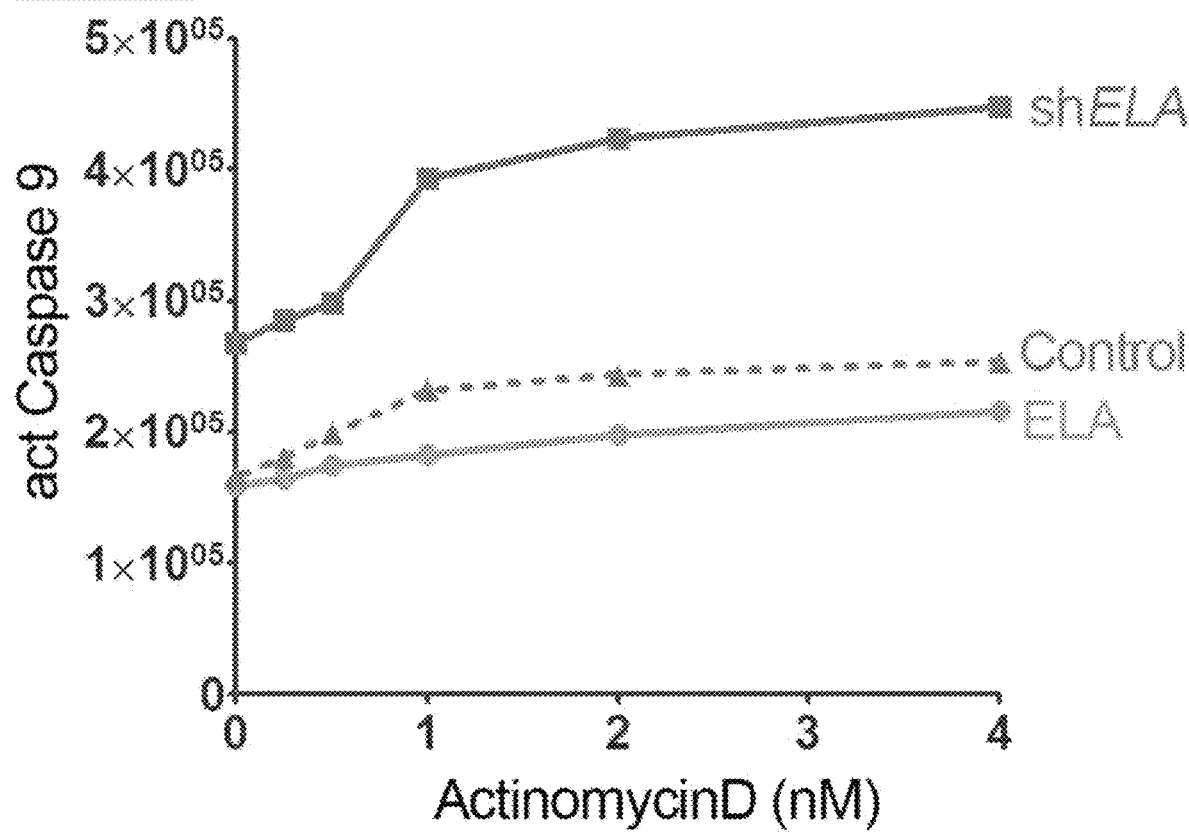

PI3K/AKT is most recognized for its anti-apoptotic properties in both normal and cancer stem cells (Brons et al., 2007). AKT inhibits apoptosis by phosphorylation and inactivation of numerous pro-apoptotic molecules, such as BAD and FOXO, while activating pro-survival pathways such as NK-kB (Brons et al., 2007). For this reason, we hypothesized that ELA may prevent apoptosis and thereby potentiate hESC growth. In line with our observation that shELA hESCs have impaired AKT signaling and growth, we found that following passaging, a significantly higher proportion of shELA hESCs underwent apoptosis, as marked by surface expression of ANNEXIN V (FIG. 17C) and intracellular activated CASPASE 3 (FIG. 17D), which was also observed by immunofluorescence staining (FIG. 17E). This suggests that endogenous ELA is required to protect against apoptosis induced by routine in vitro culture conditions, such as dissociation-induced cell death namely anoikis (Bendall et al., 2007; Wang et al., 2007b). In line with this observation, shELA hESCs do not survive single-cell dissociation in the absence of Y-27632, which inhibits anoikis by inhibition of Rho-associated kinase (ROCK) (Hanahan and Coussens, 2012) (FIG. 18D). Conversely, synthetic ELA peptide was able to increase survival following dissociation compared to untreated hESCs, partially replacing Y-27632 (FIG. 18D). To further document the protective role of ELA against cellular stress, we exposed hESCs to ionizing radiation to stimulate DNA damage (FIG. 17F). shELA hESCs were twice as sensitive to gamma irradiation relative to control, while ELA-treated hESCs were 5 times more resistant. Addition of exogenous ELA to shELA hESCs rescued this phenotype (FIG. 17F). Consistent with these results, 3 hours after exposure to 1 Gray of γ irradiation, higher levels of activated CASPASE 3 was detected in shELA hESCs compared to control, but were almost undetectable in ELA treated hESCs, despite comparable numbers of γH2AX foci, marking DNA double-stranded breaks (FIG. 17G). Similar results were obtained, when hESCs were treated with nanomolar concentrations of ActinomycinD, which inflicts translational stress (Junttila and de Sauvage, 2013) with P53-dependent cell cycle arrest and apoptosis (Moral and Paramio, 2008). ShELA hESCs were more sensitive compared to control while addition of ELA conferred significant resistance to control hESCs and completely rescued shELA hESCs (FIG. 17H). Mutant ELA$^{RR>GG}$ had no protective effect (FIG. 18E). ELA had no apparent effect on the levels of P53 protein following exposure to stress (FIG. 18F). shELA hESCs had lower levels of the anti-apoptotic BCL-2 family member MCL-1, which was rescued with exogenous ELA (FIG. 18F). At the same time, shELA cells had higher levels of BAX in the mitochondria, while it remained primarily in the cytoplasm in ELA-treated cells (FIG. 18G). Consequentially, shELA hESCs had increased levels of activated CASPASE3/7 consistent with complete leakage of CYT C (FIGS. 17I and 18G) and CASPASE 9 which is mediated by BAX (Pickering et al., 2014). This was entirely suppressed by addition of exogenous ELA (FIG. 18H). Altogether, our results indicate that exogenous ELA protects against the intrinsic apoptosis pathway activated by cellular stress, while hESCs depleted of ELA are highly sensitized to stress.

Figure 17J:
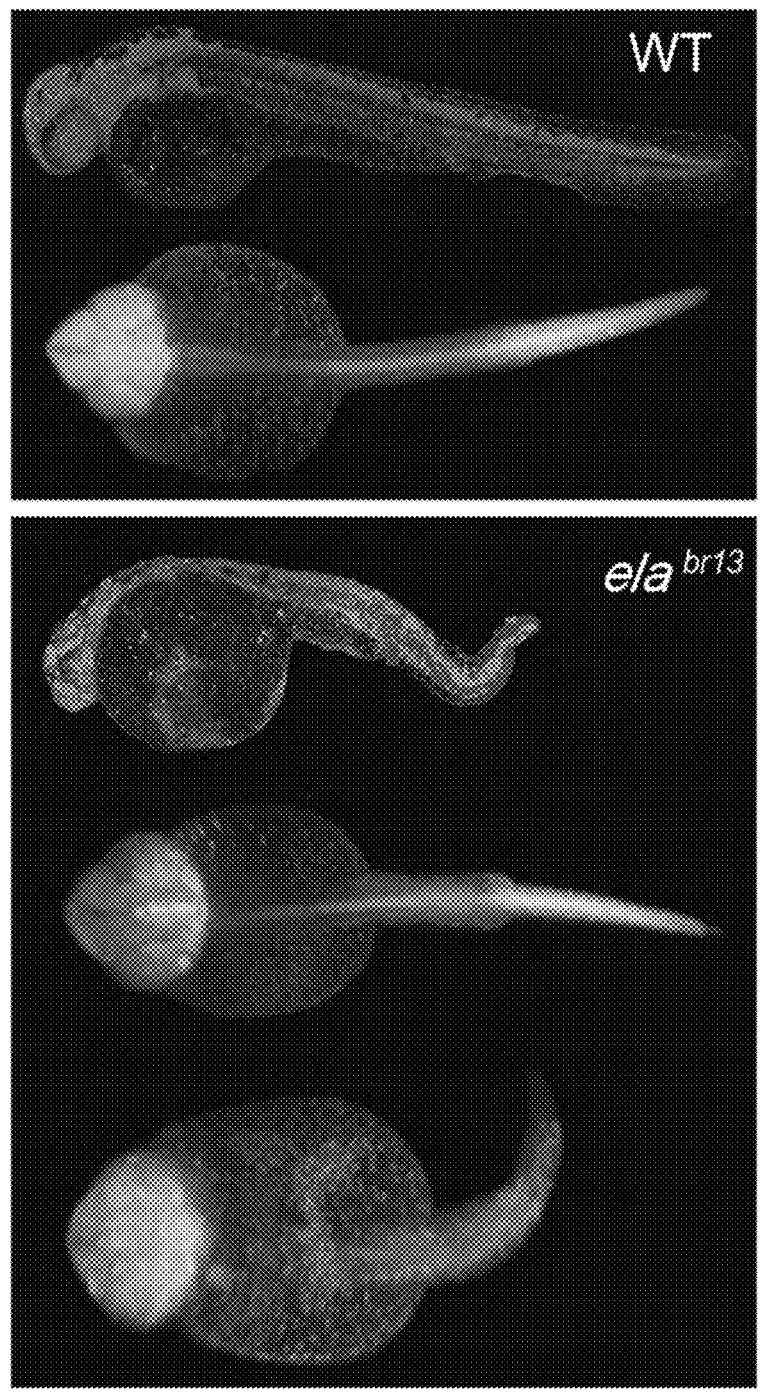

We next sought to determine if the protective effect of ELA against cell death observed in cultured hESCs were also relevant in vivo. In ela mutant zebrafish embryos carrying a recessive null allele (Gaggioli et al., 2007), we observed a generalized increase in the numbers of activated Caspase3-positive cells at 24 hours post-fertilization (hpf), with clusters of apoptotic cells in the trunk, brain and peri-ocular areas of ela$^{br13}$ but not wildtype embryos (FIG. 17J). This suggests that Ela's anti-apoptotic activity is also relevant during embryogenesis.

Example 51. Discussion: An Alternate Receptor for ELA Mediates its Function in hESCs Our observation that recombinant ELA is rapidly taken up by hESCs and that endogenous ELA can be found in the cytoplasm suggests that it has a dedicated receptor in these cells. We do not favor the possibility that ELA behaves a self-penetrating peptide (Green and Loewenstein, 1988) despite its very basic amino-acid make-up (Chng et al) because its rapid cellular uptake is only observed in hESCs and not in other tested cell types. As previously reported and confirmed by us, APLNR is silent in hESCs. We therefore believe that another cell surface receptor mediates ELA's activity in hESCs. Furthermore, APELIN-13, which activates the PI3K/AKT via APLNR in certain cell types (Tang et al., 2007) has no effect on hESCs (data not shown). Since ELA's known receptor APLNR belongs to the G-protein coupled receptor (GPCR) family, we surmise that the alternate and earlier receptor might also be a GPCR, although we cannot rule out other receptor types such as receptor tyrosine kinases (RTKs).

Example 52. Discussion: Regulation of Embryonic Growth Potential by ELA

A disproportionate emphasis has been placed on transcription factors for the maintenance of the pluripotency circuit. In recent years, a plethora of transcription factors has been shown to be critical for the pluripotent state and to enhance reprogramming (Takahashi and Yamanaka, 2006). However, besides the well-studied roles of NODAL/BMP, IGF/FGF and WNT that are established factors for pluripotency, very few new secreted factors with proven roles in pluripotency have been discovered in the last 20 years. INSULIN/INSULIN-LIKE GROWTH FACTORS (IGF-1 and IGF-2) are well-known to stimulate preimplantation embryonic growth in vitro, increasing the number of cells in the inner cell mass of mouse embryos and protecting them against apoptosis induced by oxidative stress (Kurzawa et al., 2002; Markham and Kaye, 2003; Rappolee et al., 1992). In both humans and mice, IGF-2 is produced by the embryo and acts in an autocrine fashion, while INSULIN and IGF-1 are undetectable in the preimplantation embryo but are believed to be supplied by the maternal environment (Lighten et al., 1997; Schultz et al., 1993).

Here we present evidence that a new extracellular molecule, ELA exists and plays an important role in stemness. ELA, like INSULIN and IGFs, can activate the PI3K/AKT pathway and is either the endogenous or an alternate activator of this crucial pathway during early embryogenesis. Unlike FGFs which needs to be added exogenously, or secreted by feeder cells to maintain pluripotency in hESCs, ELA is endogenously synthesized and secreted by hESCs in sufficient quantities. The inhibition of ELA causes rapid apoptosis suggesting that it serves as a pro-survival factor to counteract the high levels of spontaneous apoptosis inherent to hESC cultures. In line with this, we note that the depletion of ELA in hESCs grown as single cells is more detrimental than hESCs grown in colonies due to the higher rate of anoikis following dissociation (Wang et al., 2009; Watanabe et al., 2007). Alternatively, this might point to the extracellular activity of the peptide, which may be more readily captured in a paracrine manner by hESC colonies than it is by single cells. Also, we note that while endogenous ELA is present in hESC-conditioned media in the nM range, our recombinant peptide, although specific and bioactive, works in the μM range. This finding suggests existence of possible post-translational modifications on endogenous ELA that are required for its full potency, as is the case for other peptide hormones such as GHRELIN (Kojima et al., 1999).

Taken together, our data suggest that mature ELA functions as an endogenous hormonal peptide secreted by hESCs, taken up by hESCs in a paracrine manner, and signalling through an unknown receptor to the PI3K/AKT pathway to sustain survival and self-renewal of ES cells and early embryos. As ELA is highly expressed in the human blastocyst, the stage from which hESCs are derived, we conjecture that it may play a similar protective role in mammalian pre-implantation embryos as it does in zebrafish embryos. What endogenous stress signal in the mammalian embryo ELA might protect against is not entirely clear. Normoxia, replicative stress, nutrient deprivation, temperature, are potential stimuli which could equally solicit the need for ELA during embryogenesis.

Example 53. ELA Mouse Knockout: Introduction

We recently reported the discovery of ELABELA (ELA) as a novel and early endogenous ligand for the APELIN RECEPTOR (APLNR). Mice deficient for Aplnr (or Apj) display cardiovascular defects and succumb around 10.5 days of gestation due to the lack of a proper circulation (Charo et al., 2009). However, mice deficient for Apelin, the known ligand of Apj, are phenotypically normal (Charo et al., 2009). This suggests that cardiovascular functions of Apj are mediated by Ela rather Apelin, and prompted us to investigate the contribution of Ela to mouse embryonic development.

Example 54. ELA Mouse Knockout: Materials and Methods

Construction of Conditional Ela Knockout Mouse

A linearized targeting vector containing homology arms and exon 2 of Elabela, flanked by lox-p sites together with a neo cassette flanked by FRT sites was electroporated into 129Sv mouse embryonic stems cells. Targeting was verified by southern blotting. Verified clones were transfected with Flp recombinase to remove the neo cassette, and were subsequently injected into C57BL6 recipient blastocysts and implanted into pseudopregnant females. F0 founders with >50% chimerism were backcrossed to C57BL6. The F1 generation, upon confirmation of stable $ELA^{Flox}$ germline transmission, were crossed with ZP3-cre recombinase-containing transgenic mice to remove Exon 2 to generate the $Ela^4$ null allele. $Ela^{\Delta/+}$ heterozygous mice were subsequently backcrossed for 8 generations to C57BL6 before phenotypic analysis.

Phenotypic Characterization of Ela-Deficient Embryos $Ela^{\Delta/+}$ mice were intercrossed to generate $Ela^{\Delta/\Delta}$, $Ela^{\Delta/+}$ and wildtype embryos for phenotypic analysis. Embryos were harvested at e10.5. Yolk sacs and embryos were fixed for 1 hour with 4% PFA, followed by immunohistochemistry for Pecam-1 (MEC13.3, Biolegend). Embryos and yolk sacs were also paraffin-embedded and sectioned for hematoxylin and eosin (H&E) staining to observe the morphology of cardiovascular structures.

Example 55. ELA Mouse Knockout: Results

Figure 1E:
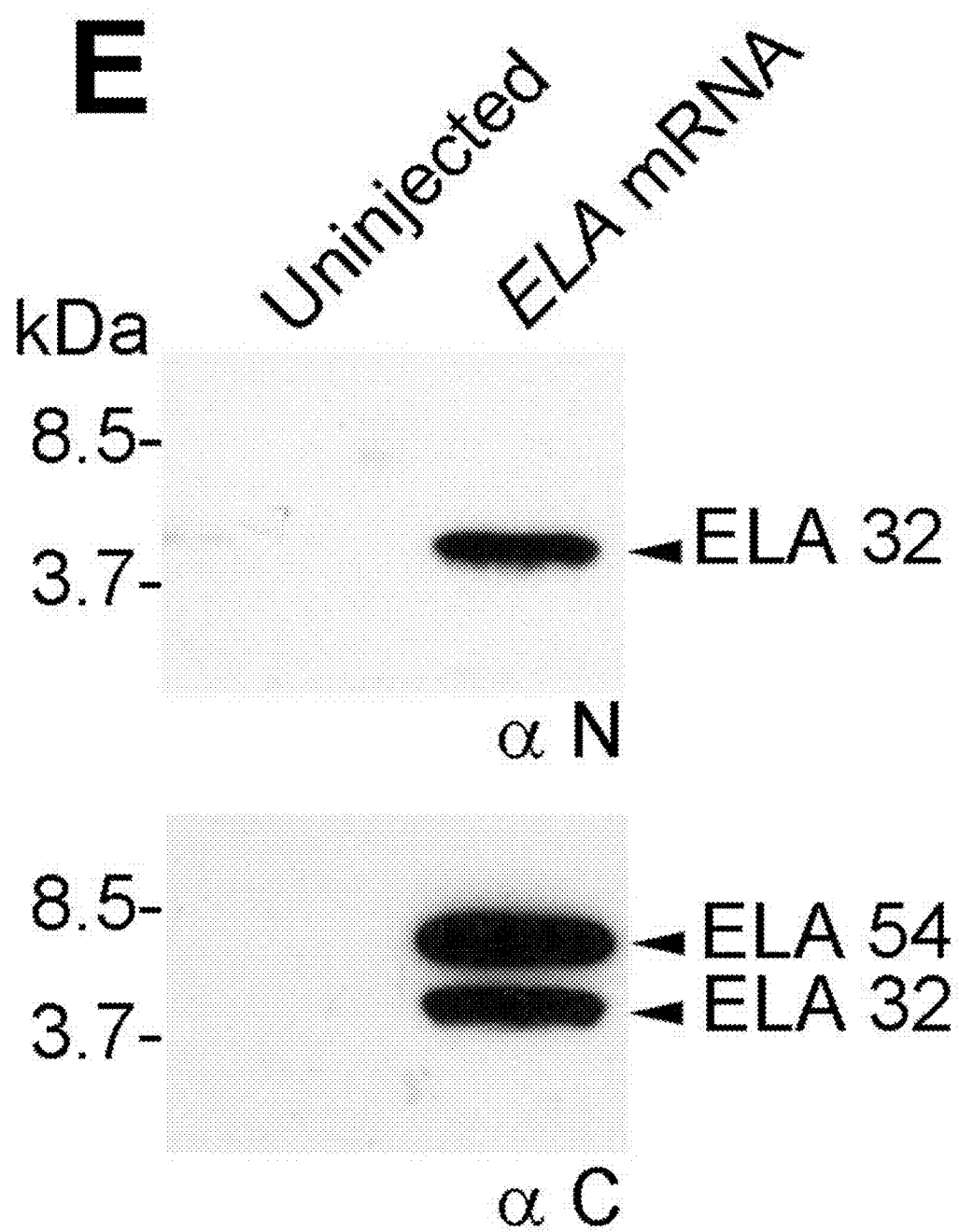

We successfully generated Ela knockout mice ($Ela^{\Delta/\Delta}$) according to the schematic shown in FIG. 1A. Ela knockout mice are viable and fertile, but showed a statistically significant reduction in Mendelian ratio at the time of weaning, suggesting partial embryonic lethality (FIG. 1B). Analysis of e10.5 embryos revealed that a portion of Ela knockouts have severe cardiovascular malformations, reminiscent of the phenotype of Apj knockout mice. These include including a hypovascularized yolk sac (FIG. 1C), cardiac edema (FIG. 1C) and dysgenesis of the heart tube (FIG. 1F). Pecam-1 staining, which marks endothelial cells, showed that Ela knockout mice developed endothelial cells and an immature vascular plexus, but these did not mature and coalesce into functional vessels (FIG. 1D). Furthermore, the endodermal and mesodermal layers of the yolk sac, which is the first site of blood formation, were not correctly fused and lined with endothelial cells compared to control littermates (FIG. 1E). Lastly, examination of the mis-formed hearts in Ela knockout mice revealed a severely underformed endocardium which lacked visible trabeculation. Taken together, our results reveal that Ela and not Apelin acts in concert with Apj to mediate correct cardiovascular morphogenesis.

Example 56. HIV Inhibition: Materials and Methods

ELA Receptor Binding Assay

Secreted ELA-Alkaline Phosphatase (ELA-AP) was produced by transfecting a construct encoding ELA-AP into 293T cells, as described previously (Chng et al., 2013). Conditioned medium from ELA-AP expressing cells was then incubated for 3 hours with 293T cells transfected with plasmids encoding full-length ORFs of putative receptors. Unbound ELA-AP was washed away and cells were lysed with 1% Triton-X/PBS. Lysates were cleared and incubated with an AP substrate BCIP/NBT at 37° C. for 15 minutes. Optical density was read at 495 nm, and the intensity of blue coloration is directly proportional to the affinity of ELA-AP to the over-expressed receptor.

ELA-CXCR4 Binding Assays

To detect activation of CXCR4 by ELA or SDF-1, recombinant ELA or SDF-1 were added in increasing concentrations for 90-180 minutes to cells stably expressing CXCR4 coupled to a downstream reporter. β-Arrestin recruitment was measured using the PathHunter® β-Arrestin CXCR4 assay (DiscoveRx). Interaction of CXCR4 with Arrestin was detected by Enzyme Fragment Complementation (EFC) between two complementary domains of β-galactosidase (β-Gal), one fused to CXCR4 and the other fused to β-Arrestin. β-Arrestin recruitment to CXCR4 results in complementation of the two domains to generate β-Gal activity. % Activity=100%×(mean RLU of test sample−mean RLU of vehicle control)/(mean MAX control ligand−mean RLU of vehicle control). To detect antagonism of SDF-1 by ELA, the assay was run in antagonist mode by measuring the EC50 of ELA in the presence of SDF-1 at EC80 concentration. To detect synergism between ELA and SDF-1, the assay was run in positive allosteric mode by measuring the EC50 of ELA in the presence of SDF-1 at EC20 concentration.

HIV Inhibition Assay

HIV-1 (NL43, JRCSF, and NLAD8 strains) and HIV (VSV), a defective HIV-1 with the env gene deleted and pseudotyped with the VSV-G envelope, were produced, and infections were performed as described previously (Marechal et al., 1998; Oberlin et al., 1996; Schwartz et al., 1998). P4C5 cells (HeLa CD4$^+$ CXCR4$^+$ CCR5$^+$ LTR-lacZ) (Marechal et al., 1998) were grown in Dulbecco modified Eagle medium (DMEM) supplemented with 10% fetal calf serum. P4C5 cells ($10^4$ per well) in 96-well plates were cultured for 24 h before infection with 200 μl of viral supernatants (in triplicate) in the absence or in the presence of ELA and with 20 ng of DEAE dextran/ml and 20 mM HEPES buffer (pH 7.3) as described previously (Schwartz et al., 1998). The viral inoculum corresponded to 2 and 2.5 ng of p24 for NL43 and JRCSF viruses, respectively. After viral exposure (2 h at 37° C.) and every following day, the supernatants were harvested and replaced with fresh medium containing or not containing ELA. After the indicated periods, the cells were washed to remove unbound virus. After 24 h, β-gal activity was measured. The cells were lysed in 100 μl of 60 mM $Na_2HPO_4$, 40 mM $NaH_2PO_4$, 10 mM KCl, 10 mM $MgSO_4$, 2.5 mM EDTA, 50 mM β-mercaptoethanol, and 0.125% Nonidet P-40. The lysates were mixed with 100 μl of 80 mM $NaPO_4$ (pH 7.4), 10 mM $MgCl2$, 50 mM β-mercaptoethanol, and 6 mM chlorophenol red-β-galactopyranoside mono-Na salt and incubated at 37° C. before the optical density at 540 nm was measured.

Example 57. HIV Inhibition: Results

The results of the experiments described above are shown in FIGS. 20A to 20D.

FIG. 20A shows that CXCR4 is an alternate receptor for ELA. The figure shows a binding assay for ELABELA, where colour intensity correlates with the extent of binding. Like APLNR, the GPCR CXCR4, one of the most prominent HIV receptor, confers cell surface binding to ELA. Other tested GPCRs did not confer binding proving assay specificity.

FIG. 20B shows that CXCR4 is not activated by ELA. Unlike CXCR4's cognate ligand SDF1 (a.k.a CXCL12), ELA cannot activate CXCR4.

FIG. 20C shows that CXCR4 is antagonised by ELA. ELA behaves as a CXCR4 antagonistic ligand, by preventing SDF1-mediated CXCR4 activation.

FIG. 20D shows that ELA inhibits a CXCR4-tropic HIV strain in HeLa cells. ELA inhibits infection with NL (HIV-1 NL43: a CXCR4-tropic strain), but not with AD8 (HIV-1 NLAD8: a CCR5-tropic virus) or a VSV-G pseudotyped virus. HIV-1 infection is measured by a colorimetric assay (B-Gal activity) after 36-48 hrs of infection. ELA inhibits HIV at 10-40 µM. Nevirapine, a reverse transcriptase inhibitor, blocks all viruses tested.

REFERENCES

Alexander, J., and Stainier, D. Y. (1999). A molecular pathway leading to endoderm formation in zebrafish. *Current biology: CB* 9, 1147-1157.

Armstrong, L., Hughes, O., Yung, S., Hyslop, L., Stewart, R., Wappler, I., Peters, H., Walter, T., Stojkovic, P., Evans, J., et al. (2006). The role of PI3K/AKT, MAPK/ERK and NFkappabeta signalling in the maintenance of human embryonic stem cell pluripotency and viability highlighted by transcriptional profiling and functional analysis. Human molecular genetics 15, 1894-1913.

Ashley, E. A., Powers, J., Chen, M., Kundu, R., Finsterbach, T., Caffarelli, A., Deng, A., Eichhorn, J., Mahajan, R., Agrawal, R., et al. (2005). The endogenous peptide apelin potently improves cardiac contractility and reduces cardiac loading in vivo. Cardiovascular research 65, 73-82.

Bendall, S. C., Stewart, M. H., Menendez, P., George, D., Vijayaragavan, K., Werbowetski-Ogilvie, T., Ramos-Mejia, V., Rouleau, A., Yang, J., Bosse, M., et al. (2007). IGF and FGF cooperatively establish the regulatory stem cell niche of pluripotent human cells in vitro. Nature 448, 1015-1021.

Birnbaum Y, Hale S L, Kloner R A. Differences in reperfusion length following 30 minutes of ischemia in the rabbit influence infarct size, as measured by triphenyltetrazolium chloride staining. J Mol Cell Cardiol. 1997; 29(2): 657-666.

Bonecchi, R., Galliera, E., Borroni, E. M., Corsi, M. M., Locati, M., and Mantovani, A. (2009). Chemokines and chemokine receptors: an overview. Front Biosci (Landmark Ed) 14, 540-551.

Brons, I. G., Smithers, L. E., Trotter, M. W., Rugg-Gunn, P., Sun, B., Chuva de Sousa Lopes, S. M., Howlett, S. K., Clarkson, A., Ahrlund-Richter, L., Pedersen, R. A., et al. (2007). Derivation of pluripotent epiblast stem cells from mammalian embryos. Nature 448, 191-195.

Cederlund, A., Gudmundsson, G. H., and Agerberth, B. (2011). Antimicrobial peptides important in innate immunity. FEBS J 278, 3942-3951.

Charo, D. N., Ho, M., Fajardo, G., Kawana, M., Kundu, R. K., Sheikh, A. Y., Finsterbach, T. P., Leeper, N. J., Ernst, K. V., Chen, M. M., et al. (2009). Endogenous regulation of cardiovascular function by apelin-APJ. American journal of physiology Heart and circulatory physiology 297, H1904-1913.

Chen, X., Vega, V. B., and Ng, H. H. (2008). Transcriptional regulatory networks in embryonic stem cells. Cold Spring Harbor symposia on quantitative biology 73, 203-209.

Chenoweth, J. G., McKay, R. D., and Tesar, P. J. (2010). Epiblast stem cells contribute new insight into pluripotency and gastrulation. Development, growth & differentiation 52, 293-301.

Chng, S. C., Ho, L., Tian, J., and Reversade, B. (2013). ELABELA: a hormone essential for heart development signals via the apelin receptor. Developmental cell 27, 672-680.

Cohen, D. E., and Melton, D. (2011). Turning straw into gold: directing cell fate for regenerative medicine. Nature reviews Genetics 12, 243-252.

Cox, J., and Mann, M. (2008). MaxQuant enables high peptide identification rates, individualized p.p.b.-range mass accuracies and proteome-wide protein quantification. Nature biotechnology 26, 1367-1372.

Cox, J., Matic, I., Hilger, M., Nagaraj, N., Selbach, M., Olsen, J. V., and Mann, M. (2009). A practical guide to the MaxQuant computational platform for SILAC-based quantitative proteomics. Nature protocols 4, 698-705.

Cummings, D. E., Clement, K., Purnell, J. Q., Vaisse, C., Foster, K. E., Frayo, R. S., Schwartz, M. W., Basdevant, A., and Weigle, D. S. (2002). Elevated plasma ghrelin levels in Prader Willi syndrome. Nat Med 8, 643-644.

D'Aniello, C., Lonardo, E., Iaconis, S., Guardiola, O., Liguoro, A. M., Liguori, G. L., Autiero, M., Carmeliet, P., and Minchiotti, G. (2009). G protein-coupled receptor APJ and its ligand apelin act downstream of Cripto to specify embryonic stem cells toward the cardiac lineage through extracellular signal-regulated kinase/p70S6 kinase signaling pathway. Circulation research 105, 231-238.

Daheron, L., Opitz, S. L., Zaehres, H., Lensch, M. W., Andrews, P. W., Itskovitz-Eldor, J., and Daley, G. Q. (2004). LIF/STAT3 signaling fails to maintain self-renewal of human embryonic stem cells. Stem Cells 22, 770-778.

Dalton, S. (2013). Signaling networks in human pluripotent stem cells. Curr Opin Cell Biol 25, 241-246.

Day, A., Dong, J., Funari, V. A., Harry, B., Strom, S. P., Cohn, D. H., and Nelson, S. F. (2009). Disease gene characterization through large-scale co-expression analysis. PloS one 4, e8491.

Dreesen, O., and Brivanlou, A. H. (2007). Signaling pathways in cancer and embryonic stem cells. Stem cell reviews 3, 7-17.

Ficarro, S. B., Adelmant, G., Tomar, M. N., Zhang, Y., Cheng, V. J., and Marto, J. A. (2009). Magnetic bead processor for rapid evaluation and optimization of parameters for phosphopeptide enrichment. Analytical chemistry 81, 4566-4575.

Frith, M. C., Forrest, A. R., Nourbakhsh, E., Pang, K. C., Kai, C., Kawai, J., Carninci, P., Hayashizaki, Y., Bailey, T. L., and Grimmond, S. M. (2006). The abundance of short proteins in the mammalian proteome. PLoS Genet 2, e52.

Gaggioli, C., Hooper, S., Hidalgo-Carcedo, C., Grosse, R., Marshall, J. F., Harrington, K., and Sahai, E. (2007). Fibroblast-led collective invasion of carcinoma cells with differing roles for RhoGTPases in leading and following cells. Nature cell biology 9, 1392-1400.

Green, M., and Loewenstein, P. M. (1988). Autonomous functional domains of chemically synthesized human immunodeficiency virus tat trans-activator protein. Cell 55, 1179-1188.

Hanahan, D., and Coussens, L. M. (2012). Accessories to the crime: functions of cells recruited to the tumor microenvironment. Cancer cell 21, 309-322.

Hikasa, H., Shibata, M., Hiratani, I., and Taira, M. (2002). The Xenopus receptor tyrosine kinase Xror2 modulates morphogenetic movements of the axial mesoderm and neuroectoderm via Wnt signaling. Development 129, 5227-5239.

Hughes, C. S., Nuhn, A. A., Postovit, L. M., and Lajoie, G. A. (2011). Proteomics of human embryonic stem cells. Proteomics 11, 675-690.

Humphrey, R. K., Beattie, G. M., Lopez, A. D., Bucay, N., King, C. C., Firpo, M. T., Rose-John, S., and Hayek, A. (2004). Maintenance of pluripotency in human embryonic stem cells is STAT3 independent. Stem Cells 22, 522-530.

Inniss, K., and Moore, H. (2006). Mediation of apoptosis and proliferation of human embryonic stem cells by sphingosine-1-phosphate. Stem cells and development 15, 789-796.

Junttila, M. R., and de Sauvage, F. J. (2013). Influence of tumour micro-environment heterogeneity on therapeutic response. Nature 501, 346-354.

Kojima, M., Hosoda, H., Date, Y., Nakazato, M., Matsuo, H., and Kangawa, K. (1999). Ghrelin is a growth-hormone-releasing acylated peptide from stomach. Nature 402, 656-660.

Kuba, K., Zhang, L., Imai, Y., Arab, S., Chen, M., Maekawa, Y., Leschnik, M., Leibbrandt, A., Markovic, M., Schwaighofer, J., et al. (2007). Impaired heart contractility in Apelin gene-deficient mice associated with aging and pressure overload. Circulation research 101, e32-42.

Kurzawa, R., Glabowski, W., Baczkowski, T., and Brelik, P. (2002). Evaluation of mouse preimplantation embryos exposed to oxidative stress cultured with insulin-like growth factor I and II, epidermal growth factor, insulin, transferrin and selenium. Reproductive biology 2, 143-162.

Lian, X., Zhang, J., Azarin, S. M., Zhu, K., Hazeltine, L. B., Bao, X., Hsiao, C., Kamp, T. J., and Palecek, S. P. (2013). Directed cardiomyocyte differentiation from human pluripotent stem cells by modulating Wnt/beta-catenin signaling under fully defined conditions. Nature protocols 8, 162-175.

Lighten, A. D., Hardy, K., Winston, R. M., and Moore, G. E. (1997). Expression of mRNA for the insulin-like growth factors and their receptors in human preimplantation embryos. Molecular reproduction and development 47, 134-139.

Link, V., Shevchenko, A., and Heisenberg, C. P. (2006). Proteomics of early zebrafish embryos. BMC Dev Biol 6, 1.

Louvi, A., Accili, D., and Efstratiadis, A. (1997). Growth-promoting interaction of IGF-II with the insulin receptor during mouse embryonic development. Developmental biology 189, 33-48.

Maguire, J. J., Kleinz, M. J., Pitkin, S. L., and Davenport, A. P. (2009). [Pyr1]apelin-13 identified as the predominant apelin isoform in the human heart: vasoactive mechanisms and inotropic action in disease. Hypertension 54, 598-604.

Marechal, V., Clavel, F., Heard, J. M., and Schwartz, O. (1998). Cytosolic Gag p24 as an index of productive entry of human immunodeficiency virus type 1. Journal of virology 72, 2208-2212.

Markham, K. E., and Kaye, P. L. (2003). Growth hormone, insulin-like growth factor I and cell proliferation in the mouse blastocyst. Reproduction 125, 327-336.

Matys, V., Kel-Margoulis, O. V., Fricke, E., Liebich, I., Land, S., Barre-Dirrie, A., Reuter, I., Chekmenev, D., Krull, M., Hornischer, K., et al. (2006). TRANSFAC and its module TRANSCompel: transcriptional gene regulation in eukaryotes. Nucleic acids research 34, D108-110.

McLatchie, L. M., Fraser, N. J., Main, M. J., Wise, A., Brown, J., Thompson, N., Solari, R., Lee, M. G., and Foord, S. M. (1998). RAMPs regulate the transport and ligand specificity of the calcitonin-receptor-like receptor. Nature 393, 333-339.

Miura, T., Luo, Y., Khrebtukova, I., Brandenberger, R., Zhou, D., Thies, R. S., Vasicek, T., Young, H., Lebkowski, J., Carpenter, M. K., et al. (2004). Monitoring early differentiation events in human embryonic stem cells by massively parallel signature sequencing and expressed sequence tag scan. Stem Cells Dev 13, 694-715.

Miura, T., Luo, Y., Khrebtukova, I., Brandenberger, R., Zhou, D., Thies, R. S., Vasicek, T., Young, H., Lebkowski, J., Carpenter, M. K., et al. (2004). Monitoring early differentiation events in human embryonic stem cells by massively parallel signature sequencing and expressed sequence tag scan. *Stem Cells Dev* 13, 694-715.

Montague, C. T., Farooqi, I. S., Whitehead, J. P., Soos, M. A., Rau, H., Wareham, N. J., Sewter, C. P., Digby, J. E., Mohammed, S. N., Hurst, J. A., et al. (1997). Congenital leptin deficiency is associated with severe early-onset obesity in humans. Nature 387, 903-908.

Moral, M., and Paramio, J. M. (2008). Akt pathway as a target for therapeutic intervention in HNSCC. Histology and histopathology 23, 1269-1278.

Nichols, J., and Smith, A. (2012). Pluripotency in the embryo and in culture. Cold Spring Harbor perspectives in biology 4, a008128.

Niehrs, C. (2012). The complex world of WNT receptor signalling. Nature reviews Molecular cell biology 13, 767-779.

Niehrs, C., and Pollet, N. (1999). Synexpression groups in eukaryotes. Nature 402, 483-487.

Nishino, S., Ripley, B., Overeem, S., Lammers, G. J., and Mignot, E. (2000). Hypocretin (orexin) deficiency in human narcolepsy. Lancet 355, 39-40.

Niwa, H., Ogawa, K., Shimosato, D., and Adachi, K. (2009). A parallel circuit of LIF signalling pathways maintains pluripotency of mouse ES cells. Nature 460, 118-122.

Oberlin, E., Amara, A., Bachelerie, F., Bessia, C., Virelizier, J. L., Arenzana-Seisdedos, F., Schwartz, O., Heard, J. M., Clark-Lewis, I., Legler, D. F., et al. (1996). The CXC chemokine SDF-1 is the ligand for LESTR/fusin and prevents infection by T-cell-line-adapted HIV-1. Nature 382, 833-835.

Paling, N. R., Wheadon, H., Bone, H. K., and Welham, M. J. (2004). Regulation of embryonic stem cell self-renewal by phosphoinositide 3-kinase-dependent signaling. The Journal of biological chemistry 279, 48063-48070.

Pauli, A., Norris, M. L., Valen, E., Chew, G. L., Gagnon, J. A., Zimmerman, S., Mitchell, A., Ma, J., Dubrulle, J., Reyon, D., et al. (2014). Toddler: an embryonic signal that promotes cell movement via Apelin receptors. Science 343, 1248636.

Peterson, R. T., Desai, B. N., Hardwick, J. S., and Schreiber, S. L. (1999). Protein phosphatase 2A interacts with the 70-kDa S6 kinase and is activated by inhibition of FKBP12-rapamycinassociated protein. Proceedings of the National Academy of Sciences of the United States of America 96, 4438-4442.

Peyron, C., Faraco, J., Rogers, W., Ripley, B., Overeem, S., Charnay, Y., Nevsimalova, S., Aldrich, M., Reynolds, D., Albin, R., et al. (2000). A mutation in a case of early onset narcolepsy and a generalized absence of hypocretin peptides in human narcoleptic brains. Nat Med 6, 991-997.

Pickering, C. R., Zhou, J. H., Lee, J. J., Drummond, J. A., Peng, S. A., Saade, R. E., Tsai, K. Y., Curry, J., Tetzlaff, M. T., Lai, S. Y., et al. (2014). Mutational landscape of aggressive cutaneous squamous cell carcinoma. Clinical cancer research: an official journal of the American Association for Cancer Research.

Rappolee, D. A., Sturm, K. S., Behrendtsen, O., Schultz, G. A., Pedersen, R. A., and Werb, Z. (1992). Insulin-like growth factor II acts through an endogenous growth pathway regulated by imprinting in early mouse embryos. Genes & development 6, 939-952.

Rappsilber, J., Mann, M., and Ishihama, Y. (2007). Protocol for micro-purification, enrichment, pre-fractionation and storage of peptides for proteomics using StageTips. Nature protocols 2, 1896-1906.

Rasmussen, S. G., Choi, H. J., Rosenbaum, D. M., Kobilka, T. S., Thian, F. S., Edwards, P. C., Burghammer, M., Ratnala, V. R., Sanishvili, R., Fischetti, R. F., et al. (2007). Crystal structure of the human beta2 adrenergic G-protein-coupled receptor. Nature 450, 383-387.

Reiter, J. F., Alexander, J., Rodaway, A., Yelon, D., Patient, R., Holder, N., and Stainier, D. Y. (1999). Gata5 is required for the development of the heart and endoderm in zebrafish. Genes Dev 13, 2983-2995.

Reversade, B., and De Robertis, E. M. (2005). Regulation of ADMP and BMP2/4/7 at opposite embryonic poles generates a self-regulating morphogenetic field. Cell 123, 1147-1160.

Rubin, R., Arzumanyan, A., Soliera, A. R., Ross, B., Peruzzi, F., and Prisco, M. (2007). Insulin receptor substrate (IRS)-1 regulates murine embryonic stem (mES) cells self-renewal. Journal of cellular physiology 213, 445-453.

Sancak, Y., Thoreen, C. C., Peterson, T. R., Lindquist, R. A., Kang, S. A., Spooner, E., Carr, S. A., and Sabatini, D. M. (2007). PRAS40 is an insulin-regulated inhibitor of the mTORC1 protein kinase. Molecular cell 25, 903-915.

Schier, A. F. (2003). Nodal signaling in vertebrate development. Annu Rev Cell Dev Biol 19, 589-621.

Schoenebeck, J. J., and Yelon, D. (2007). Illuminating cardiac development: Advances in imaging add new dimensions to the utility of zebrafish genetics. Semin Cell Dev Biol 18, 27-35.

Schulte-Merker, S., van Eeden, F. J., Halpern, M. E., Kimmel, C. B., and Nusslein-Volhard, C. (1994). no tail (ntl) is the zebrafish homologue of the mouse T (Brachyury) gene. Development 120, 1009-1015.

Schultz, G. A., Hahnel, A., Arcellana-Panlilio, M., Wang, L., Goubau, S., Watson, A., and Harvey, M. (1993). Expression of IGF ligand and receptor genes during preimplantation mammalian development. Molecular reproduction and development 35, 414-420.

Schwartz, O., Marechal, V., Friguet, B., Arenzana-Seisdedos, F., and Heard, J. M. (1998). Antiviral activity of the proteasome on incoming human immunodeficiency virus type 1. Journal of virology 72, 3845-3850.

Scimia, M. C., Hurtado, C., Ray, S., Metzler, S., Wei, K., Wang, J., Woods, C. E., Purcell, N. H., Catalucci, D., Akasaka, T., et al. (2012). APJ acts as a dual receptor in cardiac hypertrophy. Nature 488, 394-398.

Scott, I. C., Masri, B., D'Amico, L. A., Jin, S. W., Jungblut, B., Wehman, A. M., Baier, H., Audigier, Y., and Stainier, D. Y. (2007). The g protein-coupled receptor agtrllb regulates early development of myocardial progenitors. Developmental cell 12, 403-413.

Sorrells, S., Toruno, C., Stewart, R. A., and Jette, C. (2013). Analysis of apoptosis in zebrafish embryos by whole-mount immunofluorescence to detect activated Caspase 3. Journal of visualized experiments: JoVE, e51060.

Steendijk P, Baan J, Jr., Van der Velde E T, Baan J. Effects of critical coronary stenosis on global systolic left ventricular function quantified by pressure-volume relations during dobutamine stress in the canine heart. J Am Coll Cardiol. 1998; 32(3):816-826.

Swoger, J., Pampaloni, F., and Stelzer, E. H. (2014). Light-sheet-based fluorescence microscopy for three-dimensional imaging of biological samples. Cold Spring Harbor protocols 2014, 1-8.

Takahashi, K., and Yamanaka, S. (2006). Induction of pluripotent stem cells from mouse embryonic and adult fibroblast cultures by defined factors. Cell 126, 663-676.

Tang, S. Y., Xie, H., Yuan, L. Q., Luo, X. H., Huang, J., Cui, R. R., Zhou, H. D., Wu, X. P., and Liao, E. Y. (2007). Apelin stimulates proliferation and suppresses apoptosis of mouse osteoblastic cell line MC3T3-E1 via JNK and PI3-K/Akt signaling pathways. Peptides 28, 708-718.

Tesar, P. J., Chenoweth, J. G., Brook, F. A., Davies, T. J., Evans, E. P., Mack, D. L., Gardner, R. L., and McKay, R. D. (2007). New cell lines from mouse epiblast share defining features with human embryonic stem cells. Nature 448, 196-199.

Timmers L, Sluijter J P, Verlaan C W, Steendijk P, Cramer M J, Emons M, Strijder C, Grundeman P F, Sze S K, Hua L, Piek J J, Borst C, Pasterkamp G, de Kleijn D P. Cyclooxygenase-2 inhibition increases mortality, enhances left ventricular remodeling, and impairs systolic function after myocardial infarction in the pig. Circulation. 2007; 115(3):326-332.

Tiscornia, G., Singer, O., and Verma, I. M. (2006a). Design and cloning of lentiviral vectors expressing small interfering RNAs. Nature protocols 1, 234-240.

Tiscornia, G., Singer, O., and Verma, I. M. (2006b). Production and purification of lentiviral vectors. Nature protocols 1, 241-245.

Vallier, L., Alexander, M., and Pedersen, R. A. (2005). Activin/Nodal and FGF pathways cooperate to maintain pluripotency of human embryonic stem cells. Journal of cell science 118, 4495-4509.

van den Pol, A. N. (2012). Neuropeptide transmission in brain circuits. Neuron 76, 98-115.

Vander Haar, E., Lee, S. I., Bandhakavi, S., Griffin, T. J., and Kim, D. H. (2007). Insulin signalling to mTOR mediated by the Akt/PKB substrate PRAS40. Nature cell biology 9, 316-323.

Vassilatis, D. K., Hohmann, J. G., Zeng, H., Li, F., Ranchalis, J. E., Mortrud, M. T., Brown, A., Rodriguez, S. S., Weller, J. R., Wright, A. C., et al. (2003). The G protein-coupled receptor repertoires of human and mouse. Proc Natl Acad Sci USA 100, 4903-4908.

Vodyanik, M. A., Yu, J., Zhang, X., Tian, S., Stewart, R., Thomson, J. A., and Slukvin, II (2010). A mesoderm-derived precursor for mesenchymal stem and endothelial cells. Cell Stem Cell 7, 718-729.

Voskas, D., Ling, L. S., and Woodgett, J. R. (2014). Signals controlling undifferentiated states in embryonic stem and cancer cells: role of the phosphatidylinositol 3' kinase pathway. Journal of cellular physiology 229, 1312-1322.

Wang, H., Zhang, Q., Wen, Q., Zheng, Y., Lazarovici, P., Jiang, H., Lin, J., and Zheng, W. (2012). Proline-rich Akt substrate of 40 kDa (PRAS40): a novel downstream target of PI3k/Akt signaling pathway. Cellular signalling 24, 17-24.

Wang, L., Harris, T. E., Roth, R. A., and Lawrence, J. C., Jr. (2007a). PRAS40 regulates mTORC1 kinase activity by functioning as a direct inhibitor of substrate binding. The Journal of biological chemistry 282, 20036-20044.

Wang, L., Schulz, T. C., Sherrer, E. S., Dauphin, D. S., Shin, S., Nelson, A. M., Ware, C. B., Zhan, M., Song, C. Z., Chen, X., et al. (2007b). Self-renewal of human embryonic stem cells requires insulin-like growth factor-1 receptor and ERBB2 receptor signaling. Blood 110, 4111-4119.

Wang, X., Lin, G., Martins-Taylor, K., Zeng, H., and Xu, R. H. (2009). Inhibition of caspase-mediated anoikis is critical for basic fibroblast growth factor-sustained culture of human pluripotent stem cells. The Journal of biological chemistry 284, 34054-34064.

Warmflash, A., Arduini, B. L., and Brivanlou, A. H. (2012). The molecular circuitry underlying pluripotency in embryonic stem cells. Wiley interdisciplinary reviews Systems biology and medicine 4, 443-456.

Watanabe, K., Ueno, M., Kamiya, D., Nishiyama, A., Matsumura, M., Wataya, T., Takahashi, J. B., Nishikawa, S., Muguruma, K., and Sasai, Y. (2007). A ROCK inhibitor permits survival of dissociated human embryonic stem cells. Nature biotechnology 25, 681-686.

Watanabe, S., Umehara, H., Murayama, K., Okabe, M., Kimura, T., and Nakano, T. (2006). Activation of Akt signaling is sufficient to maintain pluripotency in mouse and primate embryonic stem cells. Oncogene 25, 2697-2707.

Xu, C., Rosler, E., Jiang, J., Lebkowski, J. S., Gold, J. D., O'Sullivan, C., Delavan-Boorsma, K., Mok, M., Bronstein, A., and Carpenter, M. K. (2005). Basic fibroblast growth factor supports undifferentiated human embryonic stem cell growth without conditioned medium. Stem Cells 23, 315-323.

Yu, Q. C., Hirst, C. E., Costa, M., Ng, E. S., Schiesser, J. V., Gertow, K., Stanley, E. G., and Elefanty, A. G. (2012). APELIN promotes hematopoiesis from human embryonic stem cells. Blood 119, 6243-6254.

Zafarana, G., Avery, S. R., Avery, K., Moore, H. D., and Andrews, P. W. (2009). Specific knockdown of OCT4 in human embryonic stem cells by inducible short hairpin RNA interference. Stem Cells 27, 776-782.

Zeng, X. X., Wilm, T. P., Sepich, D. S., and Solnica-Krezel, L. (2007). Apelin and its receptor control heart field formation during zebrafish gastrulation. Developmental cell 12, 391-402.

Zhou, J., Su, P., Wang, L., Chen, J., Zimmermann, M., Genbacev, O., Afonja, O., Horne, M. C., Tanaka, T., Duan, E., et al. (2009). mTOR supports long-term self-renewal and suppresses mesoderm and endoderm activities of human embryonic stem cells. Proceedings of the National Academy of Sciences of the United States of America 106, 7840-7845.

Zou, M. X., Liu, H. Y., Haraguchi, Y., Soda, Y., Tatemoto, K., and Hoshino, H. (2000). Apelin peptides block the entry of human immunodeficiency virus (HIV). FEBS letters 473, 15-18.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

---

INFORMAL SEQUENCE LISTING

SEQ ID NO: 1

ELABELA polypeptide signature sequence
CXXXRCXXXHSRVPFP

SEQ ID NO: 2

Homo ELABELA mature polypeptide
QRPVNLTMRRKLRKHNCLQRRCMPLHSRVPFP

SEQ ID NO: 3

Peromyscus ELABELA mature polypeptide
QRPVNFPKKRKVYRHNCFRRRCVPLHSRVPFP

SEQ ID NO: 4

Rattus ELABELA mature polypeptide
EKSVNFPRRRKLYRHNCFRRRCISLHSRVPFP

| INFORMAL SEQUENCE LISTING |
| --- |
| SEQ ID NO: 5 |
| Mus ELABELA mature polypeptide |
| QKPVNFPRRRKLYRHNCFRRRCIPLHSRVPFP |
| SEQ ID NO: 6 |
| Bos ELABELA mature polypeptide |
| QRQANLAMRRKLHRHNCLQRRCMPLHSRVPFP |
| SEQ ID NO: 7 |
| Sus ELABELA mature polypeptide |
| QRPANLAVRRKLHRHNCLQRRCMPLHSRVPFP |
| SEQ ID NO: 8 |
| Dasypus ELABELA mature polypeptide |
| QRPANLAMRRKLHRHNCFQRRCMPLHSRVPFP |
| SEQ ID NO: 9 |
| Trichosurus ELABELA mature polypeptide |
| QRPGNLALRRKPHRHICPQRRCMPLHSRVPFP |
| SEQ ID NO: 10 |
| Gallus ELABELA mature polypeptide |
| QRPANLALRRKLHRHNCSHRRCMPLHSRVPFP |
| SEQ ID NO: 11 |
| Gekko ELABELA mature polypeptide |
| QRPANLSLRRKLHRQHCSHRRCMPLHSRVPFP |
| SEQ ID NO: 12 |
| Anolis ELABELA mature polypeptide |
| QRPANLASRRKLHRHHCSHRRCMPLHSRVPFP |
| SEQ ID NO: 13 |
| Xenopus ELABELA mature polypeptide |
| QKPANLAQRRIHRHNCFLKRCIPLHSRVPFP |
| SEQ ID NO: 14 |
| Ambystoma ELABELA mature polypeptide |
| QRPVNAAHRRRLHRHNCSLRRCMPLHSRVPFP |
| SEQ ID NO: 15 |
| Oryzias ELABELA mature polypeptide |
| ARPDFLNLRRKYHRHHCLHRRCMPLHSRVPFP |
| SEQ ID NO: 16 |
| Callorhinchus ELABELA mature polypeptide |
| QKSGNSWRRKKMQRRNCWHRRCLPFHSRVPFP |
| SEQ ID NO: 17 |
| Oncorhynchus ELABELA mature polypeptide |
| VRPDILNIRRRYHRHHCPHRRCMPLHSRVPFP |
| SEQ ID NO: 18 |
| Danio ELABELA mature polypeptide |
| DKHGTKHDFLNLRRKYRRHNCPKKRCLPLHSRVPFP |
| SEQ ID NO: 19 |
| Human ELABELA signal sequence |
| MRFQQFLFAFFIFIMSLLLISG |
| SEQ ID NO: 20 |
| Homo ELABELA polypeptide with signal sequence (bold) |
| MRFQQFLFAFFIFIMSLLLISGQRPVNLTMRRKLRKHNCLQRRCMPLHSRVPFP |
| SEQ ID NO: 21 |
| Peromyscus ELABELA polypeptide with signal sequence (bold) |
| MRFQHYFLVFFIFAMSLLFITEQRPVNFPKKRKVYRHNCFRRRCVPLHSRVPFP |
| SEQ ID NO: 22 |
| Rattus ELABELA polypeptide with signal sequence (bold) |
| MRFQPLFWVFFIFAMSLLFITEEKSVNFPRRRKLYRHNCFRRRCISLHSRVPFP |
| SEQ ID NO: 23 |
| Mus ELABELA polypeptide with signal sequence (bold) |
| MRFQPLFWVFFIFAMSLLFISEQKPVNFPRRRKLYRHNCFRRRCIPLHSRVPFP |
| SEQ ID NO: 24 |
| Bos ELABELA polypeptide with signal sequence (bold) |
| MRFHQFFLLFVIFMLSLLLIHGQRQANLAMRRKLHRHNCLQRRCMPLHSRVPFP |
| SEQ ID NO: 25 |
| Sus ELABELA polypeptide with signal sequence (bold) |
| MRFRQFFLVFFIFMMNLLLICGQRPANLAVRRKLHRHNCLQRRCMPLHSRVPFP |
| SEQ ID NO: 26 |
| Dasypus ELABELA polypeptide with signal sequence (bold) |
| MKFQQFFYVFFVFIMSLLLINGQRPANLAMRRKLHRHNCFQRRCMPLHSRVPFP |
| SEQ ID NO: 27 |
| Trichosurus ELABELA polypeptide with signal sequence (bold) |
| MRFQLLFFLFLFFTMGILLIDGQRPGNLALRRKPHRHICPQRRCMPLHSRVPFP |
| SEQ ID NO: 28 |
| Gallus ELABELA polypeptide with signal sequence (bold) |
| MRLRRLLCVVFLLLVSLLPAAAQRPANLALRRKLHRHNCSHRRCMPLHSRVPFP |
| SEQ ID NO: 29 |
| Gekko ELABELA polypeptide with signal sequence (bold) |
| MRLQLLLLTCFLILTGVLLGNGQRPANLSLRRKLHRQHCSHRRCMPLHSRVPFP |

| INFORMAL SEQUENCE LISTING | |
|---|---|
| *Anolis* ELABELA polypeptide with signal sequence (bold)<br>MRLQQLLLTWFLLLAGALLINGQRPANLASRRKLHRHHCSHRRCMPLHSRVPFP | SEQ ID NO: 30 |
| *Xenopus* ELABELA polypeptide with signal sequence (bold)<br>MDFQKLLYALFFILMSLLLINGQKPANLAQRRRIHRHNCFLKRCIPLHSRVPFP | SEQ ID NO: 31 |
| *Ambystoma* ELABELA polypeptide with signal sequence (bold)<br>MKWQKLLAILFWILMGALLVNGQRPVNAAHRRRLHRHNCSLRRCMPLHSRVPFP | SEQ ID NO: 32 |
| *Oryzias* ELABELA polypeptide with signal sequence (bold)<br>MRVTANLLYLLLLLAAALAPVFSARPDFLNLRRKYHRHHCLHRRCMPLHSRVPFP | SEQ ID NO: 33 |
| *Callorhinchus* ELABELA polypeptide with signal sequence (bold)<br>MRFQHLLHIILLLCTSLLLISGQKSGNSWRRKKMQRRNCWHRRCLPFHSRVPFP | SEQ ID NO: 34 |
| *Oncorhynchus* ELABELA polypeptide with signal sequence (bold)<br>MRIISLLYLLLLVTVLGSVSSVRPDILNIRRRYHRHHCPHRRCMPLHSRVPFP | SEQ ID NO: 35 |
| *Danio* ELABELA polypeptide with signal sequence (bold)<br>MRFFHPLYLLLLLLTVLVLISADKHGTKHDFLNLRRKYRRHNCPKKRCLPHSRVPFP | SEQ ID NO: 36 |
| Human (*Homo sapiens*) ELABELA cDNA sequence<br>ATGAGATTTCAGCAATTCCTTTTTGCATTTTTTATTTTTATTATGAGTCTTCTCC<br>TTATCAGCGGACAGAGACCAGTTAATTTGACCATGAGAAGAAAACTGCGCAAACA<br>CAATTGCCTTCAGAGGAGATGTATGCCTCTCCATTCACGAGTACCCTTCCCCTGA | SEQ ID NO: 37 |
| Mouse (*Mus musculus*) ELABELA cDNA sequence<br>ATGCGATTCCAGCCCCTTTTTGGGTATTTTTATTTTTGCCATGAGTCTCCTTTTT<br>ATCAGTGAACAGAAACCAGTTAACTTTCCCAGGAGAAGAAAACTATACAGACACAAC<br>TGCTTTCGCAGGAGATGCATTCCACTTCATTCTCGAGTGCCCTTCCCATGA | SEQ ID NO: 38 |
| Chicken (*Gallus gallus*) ELABELA cDNA sequence<br>ATGAGGCTCCGGCGGCTGCTGTGCGTCGTGTTCCTGCTCCTGGTCAGCCTGCTACCT<br>GCCGCCGCGCAGAGACCGGCCAACCTGGCCCTGCGCAGGAAGCTGCACCGACACAAC<br>TGCTCGCACCGGCGGTGCATGCCGCTCCACTCCCGCGTGCCCTTTCCCTGA | SEQ ID NO: 39 |
| *Xenopus* (*Xenopus laevis*) ELABELA cDNA sequence<br>ATGGATTTTCAGAAATTATTGTATGCCTTATTTTTCATTCTGATGAGTCTACTGCTG<br>ATTAATGGCCAGAAACCAGCCAACCTCGCACAGCGCCGGAGGATACACAGACACAAC<br>TGCTTCCTCAAGAGGTGCATACCACTACATTCAAGAGTTCCATTTCCATGA | SEQ ID NO: 40 |
| Zebrafish (*Danio rerio*) ELABELA cDNA sequence<br>ATGAGATTCTTCCACCCGCTGTATCTGCTGCTGCTGCTGCTGACAGTGCTGGTCCTC<br>ATCAGCGCAGATAAACATGGTACAAAACACGATTTTCTCAACTTGAGGCGGAAATAT<br>CGCAGACACAACTGCCCGAAGAAACGCTGTCTACCTCTTCACTCCAGAGTACCTTTC<br>CCTTGA | SEQ ID NO: 41 |
| Human (*Homo sapiens*) ELABELA genomic sequence<br>AK092578; LOC100506013; cDNA FLJ35259 fis; clone PROST2004251; Hs.<br>105196<br>>gi\|21751202\|dbj\|AK092578.1\| *Homo sapiens* cDNA FLJ35259 fis, clone<br>PROST2004251<br>ATCATTAACCTTCCTGCAAAACACAGCTGGCAGTTCTCTGAGGCTTGTCACTAGAATGTGAAGACAGCCA<br>CACAGATATTGCACAGACTATTTACAGATCGTTTGGCTTACATTGAGAGTCATTGCTCTACTTTTGTGCG<br>GTAGGAAA*ATGAGATTTCAGCAATTCCTTTTTGCATTTTTTATTTTTATTATGAGTCTTCTCCTTATCAG*<br>*CGGACAGAGACCAGTTAATTTGACCATGAGAAGAAAACTGCGCAAACACAATTGCCTTCAGAGGAGATGT*<br>*ATGCCTCTCCATTCACGAGTACCCTTCCCCTGAGATCTCTCTAGCTAACTTTACTGGATCTATCAGAAGA<br>AGAAGAGGAGTGAAGGAAAGACACCCAGCCACACAAAAGAACTTCATGATGCCAACAGCGTGATTGCTTA | SEQ ID NO: 42 |

| INFORMAL SEQUENCE LISTING |
|---|
| GAAGTTCCTACACAAAAAAAGGATCATTTGAAAGCACCTGGAATGGTTTATTAGCTTCACAGGATTTTAT |
| TCTTCTTGGCTTCTATTTGGAGGGAAAATAACATAAATTCAAAAGGATTCCAATCTGAAGCCCAAATTGT |
| TTGCCTACATAACAAAAATATCTCATCTTTTCCTGCACATTATTATTCTTTTATGGGTTAAAAAGAAAAA |
| TACCTTTTAGTGTTTTAGAACTCTCTCATGGTAAAAAGTGCAAGAATTTAAAATGTTGCTTTCATATTCC |
| TATAATTCTCCAAAAGTATTAAATTCGTATATGTTTGAGTGATTTTCTAAAAACTGCTCAACCTGGAATC |
| AATTGCATTGACCATTTGGCTTCGCACAATAGGGAGAAATAATTGGTTCATTGATTATATAGAGAGAAA |
| GACTAAGAAAAGCTATTAATTGCTACCAATTTTATGATAAGCTTTAAGGTTTATGAAAGTATGTTTTTTT |
| ATTTAATGAGTAATGTCCATTTGAAGTTGAAAGAAAACATGAAATCCTAATTGTAGTTCATTTTATGTTC |
| AAATGAAACCATTGTTTTTGTTTTTGTTTTGAAACAGAGTCTCACTCTGTTGCCCAAGGTGGAGAGAAGT |
| GGCACGCTTTTGTCTCACTGCAACCTCCACCTCCCGAGTTCAAGTGATTCTCGTGCCTCAACCTCCCAAT |
| TATAGGCTGGGATTACAGGTGTGCACCACTACACCCAGCTAATTCTTGTATTTTTTGTAGAGATGAGGTT |
| TTACCCTGTTGCCCAGGCTGGTCTTGAACTCAGGCTGGAACCATTCATTTTTTAACCTTTCTCATCATGT |
| AATTATAGGAACCCAACGTTTGATTTCCTTTGAAGTTTTGTTATGTCCTTTATTATTTTGTATGGATAAT |
| TTCTTTAAAAGTCTTACTTAAAGTCGACATCTAAAATACAGTTATGCCAATGAAGTCCCACTCAGGGTGA |
| TATCTGTATCTAAAAGATGAGTGCTCATCATCCTATTAGGCTTTGTCTTGGTGGTGTTCATCCTGAGATG |
| CTGAGACATGGAAATAAAAAATCAGAAGGAATTTAGGGATATGATTACTCAAAAAGAAACTATCCTGTC |
| TAAATTTGAATTGTGTTGATAACTAGGTGTTCCCCAGATGCTAAGATGTTCTTAATTTGTATTTATTGAA |
| GGATTGTTAGCTTAGTGCCACAAAATTTTTCTTACTTTATGTTAATTCCAGATAAGAAATTTACAAGTTT |
| ATATCTTTTTTTTCTTTTTTTTAAGATGAGATCTGGCTCTATCACCCAGGCTAAAGTGCAGTGGCATGA |
| TCTAGGCTAACTCCCTGGCTCAAGCGATCCTTCCACCTCAGCCTCCCAAGTACCTGGGACTACAGGCACT |
| CACGGCCACACCTGACTAATTTTGTATTTTTTGTAGAGATGGAGTATCGCCATGTTGCCCAGGTTGGT |
| CTCAAACTCAGGCTGGTGAGCTCAAGTGATCCGCCTCCTTGGCCTCCCAAAATACTGGGATTACAGGCAT |
| GTGCCACCATGCTGGGCCACAAGTTCATATCTGGAGTAGAAGTTTTACTTTGTAAATATTATAAAGTAGA |
| AGAAACCATAAACCATTTTGCTAAAATGAAAGGTTGGGGTTAATATAAATGTAATTTTAAATAGAAAATC |
| TGACAACACTGTCGAGTTTGTCTTCCTGTCAAAGCTTATTAAAAGTGTCTTTGCGGATGAATGGTACTTT |
| CCACAAGTGCATTTGAGTAGAAGCATAACCTATTCTCAGTTATATTTATGTTTAAAACATGTACTGGTTT |
| GTATATTTTGTACTGAAAAGAAAACACTTTATAGTCAAGATACATCTCATTCAATACAAGTCTAAACTC |
| TTTCAAATACAAATTCGCATATTCACAGAAAAAGTTACAAATCAGTTTTACTATTGTAAAGTAATGAAAT |
| GGTTATACATTTCTTAATTGTTCAATAAAACACTCAATGATT |

SEQ ID NO: 43
Mouse (*Mus musculus*) ELABELA genomic sequence
Mouse Gene AK014119; XM_003084771.1; Mm.58847
>gi|74182885|dbj|AK014119.1| *Mus musculus* 13 days embryo head cDNA, RIKEN
full-length enriched library, clone:3110033I20 product:hypothetical
protein, full insert sequence

| |
|---|
| CGGACTCTCCTTGGAGCTTTGCAGAGACTTCCCGCTTAAGTTACTGCGTGCCTGAATGGAAAAGGCAGCT |
| GGCAGCCCTCTGAGTTCTGGCCATAGGATGTGGGGTGAGCCGGACAGATACTGCGATTTACAGACGATTT |
| CTCTACTTGAAGAGCTATTGTTCACTTGCGTGTAAGAAAAAGAAAAACAAAAGGAAAGAAAAAGAAGAA |
| <u>AAGAAAAAGAGAAAGAAAAGAAAAG</u>ATGCGATTCCAGCCCCTTTTTGGGTATTTTTATTTTTGCCAT |
| GAGTCTCCTTTTTATCAGTGAACAGAAACCAG<u>TTAACTTTCCCAGGAGAAGAAAACTATACAGACACAAC</u> |
| <u>TGCTTTCGCAGGAGATGCATTCCACTTCATTCTCGAGTGCCCTTCCC</u>ATGAGGAAACCTCTAATTTCCT |
| TGGCTCTACCAGAAGAAGGGTGAAAGCAAAGATACCCAATCACCGGAAAAACAACCTCAGGATGGCAACA |

```
GGATGGCAGCTCAGGAGTTACTACGCAACAGAGGCTGTTTCAGAGTACCGTGGATGGCTTTTCAGACTGCTCT

TCCTGGATTCTCTTTGACAAGAAAATGATAGAAAGGGAAAACAGACGAGGTTAAAGCACATGCGTTTGTC

TGAATAACAATCTCTCCTGCTGTTCTGCACGTTCTTTGCGTATAATGTATGAATTACACATAGTGGTGGG

TTTCACAAAGGCATTTACATACCAGTACATCACGTCCTATGGCCGTCTTTCCACACATGTGCATCATATA

CACCGATTCTTTACAGGCATGCATGCCATATACACTGACTACATTTGCACACACATACCTTCCCCTTTCT

CTCCCCTCACCCTCCTGCAGGTCTCTTTTATTCACCTGGGCAGTTTTGTTTCTATTTTAATGGTTTGTAC

ACATGAATGATTTTATTGCACATTATTATTCTTACATGGATTAAAAGAAAACTACTTTAAT
                                                                SEQ ID NO: 44
```

Chicken (*Gallus gallus*) ELABELA genomic sequence
Gga.39575; gene in ensembl: ENSGALT00000038777; *Gallus gallus* hypothetical
protein LOC770154 (LOC770154), mRNA
LOCUS XM_001233479 482 bp mRNA linear VRT 16-NOV-
2006
DEFINITION PREDICTED: *Gallus gallus* hypothetical protein LOC770154
(LOC770154), mRNA.
ACCESSION XM_001233479
VERSION XM_001233479.1 GI:118089826/
ORIGIN

```
        1 ggcgagtgcc acggacgctt ctgtacacac gcggaccgca ggg atg aggc tccggcggct
       61 gctgtgcgtc gtgttcctgc tcctggtcag cctgctacct gccgccgcgc agagaccggc
      121 caacctggcc ctgcgcagga agctgcaccg acacaactgc tcgcaccggc ggtgcatgcc
      181 gctccactcc cgcgtgccct ttccc tgag c gcccggccca gctcggcaag caatttcgta
      241 acgggctttt cagtgtctta aaggaggaag ctgcaacaac tgcactgata gagaagctca
      301 ttctaagtac tgcttaccaa cagttgacct ggtggagcca cagcaatcct gttttgaggg
      361 agtccatctg aaatgaacac tttcagtggt cctgtgtatc acattctgca tgacctggaa
      421 caaaggccca tgactcatat cctagaagca gggggaaggg agaaacgggg aaggtgattg
      481 gg
                                                                SEQ ID NO: 45
```

*Xenopus* (*Xenopus laevis*) ELABELA genomic sequence
Xl.40684; UGID: 1257954; UniGene Xl.40684
dbEST Id: 30218202
EST name: AGENCOURT_54833116
GenBank Acc: DR729415
GenBank gi: 70903527
CLONE INFO
Clone Id: IMAGE: 7975974(5')
Plate:LLAM17099 Row: n Column: 04
DNA type: cDNA
PRIMERS
PolyA Tail: Unknown
SEQUENCE
GTTTCGGTCCGGATTCCCGGGATCCAGACCTGATCTAATAGTTGCCTATCTCTGAAGAGC

AATATGGATTTTCAGAAATTATTGTATGCCTTATTTTTCATTCTGATGAGTCTACTGCTG

ATTAATGCCAGAAACCAGCCAACCTCGCACAGCGCCGAGGATACACAGACACAACTGC

TTCCTCAAGAGGTGCATACCACTACATTCAAGAGTTCCATTTCCATGAGACCACTGAGGA

ATCTCATCATGATGTAACATAGGATCTGACTCAAATCTACAGAAATAATATTTATTTTGA

ACAGTGTTTAAGTTGTTCTTTGACTTATAAGTGGATGTTTCTTAAATGAGCTGCCCACAA

GAATGGGCACAGACAAGCTCCAACCCATGTAACTGGCTGTGAAACTGGCACAGGAGCTGC

CGAAAGCAATGTCCCTCCATGAAACTGATCCAGGAGACATCTACAGCAACCTTTGTTCCA

CCAAAACAGACAAGAGAGCAGATTCTCCATCACATTCCAAGGAAGTGAATGTTCAAAGGC

TTGCATTTATTATCAAACTGAAATGAAGCATATCATAATAAGGCTCAATGTCCTGTACCT

CAAAAGATTTAAAATATGGGGATAAAATGAAGAAAAACAGAAGATGGTTTTTGGACAATC

TGGTCATATTTTTAAATATTGCCCCGTGTGCAAAAAAGA
                                                                SEQ ID NO: 46

Zebrafish (*Danio rerio*) ELABELA genomic sequence
Dr.81857; UGID:2443131; UniGene Dr.81857; GenBank: AW777215.1; NCBI
Reference Sequence: XP_001335186.1; gi|125803442|ref|XP_001335186.1|
        1 CATCAGGTCATCTGTCTATCTATCCATCCCTCAGAGGACAGAGAGAGAAGAGAGAGTGAA

| INFORMAL SEQUENCE LISTING |
|---|
| 61 TATCGCCATCTCAAACTTTGAAAAAGTTGGAGAGACCGAGAGCTGGCTAGAACTGCGCGT |
| 121 CTTCTATATAACTCAACTTATACGAGATCTGAGAACACTTGCTGAGAGCGACAGACACAT |
| 181 AAGAGGATTTCTACAGTCCGTTACCTGCACATCCGACAGAATTTATCGTCTGAGGAACCG |
| 241 CGGACATCCTGTGAGGAGAGTCGAGTCTGCGCCGCGGACCAAACCACCCTGAGCATCACC |
| 301 ATGAGATTCTTCCACCCGCTGTATCTGCTGCTGCTGCTGACAGTGCTGGTCCTCATC |
| 361 AGCGCAGATAAACATGGTACAAAACACGATTTTCTCAACTTGAGGCGGAAATATCGCAGA |
| 421 CACAACTGCCCGAAGAAACGCTGTCTACCTCTTCACTCCAGAGTACCTTTCCCTTGAGGT |
| 481 TTTATGATGCTCCGGGCAAGCATTAAGAAAAACCAAAGACCAGCCTTGGATTGGAAATGA |
| 541 GAAAAGATTTATGTCAGATGTGCCGAGGACTGTTTTATTCGCACATGTATTGTAATCAAA |
| 601 GCCATGTTTGTCACTTCTGTAGCAGAAGTGTTTTTGTTTTGTTTTGTTTTTTAAATGAA |
| 661 TGTAAGTGAATGAGCCATGGAGATCCTACTGCTGCCAAACATGCTGCAAACTCATCACTC |
| 721 AATCAGGTTGAGTTGGAGCAGAATCATTGTAAATAGTGAGGACTGAATGAAATGTGTTTA |
| 781 TATGTAAGTTATGCACTTCAAATGTTTTATTATTATCTTGATTTATTAAAAGTGTATTGT |
| 841 CTTTTCAGA                                                                                                    SEQ ID NO: 47 |
| Anti-ELABELA shRNA sequence A |
| GACACCCAGCCACACAAAA                                                                                SEQ ID NO: 48 |
| Anti-ELABELA shRNA sequence B |
| CCCAGCCACACAAAGAAC                                                                                   SEQ ID NO: 49 |
| Anti-ELABELA shRNA sequence C |
| GTGATTCTCGTGCCTCAAC                                                                                    SEQ ID NO: 50 |
| Anti-ELABELA shRNA sequence D |
| CTCACGGCCACACCTGACT                                                                                   SEQ ID NO: 51 |
| Anti-ELABELA shRNA sequence E |
| TTGCCTTCAGAGGAGATGT |

I claim:

1. A method for the treatment of an ELABELA associated condition, the method comprising administering a therapeutically effective amount of an ELABELA polypeptide selected from the group consisting of polypeptides of SEQ ID NOs: 2 to 18 to a subject having an ELABELA associated condition, wherein the ELABELA associated condition is selected from the group consisting of: hypertension-associated cardiac hypertrophy, pressure-overload heart failure, and pulmonary arterial hypertension, thereby treating the ELABELA associated condition in the subject.

* * * * *

SEQUENCE LISTING

<160> NUMBER OF SEQ ID NOS: 197

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      ELABELA polypeptide signature sequence
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (7)..(9)
<223> OTHER INFORMATION: Any amino acid

<400> SEQUENCE: 1

Cys Xaa Xaa Xaa Arg Cys Xaa Xaa Xaa His Ser Arg Val Pro Phe Pro
1               5                   10                  15

<210> SEQ ID NO 2
<211> LENGTH: 32
<212> TYPE: PRT
<213> ORGANISM: Homo sapiens

```
<400> SEQUENCE: 2

Gln Arg Pro Val Asn Leu Thr Met Arg Arg Lys Leu Arg Lys His Asn
1               5                   10                  15

Cys Leu Gln Arg Arg Cys Met Pro Leu His Ser Arg Val Pro Phe Pro
            20                  25                  30

<210> SEQ ID NO 3
<211> LENGTH: 32
<212> TYPE: PRT
<213> ORGANISM: Peromyscus sp.

<400> SEQUENCE: 3

Gln Arg Pro Val Asn Phe Pro Lys Lys Arg Lys Val Tyr Arg His Asn
1               5                   10                  15

Cys Phe Arg Arg Arg Cys Val Pro Leu His Ser Arg Val Pro Phe Pro
            20                  25                  30

<210> SEQ ID NO 4
<211> LENGTH: 32
<212> TYPE: PRT
<213> ORGANISM: Rattus sp.

<400> SEQUENCE: 4

Glu Lys Ser Val Asn Phe Pro Arg Arg Lys Leu Tyr Arg His Asn
1               5                   10                  15

Cys Phe Arg Arg Arg Cys Ile Ser Leu His Ser Arg Val Pro Phe Pro
            20                  25                  30

<210> SEQ ID NO 5
<211> LENGTH: 32
<212> TYPE: PRT
<213> ORGANISM: Mus musculus

<400> SEQUENCE: 5

Gln Lys Pro Val Asn Phe Pro Arg Arg Lys Leu Tyr Arg His Asn
1               5                   10                  15

Cys Phe Arg Arg Arg Cys Ile Pro Leu His Ser Arg Val Pro Phe Pro
            20                  25                  30

<210> SEQ ID NO 6
<211> LENGTH: 32
<212> TYPE: PRT
<213> ORGANISM: Bos sp.

<400> SEQUENCE: 6

Gln Arg Gln Ala Asn Leu Ala Met Arg Arg Lys Leu His Arg His Asn
1               5                   10                  15

Cys Leu Gln Arg Arg Cys Met Pro Leu His Ser Arg Val Pro Phe Pro
            20                  25                  30

<210> SEQ ID NO 7
<211> LENGTH: 32
<212> TYPE: PRT
<213> ORGANISM: Sus sp.

<400> SEQUENCE: 7

Gln Arg Pro Ala Asn Leu Ala Val Arg Arg Lys Leu His Arg His Asn
1               5                   10                  15

Cys Leu Gln Arg Arg Cys Met Pro Leu His Ser Arg Val Pro Phe Pro
            20                  25                  30
```

<210> SEQ ID NO 8
<211> LENGTH: 32
<212> TYPE: PRT
<213> ORGANISM: Dasypus sp.

<400> SEQUENCE: 8

Gln Arg Pro Ala Asn Leu Ala Met Arg Arg Lys Leu His Arg His Asn
1               5                   10                  15

Cys Phe Gln Arg Arg Cys Met Pro Leu His Ser Arg Val Pro Phe Pro
            20                  25                  30

<210> SEQ ID NO 9
<211> LENGTH: 32
<212> TYPE: PRT
<213> ORGANISM: Trichosurus sp.

<400> SEQUENCE: 9

Gln Arg Pro Gly Asn Leu Ala Leu Arg Arg Lys Pro His Arg His Ile
1               5                   10                  15

Cys Pro Gln Arg Arg Cys Met Pro Leu His Ser Arg Val Pro Phe Pro
            20                  25                  30

<210> SEQ ID NO 10
<211> LENGTH: 32
<212> TYPE: PRT
<213> ORGANISM: Gallus gallus

<400> SEQUENCE: 10

Gln Arg Pro Ala Asn Leu Ala Leu Arg Arg Lys Leu His Arg His Asn
1               5                   10                  15

Cys Ser His Arg Arg Cys Met Pro Leu His Ser Arg Val Pro Phe Pro
            20                  25                  30

<210> SEQ ID NO 11
<211> LENGTH: 32
<212> TYPE: PRT
<213> ORGANISM: Gekko sp.

<400> SEQUENCE: 11

Gln Arg Pro Ala Asn Leu Ser Leu Arg Arg Lys Leu His Arg Gln His
1               5                   10                  15

Cys Ser His Arg Arg Cys Met Pro Leu His Ser Arg Val Pro Phe Pro
            20                  25                  30

<210> SEQ ID NO 12
<211> LENGTH: 32
<212> TYPE: PRT
<213> ORGANISM: Anolis sp.

<400> SEQUENCE: 12

Gln Arg Pro Ala Asn Leu Ala Ser Arg Arg Lys Leu His Arg His His
1               5                   10                  15

Cys Ser His Arg Arg Cys Met Pro Leu His Ser Arg Val Pro Phe Pro
            20                  25                  30

<210> SEQ ID NO 13
<211> LENGTH: 32
<212> TYPE: PRT
<213> ORGANISM: Xenopus laevis

<400> SEQUENCE: 13

Gln Lys Pro Ala Asn Leu Ala Gln Arg Arg Arg Ile His Arg His Asn

```
                1               5                   10                  15
Cys Phe Leu Lys Arg Cys Ile Pro Leu His Ser Arg Val Pro Phe Pro
                20                  25                  30
```

<210> SEQ ID NO 14
<211> LENGTH: 32
<212> TYPE: PRT
<213> ORGANISM: Ambystoma sp.

<400> SEQUENCE: 14

```
Gln Arg Pro Val Asn Ala Ala His Arg Arg Leu His Arg His Asn
1               5                   10                  15

Cys Ser Leu Arg Arg Cys Met Pro Leu His Ser Arg Val Pro Phe Pro
                20                  25                  30
```

<210> SEQ ID NO 15
<211> LENGTH: 32
<212> TYPE: PRT
<213> ORGANISM: Oryzias sp.

<400> SEQUENCE: 15

```
Ala Arg Pro Asp Phe Leu Asn Leu Arg Arg Lys Tyr His Arg His His
1               5                   10                  15

Cys Leu His Arg Arg Cys Met Pro Leu His Ser Arg Val Pro Phe Pro
                20                  25                  30
```

<210> SEQ ID NO 16
<211> LENGTH: 32
<212> TYPE: PRT
<213> ORGANISM: Callorhinchus sp.

<400> SEQUENCE: 16

```
Gln Lys Ser Gly Asn Ser Trp Arg Arg Lys Lys Met Gln Arg Arg Asn
1               5                   10                  15

Cys Trp His Arg Arg Cys Leu Pro Phe His Ser Arg Val Pro Phe Pro
                20                  25                  30
```

<210> SEQ ID NO 17
<211> LENGTH: 32
<212> TYPE: PRT
<213> ORGANISM: Oncorhynchus sp.

<400> SEQUENCE: 17

```
Val Arg Pro Asp Ile Leu Asn Ile Arg Arg Tyr His Arg His His
1               5                   10                  15

Cys Pro His Arg Arg Cys Met Pro Leu His Ser Arg Val Pro Phe Pro
                20                  25                  30
```

<210> SEQ ID NO 18
<211> LENGTH: 36
<212> TYPE: PRT
<213> ORGANISM: Danio rerio

<400> SEQUENCE: 18

```
Asp Lys His Gly Thr Lys His Asp Phe Leu Asn Leu Arg Arg Lys Tyr
1               5                   10                  15

Arg Arg His Asn Cys Pro Lys Lys Arg Cys Leu Pro Leu His Ser Arg
                20                  25                  30

Val Pro Phe Pro
        35
```

```
<210> SEQ ID NO 19
<211> LENGTH: 22
<212> TYPE: PRT
<213> ORGANISM: Homo sapiens

<400> SEQUENCE: 19

Met Arg Phe Gln Gln Phe Leu Phe Ala Phe Phe Ile Phe Ile Met Ser
1               5                   10                  15

Leu Leu Leu Ile Ser Gly
            20

<210> SEQ ID NO 20
<211> LENGTH: 54
<212> TYPE: PRT
<213> ORGANISM: Homo sapiens

<400> SEQUENCE: 20

Met Arg Phe Gln Gln Phe Leu Phe Ala Phe Phe Ile Phe Ile Met Ser
1               5                   10                  15

Leu Leu Leu Ile Ser Gly Gln Arg Pro Val Asn Leu Thr Met Arg Arg
            20                  25                  30

Lys Leu Arg Lys His Asn Cys Leu Gln Arg Arg Cys Met Pro Leu His
        35                  40                  45

Ser Arg Val Pro Phe Pro
    50

<210> SEQ ID NO 21
<211> LENGTH: 54
<212> TYPE: PRT
<213> ORGANISM: Peromyscus sp.

<400> SEQUENCE: 21

Met Arg Phe Gln His Tyr Phe Leu Val Phe Ile Phe Ala Met Ser
1               5                   10                  15

Leu Leu Phe Ile Thr Glu Gln Arg Pro Val Asn Phe Lys Lys Arg
            20                  25                  30

Lys Val Tyr Arg His Asn Cys Phe Arg Arg Arg Cys Val Pro Leu His
        35                  40                  45

Ser Arg Val Pro Phe Pro
    50

<210> SEQ ID NO 22
<211> LENGTH: 54
<212> TYPE: PRT
<213> ORGANISM: Rattus sp.

<400> SEQUENCE: 22

Met Arg Phe Gln Pro Leu Phe Trp Val Phe Ile Phe Ala Met Ser
1               5                   10                  15

Leu Leu Phe Ile Thr Glu Glu Lys Ser Val Asn Phe Pro Arg Arg Arg
            20                  25                  30

Lys Leu Tyr Arg His Asn Cys Phe Arg Arg Cys Ile Ser Leu His
        35                  40                  45

Ser Arg Val Pro Phe Pro
    50

<210> SEQ ID NO 23
<211> LENGTH: 54
<212> TYPE: PRT
<213> ORGANISM: Mus musculus
```

```
<400> SEQUENCE: 23

Met Arg Phe Gln Pro Leu Phe Trp Val Phe Phe Ile Phe Ala Met Ser
1               5                   10                  15

Leu Leu Phe Ile Ser Glu Gln Lys Pro Val Asn Phe Pro Arg Arg Arg
            20                  25                  30

Lys Leu Tyr Arg His Asn Cys Phe Arg Arg Arg Cys Ile Pro Leu His
        35                  40                  45

Ser Arg Val Pro Phe Pro
    50

<210> SEQ ID NO 24
<211> LENGTH: 54
<212> TYPE: PRT
<213> ORGANISM: Bos sp.

<400> SEQUENCE: 24

Met Arg Phe His Gln Phe Phe Leu Leu Phe Val Ile Phe Met Leu Ser
1               5                   10                  15

Leu Leu Leu Ile His Gly Gln Arg Gln Ala Asn Leu Ala Met Arg Arg
            20                  25                  30

Lys Leu His Arg His Asn Cys Leu Gln Arg Arg Cys Met Pro Leu His
        35                  40                  45

Ser Arg Val Pro Phe Pro
    50

<210> SEQ ID NO 25
<211> LENGTH: 54
<212> TYPE: PRT
<213> ORGANISM: Sus sp.

<400> SEQUENCE: 25

Met Arg Phe Arg Gln Phe Phe Leu Val Phe Phe Ile Phe Met Met Asn
1               5                   10                  15

Leu Leu Leu Ile Cys Gly Gln Arg Pro Ala Asn Leu Ala Val Arg Arg
            20                  25                  30

Lys Leu His Arg His Asn Cys Leu Gln Arg Arg Cys Met Pro Leu His
        35                  40                  45

Ser Arg Val Pro Phe Pro
    50

<210> SEQ ID NO 26
<211> LENGTH: 54
<212> TYPE: PRT
<213> ORGANISM: Dasypus sp.

<400> SEQUENCE: 26

Met Lys Phe Gln Gln Phe Phe Tyr Val Phe Val Phe Ile Met Ser
1               5                   10                  15

Leu Leu Leu Ile Asn Gly Gln Arg Pro Ala Asn Leu Ala Met Arg Arg
            20                  25                  30

Lys Leu His Arg His Asn Cys Phe Gln Arg Arg Cys Met Pro Leu His
        35                  40                  45

Ser Arg Val Pro Phe Pro
    50

<210> SEQ ID NO 27
<211> LENGTH: 54
<212> TYPE: PRT
<213> ORGANISM: Trichosurus sp.
```

<400> SEQUENCE: 27

Met Arg Phe Gln Leu Leu Phe Phe Leu Phe Leu Phe Thr Met Gly
1               5                   10                  15

Ile Leu Leu Ile Asp Gly Gln Arg Pro Gly Asn Leu Ala Leu Arg Arg
            20                  25                  30

Lys Pro His Arg His Ile Cys Pro Gln Arg Arg Cys Met Pro Leu His
        35                  40                  45

Ser Arg Val Pro Phe Pro
    50

<210> SEQ ID NO 28
<211> LENGTH: 54
<212> TYPE: PRT
<213> ORGANISM: Gallus gallus

<400> SEQUENCE: 28

Met Arg Leu Arg Leu Leu Cys Val Val Phe Leu Leu Val Ser
1               5                   10                  15

Leu Leu Pro Ala Ala Ala Gln Arg Pro Ala Asn Leu Ala Leu Arg Arg
            20                  25                  30

Lys Leu His Arg His Asn Cys Ser His Arg Arg Cys Met Pro Leu His
        35                  40                  45

Ser Arg Val Pro Phe Pro
    50

<210> SEQ ID NO 29
<211> LENGTH: 54
<212> TYPE: PRT
<213> ORGANISM: Gekko sp.

<400> SEQUENCE: 29

Met Arg Leu Gln Leu Leu Leu Thr Cys Phe Leu Ile Leu Thr Gly
1               5                   10                  15

Val Leu Leu Gly Asn Gly Gln Arg Pro Ala Asn Leu Ser Leu Arg Arg
            20                  25                  30

Lys Leu His Arg Gln His Cys Ser His Arg Arg Cys Met Pro Leu His
        35                  40                  45

Ser Arg Val Pro Phe Pro
    50

<210> SEQ ID NO 30
<211> LENGTH: 54
<212> TYPE: PRT
<213> ORGANISM: Anolis sp.

<400> SEQUENCE: 30

Met Arg Leu Gln Gln Leu Leu Leu Thr Trp Phe Leu Leu Ala Gly
1               5                   10                  15

Ala Leu Leu Ile Asn Gly Gln Arg Pro Ala Asn Leu Ala Ser Arg Arg
            20                  25                  30

Lys Leu His Arg His His Cys Ser His Arg Arg Cys Met Pro Leu His
        35                  40                  45

Ser Arg Val Pro Phe Pro
    50

<210> SEQ ID NO 31
<211> LENGTH: 54
<212> TYPE: PRT

<213> ORGANISM: Xenopus laevis

<400> SEQUENCE: 31

Met Asp Phe Gln Lys Leu Leu Tyr Ala Leu Phe Phe Ile Leu Met Ser
1               5                   10                  15

Leu Leu Leu Ile Asn Gly Gln Lys Pro Ala Asn Leu Ala Gln Arg Arg
            20                  25                  30

Arg Ile His Arg His Asn Cys Phe Leu Lys Arg Cys Ile Pro Leu His
        35                  40                  45

Ser Arg Val Pro Phe Pro
    50

<210> SEQ ID NO 32
<211> LENGTH: 54
<212> TYPE: PRT
<213> ORGANISM: Ambystoma sp.

<400> SEQUENCE: 32

Met Lys Trp Gln Lys Leu Leu Ala Ile Leu Phe Trp Ile Leu Met Gly
1               5                   10                  15

Ala Leu Leu Val Asn Gly Gln Arg Pro Val Asn Ala Ala His Arg Arg
            20                  25                  30

Arg Leu His Arg His Asn Cys Ser Leu Arg Arg Cys Met Pro Leu His
        35                  40                  45

Ser Arg Val Pro Phe Pro
    50

<210> SEQ ID NO 33
<211> LENGTH: 54
<212> TYPE: PRT
<213> ORGANISM: Oryzias sp.

<400> SEQUENCE: 33

Met Arg Val Trp Asn Leu Leu Tyr Leu Leu Leu Leu Leu Ala Ala Ala
1               5                   10                  15

Leu Ala Pro Val Phe Ser Ala Arg Pro Asp Phe Leu Asn Leu Arg Arg
            20                  25                  30

Lys Tyr His Arg His His Cys Leu His Arg Arg Cys Met Pro Leu His
        35                  40                  45

Ser Arg Val Pro Phe Pro
    50

<210> SEQ ID NO 34
<211> LENGTH: 54
<212> TYPE: PRT
<213> ORGANISM: Callorhinchus sp.

<400> SEQUENCE: 34

Met Arg Phe Gln His Leu Leu His Ile Ile Leu Leu Leu Cys Thr Ser
1               5                   10                  15

Leu Leu Leu Ile Ser Gly Gln Lys Ser Gly Asn Ser Trp Arg Arg Lys
            20                  25                  30

Lys Met Gln Arg Arg Asn Cys Trp His Arg Arg Cys Leu Pro Phe His
        35                  40                  45

Ser Arg Val Pro Phe Pro
    50

<210> SEQ ID NO 35
<211> LENGTH: 53

```
<212> TYPE: PRT
<213> ORGANISM: Oncorhynchus sp.

<400> SEQUENCE: 35

Met Arg Ile Ile Ser Leu Leu Tyr Leu Leu Leu Val Thr Val Leu
1               5                   10                  15

Gly Ser Val Ser Ser Val Arg Pro Asp Ile Leu Asn Ile Arg Arg
            20                  25                  30

Tyr His Arg His His Cys Pro His Arg Arg Cys Met Pro Leu His Ser
        35                  40                  45

Arg Val Pro Phe Pro
    50

<210> SEQ ID NO 36
<211> LENGTH: 58
<212> TYPE: PRT
<213> ORGANISM: Danio rerio

<400> SEQUENCE: 36

Met Arg Phe Phe His Pro Leu Tyr Leu Leu Leu Leu Leu Thr Val
1               5                   10                  15

Leu Val Leu Ile Ser Ala Asp Lys His Gly Thr Lys His Asp Phe Leu
            20                  25                  30

Asn Leu Arg Arg Lys Tyr Arg Arg His Asn Cys Pro Lys Lys Arg Cys
        35                  40                  45

Leu Pro Leu His Ser Arg Val Pro Phe Pro
    50                  55

<210> SEQ ID NO 37
<211> LENGTH: 165
<212> TYPE: DNA
<213> ORGANISM: Homo sapiens

<400> SEQUENCE: 37
atgagatttc agcaattcct ttttgcattt tttattttta ttatgagtct ctcccttatc      60
agcggacaga gaccagttaa tttgaccatg agaagaaaac tgcgcaaaca caattgcctt    120
cagaggagat gtatgcctct ccattcacga gtacccttcc cctga                    165

<210> SEQ ID NO 38
<211> LENGTH: 165
<212> TYPE: DNA
<213> ORGANISM: Mus musculus

<400> SEQUENCE: 38
atgcgattcc agccccttt ttgggtattt tttattttg ccatgagtct ccttttatc       60 agtgaacaga aaccagttaa ctttcccagg agaagaaaac tatacagaca caactgcttt    120
cgcaggagat gcattccact tcattctcga gtgcccttcc catga                    165

<210> SEQ ID NO 39
<211> LENGTH: 165
<212> TYPE: DNA
<213> ORGANISM: Gallus gallus

<400> SEQUENCE: 39
atgaggctcc ggcggctgct gtgcgtcgtg ttcctgctcc tggtcagcct gctacctgcc     60
gccgcgcaga gaccggccaa cctggccctg cgcaggaagc tgcaccgaca caactgctcg    120
caccggcggt gcatgccgct ccactcccgc gtgcccttc cctga                     165
```

<210> SEQ ID NO 40
<211> LENGTH: 165
<212> TYPE: DNA
<213> ORGANISM: Xenopus laevis

<400> SEQUENCE: 40

| | | |
|---|---|---|
| atggattttc agaaattatt gtatgcctta tttttcattc tgatgagtct actgctgatt | 60 |
| aatggccaga aaccagccaa cctcgcacag cgccggagga tacacagaca caactgcttc | 120 |
| ctcaagaggt gcataccact acattcaaga gttccatttc catga | 165 |

<210> SEQ ID NO 41
<211> LENGTH: 177
<212> TYPE: DNA
<213> ORGANISM: Danio rerio

<400> SEQUENCE: 41

| | | |
|---|---|---|
| atgagattct tccacccgct gtatctgctg ctgctgctgc tgacagtgct ggtcctcatc | 60 |
| agcgcagata aacatggtac aaaacacgat tttctcaact tgaggcggaa atatcgcaga | 120 |
| cacaactgcc cgaagaaacg ctgtctacct cttcactcca gagtacctt cccttga | 177 |

<210> SEQ ID NO 42
<211> LENGTH: 2422
<212> TYPE: DNA
<213> ORGANISM: Homo sapiens

<400> SEQUENCE: 42

| | | |
|---|---|---|
| atcattaacc ttcctgcaaa acacagctgg cagttctctg aggcttgtca ctagaatgtg | 60 |
| aagacagcca cacagatatt gcacagacta tttacagatc gtttggctta cattgagagt | 120 |
| cattgctcta cttttgtgcg gtaggaaaat gagatttcag caattccttt ttgcattttt | 180 |
| tattttattt atgagtcttc tccttatcag cggacagaga ccagttaatt tgaccatgag | 240 |
| aagaaaactg cgcaaacaca attgccttca gaggagatgt atgcctctcc attcacgagt | 300 |
| acccttcccc tgagatctct ctagctaact ttactggatc tatcagaaga agaagaggag | 360 |
| tgaaggaaag acacccagcc acacaaaaga acttcatgat gccaacagcg tgattgctta | 420 |
| gaagttccta cacaaaaaaa ggatcatttg aaagcacctg gaatggttta ttagcttcac | 480 |
| aggattttat tcttcttggc ttctatttgg agggaaaata acataaattc aaaaggattc | 540 |
| caatctgaag cccaaattgt tgcctacat aacaaaaata tctcatcttt tcctgcacat | 600 |
| tattattctt ttatgggtta aaagaaaaa tacctttag tgttttagaa ctctctcatg | 660 |
| gtaaaaagtg caagaattta aaatgttgct ttcatattcc tataattctc caaaagtatt | 720 |
| aaattcgtat atgtttgagt gattttctaa aaactgctca acctggaatc aattgcattg | 780 |
| accatttggc ttcgcacaat agggagaaaa taattggttc attgattata tagagagaaa | 840 |
| gactaagaaa agctattaat tgctaccaat tttatgataa gctttaaggt ttatgaaagt | 900 |
| atgttttttt atttaatgag taatgtccat ttgaagttga agaaaacat gaaatcctaa | 960 |
| ttgtagttca ttttatgttc aaatgaaacc attgtttttg ttttgtttt gaaacagagt | 1020 |
| ctcactctgt tgcccaaggt ggagagaagt ggcacgcttt tgtctcactg caacctccac | 1080 |
| ctcccgagtt caagtgattc tcgtgcctca acctcccaat ataggctgg gattacaggt | 1140 |
| gtgcaccact acacccagct aattcttgta tttttttgtag agatgaggtt ttaccctgtt | 1200 |
| gcccaggctg gtcttgaact caggctggaa ccattcattt tttaaccttt ctcatcatgt | 1260 |
| aattatagga acccaacgtt tgatttcctt tgaagttttg ttatgtcctt tattattttg | 1320 |

```
tatggataat ttctttaaaa gtcttactta aagtcgacat ctaaaataca gttatgccaa    1380
tgaagtccca ctcagggtga tatctgtatc taaaagatga gtgctcatca tcctattagg    1440
ctttgtcttg gtggtgttca tcctgagatg ctgagacatg gaaataaaaa atcagaagga    1500
atttagggat atgattactc aaaaaagaaa ctatcctgtc taaatttgaa ttgtgttgat    1560
aactaggtgt tccccagatg ctaagatgtt cttaatttgt atttattgaa ggattgttag    1620
cttagtgcca caaaattttt cttactttat gttaattcca gataagaaat ttacaagttt    1680 atatctttt ttttctttt tttaagatga gatctggctc tatcacccag gctaaagtgc    1740
agtggcatga tctaggctaa ctccctggct caagcgatcc ttccacctca gcctcccaag    1800
tacctgggac tacaggcact cacggccaca cctgactaat ttttgtattt ttttgtagag    1860
atggagtatc gccatgttgc ccaggttggt ctcaaactca ggctggtgag ctcaagtgat    1920
ccgcctcctt ggcctcccaa aatactggga ttacaggcat gtgccaccat gctgggccac    1980
aagttcatat ctggagtaga agttttactt tgtaaatatt ataaagtaga agaaaccata    2040
aaccattttg ctaaaatgaa aggttggggt taatataaat gtaattttaa atagaaaatc    2100
tgacaacact gtcgagtttg tcttcctgtc aaagcttatt aaaagtgtct ttgcggatga    2160
atggtacttt ccacaagtgc atttgagtag aagcataacc tattctcagt tatatttatg    2220
tttaaaacat gtactggttt gtatattttg tactgaaaaa gaaaacactt tatagtcaag    2280
atacatctca ttcaatacaa gtctaaactc tttcaaatac aaattcgcat attcacagaa    2340
aaagttacaa atcagttta ctattgtaaa gtaatgaaat ggttatacat ttcttaattg    2400
ttcaataaaa cactcaatga tt                                            2422

<210> SEQ ID NO 43
<211> LENGTH: 975
<212> TYPE: DNA
<213> ORGANISM: Mus musculus

<400> SEQUENCE: 43
cggactctcc ttggagcttt gcagagactt cccgcttaag ttactgcgtg cctgaatgga      60
aaaggcagct ggcagccctc tgagttctgg ccataggatg tggggtgagc cggacagata     120
ctgcgattta cagacgattt ctctacttga agagctattg ttcacttgcg tgtaagaaaa     180
aagaaaaaca aaggaaaga aaagaagaa agaaaaaag agaaagaaaa gaaagatgc      240 gattccagcc cctttttgg gtatttttta ttttgccat gagtctcctt tttatcagtg     300
aacagaaacc agttaacttt cccaggagaa gaaaactata cagacacaac tgctttcgca     360
ggagatgcat tccacttcat tctcgagtgc ccttcccatg aggaaaacct ctaatttcct     420
tggctctacc agaagaaggg tgaaagcaaa gatacccaat caccggaaaa acaacctcag     480
gatggcaaca ggatggcagc tcaggagtta ctacgcaaca gaggctgttt cagagtaccg     540
tggatggctt ttcagactgc tcttcctgga ttctcttga caagaaaatg atagaaaggg     600
aaaacagacg aggttaaagc acatgcgttt gtctgaataa caatctctcc tgctgttctg     660
cacgttcttt gcgtataatg tatgaattac acatagtggt gggtttcaca aaggcattta     720
cataccagta catcacgtcc tatggccgtc tttccacaca tgtgcatcat atacaccgat     780 tcttacagg catgcatgcc atatacactg actacatttg cacacacata ccttcccctt     840 tctctccct caccctcctg caggtctctt ttattcaccct gggcagtttt gtttctattt     900
taatggtttg tacacatgaa tgatttatt gcacattatt attcttacat ggattaaaaa     960
```
gaaaactact ttaat                                                            975

<210> SEQ ID NO 44
<211> LENGTH: 482
<212> TYPE: DNA
<213> ORGANISM: Gallus gallus

<400> SEQUENCE: 44
ggcgagtgcc acggacgctt ctgtacacac gcggaccgca gggatgaggc tccggcggct    60
gctgtgcgtc gtgttcctgc tcctggtcag cctgctacct gccgccgcgc agagaccggc   120
caacctggcc ctgcgcagga agctgcaccg acacaactgc tcgcaccggc ggtgcatgcc   180
gctccactcc cgcgtgccct tccctgagc gcccggccca gctcggcaag caatttcgta   240
acgggctttt cagtgtctta aaggaggaag ctgcaacaac tgcactgata gagaagctca   300
ttctaagtac tgcttaccaa cagttgacct ggtggagcca cagcaatcct gttttgaggg   360
agtccatctg aaatgaacac tttcagtggt cctgtgtatc acattctgca tgacctggaa   420
caaaggccca tgactcatat cctagaagca gggggaaggg agaaacgggg aaggtgattg   480
gg                                                                  482

<210> SEQ ID NO 45
<211> LENGTH: 700
<212> TYPE: DNA
<213> ORGANISM: Xenopus laevis

<400> SEQUENCE: 45
gtttcggtcc ggattcccgg gatccagacc tgatctaata gttgcctatc tctgaagagc    60
aatatggatt ttcagaaatt attgtatgcc ttattttca ttctgatgag tctactgctg   120
attaatggcc agaaaccagc caacctcgca cagcgccgga ggatacacag acacaactgc   180
ttcctcaaga ggtgcatacc actacattca agagttccat ttccatgaga ccactgagga   240
atctcatcat gatgtaacat aggatctgac tcaaatctac agaaataata tttattttga   300
acagtgttta agttgttctt tgacttataa gtggatgttt cttaaatgag ctgcccacaa   360
gaatgggcac agacaagctc caacccatgt aactggctgt gaaactggca caggagctgc   420
cgaaagcaat gtccctccat gaaactgatc caggagacat ctacagcaac ctttgttcca   480
ccaaaacaga caagagagca gattctccat cacattccaa ggaagtgaat gttcaaaggc   540
ttgcatttat tatcaaactg aaatgaagca tatcataata aggctcaatg tcctgtacct   600
caaaagattt aaaatatggg gataaaatga agaaaaacag aagatggttt ttggacaatc   660
tggtcatatt tttaaatatt gccccgtgtg caaaaaaga                           700

<210> SEQ ID NO 46
<211> LENGTH: 849
<212> TYPE: DNA
<213> ORGANISM: Danio rerio

<400> SEQUENCE: 46
catcaggtca tctgtctatc tatccatccc tcagaggaca gagagagaag agagagtgaa    60
tatcgccatc tcaaactttg aaaaagttgg agagaccgag agctggctag aactgcgcgt   120
cttctatata actcaactta tacgagatct gagaacactt gctgagagcg acagacacat   180
aagaggattt ctacagtccg ttacctgcac atccgacaga atttatcgtc tgaggaaccg   240
cggacatcct gtgaggagag tcgagtctgc gccgcggacc aaaccaccct gagcatcacc   300
atgagattct tccacccgct gtatctgctg ctgctgctgc tgacagtgct ggtcctcatc   360

```
agcgcagata aacatggtac aaaacacgat tttctcaact tgaggcggaa atatcgcaga    420
cacaactgcc cgaagaaacg ctgtctacct cttcactcca gagtaccttt cccttgaggt    480
tttatgatgc tccgggcaag cattaagaaa aaccaaagac cagccttgga ttggaaatga    540
gaaaagattt atgtcagatg tgccgaggac tgttttattc gcacatgtat tgtaatcaaa    600
gccatgtttg tcacttctgt agcagaagtg ttttttgttt tgttttgttt tttaaatgaa    660
tgtaagtgaa tgagccatgg agatcctact gctgccaaac atgctgcaaa ctcatcactc    720
aatcaggttg agttggagca gaatcattgt aaatagtgag gactgaatga aatgtgttta    780
tatgtaagtt atgcacttca aatgttttat tattatcttg atttattaaa agtgtattgt    840
cttttcaga                                                            849
```

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: Synthetic
      Anti-ELABELA shRNA sequence A oligonucleotide

<400> SEQUENCE: 47
gacacccagc cacacaaaa                                                 19

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      Anti-ELABELA shRNA sequence B oligonucleotide

<400> SEQUENCE: 48
cccagccaca caaaagaac                                                 19

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: Synthetic
      Anti-ELABELA shRNA sequence C oligonucleotide

<400> SEQUENCE: 49
gtgattctcg tgcctcaac                                                 19

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
      Anti-ELABELA shRNA sequence D oligonucleotide

<400> SEQUENCE: 50
ctcacggcca cacctgact                                                 19

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Synthetic
      Anti-ELABELA shRNA sequence E oligonucleotide -continued

<400> SEQUENCE: 51
ttgccttcag aggagatgt                                                    19

<210> SEQ ID NO 52
<211> LENGTH: 11
<212> TYPE: PRT
<213> ORGANISM: Homo sapiens

<400> SEQUENCE: 52

Cys Met Pro Leu His Ser Arg Val Pro Phe Pro
1               5                   10

<210> SEQ ID NO 53
<211> LENGTH: 17
<212> TYPE: PRT
<213> ORGANISM: Homo sapiens

<400> SEQUENCE: 53

Gln Arg Pro Val Asn Leu Thr Met Arg Arg Lys Leu Arg Lys His Asn
1               5                   10                  15

Cys

<210> SEQ ID NO 54
<211> LENGTH: 10
<212> TYPE: PRT
<213> ORGANISM: Unknown
<220> FEATURE:
<223> OTHER INFORMATION: Description of Unknown:
      ELABELA peptide

<400> SEQUENCE: 54

Met Pro Leu His Ser Arg Val Pro Phe Pro
1               5                   10

<210> SEQ ID NO 55
<211> LENGTH: 16
<212> TYPE: PRT
<213> ORGANISM: Unknown
<220> FEATURE:
<223> OTHER INFORMATION: Description of Unknown:
      ELABELA peptide

<400> SEQUENCE: 55

Gln Arg Pro Val Asn Leu Thr Met Arg Arg Lys Leu Arg Lys His Asn
1               5                   10                  15

<210> SEQ ID NO 56
<211> LENGTH: 54
<212> TYPE: PRT
<213> ORGANISM: Artificial Sequence
<220> FEATURE:
<223> OTHER INFORMATION: Description of Artificial Sequence: Synthetic
      consensus polypeptide
<220> FEATURE:
<221> NAME/KEY: MOD_RES
<222> LOCATION: (2)..(2)
<223> OTHER INFORMATION: Arg, Lys or Asp
<220> FEATURE:
<221> NAME/KEY: MOD_RES
<222> LOCATION: (3)..(3)
<223> OTHER INFORMATION: Phe, Leu, Trp or Val
<220> FEATURE:
<221> NAME/KEY: MOD_RES
<222> LOCATION: (4)..(4)
<223> OTHER INFORMATION: Gln, His, Arg or Trp
<220> FEATURE:
<221> NAME/KEY: MOD_RES

```
-continued

<222> LOCATION: (5)..(5)
<223> OTHER INFORMATION: Gln, His, Pro, Leu, Arg, Lys or Asn
<220> FEATURE:
<221> NAME/KEY: MOD_RES
<222> LOCATION: (6)..(6)
<223> OTHER INFORMATION: Phe, Tyr or Leu
<220> FEATURE:
<221> NAME/KEY: MOD_RES
<222> LOCATION: (7)..(7)
<223> OTHER INFORMATION: Leu or Phe
<220> FEATURE:
<221> NAME/KEY: MOD_RES
<222> LOCATION: (8)..(8)
<223> OTHER INFORMATION: Phe, Leu, Trp, Tyr, Cys, Ala or His
<220> FEATURE:
<221> NAME/KEY: MOD_RES
<222> LOCATION: (9)..(9)
<223> OTHER INFORMATION: Ala, Val, Leu, Thr or Ile
<220> FEATURE:
<221> NAME/KEY: MOD_RES
<222> LOCATION: (10)..(10)
<223> OTHER INFORMATION: Phe, Val, Cys, Trp, Leu or Ile
<220> FEATURE:
<221> NAME/KEY: MOD_RES
<222> LOCATION: (11)..(11)
<223> OTHER INFORMATION: Phe, Val or Leu
<220> FEATURE:
<221> NAME/KEY: MOD_RES
<222> LOCATION: (12)..(12)
<223> OTHER INFORMATION: Ile, Val, Phe, Leu or Trp
<220> FEATURE:
<221> NAME/KEY: MOD_RES
<222> LOCATION: (13)..(13)
<223> OTHER INFORMATION: Phe, Leu or Ile
<220> FEATURE:
<221> NAME/KEY: MOD_RES
<222> LOCATION: (14)..(14)
<223> OTHER INFORMATION: Ile, Ala, Met, Thr, Leu or Cys
<220> FEATURE:
<221> NAME/KEY: MOD_RES
<222> LOCATION: (15)..(15)
<223> OTHER INFORMATION: Met, Leu, Val, Thr or Ala
<220> FEATURE:
<221> NAME/KEY: MOD_RES
<222> LOCATION: (16)..(16)
<223> OTHER INFORMATION: Ser, Asn, Gly or Ala
<220> FEATURE:
<221> NAME/KEY: MOD_RES
<222> LOCATION: (17)..(17)
<223> OTHER INFORMATION: Leu, Ile, Val or Ala
<220> FEATURE:
<221> NAME/KEY: MOD_RES
<222> LOCATION: (18)..(18)
<223> OTHER INFORMATION: Leu or Ala
<220> FEATURE:
<221> NAME/KEY: MOD_RES
<222> LOCATION: (19)..(19)
<223> OTHER INFORMATION: Leu, Phe or Pro
<220> FEATURE:
<221> NAME/KEY: MOD_RES
<222> LOCATION: (20)..(20)
<223> OTHER INFORMATION: Ile, Ala, Gly or Val
<220> FEATURE:
<221> NAME/KEY: MOD_RES
<222> LOCATION: (21)..(21)
<223> OTHER INFORMATION: Ser, Thr, His, Cys, Asn, Asp, Ala or Phe
<220> FEATURE:
<221> NAME/KEY: MOD_RES
<222> LOCATION: (22)..(22)
<223> OTHER INFORMATION: Gly, Glu, Ala or Ser
<220> FEATURE:
<221> NAME/KEY: MOD_RES
<222> LOCATION: (23)..(23)
<223> OTHER INFORMATION: Gln, Glu or Ala
<220> FEATURE:
<221> NAME/KEY: MOD_RES
<222> LOCATION: (24)..(24)
<223> OTHER INFORMATION: Arg or Lys
<220> FEATURE:
```

```
<221> NAME/KEY: MOD_RES
<222> LOCATION: (25)..(25)
<223> OTHER INFORMATION: Pro, Ser or Gln
<220> FEATURE:
<221> NAME/KEY: MOD_RES
<222> LOCATION: (26)..(26)
<223> OTHER INFORMATION: Val, Ala, Gly or Asp
<220> FEATURE:
<221> NAME/KEY: MOD_RES
<222> LOCATION: (27)..(27)
<223> OTHER INFORMATION: Asn or Phe
<220> FEATURE:
<221> NAME/KEY: MOD_RES
<222> LOCATION: (28)..(28)
<223> OTHER INFORMATION: Leu, Phe, Ala or Ser
<220> FEATURE:
<221> NAME/KEY: MOD_RES
<222> LOCATION: (29)..(29)
<223> OTHER INFORMATION: Thr, Pro, Ala, Ser, Asn or Trp
<220> FEATURE:
<221> NAME/KEY: MOD_RES
<222> LOCATION: (30)..(30)
<223> OTHER INFORMATION: Met, Lys, Arg, Val, Leu, Ser, Gln or His
<220> FEATURE:
<221> NAME/KEY: MOD_RES
<222> LOCATION: (31)..(31)
<223> OTHER INFORMATION: Arg or Lys
<220> FEATURE:
<221> NAME/KEY: MOD_RES
<222> LOCATION: (32)..(32)
<223> OTHER INFORMATION: Arg or Lys
<220> FEATURE:
<221> NAME/KEY: MOD_RES
<222> LOCATION: (33)..(33)
<223> OTHER INFORMATION: Lys or Arg
<220> FEATURE:
<221> NAME/KEY: MOD_RES
<222> LOCATION: (34)..(34)
<223> OTHER INFORMATION: Leu, Val, Pro, Ile, Tyr or Met
<220> FEATURE:
<221> NAME/KEY: MOD_RES
<222> LOCATION: (35)..(35)
<223> OTHER INFORMATION: Arg, Tyr, His or Gln
<220> FEATURE:
<221> NAME/KEY: MOD_RES
<222> LOCATION: (36)..(36)
<223> OTHER INFORMATION: Lys or Arg
<220> FEATURE:
<221> NAME/KEY: MOD_RES
<222> LOCATION: (37)..(37)
<223> OTHER INFORMATION: His, Gln or Arg
<220> FEATURE:
<221> NAME/KEY: MOD_RES
<222> LOCATION: (38)..(38)
<223> OTHER INFORMATION: Asn, Ile or His
<220> FEATURE:
<221> NAME/KEY: MOD_RES
<222> LOCATION: (40)..(40)
<223> OTHER INFORMATION: Leu, Phe, Pro, Ser or Trp
<220> FEATURE:
<221> NAME/KEY: MOD_RES
<222> LOCATION: (41)..(41)
<223> OTHER INFORMATION: Gln, Arg, His or Leu
<220> FEATURE:
<221> NAME/KEY: MOD_RES
<222> LOCATION: (42)..(42)
<223> OTHER INFORMATION: Arg or Lys
<220> FEATURE:
<221> NAME/KEY: MOD_RES
<222> LOCATION: (45)..(45)
<223> OTHER INFORMATION: Met, Val, Ile or Leu
<220> FEATURE:
<221> NAME/KEY: MOD_RES
<222> LOCATION: (46)..(46)
<223> OTHER INFORMATION: Pro or Ser
<220> FEATURE:
<221> NAME/KEY: MOD_RES
<222> LOCATION: (47)..(47)
<223> OTHER INFORMATION: Leu or Phe
```

```
<400> SEQUENCE: 56

Met Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Cys Xaa Xaa Xaa Arg Cys Xaa Xaa Xaa His
        35                  40                  45

Ser Arg Val Pro Phe Pro
    50

<210> SEQ ID NO 57
<211> LENGTH: 4
<212> TYPE: PRT
<213> ORGANISM: Danio rerio

<400> SEQUENCE: 57

Asp Lys His Gly
1

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      ELABELA polypeptide signature sequence

<400> SEQUENCE: 58

His Ser Arg Val Pro Phe Pro
1               5

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      ELABELA polypeptide signature sequence
<220> FEATURE:
<221> NAME/KEY: MOD_RES
<222> LOCATION: (3)..(5)
<223> OTHER INFORMATION: Any amino acid

<400> SEQUENCE: 59

Arg Cys Xaa Xaa Xaa His Ser Arg Val Pro Phe Pro
1               5                   10

<210> SEQ ID NO 60
<211> LENGTH: 16
<212> TYPE: PRT
<213> ORGANISM: Homo sapiens

<400> SEQUENCE: 60

Cys Leu Gln Arg Arg Cys Met Pro Leu His Ser Arg Val Pro Phe Pro
1               5                   10                  15

<210> SEQ ID NO 61
<211> LENGTH: 16
<212> TYPE: PRT
<213> ORGANISM: Peromyscus sp.

<400> SEQUENCE: 61

Cys Phe Arg Arg Arg Cys Val Pro Leu His Ser Arg Val Pro Phe Pro
1               5                   10                  15
```

```
<210> SEQ ID NO 62
<211> LENGTH: 16
<212> TYPE: PRT
<213> ORGANISM: Rattus sp.

<400> SEQUENCE: 62

Cys Phe Arg Arg Arg Cys Ile Ser Leu His Ser Arg Val Pro Phe Pro
1               5                   10                  15

<210> SEQ ID NO 63
<211> LENGTH: 16
<212> TYPE: PRT
<213> ORGANISM: Mus musculus

<400> SEQUENCE: 63

Cys Phe Arg Arg Arg Cys Ile Pro Leu His Ser Arg Val Pro Phe Pro
1               5                   10                  15

<210> SEQ ID NO 64
<211> LENGTH: 16
<212> TYPE: PRT
<213> ORGANISM: Bos sp.

<400> SEQUENCE: 64

Cys Leu Gln Arg Arg Cys Met Pro Leu His Ser Arg Val Pro Phe Pro
1               5                   10                  15

<210> SEQ ID NO 65
<211> LENGTH: 16
<212> TYPE: PRT
<213> ORGANISM: Sus sp.

<400> SEQUENCE: 65

Cys Leu Gln Arg Arg Cys Met Pro Leu His Ser Arg Val Pro Phe Pro
1               5                   10                  15

<210> SEQ ID NO 66
<211> LENGTH: 16
<212> TYPE: PRT
<213> ORGANISM: Dasypus sp.

<400> SEQUENCE: 66

Cys Phe Gln Arg Arg Cys Met Pro Leu His Ser Arg Val Pro Phe Pro
1               5                   10                  15

<210> SEQ ID NO 67
<211> LENGTH: 16
<212> TYPE: PRT
<213> ORGANISM: Trichosurus sp.

<400> SEQUENCE: 67

Cys Pro Gln Arg Arg Cys Met Pro Leu His Ser Arg Val Pro Phe Pro
1               5                   10                  15

<210> SEQ ID NO 68
<211> LENGTH: 16
<212> TYPE: PRT
<213> ORGANISM: Gallus gallus

<400> SEQUENCE: 68

Cys Ser His Arg Arg Cys Met Pro Leu His Ser Arg Val Pro Phe Pro
1               5                   10                  15
```

```
<210> SEQ ID NO 69
<211> LENGTH: 16
<212> TYPE: PRT
<213> ORGANISM: Gekko sp.

<400> SEQUENCE: 69

Cys Ser His Arg Arg Cys Met Pro Leu His Ser Arg Val Pro Phe Pro
1               5                   10                  15

<210> SEQ ID NO 70
<211> LENGTH: 16
<212> TYPE: PRT
<213> ORGANISM: Anolis sp.

<400> SEQUENCE: 70

Cys Ser His Arg Arg Cys Met Pro Leu His Ser Arg Val Pro Phe Pro
1               5                   10                  15

<210> SEQ ID NO 71
<211> LENGTH: 16
<212> TYPE: PRT
<213> ORGANISM: Xenopus laevis

<400> SEQUENCE: 71

Cys Phe Leu Lys Arg Cys Ile Pro Leu His Ser Arg Val Pro Phe Pro
1               5                   10                  15

<210> SEQ ID NO 72
<211> LENGTH: 16
<212> TYPE: PRT
<213> ORGANISM: Ambystoma sp.

<400> SEQUENCE: 72

Cys Ser Leu Arg Arg Cys Met Pro Leu His Ser Arg Val Pro Phe Pro
1               5                   10                  15

<210> SEQ ID NO 73
<211> LENGTH: 16
<212> TYPE: PRT
<213> ORGANISM: Oryzias sp.

<400> SEQUENCE: 73

Cys Leu His Arg Arg Cys Met Pro Leu His Ser Arg Val Pro Phe Pro
1               5                   10                  15

<210> SEQ ID NO 74
<211> LENGTH: 16
<212> TYPE: PRT
<213> ORGANISM: Callorhinchus sp.

<400> SEQUENCE: 74

Cys Trp His Arg Arg Cys Leu Pro Phe His Ser Arg Val Pro Phe Pro
1               5                   10                  15

<210> SEQ ID NO 75
<211> LENGTH: 16
<212> TYPE: PRT
<213> ORGANISM: Oncorhynchus sp.

<400> SEQUENCE: 75

Cys Pro His Arg Arg Cys Met Pro Leu His Ser Arg Val Pro Phe Pro
1               5                   10                  15

<210> SEQ ID NO 76
<211> LENGTH: 16
```

```
<212> TYPE: PRT
<213> ORGANISM: Danio rerio

<400> SEQUENCE: 76

Cys Pro Lys Lys Arg Cys Leu Pro Leu His Ser Arg Val Pro Phe Pro
1               5                   10                  15

<210> SEQ ID NO 77
<211> LENGTH: 23
<212> TYPE: PRT
<213> ORGANISM: Unknown
<220> FEATURE:
<223> OTHER INFORMATION: Description of Unknown:
      ELABELA peptide
<220> FEATURE:
<221> NAME/KEY: MOD_RES
<222> LOCATION: (1)..(1)
<223> OTHER INFORMATION: Arg or Lys
<220> FEATURE:
<221> NAME/KEY: MOD_RES
<222> LOCATION: (2)..(7)
<223> OTHER INFORMATION: Any amino acid
<220> FEATURE:
<221> NAME/KEY: MOD_RES
<222> LOCATION: (9)..(11)
<223> OTHER INFORMATION: Any amino acid
<220> FEATURE:
<221> NAME/KEY: MOD_RES
<222> LOCATION: (14)..(16)
<223> OTHER INFORMATION: Any amino acid

<400> SEQUENCE: 77

Xaa Xaa Xaa Xaa Xaa Xaa Xaa Cys Xaa Xaa Xaa Arg Cys Xaa Xaa Xaa
1               5                   10                  15

His Ser Arg Val Pro Phe Pro
            20

<210> SEQ ID NO 78
<211> LENGTH: 24
<212> TYPE: PRT
<213> ORGANISM: Unknown
<220> FEATURE:
<223> OTHER INFORMATION: Description of Unknown:
      ELABELA peptide
<220> FEATURE:
<221> NAME/KEY: MOD_RES
<222> LOCATION: (1)..(1)
<223> OTHER INFORMATION: Arg or Lys
<220> FEATURE:
<221> NAME/KEY: MOD_RES
<222> LOCATION: (2)..(8)
<223> OTHER INFORMATION: Any amino acid
<220> FEATURE:
<221> NAME/KEY: MOD_RES
<222> LOCATION: (10)..(12)
<223> OTHER INFORMATION: Any amino acid
<220> FEATURE:
<221> NAME/KEY: MOD_RES
<222> LOCATION: (15)..(17)
<223> OTHER INFORMATION: Any amino acid

<400> SEQUENCE: 78

Xaa Xaa Xaa Xaa Xaa Xaa Xaa Xaa Cys Xaa Xaa Xaa Arg Cys Xaa Xaa
1               5                   10                  15

Xaa His Ser Arg Val Pro Phe Pro
            20

<210> SEQ ID NO 79
<211> LENGTH: 24
<212> TYPE: PRT
<213> ORGANISM: Unknown
```

```
<220> FEATURE:
<223> OTHER INFORMATION: Description of Unknown:
      ELABELA peptide
<220> FEATURE:
<221> NAME/KEY: MOD_RES
<222> LOCATION: (1)..(1)
<223> OTHER INFORMATION: Arg or Lys
<220> FEATURE:
<221> NAME/KEY: MOD_RES
<222> LOCATION: (2)..(2)
<223> OTHER INFORMATION: Arg or Lys
<220> FEATURE:
<221> NAME/KEY: MOD_RES
<222> LOCATION: (3)..(8)
<223> OTHER INFORMATION: Any amino acid
<220> FEATURE:
<221> NAME/KEY: MOD_RES
<222> LOCATION: (10)..(12)
<223> OTHER INFORMATION: Any amino acid
<220> FEATURE:
<221> NAME/KEY: MOD_RES
<222> LOCATION: (15)..(17)
<223> OTHER INFORMATION: Any amino acid

<400> SEQUENCE: 79

Xaa Xaa Xaa Xaa Xaa Xaa Xaa Xaa Cys Xaa Xaa Xaa Arg Cys Xaa Xaa
1               5                   10                  15

Xaa His Ser Arg Val Pro Phe Pro
            20

<210> SEQ ID NO 80
<211> LENGTH: 22
<212> TYPE: PRT
<213> ORGANISM: Peromyscus sp.

<400> SEQUENCE: 80

Met Arg Phe Gln His Tyr Phe Leu Val Phe Phe Ile Phe Ala Met Ser
1               5                   10                  15

Leu Leu Phe Ile Thr Glu
            20

<210> SEQ ID NO 81
<211> LENGTH: 22
<212> TYPE: PRT
<213> ORGANISM: Rattus sp.

<400> SEQUENCE: 81

Met Arg Phe Gln Pro Leu Phe Trp Val Phe Phe Ile Phe Ala Met Ser
1               5                   10                  15

Leu Leu Phe Ile Thr Glu
            20

<210> SEQ ID NO 82
<211> LENGTH: 22
<212> TYPE: PRT
<213> ORGANISM: Mus musculus

<400> SEQUENCE: 82

Met Arg Phe Gln Pro Leu Phe Trp Val Phe Phe Ile Phe Ala Met Ser
1               5                   10                  15

Leu Leu Phe Ile Ser Glu
            20

<210> SEQ ID NO 83
<211> LENGTH: 22
<212> TYPE: PRT
<213> ORGANISM: Bos sp.
```

<400> SEQUENCE: 83

Met Arg Phe His Gln Phe Phe Leu Leu Phe Val Ile Phe Met Leu Ser
1               5                   10                  15

Leu Leu Leu Ile His Gly
            20

<210> SEQ ID NO 84
<211> LENGTH: 22
<212> TYPE: PRT
<213> ORGANISM: Sus sp.

<400> SEQUENCE: 84

Met Arg Phe Arg Gln Phe Phe Leu Val Phe Phe Ile Phe Met Met Asn
1               5                   10                  15

Leu Leu Leu Ile Cys Gly
            20

<210> SEQ ID NO 85
<211> LENGTH: 22
<212> TYPE: PRT
<213> ORGANISM: Dasypus sp.

<400> SEQUENCE: 85

Met Lys Phe Gln Gln Phe Phe Tyr Val Phe Phe Val Phe Ile Met Ser
1               5                   10                  15

Leu Leu Leu Ile Asn Gly
            20

<210> SEQ ID NO 86
<211> LENGTH: 22
<212> TYPE: PRT
<213> ORGANISM: Trichosurus sp.

<400> SEQUENCE: 86

Met Arg Phe Gln Leu Leu Phe Phe Leu Phe Leu Phe Thr Met Gly
1               5                   10                  15

Ile Leu Leu Ile Asp Gly
            20

<210> SEQ ID NO 87
<211> LENGTH: 22
<212> TYPE: PRT
<213> ORGANISM: Gallus gallus

<400> SEQUENCE: 87

Met Arg Leu Arg Arg Leu Leu Cys Val Val Phe Leu Leu Val Ser
1               5                   10                  15

Leu Leu Pro Ala Ala Ala
            20

<210> SEQ ID NO 88
<211> LENGTH: 22
<212> TYPE: PRT
<213> ORGANISM: Gekko sp.

<400> SEQUENCE: 88

Met Arg Leu Gln Leu Leu Leu Thr Cys Phe Leu Ile Leu Thr Gly
1               5                   10                  15

Val Leu Leu Gly Asn Gly
            20

-continued

<210> SEQ ID NO 89
<211> LENGTH: 22
<212> TYPE: PRT
<213> ORGANISM: Anolis sp.

<400> SEQUENCE: 89

Met Arg Leu Gln Gln Leu Leu Thr Trp Phe Leu Leu Leu Ala Gly
1               5                   10                  15

Ala Leu Leu Ile Asn Gly
            20

<210> SEQ ID NO 90
<211> LENGTH: 22
<212> TYPE: PRT
<213> ORGANISM: Xenopus laevis

<400> SEQUENCE: 90

Met Asp Phe Gln Lys Leu Leu Tyr Ala Leu Phe Phe Ile Leu Met Ser
1               5                   10                  15

Leu Leu Leu Ile Asn Gly
            20

<210> SEQ ID NO 91
<211> LENGTH: 22
<212> TYPE: PRT
<213> ORGANISM: Ambystoma sp.

<400> SEQUENCE: 91

Met Lys Trp Gln Lys Leu Leu Ala Ile Leu Phe Trp Ile Leu Met Gly
1               5                   10                  15

Ala Leu Leu Val Asn Gly
            20

<210> SEQ ID NO 92
<211> LENGTH: 22
<212> TYPE: PRT
<213> ORGANISM: Oryzias sp.

<400> SEQUENCE: 92

Met Arg Val Trp Asn Leu Leu Tyr Leu Leu Leu Leu Ala Ala Ala
1               5                   10                  15

Leu Ala Pro Val Phe Ser
            20

<210> SEQ ID NO 93
<211> LENGTH: 22
<212> TYPE: PRT
<213> ORGANISM: Callorhinchus sp.

<400> SEQUENCE: 93

Met Arg Phe Gln His Leu Leu His Ile Ile Leu Leu Leu Cys Thr Ser
1               5                   10                  15

Leu Leu Leu Ile Ser Gly
            20

<210> SEQ ID NO 94
<211> LENGTH: 24
<212> TYPE: PRT
<213> ORGANISM: Unknown
<220> FEATURE:
<223> OTHER INFORMATION: Description of Unknown:
      ELABELA peptide
<220> FEATURE:

```
<221> NAME/KEY: MOD_RES
<222> LOCATION: (1)..(1)
<223> OTHER INFORMATION: Arg or Lys
<220> FEATURE:
<221> NAME/KEY: MOD_RES
<222> LOCATION: (2)..(2)
<223> OTHER INFORMATION: Ala or Gly
<220> FEATURE:
<221> NAME/KEY: MOD_RES
<222> LOCATION: (3)..(8)
<223> OTHER INFORMATION: Any amino acid
<220> FEATURE:
<221> NAME/KEY: MOD_RES
<222> LOCATION: (10)..(12)
<223> OTHER INFORMATION: Any amino acid
<220> FEATURE:
<221> NAME/KEY: MOD_RES
<222> LOCATION: (15)..(17)
<223> OTHER INFORMATION: Any amino acid

<400> SEQUENCE: 94

Xaa Xaa Xaa Xaa Xaa Xaa Xaa Xaa Cys Xaa Xaa Xaa Arg Cys Xaa Xaa
1               5                   10                  15

Xaa His Ser Arg Val Pro Phe Pro
            20

<210> SEQ ID NO 95
<211> LENGTH: 24
<212> TYPE: PRT
<213> ORGANISM: Unknown
<220> FEATURE:
<223> OTHER INFORMATION: Description of Unknown:
      ELABELA peptide
<220> FEATURE:
<221> NAME/KEY: MOD_RES
<222> LOCATION: (1)..(1)
<223> OTHER INFORMATION: Ala or Gly
<220> FEATURE:
<221> NAME/KEY: MOD_RES
<222> LOCATION: (2)..(2)
<223> OTHER INFORMATION: Arg or Lys
<220> FEATURE:
<221> NAME/KEY: MOD_RES
<222> LOCATION: (3)..(8)
<223> OTHER INFORMATION: Any amino acid
<220> FEATURE:
<221> NAME/KEY: MOD_RES
<222> LOCATION: (10)..(12)
<223> OTHER INFORMATION: Any amino acid
<220> FEATURE:
<221> NAME/KEY: MOD_RES
<222> LOCATION: (15)..(17)
<223> OTHER INFORMATION: Any amino acid

<400> SEQUENCE: 95

Xaa Xaa Xaa Xaa Xaa Xaa Xaa Xaa Cys Xaa Xaa Xaa Arg Cys Xaa Xaa
1               5                   10                  15

Xaa His Ser Arg Val Pro Phe Pro
            20

<210> SEQ ID NO 96
<211> LENGTH: 24
<212> TYPE: PRT
<213> ORGANISM: Unknown
<220> FEATURE:
<223> OTHER INFORMATION: Description of Unknown:
      ELABELA peptide
<220> FEATURE:
<221> NAME/KEY: MOD_RES
<222> LOCATION: (1)..(1)
<223> OTHER INFORMATION: Ala or Gly
<220> FEATURE:
<221> NAME/KEY: MOD_RES
```

```
<222> LOCATION: (2)..(2)
<223> OTHER INFORMATION: Ala or Gly
<220> FEATURE:
<221> NAME/KEY: MOD_RES
<222> LOCATION: (3)..(8)
<223> OTHER INFORMATION: Any amino acid
<220> FEATURE:
<221> NAME/KEY: MOD_RES
<222> LOCATION: (10)..(12)
<223> OTHER INFORMATION: Any amino acid
<220> FEATURE:
<221> NAME/KEY: MOD_RES
<222> LOCATION: (15)..(17)
<223> OTHER INFORMATION: Any amino acid

<400> SEQUENCE: 96

Xaa Xaa Xaa Xaa Xaa Xaa Xaa Xaa Cys Xaa Xaa Xaa Arg Cys Xaa Xaa
1               5                   10                  15

Xaa His Ser Arg Val Pro Phe Pro
            20

<210> SEQ ID NO 97
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 97

His His His His His His
1               5

<210> SEQ ID NO 98
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
agcaaaaccc ggaggagt                                                 18

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
cacgagtacc ctttccctga                                               20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
tccagcagat gcaagaactc                                               20

<210> SEQ ID NO 101
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
ggaagcccaa gaacctgaat                                                    20

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
aatacttccc ccacaacaca a                                                  21

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
cgccctactc gtacatctcg                                                    20

<210> SEQ ID NO 104
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
gtggggaggt cgaggttc                                                      18

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
gctgtgacag gtacccaacc                                                    20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
tgcgggctac tgaaaagttc                                                    20

<210> SEQ ID NO 107
<211> LENGTH: 19
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 107
agccacatcg ctcagacac                                            19

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
atcttgaccc tccctggaat                                           20

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
aatgggcgga gttatgatac c                                         21

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
gatcttcact ccccttgttc a                                         21

<210> SEQ ID NO 111
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
gctgtgttca gccagtgct                                            19

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
cgtctgctac tgcttcatcg                                           20

<210> SEQ ID NO 113
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 113
cctcttgcgc tatggacttc                                                 20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
ttcttccacc cgctgtatct                                                 20

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
ccacatcggc ctgtgtatat c                                               21

<210> SEQ ID NO 116
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
ggctgggtgt ctttccttc                                                  19

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
ttgctattct tcggccagtt                                                 20

<210> SEQ ID NO 118
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
gctggagttg ctggaagc                                                   18

<210> SEQ ID NO 119
<211> LENGTH: 18
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 119
ctctcccgca ccagtcat                                                      18

<210> SEQ ID NO 120
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
agcgtcagca tcttgttgg                                                     19

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
tgttctggag gtccatggta g                                                  21

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
catgcaggtg agttgtcaga a                                                  21

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
tgtaggccct gtttctcctg                                                    20

<210> SEQ ID NO 124
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
gcccaatacg accaaatcc                                                     19

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 125
atggggagac taggctgtga                                          20

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
catatcaggt tcacttccgg g                                        21

<210> SEQ ID NO 127
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
ggcagcgatt tcctcatc                                            18

<210> SEQ ID NO 128
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
ttctgccgca aaggagtc                                            18

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129 gcttttttctg gtcttccttg c                                       21

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
gcctgcaatc cagtaggtct                                          20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
ccggagcatc ataaaacctc                                              20

<210> SEQ ID NO 132
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
gtgattctcg tgcctcaac                                               19

<210> SEQ ID NO 133
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
tccacccgct gtatct                                                  16

<210> SEQ ID NO 134
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
gctgctgctg acagt                                                   15

<210> SEQ ID NO 135
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
aacacttgct gagagcgaca g                                            21

<210> SEQ ID NO 136
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
agatgtggtg gtgttgagta gc                                           22

<210> SEQ ID NO 137
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 137
atggagccaa cgccggaat                                                  19

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
atgaatgcca tggacaacat                                                 20

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
acacacatcc cagccttttc                                                 20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
ccatccctca gaggacagag                                                 20

<210> SEQ ID NO 141
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
tcacactttg gtggccagc                                                  19

<210> SEQ ID NO 142
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
tcacaccttc gtagccagc                                                  19

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
```
ccaatttcat tcggcaatct                                                    20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
catgtttggc agcagtagga                                                    20

<210> SEQ ID NO 145
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
ctttgtggtg accctgcccc tgttggccgt ctacactgct ctg                          43

<210> SEQ ID NO 146
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
cagagcagtg tagacggcca acaggggcag ggtcaccaca aag                          43

<210> SEQ ID NO 147
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
atggaggaag gtggtgattt tga                                                23

<210> SEQ ID NO 148
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
atggacccag aagaaacttc ag                                                 22

<210> SEQ ID NO 149
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149

```
atgagattct tccacccgc                                              19

<210> SEQ ID NO 150
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
ggagaccctt gtggttgact ag                                          22

<210> SEQ ID NO 151
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
ttagagtgac acagacctct tcc                                         23

<210> SEQ ID NO 152
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
tcaagggaaa ggtactctgg ag                                          22

<210> SEQ ID NO 153
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
acacgtaccg ggactatga                                              19

<210> SEQ ID NO 154
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
ccatcatgct gacctgtta                                              19

<210> SEQ ID NO 155
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
gacctctgcg cctaattat                                              19
```

<210> SEQ ID NO 156
<211> LENGTH: 57
<212> TYPE: DNA
<213> ORGANISM: Danio rerio

<400> SEQUENCE: 156
atgagattct tccacccgct gtatctgctg ctgctgctgc tgacagtgct ggtcctc        57

<210> SEQ ID NO 157
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Met Arg Phe Phe His Pro Leu Tyr Leu Leu Val Leu Ile Ser Ala Asp
1               5                   10                  15

Lys His Gly Thr Lys His Asp Phe Leu Asn Leu Arg Arg Lys Tyr Arg
            20                  25                  30

Arg His Asn Cys Pro Lys Lys Arg Cys Leu Pro Leu His Ser Arg Val
        35                  40                  45

Pro Phe Pro
    50

<210> SEQ ID NO 158
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Met Arg Phe Phe His Pro Leu Tyr Leu Cys Gln Cys Trp Ser Ser Ser
1               5                   10                  15

Ala Gln Ile Asn Met Val Gln Asn Thr Ile Phe Ser Thr
            20                  25

<210> SEQ ID NO 159
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Met Arg Phe Phe His Pro Leu
1               5

<210> SEQ ID NO 160
<211> LENGTH: 33
<212> TYPE: PRT
<213> ORGANISM: Homo sapiens

<400> SEQUENCE: 160

Gly Gln Arg Pro Val Asn Leu Thr Met Arg Arg Lys Leu Arg Lys His
1               5                   10                  15

Asn Cys Leu Gln Arg Arg Cys Met Pro Leu His Ser Arg Val Pro Phe
            20                  25                  30

```
<210> SEQ ID NO 161
<211> LENGTH: 36
<212> TYPE: PRT
<213> ORGANISM: Unknown
<220> FEATURE:
<223> OTHER INFORMATION: Description of Unknown:
      apelin peptide

<400> SEQUENCE: 161

Leu Val Gln Pro Arg Gly Ser Arg Asn Gly Pro Gly Pro Trp Gln Gly
1               5                   10                  15

Gly Arg Arg Lys Phe Arg Arg Gln Arg Pro Arg Leu Ser His Lys Gly
            20                  25                  30

Pro Met Pro Phe
        35

<210> SEQ ID NO 162
<211> LENGTH: 23
<212> TYPE: PRT
<213> ORGANISM: Unknown
<220> FEATURE:
<223> OTHER INFORMATION: Description of Unknown:
      ELABELA peptide
<220> FEATURE:
<221> NAME/KEY: MOD_RES
<222> LOCATION: (1)..(7)
<223> OTHER INFORMATION: Any amino acid
<220> FEATURE:
<221> NAME/KEY: MOD_RES
<222> LOCATION: (9)..(11)
<223> OTHER INFORMATION: Any amino acid
<220> FEATURE:
<221> NAME/KEY: MOD_RES
<222> LOCATION: (14)..(16)
<223> OTHER INFORMATION: Any amino acid

<400> SEQUENCE: 162

Xaa Xaa Xaa Xaa Xaa Xaa Xaa Cys Xaa Xaa Xaa Arg Cys Xaa Xaa Xaa
1               5                   10                  15

His Ser Arg Val Pro Phe Pro
            20

<210> SEQ ID NO 163
<211> LENGTH: 24
<212> TYPE: PRT
<213> ORGANISM: Unknown
<220> FEATURE:
<223> OTHER INFORMATION: Description of Unknown:
      ELABELA peptide
<220> FEATURE:
<221> NAME/KEY: MOD_RES
<222> LOCATION: (1)..(8)
<223> OTHER INFORMATION: Any amino acid
<220> FEATURE:
<221> NAME/KEY: MOD_RES
<222> LOCATION: (10)..(12)
<223> OTHER INFORMATION: Any amino acid
<220> FEATURE:
<221> NAME/KEY: MOD_RES
<222> LOCATION: (15)..(17)
<223> OTHER INFORMATION: Any amino acid

<400> SEQUENCE: 163

Xaa Xaa Xaa Xaa Xaa Xaa Xaa Xaa Cys Xaa Xaa Xaa Arg Cys Xaa Xaa
1               5                   10                  15

Xaa His Ser Arg Val Pro Phe Pro
            20
```

<210> SEQ ID NO 164
<211> LENGTH: 24
<212> TYPE: PRT
<213> ORGANISM: Homo sapiens

<400> SEQUENCE: 164

Arg Arg Lys Leu Arg Lys His Asn Cys Leu Gln Arg Arg Cys Met Pro
1               5                   10                  15

Leu His Ser Arg Val Pro Phe Pro
            20

<210> SEQ ID NO 165
<211> LENGTH: 24
<212> TYPE: PRT
<213> ORGANISM: Peromyscus sp.

<400> SEQUENCE: 165

Lys Arg Lys Val Tyr Arg His Asn Cys Phe Arg Arg Cys Val Pro
1               5                   10                  15

Leu His Ser Arg Val Pro Phe Pro
            20

<210> SEQ ID NO 166
<211> LENGTH: 24
<212> TYPE: PRT
<213> ORGANISM: Rattus sp.

<400> SEQUENCE: 166

Arg Arg Lys Leu Tyr Arg His Asn Cys Phe Arg Arg Cys Ile Ser
1               5                   10                  15

Leu His Ser Arg Val Pro Phe Pro
            20

<210> SEQ ID NO 167
<211> LENGTH: 24
<212> TYPE: PRT
<213> ORGANISM: Mus musculus

<400> SEQUENCE: 167

Arg Arg Lys Leu Tyr Arg His Asn Cys Phe Arg Arg Cys Ile Pro
1               5                   10                  15

Leu His Ser Arg Val Pro Phe Pro
            20

<210> SEQ ID NO 168
<211> LENGTH: 24
<212> TYPE: PRT
<213> ORGANISM: Bos sp.

<400> SEQUENCE: 168

Arg Arg Lys Leu His Arg His Asn Cys Leu Gln Arg Arg Cys Met Pro
1               5                   10                  15

Leu His Ser Arg Val Pro Phe Pro
            20

<210> SEQ ID NO 169
<211> LENGTH: 24
<212> TYPE: PRT
<213> ORGANISM: Sus sp.

<400> SEQUENCE: 169

Arg Arg Lys Leu His Arg His Asn Cys Leu Gln Arg Arg Cys Met Pro
1               5                   10                  15

Leu His Ser Arg Val Pro Phe Pro
            20

<210> SEQ ID NO 170
<211> LENGTH: 24
<212> TYPE: PRT
<213> ORGANISM: Dasypus sp.

<400> SEQUENCE: 170

Arg Arg Lys Leu His Arg His Asn Cys Phe Gln Arg Arg Cys Met Pro
1               5                   10                  15

Leu His Ser Arg Val Pro Phe Pro
            20

<210> SEQ ID NO 171
<211> LENGTH: 24
<212> TYPE: PRT
<213> ORGANISM: Trichosurus sp.

<400> SEQUENCE: 171

Arg Arg Lys Pro His Arg His Ile Cys Pro Gln Arg Arg Cys Met Pro
1               5                   10                  15

Leu His Ser Arg Val Pro Phe Pro
            20

<210> SEQ ID NO 172
<211> LENGTH: 24
<212> TYPE: PRT
<213> ORGANISM: Gallus gallus

<400> SEQUENCE: 172

Arg Arg Lys Leu His Arg His Asn Cys Ser His Arg Arg Cys Met Pro
1               5                   10                  15

Leu His Ser Arg Val Pro Phe Pro
            20

<210> SEQ ID NO 173
<211> LENGTH: 24
<212> TYPE: PRT
<213> ORGANISM: Gekko sp.

<400> SEQUENCE: 173

Arg Arg Lys Leu His Arg Gln His Cys Ser His Arg Arg Cys Met Pro
1               5                   10                  15

Leu His Ser Arg Val Pro Phe Pro
            20

<210> SEQ ID NO 174
<211> LENGTH: 24
<212> TYPE: PRT
<213> ORGANISM: Anolis sp.

<400> SEQUENCE: 174

Arg Arg Lys Leu His Arg His His Cys Ser His Arg Arg Cys Met Pro
1               5                   10                  15

Leu His Ser Arg Val Pro Phe Pro
            20

<210> SEQ ID NO 175
<211> LENGTH: 24

<212> TYPE: PRT
<213> ORGANISM: Xenopus laevis

<400> SEQUENCE: 175

Arg Arg Arg Ile His Arg His Asn Cys Phe Leu Lys Arg Cys Ile Pro
1               5                   10                  15

Leu His Ser Arg Val Pro Phe Pro
            20

<210> SEQ ID NO 176
<211> LENGTH: 24
<212> TYPE: PRT
<213> ORGANISM: Ambystoma sp.

<400> SEQUENCE: 176

Arg Arg Arg Leu His Arg His Asn Cys Ser Leu Arg Arg Cys Met Pro
1               5                   10                  15

Leu His Ser Arg Val Pro Phe Pro
            20

<210> SEQ ID NO 177
<211> LENGTH: 24
<212> TYPE: PRT
<213> ORGANISM: Oryzias sp.

<400> SEQUENCE: 177

Arg Arg Lys Tyr His Arg His His Cys Leu His Arg Cys Met Pro
1               5                   10                  15

Leu His Ser Arg Val Pro Phe Pro
            20

<210> SEQ ID NO 178
<211> LENGTH: 24
<212> TYPE: PRT
<213> ORGANISM: Callorhinchus sp.

<400> SEQUENCE: 178

Arg Lys Lys Met Gln Arg Arg Asn Cys Trp His Arg Arg Cys Leu Pro
1               5                   10                  15

Phe His Ser Arg Val Pro Phe Pro
            20

<210> SEQ ID NO 179
<211> LENGTH: 24
<212> TYPE: PRT
<213> ORGANISM: Oncorhynchus sp.

<400> SEQUENCE: 179

Arg Arg Arg Tyr His Arg His His Cys Pro His Arg Cys Met Pro
1               5                   10                  15

Leu His Ser Arg Val Pro Phe Pro
            20

<210> SEQ ID NO 180
<211> LENGTH: 24
<212> TYPE: PRT
<213> ORGANISM: Danio rerio

<400> SEQUENCE: 180

Arg Arg Lys Tyr Arg Arg His Asn Cys Pro Lys Lys Arg Cys Leu Pro
1               5                   10                  15

Leu His Ser Arg Val Pro Phe Pro

<210> SEQ ID NO 181
<211> LENGTH: 23
<212> TYPE: PRT
<213> ORGANISM: Homo sapiens

<400> SEQUENCE: 181

Arg Lys Leu Arg Lys His Asn Cys Leu Gln Arg Arg Cys Met Pro Leu
1               5                   10                  15

His Ser Arg Val Pro Phe Pro
            20

<210> SEQ ID NO 182
<211> LENGTH: 23
<212> TYPE: PRT
<213> ORGANISM: Peromyscus sp.

<400> SEQUENCE: 182

Arg Lys Val Tyr Arg His Asn Cys Phe Arg Arg Cys Val Pro Leu
1               5                   10                  15

His Ser Arg Val Pro Phe Pro
            20

<210> SEQ ID NO 183
<211> LENGTH: 23
<212> TYPE: PRT
<213> ORGANISM: Rattus sp.

<400> SEQUENCE: 183

Arg Lys Leu Tyr Arg His Asn Cys Phe Arg Arg Cys Ile Ser Leu
1               5                   10                  15

His Ser Arg Val Pro Phe Pro
            20

<210> SEQ ID NO 184
<211> LENGTH: 23
<212> TYPE: PRT
<213> ORGANISM: Mus musculus

<400> SEQUENCE: 184

Arg Lys Leu Tyr Arg His Asn Cys Phe Arg Arg Cys Ile Pro Leu
1               5                   10                  15

His Ser Arg Val Pro Phe Pro
            20

<210> SEQ ID NO 185
<211> LENGTH: 23
<212> TYPE: PRT
<213> ORGANISM: Bos sp.

<400> SEQUENCE: 185

Arg Lys Leu His Arg His Asn Cys Leu Gln Arg Arg Cys Met Pro Leu
1               5                   10                  15

His Ser Arg Val Pro Phe Pro
            20

<210> SEQ ID NO 186
<211> LENGTH: 23
<212> TYPE: PRT
<213> ORGANISM: Sus sp.

<400> SEQUENCE: 186

Arg Lys Leu His Arg His Asn Cys Leu Gln Arg Arg Cys Met Pro Leu
1               5                   10                  15

His Ser Arg Val Pro Phe Pro
            20

<210> SEQ ID NO 187
<211> LENGTH: 23
<212> TYPE: PRT
<213> ORGANISM: Dasypus sp.

<400> SEQUENCE: 187

Arg Lys Leu His Arg His Asn Cys Phe Gln Arg Arg Cys Met Pro Leu
1               5                   10                  15

His Ser Arg Val Pro Phe Pro
            20

<210> SEQ ID NO 188
<211> LENGTH: 23
<212> TYPE: PRT
<213> ORGANISM: Trichosurus sp.

<400> SEQUENCE: 188

Arg Lys Pro His Arg His Ile Cys Pro Gln Arg Arg Cys Met Pro Leu
1               5                   10                  15

His Ser Arg Val Pro Phe Pro
            20

<210> SEQ ID NO 189
<211> LENGTH: 23
<212> TYPE: PRT
<213> ORGANISM: Gallus gallus

<400> SEQUENCE: 189

Arg Lys Leu His Arg His Asn Cys Ser His Arg Arg Cys Met Pro Leu
1               5                   10                  15

His Ser Arg Val Pro Phe Pro
            20

<210> SEQ ID NO 190
<211> LENGTH: 23
<212> TYPE: PRT
<213> ORGANISM: Gekko sp.

<400> SEQUENCE: 190

Arg Lys Leu His Arg Gln His Cys Ser His Arg Arg Cys Met Pro Leu
1               5                   10                  15

His Ser Arg Val Pro Phe Pro
            20

<210> SEQ ID NO 191
<211> LENGTH: 23
<212> TYPE: PRT
<213> ORGANISM: Anolis sp.

<400> SEQUENCE: 191

Arg Lys Leu His Arg His His Cys Ser His Arg Arg Cys Met Pro Leu
1               5                   10                  15

His Ser Arg Val Pro Phe Pro
            20

<210> SEQ ID NO 192

```
<211> LENGTH: 23
<212> TYPE: PRT
<213> ORGANISM: Xenopus laevis

<400> SEQUENCE: 192

Arg Arg Ile His Arg His Asn Cys Phe Leu Lys Arg Cys Ile Pro Leu
1               5                   10                  15

His Ser Arg Val Pro Phe Pro
            20

<210> SEQ ID NO 193
<211> LENGTH: 23
<212> TYPE: PRT
<213> ORGANISM: Ambystoma sp.

<400> SEQUENCE: 193

Arg Arg Leu His Arg His Asn Cys Ser Leu Arg Arg Cys Met Pro Leu
1               5                   10                  15

His Ser Arg Val Pro Phe Pro
            20

<210> SEQ ID NO 194
<211> LENGTH: 23
<212> TYPE: PRT
<213> ORGANISM: Oryzias sp.

<400> SEQUENCE: 194

Arg Lys Tyr His Arg His His Cys Leu His Arg Arg Cys Met Pro Leu
1               5                   10                  15

His Ser Arg Val Pro Phe Pro
            20

<210> SEQ ID NO 195
<211> LENGTH: 23
<212> TYPE: PRT
<213> ORGANISM: Callorhinchus sp.

<400> SEQUENCE: 195

Lys Lys Met Gln Arg Arg Asn Cys Trp His Arg Arg Cys Leu Pro Phe
1               5                   10                  15

His Ser Arg Val Pro Phe Pro
            20

<210> SEQ ID NO 196
<211> LENGTH: 23
<212> TYPE: PRT
<213> ORGANISM: Oncorhynchus sp.

<400> SEQUENCE: 196

Arg Arg Tyr His Arg His His Cys Pro His Arg Arg Cys Met Pro Leu
1               5                   10                  15

His Ser Arg Val Pro Phe Pro
            20

<210> SEQ ID NO 197
<211> LENGTH: 23
<212> TYPE: PRT
<213> ORGANISM: Danio rerio
```

-continued

```
<400> SEQUENCE: 197

Arg Lys Tyr Arg Arg His Asn Cys Pro Lys Lys Arg Cys Leu Pro Leu
1               5                   10                  15

His Ser Arg Val Pro Phe Pro
                20
```